US009255264B2

(12) United States Patent
Taguchi et al.

(10) Patent No.: US 9,255,264 B2
(45) Date of Patent: Feb. 9, 2016

(54) HAIR SHAPE SUSCEPTIBILITY GENE

(75) Inventors: Hiroyuki Taguchi, Tochigi (JP); Hiroshi Yoshida, Tochigi (JP); Chie Fuse, Tochigi (JP); Tadao Arinami, Ibaraki (JP)

(73) Assignee: Kao Corporation, Tokyo (JP)

( * ) Notice: Subject to any disclaimer, the term of this patent is extended or adjusted under 35 U.S.C. 154(b) by 228 days.

(21) Appl. No.: 13/500,462

(22) PCT Filed: Oct. 5, 2010

(86) PCT No.: PCT/JP2010/067444
§ 371 (c)(1),
(2), (4) Date: Jun. 1, 2012

(87) PCT Pub. No.: WO2011/043333
PCT Pub. Date: Apr. 14, 2011

(65) Prior Publication Data

US 2012/0276536 A1 Nov. 1, 2012

(30) Foreign Application Priority Data

Oct. 5, 2009 (JP) ................................ 2009-231998
Oct. 5, 2009 (JP) ................................ 2009-232000
Oct. 5, 2009 (JP) ................................ 2009-232030
Oct. 5, 2009 (JP) ................................ 2009-232031
Oct. 5, 2009 (JP) ................................ 2009-232034

(51) Int. Cl.
*C12N 15/09* (2006.01)
*C12Q 1/68* (2006.01)
*G01N 33/15* (2006.01)
*G01N 33/50* (2006.01)
*G01N 33/53* (2006.01)

(52) U.S. Cl.
CPC *C12N 15/09* (2013.01); *C12Q 1/68* (2013.01); *G01N 33/15* (2013.01); *G01N 33/50* (2013.01); *G01N 33/53* (2013.01)

(58) Field of Classification Search
None
See application file for complete search history.

(56) References Cited

U.S. PATENT DOCUMENTS

| | | | | |
|---|---|---|---|---|
| 6,812,330 | B2 | 11/2004 | Burton et al. | |
| 6,812,339 | B1 | 11/2004 | Venter et al. | |
| 2002/0045188 | A1 * | 4/2002 | Kamb et al. | 435/7.1 |
| 2005/0208010 | A1 | 9/2005 | De Lacharriere et al. | |
| 2005/0250180 | A1 | 11/2005 | Jacobs et al. | |
| 2007/0065389 | A1 | 3/2007 | De Lacharriere et al. | |
| 2012/0231094 | A1 | 9/2012 | Taguchi et al. | |
| 2012/0329726 | A1 | 12/2012 | Taguchi et al. | |

FOREIGN PATENT DOCUMENTS

| | | |
|---|---|---|
| JP | 2002-238577 | 8/2002 |
| JP | 2005-532407 | 10/2005 |
| JP | 2006-042735 | 2/2006 |
| JP | 2006-254735 | 9/2006 |
| WO | WO 02/068649 A2 | 9/2002 |
| WO | WO 2007/086526 A1 | 8/2007 |
| WO | WO 2008/016356 A2 | 2/2008 |
| WO | WO 2008/021290 A2 | 2/2008 |
| WO | WO 2008/043644 A1 | 4/2008 |

OTHER PUBLICATIONS

Jiang et al., Oral cancer overexpressed 1 (ORAOV1): A regulator for the cell growth and tumor angiogenesis in oral squamous cell carcinoma; Int. J. Cancer, vol. 123, ppl 1779-1786, 2008.*
Ku et al., Genomic profiling of decreased DNA damage response in human squamous carcinoma cells; Molecular Medicine Reports, vol. 1, pp. 105-117, 2008.*
Hattori et al., GenBank Accession No. AP001888.4, submitted Mar. 15, 2003; Accessed Sep. 3, 2014.*
GenBank Accession No. NM_153451.2, ORAOV1 nucleotide sequence, accessed Sep. 3, 2014.*
GenPept Accession No. NP_703152.1 ORAOV1 protein sequence, accessed Sep. 3, 2014.*
Extended European search report including the supplementary European search report and the European search opinion, mailed May 17, 2013, for EP Application No. 10822000.5, the European Patent Office, Rijswijk, Netherlands.
Yusuke: "Submitted SNP (ss) Details: ss4940242," NCBI-dbSNP database, NCBI, Bethesda, MD, submitted Aug. 1, 2002, retrieved from the internet: www.ncbi.nlm.nih.gov/SNP/snp_ss.cgi?subsnp_id=4940242 retrieved on Apr. 16, 2013.
International Search Report (ISR) for PCT/JP2010/067444, I.A. fd: Oct. 5, 2010, mailed Dec. 7, 2010 from the Japanese Patent Office, Tokyo, Japan.
International Preliminary Report on Patentability (IPRP), Chapter I of the Patent Cooperation Treaty, including the Written Opinion for PCT/JP2010/067444, I.A. fd: Oct. 5, 2010, issued May 8, 2012, from the International Bureau of WIPO, Geneva, Switzerland.
*Homo sapiens* organic anion transporter 3 (OAT3), mRNA, complete cds. Uploaded Mar. 9, 1999. NCBI Entrez Nucleotide, Accession No. AF097491 (GI:4378058), retrieved on Nov. 29, 2010, from the internet, www.ncbi.nlm.nih.gov/nuccore/4378058>.

(Continued)

*Primary Examiner* — Addison D Ault
(74) *Attorney, Agent, or Firm* — Sterne, Kessler, Goldstein & Fox P.L.L.C.

(57) ABSTRACT

A genetic polymorphism and a hair shape susceptibility gene that are related to hair shape, and a method for determining the genetic susceptibility to hair shape in individual test subjects are provided. Disclosed is a hair shape susceptibility gene, which overlaps with a haplotype block in in the 11q12.2 to 11q13.2 region (D11S4191 and D11S987) of human chromosome 11 and comprises a portion or the entirety of the base sequence of the haplotype block, wherein the haplotype block is determined by a linkage disequilibrium analysis conducted on a single nucleotide polymorphism (SNP) marker whose allele frequency differs statistically significantly between a group having a curly hair trait and a group having a non-curly hair trait, and consists of a base sequence set forth in any one of SEQ ID NO: 1 to NO: 5.

17 Claims, 14 Drawing Sheets

(56) References Cited

OTHER PUBLICATIONS

*Homo sapiens* phosphofurin acidic cluster sorting protein 1 (PACS1), mRNA, complete cds. Uploaded Sep. 20, 2009, NCBI Entrez Nucleotide, Accession No. NM_018026 (GI:30089915), retrieved on Nov. 29, 2010, from the internet, www.ncbi.nlm.nih.gov/nuccore/30089915?sat=NCBI&satkey=32698503>.

*Homo sapiens* kinesin light chain 2 (KLC2), transcript variant 2, mRNA, Uploaded Sep. 3, 2009, NCBI Entrez Nucleotide, Accession No. NM_001134774 (GI:198041727), retrieved on Nov. 29, 2010, from the internet, www.ncbi.nlm.nih.gov/nuccore/198041727?sat=NCBI&satkey=32519240>.

*Homo sapiens* RAB1B, member RS oncogene family (RAB1B), mRNA, Uploaded Feb. 1, 2009, NCBI Entrez Nucleotide, Accession No. NM_030981 (GI:116014337), retrieved on Nov. 29, 2010, from the internet, www.ncbi.nlm.nih.gov/nuccore/116014337?sat=NCBI &satkey=27780408>.

*Homo sapiens* cornichon homolog 2 (*Drosophila*) (CNIH2), mRNA, Uploaded Aug. 6, 2009, NCBI Entrez Nucleotide, Accession No. NM_182553 (GI:32698937), retrieved on Nov. 29, 2010, from the internet, www.ncbi.nlm.nih.gov/nuccore/32698937?sat=NCBI &satkey=31931907>.

*Homo sapiens* Yip1 interacting factor homolog A (*S. cerevisiae*) (YIF1A), mRNA, Uploaded Aug. 2, 2009, NCBI Entrez Nucleotide, Accession No. NM_020470 (GI:170932463), retrieved on Nov. 29, 2010, from the internet, www.ncbi.nlm.nih.gov/nuccore/170932463?sat=NCBI&satkey=31767219>.

*Homo sapiens* transmembrance protein 151A (TMEM151A), mRNA, Uploaded Aug. 6, 2009, NCBI Entrez Nucleotide, Accession No. NM_153266 (GI:221136815), retrieved on Nov. 29, 2010, from the internet, www.ncbi.nlm.nih.gov/nuccore/NM_153266.3.

*Homo sapiens* CD248 molecule, endosialin (CD248), mRNA, Uploaded Feb. 1, 2009, NCBI Entrez Nucleotide, Accession No. NM_020404 (GI:45387956), retrieved on Nov. 29, 2010, from the internet, www.ncbi.nlm.nih.gov/nuccore/45387956?sat=NCBI &satkey=27783461>.

*Homo sapiens* oral cancer overexpressed 1 (ORAOV1), mRNA, Uploaded Aug. 6, 2009, NCBI Entrez Nucleotide, Accession No. NM_153451 (GI:56676315), retrieved on Nov. 29, 2010, from the internet, www.ncbi.nlm.nih.gov/nuccore/56676315?sat=NCBI &satkey=31931818>.

*Homo sapiens* keratin associated protein 5-8 (KRTAP5-8), mRNA, Uploaded May 1, 2008, NCBI Entrez Nucleotide, Accession No. NM_021046 (GI:123173776), retrieved on Nov. 29, 2010, from the internet, www.ncbi.nlm.nih.gov/nuccore/123173776?sat=NCBI &satkey=22245774>.

*Homo sapiens* keratin associated protein 5-9 (KRTAP5-9), mRNA, Uploaded Feb. 26, 2008, NCBI Entrez Nucleotide, Accession No. NM_005553 (GI:123702037), retrieved on Nov. 29, 2010, from the internet, www.ncbi.nlm.nih.gov/nuccore/123702037?sat=NCBI &satkey=20831141>.

*Homo sapiens* keratin associated protein 5-10 (KRTAP5-10), mRNA, Uploaded May 1, 2008, NCBI Entrez Nucleotide, Accession No. NM_001012710 (GI:60593039), retrieved on Nov. 29, 2010, from the internet, www.ncbi.nlm.nih.gov/nuccore/60593039?sat=NCBI&satkey=22247595>.

Altshuler, D et al., "The common PPARgamma Pro12Ala polymorphism is associated with decreased risk of type 2 diabetes," Nat Genet 26(1): 76-80 (Sep. 2000), Nature Pub. Co, New York, NY.

Cullen SI et al, "Acquired Progressive Kinking of the Hair," Arch Dermatol 125: 252-255 (Feb. 1989), American Medical Assn, Chicago, IL.

Du, X et al., "Velvet, a Dominant Egfr Mutation That Causes Wavy Hair and Defective Eyelid Development in Mice," Genetics 166: 331-340 (Jan. 2004), Genetics Society of America, Bethesda, MD.

Fujimoto, A, et al., "A scan for genetic determinants of human hair morphology: EDAR is associated with Asian hair thickness," Hum Mol Genet 17: 835-843 (Mar. 2008), IRL Press at Oxford University Press, Oxford, England.

Hanis, CL et al., "A genome-wide search for human non-insulin-dependent (type 2) diabetes genes reveals a major susceptibility locus on chromosome 2," Nat Genet 13(2): 161-166 (Jun. 1996), Nature Pub. Co, New York, NY.

Kjaer, KW et al., "Novel Connexin 43 (GJA1) mutation causes ocuio-dento-digital dysplasia with curly hair,"Am J Med Genet A, 127A(2): 152-157 (Jun. 2004), Wiley-Blackwell, Hoboken, N.J.

Mann, GB et al., "Mice with a null mutation of the TGF alpha gene have abnormal skin architecture, wavy hair, and curly whiskers and often develop corneal inflammation," Cell 73(2): 249-261 (Apr. 1993), MIT Press, Cambridge, MA.

Medland, SE et al., "Common variants in the trichohyalin gene are associated with straight hair in Europeans," Am J Hum Genet 85(5): 750-755 (Nov. 2009), American Society of Human Genetics, Baltimore, MD.

Møller, LB et al., "Identification and analysis of 21 novel disease-causing amino acid substitutions in the conserved part of ATP7A," Hum Mutat 26(2): 84-93 (Aug. 2005), Wiley-Liss, New York, NY.

Norgett, EE et al., "Recessive mutation in desmoplakin disrupts desmoplakin-intermediate filament interactions and causes dilated cardiomyopathy, woolly hair and keratoderma," Hum Mol Genet 9: 2761-2766 (Nov. 2000), IRL Press at Oxford University Press, Oxford, England.

Rostand, J et al., "An Atlas of Human Genetics," Hutchinson Scientific & Technical, London, England, pp. 26-29, 1964.

Sabeti, PC et al., "Genome-wide detection and characterization of positive selection in human populations," Nature 449(7164): 913-918 (Oct. 2007), Nature Publishing Group, Basingstoke, England.

Sulem, P et al., "Genetic determinants of hair, eye and skin pigmentation in Europeans," Nat Genet 39(12): 1443-1452 (Dec. 2007), Nature Pub. Co., New York, NY.

Thibaut, S, et al., "Human hair shape is programmed from the bulb," Br J Dermatol 152(4): 632-638 (Apr. 2005), Blackwell Scientific Publications, Oxford, England.

Extended European search report including the supplementary European search report and the European search opinion, mailed Jun. 7, 2013, for EP Application No. 10822003.9, the European Patent Office, Munich, Germany.

International Search Report (ISR) for PCT/JP2010/067441, I.A. fd: Oct. 5, 2010, mailed Nov. 30, 2010 from the Japanese Patent Office, Tokyo, Japan (PCT phase of U.S. Appl. No. 13/500,439).

International Preliminary Report on Patentability (IPRP), Chapter I of the Patent Cooperation Treaty, including the Written Opinion for PCT/JP2010/067441, I.A. fd: Oct. 5, 2010, issued May 8, 2012, from the International Bureau of WIPO, Geneva, Switzerland (PCT phase of U.S. Appl. No. 13/500,439).

International Search Report (ISR) for PCT/JP2010/067443, I.A. fd: Oct. 5, 2010, mailed Dec. 7, 2010, from the Japanese Patent Office, Tokyo, Japan (PCT phase of U.S. Appl. No. 13/500,442).

International Preliminary Report on Patentability (IPRP), Chapter I of the Patent Cooperation Treaty, including the Written Opinion for PCT/JP2010/067443, I.A. fd: Oct. 5, 2010, issued May 8, 2012, from the International Bureau of WIPO, Geneva, Switzerland (PCT phase of U.S. Appl. No. 13/500,442).

Notification of First Office Action, for Chinese Patent Application No. CN 201080044858.8, mailed Dec. 24, 2012, from the Patent Office of the People's Republic of China, Beijing, China (counterpart to U.S. Appl. No. 13/500,439).

Extended European search report for EP Appl. No. 10822002.1, including the supplementary European search report and the European search opinion, dated Feb. 12, 2013, European Patent Office, Munich, Germany (counterpart to U.S. Appl. No. 13/500,442).

*Homo sapiens* annexin A9 (ANXA9), mRNA, Uploaded May 1, 2008, NCBI Entrez Nucleotide, Accession No. NM_003568 (GI:145864464), retrieved on Nov. 15, 2010, from the internet, www.ncbi.nlm.nih.gov/nuccore/145864464?sat=NCBI &satkey=22246716>.

*Homo sapiens* family with sequence similarity 63, member A (FAM63A), transcript variant 2, mRNA, Uploaded Aug. 5, 2009, NCBI Entrez Nucleotide, Accession No. NM_001040217 (GI:253795485), retrieved on Nov. 15, 2010, from the internet, www.ncbi.nlm.nih.gov/nuccore/NM_001040217.2>.

(56) References Cited

OTHER PUBLICATIONS

*Homo sapiens* late cornified envelope 5A (LCE5A), mRNA, Uploaded Sep. 20, 2009, NCBI Entrez Nucleotide, Accession No. NM_178438 (GI:110578661), retrieved on Nov. 15, 2010, from the internet, www.ncbi.nlm.nih.gov/nuccore/110578661?sat=NCBI &satkey=32699481>.
*Homo sapiens* cysteine-rich C-terminal 1 (CRCT1), mRNA, Uploaded Oct. 9, 2008, NCBI Entrez Nucleotide, Accession No. NM_019060 (GI:209180483), retrieved on Nov. 15, 2010, from the internet, www.ncbi.nlm.nih.gov/nuccore/209180483?sat=NCBI &satkey=25519550>.
*Homo sapiens* late cornified envelope 2B (LCE2B), mRNA, Uploaded Feb. 22, 2009, NCBI Entrez Nucleotide, Accession No. NM_014357 (GI:223633914), retrieved on Nov. 15, 2010, from the internet, www.ncbi.nlm.nih.gov/nuccore/223633914?sat=NCBI &satkey=28460288>.
*Homo sapiens* late cornified envelope 2A (LCE2A), mRNA, Uploaded Feb. 13, 2009, NCBI Entrez Nucleotide, Accession No. NM_178428 (GI:57242769), retrieved on Nov. 15, 2010, from the internet, www.ncbi.nlm.nih.gov/nuccore/57242769?sat=NCBI &satkey=283933204>.
*Homo sapiens* sperm mitochondria-associated cysteine-rich protein (SMCP), nuclear gene encoding mitochondrial protein, mRNA, Uploaded Feb. 11, 2008, NCBI Entrez Nucleotide, Accession No. NM_030663 (GI:25121988), retrieved on Nov. 15, 2010, from the internet, www.ncbi.nlm.nih.gov/nuccore/25121988?sat=NCBI &satkey=20570171>.
*Homo sapiens* involucrin (IVL), mRNA, Uploaded Sep. 20, 2009, NCBI Entrez Nucleotide, Accession No. NM_005547 (GI:44890058), retrieved on Nov. 15, 2010, from the internet, www.ncbi.nlm.nih.gov/nuccore/44890058?sat=NCBI &satkey=32698100>.
*Homo sapiens* cysteine and glycine-rich protein 1, mRNA (cDNA clone MGC:40335 IMAGE:5244276, complete cds. Uploaded Jul. 15, 2006, NCBI Entrez Nucleotide, Accession No. BC032493 (GI:21595351) [Retrieved on Nov. 24, 2010, from the internet, www.ncbi.nlm.nih.gov/nuccore/21595351>.
*Homo sapiens* neuron navigator 1 (NAV1) mRNA, complete cds. Uploaded Jul. 1, 2002, NCBI Entrez Nucleotide, Accession No. AY043013 (GI:21654876) [Retrieved on Nov. 24, 2010, from the internet, www.ncbi.nlm.nih.gov/nuccore/21654876>.
*Homo sapiens* importin 9 (IPO9), mRNA, Uploaded Feb. 11, 2008, NCBI Entrez Nucleotide, Accession No. NM_018085 (GI:112734865) [Retrieved on Nov. 24, 2010, from the internet, www.ncbi.nlm.nih.gov/nuccore/112734865?sat=NCBI &satkey=20569420>.
*Homo sapiens* shisa homolog 4 (*Xenopus laevis*) (SHISA4), mRNA, Uploaded Sep. 3, 2009, NCBI Entrez Nucleotide, Accession No. NM_198149 (GI:39930574) [Retrieved on Nov. 24, 2010, from the internet, www.ncbi.nlm.nih.gov/nuccore/39930574?sat=NCBI &satkey=32433675>.
*Homo sapiens* nuclear casein kinase and cyclin-dependent kinase substrate 1 (NUCKS1), mRNA, Uploaded Feb. 1, 2009, NCBI Entrez Nucleotide, Accession No. NM_022731 (GI:181336713) [Retrieved on Nov. 24, 2010, from the internet, www.ncbi.nlm.nih.gov/nuccore/181336713?sat=NCBI&satkey=27783208>.
Botchkarev, VA et al., "Edar signaling in the control of hair follicle development," J Investig Dermatol Symp Proc 10(3): 247-251, Dec. 2005), Nature Publishing Group, New York, New York.
Kimura, K. et al., "Diversification of transcriptional modulation: Large-scale identification and characterization of putative alternative promoters of human gene," Genome Research 16: 55-65, Jan. 2006, Cold Spring Harbor Laboratory Press, Woodbury, NY.
Klacansky, I. et al., "Cell-type-specific patterns of gene expression, GenBank: lucus FW48121.1" Feb. 21, 2008, XP055052019, Retrieved from the internet: www.ncbi.nlm.nih.gov/nuccore/fw548121, retrieved Feb. 1, 2013.
Mou, C, et al., "Enhanced ectodysplasin-A receptor (EDAR) signaling alters multiple fiber characteristics to produce the East Asian hair form," Hum Mutat, 29(12): 1405-1411 (Dec. 2008), Wiley-Liss, New York, NY.
Notification of First Office Action, for Chinese Patent Application No. CN 201080044857.3, mailed Dec. 24, 2012, from the Patent Office of the People's Republic of China, Beijing, China (counterpart to U.S. Appl. No. 13/500,462).
Notification of First Office Action, for Chinese Patent Application No. CN 201080044856.9, mailed Dec. 25, 2012, from the Patent Office of the People's Republic of China, Beijing, China (counterpart to U.S. Appl. No. 13/500,442).
Tand, D. et al., "Advances in Methods for SNP Detection," J. Shanghai Jiaotong University (Agricultural Science) 25(2):405-418 (Apr. 2007), China Academic Journal Electronic Publishing House, Beijing, China.
Wang, Q-s. et al., "Review of Association Analyses of Haplotype with Traits," J. Shanghai Jiaotong University (Agricultural Science) 26(3):255-257 (Jun. 2008),China Academic Journal Electronic Publishing House, Beijing, China.
Stoll, M et al., "Genetic variation in DLG5 is associated with inflammatory bowel disease," Nat Genet, May 2004; 36(5): 476-480, Nature Pub. Co, New York, NY.
Shimomura, Y et al., "Disruption of P2RY5, an orphan G protein-coupled receptor, underlies autosomal recessive woolly hair," Nat Genet, Mar. 2008; 40(3): 335-339, Nature Pub. Co, New York, NY.
Schlake, T, "Segmental Igfbp5 expression is specifically associated with the bent structure of zigzag hairs," Mech Dev, Sep. 2005; 122(9): 988-997, Elsevier, Limerick, Ireland.
Excerpted file history of U.S. Appl. No. 13/500,439: Final Office action mailed Nov. 24, 2014; Amendment and Reply filed Oct. 17, 2014; Office action mailed Apr. 22, 2014; reply to Restriction/election of species requirements filed Jan. 23, 2014 and Restriction/election of species requirements mailed Nov. 27, 2013.
Excerpted file history of U.S. Appl. No. 13/500,442: Final Office action mailed Sep. 10, 2014; Reply to Office action filed Aug. 21, 2014; Office action mailed Apr. 21, 2014; reply to Restriction/election of species requirements filed Jan. 23, 2014; and Restriction/election of species requirement mailed Nov. 27, 2013.
Hindorff, LA et al., "Genetic architecture of cancer and other complex diseases: lessons learned and future directions," Carcinogenesis, Jul. 2011; 32: 945-954, IRL Press, Oxford, England.
Liu, X et al., "Genetic variants at 5p12 and risk of breast cancer in Han Chinese," J Hum Genet, Oct. 2012; 57(10): 638-641, Nature Pub. Group, London, England.
*Homo sapiens* cysteine and glycine-rich protein 1 (CSRP1), transcript variant 1, mRNA, NCBI Accession NM_004078, version NM_004078.2 (GI:221316625), Jun. 24, 2009, last modification Feb. 26, 2014, printed from www.ncbi.nlm.nih.gov/nuccore/NM_004078.
Xie, Ji-sheng et al., "Difference in the polymorphism of exon 5 +3953C/T of interleukin-1 beta gene between Guangxi Zhuang population and Han population," Chinese J Clin. Rehabilitation 10:154-156 (Oct. 2006), Shenyang Shi, China.
Excerpted file history of U.S. Appl. No. 13/500,442: Amendment and reply filed Mar. 9, 2015.
Excerpted file history of U.S. Appl. No. 13/500,439: Amendment and Reply filed Mar. 20, 2015, filed with the United States Patent and Trademark Office, Alexandria, VA.

* cited by examiner

HAIR SHAPE SUSCEPTIBILITY GENE

REFERENCE TO SEQUENCE LISTING SUBMITTED ELECTRONICALLY

The content of the electronically submitted substitute sequence listing, file name 2537_0690005SequenceListing_ascii.txt; size 431,187 bytes; and date of creation Apr. 4, 2012, filed herewith, is incorporated herein by reference in its entirety.

FIELD OF THE INVENTION

The present invention relates to a gene related to hair shape, determination of genetic susceptibility to hair shape, detection and/or determination of the type of hair shape, a marker for screening an ingredient effective for the regulation of hair shape, and a use of the marker.

BACKGROUND OF THE INVENTION

The natural shape of human hair is generally classified into straight hair, wavy hair (wave hair), curled hair, and kinky hair (or coiled hair), depending on the degree of curl of the hair. Since the shape of hair and hairstyle constitutes one of the traits that can be easily recognized as physical features of human being, and also serve as an important factor that determines the first impression of a person, the shape of hair and hairstyle is a matter of great interest from a cosmetic viewpoint, irrespective of gender and age. In the case of kinky hair or curled hair with a high degree of curl, the person has trouble that the degree of freedom in hairstyle is limited so that desired styling cannot be achieved. On the other hand, even in the case of straight hair, the person also has trouble that the hair cannot be volumized, and bare skin is easily shown through.

As methods for changing the shape of hair and hairstyle, hairdressing using various hairstyling agents or hair dryers/hair irons, wave/straight permanent treatments, and the like are being extensively carried out. However, although these operations can effectively modify the shape of hair, the operations have no effect on the causative factor that determines the hair shape. These operations, which are solutions to the above described troubles, are not fundamental solutions but are merely temporary, and in order to maintain the shape of hair and hairstyle, these operations must be repeated frequently. However, on the contrary, these operations cause increased damage to hair, and consequently impair the cosmetic value. For this reason, there is a demand for the development of a method for the intrinsic regulation of hair shape, by which the hair shape can be changed from the beginning of hair growth.

Searching for a causative factor that determines the hair shape and identifying a causative gene thereof are expected to provide useful information in the development of a method for the intrinsic regulation of hair shape. In regard to the factors or genes related to hair shape, there have been reports on the genetic diseases that bring changes to the shape of hair (Non-Patent Documents 1 to 3), acquired kinky hair caused by drugs (Non-Patent Document 4), curly hair model animals (Non-Patent Documents 5 and 6), and the like. However, the factors or genes disclosed in these documents are merely a special example that affect the hair shape, and are not adequate to be considered as causative factors that determine the natural shape of human hair.

Meanwhile, along with the rapid progress in the genome analysis technology in recent years, the correlation between diseases and genes is being gradually clarified. Particularly, not only for so-called genetic diseases that are defined by variation or abnormality of a single gene, but also for polygenic diseases characterized by low penetrance (the ratio of onset of a certain disease in an individual having a variation in a certain gene), such as highly frequent common diseases including lifestyle diseases such as diabetes and hypertension, search for causative genes using non-parametric linkage analysis techniques such as affected sib-pair linkage analysis is frequently carried out (see, for example, Non-Patent Document 7). Further, based on the hypothesis that the variation of a disease-associated gene for a common disease is a highly frequent genetic polymorphism (common variant), and that although the variation is present in healthy persons as well, the prevalence is significantly high in patients (Common Disease-Common Variant), search for causative genes by means of linkage disequilibrium analysis using a genetic polymorphism (for example, SNP (Single Nucleotide Polymorphism)) is also actively carried out throughout the world (see, for example, Non-Patent Document 8).

More recently, with the progress in the international HapMap Project, a database of general polymorphisms (SNP) of high frequencies such as one million loci or more in four human populations has been established, and research is being conducted on common diseases as well as on general traits in which the phenotype varies with the human race or population, for example, skin color, hair color, and eye color (see, for example, Non-Patent Documents 9 and 10).

Similarly, also in regard to the natural shape of human hair, it can be contemplated that the natural hair shape is a general trait in which the phenotype varies with the human race or population. In general, many Asian people have straight hair, while African people predominantly have kinky hair (or curled hair). Indo-European people have a high ratio of having a trait of wavy hair (wave hair), which is intermediate of the two. The mode of inheritance was first observed by Rostand, J., et al., and they reported that curly hair is an autosomal (semi) dominant trait over straight hair (Non-Patent Document 11). Furthermore, descriptions on the curly hair trait may also be found in the human Mendelian inheritance database of the NCBI (OMIM, http://www.ncbi.nlm.nih.gov/omim/). However, in regard to causative genes that determine the natural shape of human hair, systematic research on genome analysis has not been completed, and no such genes have been found yet.

PRIOR ART DOCUMENTS

Non-Patent Documents

Non-Patent Document 1: Norgett E E et al., Hum. Mol. Genet. 9(18), p. 2761-2766, 2000

Non-Patent Document 2: Moller L B et al., Hum. Mutat. 26 (2), p. 84-93, 2005

Non-Patent Document 3: Kjaer K W et al., Am. J. Med. Genet. A. 127A(2), p. 152-157, 2004

Non-Patent Document 4: Cullen S I et al., Arch. Dermatol. 125(2), p. 252-255, 1989

Non-Patent Document 5: Du X at al. Genetics. 166(1), p. 331-340, 2004

Non-Patent Document 6: Mann G B at al., Cell. 73(2), p. 249-61, 1993

Non-Patent Document 7: Hanis C L et al., Nat. Genet. 13(2), p 161-166, 1996

Non-Patent Document 8: Altshuler D et al., Nat. Genet. 26(1), p. 76-80, 2000

Non-Patent Document 9: Sulem P et al., Nat. Genet. 39(12), p. 1443-1452, 2007

Non-Patent Document 10: Sabeti P C et al., Nature. 449 (7164), p. 913-918, 2007

Non-Patent Document 11: Rostand J at al., "An Atlas of Human Genetics", Hutchinson Scientific & Technical, London, pp. 26-29, 1964

SUMMARY OF THE INVENTION

The present invention provides a hair shape susceptibility gene, which overlaps with a haplotype block in the 11q12.2 to 11q13.2 region (D11S4191 and D11S987) of human chromosome 11 and includes a portion or the entirety of the base sequence of the haplotype block, wherein the haplotype block is determined by a linkage disequilibrium analysis conducted on a single nucleotide polymorphism (SNP) marker whose allele frequency differs statistically significantly between a group having a curly hair trait and a group having a non-curly hair trait, and consists of a base sequence set forth in any one of SEQ ID NO:1 to NO:5.

The present invention also provides a hair shape determining marker, which is an oligo- or polynucleotide containing a partial base sequence of the base sequence of the haplotype block described above, or a complementary strand thereof, wherein the partial base sequence consists of a contiguous base sequence containing one or more single nucleotide polymorphisms (SNPs), wherein the SNPs include an SNP whose allele frequency differs statistically significantly between a group having a curly hair trait and a group having a non-curly hair trait and an SNP linked to the SNP.

Furthermore, the present invention provides a method for determining the genetic susceptibility of a test subject to hair shape, the method including the following steps (a) to (c):

(a) preparing a genomic DNA derived from a test subject;

(b) detecting, from the genomic DNA, in the haplotype block, a single nucleotide polymorphism (SNP) which exists in the haplotype block described above and whose allele frequency differs statistically significantly between a group having a curly hair trait and a group having a non-curly hair trait, and a single nucleotide polymorphism (SNP) that is linked to the SNP; and (c) determining, if the allele frequency of the detected relevant SNP is statistically significantly higher in the group of curly hair people than in the group of non-curly hair people, that the test subject has a genetic predisposition to curly hair, and if the allele frequency of the detected SNP is statistically significantly higher in an arbitrary group of non-curly hair people than in the group of curly hair people, that the test subject does not have a genetic predisposition to curly hair.

The present invention also provides a method for determining the genetic susceptibility of a test subject to hair shape, the method including:

identifying, for any one or more nucleotides of the nucleotide numbers as indicated in the following table that are present in the base sequences set forth in SEQ ID NO:1 to NO:5 in the genomic DNA derived from a test subject, whether the nucleotide is nucleotide (i) or nucleotide (ii); and determining, when the nucleotide is nucleotide (i), that the test subject has a predisposition to curly hair, and when the nucleotide is nucleotide (ii), that the test subject does not have a predisposition to curly hair.

TABLE 1

| SEQ ID NO. | Nucleotide Number | Nucleotide (i) (having predisposition) | Nucleotide (ii) (no predisposition) |
|---|---|---|---|
| 1 | 1 | C | G |
| | 7633 | T | A |
| | 9315 | C | G |
| 2 | 1 | T | C |
| | 16722 | C | A |
| | 19992 | C | T |
| | 21051 | C | T |
| | 21927 | A | T |
| | 25269 | G | A |
| | 27032 | T | C |
| | 35997 | G | C |
| | 49537 | G | A |
| | 55405 | A | T |
| | 69180 | C | T |
| | 84627 | G | A |
| | 86185 | C | A |
| | 90221 | T | C |
| | 91247 | T | A |
| | 92398 | T | C |
| | 98150 | A | G |
| | 100779 | C | T |
| | 101730 | G | A |
| | 102920 | T | G |
| | 105310 | A | G |
| | 126741 | G | A |
| | 133917 | T | C |
| | 134786 | G | C |
| | 142991 | C | T |
| | 144254 | G | A |
| | 147896 | G | C |
| | 150043 | G | A |
| | 152853 | T | C |
| | 168931 | C | T |
| | 172500 | C | T |
| | 175003 | C | T |
| | 184535 | G | A |
| | 189853 | G | C |
| | 194405 | C | G |
| | 202111 | G | T |
| 3 | 5297 | C | A |
| | 18280 | C | T |
| | 18933 | A | G |
| 4 | 1 | G | A |
| | 8378 | T | G |
| | 12624 | C | T |
| | 20147 | C | G |
| | 22309 | T | A |
| | 24512 | C | T |
| | 26599 | C | T |
| 5 | 17000 | C | T |
| | 18895 | G | T |
| | 26143 | A | G |
| | 26545 | G | A |
| | 27090 | T | C |
| | 27751 | A | G |
| | 30274 | C | T |

Furthermore, the present invention provides a reagent for the determination of the genetic susceptibility of a test subject to hair shape, the reagent including a probe and/or a primer, which hybridizes with the hair shape determining marker of the present invention under stringent conditions.

The present invention also provides a kit for the determination of the genetic susceptibility of a test subject to hair shape, the kit including the reagent described above.

Furthermore, the present invention provides a method for screening a hair shape regulating agent, the method including the following steps (a) and (b):

(a) administering a test substance to a cell containing the hair shape susceptibility gene of the present invention; and (b) selecting, among the administered test substances, a substance which converts the type of the polymorphism of the nucleotide in a marker with a single nucleotide polymorphism (SNP) that is present on the hair shape susceptibility gene or in the vicinity thereof, and the allele frequency of which differs statistically significantly between a group having a curly hair trait and a group having a non-curly hair trait, or a single nucleotide polymorphism (SNP) that is linked to the SNP, to other polymorphisms, as a hair shape regulating agent.

Furthermore, the present invention provides a marker for the type of hair shape, consisting of a polynucleotide consisting of a base sequence set forth in SEQ ID NO:34, SEQ ID NO:36, SEQ ID NO:38 or SEQ ID NO:40, or a base sequence complementary thereto, or a partial polynucleotide of the polynucleotide, or consisting of a polypeptide consisting of an amino acid sequence set forth in SEQ ID NO:35, SEQ ID NO:37, SEQ ID NO: 39 or SEQ ID NO: 41, or a partial polypeptide thereof.

The present invention also provides a primer for amplifying the marker for the type of hair shape of the present invention, the primer including a partial polynucleotide of a polynucleotide consisting of a base sequence set forth in SEQ ID NO:34, SEQ ID NO:36, SEQ ID NO:38 or SEQ ID NO:40, or a base sequence complementary thereto.

The present invention also provides a probe for detecting the marker for the type of hair shape of the present invention, the probe including a polynucleotide consisting of a base sequence set forth in SEQ ID NO:34, SEQ ID NO:36, SEQ ID NO:38 or SEQ ID NO:40, or a base sequence complementary thereto, or a partial polynucleotide of these polynucleotides.

The present invention also provides an antibody for detecting the marker for the type of hair shape of the present invention, the antibody being capable of specifically recognizing a polypeptide consisting of an amino acid sequence set forth in SEQ ID NO:35, SEQ ID NO:47, SEQ ID NO:39 or SEQ ID NO:41, or a partial polypeptide of the polypeptide.

Furthermore, the present invention provides a method for detecting and/or determining the type of hair shape, the method including the following steps (a) to (c):

(a) measuring the amount of expression of the marker for the type of hair shape of the present invention in a sample derived from a test subject;

(b) comparing the measurement results obtained from step (a) with the measurement results of non-curly hair people; and (c) determining the type of hair shape based on the results obtained from (b).

The present invention also provides a method for evaluating or selecting a hair shape regulating agent, the method including the following steps (a) to (d):

(a) contacting a test substance with a cell capable of expressing the hair shape susceptibility gene of the present invention or a protein encoded by the gene;

(b) measuring the amount of expression of the gene or the protein in the cell contacted with the test substance;

(c) comparing the amount of expression measured in step (b) with the amount of expression of the gene or the protein in a control cell that has not been contacted with the test substance; and (d) selecting, based on the results obtained in step (c), a test substance which increases or decreases the amount of expression of the gene or the protein, as a hair shape regulating agent.

The present invention also provides a method for evaluating or selecting a hair shape regulating agent, the method including the following steps (a) to (c):

(a) introducing, to a cell capable of expressing the hair shape susceptibility gene for the type of hair shape of the present invention, a fusion gene of the regulatory region of the hair shape susceptibility gene and a reporter gene, and culturing the cell in the presence and in the absence of a test substance;

(b) measuring the amount of expression of an expression product of the reporter gene in the cell culture cultured in the presence of the test substance, and comparing the amount with the amount of expression of an expression product of the reporter gene in the cell culture cultured in the absence of the test substance; and (c) selecting, based on the comparison results obtained from step (b), a test substance which increases or decreases the amount of the expression product of the reporter gene, as a hair shape regulating agent.

The present invention also provides a method for evaluating or selecting a hair shape regulating agent, the including the following steps (a) to (c):

(a) contacting a test substance with an aqueous solution, a cell or a cell fraction prepared from the cell containing a protein encoded by the hair shape susceptibility gene of the present invention;

(b) measuring the function or activity of the protein in the aqueous solution, cell or cell fraction that has been contacted with the test substance, and comparing the function or activity with that in a control aqueous solution, a control cell or a control cell fraction, which has not been contacted with the test substance; and (c) selecting, based on the comparison results obtained from step (b), a test substance which increases or decreases the function or activity of the protein, as a hair shape regulating agent.

The present invention also provides a method for regulating the type of hair shape, the method including controlling the expression of the hair shape susceptibility gene of the present invention in the human hair root area.

According to an embodiment, the hair shape susceptibility gene of the present invention is selected from SLC22A8, PACS1, KLC2, RAB1B, CNIH2, YIF1A, MGC33486, CD248, ORAOV1, KRTAP5-8, KRTAP5-9, and KRTAP5-10.

According to an embodiment of the hair shape determining marker of the present invention, the SNP is a SNP for a nucleotide selected from the group consisting of the following bases:

(1) in the base sequence set forth in SEQ ID NO:1, nucleotides represented by Nucleotide Numbers 1 (dbSNP Database ID:rs10792367, G or C), 7633 (rs2276299, A or T), and 9315 (rs4149182, G or C);

(2) in the base sequence set forth in SEQ ID NO:2, nucleotides represented by Nucleotide Numbers 1 (rs11227403, C or T), 16722 (rs11607393, A or C), 19992 (rs3825067, T or C), 21051 (rs11227411, T or C), 21927 (rs10896081, T or A), 25269 (rs11227413, A or G), 27032 (rs11227415, C or T), 35997 (rs3862386, C or G), 49537 (rs9645684, A or G), 55405 (rs10896085, T or A), 69180 (rs918299, T or C), 84627 (rs7943911, A or G), 86185 (rs2177054, A or C), 90221 (rs10750778, C or T), 91247 (rs6591207, A or T), 92398 (rs10896091, C or T), 98150 (rs7946917, G or A), 100779 (rs10896094, T or C), 101730 (rs7941431, A or G), 102920 (rs2293121, G or T), 105310 (rs10791855, G or A), 126741 (rs512421, A or G), 133917 (rs2155201, C or T), 134786 (rs7925123, C or G), 142991 (rs2236651, T or C), 144254 (rs2236652, A or G), 147896 (rs476551, C or G), 150043 (rs10791861, A or G), 152853 (rs2298466, C or T), 168931 (rs10791863, T or C), 172500 (rs2155031, T or C), 175003

(rs2276036, T or C), 184535 (rs2298468, A or G), 189853 (rs11227447, C or G), 194405 (rs2282568, G or C), and 202111 (rs3814738, T or G);

(3) in the base sequence set forth in SEQ ID NO:3, nucleotides represented by Nucleotide Numbers 5297 (rs523583, A or C), 18280 (rs3741367, T or C), and 18933 (rs3741368, G or A);

(4) in the base sequence set forth in SEQ ID NO:4, nucleotides represented by Nucleotide Numbers 1 (rs1789165, A or G), 8378 (rs10796828, G or T), 12624 (rs1789172, T or C), 20147 (rs1192921, G or C), 22309 (rs1192923, A or T), 24512 (rs1192924, T or C), and 26599 (rs1789168, T or C); and (5) in the base sequence set forth in SEQ ID NO:5, nucleotides represented by Nucleotide Numbers 17000 (rs2664, T or C), 18895 (rs7934055, T or G), 26143 (rs17363723, G or A), 26545 (rs11234174, A or G), 27090 (rs10792781, C or T), 27751 (rs7107678, G or A), and 30274 (rs7106362, T or C).

According to another embodiment, the hair shape determining marker consists of a contiguous base sequence having a length of 10 to 601 nucleotides.

According to an embodiment of the reagent of the present invention for the determination of the genetic susceptibility of a test subject to hair shape, the probe and/or the primer hybridizes with a region containing the SNP described in the items (1) to (5) described above.

According to an embodiment of the marker for the type of hair shape of the present invention, the partial polynucleotide is a polynucleotide of 15 bases or more in length.

According to an embodiment of the method of the present invention for detecting and/or determining the type of hair shape, the sample derived from a test subject is an RNA prepared from a biological sample collected from the test subject, or a complementary polynucleotide transcribed from the RNA.

According to another embodiment of the method of the present invention for detecting and/or determining the type of hair shape, the step (a) is a step of bringing a biological sample collected from a test subject into contact with an antibody for detecting the marker for the type of hair shape of the present invention, and measuring the amount of the marker for the type of hair shape of the present invention in the biological sample that has been bound with the antibody.

According to another embodiment of the method of the present invention for detecting and/or determining the type of hair shape, the biological sample collected from the test subject is derived from an epithelial tissue or epithelial cell.

BRIEF DESCRIPTION OF THE DRAWINGS

FIG. 10-1 is a graph showing the amounts of expression of the hair shape susceptibility gene in the scalp hair roots of a curly hair group and a straight hair group, A: CNIH2 gene, B: YIF1A gene;

FIG. 10-2 is a graph showing the amounts of expression of the hair shape susceptibility gene in the scalp hair roots of a curly hair group and a straight hair group, C: ORAOV1 gene, D: KRTAP5-9 gene;

DETAILED DESCRIPTION OF THE INVENTION

Figure 1:
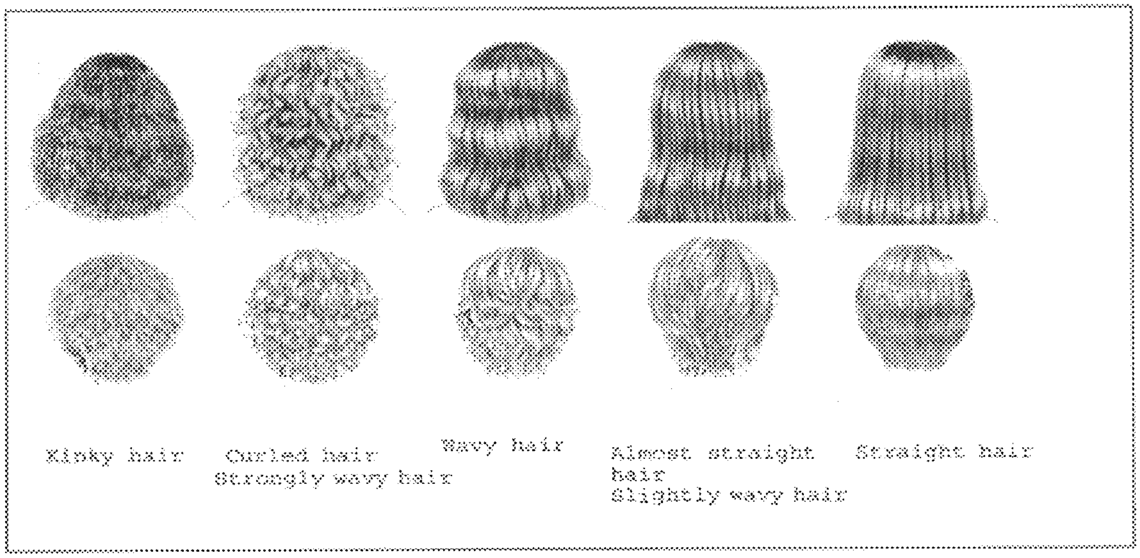
FIG. 1 is a set of images of the phenotypes of hair shape.

The present invention relates to the provision of a genetic polymorphism and a hair shape susceptibility gene that are related to the natural shape of human hair such as curly hair or straight hair, and the provision of a method for determining the genetic susceptibility of individual test subjects to hair shape based on this information. Furthermore, the present invention relates to the provision of a reagent and a reagent kit, which are useful for conveniently carrying out the method. In addition, the present invention relates to the provision of a marker (polynucleotide or polypeptide) for detecting and determining the natural shape of human hair such as curly hair or straight hair, and to the use of the marker, such as the detection and/or determination of the type of hair shape, or the evaluation and selection of an ingredient effective for the regulation of hair shape using the marker.

The inventors of the present invention set a goal of finding a causative gene that determines the natural shape of human hair, and conducted a genome analysis directed to Japanese family lines having curly hair, a group of Japanese curly hair people and a group of Japanese non-curly hair people. As a result, the inventors identified genetic polymorphisms related to hair shape, that is, hair shape susceptibility SNP markers, and also identified hair shape susceptibility genes in the 11q12.2 to 11q13.2 region of chromosome 11. The inventors of the present invention also investigated the relations between hair shape and the gene expression of various genes in the hair root area, and found that the amount of expression of the hair shape susceptibility genes in the hair root area differs significantly between non-curly hair people and curly hair people. These genes are hair shape susceptibility genes, and can serve as markers for detecting and/or determining the type of hair shape. Based on these findings, the inventors of the present invention finally completed the present invention.

According to the present invention, a hair shape susceptibility gene related to the natural shape of human hair such as curly hair or straight hair, a hair shape susceptibility SNP marker, and a hair shape determining marker utilizing these are provided. When the hair shape susceptibility gene, the SNP marker, and the hair shape determining marker of the present invention are analyzed in detail, research on the mechanism of the hair formation related to the hair shape, and application research such as the development of an adequate method for promoting the regulation of hair shape are made available.

According to the method for determining the genetic susceptibility to hair shape of a test subject of the present invention, search for a gene that serves as a main factor that determines the hair shape of individual test subjects, and determination of the susceptibility of individual test subjects to the acquired changes of hair shape, that is, the degree of risk of the future change in the hair shape, can be more conveniently and rapidly carried out. Furthermore, based on the results, an adequate method for regulating the hair shape for individual persons can be provided. Further, the determination method can be carried out more conveniently and rapidly, by the reagent for the determination of genetic susceptibility of a test subject to hair shape of the present invention and the kit including the reagent.

According to the present invention, the shape or nature of hair such as curly hair or kinky hair can be detected and determined without damaging the hair. Furthermore, a substance selected according to the method of the present invention for screening an ingredient effective for the regulation of hair shape can be used as a hair shape regulating agent that is effective for the regulation of hair shape, and can also be used for the preparation of a pharmaceutical product, a quasi-drugs, cosmetic materials, health foods and the like, which all contain the agent. Further, according to the present invention, a method for regulating the hair shape using the hair shape susceptibility SNP marker obtained by the present invention can be provided.

1. DEFINITIONS OF TERMS USED IN PRESENT INVENTION

The indication of base sequences (nucleotide sequences), nucleic acids and the like by means of abbreviations in the present specification is as recommended by the specifications of IUPAC-IUB (IUPAC-IUB Communication on Biological Nomenclature (Eur. J. Biochem. 138, 9, 1984), "Guidelines for the preparation of specifications containing base sequences or amino acid sequences" (edited by the Japanese Patent Of f ice), and the symbols conventionally used in the art.

The term "DNA" as used in the present specification encompasses not only a double-strand DNA, but also single-strand DNAs such as a sense strand, and an anti-sense strand constituting the double-strand DNA. Unless particularly stated otherwise, the term "gene" as used herein encompasses all of a double-stranded DNA including human genome DNA, a single-stranded DNA (sense strand) and a single-stranded DNA having a sequence complementary to the sense strand (anti-sense strand), and fragments thereof. Unless particularly stated otherwise, the term "gene" as used herein is, unless particularly stated otherwise, intended to indicate any of a regulatory region, a coding region, an exon and an intron without discrimination. Further, the "gene" or "DNA" encompasses a "gene" or "DNA" represented by a specific base sequence, as well as a "gene" or "DNA" which encodes a homologue, a derivative or a variant of a protein encoded by the "gene" or "DNA" represented by a specific base sequence, provided that they have a biological function equivalent to that of the protein.

Furthermore, according to the present invention, the terms "nucleotide", "oligonucleotide" and "polynucleotide" have the same meanings as nucleic acid, and they are intended to encompass both DNA and RNA. The DNA encompasses all of cDNA, genomic DNA and synthetic DNA. The RNA encompasses all of total RNA, mRNA, rRNA and synthetic RNA. Further, the "nucleotide", "oligonucleotide" and "polynucleotide" may be double-stranded or single-stranded, and in the case of a "nucleotide" (or an "oligonucleotide" or "polynucleotide") having a certain sequence, unless particularly stated otherwise, the "nucleotide" is intended to collectively mean "nucleotide" (or an "oligonucleotide" or "polynucleotide") having a sequence complementary to the sequence. Furthermore, when the "nucleotide" (or "oligonucleotide" or "polynucleotide") is RNA, the nucleotide symbol "T" indicated in the base sequence may be replaced with "U".

The term "polynucleotide having a complementary base sequence" means a polynucleotide that is in a complementary relation in terms of nucleotide (i.e., complementary strand or anti-sense strand), to a polynucleotide having an arbitrary base sequence (sense strand). A complementary base sequence encompasses a sequence that is completely complementary to the subject base sequence, as well as a base sequence that can be hybridized with the subject base sequence under stringent conditions. Here, the stringent conditions may conventionally refer to washing conditions of approximately "1×SSC, 0.1% SDS, 37° C.", and more stringent hybridization conditions may be approximately "0.5×SSC, 0.1% SDS, 42° C.", and even more stringent hybridization conditions may be approximately "0.1×SSC, 0.1% SDS, 65° C.". Furthermore, a person having ordinary skill in the art can determine stringent hybridization conditions according to general textbooks (for example, Sambrook, J. & Russell, D., 2001, Molecular Cloning: a Laboratory Manual, $3^{rd}$ edition, Cold Spring Harbor, N.Y.: cold Spring Harbor Laboratory). An example of a base sequence that can be hybridized with a subject base sequence under stringent conditions may be a base sequence having a homology of 90% or higher, and preferably 95% or higher, with the subject base sequence.

The term "protein" or "polypeptide" encompasses a "protein" or "polypeptide" represented by a specific base sequence or amino acid sequence, as well as a fragment, a homologue, a derivative and a variant thereof, provided that they all have a biological function equivalent to that of the "protein" or "polypeptide". Meanwhile, the variant encompasses a naturally occurring allele variant, a variant that does not occur naturally, and a variant having an amino acid sequence modified by artificial deletion, substitution, addition and insertion. In addition, examples of the variant include those having a homology in the amino acid sequence of 80% or higher, preferably 90% or higher, more preferably 95% or higher, and even more preferably 98% or higher, with a protein or polypeptide having no variation.

According to the present specification, the homology of amino acid sequences and base sequences is calculated by the Lipman-Pearson method (Science, 227, 1435, 1985). Specifically, the homology is calculated by performing an analysis using a homology analysis (Search homology) program in the genetic information processing software Genetyx-Win (Software Development Co., Ltd.), and by setting the parameter, Unit size to compare (ktup), at 2.

The term "antibody" encompasses a polyclonal antibody, a monoclonal antibody, a chimeric antibody, a single-chain antibody, and portions of the antibodies described above, which have antigen-binding properties, such as Fab fragments, and fragments produced by a Fab expression library.

In regard to the term "genetic polymorphism" as used herein, when there are two or more genetically determined alleles, the term refers to such an allele gene. Specifically, in a human population, when variations such as substitution, deletion, insertion, dislocation, and inversion of one or plural nucleotides exist at a specific region in the genome of one or plural individuals, with respect to the genomic sequence of one certain individual, the variation is called "genetic polymorphism" if it is statistically ensured that the variation is not a mutation occurring in the one or plural individuals, or if it can be genetically demonstrated that the variation is not a specific variation in the individuals but occurs in the population at a frequency of 1% or greater. Examples of the "genetic polymorphism" as used herein include substitution of one nucleotide with another nucleotide, that is, a single nucleotide polymorphism (SNP); deletion or insertion of one to several tens of nucleotides (DIP); a region includes repetition of units of sequence consisting of 2 to several tens of nucleotides as one unit, where the number of the repetition is different (when the unit repeated in the region consists of 2 to 4 nucleotides, it is referred to as a microsatellite polymorphism, and when the unit repeated in the region consists of several to several tens of nucleotides, it is referred to as a VNTR (Variable Number of Tandem Repeat); and the like.

The term "hair shape" as used herein refers to the tendency of the overall shape of hair in the head area, which attributes to the shape of individual hairs, such as straight hair, wavy hair or wave hair, curled hair, or kinky hair or coiled hair.

The term "curly hair" as used herein is, unless particularly stated otherwise, a term which collectively refers to the shape other than straight hair in the case of contrasting with straight hair. Therefore, according to the present specification, in the case of contrasting with the "curly hair", unless particularly stated otherwise, the "straight hair" and the "non-curly hair" are considered to have the same meaning.

The "curly hair", "non-curly hair" and "straight hair" are of relative nature, and can be defined by various methods that will be described below. The "curly hair trait", "non-curly hair trait", and "straight hair trait" refer to the phenotypes representing the "curly hair", "non-curly hair" and "straight hair", respectively.

The term "hair shape susceptibility gene" as used herein refers to a causative gene that determines the hair shape which is a polygenic trait, and the term "hair shape susceptibility SNP marker" refers to the nucleotide at a site which represents an SNP associated with the trait of hair shape of the individual.

According to the present specification, the terms "genetic susceptibility to hair shape", "hair shape determining marker" and "marker for the type of hair shape" respectively refer to the genetic predisposition related to the specific hair shape possessed by an individual, and a marker for determining the predisposition.

The term "Affected Sib-Pair Linkage Analysis" as used herein refers to one technique for estimating the location of a target gene (e.g., disease susceptibility gene or the like) using linkage, and is a representative analysis technique for non-parametric linkage analysis which does not assume any mode of inheritance (e.g., autosomal dominant inheritance, recessive heredity, sex-linked gene, or the like) or the penetrance. In the affected sib-pair linkage analysis, family lines including sibs (e.g., brothers and sisters) that are affected (or have a particular trait) are collected, calculation of the likelihood is carried out on the basis of the data obtained by observation of these family lines, and the genetic locus regions of the marker linked to the disease (or the particular trait) are narrowed down. In the case of a group of general (i.e., not affected, or not having a particular trait) sibs, in one genetic locus, a child receives one of the two alleles of one parent (even if the one parent is a homozygote, the alleles are considered to be different from each other). Therefore, in this case, there exist a case in which the sibs receive the same allele, and a case in which the sibs receive different alleles. Since each of the two alleles of a child originates one allele from each of the parents, when the question of how many identical alleles sibs will receive from their parents is considered, there are three cases such as 0, 1 and 2. These three cases are said to have an IBD (Identity By Descent) of 0, 1 and 2, respectively. When a number of sib-pairs are considered, the numbers of the pairs having an IBD=0, the pairs having an IBD=1, and the pairs having an IBD=2 should be counted, and the proportion of the numbers constitutes a certain proportion (1:2:1) according to the probability laws. On the contrary, when sibs that are affected (or have a particular trait) are collected, and the same investigation is carried out with this group, if an observed marker gene is linked to the disease (or the particular trait), this ratio (1:2:1) is deviated (i.e., the number of the pairs having an IBD=2 increases, and the number of the pairs having an IBD=0 decreases). In addition, for a marker gene which is not linked to a gene that is related to the disease (or the particular trait), it can be considered that the ratio has the same distribution (1:2:1) as any arbitrary sib. In the affected sib-pair linkage analysis, the likelihood of observation data is calculated by utilizing this hypothesis, by taking the difference of the ratio of shared alleles in affected sib-pairs as an index. The likelihood is represented by the following formula:

$$L(Z) = \prod_{j=1}^{N} \sum_{i=0}^{2} ZiWij$$

wherein Wij represents the probability that the affected sib-pair of the $j^{th}$ family line has an IBD=i. The variable is Z=(Z0, Z1, Z2), and the degree of freedom is 2 (Z2=1−Z1−Z0, there are only two independent variables of Z0 and Z1). The ratio with the likelihood in the case where a marker gene and a gene associated with a disease (or a particular trait) are not linked (that is, Z0=0.25, Z1=0.5, Z2=0.25) is taken, and the value of Z which gives the maximum likelihood is determined by the likelihood maximization method (maximum likelihood estimation).

The term "gene frequency" as used herein refers to the proportion occupied by the allele at a genetic locus among the total number of genes present in a group.

The term "haplotype" as used herein means a combination of genetic variations existing in one allele (haploid).

The term "linkage disequilibrium analysis" or "haplotype analysis" as used herein means an analysis of the degree of the intensity of linkage disequilibrium in a genomic region.

The term "linkage disequilibrium" as used herein refers to a phenomenon in the population genetics, in which a non-random correlation is observed in a group between alleles or genetic markers (polymorphisms) at plural genetic loci, that is, the frequency of such a particular combination (haplotype) is significantly increased. They are generally on the same chromosome and constitute genetic linkage, but there are occasions in which even if the alleles are linked, linkage disequilibrium is not observed. Further, in some exceptional cases, linkage disequilibrium may be seen over different chromosomes. For example, when a genetic locus X has alleles a and b (these exist at the same frequency), and a neighboring genetic locus Y has alleles c and d (these exist at the same frequency), the haplotype ac, which is a combination of the respective genetic polymorphisms, is expected to exist at a frequency of 0.25 in the group. When the frequency of the haplotype ac is higher than such an expected value, that is, when a specific genotype denoted as ac appears frequently, it is said that the allele ac is in linkage disequilibrium. Linkage disequilibrium is occurred as a result that the time of natural selection or introduction into a group of a particular combination of alleles is evolutionarily recent, and may be occurred as a result that linked alleles have not reached equilibrium. Therefore, the mode of linkage disequilibrium varies with different groups, such as nations or races, and even in the case where the allele ac in a certain group is in linkage disequilibrium, there are occasions in which the allele ad is in a relation of linkage disequilibrium in other groups. The detection of genetic polymorphism in the linkage disequilibrium is effective in detecting the susceptibility to a disease, regardless of whether the polymorphism itself directly causes the disease. For example, in regard to an allele a of a certain genetic locus X, although the allele is not a causative genetic factor of a disease, the allele may exhibit susceptibility to a disease through the linkage disequilibrium with an allele c of a genetic locus Y.

The "haplotype block" as used herein is defined as a region that is categorized as a genome region for which most of the historical recombination has not been acknowledged, and includes strong linkage disequilibrium. Identification of a haplotype block can be appropriately achieved by those having ordinary skill in the art based on the strength of the linkage disequilibrium, but for example, the identification can be carried out according to the report of Gabriel, et al. (Gabriel, S. B., et al., Science, 296 (5576), p. 2225-2229, 2002). The term "strong linkage disequilibrium" as used herein means the state in which the upper limit of the 95% confidence interval of the linkage disequilibrium coefficient D', which is calculated in a linkage disequilibrium analysis, exceeds 0.98, and the lower limit is higher than 0.7. The phrase "there is an evidence of strong historical recombination" means a state in which the upper limit of the 95% confidence interval of the linkage disequilibrium coefficient D' is lower than 0.9.

The term "minor allele" as used herein means an allele having a low gene frequency when two alleles exist in one genetic locus.

According to the present specification, the terms "gene frequency" and "allele frequency" are used for the same meaning, and are terms meaning the proportion occupied by a particular allele in an arbitrary group of genes.

The phrase "statistically significantly different" as used herein means a state in which when a test is carried out according to any statistical technique, the risk (p value) is less than 0.1%, preferably less than 0.07%, even more preferably less than 0.05%, and still more preferably less than 0.01%.

2. IDENTIFICATION OF HAIR SHAPE SUSCEPTIBILITY GENE AND HAIR SHAPE SUSCEPTIBILITY SNP MARKER

Search and identification of a causative gene that determines the natural shape of human hair which is a multifactorial general trait (hair shape susceptibility gene), can be carried out by a genetic statistical analysis using a technique for trait mapping. That is, SNP(s) that are in the linkage disequilibrium state with the hair shape susceptibility gene can be effectively selected through the identification of curly hair trait loci by an affected sib-pair linkage analysis, and a case-control association analysis on the curly hair trait loci, and a gene present in a haplotype block containing the SNP(s) can be identified as a hair shape susceptibility gene.

The identification of the hair shape susceptibility gene and the hair shape susceptibility SNP marker of the present invention can be carried out, as will be described specifically in Examples below, by performing an identification method having the following steps:

(i) a step of defining hair shapes, and collecting curly hair family lines, people having a curly hair trait (case), and people having a straight hair trait (control);

(ii) a step of performing an affected sib-pair linkage analysis directed to the entire genome using samples derived from the curly hair family lines, and identifying a curly hair trait locus;

(iii) a step of selecting plural SNP markers which are not unevenly distributed over the entire region in the curly hair trait locus identified in step (ii);

(iv) a step of performing typing of the SNP markers selected in step (iii) using case-derived and control-derived samples, comparing the results of the typing through a statistical processing, and identifying a SNP marker that is recognized to have a significant difference, as a hair shape susceptibility SNP marker;

(v) a step of determining, in the hair shape susceptibility SNP marker, a region (haplotype block) where linkage disequilibrium is recognized within the object candidate region and a hair shape susceptibility SNP marker is contained (Haplotype block), using the HapMap PHASE data of the International HapMap Project Database, and thereby identifying a hair shape susceptibility gene; and (vi) a step of determining, for the haplotype extracted from the haplotype block specified in step (v), aSNP locus that is linked with the hair shape susceptibility SNP marker locus determined in step (iv) using the HapMap PHASE data of the International HapMap Project Database, and additionally identifying the SNP thus-determined as an additional hair shape susceptibility SNP marker.

The step (i) is a step of defining hair shapes (curly hair or straight hair) and collecting analysis objects for trait mapping. In regard to the trait mapping, it is necessary to handle the subject trait quantitatively to a certain extent, and thus, the operation of defining hair shape, by which the objects are defined to have a curly hair trait or a straight hair trait, constitutes an important step when the trait mapping is carried out. There are a variety of human hair shapes, and the method for measurement thereof and the method for classification or defining are also various. For instance, examples of the method of defining hair shapes include a method of binarizing the hair shape, in such a manner that curly hair=1 and straight hair=0; a method of measuring the degree of curly hair by any method and quantifying the degree; and a method that is well known to those having ordinary skill in the art (for example, see, Japanese Patent Application Laid-Open (JP-A) No. 2005-350801, JP-A No. 2008-268229, Japanese Patent No. 4159515, and the like), but the method is not limited to these. As a more specific example of the method of defining hair shapes, there may be mentioned a method of classifying hair shapes into several grades (for example, 2 to 10 grades, preferably 3 to 8 grades, and more preferably 5 to 7 grades) based on the features such as the overall shape, the degree of curl of the hair (radius of curl), the frequency of the appearance of curl, and/or the synchrony of curl with the groups of hair in the surroundings; and defining, in regard to such classifications, a hair shape having a tendency of a small radius of curl, such as kinky hair and curled hair or strongly wavy hair, as a curly hair trait, and defining a hair shape having a tendency of a large radius of curl, such as wavy hair, almost straight hair or slightly wavy hair, or straight hair, as a straight hair trait.

The step (ii) is a step of carrying out an affected sib-pair linkage analysis on the entire genome using samples derived from a curly hair family line. The constituent members of the curly hair family line for carrying out the affected sib-pair linkage analysis are sibs (a pair among brothers and sisters, two people) determined to have the curly hair trait by the step (i). More preferably, the constituent members consist of a family of 4 people (or 3 people) including the parents of the sibs, and other brothers and sisters (irrespective of the hair shape) or grandparents may also be further added. Furthermore, the number of the curly hair family lines needed to carry out the affected sib-pair linkage analysis can be determined by estimating and/or observing the frequency in the population of the curly hair trait, the frequency of the causative gene (allele frequency), the sib relative risk, or the like, and calculating the number by through simulation. However, the number of the curly hair family line needed is generally 50 family lines to several hundred family lines.

The genetic marker used in the affected sib-pair linkage analysis is not particularly limited as long as it is a genetic polymorphism, but a microsatellite that exists uniformly in the genome and has a large number of alleles is used with preference. A kit for amplifying and detecting a microsatellite (linkage mapping set) is commercially available from Applied Biosystems Corp. (ABI). Meanwhile, in the present invention, ABI PRISM Linkage Mapping Set-MD 10 v2.5 (manufactured by ABI) which covers human chromosome at an average interval of 9.2 cM, and ABI PRISM Linkage Mapping Set-HD 5 v2.5 (manufactured by ABI) which covers human chromosome at an average interval of 5 cM were used.

Furthermore, the microsatellite that serves as a genetic marker can be arbitrarily selected, and can be retrieved from the Comprehensive Human Genetic Maps of the Mammalian Genotyping Service (http://research.marshfieldclinic.org/genetics/GeneticResearch/compMaps.asp), NCBI (http://www.ncbi.nlm.nih.gov/) and the like. In this case, it is preferable to select a microsatellite which exists in the genome at an interval of 0.1 to several cM, and has many alleles and high heterozygosity. Furthermore, microsatellite markers can be added to a chromosome in which linkage has been recognized, and the linkage region can be narrowed (detailed mapping). Meanwhile, for the PCR primer for amplifying and detecting the microsatellites that have been arbitrarily selected and added, the base sequence can be retrieved from the NCBI (http://www.ncbi.nlm.nih/gov/), and the primer can be produced based on the retrieved sequence according to an ordinary method using, for example, a commercially available nucleotide synthesizer. At this time, it is preferable to label the probe with a radioactive substance, a fluorescent substance, a chemiluminescent substance, an enzyme or the like so that the detection of the amplification product can be achieved rapidly and easily.

In the affected sib-pair linkage analysis, PCR is carried out using a genomic DNA derived from a curly hair family line as a template, and using a linkage mapping set (ABI) or an amplification primer of a microsatellite marker arbitrarily selected, and thus an amplification product (fragment) is detected. The operations of PCR and the detection of the amplification product can be carried out according to ordinary methods. At this time, when various amplification primers are labeled with different fluorescent dyes (for example, any dyes emitting different fluorescent light, such as 6-FAM (blue), VIC (green), or NED (yellow)), even if amplification products having an identical size are obtained, plural amplification primers can be rapidly detected by separately discriminating the various fluorescent colors.

A statistical test of the linkage can be carried out using commercially available or publicly disclosed genetic statistic software programs which are capable of non-parametric analysis (for example, Genehunter, Linkage Package, Mapmaker/sibs, and the like).

The determination of the region where linkage is recognized was based on the criteria for obtaining a false positive linkage, according to the guidelines provided by Lander and Kruglyak (Nat. Genet., 11(3), 241-247, 1995) shown below. The guidelines by Lander and Kruglyak (linkage analysis over the entire genome in a multifactorial disease) have come to be actively carried out, but in the linkage analysis of individual genes, the determination of whether the gene function can be causative is also added. However, since the gene function is not taken into consideration in that stage in the analysis of the entire genome, determination criteria (threshold) of significant purely in terms of mathematical genetics are required. Thus, they provided criteria for significance of linkage as shown in the following Table 2 according to simulations.

TABLE 2

| | |
|---|---|
| Suggestive Linkage | $P < 7.4 \times 10^{-4}$ |
| (Criteria for obtaining a result of one false positive linkage from the entire genome) | LOD > 2.2 |
| Significant Linkage | $P < 2.2 \times 10^{-5}$ |
| (Criteria for obtaining a result of 0.05 false positive linkages from the entire genome) | LOD > 3.6 |
| High Significant Linkage | $P < 3.0 \times 10^{-7}$ |
| (Criteria for obtaining a result of 0.01 false positive linkages from the entire genome) | LOD > 5.4 |

Through this process, the whole chromosome can be screened, and a region on the chromosome where linkage with the curly hair trait is recognized can be detected. Through further detailed mapping, a specific region on the chromosome can be identified as a curly hair trait locus. The region identified as such is a region where the presence of a hair shape susceptibility gene is strongly suggested.

The step (iii) is a step of selecting, in the curly hair trait locus region identified in the step (ii), plural SNP markers which are not unevenly distributed over the entire region. The SNP markers can be selected by using various databases related to SNP, such as the dbSNP database (http://www.ncbi.nlm.nih.gov/SNP/) and the JSNP database (http://snp.ims.u-tokyo.ac.jp/index_ja.html).

Upon the selection of the SNP marker, a SNP which is useful for the identification of a hair shape susceptibility gene is selected. Specifically, in a Japanese group, a SNP having a gene frequency of minor allele of 10% or greater, and more preferably 15% or greater, is selected. When a SNP having such a gene frequency is used, a SNP marker having high reliability can be selected.

In addition, when a SNP marker is selected by using the gene frequency as an index, there are occasions in which the SNP marker is unevenly distributed in a specific narrow region. In this case, if all of the selected SNP markers are used in the identification of a hair shape susceptibility gene, the experiment becomes complicated, and it is also not very effective that SNPs which are neighboring with each other are in the state of linkage disequilibrium. Therefore, it is preferable to select and use SNP markers which are present at a certain interval from one another. As such, when uneven distribution of markers is eliminated by providing a certain interval between them, a comprehensive association analysis can be carried out over the entire object candidate region, and the identification of the hair shape susceptibility gene can be easily carried out. The distance between adjacent SNP markers that are selected as such is preferably 5 kb or greater, and more preferably 5 kb to 10 kb. If this distance is too long, there is a possibility that a region may occur where the extent of the strength of mutual linkage disequilibrium between SNP markers cannot be checked. Furthermore, if this distance is too short, there are so many SNPs for which strong mutual linkage disequilibrium is recognized, and therefore, it is not efficient.

In the comprehensive selection of SNP markers over the entire object candidate region, apart from this distance between SNP markers, the state of scattering of markers in the object candidate region, that is, the number of markers per unit distance of genome, can be expressed as "marker density." The marker density is 0.5 SNPs or more, preferably 1 SNP or more, and more preferably 1 SNP to 2 SNPs, per 10 kb of genome. If the marker density is too low, the distance between markers is too long, and there is a possibility that a region may occur where the degree of the strength of linkage disequilibrium between SNP markers cannot be checked, as described above. On the other hand, if the marker density is too high, the distance between markers is too short, and as described above, markers are selected overcrowdedly, so that in the case of identifying a hair shape susceptibility gene, a large amount of experiment is needed, which is not so efficient.

The step (iv) is a step of carrying out a case-control association analysis for the SNP markers selected in step (iii). The case-control association analysis is a method of comparing the allele frequencies for a certain hereditary marker between a case (affected people: people having the curly hair trait) group and a control (control people: people having the straight hair trait), and detecting a marker which can exhibit a significant difference in the allele frequency between the two groups. For example, samples derived from people having the curly hair trait (case) and people having the straight hair trait (control) are used, and typing is carried out. The results are compared by statistical processing, and a SNP marker with which a significant difference is recognized is identified as a hair shape susceptibility SNP marker. The sample required for trait mapping is not particularly limited as long as the sample contains genomic DNA, but examples include blood such as peripheral blood, body fluids such as saliva and sweat, somatic cells, and tissues or organs including somatic cells. The number of case-control required to perform a case control association analysis can be estimated based on the frequency in a population having the curly hair trait, the gene frequency (allele frequency) causative of the trait, the genotype relative risk, and the like, but the number is generally 50 to several thousand people. Furthermore, it is possible to obtain a relatively high power of test by a stepwise refinement method under the conditions of limited sample size, limited number of typing operations or the like. Furthermore, the case and the control are preferably constituted of the same human race as the race for which the hair shape susceptibility gene is specified, and for example, in order to identify a hair shape susceptibility gene of Japanese people, it is preferable that the object of analysis be constituted of Japanese people.

As the method for SNP typing, methods that are well known to those having ordinary skill in the art, such as PCR-SSCP, PCR-RLFP, PCR-SSO, PCR-ASP, a direct sequencing method, SNaPshot, dHPLC, a Sniper method, and a MALDI-TOF/MS method, can be used (see, for example, Nojima, Hiroshi, Ed., "Forefront of Genomic Drug Discovery", p. 44-p. 54, Yodosha Co., Ltd., 2001). For example, it is effective to utilize TaqMan SNP Genotyping Assays (registered trademark) (manufactured by ABI), and to employ a SNP typing method which utilizes a TaqMan system.

The association analysis is typically achieved by comparing the gene frequency of each of the SNP markers between the case group and the control group, and carrying out a $\chi^2$ test on whether the difference in the frequency is statistically meaningful or not (see, University of Tokyo, College of Arts and Sciences, Department of Social Sciences, Statistics Section, Edited, "Tokeigaku Nyumon—Kisotokeigaku I (Introduction to Statistics—Fundamental Statistics I)", University of Tokyo Press, 1991). However, the association analysis may also be carried out based on the genotype frequency for each SNP marker, the genotype frequency in the case of employing a dominant (or recessive) model, the frequency of allele in terms of positive ratio, and the like. Furthermore, in addition to the $\chi^2$ test, the association analysis can be carried out by any other well-known statistical processing, as long as it is possible to compare the case group and the control group, that is, to test the relations between a phenotype that can be divided into plural groups, such as a trait and a disease, and a genetic polymorphism.

Meanwhile, in order to evaluate the typing error of a genotype, and the validity of sampling, a Hardy-Weinberg equilibrium test is carried out. Hardy-Weinberg equilibrium is well known in the field of genome statistics, and in which when two alleles (for example, C and T) exists as in an SNP or the like, and the respective frequencies in a group are represented by p and q ($p+q=1$), the genotype frequencies of C/C homo, C/T hetero and T/T homo may be represented by $p^2$, $2pq$ and $q^2$, respectively ($p^2+2pq+q^2=1$). When an association analysis is carried out, it is desirable that the Hardy-Weinberg equilibrium is established for the control group. However, the selected SNP marker can be evaluated as valid as long as the number of alleles, whose genotype frequency is statistically significantly different from Hardy-Weinberg equilibrium, is in a predictable range of the significance level (typically, $p=0.01$ to $0.05$).

According to an embodiment, typing is carried out for the respective samples obtained from a case group and a control group, and a significant difference test is carried out by a $\chi^2$ test by four methods involving the genotype, allele type, dominance model and recessive model. That is, if a certain genetic variation is causative of hair shape change, the difference in the allele frequency or the like between the case and the control can be predicted. In regard to the test, when the association analysis is carried out on a relatively small number of objects, or when the power of test of the significant difference between the objects is increased, the level of significance is set loose. When the number of objects is relatively large, or when the significant difference is strictly determined, the level of significance can be set strict. A SNP which exhibits a significant difference in the gene frequency by a test is identified as a hair shape susceptibility SNP marker.

The step (v) that is subsequently carried out is a step of identifying a hair shape susceptibility gene by determining, in connection with the hair shape susceptibility SNP marker determined as described above, a region where linkage disequilibrium is recognized in an object candidate region and the hair susceptibility SNP marker is included (haplotype block), using the HapMap PHASE data of the International HapMap Project Database.

The analysis of haplotype (linkage disequilibrium analysis) is a method well known to those having ordinary skill in the art, and can be carried out by various linkage disequilibrium analyses that are conventionally carried out (for example, Kamatani, Naoyuki, Edited., "Post-Genome Jidai no Iden Tokeigaku (Genetic Statistics in Post-Genomic Era)", p. 183-201, Yodosha Co., Ltd., 2002). The haplotype analysis can be carried out using various genetic statistics software programs that are commercially available or made public (for example, Haploview, Arlequin, SNP disease-associated analysis software, SNPalyze (registered trademark) (manufactured by Dynacom Co., Ltd.), and the like). More specifically, the linkage disequilibrium coefficient D' (pair-wise LD coefficient) is calculated and an analysis is carried out, through a linkage disequilibrium analysis based on the EM algorithm (Laird, N.: "The EM Algorithm", Chap. 14, pp. 509-520, Handbook of Statistics, Vol. 9, Computational Statistics, C. R. Rao (ed.), Elsevier Science Publishers B.V., 1993). More specifically, in the haplotype analysis, it is analyzed whether linkage disequilibrium exists between the hair shape susceptibility SNP marker specified above and another SNP marker, and the region where linkage disequilibrium exists is identified as the haplotype block. The other SNP marker used in the linkage disequilibrium analysis can be freely selected among the SNPs existing in the upstream and the downstream of the genome sequence with respect to the hair shape susceptibility SNP marker. For example, the linkage disequilibrium analysis may be sequentially carried out for the SNPs present from proximal positions to distal positions of the hair shape susceptibility SNP marker, or the linkage disequilibrium analysis may be carried out for arbitrarily selected SNPs at distal positions to determine an approximate haplotype block region, and then be carried out for SNPs at more proximal positions to determine a more specific haplotype block region. The number of the other SNP markers used in the linkage disequilibrium analysis is 4 SNPs or more including the hair shape susceptibility SNP marker, preferably 20 SNPs or more, and even more preferably 32 SNPs or more, and the analysis is carried out for a series of SNP marker groups including these plural SNP markers. Here, the linkage disequilibrium coefficient D' is obtained from the following equation when, in two SNPs, the respective alleles of a first SNP are designated as (A, a), the respective alleles of a second SNP are designated as (B, b), and the respective frequencies of four haplotypes (AB, Ab, aB, ab) are designated as $P_{AB}$, $P_{Ab}$, $P_{aB}$, and $P_{ab}$. Furthermore, Min $[(P_{AB}+P_{ab})\ (P_{aB}+P_{ab}),\ (P_{AB}+P_{Ab})\ (P_{Ab}+P_{ab})]$ in the equation means that the smaller value between the values of $(P_{AB}+(P_{aB})(P_{aB}+P_{ab})$ and $(P_{AB}+P_{Ab})\ (P_{Ab}+P_{ab})$ is taken.

$$D'=(P_{AB}P_{ab}-P_{Ab}P_{aB})/\mathrm{Min}[(P_{AB}+P_{aB})(P_{aB}+P_{ab}),\ (P_{AB}+P_{Ab})(P_{Ab}+P_{ab})]$$

The number of markers in the SNP marker group may appropriately vary with the size of the region forming the haplotype block related to the hair shape susceptibility gene to be identified (linkage disequilibrium block). Furthermore, when a discontinuity of blocks can be predicted in advance, it is also possible to carry out the analysis on about 6 SMPs located over the blocks. Furthermore, it is also acceptable to carry out a linkage disequilibrium analysis for a hair susceptibility SNP marker and 5 SNPs each existing on both sides of the SNP marker, 11 SNPs in total. If necessary, the number of markers to be analyzed may be increased.

As the linkage disequilibrium analysis is carried out, a region where SNPs are linked within an object candidate region (a haplotype block including the group of SNP markers among which strong linkage disequilibrium is recognized) is determined. For example, the linkage disequilibrium coefficient D' is calculated for all combinations between 2 SNPs for the selected SNP markers, combinations showing the relation: D'>0.9 are selected, and a series of regions including a region sandwiched between the remotest SNPs among them are detected. Subsequently, D' is calculated between three consecutive SNPs that are adjacent to the region in the outside of the detected region, and the SNPs in the region. Even among any combinations thus calculated, when it is verified that D' is 0.9 or less, the region is specified as a "haplotype block."

When a haplotype block is determined in this manner, for example, in connection with that region, genes present in the haplotype block under attention can be determined using a database associated with the genome, or the like. Furthermore, even in the case of not using a database, the base sequence in the vicinity of SNP markers present in the haplotype block region are determined by an ordinary methods, and genes can also be determined from the base sequence.

The step (vi) is a step of determining, for the haplotype extracted from the haplotype block specified in step (v), a SNP locus that is linked to the locus of the hair shape susceptibility SNP marker identified in the step (iv) using the HapMap PHASE data of the International HapMap Project Database, and additionally identifying the SNP thus-determined as an additional hair shape susceptibility SNP marker.

In the step (v), it is possible to extract all haplotypes consisting of the respective nucleotides of the SNP marker group used in the haplotype analysis, while simultaneously determining the haplotype block, and to thereby determine the frequency of the haplotype or the like.

When the combinations of the respective nucleotides of the extracted haplotype, that is, the SNP marker group, are compared, a SNP locus that is linked to the locus of the hair shape susceptibility SNP marker identified in the step (iv) can be identified, and the SNP locus thus identified can be designated as an additional hair shape susceptibility SNP marker.

Through the steps (i) to (vi), a chromosome region where linkage with curly hair is recognized is determined, and then a hair shape susceptibility SNP marker is selected from the chromosome region. Furthermore, through a haplotype analysis of the selected SNP marker, a haplotype block and gene in the chromosome region that are related to hair shape in the chromosome region are identified. Thereafter, a SNP locus that is linked to the locus of the hair shape susceptibility SNP marker is further determined, and thereby, a hair shape susceptibility SNP marker that is present in the haplotype block or gene can be identified.

Examples of the chromosome region where linkage to curly hair is recognized, which region is determined in the steps described above, include chromosome 1 and chromosome 11, more specifically the 11q12.2 to 11q13.2 region of chromosome 11 (a region between microsatellites D11S4191 and D11S987) (maximum LOD score=2.81). These regions are determined as curly hair trait loci, and it is strongly suggested that hair shape susceptibility genes exist in these regions.

Examples of the haplotype block specified by the steps described above include, among the genomic regions of human chromosome 11, a 12,590-bp region represented by the base sequence set forth in SEQ ID NO:1, a 202,111-bp region represented by the base sequence set forth in SEQ ID NO:2, a 18, 933-bp region represented by the base sequence set forth in SEQ ID NO: 3, a 27, 375-bp region represented by the base sequence set forth in SEQ ID NO:4, and a 35,979-bp region represented by the base sequence set forth in SEQ ID NO:5.

A gene which overlaps with such a haplotype block, and contains a portion or the entirety of the base sequence of the haplotype block, is identified as a hair shape susceptibility gene. Here, the "gene which overlaps with the haplotype block" means both a gene which has the same base sequence as that of a partial region of the haplotype block, and a gene which has the same base sequence as the base sequence of the entire region of the haplotype block. Further, a single nucleotide polymorphism (SNP) which exists in such a haplotype block, and whose allele frequency is statistically significantly different between a group having a curly hair trait and a group having a non-curly hair trait, and an SNP that is linked to the SNP, are identified as hair shape susceptibility SNP markers.

An example of the gene which overlaps with the 12,590-bp haplotype block represented by the base sequence set forth in SEQ ID NO: 1, may be SLC22A8 gene on human chromosome 11. SLC22A8 gene is a gene represented by GeneID: 9376 in the Entrez Gene Database (http://www.ncbi.nlm.nih.gov/gene), and as shown in Example 5 and FIG. 5, a portion of the base sequence overlaps with the haplotype block described above.

Examples of the hair shape susceptibility SNP marker present in the base sequence set forth in SEQ ID NO:1 include nucleotides represented by Nucleotide Numbers 1 (dbSNP Database ID:rs10792367, G or C), 7633 (rs2276299, A or T), and 9315 (rs4149182, G or C). A preferred example is a nucleotide represented by Nucleotide Number 7633 (rs2276299, A or T).

Examples of the gene which overlaps with the 202,111-bp haplotype block represented by the base sequence represented by SEQ ID NO:2 include PACS1 gene, KLC2 gene, RAB1B gene, CNIH2 gene, YIF1A gene, and MGC33486 gene on human chromosome 11. PACS1 gene is a gene represented by GeneID:55690 in the Entrez Gene Database, and as shown in Example 5 and FIG. 6, a portion of the base sequence overlaps with the haplotype block described above. Further, KLC2 gene is a gene represented by GeneID:64837 in the Entrez Gene Database, and as shown in Example 5 and FIG. 6, the entire length of the base sequence overlaps with the haplotype block described above. RAB1B gene is a gene represented by GeneID:81876 in the Entrez Gene Database, and as shown in Example 5 and FIG. 6, the entire length of the base sequence overlaps with the haplotype block described above. CNIH2 gene is a gene represented by GeneID: 254263 in the Entrez Gene Database, and as shown in Example 5 and FIG. 6, the entire length of the base sequence overlaps with the haplotype block described above. YIF1A gene gene is a gene represented by GeneID:10897 in the Entrez Gene Database, and as shown in Example 5 and FIG. 6, the entire length of the base sequence overlaps with the haplotype block described above. Furthermore, MGC33486 gene is a gene represented by GeneID:256472 in the Entrez Gene Database, and as shown in Example 5 and FIG. 6, a portion of the base sequence overlaps with the haplotype block described above.

Examples of the hair shape susceptibility SNP marker present in the base sequence set forth in SEQ ID NO:2 include nucleotides represented by Nucleotide Numbers 1 (rs11227403, C or T), 16722 (rs11607393, A or C), 19992 (rs3825067, T or C), 21051 (rs11227411, T or C), 21927 (rs10896081, T or A), 25269 (rs11227413, A or G), 27032 (rs11227415, C or T), 35997 (rs3862386, C or G), 49537 (rs9645684, A or G), 55405 (rs10896085, T or A), 69180 (rs918299, T or C), 84627 (rs7943911, A or G), 86185 (rs2177054, A or C), 90221 (rs10750778, C or T), 91247 (rs6591207, A or T), 92398 (rs10896091, C or T), 98150 (rs7946917, G or A), 100779 (rs10896094, T or C), 101730 (rs7941431, A or G), 102920 (rs2293121, G or T), 105310 (rs10791855, G or A), 126741 (rs512421, A or G), 133917 (rs2155201, C or T), 134786 (rs7925123, C or G), 142991 (rs2236651, T or C), 144254 (rs2236652, A or G), 147896 (rs476551, C or G), 150043 (rs10791861, A or G), 152853 (rs2298466, C or T), 168931 (rs10791863, T or C), 172500 (rs2155031, T or C), 175003 (rs2276036, T or C), 184535 (rs2298468, A or G), 189853 (rs11227447, C or G), 194405 (rs2282568, G or C), and 202111 (rs3814738, T or G). Preferred examples include nucleotides represented by Nucleotide Numbers 189853 (rs11227447, C or G), and 194405 (rs2282568, G or C).

Examples of the gene which overlaps with the 18,933-bp haplotype block represented by the base sequence set forth in SEQ ID NO:3 include CD248 gene on human chromosome 11. CD248 gene is a gene represented by GeneID:57124 in the Entrez Gene Database, and as shown in Example 5 and FIG. 7, a portion of the base sequence overlaps with the haplotype block described above.

Examples of the hair shape susceptibility SNP marker present in the base sequence set forth in SEQ ID NO:3 include nucleotides represented by Nucleotide Numbers 5297 (rs523583, A or C), 18280 (rs3741367, T or C), and 18933 (rs3741368, G or A). Preferred examples include nucleotides represented by Nucleotide Numbers 18280 (rs3741367, T or C), and 18933 (rs3741368, G or A).

Examples of the gene which overlaps with the 27,375-bp haplotype block represented by the base sequence set forth in SEQ ID NO:4 include ORAOV1 gene on human chromosome 11. ORAOV1 gene is a gene represented by GeneID: 220064 in the Entrez Gene Database, and as shown in Example 5 and FIG. 8, a portion of the base sequence overlaps with the haplotype block described above.

Examples of the hair shape susceptibility SNP marker present in the base sequence set forth in SEQ ID NO:4 include nucleotides represented by Nucleotide Numbers 1 (rs1789165, A or G), 8378 (rs10796828, G or T), 12624 (rs1789172, T or C), 20147 (rs1192921, G or C), 22309 (rs1192923, A or T), 24512 (rs1192924, T or C), and 26599 (rs1789168, T or C). A preferred example may be a nucleotide represented by Nucleotide Number 1 (rs1789165, A or G).

Examples of the gene which overlaps with the 35,979-bp haplotype block represented by the base sequence set forth in SEQ ID NO:5 include KRTAP5-8 gene, KRTAP5-9 gene, and KRTAP5-10 gene on human chromosome 11. KRTAP5-8 gene is a gene represented by GeneID:57830 in the Entrez Gene Database, and as shown in Example 5 and FIG. 9, a portion of the base sequence overlaps with the haplotype block described above. KRTAP5-9 gene is a gene represented by GeneID:3846 in the Entrez Gene Database, and as shown in Example 5 and FIG. 9, the entire length of the base sequence overlaps with the haplotype block described above. Furthermore, KRTAP5-10 gene is a gene represented by GeneID:387273 in the Entrez Gene Database, and as shown in Example 5 and FIG. 9, the entire length of the base sequence overlaps with the haplotype block described above.

Examples of the hair shape susceptibility SNP marker present in the base sequence set forth in SEQ ID NO:5 include nucleotides represented by Nucleotide Numbers 17000 (rs2664, T or C), 18895 (rs7934055, T or G), 26143 (rs17363723, G or A), 26545 (rs11234174, A or G), 27090 (rs10792781, C or T), 27751 (rs7107678, G or A), and 30274 (rs7106362, T or C). A preferred example may be a nucleotide represented by Nucleotide Number 17000 (rs2664, T or C).

3. HAIR SHAPE DETERMINING MARKER

The present invention also provides a hair shape determining marker which is an oligo- or polynucleotide in the 11q12.2 to 11q13.2 region (D11S4191 and D11S987) of human chromosome 11, or a complementary strand thereof, wherein in the oligo- or polynucleotide contains a partial base sequence of the base sequence of a haplotype block that is determined by a linkage disequilibrium analysis for a SNP marker whose allele frequency is statistically significantly different between a group having a curly hair trait and a group having a non-curly hair trait and consists of abase sequence set forth in any one of SEQ ID NO:1 to NO:5, and wherein the partial base sequence consisting of a contiguous base sequence containing one or more single nucleotide polymorphisms (SNPs) wherein the SNPs include an SNP whose allele frequency is statistically significantly different between a group having a curly hair trait and a group having a non-curly hair trait, and an SNPs linked to the SNP.

The oligo- or polynucleotides, or complementary strands thereof, defined by these base sequences contain one or more a hair shape susceptibility SNP marker that is a single nucleotide polymorphism (SNP) which is present in a haplotype block represented by a base sequence set forth in any one of SEQ ID NO: 1 to NO: 5, and whose allele frequency is statistically significantly different between a group having a curly hair trait and a group having a non-curly hair trait, or an SNP linked to the SNP. When these oligo- or polynucleotides, or complementary strands thereof, are detected, the genetic predisposition of hair shape in a test subject can be examined and/or determined. Therefore, these oligo- or polynucleotides, or complementary strand thereof can be defined and used as markers for determining the genetic predisposition of hair shape possessed by an individual.

The length (nucleotide length) of these oligo- or polynucleotides, or complementary strands, is desirably a length which is specifically recognized in human genome, and there are no particular limitations on the limit. The length is usually equal to or more than 10-mers and equal to or fewer than 1000-mers, preferably equal to or more than 20-mers and equal to or fewer than 500-mers, and more preferably equal to or more than 20-mers and equal to or fewer than 100-mers. Therefore, if necessary, the length can be set to, for example, 11 nucleotides containing a hair shape susceptibility SNP marker present in a haplotype block represented by a base sequence set forth in SEQ ID NO:1 to NO:5 (preferably, 5 nucleotides each on the 5' side and the 3' side of the hair shape susceptibility SNP marker), 21 nucleotides (preferably including 10 nucleotides each on the 5' side and the 3' side of the hair shape susceptibility SNP marker), 101 nucleotides (preferably including 50 nucleotides each on the 5' side and the 3' side of the hair shape susceptibility SNP marker), 601 nucleotides (preferably including 300 nucleotides each on the 5' side and the 3' side of the hair shape susceptibility SNP marker), or the like.

Examples of the hair shape susceptibility SNP marker used in the present invention, which should be included in the hair shape determining marker of the present invention, include the following:

(1) nucleotides represented by Nucleotide Numbers 1 (dbSNP Database ID:rs10792367, G or C), 7633 (rs2276299, A or T), and 9315 (rs4149182, G or C) in the base sequence set forth in SEQ ID NO:1;

(2) nucleotides represented by Nucleotide Numbers 1 (rs11227403, C or T), 16722 (rs11607393, A or C), 19992 (rs3825067, T or C), 21051 (rs11227411, T or C), 21927 (rs10896081, T or A), 25269 (rs11227413, A or G), 27032 (rs11227415, C or T), 35997 (rs3862386, C or G), 49537 (rs9645684, A or G), 55405 (rs10896085, T or A), 69180 (rs918299, T or C), 84627 (rs7943911, A or G), 86185 (rs2177054, A or C), 90221 (rs10750778, C or T), 91247 (rs6591207, A or T), 92398 (rs10896091, C or T), 98150 (rs7946917, G or A), 100779 (rs10896094, T or C), 101730 (rs7941431, A or G), 102920 (rs2293121, G or T), 105310 (rs10791855, G or A), 126741 (rs512421, A or G), 133917 (rs2155201, C or T), 134786 (rs7925123, C or G), 142991 (rs2236651, T or C), 144254 (rs2236652, A or G), 147896 (rs476551, C or G), 150043 (rs10791861, A or G), 152853 (rs2298466, C or T), 168931 (rs10791863, T or C), 172500 (rs2155031, T or C), 175003 (rs2276036, T or C), 184535 (rs2298468, A or G), 189853 (rs11227447, C or G), 194405 (rs2282568, G or C), and 202111 (rs3814738, T or G) in the base sequence set forth in SEQ ID NO:2;

(3) nucleotides represented by Nucleotide Numbers 5297 (rs523583, A or C), 18280 (rs3741367, T or C), and 18933 (rs3741368, G or A) in the base sequence set forth in SEQ ID NO:3;

(4) nucleotides represented by Nucleotide Numbers 1 (rs1789165, A or G) 8378 (rs10796828, G or T), 12624 (rs1789172, T or C), 20147 (rs1192921, G or C), 22309 (rs1192923, A or T), 24512 (rs1192924, T or C), and 26599 (rs1789168, T or C) in the base sequence set forth in SEQ ID NO:4; and (5) nucleotides represented by Nucleotide Numbers 17000 (rs2664, T or C), 18895 (rs7934055, T or G), 26143 (rs17363723, G or A), 26545 (rs11234174, A or G), 27090 (rs10792781, C or T), 27751 (rs7107678, G or A), and 30274 (rs7106362, T or C) in the base sequence set forth in SEQ ID NO:5.

Among the nucleotides described above, the nucleotide represented by Nucleotide Number 7633 (rs2276299, A or T) in the base sequence set forth in SEQ ID NO:1; the nucleotides represented by Nucleotide Numbers 189853 (rs11227447, C or G) and 194405 (rs2282568, G or C) in the base sequence set forth in SEQ ID NO:2; the nucleotides represented by Nucleotide Numbers 18280 (rs3741367, T or C) and 18933 (rs3741368, G or A) in the base sequence set forth in SEQ ID NO:3; the nucleotide represented by Nucleotide Number 1 (rs1789165, A or G) in the base sequence set forth in SEQ ID NO:4; and the nucleotide represented by Nucleotide Number 17000 (rs2664, T or C) in the base sequence set forth in SEQ ID NO:5 are preferred.

It is desirable that the hair shape susceptibility SNP marker be located at the center or near the center of the hair shape determining marker of the present invention (for example, within 100 nucleotides, preferably 50 nucleotides, more preferably 30 nucleotides, even more preferably 10 nucleotides, and still more preferably 5 nucleotides, from the center), but it is not necessarily required. Furthermore, when two or more hair shape susceptibility SNP markers are included in the hair shape determining marker of the present invention, all of the hair shape susceptibility SNP markers may be located at the center or near the center of the hair shape determining marker of the present invention; one of the hair shape susceptibility SNP markers is located at the center or near the center, while the others may be located at any positions; or all of the hair shape susceptibility SNP markers may not be located at the center or near the center.

Specific examples of the hair shape determining marker of the present invention in which the hair shape susceptibility SNP marker is located at the center include, for example, in the case where a SNP is contained in the nucleotide represented by Nucleotide Number 1 (dbSNP Database ID:rs10792367, G or C) in the base sequence set forth in SEQ ID NO:1, a 11-mer polynucleotide consisting of from 5 nucleotides upstream of SEQ ID NO:1 to Nucleotide Number 6, a 21-mer polynucleotide consisting of from 10 nucleotides upstream of SEQ ID NO:1 to Nucleotide Number 11, a 101-mer polynucleotide consisting of from 50 nucleotides upstream of SEQ ID NO: 1 to Nucleotide Number 51, and a 601-mer polynucleotide having a base sequence consisting of from 300 nucleotides upstream of SEQ ID NO:1 to Nucleotide Number 11.

4. METHOD FOR DETERMINING GENETIC SUSCEPTIBILITY TO HAIR SHAPE

The present invention also provides a method for determining the genetic susceptibility (genetic predisposition) of a test subject to hair shape. The method for determining the genetic susceptibility to hair shape of the present invention includes the following steps (a) and (b), and there are no particular limitations on the limit:

(a) a step of preparing a genomic DNA derived from a test subject; and (b) a step of detecting, from the genomic DNA, a single nucleotide polymorphism (SNP) whose allele frequency is statistically significantly different between a group having a curly hair trait and a group having a non-curly hair trait, and being present in a haplotype block in the 11q12.2 to 11q13.2 region (D11S4191 and D11S987) of human chromosome 11 that is determined by a linkage disequilibrium analysis on a single nucleotide polymorphism (SNP) marker whose allele frequency is statistically significantly different between a group having a curly hair trait and a group having a non-curly hair trait, and that consists of a base sequence set forth in any one of SEQ ID NO:1 to NO:5, and a single nucleotide polymorphism (SNP) linked to the SNP.

The step (a) (extraction of a genomic DNA) and the step (b) (detection of SNPs) can be carried out using a known method (for example, Birren Bruce et al., Genome Analysis, Vol. 4/A Laboratory Manual Mapping Genomes, Cold Spring Harbor Laboratory, NY, 1999).

In the step (a), the genomic DNA derived from a test subject can be obtained from a material such as all cells (including cultured cells; however, reproductive cells are excluded), tissues (including cultured tissues), organs, or body fluids (for example, blood, saliva, lymph fluid, respiratory tract mucosa, semen, sweat, urine, and the like), which have been isolated from the test subject, clinical specimens therefrom, and the like. The material is preferably leukocytes or monocytes separated from peripheral blood, and is more suitably leukocytes. These materials can be isolated according to those methods usually used in clinical tests.

For example, in the case of using leukocytes as the material, first, leukocytes are separated from the peripheral blood isolated from a test subject, according to an ordinary method. Subsequently, Proteinase K and sodium dodecyl sulfate (SDS) are added to the leukocytes thus obtained to degrade and denature proteins, and then phenol/chloroform extraction is carried out to thereby obtain genomic DNA (including RNA). The RNA can be eliminated with an RNase as necessary. Meanwhile, the extraction of genomic DNA is not limited to the method described above, and can be carried out using a method well-known in the art (for example, Joseph Sambrook et al., Molecular Cloning: A Laboratory Manual (3 Vol. set), Cold Spring Harbor Laboratory, NY, 2001) or using a commercially available DNA extraction kit or the like. Furthermore, if necessary, the DNA containing the 11q12.2 to 11q13.2 region of human chromosome 11, or a DNA containing a haplotype block represented by a base sequence set forth in any one of SEQ ID NO: 1 to NO: 5 in the genomic region of human chromosome 11, may be isolated. The isolation of the DNA can be carried out by PCR using a primer which hybridizes with the 11q12.2 to 11q.13.2 region or with the corresponding haplotype block and using the genomic DNA as a template, or the like.

In the step (b), detected from the genomic DNA obtained in the step (a) is an SNP which is a polymorphism present in a haplotype block in the 11q12.2 to 11q13.2 region (D11S4191 and D11S987) of human chromosome 11 and that is determined by a linkage disequilibrium analysis on a single nucleotide polymorphism (SNP), whose allele frequency is statistically different between a group having a curly hair trait and a group having a non-curly hair trait, and the allele frequency of which SNP is higher in any curly hair people group than in any non-curly hair people group, or a SNP that is linked to the SNP. The base sequences set forth in SEQ ID NO:1 to NO:5 include the 12,590-bp base sequence set forth in SEQ ID NO:1, the 202,111-bp base sequence set forth in SEQ ID NO:2, the 18,933-bp base sequence set forth in SEQ ID NO:3, the 27,375-bp base sequence set forth in SEQ ID NO:4, and the 35,979-bp base sequence set forth in SEQ ID NO:5, in the genomic region of human chromosome 11.

The method for determination of the present invention preferably further includes the following step (c):

(c) a step of determining, if the allele frequency of the detected SNP is statistically significantly higher in the curly hair people group than in the non-curly hair people group, that the test subject has a genetic predisposition to curly hair, and if the allele frequency of the detected SNP is statistically significantly higher in any non-curly hair people group than in the curly hair people group, that the test subject does not have a genetic predisposition to curly hair.

An example of the step (c) may be a step of identifying, for any one or more nucleotides of the nucleotide numbers as indicated in the following table that are present in the base sequences set forth in SEQ ID NO:1 to NO:5 in the genomic DNA derived from a test subject, whether the nucleotide is nucleotide (i) or nucleotide (ii); and determining, when the nucleotide is nucleotide (i), that the test subject has a predisposition to curly hair, and when the nucleotide is nucleotide (ii), that the test subject does not have a predisposition to curly hair.

TABLE 3

| SEQ ID NO. | Nucleotide Number | Nucleotide (i) (having predisposition) | Nucleotide (ii) (No predisposition) |
|---|---|---|---|
| 1 | 1 | C | G |
| | 7633 | T | A |
| | 9315 | C | G |
| 2 | 1 | T | C |
| | 16722 | C | A |
| | 19992 | C | T |
| | 21051 | C | T |
| | 21927 | A | T |
| | 25269 | G | A |
| | 27032 | T | C |
| | 35997 | G | C |
| | 49537 | G | A |
| | 55405 | A | T |
| | 69180 | C | T |
| | 84627 | G | A |
| | 86185 | C | A |
| | 90221 | T | C |
| | 91247 | T | A |
| | 92398 | T | C |
| | 98150 | A | G |
| | 100779 | C | T |
| | 101730 | G | A |
| | 102920 | T | G |
| | 105310 | A | G |
| | 126741 | G | A |
| | 133917 | T | C |
| | 134786 | G | C |
| | 142991 | C | T |

TABLE 3-continued

| SEQ ID NO. | Nucleotide Number | Nucleotide (i) (having predisposition) | Nucleotide (ii) (No predisposition) |
|---|---|---|---|
| | 144254 | G | A |
| | 147896 | G | C |
| | 150043 | G | A |
| | 152853 | T | C |
| | 168931 | C | T |
| | 172500 | C | T |
| | 175003 | C | T |
| | 184535 | G | A |
| | 189853 | G | C |
| | 194405 | C | G |
| | 202111 | G | T |
| 3 | 5297 | C | A |
| | 18280 | C | T |
| | 18933 | A | G |
| 4 | 1 | G | A |
| | 8378 | T | G |
| | 12624 | C | T |
| | 20147 | C | G |
| | 22309 | T | A |
| | 24512 | C | T |
| | 26599 | C | T |
| 5 | 17000 | C | T |
| | 18895 | G | T |
| | 26143 | A | G |
| | 26545 | G | A |
| | 27090 | T | C |
| | 27751 | A | G |
| | 30274 | C | T |

More specifically, the method of the present invention for determining genetic susceptibility of a test subject to hair shape includes any one step of the following (1) to (56).

(1) In the base sequence set forth in SEQ ID NO:1, it is identified whether the nucleotide represented by Nucleotide Number 1 is G or C, and it is determined, when the nucleotide is C, that the test subject has a predisposition to curly hair, or when the nucleotide is G, the test subject does not have a predisposition to curly hair;

(2) in the base sequence set forth in SEQ ID NO:1, it is identified whether the nucleotide represented by Nucleotide Number 7633 is A or T, and it is determined, when the nucleotide is T, that the test subject has a predisposition to curly hair, or when the nucleotide is A, the test subject does not have a predisposition to curly hair;

(3) in the base sequence set forth in SEQ ID NO:1, it is identified whether the nucleotide represented by Nucleotide Number 9315 is G or C, and it is determined, when the nucleotide is C, that the test subject has a predisposition to curly hair, or when the nucleotide is G, the test subject does not have a predisposition to curly hair;

(4) in the base sequence set forth in SEQ ID NO:2, it is identified whether the nucleotide represented by Nucleotide Number 1 is C or T, and it is determined, when the nucleotide is T, that the test subject has a predisposition to curly hair, or when the nucleotide is C, the test subject does not have a predisposition to curly hair;

(5) in the base sequence set forth in SEQ ID NO:2, it is identified whether the nucleotide represented by Nucleotide Number 16722 is A or C, and it is determined, when the nucleotide is C, that the test subject has a predisposition to curly hair, or when the nucleotide is A, the test subject does not have a predisposition to curly hair;

(6) in the base sequence set forth in SEQ ID NO:2, it is identified whether the nucleotide represented by Nucleotide Number 19992 is T or C, and it is determined, when the nucleotide is C, that the test subject has a predisposition to curly hair, or when the nucleotide is T, the test subject does not have a predisposition to curly hair;

(7) in the base sequence set forth in SEQ ID NO:2, it is identified whether the nucleotide represented by Nucleotide Number 21051 is T or C, and it is determined, when the nucleotide is C, that the test subject has a predisposition to curly hair, or when the nucleotide is T, the test subject does not have a predisposition to curly hair;

(8) in the base sequence set forth in SEQ ID NO:2, it is identified whether the nucleotide represented by Nucleotide Number 21927 is T or A, and it is determined, when the nucleotide is A, that the test subject has a predisposition to curly hair, or when the nucleotide is T, the test subject does not have a predisposition to curly hair;

(9) in the base sequence set forth in SEQ ID NO:2, it is identified whether the nucleotide represented by Nucleotide Number 25269 is A or G, and it is determined, when the nucleotide is G, that the test subject has a predisposition to curly hair, or when the nucleotide is A, the test subject does not have a predisposition to curly hair;

(10) in the base sequence set forth in SEQ ID NO:2, it is identified whether the nucleotide represented by Nucleotide Number 27032 is C or T, and it is determined, when the nucleotide is T, that the test subject has a predisposition to curly hair, or when the nucleotide is C, the test subject does not have a predisposition to curly hair;

(11) in the base sequence set forth in SEQ ID NO:2, it is identified whether the nucleotide represented by Nucleotide Number 35997 is C or G, and it is determined, when the nucleotide is G, that the test subject has a predisposition to curly hair, or when the nucleotide is C, the test subject does not have a predisposition to curly hair;

(12) in the base sequence set forth in SEQ ID NO:2, it is identified whether the nucleotide represented by Nucleotide Number 49537 is A or G, and it is determined, when the nucleotide is G, that the test subject has a predisposition to curly hair, or when the nucleotide is A, the test subject does not have a predisposition to curly hair;

(13) in the base sequence set forth in SEQ ID NO:2, it is identified whether the nucleotide represented by Nucleotide Number 55405 is T or A, and it is determined, when the nucleotide is A, that the test subject has a predisposition to curly hair, or when the nucleotide is T, the test subject does not have a predisposition to curly hair;

(14) in the base sequence set forth in SEQ ID NO:2, it is identified whether the nucleotide represented by Nucleotide Number 69180 is T or C, and it is determined, when the nucleotide is C, that the test subject has a predisposition to curly hair, or when the nucleotide is T, the test subject does not have a predisposition to curly hair;

(15) in the base sequence set forth in SEQ ID NO:2, it is identified whether the nucleotide represented by Nucleotide Number 84627 is A or G, and it is determined, when the nucleotide is G, that the test subject has a predisposition to curly hair, or when the nucleotide is A, the test subject does not have a predisposition to curly hair;

(16) in the base sequence set forth in SEQ ID NO:2, it is identified whether the nucleotide represented by Nucleotide Number 86185 is A or C, and it is determined, when the nucleotide is C, that the test subject has a predisposition to curly hair, or when the nucleotide is A, the test subject does not have a predisposition to curly hair;

(17) in the base sequence set forth in SEQ ID NO:2, it is identified whether the nucleotide represented by Nucleotide Number 90221 is C or T, and it is determined, when the nucleotide is T, that the test subject has a predisposition to curly hair, or when the nucleotide is C, the test subject does not have a predisposition to curly hair;

(18) in the base sequence set forth in SEQ ID NO:2, it is identified whether the nucleotide represented by Nucleotide Number 91247 is A or T, and it is determined, when the nucleotide is T, that the test subject has a predisposition to curly hair, or when the nucleotide is A, the test subject does not have a predisposition to curly hair;

(19) in the base sequence set forth in SEQ ID NO:2, it is identified whether the nucleotide represented by Nucleotide Number 92398 is C or T, and it is determined, when the nucleotide is T, that the test subject has a predisposition to curly hair, or when the nucleotide is C, the test subject does not have a predisposition to curly hair;

(20) in the base sequence set forth in SEQ ID NO:2, it is identified whether the nucleotide represented by Nucleotide Number 98150 is G or A, and it is determined, when the nucleotide is A, that the test subject has a predisposition to curly hair, or when the nucleotide is G, the test subject does not have a predisposition to curly hair;

(21) in the base sequence set forth in SEQ ID NO:2, it is identified whether the nucleotide represented by Nucleotide Number 100779 is T or C, and it is determined, when the nucleotide is C, that the test subject has a predisposition to curly hair, or when the nucleotide is T, the test subject does not have a predisposition to curly hair;

(22) in the base sequence set forth in SEQ ID NO:2, it is identified whether the nucleotide represented by Nucleotide Number 101730 is A or G, and it is determined, when the nucleotide is G, that the test subject has a predisposition to curly hair, or when the nucleotide is A, the test subject does not have a predisposition to curly hair;

(23) in the base sequence set forth in SEQ ID NO:2, it is identified whether the nucleotide represented by Nucleotide Number 102920 is G or T, and it is determined, when the nucleotide is T, that the test subject has a predisposition to curly hair, or when the nucleotide is G, the test subject does not have a predisposition to curly hair;

(24) in the base sequence set forth in SEQ ID NO:2, it is identified whether the nucleotide represented by Nucleotide Number 105310 is G or A, and it is determined, when the nucleotide is A, that the test subject has a predisposition to curly hair, or when the nucleotide is G, the test subject does not have a predisposition to curly hair;

(25) in the base sequence set forth in SEQ ID NO:2, it is identified whether the nucleotide represented by Nucleotide Number 126741 is A or G, and it is determined, when the nucleotide is G, that the test subject has a predisposition to curly hair, or when the nucleotide is A, the test subject does not have a predisposition to curly hair;

(26) in the base sequence set forth in SEQ ID NO:2, it is identified whether the nucleotide represented by Nucleotide Number 133917 is C or T, and it is determined, when the nucleotide is T, that the test subject has a predisposition to curly hair, or when the nucleotide is C, the test subject does not have a predisposition to curly hair;

(27) in the base sequence set forth in SEQ ID NO:2, it is identified whether the nucleotide represented by Nucleotide Number 134786 is C or G, and it is determined, when the nucleotide is G, that the test subject has a predisposition to curly hair, or when the nucleotide is C, the test subject does not have a predisposition to curly hair;

(28) in the base sequence set forth in SEQ ID NO:2, it is identified whether the nucleotide represented by Nucleotide Number 142991 is T or C, and it is determined, when the nucleotide is C, that the test subject has a predisposition to curly hair, or when the nucleotide is T, the test subject does not have a predisposition to curly hair;

(29) in the base sequence set forth in SEQ ID NO:2, it is identified whether the nucleotide represented by Nucleotide Number 144254 is A or G, and it is determined, when the nucleotide is G, that the test subject has a predisposition to curly hair, or when the nucleotide is A, the test subject does not have a predisposition to curly hair;

(30) in the base sequence set forth in SEQ ID NO:2, it is identified whether the nucleotide represented by Nucleotide Number 147896 is C or G, and it is determined, when the nucleotide is G, that the test subject has a predisposition to curly hair, or when the nucleotide is C, the test subject does not have a predisposition to curly hair;

(31) in the base sequence set forth in SEQ ID NO:2, it is identified whether the nucleotide represented by Nucleotide Number 150043 is A or G, and it is determined, when the nucleotide is G, that the test subject has a predisposition to curly hair, or when the nucleotide is A, the test subject does not have a predisposition to curly hair;

(32) in the base sequence set forth in SEQ ID NO:2, it is identified whether the nucleotide represented by Nucleotide Number 152853 is C or T, and it is determined, when the nucleotide is T, that the test subject has a predisposition to curly hair, or when the nucleotide is C, the test subject does not have a predisposition to curly hair;

(33) in the base sequence set forth in SEQ ID NO:2, it is identified whether the nucleotide represented by Nucleotide Number 168931 is T or C, and it is determined, when the nucleotide is C, that the test subject has a predisposition to curly hair, or when the nucleotide is T, the test subject does not have a predisposition to curly hair;

(34) in the base sequence set forth in SEQ ID NO:2, it is identified whether the nucleotide represented by Nucleotide Number 172500 is T or C, and it is determined, when the nucleotide is C, that the test subject has a predisposition to curly hair, or when the nucleotide is T, the test subject does not have a predisposition to curly hair;

(35) in the base sequence set forth in SEQ ID NO:2, it is identified whether the nucleotide represented by Nucleotide Number 175003 is T or C, and it is determined, when the nucleotide is C, that the test subject has a predisposition to curly hair, or when the nucleotide is T, the test subject does not have a predisposition to curly hair;

(36) in the base sequence set forth in SEQ ID NO:2, it is identified whether the nucleotide represented by Nucleotide Number 184535 is A or G, and it is determined, when the nucleotide is G, that the test subject has a predisposition to curly hair, or when the nucleotide is A, the test subject does not have a predisposition to curly hair;

(37) in the base sequence set forth in SEQ ID NO:2, it is identified whether the nucleotide represented by Nucleotide Number 189853 is C or G, and it is determined, when the nucleotide is G, that the test subject has a predisposition to curly hair, or when the nucleotide is C, the test subject does not have a predisposition to curly hair;

(38) in the base sequence set forth in SEQ ID NO:2, it is identified whether the nucleotide represented by Nucleotide Number 194405 is G or C, and it is determined, when the nucleotide is C, that the test subject has a predisposition to curly hair, or when the nucleotide is G, the test subject does not have a predisposition to curly hair;

(39) in the base sequence set forth in SEQ ID NO:2, it is identified whether the nucleotide represented by Nucleotide Number 202111 is T or G, and it is determined, when the nucleotide is G, that the test subject has a predisposition to curly hair, or when the nucleotide is T, the test subject does not have a predisposition to curly hair;

(40) in the base sequence set forth in SEQ ID NO:3, it is identified whether the nucleotide represented by Nucleotide Number 5297 is A or C, and it is determined, when the nucleotide is C, that the test subject has a predisposition to curly hair, or when the nucleotide is A, the test subject does not have a predisposition to curly hair;

(41) in the base sequence set forth in SEQ ID NO:3, it is identified whether the nucleotide represented by Nucleotide Number 18280 is T or C, and it is determined, when the nucleotide is C, that the test subject has a predisposition to curly hair, or when the nucleotide is T, the test subject does not have a predisposition to curly hair;

(42) in the base sequence set forth in SEQ ID NO:3, it is identified whether the nucleotide represented by Nucleotide Number 18933 is G or A, and it is determined, when the nucleotide is A, that the test subject has a predisposition to curly hair, or when the nucleotide is G, the test subject does not have a predisposition to curly hair;

(43) in the base sequence set forth in SEQ ID NO:4, it is identified whether the nucleotide represented by Nucleotide Number 1 is A or G, and it is determined, when the nucleotide is G, that the test subject has a predisposition to curly hair, or when the nucleotide is A, the test subject does not have a predisposition to curly hair;

(44) in the base sequence set forth in SEQ ID NO:4, it is identified whether the nucleotide represented by Nucleotide Number 8378 is G or T, and it is determined, when the nucleotide is T, that the test subject has a predisposition to curly hair, or when the nucleotide is G, the test subject does not have a predisposition to curly hair;

(45) in the base sequence set forth in SEQ ID NO:4, it is identified whether the nucleotide represented by Nucleotide Number 12624 is T or C, and it is determined, when the nucleotide is C, that the test subject has a predisposition to curly hair, or when the nucleotide is T, the test subject does not have a predisposition to curly hair;

(46) in the base sequence set forth in SEQ ID NO:4, it is identified whether the nucleotide represented by Nucleotide Number 20147 is G or C, and it is determined, when the nucleotide is C, that the test subject has a predisposition to curly hair, or when the nucleotide is G, the test subject does not have a predisposition to curly hair;

(47) in the base sequence set forth in SEQ ID NO:4, it is identified whether the nucleotide represented by Nucleotide Number 22309 is A or T, and it is determined, when the nucleotide is T, that the test subject has a predisposition to curly hair, or when the nucleotide is A, the test subject does not have a predisposition to curly hair;

(48) in the base sequence set forth in SEQ ID NO:4, it is identified whether the nucleotide represented by Nucleotide Number 24512 is T or C, and it is determined, when the nucleotide is C, that the test subject has a predisposition to curly hair, or when the nucleotide is T, the test subject does not have a predisposition to curly hair;

(49) in the base sequence set forth in SEQ ID NO:4, it is identified whether the nucleotide represented by Nucleotide Number 26599 is T or C, and it is determined, when the nucleotide is C, that the test subject has a predisposition to curly hair, or when the nucleotide is T, the test subject does not have a predisposition to curly hair;

(50) in the base sequence set forth in SEQ ID NO:5, it is identified whether the nucleotide represented by Nucleotide Number 17000 is T or C, and it is determined, when the nucleotide is C, that the test subject has a predisposition to curly hair, or when the nucleotide is T, the test subject does not have a predisposition to curly hair;

(51) in the base sequence set forth in SEQ ID NO:5, it is identified whether the nucleotide represented by Nucleotide Number 18895 is T or G, and it is determined, when the nucleotide is G, that the test subject has a predisposition to curly hair, or when the nucleotide is T, the test subject does not have a predisposition to curly hair;

(52) in the base sequence set forth in SEQ ID NO:5, it is identified whether the nucleotide represented by Nucleotide Number 26143 is G or A, and it is determined, when the nucleotide is A, that the test subject has a predisposition to curly hair, or when the nucleotide is G, the test subject does not have a predisposition to curly hair;

(53) in the base sequence set forth in SEQ ID NO:5, it is identified whether the nucleotide represented by Nucleotide Number 26545 is A or G, and it is determined, when the nucleotide is G, that the test subject has a predisposition to curly hair, or when the nucleotide is A, the test subject does not have a predisposition to curly hair;

(54) in the base sequence set forth in SEQ ID NO:5, it is identified whether the nucleotide represented by Nucleotide Number 27090 is C or T, and it is determined, when the nucleotide is T, that the test subject has a predisposition to curly hair, or when the nucleotide is C, the test subject does not have a predisposition to curly hair;

(55) in the base sequence set forth in SEQ ID NO:5, it is identified whether the nucleotide represented by Nucleotide Number 27751 is G or A, and it is determined, when the nucleotide is A, that the test subject has a predisposition to curly hair, or when the nucleotide is G, the test subject does not have a predisposition to curly hair; or

(56) in the base sequence set forth in SEQ ID NO:5, it is identified whether the nucleotide represented by Nucleotide Number 30274 is T or C, and it is determined, when the nucleotide is C, that the test subject has a predisposition to curly hair, or when the nucleotide is T, the test subject does not have a predisposition to curly hair.

In addition, the SNP detected in the method of the present invention for determining the genetic susceptibility (genetic predisposition) to hair shape may be any one of the SNPs described above, or may be two or more thereof. Preferably, two or more SNPs are detected, and thereby, the type or the presence or absence of the genetic predisposition of the test subject to the hair shape, which is a general polygenic trait, can be made clear, while a gene which serves as a main factor determining the hair shape of the test subject can be retrieved with higher accuracy.

The detection of the SNPs can be carried out by directly determining the base sequence of the 11q12.2 to 11q13.2 region of human chromosome 11 further isolated from a sample containing the genomic DNA, or the base sequence of the haplotype block represented by the base sequences set forth in SEQ ID NO:1 to NO:5 in the genomic regions of human chromosome 11. Alternatively, as a method for detecting a polymorphism, in addition to the method of directly determining the gene sequence of the region as described above, there are available a method of determining, when the polymorphism sequence is a restriction enzyme recognition site, the genotype by using the difference in the restriction enzyme cleavage pattern (hereinafter, called RFLP); and methods based on hybridization using a polymorphism-specific probe (for example, a method of determining the type of polymorphism by attaching particular probes on a chip, a glass slide or a nylon film and detecting the difference in the intensity of hybridization with respect to those probes, or a method of determining the genotype by detecting the efficiency of hybridization of a specific probe as the amount of the probe decomposed by a polymerase during amplification of the two strands of a template; a method of detecting the temperature difference in the fusion of two strands by tracing the temperature change of fluorescence emitted by a certain type of two-stranded specific fluorescent dye, and thereby determining the polymorphism; a method of attaching complementary sequences to the two ends of a polymorphic site-specific oligo-probe, and specifying the genotype by utilizing the difference between the case where the probe makes a secondary structure within the molecules of the probe itself due to temperature, and the case where the probe hybridizes with the target region; and the like). Further examples include methods of carrying out a nucleotide extension reaction by a polymerase from a template-specific primer, and determining a nucleotide that is accepted to the polymorphic site at that time (a method of using dideoxynucleotides, including fluorescently labeling each of them, and detecting the fluorescence of each, and a method of detecting the accepted dideoxynucleotides by mass spectrometry); a method of recognizing the presence or absence of a complementary base pair or a non-complementary base pair at a mutation site by means of an enzyme, subsequent to a template-specific primer; and the like.

Now, conventionally well-known, representative methods for detecting genetic polymorphisms will be listed below, but the present invention is not at all intended to be limited to these: (a) a RFLP (restriction enzyme-cleaved fragment length polymorphism) method; (b) a PCR-SSCP method (analysis of single-stranded DNA higher structure polymorphism, Biotechniques, 16, p. 296-297, 1994, and Biotechniques, 21, p. 510 to 514, 1996); (c) an ASO hybridization method (Clin. Chin. Acta., 189, p. 153-157, 1990); (d) a direct sequencing method (Biotechniques, 11, p. 246-249, 1991); (e) an ARMS method (Nuc. Acids Res., 19, p. 3561-3567, 1991, and Nuc. Acids Res., 20, p. 4831-4837, 1992); (f) a denaturant concentration gradient gel electrophoresis (DGGE) method (Biotechniques, 27, p. 1016-1018, 1999); (g) an RNaseA cleavage method (DNA Cell Biol., 14, p. 87-94, 1995); (h) a chemical cleavage method (Biotechniques, 21, p. 216-218, 1996); (i) a DOL method (Genome Res., 8, p. 549-556, 1998); (j) a TaqMan-PCR method (Genet. Anal., 14, p. 143-149, 1999, and J. Clin. Microbiol., 34, p. 2933-2936, 1996); (k) an invader method (Science, 5109, p. 778-783, 1993, J. Bio. Chem., 30, p. 21387-21394, 1999, and Nat. Biotechnol., 17, p. 292-296, 1999); (l) a MALDI-TOF/MS method (Genome Res., 7, p. 378-388, 1997, and Eur. J. Clin. Chem. Clin. Biochem., 35, p. 545-548, 1997); (m) a TDI method (Proc. Natl. Acad. Sci. USA, 94, p. 10756-10761, 1997); (n) a molecular beacon method (Nat. Biotechnol., 16, p. 49-53, 1998); (O) a dynamic allele specific hybridization (DASH) method (Nat. Biotechnol., 17, p. 87-88, 1999); (p) a padlock probe method (Nat. Genet., 3, p. 225-232, 1998); (q) a DNA chip or DNA microarray (Nakamura, Yusuke, et al., "SNP Idenshi Takei no Senryaku (Strategy for SNP Gene Polymorphism)", Nakayama Shoten Co., Ltd., p. 128-135, 2000); and (R) an ECA method (Anal. Chem., 72, p. 1334-1341, 2000).

Those described above are representative methods for gene polymorphism detection; however, the method of the present invention for determining the genetic susceptibility (genetic predisposition) to hair shape is not limited to these, and any other gene polymorphism detection methods that are already known or will be developed in the future can be broadly used. Furthermore, in regard to the gene polymorphism detection of the present invention, these methods for gene polymorphism detection may be used singly, or two or more methods can also be used in combination. Hereinafter, as representative methods, the TaqMan-PCR method and the invader method that are used in the Examples described below will be explained in more detail.

(1) TaqMan-PCR Method

The TaqMan-PCR method is a method of using a fluorescent-labeled, allele-specific oligonucleotide (TaqMan probe), and PCR by a Taq DNA polymerase. As the TaqMan probe, an oligonucleotide containing a contiguous base sequence of about 15 to about 30 nucleotides, which is a partial base sequence of a haplotype block represented by any one of SEQ ID NO:1 to NO:5 in the genomic region of human chromosome 11, and contains one or more polymorphic sites described above (for example, a nucleic acid probe contained in the reagent for hair shape determination of the present invention that will be described below), is used. The probe is labeled with a fluorescent dye such as FAM or VIC at the 5'-terminal, and with a quencher (quenching substance) such as TAMPA at the 3'-terminal, respectively, and in the state as received, since the quencher absorbs the fluorescent energy, fluorescence is not detected. It is preferable to produce probes for both alleles, and to label the probes with fluorescent dyes having different fluorescence wavelengths for batch detection (for example, FAM for one allele and VIC for the other). Furthermore, the 3'-terminal is phosphorylated so that a PCP extension reaction from the Taqman probe does not occur. When a PCR is carried out using a primer which is designed to amplify a partial sequence of the genomic DNA containing a region that hybridizes with the TaqMan probe, as well as a TaqDNApolymerase, the Taqman probe hybridizes with the template DNA, and at the same time, an extension reaction from the PCR primer occurs. However, when the extension reaction proceeds, the hybridized Taqman probe is cleaved due to the 5' nuclease activation of the Taq DNA polymerase, and the fluorescent dye is released and is no longer affected by the quencher, so that fluorescence is detected. With the amplification of the template, the fluorescence intensity increases exponentially. For example, in the detection of a polymorphism in the nucleotide represented by Nucleotide Number 1 (rs10792367, G or C) in the base sequence set forth in SEQ ID NO:1, when an allele-specific oligonucleotide containing the nucleotide (having a length of about 15 to about 30 nucleotides; the C allele is labeled with FAM, and the T allele is labeled with VIC, respectively, at the 5'-terminals, and the 3'-terminals are both labeled with TAMPA) is used as the TaqMan probe, if the genotype of the test subject is CC or TT, high fluorescence intensity of FAM or VIC is recognized in the respective cases, while the other fluorescence is almost unrecognizable. On the other hand, if the genotype of the test subject is CT, fluorescence of both FAM and VIC is detected.

(2) Invader Method

In the invader method, unlike the TaqMan-PCR method, the allele-specific oligonucleotide (allele probe) itself is not labeled, and the oligonucleotide has a sequence having no complementarity to the template DNA on the 5' side of the nucleotides at the polymorphic site (flap) and has a complementary sequence specific to the template on the 3' side. In the invader method, use is made of an oligonucleotide having a complementary sequence specific to the 3' side of the polymorphic site of the template (invader probe; the nucleotides corresponding to the polymorphic site, which is the 5'-terminal of the probe, are arbitrary), and a FRET (Fluorescence Resonance Energy Transfer) probe characterized in that the 5' side has a sequence capable of adopting a hairpin structure, and the sequence contiguous from the nucleotides forming pairs with the nucleotides of the 5'-terminal to the 3' side when a hairpin structure is formed, is a sequence complementary to the flap of the allele probe. The 5'-terminal of the FRET probe is fluorescent labeled (for example, FAM, VIC, or the like), and a quencher (for example, TAMRA, or the like) is bonded in the vicinity thereof, so that in the state as received (hairpin structure), fluorescence is not detected. When the template genomic DNA is allowed to react with the allele probe and the invader probe, upon the complementary binding of the three entities, the 3'-terminal of the invader probe penetrates into the polymorphic site. When the single-stranded portion of the allele probe (that is, the flap portion on the 5' side from the nucleotides of the polymorphic site) is cut using an enzyme which recognizes the structure of this polymorphic site (Cleavase), the flap complementarily binds with the FRET probe, and the polymorphic site of the flap penetrates into the hairpin structure of the FRET probe. When Cleavase recognizes and cleaves this structure, the fluorescent dye used to label the terminal of the FRET probe is released and is no longer affected by the quencher, and thus fluorescence is detected. An allele probe whose nucleotides of the polymorphic site do not match with the template is not cleaved by Cleavase, since an allele probe which is not cleaved can also hybridize with the FRET probe, fluorescence is similarly detected. However, because the reaction efficiency is different, in the allele probe whose nucleotides of the polymorphic site match the template, the fluorescence intensity is markedly stronger than that of the allele probe which does not match. Usually, it is preferable to have the template DNA amplified by PCR using a primer capable of amplifying the region containing the portions where the allele probe and the invader probe hybridize, before the template DNA is allowed to react with the three kinds of probes and Cleavase.

The hair shape of a person can be freely changed by a permanent treatment, a styling agent treatment, brushing or the like, and also can change in an acquired manner, through changes in aging, metabolism, and the like. For this reason, it is difficult to correctly determine or classify the intrinsic natural hair shape of a person based only on the phenotype. Furthermore, since the hair shape can be considered as a general trait of complicated polygenicity, it can be speculated that for individual persons, the gene which serves as a main causative factor for determining the hair shape among the hair shape susceptibility genes of the present invention described above, may vary indifferent individuals. Therefore, when the genetic predisposition to hair shape is examined and/or determined, a method for regulating the hair shape appropriate for the individuals can be provided.

Furthermore, according to the method, the susceptibility to an acquired change in the hair shape of a test subject, that is, the risk of hair shape change, can be determined. The risk of hair shape change can be mechanically determined using the polymorphisms described above as the reference (index), without requiring the judgment of a person having expertise such as a doctor. Accordingly, the method of the present invention can also be used as a method for detecting the risk of hair shape change.

Through the method of the present invention for determining the genetic susceptibility (genetic predisposition) of a test subject to hair shape, the type or the presence or absence of the genetic predisposition of the test subject to hair shape, which is a general polygenic trait, can be made clear, and a gene which serves as the main causative factor that determines the hair shape of the test subject can be searched among the hair shape susceptibility genes of the present invention. Furthermore, appropriate measures for promoting the regulation of hair shape in the test subject can be devised based on the results of the search. Therefore, the present invention is extremely useful as a method for the examination and/or determination for the fundamental regulation of hair shape.

5. REAGENT FOR DETERMINATION OF GENETIC SUSCEPTIBILITY (GENETIC PREDISPOSITION) TO HAIR SHAPE AND KIT INCLUDING THE REAGENT

The present invention also provides a reagent to be used in the determination method of the present invention, and a kit including the reagent. That is, the reagent for determination of the present invention and the kit including the reagent include a nucleic acid probe and/or a primer capable of detecting one or more SNPs selected from the group consisting of an SNP in the 11q12.2 to 11q13.2 region (D11S4191 and D11S987) of human chromosome 11, which is determined by a linkage disequilibrium analysis on a single polynucleotide polymorphism (SNP) marker whose allele frequency is statistically significantly different between a group having a curly hair trait and a group having a non-curly hair trait, and is present in a haplotype block having a 12,590-bp base sequence set forth in SEQ ID NO:1, a 202,111-bp base sequence set forth in SEQ ID NO:2, a 18,933-bp base sequence set forth in SEQ ID NO:3, a 27,375-bp base sequence set forth in SEQ ID NO:4, or a 35,979-bp base sequence set forth in SEQ ID NO:5, and which has a higher allele frequency in an arbitrary curly hair people group than in an arbitrary non-curly hair people group, and an SNP linked to the SNP.

According to an embodiment, the nucleic acid probe used in the reagent for determination of the present invention and the kit including the reagent, is a nucleic acid which specifically hybridizes with the region of a genomic DNA containing the nucleotides of the SNP site to be detected in the method for examination and/or determination of the present invention, and is, for example, a probe which specifically hybridizes with the hair shape determining marker sequence of the present invention. The nucleic acid probe is not particularly limited in the length (length of nucleotides in the portion that hybridizes with the genomic DNA), as long as the nucleic acid probe is specific to a target site to be hybridized and can easily detect polymorphisms. For example, the length is about 10 nucleotides or more, preferably about 15 nucleotides or more, more preferably about 15 to about 600 nucleotides, even more preferably about 15 to about 200 nucleotides, and still more preferably about 15 to about 50 nucleotides. Meanwhile, the phrase "specifically hybridizes with a target site (sequence)" means that cross-hybridization with another DNA does not occur significantly under standard hybridization conditions, preferably under stringent hybridization conditions (for example, conditions described in Joseph Sambrook et al., Molecular Cloning: A Laboratory Manual (3 Vol. set), Cold Spring Harbor Laboratory, NY, 2001). Suitably, the nucleic acid probe preferably has abase sequence complementary to the base sequence of a region containing nucleotides of the polymorphic site to be detected; however, if such specific hybridization is possible, the nucleic acid probe does not need to be completely complementary.

The nucleic acid probe may contain an additional sequence appropriate for the detection of polymorphism (a sequence which is not complementary to the genomic DNA). For example, the allele probe used in the invader method has an additional sequence called flap, at the 5'-terminal of the nucleotides of the polymorphic site. Furthermore, the probe may also be labeled with an appropriate labeling agent, for example, a radioisotope (for example, $^{125}I$, $^{13}I$, $^{3}H$, and $^{14}C$), an enzyme (for example, β-galactosidase, β-glucosidase, alkali phosphatase, peroxidase, malate dehydrogenase, or the like), a fluorescent substance (for example, fluorescamine, fluorescein isothiocyanate, or the like), or a luminescent substance (for example, luminol, a luminol derivative, luciferin, lucigenin, or the like). Alternatively, the probe may also be further bonded, in the vicinity of a fluorescent substance (for example, FAM, VIC, or the like), with a quencher (quenching substance) which absorbs the fluorescent energy emitted by the fluorescent substance. In such an embodiment, the fluorescent substance and the quencher are separated at the time of the detection reaction, and fluorescence is detected.

The nucleic acid probe can also be used after being immobilized on an arbitrary solid phase. For this reason, the reagent of the present invention and the kit including the reagent can be provided as an immobilized probe in which the probe is immobilized on an arbitrary solid support (for example, a gene chip, a cDNA microarray, an oligo-DNA array, a membrane filter, or the like, on which a probe is immobilized). Suitably, the immobilized probe is provided as a DNA chip for hair shape susceptibility gene detection.

The solid support used in immobilization is not particularly limited as long as nucleic acid can be immobilized thereon, and examples include a glass plate, a nylon membrane, microbeads, a silicon chip, a capillary, other supports, or the like. The immobilization of a nucleic acid on a solid support may be carried out by a method of mounting a previously synthesized nucleic acid on a solid phase, or by a method of synthesizing a target nucleic acid on a solid phase. The immobilization method is, for example, in the case of a DNA microarray, well known in the art according to the type of the immobilization probe, e.g., a commercially available spotter (manufactured by Amersham Biosciences Corp.), or the like (for example, in situ synthesis of oligonucleotides by photolithographic technology (Affymetrix, Inc.) or inkjet technology (Rosetta Inpharmatics, Inc.), and the like).

The nucleic acid primer used in the reagent for determination of the present invention and the kit including the reagent, may be any nucleic acid primer as long as it is designed to be capable of specifically hybridizing with the region of a genomic DNA containing the nucleotides of the SNP site to be detected in the method for examination and/or determination of the present invention, and specifically amplifying the nucleic acid sequence. For example, the primer is a primer which specifically hybridizes with the nucleic acid sequence of the hair shape determining marker of the present invention and amplifies the hair shape determining marker. Here, the phrase "specifically hybridizes with a target site (sequence)" means that cross-hybridization with another DNA does not occur significantly under the standard hybridization conditions, preferably under stringent hybridization conditions (for example, the conditions described in Joseph Sambrook et al., Molecular Cloning: A Laboratory Manual (3 Vol. set), Cold Spring Harbor Laboratory, NY, 2001).

The method for amplifying the nucleic acid sequence using a primer is not particularly limited as long as it is a method ordinarily used in the art. For example, generally, a PCR method is broadly used, but examples include RCA (Rolling Circle Amplification; Proc. Natl. Acad. Sci., Vol. 92, 4641-4645 (1995)), ICAN (Isothermal and Chimeric primer-initiated Amplification of Nucleic acids), LAMP (Loop-Mediated Isothermal Amplification of DNA; Bio Industry, vol. 18, No. 2 (2001)), NASBA (Nucleic acid Sequence-based Amplification method; Nature, 350, 91-(1991)), TMA (Transcription Mediated Amplification method; J. Clin. Microbiol. Vol. 31, 3270-(1993), and the like). The number and type of the nucleic acid primer required for amplification can vary depending on the amplification method. For example, in the case of using a PCR method, the required primer may be a pair of nucleic acid primers, which is a combination of a nucleic acid containing a base sequence having about 10 to about 50 nucleotides, preferably about 15 to about 50 nucleotides, and more preferably about 15 to about 30 nucleotides, that is a partial base sequence of a haplotype block represented by a base sequence set forth in any one of SEQ ID NO:1 to NO:5 in the genomic region of human chromosome 11, and specifically hybridizes with a portion of the complementary strand sequence on the 5' side relative to the nucleotides of the polymorphic site to be detected, and a nucleic acid containing a base sequence having about 10 to about 50 nucleotides, preferably about 15 to about 50 nucleotides, and more preferably about 15 to about 30 nucleotides, that is the partial base sequence and specifically hybridizes with a portion of the complementary strand sequence on the 3' side relative to the nucleotides of the polymorphic site, the fragment of the nucleic acid to be amplified by the combination of nucleic acids having a length of about 50 to about 1000 nucleotides, preferably about 50 to about 500 nucleotides, and more preferably about 50 to about 200 nucleotides.

The primer may also contain an additional sequence appropriate for the detection of polymorphism (a sequence that is not complementary to the genomic DNA), for example, a linker sequence. Further, the primer may also be labeled with an appropriate labeling agent, for example, a radioisotope (for example, $^{125}I$, $^{131}I$, $^{3}H$, or $^{14}C$), an enzyme (for example, β-galactosidase, β-glucosidase, alkali phosphatase, peroxidase, or malate dehydrogenase), a fluorescent substance (for example, fluorescamine, or fluorescein isothiocyanate), a luminescent substance (for example, luminol, a luminol derivative, luciferin, lucigenin, or the like), or the like.

Preferably, the nucleic acid probe and/or primer used in the reagent for determination of the present invention and the kit including the reagent include the hair shape susceptibility SNP marker of the present invention, that is, the nucleotides shown below:

(1) in the base sequence set forth in SEQ ID NO:1, nucleotides represented by Nucleotide Numbers 1 (dbSNP Database ID:rs10792367, G or C), 7633 (rs2276299, A or T), and 9315 (rs4149182, G or C);

(2) in the base sequence set forth in SEQ ID NO:2, nucleotides represented by Nucleotide Numbers 1 (rs11227403, C or T), 16722 (rs11607393, A or C), 19992 (rs3825067, T or C), 21051 (rs11227411, T or C), 21927 (rs10896081, T or A), 25269 (rs11227413, A or G), 27032 (rs11227415, C or T), 35997 (rs3862386, C or G), 49537 (rs9645684, A or G), 55405 (rs10896085, T or A), 69180 (rs918299, T or C), 84627 (rs7943911, A or G), 86185 (rs2177054, A or C), 90221 (rs10750778, C or T), 91247 (rs6591207, A or T), 92398 (rs10896091, C or T), 98150 (rs7946917, G or A), 100779 (rs10896094, T or C), 101730 (rs7941431, A or G), 102920 (rs2293121, G or T), 105310 (rs10791855, G or A), 126741 (rs512421, A or G), 133917 (rs2155201, C or T), 134786 (rs7925123, C or G), 142991 (rs2236651, T or C), 144254 (rs2236652, A or G), 147896 (rs476551, C or G), 150043 (rs10791861, A or G), 152853 (rs2298466, C or T), 168931 (rs10791863, T or C), 172500 (rs2155031, T or C), 175003 (rs2276036, T or C), 184535 (rs2298468, A or G), 189853 (rs11227447, C or G), 194405 (rs2282568, G or C), and 202111 (rs3814738, T or G);

(3) in the base sequence set forth in SEQ ID NO:3, nucleotides represented by Nucleotide Numbers 5297 (rs523583, A or C), 18280 (rs3741367, T or C), and 18933 (rs3741368, G or A);

(4) in the base sequence set forth in SEQ ID NO:4, nucleotides represented by Nucleotide Numbers 1 (rs1789165, A or G), 8378 (rs10796828, G or T), 12624 (rs1789172, T or C), 20147 (rs1192921, G or C), 22309 (rs1192923, A or T), 24512 (rs1192924, T or C), and 26599 (rs1789168, T or C); and (5) in the base sequence set forth in SEQ ID NO:5, nucleotides represented by Nucleotide Numbers 17000 (rs2664, T or C), 18895 (rs7934055, T or G), 26143 (rs17363723, G or A), 26545 (rs11234174, A or G), 27090 (rs10792781, C or T), 27751 (rs7107678, G or A), and 30274 (rs7106362, T or C).

More preferably, the nucleic acid probe and/or primer used in the reagent for determination of the present invention and the kit including the reagent, contains a nucleotide represented by Nucleotide Number 7633 (rs2276299, A or T) in the base sequence set forth in SEQ ID NO:1; nucleotides represented by Nucleotide Numbers 189853 (rs11227447, C or G) and 194405 (rs2282568, G or C) in the base sequence set forth in SEQ ID NO:2; nucleotides represented by Nucleotide Numbers 18280 (rs3741367, T or C) and 18933 (rs3741368, G or A) in the base sequence set forth in SEQ ID NO: 3; a nucleotide represented by Nucleotide Number 1 (rs1789165, A or G) in the base sequence set forth in SEQ ID NO:4; and a nucleotide represented by Nucleotide Number 17000 (rs2664, T or C) in the base sequence set forth in SEQ ID NO:5.

As the nucleic acid probe having the nucleotides of the polymorphic sites described above, a nucleic acid having the nucleotides of any one of the alleles for various polymorphic sites can be used, or two nucleic acids having the nucleotides each respectively corresponding to each of the alleles can also be used, depending on the method for detecting polymorphism used. Meanwhile, in regard to the invader probe used in the invader method, the nucleotides of the polymorphic site (that is, the nucleotides at the 3'-terminal) may be any arbitrary nucleotides.

The nucleic acid probe and/or primer used in the reagent for determination of the present invention and the kit including the reagent may be a DNA or an RNA, and may be single-stranded or double-stranded. In the case of being double-stranded, the nucleic acid probe and/or primer may be any one of a double-stranded DNA, a double-stranded RNA, and a DNA/RNA hybrid. The nucleic acid probe and/or primer can be produced, based on the information of the base sequence, according to an ordinary method using, for example, a commercially available nucleotide synthesizer.

The nucleic acid probe and/or primer described above can be respectively separately (or if possible, in a mixed state) dissolved in water or an appropriate buffer solution (for example, TE buffer, or the like) to an appropriate concentration (for example, 1 to 50 μM, or the like at 2 to 20× concentration), and can be stored at about −20° C. The reagent for determination of the present invention and the kit including the reagent may further include, as constituents, other components necessary for carrying out the method, for example, a buffer for hybridization reaction, an enzyme for nucleic acid amplification reaction, a buffer and other necessary reagents, a reagent for labeling, a reagent for label detection, and apparatuses needed for those reactions or procedure, depending on the method for detecting polymorphism used. For example, when the reagent and the kit including the reagent are for polymorphism detection according to a TaqMan-PCR method, the reagent and the kit including the reagent can further include a 10×PCR reaction buffer solution, a 10× aqueous solution of $MgCl_2$, a 10× aqueous solution of dNTPs, a Taq DNA polymerase (5 U/μL) and the like.

The reagent for determination of the present invention and the kit including the reagent can be used for the examination and/or determination of the genetic susceptibility (genetic predisposition) to hair shape.

6. USE OF HAIR SHAPE SUSCEPTIBILITY GENE OR PROTEIN ENCODING THE GENE

In regard to the hair shape susceptibility gene identified by the procedure described above or an expression product thereof, the expression or activity changes in association with the hair shape. Therefore, the hair shape susceptibility gene and an expression product thereof can be used as a marker for the type of hair shape for detecting and/or determining the type of hair shape of a test subject. Alternatively, when the amount of expression of the hair shape susceptibility gene or an expression product thereof is measured and evaluated, the evaluation or selection of a regulating agent for the hair shape of a person can be carried out. Furthermore, alternatively, when the amount of expression of the hair shape susceptibility gene or an expression product thereof is controlled, the hair shape of a person can be regulated.

According to the present invention, the person who can serve as an object in need of the detection and/or determination of the type of hair shape or the regulation of hair shape, is not particularly limited to a specific human race or group, but Asian race is preferred, while Japanese people are more preferred.

The hair shape susceptibility gene and an expression product thereof that are used as the hair shape determining marker may be a gene which overlaps with the haplotype block having a base sequence set forth in any one of SEQ ID NO:1 to NO:5 or an expression product thereof. However, preferred examples include SLC22A8 gene, PACS1 gene, KLC2 gene, RAB1B gene, CNIH2 gene, YIF1A gene, MGC33486 gene, CD248 gene, ORAOV1 gene, KRTAP5-8 gene, KRTAP5-9 gene and KRTAP5-10 gene, and expression products thereof, and among these, CNIH2 gene, YIF1A gene, ORAOV1 gene and KRTAP5-9 gene, and expression products thereof, are more preferred.

CNIH2 gene is a gene containing a polynucleotide set forth in SEQ ID NO:34, and CNIH2 protein encoded by the gene has an amino acid sequence set forth in SEQ ID NO:35. CNIH2 gene is reported to be participating in the transport of EGF family molecules, which are epidermal cell growth factors, from the endoplasmic reticulum to the Golgi apparatus (Castro C P et al., J. Cell. Sci., 120 (Pt14), p. 2454-66, 2007). The gene can be accessed at the NCBI gene database under GeneID: 254263. The gene can be acquired by a known technique for gene manipulation. CNIH2 protein can be obtained by expressing a gene containing a polynucleotide set forth in SEQ ID NO:34, or can also be produced by a general chemical synthesis method, according to the amino acid sequence information set forth in SEQ ID NO:35.

As shown in the Examples that will be described below, gene expression in the hair root areas of Japanese curly hair people and Japanese non-curly hair people was analyzed, and it was found that as compared with the non-curly hair group, the amount of expression of CNIH2 gene is significantly lower in the curly hair group. Further, when a substance having a hair straightening action, such as morning glory, is administered, curly hair is alleviated, and the amount of expression of CNIH2 gene is increased.

YIF1A gene is a gene containing a polynucleotide set forth in SEQ ID NO:36, and YIF1A protein encoded by the gene has an amino acid sequence set forth in SEQ ID NO:37. YIF1A gene is reported to be a gene that encodes a five-span transmembrane protein present in the endoplasmic reticulum or the Golgi apparatus (Yoshida Y. et al., Exp. Cell. Res. 314(19), p. 3427-43, 2008). The gene can be accessed at the NCBI gene database under GeneID: 10897. The gene can be acquired by a known technique for gene manipulation. YIF1A protein can be obtained by expressing a gene containing a polynucleotide set forth in SEQ ID NO:36, or can also be produced by a general chemical synthesis method according to the amino acid sequence set forth in SEQ ID NO:37.

As shown in the Examples that will be described below, gene expression in the hair root areas of Japanese curly hair people and Japanese non-curly hair people was analyzed, and it was found that as compared with the non-curly hair group, the amount of expression of YIF1A gene is significantly higher in the curly hair group. Further, when a substance having a hair straightening action, such as round cardamom, is administered, curly hair is improved, and the amount of expression of YIF1A gene is decreased.

ORAOV1 gene is a gene containing a polynucleotide set forth in SEQ ID NO:38, and ORAOV1 protein encoded by the gene has an amino acid sequence set forth in SEQ ID NO:39. It has been hitherto suggested that ORAOV1 gene is associated with oral squamous cell carcinoma (Jiang L. et al., Int. J. Cancer, 123(8), p. 1779-86, 2008). The gene can be accessed at the NCBI gene database under GeneID: 220064. The gene can be acquired by a known technique for gene manipulation. ORAOV1 protein can be obtained by expressing a gene containing a polynucleotide set forth in SEQ ID NO:38, or can also be produced by a general chemical synthesis method according to the amino acid sequence set forth in SEQ ID NO:39.

As shown in the Examples that will be described below, gene expression in the hair root areas of Japanese curly hair people and Japanese non-curly hair people was analyzed, and it was found that as compared with the non-curly hair group, the amount of expression of ORAOV1 gene is significantly lower in the curly hair group. Further, when a substance having a hair straightening action, such as round cardamom, is administered, curly hair is improved, and the amount of expression of ORAOV1 gene is increased.

KRTAP5-9 gene is a gene containing a polynucleotide set forth in SEQ ID NO:40, and KRTAP5-9 protein encoded by the gene has an amino acid sequence set forth in SEQ ID NO:41. KRTAP5-9 gene is reported to be a gene that encodes a hair keratin-binding protein that is expressed in the cuticle of hair (Rogers M A et al., Int. Rev. Cytol. 251, p. 209-63, 2006). The gene can be accessed at the NCBI gene database under GeneID: 3846. The gene can be acquired by a known technique for gene manipulation. KRTAP5-9 protein can be obtained by expressing a gene containing a polynucleotide set forth in SEQ ID NO:40, or can also be produced by a general chemical synthesis method according to the amino acid sequence set forth in SEQ ID NO:41.

As shown in the Examples that will be described below, gene expression in the hair root areas of Japanese curly hair people and Japanese non-curly hair people was analyzed, and it was found that as compared with the non-curly hair group, the amount of expression of KRTAP5-9 gene is significantly lower in the curly hair group.

(1) Polynucleotide Marker for Detecting and/or Determining Type of Hair Shape

According to the present invention, the marker for detecting and/or determining the type of hair shape (marker for the type of hair shape) may be a polynucleotide having the base sequence of the hair shape susceptibility gene of the present invention, or a partial polynucleotide thereof. Examples of the marker for the type of hair shape of the present invention include a polynucleotide consisting of the base sequences of SLC22A8 gene, PACS1 gene, KLC2 gene, RAB1B gene, CNIH2 gene, YIF1A gene, MGC33486 gene, CD248 gene, ORAOV1 gene, KRTAP5-8 gene, KRTAP5-9 gene, or KRTAP5-10 gene; preferably a polynucleotide consisting of the base sequences of ACNIH2 gene, YIF1A gene, ORAOV1 gene or KRTAP5-9 gene; and more preferably a polynucleotide consisting of the base sequences set forth in SEQ ID NO:34, SEQ ID NO:36, SEQ ID NO:38 or SEQ ID NO:40, polynucleotides having base sequences complementary to these, and partial polynucleotides thereof.

Furthermore, the marker for the type of hair shape of the present invention can contain a strain consisting of a base sequence which is in a further complementary relation with respect to the base sequence of the polynucleotide consisting of complementary base sequence or a partial polynucleotide thereof described above.

The polynucleotides described above and complementary strands thereof may be respectively used as the marker of the present invention in a single-stranded form, or may also be used as the marker of the present invention in a double-stranded form.

Examples of the partial polynucleotide include a partial polynucleotide of the polynucleotide consisting of the base sequence of the hair shape susceptibility gene of the present invention or a base sequence complementary to this, in which the partial polynucleotide has, for example, a length of contiguous 15 nucleotides or more. The length of the partial polynucleotide can be appropriately set in accordance with the use.

(2) Primer for Amplifying Marker for Type of Hair Shape, and Probe for Detecting the Marker A partial polynucleotide of the polynucleotide consisting of the base sequence of the hair shape susceptibility gene of the present invention or abase sequence complementary to this, can serve as a primer for amplifying the marker for the type of hair shape. Preferably, the primer amplifies a polynucleotide consisting of a base sequence set forth in SEQ ID NO:34, SEQ ID NO:36, SEQ ID NO:38 or SEQ ID NO:40, or a base sequence complementary to this, or a partial polynucleotide of such a polynucleotide.

Furthermore, a polynucleotide consisting of the base sequence of the hair shape susceptibility gene of the present invention or a base sequence complementary to this, or a partial polynucleotide thereof, can serve as a probe for detecting the marker for the type of hair shape. Preferably, the probe detects a polynucleotide having a base sequence set forth in SEQ ID NO:34, SEQ ID NO:36, SEQ ID NO:38, or SEQ ID NO:40, or a base sequence complementary to this, or a partial polynucleotide of such a polynucleotide.

That is, a primer for specifically recognizing and amplifying an RNA produced as a result of the expression of CNIH2 gene, YIF1A gene, ORAOV1 gene or KRTAP5-9 gene, or a polynucleotide derived therefrom, or a probe for specifically detecting the RNA or the polynucleotide derived therefrom, is included the primer or probe described above.

Specifically, the polynucleotide or partial polynucleotide can be used as a primer or a probe according to an ordinary method, in the methods known to specifically detect a particular gene, such as a Northern Blotting method, an RT-PCR method, and an in situ hybridization method.

In the case of using the polynucleotide or partial polynucleotide as a primer, the nucleotide length thereof is usually 15 to 100 nucleotides, preferably 15 to 50 nucleotides, and more preferably 15 to 35 nucleotides.

Furthermore, in the case of using the polynucleotide or partial polynucleotide as a detection probe, one having a nucleotide length of usually 15 nucleotides or more, preferably 15 to 1000 nucleotides, and more preferably 100 to 1000 nucleotides, may be used.

Here, the term “specifically recognizes” means that, as in the case where, for example, in a Northern Blotting method, a polynucleotide consisting of a base sequence set forth in SEQ ID NO:34, SEQ ID NO:36, SEQ ID NO:38 or SEQ ID NO:40, or a base sequence complementary to this, or a partial polynucleotide thereof can be specifically detected, and as in the case where, for example, in an RT-PCR method, the polynucleotide is specifically produced, the detected substance or the product can be considered as a polynucleotide consisting of a base sequence set forth in SEQ ID NO:34, SEQ ID NO:36, SEQ ID NO:38 or SEQ ID NO:40, or a base sequence complementary to this, or a partial polynucleotide thereof.

The partial polynucleotide of a polynucleotide consisting of a base sequence set forth in SEQ ID NO:34, SEQ ID NO:36, SEQ ID NO:38 or SEQ ID NO:40, or a base sequence complementary to this, can be designed based on the base sequence of CNIH2 gene, YIF1A gene, ORAOV1 gene or KRTAP5-9 gene as set forth in the sequence numbers described above, for example, through the software program of Primer 3 or Vector NTI. The candidate sequence of the primer or probe thus obtainable, or a sequence containing the sequence in a portion, can be designed as a primer or a probe.

(3) Polypeptide Marker for Detecting and/or Determining Type of Hair Shape

Like the hair shape susceptibility genes listed above, expression products of these genes (proteins encoded by the hair shape susceptibility genes, or polypeptides derived therefrom, or partial polypeptides thereof) can also serve as the marker (polypeptide) for the type of hair shape.

Examples of the expression products include SLC22A8 protein, PACS1 protein, KLC2 protein, RAB1B protein, CNIH2 protein, YIF1A protein, MGC33486 protein, CD248 protein, ORAOV1 protein, KRTAP5-8 protein, KRTAP5-9 protein and KRTAP5-10 protein (or also referred to as SLC22A8, PACS1, KLC2, RABID, CNIH2, YIF1A, MGC33486, CD248, ORAOV1, KRTAP5-8, KRTAP5-9 and KRTAP5-10), which are proteins encoded by SLC22A8 gene, PACS1 gene, KLC2 gene, RAB1B gene, CNIH2 gene, YIF1A gene, MGC33486 gene, CD248 gene, ORAOV1 gene, KRTAP5-8 gene, KRTAP5-9 gene and KRTAP5-10 gene, respectively; polypeptides derived from these proteins; and partial polypeptides thereof. Preferred examples include CNIH2, YIF1A, ORAOV1 and KRTAP5-9, polypeptides derived from these, and partial polypeptides thereof.

More preferably, the expression products are proteins encoded by polynucleotides consisting of base sequences set forth in SEQ ID NO:34, SEQ ID NO:36, SEQ ID NO:38, and SEQ ID NO:40, and even more preferably, proteins having amino acid sequences set forth in SEQ ID NO:35, SEQ ID NO:37, SEQ ID NO:38 and SEQ ID NO:41.

Furthermore, the expression products also include proteins which have amino acid sequences resulting from deletions, substitutions or additions of one or several amino acids in the amino acid sequences set forth in SEQ ID NO:35, SEQ ID NO: 37, SEQ ID NO: 38 or SEQ ID NO:41, and having biological functions equivalent to and/or having equivalent immunological activity to those of proteins consisting of the amino acid sequences set forth in SEQ ID NO: 35, SEQ ID NO:37, SEq ID NO:38, and SEQ ID NO:41 (homologues of CNIH2, YIF1A, ORAOV1, or KRTAP5-9).

Here, examples of proteins which have equivalent biological functions include proteins that are equivalent to CNIH2, YIF1A, ORAOV1 or KRTAP5-9 in terms of the biochemical or pharmacological functions. Further, examples of proteins having equivalent immunological activity include proteins that have an ability to induce a specific immune reaction in an appropriate animal or cells thereof, and to bind specifically to the antibodies to CNIH2, YIF1A, ORAOV1 or KRTAP5-9.

Meanwhile, an indicator that determines the substitution, insertion or deletion of amino acid residues can be found by using a computer program well known to those having ordinary skill in the art, for example, DNA Star software program. For example, the number of variations is typically 10% or less of the total number of amino acids, preferably 5% or less of the total number of amino acids, and more preferably 1% or less of the total number of amino acids. Furthermore, from the viewpoint of maintaining the structure of protein, the amino acid to be substituted is preferably an amino acid having properties that are similar to those of amino acids before substitution in terms of the polarity, charge, solubility, hydrophobicity, hydrophilicity, amphiphilicity and the like of the amino acid.

The partial polypeptide may be a polypeptide consisting of at least 5 contiguous amino acids, and preferably 10 to 100 amino acids, in an amino acid sequence encoded by the hair shape susceptibility gene of the present invention (for example, an amino acid sequence set forth in SEQ ID NO:35, SEQ ID NO:37, SEQ ID NO:38 or SEQ ID NO:41), and having a biological function and/or immunological activity equivalent to those of an expression product of the hair shape susceptibility gene of the present invention (for example, CNIH2, YIF1A, ORAOV1 or KRTAP5-9).

The polypeptide encoded by the hair shape susceptibility gene of the present invention can be obtained by operations of DNA cloning, establishment of various plasmids, transfection of the plasmid to a host, culture of the transformant, and collection of protein from the culture, based on the base sequence information of the hair shape susceptibility gene. These operations can be carried out according to known methods, for example, the methods described in Molecular Cloning, T. Maniatis et al., CSH Laboratory (1983); DNA Cloning, D M. Glover, IRL PRESS (1985); and the like.

Specifically, the polypeptide can be obtained by producing a recombinant DNA (e.g., expression vector) through which a gene encoding CNIH2, YIF1A, ORAOV1 or KRTAP5-9 can be expressed in a desired host cell, introducing this into a host cell to thereby transform the recombinant DNA, culturing the transformant, and collecting the target protein from the culture thus obtainable.

Furthermore, the polypeptide encoded by the hair shape susceptibility gene of the present invention can also be produced by a general chemical synthesis method in accordance with an amino acid sequence encoded by the hair shape susceptibility gene.

(4) Antibody Specifically Recognizing Marker (Polypeptide) for Type of Hair Shape An antibody which specifically recognizes a polypeptide consisting of an amino acid sequence encoded by the hair shape susceptibility gene of the present invention or a partial polypeptide thereof, may be an antibody for detecting the marker (polypeptide) for the type of hair shape described above.

As will be described below, when such an antibody is used, the presence or absence of the expression of the marker (polypeptide) for the type of hair shape (for example, CNIH2, YIF1A, ORAOV1, KRTAP5-9, or a polypeptide derived therefrom, or a partial polypeptide thereof) in a tissue of a test subject, and the level of the expression of the marker can be detected. Specifically, when a portion of the hair root area of a test subject or the like is collected by a biopsy method or the like, a protein is produced therefrom according to an ordinary method, and the antibody of the present invention is used according to an ordinary method in, for example, a known detection method such as a Western Blotting method or an ELISA method, the marker (polypeptide) for the type of hair shape present in the tissue can be detected.

The antibody for the detection of the type of hair shape may be a polyclonal antibody or a monoclonal antibody, which are both directed to the marker (polypeptide) for the type of hair shape as an immunizing antigen.

These antibodies can be produced according to known methods (Current protocols in Molecular Biology, edited by Ausubel et al., (1987) published by John Wiley and Sons, Section 11.12-11.13). Specifically, a polyclonal antibody can be obtained by immunizing a non-human animal such as a rabbit with a polypeptide consisting of an amino acid sequence encoded by the hair shape susceptibility gene of the present invention (for example, CNIH2, YIF1A, ORAOV1 or KRTAP5-9), which has been expressed in *Escherichia coli* or the like and purified by ordinary methods, or with a partial polypeptide of the polypeptide above synthesized according to an ordinary method, and collecting the polyclonal antibody from the blood serum of the immunized animal according to an ordinary method.

On the other hand, a monoclonal antibody can be obtained from a hybridoma cell prepared by immunizing a non-human animal such as a mouse with the polypeptide expressed in *Escherichia coli* or the like and purified according to ordinary methods as described above, or a partial polypeptide thereof, and subjecting spleen cells obtained from the animal and myeloma cells to cell fusion (Current protocols in Molecular Biology, edited by Ausubel et al., (1987), published by John Wiley and Sons, Section 11.4-11.11).

The partial polypeptide used herein is an oligopeptide having a partial amino acid sequence of a polypeptide consisting of an amino acid sequence encoded by the hair shape susceptibility gene of the present invention (for example, CNIH2, YIF1A, ORAOV1 or KRTAP5-9). It is not necessary for the partial polypeptide to have a functional biological activity, but it is preferable that the partial polypeptide have the same immunogenic characteristics as those of proteins consisting of the amino acid sequences described above. For example, there may be mentioned an oligopeptide consisting of at least 8 contiguous amino acids, preferably 15 amino acids, and more preferably 20 amino acids, in the amino acid sequences described above, which oligopeptide has immunogenic characteristics equivalent to those of proteins consisting of the amino acid sequences described above, and preferably CNIH2, YIF1A, ORAOV1 or KRTAP5-9.

The production of an antibody to such a partial polypeptide can be carried out by increasing the immunological response using various adjuvants depending on the host. Although there are no limitations, examples of such adjuvants include Freund's adjuvant; mineral gels such as aluminum hydroxide; surface-active substances such as lysolecithin, pluronic polyol, polyanions, peptides, oil emulsifying agents, keyhole limpet hemocyanin, and dinitrophenol; and human adjuvants such as *bacillus* Calmette-Guerin (BCG) and *corynebacterium parvum.*

(5) Detection and/or Determination of Type of Hair Shape

Detection/determination of the type of hair shape involves collecting a portion of hair root tissue or the like of a test subject by a biopsy method or the like, and detecting and/or determining the type of hair shape by using the marker for the type of hair shape of the present invention contained in the tissue as an indicator. For example, in the method described above, the type of hair shape is detected and/or determined by measuring the expression level (amount of expression) of the hair shape susceptibility gene of the present invention (for example, CNIH2 gene, YIF1A gene, ORAOV1 gene, or KRTAP5-9 gene), a complementary strand thereof, or a partial polynucleotide thereof, or the amount of expression of a protein derived from the gene (for example, CNIH2, YIF1A, ORAOV1, or KRTAP5-9), a homologue thereof, or a partial polypeptide thereof.

Furthermore, the method for detection/determination of the present invention is also used, for example, in the case where a pharmaceutical product, a cosmetic product or the like for alleviating curly hair is administered to a curly hair person, so as to determine the presence or absence or the degree of an alleviation of the curly hair.

1) Biological Sample

Examples of the biological sample used herein include epithelial tissue or epithelial cells of a test subject, for example, a tissue containing cells that are capable of expressing the hair shape susceptibility gene of the present invention (for example, CNIH2 gene, YIF1A gene, ORAOV1 gene, or KRTAP5-9 gene), such as the hair root area or skin; an RNA produced from this tissue; a polynucleotide further produced from the RNA; and a protein produced from the tissue described above. These RNA, polynucleotide and protein can be prepared, for example, by collecting a portion of the hair root area of a test subject by a biopsy method or the like, and then according to ordinary methods.

2) Detection and/or Measurement of Marker

The detection and measurement of a marker may vary depending on the type of the biological sample used as the object of measurement, and specifically, the detection and measurement are carried out as follows.

(i) Case of Using RNA as Biological Sample of Measurement

In the case of using an RNA as a biological sample, the detection and measurement is carried out by detecting and measuring the expression level of a marker (polynucleotide) for the type of hair shape of the present invention in the RNA, for example, CNIH2 gene, YIF1A gene, ORAOV1 gene, KRTAP5-9 gene, or a partial polynucleotide thereof.

Here, specifically, the measurement of the amount of expression of the marker can be carried out by carrying out a known method such as a Northern Blotting method, an RT-PCR method, a DNA chip analysis method, or an in situ hybridization analysis method, using a primer for amplifying a polynucleotide that can serve as the marker of the present invention described above, or a probe for detecting the polynucleotide.

In the case of using a Northern Blotting method, when the probe of the present invention is used, the presence or absence of the expression of the marker (for example, CNIH2 gene, YIF1A gene, ORAOV1 gene, KRTAP5-9 gene, or a partial polynucleotide thereof) in the RNA, and the level of the expression can be detected and measured.

Specifically, there may be mentioned a method in which, first, the probe DNA is labeled with a radioisotope ($^{32}P$, $^{33}P$, or the like; RI), a fluorescent substance or the like; subsequently, the labeled disease marker thus obtainable is hybridized with an RNA derived from a biological tissue of a test subject that has been transferred onto a nylon membrane or the like according to an ordinary method; and then the double strand of the labeled disease marker (DNA) and the RNA thus formed is detected and measured by measuring the signal originating from the labeled material (RI, a fluorescent substance or the like) of the labeled disease marker with a radiation detector (BAS-1800 II, manufactured by Fujifilm Holdings Corp.), a fluorescence detector or the like.

Furthermore, a method using an AlkPhos Direct™ Labelling and Detection System (manufactured by Amersham Pharamcia Biotech, Inc.) can also be available, in which the method includes labeling a probe DNA according to the protocol of AlkPhos Direct™, hybridizing the probe DNA with an RNA derived from a biological tissue of a test subject, and then detecting and measuring the signal originating from the labeled material of the probe DNA with a multibioimager STORM860 (manufactured by Amersham Pharmacia Biotech, Inc.).

In the case of using an RT-PCR method, the presence or absence of the expression of the marker in the RNA, and the level of the expression can be detected and measured using the primer of the present invention. Specifically, first, a cDNA is prepared from an RNA derived from a biological tissue of a test subject according to an ordinary method, and by using this cDNA as a template, a pair of primers (a forward strand which binds to the cDNA (minus strand) and a reverse strand which binds to the plus strand) prepared from the marker polynucleotide of the present invention is hybridized with the cDNA, so that the region of the target marker can be amplified. Thereafter, a PCR method is carried out according to an ordinary method, and thus the amplified double-stranded DNA thus obtained is detected.

For the detection of the amplified double-stranded DNA, a method of detecting a labeled double-stranded DNA produced by carrying out the PCR using primers which have been labeled in advance with RI, a fluorescent substance or the like; a method of transferring the produced double-stranded DNA onto a nylon membrane or the like according to an ordinary method, hybridizing this double-stranded DNA by using a labeled disease marker as a probe, and detecting the hybridization product; and the like can be used. The labeled double-stranded DNA product thus produced can be measured with an Agilent 2100 Bioanalyzer (manufactured by Yokogawa Analytical Systems, Inc.) or the like. Furthermore, an RT-PCR reaction solution is prepared using SYBR (registered trademark) Green RT-PCR Reagents (manufactured by Applied Biosystems, Inc.) according to the protocol, the reaction solution is allowed to react with ABI PRIME (registered trademark) 7700 Sequence Detection System (manufactured by Applied Biosystems), and the reaction product may be detected. The detection and measurement of the level of expression of the marker (polynucleotide) for the type of hair shape of the present invention in the RNA of a test subject using such an RT-PCR method, will be described in Examples.

In the case of using a DNA chip analysis, a DNA chip bonded with the DNA probe (single-stranded or double-stranded) of the present invention is provided, and this is hybridized with a cRNA prepared from an RNA derived from a biological tissue of a test subject according to a conventional method, the two strands of the DNA and cRNA thus formed are bound with a labeled probe prepared from the marker polynucleotide of the present invention, and thereby, the presence or absence of the expression of the marker of the present invention and the level of the expression can be detected and measured.

Furthermore, a DNA chip capable of detecting and measuring the level of expression of the marker of the present invention can also be used as the DNA chip. As the DNA chip, for example, GeneChip (registered trademark) Human Genome U133 plus 2 manufactured by Affymetrix, Inc. may be used.

(ii) Case of Using Protein as Biological Sample of Object of Measurement

When a protein is used as an object of measurement, the measurement is carried out by bringing the antibody of the present invention into contact with a biological sample, detecting the marker (polypeptide) for the type of hair shape of the present invention in the biological sample, which has been bound to the antibody, for example, CNIH2, YIF1A, ORAOV1, KRTAP5-9, or a partial polypeptide thereof, and measuring the amount (level) of the marker.

Here, the measurement of the amount of protein binding can be carried out by using a known method such as a Western Blotting method.

The Western Blotting method can be carried out by using the antibody of the present invention as a primary antibody, subsequently; labeling the primary antibody using, as a secondary antibody, an antibody which binds to the primary antibody labeled with a radioisotope such as $^{125}I$, a fluorescent substance, an enzyme such as horse radish peroxidase (HRP), or the like; and determining the signals originating from these labeled substances with a radiation meter, a fluorescence detector or the like. Furthermore, after using the antibody of the present invention as the primary antibody, the primary antibody is detected using an ECL Plus Western Blotting Detection System (manufactured by Amersham Pharmacia Biotech, Inc.) according to the protocol, and measurement can be made using a multibioimager STORM 860 (manufactured by Amersham Pharmacia Biotech, Inc.).

3) Determination of Type of Hair Shape

The determination of the type of hair shape can be carried out by comparing the level of the marker of the present invention (for example, the level of gene expression of CNIH2 gene, YIF1A gene, ORAOV1 gene or KRTAP5-9 gene, or the amount of CNIH2, YIF1A, ORAOV1 or KRTAP5-9) in a biological sample of a test subject, which has been measured as described above, with the corresponding level of a non-curly hair person, and determining the difference between the two levels.

The comparison of the level of expression of the marker polynucleotide or polypeptide between the biological sample of a test subject and the biological sample of a non-curly hair person can be carried out by carrying out the measurements directed to the biological sample of a test subject and the biological sample of a non-curly hair person in parallel. Furthermore, even if the measurements are not carried out in parallel, the average value or a statistical median value of the level of gene expression of the marker polynucleotide (CNIH2 gene, YIF1A gene, ORAOV1 gene, KRTAP5-9 gene, a partial polynucleotide thereof, or the like) or the level of expression of the marker polypeptide (CNIH2, YIF1A, ORAOV1, KRTAP5-9, a partial polypeptide thereof, or the like), which has been determined in advance in the tissues of plural (at least 2, preferably 3 or more, and more preferably 5 or more) non-curly hair persons under the same measurement conditions, can be used for the comparison with the test subjects, as the measured value for the test subject with the level of expression of the marker polynucleotide or polypeptide of a non-curly hair person.

The determination of the type of hair shape of a test subject can be carried out by using, as an index, the extent of increase or decrease (for example, higher or lower by two times or more, and preferably three times or more) in the case of comparing the gene expression level of the marker polynucleotide (CNIH2 gene, YIF1A gene, ORAOV1 gene, KRTAP5-9 gene, a partial polynucleotide thereof, or the like) or the expression level of the marker polypeptide (CNIH2, YIF1A, ORAOV1, KRTAP5-9, a partial polypeptide thereof, or the like) in the tissue of the test subject, with the levels of a non-curly hair person.

For example, if the expression level of CNIH2 gene or CNIH2 protein of the test subject is lower than such a level of a non-curly hair person, the test subject can be considered as a curly hair person, or is suspected to have the onset of curly hair in the future.

Furthermore, for example, if the expression level of YIF1A gene or YIF1A protein of the test subject is lower than such a level of a non-curly hair person, the test subject can be considered as a curly hair person, or is suspected to have the onset of curly hair in the future.

For example, if the expression level of ORAOV1 gene or ORAOV1 protein of the test subject is lower than such a level of a non-curly hair person, the test subject can be considered as a curly hair person, or is suspected to have the onset of curly hair in the future.

For example, if the expression level of KRTAP5-9 gene or KRTAP5-9 protein of the test subject is lower than such a level of a non-curly hair person, the test subject can be considered as a curly hair person, or is suspected to have the onset of curly hair in the future.

7. Method for Regulating Hair Shape

When the nucleotides located at the hair shape susceptibility SNP marker of the present invention are modified, the hair shape of individuals can be regulated.

That is, the present invention also provides a method for regulating the hair shape of an individual. According to an embodiment, the method may be a non-therapeutic method for regulating hair shape for cosmetic purposes, and can be carried out by a beautician or a barber. Meanwhile, according to the present specification, the term "non-therapeutic" is a concept which does not encompass medical acts, that is, acts of remedy to human body through treatment.

The method can be achieved by modifying the nucleotides located at the hair shape susceptibility SNP markers of the present invention listed above. The specific technique is not particularly limited as long as it is a method capable of achieving the purpose described above, and conventionally known methods and techniques that will be developed in the future can all be used; however, for example, a method of utilizing genetic recombination may be used.

Alternatively, the method for regulating hair shape of the present invention is carried out by controlling the expression of the hair shape susceptibility gene of the present invention in the hair root area of a person in need of regulation of hair shape (for example, suppression of curly hair or kinky hair, or waving of scalp hair).

For example, in a person who is concerned about having curly hair or kinky hair, curly hair or kinky hair can be suppressed by inducing or promoting the expression of a hair shape susceptibility gene whose expression contributes to the phenotype of straight hair, for example, CNIH2 gene, ORAOV1 gene, or KRTAP5-9 gene. Alternatively, curly hair or kinky hair can be suppressed by inhibiting the expression of a hair shape susceptibility gene whose expression contributes to the phenotype of curly hair or kinky hair, for example, YIF1A gene. On the other hand, in a person who wishes for waving of the scalp hair, waving can be expressed or promoted by inducing or promoting the expression of a hair shape susceptibility gene whose expression contributes to the phenotype of curly hair or kinky hair, for example, YIF1A gene. Alternatively, waving can be expressed or promoted by inhibiting the expression of a hair shape susceptibility gene whose expression contributes the phenotype of straight hair, for example, CNIH2 gene, ORAOV1 gene or KRTAP5-9 gene.

For example, in the case of suppressing curly hair or kinky hair, the expression level of CNIH2 gene, ORAOV1 gene, or KRTAP5-9 gene in the human hair root area may be brought to a value equal to or higher than the mRNA expression level of the gene in a non-curly hair person, and for example, it is desirable to increase the expression level to a value of about 3 to 10 times higher or more. On the other hand, in the case of intending to promote waving, the expression level of CNIH2 gene, ORAOV1 gene or KRTAP5-9 gene may be brought to a value lower than the mRNA expression level of the gene in a non-curly hair person, and for example, it is desirable to decrease the expression level to a value of about 3 to 10 times lower or less.

Furthermore, for example, in the case of suppressing curly hair or kinky hair, the expression level of YIF1A gene in the human hair root area may be brought to a value equal to or lower than the mRNA expression level of the gene in a non-curly hair person, and for example, it is desirable to decrease the expression level to a value of about 3 to 10 times lower or less. On the other hand, in the case of intending to promote waving, the expression level of YIF1A gene may be brought to a value higher than the mRNA expression level of the gene in a non-curly hair person, and for example, it is desirable to increase the expression level to a value of about 3 to 10 times higher or more.

The suppression, induction or promotion of the expression of a hair shape susceptibility gene in the human hair root area can be carried out according to an ordinary method. For example, in the suppression of gene, a method based on an antisense nucleotide, for example, a technique based on a method of inhibiting the translation from mRNA, or the like, may be used, and in the induction or promotion, a technique of expressing a hair shape susceptibility gene through gene transduction by means of a viral vector or the like may be used, or the like. Furthermore, in the suppression of the expression of a protein encoded by a hair shape susceptibility gene can be basically realized by a technique of suppressing the expression of the gene, and in the induction or promotion of the expression of the protein, a technique of expressing the gene at a high level, as well as a technique of direct intracutaneous injection of a human recombinant protein of the protein, or the like may be used.

The gene transduction utilizing an antisense nucleotide can be carried out in the same manner as in the methods ordinarily used in gene therapy. For example, gene transduction can be carried out by a method of directly administering an antisense oligonucleotide or a chemical modification product thereof into the body of a test subject and thereby suppressing the expression of the hair shape susceptibility gene of the present invention, or a method of introducing an antisense RNA to a target cell of a patient and thereby suppressing the expression of the hair shape susceptibility gene of the present invention in the cell.

Here, the term "antisense nucleotide" encompasses an antisense oligonucleotide, an antisense RNA, an antisense DNA and the like, which all correspond to a portion of at least 8 nucleotides or more in a hair shape susceptibility gene of the present invention. Examples of the chemical modification products thereof include derivatives which are capable of increasing the transferability into cells or stability in the cells, such as phosphorothioates, phosphorodithioates, alkyl phosphotriesters, alkylphosphonates, and alkyl phosphoamidates ("Antisense RNA and DNA", published by WILEY-LISS, 1992, pp. 1-50; J. Med. Chem. 36, 1923-1937 (1993)).

The antisense nucleotide or a chemical modification product thereof can suppress the expression of a hair shape susceptibility gene, that is, the expression of a protein encoded by a hair shape susceptibility gene, by binding to a sense strand mRNA in a cell, and can thereby control the function (activity) of the protein.

In the method of directly administering an antisense oligonucleotide or a chemical modification product thereof into a living body, an antisense oligonucleotide or a chemical modification product thereof used therein may have a length of preferably 5 to 200 nucleotides, more preferably 8 to 25 nucleotides, and most preferably 12 to 25 nucleotides. Upon the administration, the antisense oligonucleotide or a chemical modification product thereof can be formulated into a preparation using a stabilizer, a buffer solution, a solvent and the like that are ordinarily used.

In the method of introducing an antisense RNA into a target cell of a test subject, the antisense RNA used therein may have a length of preferably 100 nucleotides or more, more preferably 300 nucleotides or more, and even more preferably 500 nucleotides or more. Furthermore, this method encompasses an in vivo method of introducing an antisense gene into the cells of a living body, and an ex vivo method of first introducing an antisense gene into the cells that have been extracted out of body, and returning the cells into the body (see Nikkei Science, April 1994, pp. 20-45; Gekkan Yakuji (Pharmaceuticals Monthly) 36(1), 23-48 (1994); Jikken Igaku (Experimental Medicine) Special Issue, 12(15) (1994), whole page; and the like). Among these, an in vivo method is preferred, and examples thereof include a viral transduction method (a method of using a recombinant virus) and a non-viral transduction method (see the various documents described above).

As the method of using a recombinant virus, for example, methods of inserting an antisense nucleotide of MLTK gene into the genome of a virus such as retrovirus, adenovirus, adeno-associated virus, herpes virus, vaccinia virus, polio virus, or Sindbis virus, and introducing the product into the living body, may be used. Among these methods, methods of using retrovirus, adenovirus, adeno-associated virus and the like are particularly preferred. As the non-viral transduction method, a liposome method, a lipofectin method and the like may be used, and particularly, a liposome method is preferred. As other non-viral transduction methods, for example, a microinjection method, a calcium phosphate method, an electroporation method and the like may also be used.

A preparation composition for gene transduction contains, as active ingredients, the antisense nucleotide described above or a chemical modification product thereof, recombinant viruses containing these, infected cells to which these viruses have been introduced, and the like.

The administration of the composition to a test subject can be carried by, for example, intravenous, intraarterial, subcutaneous, or intramuscular administration in an appropriate dosage form such as an injection, and can be introduced by directly administering the composition through the skin of a patient. In the case of employing an in vivo method, the composition for gene transduction can be formulated into a dosage form such as an injection containing an antisense nucleotide of a hair shape susceptibility gene, as well as a form in which, for example, a viral vector containing an antisense nucleotide of a hair shape susceptibility gene that is embedded in a liposome or a membrane-fused liposome (Sendai virus (HVJ)-liposome, or the like). These liposome dosage forms include a suspending agent, a freezing agent, a centrifuge concentration freezing agent, and the like. Furthermore, the composition for gene transduction can also be formulated into a form of a culture fluid of cells infected with a virus to which a vector containing the antisense nucleotide of a hair shape susceptibility gene has been introduced. The amount of administration of the active ingredient in these various preparation forms can be appropriately adjusted on the basis of the severity of the disease intended to treat, the age and body weight of the patient, and the like. Usually, in the case of an antisense nucleotide for a hair shape susceptibility gene, the amount of administration may be an amount by which about 0.0001 to 100 mg, and preferably about 0.001 to 10 mg, is administered once in several days to several months to an adult as a test subject.

In the case of a retrovirus vector containing an antisense nucleotide, the amount can be selected in the range of an amount which gives a retrovirus titer of about $1\times10^3$ pfu to $1\times101^5$ pfu per day per kg of the patient's body weight. In the case of a cell having an antisense nucleotide introduced therein, an amount of about $1\times10^4$ cells/body to $1\times10^{15}$ cells/body may be administered.

8. Method for Evaluation or Selection of Hair Shape Regulating Agent

The present invention also provides a method for evaluating or selecting a hair shape regulating agent (screening method).

The screening method may be carried out by, for example, steps such as described below:

(a) a step of administering a test substance into a cell containing the hair shape susceptibility gene of the present invention; and (b) a step of selecting, among the administered test substances, a substance which converts a nucleotide polymorphism of the hair shape susceptibility SNP marker of the present invention present on the hair shape susceptibility gene or the vicinity thereof, for example, on the haplotype block containing the gene, to another polymorphism, as a hair shape regulating agent.

The cell used in the step (a) (step of administering a test substance) may be any cell which can be introduced a haplotype block in the genomic region of human chromosome 11 represented by a base sequence set forth in any one of SEQ ID NO: 1 to NO: 5, or a gene which at least overlaps with the haplotype block, that is, the hair shape susceptibility gene of the present invention, and can retain the gene stably, and there are no particular limitations on the origin of the cell (for example, the cell is not limited to a prokaryotic cell or a eukaryotic cell, or an insect cell or an animal cell, or the like). Meanwhile, gene transduction, cell culture and the like can be carried out by arbitrarily using any methods conventionally known in the art (for example, Joseph Sambrook et al., Molecular Cloning: A Laboratory Manual (3 Vol. Set), Cold Spring Harbor Laboratory, NY, 2001; The Japanese Tissue Culture Association, Ed., "Technology of Tissue Culture, 3rd Edition, Fundamentals and Applications", Asakura Shoten, 1996; and the like). The cell can be effectively utilized as a screening tool in the method for evaluating or selecting a substance effective for regulating the hair shape (screening method).

There are no particular limitations on the test substance that is administered. Examples include single compounds such as a natural compound, an organic compound, an inorganic compound, a protein and a peptide; and arbitrary compounds or compositions such as a compound library, expression products of a gene library, a cell extract, a cell culture supernatant, products of a fermentation microorganism, a marine extract, and a vegetable extract.

In regard to the step (b) (step of selecting a hair shape regulating agent), the presence or absence of the conversion of a nucleotide polymorphism and the type of the nucleotide after conversion are detected. The method for detecting the presence or absence of the conversion of a nucleotide polymorphism and the type of the converted nucleotide may be a method of directly measuring the type of nucleotides, or a method capable of indirectly evaluating the change of nucleotides. Examples of the method of directly measuring nucleotides include methods that are well known to those having ordinary skill in the art, such as PCR-SSCP, PCR-RLFP, PCR-SSO, PCR-ASP, a direct sequencing method, SNaP-shot, dHPLC, a Sniper method, and a MALDI-TOF/MS method. Examples of the method of indirectly evaluating nucleotides includes methods of measuring a function, activity, the amount of a specific mRNA, or the amount of a protein, which may be produced/increased, or lost/decreased as a result of the conversion of the target nucleotides.

The substance selected by the method can be used as a hair shape regulating agent effective for the regulation of hair shape, and can also be used for the preparation of a pharmaceutical product, a quasi-drug, a cosmetic material, a health food, or the like, which all contain the agent. When the selected substance is further subjected to other pharmacological tests, clinical tests and toxicology tests as necessary, a hair shape regulating agent that is more effective and safe to human beings can be obtained.

Alternatively, the screening method described above can be carried out by using, for example, the expression of a hair shape susceptibility gene of the present invention or a protein encoded by the gene in a tissue or cell capable of expressing the gene or protein, as an indicator.

Specifically, the screening method can be carried out by the following steps (a) to (d):

(a) a step for contacting a test substance with a tissue or cell capable of expressing the hair shape susceptibility gene of the present invention or a protein encoded by the gene;

(b) a step of measuring the amount of expression of the gene or the protein in the tissue or cell;

(c) a step of comparing the amount of expression measured in step (b) with the amount of expression of the gene or the protein in a control tissue or cell which has not been contacted with the test substance; and (d) a step of selecting, based on the results of step (c), a test substance which decreases or increases the amount of expression of the gene or the protein, as a hair shape regulating agent.

Here, as the tissue or cell capable of expressing the hair shape susceptibility gene of the present or a protein encoded by the gene, the type of the tissue or cell does not matter as long as the tissue or cell which expresses the gene or the protein. However, examples include a tissue or a cell of a mammal, for example, the skin tissue, hair root area tissue (hair follicle tissue), epidermal keratinocytes, hair root area-derived cells, an established epithelial cell line, and the like, all collected from a human being. The cell also includes a transformant which has been transformed with the hair shape susceptibility gene of the present invention (an expression vector having the gene).

The contact between the tissue or cell and a test substance can be carried out by, for example, adding the test substance in advance to a culture fluid to a predetermined concentration, and then placing the tissue or cell in the culture fluid, or by adding the test substance to a culture fluid in which the tissue or cell is placed, to a predetermined concentration.

Examples of the culture fluid include DMEM medium, MCDB medium, Willams' E medium, RPMI1640 medium, DMEM/HamF12 (1:1) medium, various commercially available media for epithelial cells, and the like, and appropriately agar or gelatin may also be added. Furthermore, if necessary, an antibiotic substance, an amino acid, blood serum, a growth factor, a biological extract, and the like may also be added.

Tissue culture can be carried out by, for example, inserting a collected hair root area tissue (hair follicle tissue) into a 24-well plate to which a culture fluid has been added, and culturing the tissue usually for 10 to 30 days, and preferably 1 to 21 days, in a gas phase of air containing $CO_2$ at a temperature of 37° C.

Furthermore, cell culture can be carried out by, for example, inserting cells into a 24-well plate to which a culture fluid has been added, and culturing the cells usually for 1 to 7 days, and preferably 1 to 3 days, in a gas phase of air containing $CO_2$ at a temperature of 37° C.

The measurement (quantification) of the expression of the gene can be carried out according to the method described in connection with the detection/measurement of a marker for the type of hair shape described above ((5)-2)-(i)). That is, the measurement can be carried out by performing a known method such as a Northern Blotting method, an RT-PCR method, a DNA chip analysis method, or an in situ hybridization analysis method, using a primer for amplifying a polynucleotide that can serve as the marker of the present invention, or a probe for detecting the polynucleotide.

Furthermore, the measurement (quantification) of the expression of the protein can be carried out according to the method described in connection with the detection/measurement of a marker for the type of hair shape described above ((5)-2)-(ii)). That is, the measurement can be achieved according to a known method such as a Western Blotting method, using an antibody which recognizes the marker (polypeptide) for the type of hair shape of the present invention.

2) The measurement of the expression level of the hair shape susceptibility gene of the present invention can also be carried out by introducing into a cell line a fusion gene in which a reporter gene such as, for example, luciferase gene, is linked to a gene region controlling the expression of the gene (regulatory region), and measuring the amount or activity of a protein derived from the reporter gene.

That is, the method for evaluating or selecting a hair shape regulating agent according to the present invention can be carried out by the following steps of (a) to (c):

(a) a step of introducing a fusion gene of the regulatory region of a hair shape susceptibility gene of the present invention and a reporter gene, into a cell capable of expressing the hair shape susceptibility gene of the present invention, and culturing the cell in the presence and in the absence of a test substance;

(b) a step of measuring the amount of expression of an expression product of the reporter gene in the cell culture cultured in the presence of the test substance, and comparing the amount with the amount of expression of an expression product of the reporter gene in the cell culture cultured in the absence of the test substance; and (c) a step of selecting, based on the comparison results obtained in step (b), a test substance which increases or decreases the amount of expression of the reporter gene expression product, as a hair shape regulating agent.

As the reporter gene, a structural gene of an enzyme which catalyzes a light emission reaction or a color reaction is preferred. Specifically, examples include the luciferase gene described above, secreted alkali phosphatase gene, chloramphenichol acetyltransferase gene, β-glucuronidase gene, β-galactosidase gene, aequorin gene, and the like.

Furthermore, as the regulatory region of the hair shape susceptibility gene, for example, about 1 kb to about 10 kb, and preferably about 2 kb, upstream of the transcription initiation site of the gene can be used, and for example, the regions having base sequences set forth in SEQ ID NO: 42 to NO: 45 in CNIH2 gene, YIF1A gene, ORAOV1 gene or KRTAP5-9 gene, respectively, may be used.

A substance which decreases the amount of expression of the hair shape susceptibility gene may be a substance which suppresses the expression of or promotes the degradation of a mRNA complementary to the polynucleotide constituting the gene, and a substance which decreases the amount of expression of a protein encoded by the hair shape susceptibility gene may be a substance which suppresses the expression of the hair shape susceptibility gene or a protein thereof, or promotes the degradation of the gene or a protein thereof, and consequently decreases the amount of expression of the protein.

A substance which increases the amount of expression of the hair shape susceptibility gene of the present invention may be a substance which promotes the expression of or suppresses the degradation of a mRNA complementary to the polynucleotide constituting the gene, and a substance which increases the amount of expression of a protein encoded by the hair shape susceptibility gene may be a substance which promotes the expression of the hair shape susceptibility gene or a protein thereof, or suppresses the degradation of the gene or a protein thereof, and consequently increases the amount of expression of the protein.

A substance which increases the amount of expression of the hair shape susceptibility gene or a protein encoded by the gene, serves as a reducing or promoting agent for curly hair or kinky hair. For example, a substance which increases the amount of expression of CNIH2 gene, YIF1A gene, ORAOV1 gene or KRTAP5-9 gene, or a protein encoded thereby, can serve as an agent capable of reducing or improving curly hair or kinky hair, while a substance which decreases the expression of such a gene or protein can serve as an agent capable of promoting curly hair or kinky hair, or a waving promoting agent. Furthermore, for example, a substance which increases the amount of expression of IVL gene or a protein encoded thereby, can serve as a promoting agent for curly hair or kinky hair, or a waving promoting agent, while a substance which decreases the expression of the gene or protein can serve as a reducing or improving agent for curly hair or kinky hair. Such a hair shape regulating agent can function as a pharmaceutical product, a cosmetic product or the like for an amelioration of curly hair or kinky hair, or for the promotion of waving of scalp hair, when administered to a human being.

3) Furthermore, the method for evaluating or selecting the hair shape regulating agent of the present invention can be carried out by using the function (activity) of a protein encoded by the hair shape susceptibility gene of the present invention as an indicator.

Examples of the function or activity of the protein include the acetylcholine receptor activity (Nguyen V T et al., J. Biol. Chem., 275(38), p. 29466-76, 2000), and phosphatidylserine binding ability (Goebeler V et al., FEBS Lett. 546(2-3), p. 359-64, 2003). The amount of the protein and the function or activity thereof have a certain correlation. Therefore, when the measurement of the function or activity of the protein described above is measured instead of the measurement of the amount of the protein, an evaluation or selection of a hair shape regulating agent can be carried out.

Specifically, the evaluation or selection is carried out by the following steps (a), (b) and (c).

(a) a step for contacting a test substance with an aqueous solution, tissue cells, or a cell fraction prepared from the tissue cells containing a protein encoded by the hair shape susceptibility gene of the present invention;

(b) a step of measuring the function or activity of the protein in the aqueous solution, tissue cells or cell fraction that has been contacted with the test substance, and comparing the function or activity with the function or activity of the protein in a control aqueous solution, control cells or control cell fraction, which has not been contacted with the test substance; and (c) a step of selecting, based on the comparison results of the step (b), a test substance which increases or decrease the function or activity of the protein.

As the aqueous solution containing a protein encoded by the hair shape susceptibility gene, examples include an aqueous solution of CNIH2, YIF1A, ORAOV1 or KRTAP5-9, as well as a tissue cell lysate, a nucleus extract, and cell culture supernatant, which contain such a protein, and the like. The cell used herein may be a cell which expresses the hair shape susceptibility gene of the present invention (for example, CNIH2 gene, YIF1A gene, ORAOV1 gene, or KRTAP5-9 gene), and has a protein encoded by such a gene as an expression product. Specifically, a tissue or cell of a mammal, for example, the skin tissue, hair root area tissue (hair follicle tissue), epidermal keratinocytes, hair root area-derived cells, an established epithelial cell line, and the like, all collected from a human being, can be used. The cell also includes a transformant which has been transformed with the hair shape susceptibility gene of the present invention (or an expression vector having the gene). Examples of host cells used in the transformation include well known cells such as Hela cell, COS cell, HEK293 cell, MDCK cell, CHO cell, and HL60 cell. Furthermore, a cell fraction means one of various fractions derived from the cells described above, and includes, for example, a cell membrane fraction, a cell cytoplasm fraction, a cell nucleus fraction, and the like.

The activity of a protein encoded by the hair susceptibility gene of the present invention can be measured, for example, in the case of measuring the acetylcholine receptor activity or the phosphatidylserine binding ability, by known methods such as a binding assay, a co-immunoprecipitation method, a pulldown assay, a two-hybrid method (Y2H), a fluorescence polarization method, and a time-resolved fluorescence resonance energy transfer (TR-FRET) method (for example, Hiromitsu Nakauchi, Ed., "Immunological Protocol", Yodosha Co., Ltd., 2004; Tadaomi Takenawa, Ed., "Optimal Methods Clarifying Protein Interaction", Biotechnology Journal, Vol. 5, No. 6, Yodosha Co., Ltd., 2005). That is, the activity can be measured by immobilizing a protein encoded by a hair shape susceptibility gene on a membrane or a plate using an aqueous solution containing the protein, and detecting the amount of radioisotope-labeled acetylcholine or phosphatidylserine binding to the protein. A substance which suppresses (decreases) the function (activity) of the protein may be a substance which decreases the acetylcholine receptor activity or the phosphatidylserine binding ability, while a substance which enhances (increases) the function (activity) of the protein may be a substance which increases the acetylcholine receptor activity or the phosphatidylserine binding ability. For example, a substance which enhances the function (activity) of CNIH2, YIF1A, ORAOV1 or KRTAP5-9 can serve as an agent for ameliorating curly hair or kinky hair, and a substance which suppresses the function (activity) of such a protein can serve as a waving promoting agent.

EXAMPLES

Hereinafter, the present invention will be described by way of Examples.

Example 1

Definition of Hair Shape and Collection of Curly Hair Family Lines

In the present Example, an affected sib-pair linkage analysis and a case-control association analysis were carried out on a Japanese group, in order to identify the hair shape susceptibility gene.

In general, hair shape varies with the human race, and the people of the Asian race relatively more frequently have straight hair, while the people of the African race mainly have kinky hair (or curled hair). A large proportion of the people of the Indo-European race have a trait of wavy hair (wave hair) which is intermediate of the two. Since a Japanese group is a straight hair-dominant group, people having a curly hair trait as the hair shape were defined as the affected (case), while the straight hair trait was defined as the control (control). In a genetic analysis such as a linkage analysis, it is necessary to handle the object traits quantitatively to a certain extent, and thus, for example, a method of binarizing the traits in such a manner that curly hair=1 and straight hair=0, or a method of measuring the degree of curly hair by a certain method, and quantifying the degree were considered. However, in the current situation, due to a variety of hair shapes of human being, the method for measurement or classification has not sufficiently established. Thus, first, an accurate classification of the phenotypes of hair shape was carried out. The hair shape is defined by the overall feature of the hair and the degree of curl (curl radius). Furthermore, factors defining the hair shape include not only the curl characteristics of a single hair, but also the synchrony of curl with the groups of hair in the surroundings. Thus, the phenotypes of hair shape were classified as indicated in Table 4, based on the actual states of hair shape in various human races. This classification is applicable to various racial groups, including Japanese groups. Furthermore, FIG. 1 presents images of the phenotypes of hair shape.

TABLE 4

Classification of phenotypes of hair shape

| | Feature | Curl radius | Type of hair shape |
|---|---|---|---|
| Type 1 | Hair which exhibits one curl in overall even if the length of the hair changes, or has one curl only at the hair tips | 9.5 cm or larger over the entire hair, or 3 cm or larger only at the hair tip | Straight hair |
| | | Smaller than 9.5 cm over the entire hair, or smaller than 3 cm only at the hair tip | Almost straight hair, or slightly wavy hair |
| Type 2 | Hair which has several repeated curls along the length of the hair with an inherent curl radius, and has a curl period synchronizing with the hair in the surroundings | 9.5 cm or larger over the entire hair | Almost straight hair, or slightly wavy hair |
| | | Equal to or larger of 3 cm and smaller than 9.5 cm over the entire hair | Wavy hair |
| | | Smaller than 3 cm in the entire hair | Curly hair, or strongly wavy hair |
| Type 3 | Hair in which individual hairs have finely repeated curls, and the curl period does not synchronize with the hair in the surroundings | | Kinky hair |

On the other hand, the phenotype is the hair shape is a quantitative trait which can be continuously changed in a group, and it has been not established to which extent should be determined as the curly hair trait or as the straight hair trait. In the present invention, among the classifications based on the actual states of hair shape, kinky hair, and curly hair or strongly wavy hair are defined as the curly hair traits, and wavy hair, almost straight hair or slightly wavy hair, and straight hair are defined as the straight hair (non-curly hair) traits.

As such, the phenotypes of hair shape could be accurately classified, but in regard to the collection of the objects of genetic analysis, the following problem to be solved emerged. That is, problems arise when the hair at the time point of collection is markedly short and it is impossible to evaluate the shape, and when the original hair shape has changed by permanent treatment, hair dyeing, and chemical treatments by various styling agents. For this reason, all candidates who could become the objects of a genetic analysis were each requested to submit a photograph of the candidate himself/herself that was taken at a time when the phenotype of the hair shape could be discriminated (for example, childhood). That is, it is a photograph of a hair state which is not a markedly short hair and has not been subjected to a chemical treatment of hair. At the same time, all of the candidates were requested to submit several hair strands. The submitted hair strands were subjected to a detailed shape evaluation of torsion or kink of the hair, crimp, curl characteristics, and the like under water immersion conditions by which the effect of chemical treatment is lost. The objects of a genetic analysis were determined based on the evaluation of hair shape from the submitted photographs of the candidates themselves, and the evaluation of the shape of the submitted hair, and finally based on an investigation of hair shape through interviews.

As such, it took about two years to collect curly hair family lines of 68 families with 283 members among 3000 or more candidates applied from all over Japan. The specific details include 41 groups of two siblings, 22 groups of three siblings, 4 groups of four siblings, and one group of five siblings, and 100 pairs were defined as the final affected sib-pairs (brothers or sisters having the curly hair trait). Since it was predicted that this number of sib-pairs was sufficient to characterize the genetic locus in consideration of the strength of the genetic factor and the risk in the siblings, it was decided to carry out an affected sib-pair linkage analysis.

In regard to the collection of specimens from the objects of the genetic analysis, specimens were collected only when an approval was granted in advance by the ethics committee, subsequently the person in charge of the implementation of informed consent explained the contents of the study to the objects using a written explanation, and written consent was obtained.

A doctor or a nurse collected about 20 mL of blood from each of the objects of the genetic analysis. The genomic DNA was extracted from the blood specimen using PUREGENE Genomic DNA Purification Kit (manufactured by Gentra Systems, Inc.) according to the manual. The genomic DNA was dissolved in 2 mL of a DNA Hydration Solution, the concentration was measured, and the solution was stored at 4° C. The average yield of the genomic DNA was 576.2 g/20 ml of blood.

Example 2

Affected Sib-Pair Linkage Analysis on Entire Genome

In the present Example, an affected sib-pair linkage analysis covering the entire genome was carried out for the first time on the Japanese curly hair family lines. To briefly describe the principle of this method, since siblings that are affected have inherited from their parents an allele causative of a disease, the siblings necessarily share the allele. On the other hand, the number of alleles shared by brothers is 1 (a value based on the null hypothesis). When many cases of allele sharing could be observed from the number of alleles based on the null hypothesis by examining the number of alleles shared by many affected sib-pairs, it was determined that linkage was recognized.

The affected sib-pair linkage analysis was carried out using a linkage mapping set (ABI PRISM Linkage Mapping Set-MD 10 v2.5) manufactured by Applied Biosystems, Inc. (ABI). This is a set of 400 fluorescent primers for typing in total, intended to amplify microsatellites, which are short repeating sequences rich in polymorphisms that are evenly scattered in the genome, and the kit covers human chromosome at an average interval of 9.2 cm.

The genomic DNA prepared in Example 1 was used as a template, and PCR (GeneAmp PCR System 9700G, manufactured by ABI) was carried out using a linkage mapping set. Detection of the amplification product (fragment) was carried out using an ABI PRISM 3100 Genetic Analyzer (manufactured by ABI). The fluorescent primer set for typing includes primers labeled with three types of fluorescent dyes such as 6-FAM (blue), VIC (green) and NED (yellow), and therefore, even with fragments of the same size, three types of colors can be separately discriminated. Accordingly, large amounts of samples could be rapidly processed.

The typing of the fragments was carried out by means of Genotyper Software v3.7 (manufactured by ABI) and GeneScan Software (manufactured by ABI).

A statistical test of the linkage was carried out using Genehunter v2.1_r5 Software (Kruglyak, L. et al., Am. J. Hum. Genet., 58(6), 1347-1363, 1996), which is a non-parametric analysis. Determination of the region where linkage is recognized was carried out according to the guidelines of Lander and Kruglyak (Nat. Genet., 11(3), 241-247, 1995) as described below, based on the criteria for obtaining false positive linkage.

A linkage analysis came to be actively carried out over the entire genome through the guidelines of Lander and Kruglyak (polygenic diseases), but in a linkage analysis of individual genes, the determination of whether the gene function can be a cause of a disease, is also needed. However, in an analysis over the entire genome, since the gene function is not taken into consideration at that stage, determination criteria (threshold values) that are purely meaningful in terms of mathematical genetics are required. Thus, they have provided significant linkage criteria as shown in the following Table 5, according to simulation results.

TABLE 5

| | |
|---|---|
| Suggestive Linkage<br>(Criteria for obtaining one false positive linkage result over the entire genome) | $P < 7.4 \times 10^{-4}$<br>LOD > 2.2 |
| Significant Linkage<br>(Criteria for obtaining 0.05 false positive linkage results over the entire genome) | $P < 2.2 \times 10^{-5}$<br>LOD > 3.6 |
| High Significant Linkage<br>(Criteria for obtaining 0.01 false positive linkage results over the entire genome) | $P < 3.0 \times 10^{-7}$<br>LOD > 5.4 |

Figure 2:
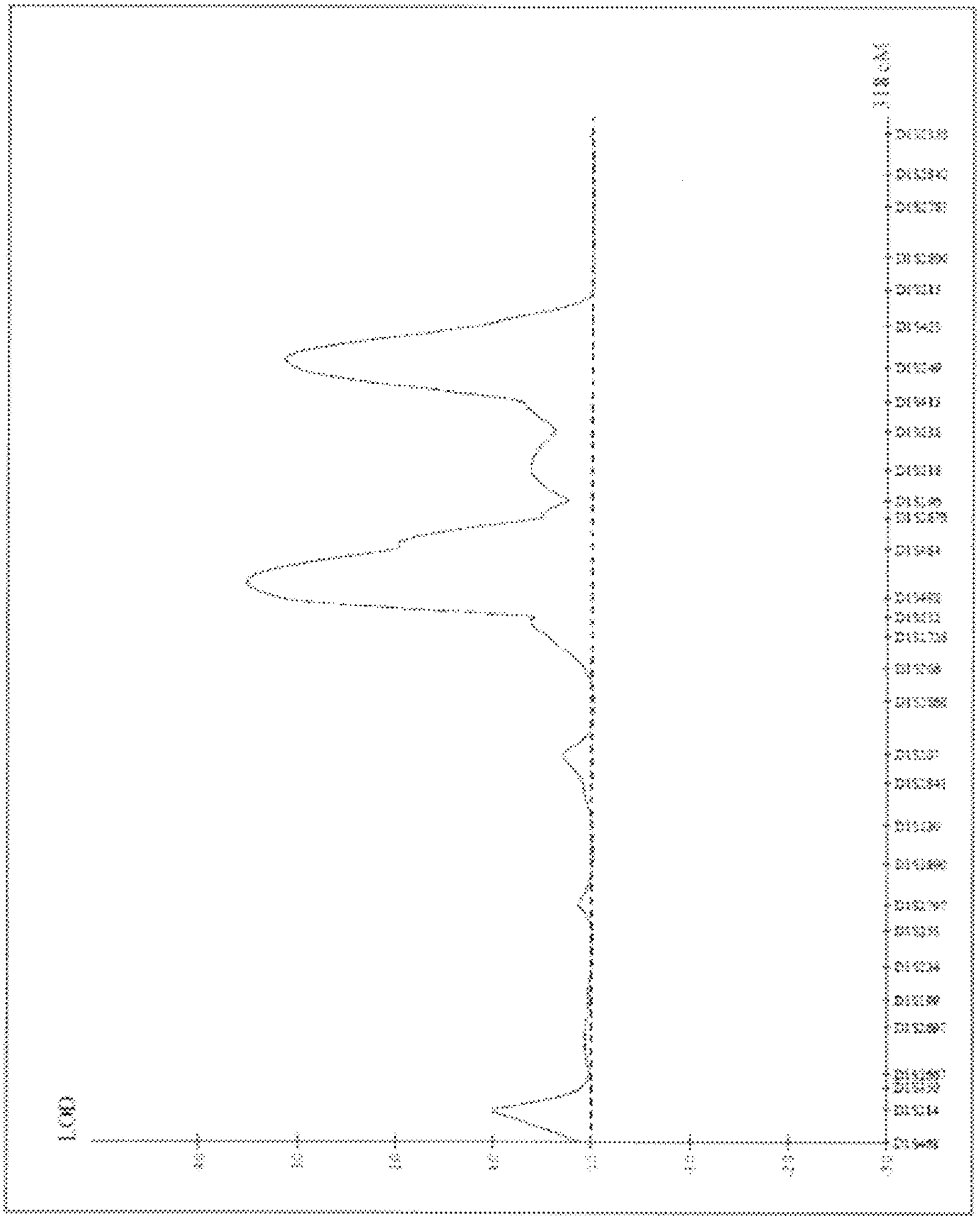
FIG. 2 is a diagram showing microsatellite markers and the maximum LODs obtained by an affected sib-pair linkage analysis on chromosome 1.
Figure 3:
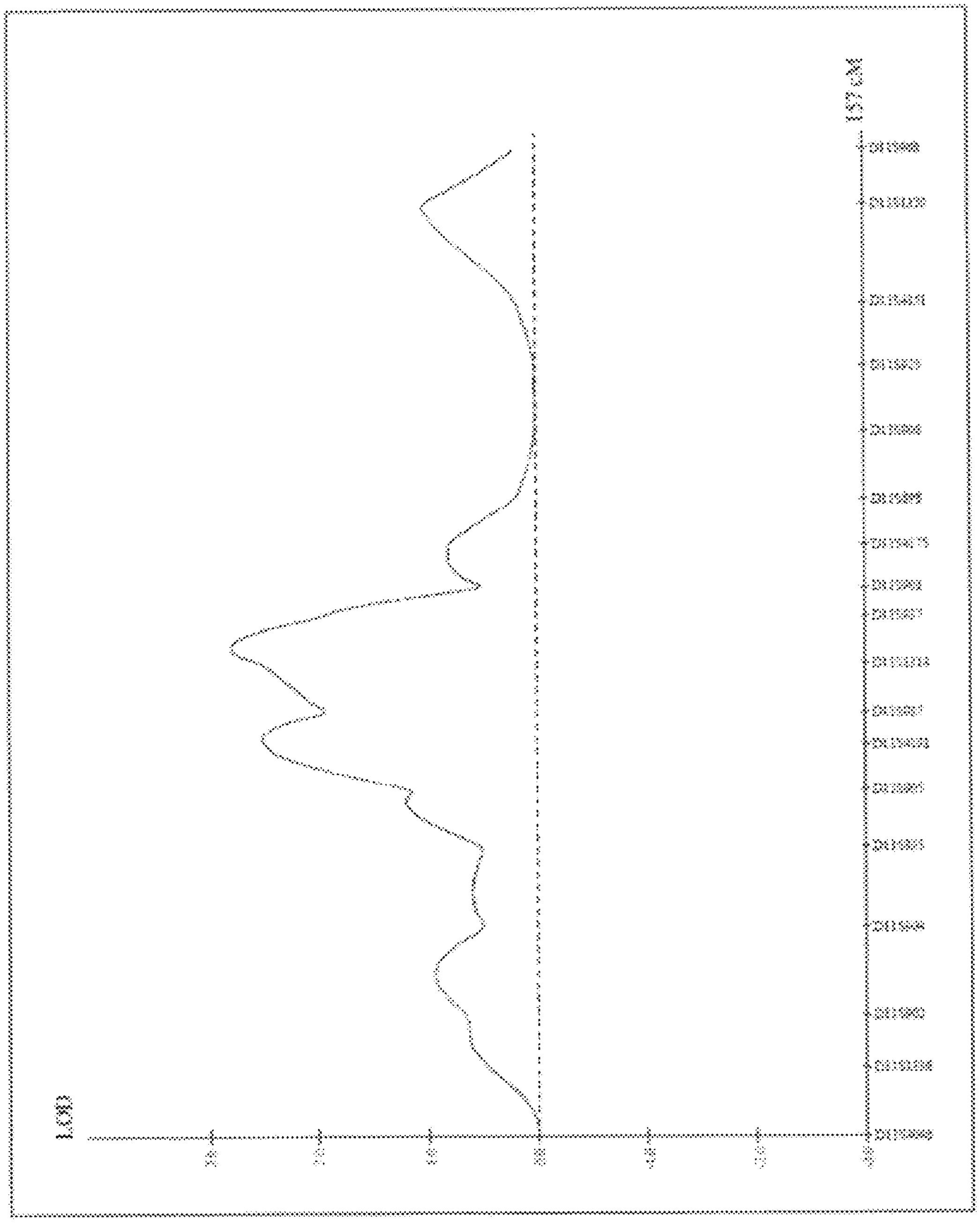
FIG. 3 is a diagram showing microsatellite markers and the maximum LODs obtained by an affected sib-pair linkage analysis on chromosome 11.

As a result of the screening of whole chromosome, linkages were recognized on chromosome 1 and chromosome 11. The results are respectively presented in FIG. 2 and FIG. 3. As shown in FIG. 2, in chromosome 1, a maximum LOD score of 3.49 was obtained in the 1q21 to 1q23.1 region (near D1S498), and a maximum LOD score of 3.13 was obtained in the 1q32 to 1q41 region (D1S249-D1S213). As shown in FIG. 3, in chromosome 11, a maximum LOD score of 2.78 was obtained in the 11812 to 11q13.5 region (D11S905 to D11S937). The values thus obtained satisfied the criteria of Suggestive Linkage defined by Lander and Kruglyak. Therefore, the curly hair trait locus could be specified on chromosome 1 and chromosome 11, and it was strongly suggested that hair shape susceptibility genes exist in these regions.

Example 3

Detailed Mapping in Candidate Regions

Subsequently, chromosome 11 that where linkages was recognized in Example 2 was subjected to an affected sib-pair linkage analysis (detailed mapping) by further using microsatellite markers, for the purpose of narrowing the linkage regions.

The microsatellites used as a marker for the detailed mapping were searched using Comprehensive human genetic maps of the Mammalian Genotyping Service (http://research-.marshfieldclinic.org/genetics/GeneticResearch/compMap-s.asp). M which were present in the genome at an interval of 1 to 2 cM and had high heterozygosity were selected. Furthermore, the fluorescent primers for typing, which were intended to amplify the microsatellites, were designed based on the Genome Database Project (GDB) (http://www.gd-b.org/). Here, although the GDB has terminated the operation, currently retrieval and design can be carried out through the NCBI (http://www.ncbi.nlm.nih.gov/). Fluorescent primers for typing manufactured by ABI were used, and for some of the fluorescent primers for typing, those included in a linkage mapping set (ABI PRISM Linkage Mapping Set-HD 5 v2.5, manufactured by ABI) were used. The microsatellites used as the markers for detailed mapping, and the fluorescent primers for typing are presented in Table 6 (see SEQ ID NO:6 to NO:33).

TABLE 6

Microsatellites used as markers for detailed mapping, and fluorescent primers for typing

| ABI | Microsatellite | | Location (cM) | GenBank Accession | Heterozygosity | Amplification product (fragment) size | Label | Forward primer | Reverse primer |
|---|---|---|---|---|---|---|---|---|---|
| MD10 | AFM254zb9 | D11S935 | 45.94 | Z17148 | 0.73 | 196-208 | 6-FAM | | |
| HD5 | AFMa218xg9 | D11S4102 | 47.61 | Z52543 | 0.76 | 142-174 | 6-FAM | | |
| | AFM362tb9 | D11S1360 | 50.88 | Z24611 | 0.61 | 103-117 | 6-FAM | AGTGGTGTGCCGACAA (SEQ ID NO: 6) | TCCAAATCAGGGCTTTCT (SEQ ID NO: 7) |
| MD10 | AFM105xb10 | D11S905 | 51.95 | Z16575 | 0.72 | 208-228 | VIC | | |
| | ATA1B07 | D11S1993 | 54.09 | G08834 | 0.77 | 224-245 | VIC | GGACAGATGCTTCCAGAAAA (SEQ ID NO: 8) | AGATTATGCATGTGTAAAGAGCC (SEQ ID NO: 9) |
| | AFM255ye1 | D11S986 | 56.76 | Z21491 | 0.79 | 137-169 | NED | GAAGGACTCGGCTCCAG (SEQ ID NO: 10) | GTAAGAGGATGGTAGGAGGG (SEQ ID NO: 11) |
| | AFM211xe1 | D11S1313 | 58.40 | Z23608 | 0.85 | 184-204 | NED | CTAAGCATGANGCCAAGTTA (SEQ ID NO: 12) | AGTTTGACATTAGGGAATTTTGA (SEQ ID NO: 13) |
| MD10 | AFM338wc1 | D11S4191 | 60.09 | Z51451 | 0.87 | 111-135 | VIC | | |
| | AFM165zc3 | D11S1765 | 61.78 | Z51076 | 0.79 | 234-252 | 6-FAM | CAGAAATGCCACCCAGAGAG (SEQ ID NO: 14) | TTCCGGAGTTTGCACAATCT (SEQ ID NO: 15) |
| | AFMa356yg5 | D11S4076 | 62.62 | Z53015 | 0.77 | 151-163 | NED | CATGAATGCTCTTGTCCC (SEQ ID NO: 16) | AACCCCCTGGAAAATAGACT (SEQ ID NO: 17) |
| | AFM039xg3 | D11S1883 | 65.05 | Z50899 | 0.73 | 250-266 | NED | TTCAGTAACAGGAGACAAAAGG (SEQ ID NO: 18) | TGGTTTCGGATCTCTTCTCA (SEQ ID NO: 19) |
| MD10 | AFMa131ye5 | D11S987 | 67.48 | Z21492 | 0.82 | 82-118 | 6-FAM | | |
| | AFMa272yb5 | D11S4113 | 68.01 | Z52723 | 0.80 | 218-262 | NED | ACCTCACGGTGTAATCCC (SEQ ID NO: 20) | CTTGAAGCCCATCTTTGC (SEQ ID NO: 21) |
| | AFM289ya9 | D11S1337 | 68.55 | Z24080 | 0.59 | 279-295 | 6-FAM | | |
| | AFMb032zg5 | D11S4136 | 71.60 | Z53163 | 0.80 | 180-202 | VIC | GAATCGCTTGAACCCAG (SEQ ID NO: 24) | CCAGGTGGTCTTAACGG (SEQ ID NO: 25) |
| MD10 | AFM212xe3 | D11S1314 | 73.64 | Z23617 | 0.76 | 209-227 | VIC | | |
| | AFMc020yd5 | D11S4184 | 75.30 | Z54028 | 0.68 | 263-277 | VIC | CCCAGCCTTACATATTCC (SEQ ID NO: 26) | GCTGATGAGCAGAGGTAG (SEQ ID NO: 27) |
| HD5 | AFMa103zf9 | D11S4207 | 76.13 | Z52030 | 0.89 | 254-288 | 6-FAM | | |
| | AFM199yh10 | D11S4128 | 77.78 | Z51124 | 0.83 | 148-168 | VIC | AAGTTGCAGTGAGCCG (SEQ ID NO: 28) | TTCCAGCCCATTAACCT (SEQ ID NO: 29) |
| MD10 | AFM256zb5 | D11S937 | 79.98 | Z17159 | 0.88 | 230-264 | 6-FAM | | |
| | AFMb334yc1 | D11S4166 | 81.26 | Z53689 | 0.67 | 110-130 | NED | GGAAGGCACCATGATACTTG (SEQ ID NO: 30) | GTGAAGTCTGGGATTTCAGC (SEQ ID NO: 31) |
| | AFMb343yf5 | D11S4172 | 82.57 | Z53759 | 0.68 | 141-153 | VIC | CCAGCTCAAATGCTCATCAG (SEQ ID NO: 32) | TTATCAGCAACATGAAAATGGAC (SEQ ID NO: 33) |
| MD10 | AFM063yg1 | D11S901 | 85.48 | Z16505 | 0.81 | 160-176 | 6-FAM | | |

Figure 4:
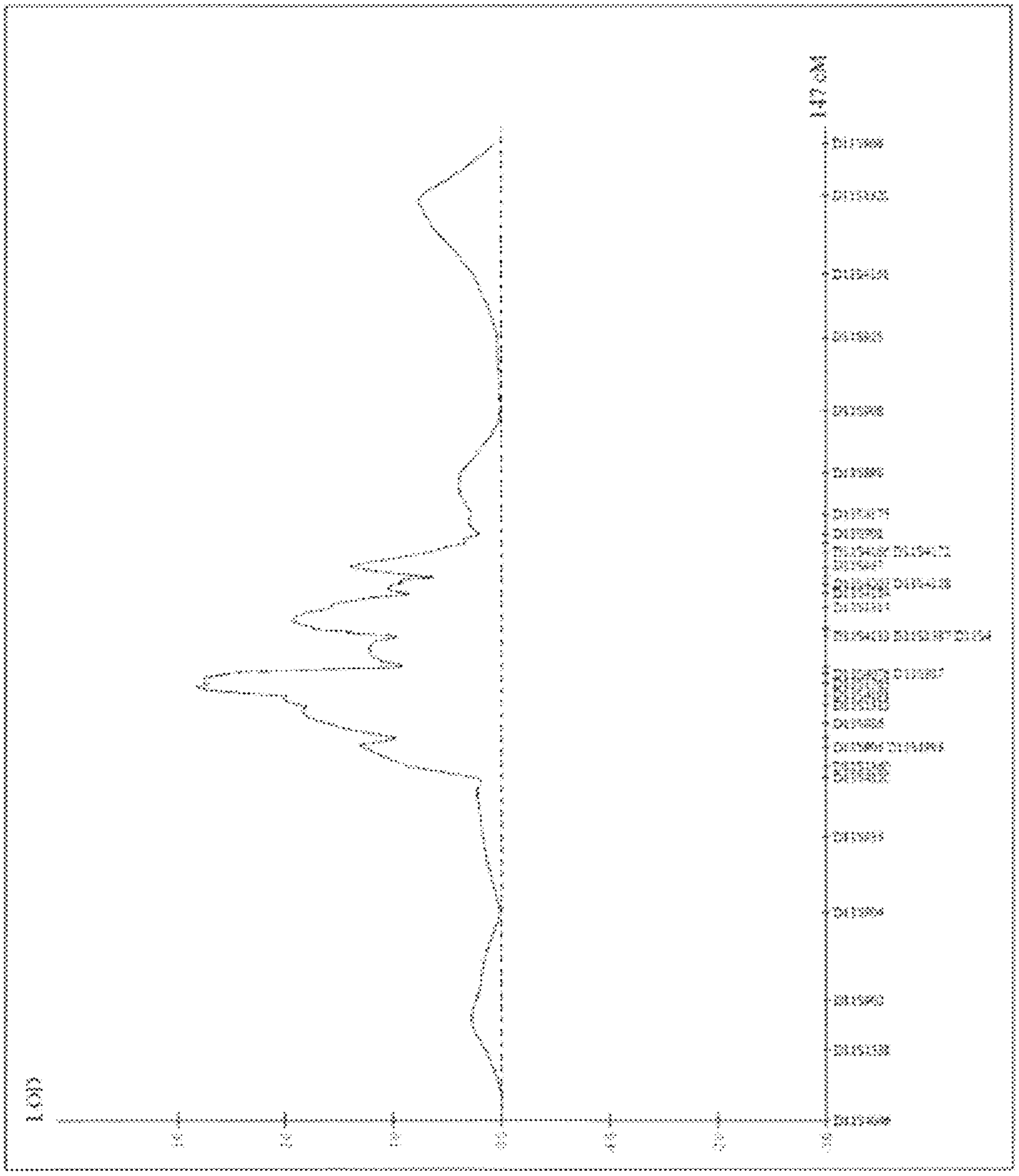
FIG. 4 is a diagram showing microsatellite markers and the maximum LODs obtained by an affected sib-pair linkage analysis on chromosome 11.

The results obtained by carrying out an affected sib-pair linkage analysis (detailed mapping) on chromosome 11 in the same manner as in Example 2, are presented in FIG. 4. As shown in FIG. 4, a maximum LOD score of 2.81 was obtained in the 11q12.2 to 11q13.2 region (D11S4191 and D11S987). The values thus obtained were considered to satisfy the criteria of Significant Linkage and Suggestive Linkage, respectively, defined by Lander and Kruglyak as described in Example 2. Therefore, the curly hair trait loci on chromosome 11 could be narrowed, and it was strongly suggested that hair shape susceptibility genes exist in these regions.

Example 4

Case-Control Association Analysis

In order to identify a hair shape susceptibility gene from the 11q12.2 to 11q13.2 region (D11S4191 and D11S987) on chromosome 11, where strong linkage was recognized in Example 3 above, a comparison of the allele frequency for the single nucleotide polymorphism (SNP) markers present in the region was made by a case-control association analysis.

Since it is necessary that the cases (affected: those having the curly hair trait) and the controls (control: those having the straight hair trait) consist of people of the same race as the race for whom the hair shape susceptibility gene is identified, in the present invention, non-family related Japanese people having the curly hair trait and non-family related Japanese people having the straight hair trait were employed as objects. Objects were collected in the same manner according to the criteria described in Example 1, and genomic DNA was obtained from each of 43 non-family related Japanese people having the curly hair trait and 51 non-family related Japanese people having the straight hair trait.

With reference to the dbSNP database (http://www.ncbi.nlm.nih.gov/SNP/) and the JSNP database (http://snp.ims.u-tokyo.ac.jp/index_ja.html), SNPs which represented certain regions in the region to be analyzed, and had a gene frequency of the minor allele of 10% or higher in a panel of Japanese people, were selected as SNPs to be typed. Thus, 38 SNPs were selected from the region to be analyzed.

The typing of SNPs was carried out according to a TaqMan PCR method, using TaqMan SNP Genotyping Assays (manufactured by ABI, formerly known as Assays-on-Demand or Assays-by-Design). Furthermore, the apparatuses of Applied Biosystems 7900HT Fast Real-time PCR System (manufactured by ABI) and Applied Biosystems 7500 Real-time PCR System (manufactured by ABI) were used. The method was carried out according to the respective manuals attached to the apparatuses.

The typing data thus obtained were totalized for each of the cases and the controls, and a significant difference test was carried out through a $\chi^2$ test by four methods involving the genotype, allele type, dominant model and recessive model. That is, if any genetic variation is causative of changes in the hair shape, differences in the allele frequency and the like are expected between the cases and the controls. Furthermore, in the present Example, since the association analysis was carried out on a relatively small number of objects, the significance level was set at $p<0.05$. Further, in some part, the significance level was set to be loose ($p<0.07$) in order to increase the power of the test.

As a result, it was found that there is a statistically significant ($p<0.05$) difference between the cases and the controls, for the two SNPs shown below.

In SNP:rs3741368 (single nucleotide polymorphism represented by Nucleotide Number 18933 in the base sequence set forth in SEQ ID NO:3), the proportion of homozygous G-allele carriers was significantly higher in the people having the straight hair trait as compared with the people having the curly hair trait, and even by the allele type, a significant difference was observed between the people having the straight hair trait and the people having the curly hair trait (Table 7-1).

In SNP:rs2664 (single nucleotide polymorphism represented by Nucleotide Number 17000 in the base sequence set forth in SEQ ID NO:5), the proportion of homozygous T-allele carriers was significantly higher in the people having the straight hair trait as compared with the people having the curly hair trait (Table 7-2).

Furthermore, it was found that even the five SNPs shown below exhibit a difference between the cases and the controls.

In SNP:rs2276299 (single nucleotide polymorphism represented by Nucleotide Number 7633 in the base sequence set forth in SEQ ID NO:1), the proportion of homozygous T-allele carriers was higher in the people having the curly hair trait as compared with the people having the straight hair trait (p=0.056), and even by the allele type, a significant difference was observed between the people having the straight hair trait and the people having the curly hair trait (p=0.058) (Table 7-3).

In SNP:rs11227447 (single nucleotide polymorphism represented by Nucleotide Number 189853 in the base sequence set forth in SEQ ID NO: 2), the proportion of homozygous C-allele carriers was higher in the people having the straight hair trait as compared with the people having the curly hair trait (p=0.061), and even by the allele type, a significant difference was observed between the people having the straight hair trait and the people having the curly hair trait (p=0.055) (Table 7-4).

In SNP:rs2282568 (single nucleotide polymorphism represented by Nucleotide Number 194405 in the base sequence set forth in SEQ ID NO: 2), the proportion of homozygous G-allele carriers was higher in the people having the straight hair trait as compared with the people having the curly hair trait (p=0.061), and even by the allele type, a significant difference was observed between the people having the straight hair trait and the people having the curly hair trait (p=0.055) (Table 7-5).

In SNP:rs3741367 (single nucleotide polymorphism represented by Nucleotide Number 18280 in the base sequence set forth in SEQ ID NO:3), the proportion of homozygous T-allele carriers was higher in the people having the straight hair trait as compared with the people having the curly hair trait (p=0.051), and even by the allele type, a significant difference was observed between the people having the straight hair trait and the people having the curly hair trait (p=0.063) (Table 7-6).

In SNP:rs1789165 (single nucleotide polymorphism represented by Nucleotide Number 1 in the base sequence set forth in SEQ ID NO:4), the proportion of homozygous A-allele carriers was higher in the people having the straight hair trait as compared with the people having the curly hair trait (p=0.062) (Table 7-7).

These seven SNPs all satisfied the Hardy-Weinberg equilibrium. Therefore, these seven SNPs were considered to be hair shape susceptibility SNPs, and their relations with hair shape were confirmed.

TABLE 7-1

Association analysis on SNP: rs3741368

| | Allele type | | Genotype | | |
|---|---|---|---|---|---|
| SNP: rs3741368 | G | A | GG | GA | AA |
| Curly hair trait | 68.4% | 31.6% | 44.7% | 47.4% | 7.9% |
| Straight hair trait (control) | 82.4% | 17.6% | 68.6% | 27.5% | 3.9% |
| p value ($\chi^2$ test) | Allele type | | 0.039 | | |
| | Genotype | | 0.076 | | |
| | GG vs GA, AA | | 0.024 | | |

TABLE 7-2

Association analysis on SNP:rs2664

| | Allele type | | Genotype | | |
|---|---|---|---|---|---|
| SNP:rs2664 | T | C | TT | TC | CC |
| Curly hair trait | 33.3% | 66.7% | 4.8% | 57.1% | 38.1% |
| Straight hair trait (control) | 41.0% | 59.0% | 20.0% | 42.0% | 38.0% |
| p value ($\chi^2$ test) | Allele type | | 0.285 | | |
| | Genotype | | 0.077 | | |
| | TT vs TC, CC | | 0.031 | | |

TABLE 7-3

Association analysis on SNP:rs2276299

| SNP:rs2276299 | Allele type | | Genotype | | |
|---|---|---|---|---|---|
| | A | T | AA | AT | TT |
| Curly hair trait | 61.6% | 38.4% | 41.9% | 39.5% | 18.6% |
| Straight hair trait (control) | 74.5% | 25.5% | 54.9% | 39.2% | 5.9% |
| p value ($\chi^2$ test) | Allele type | | | 0.058 | |
| | Genotype | | | 0.133 | |
| | AA, AT vs TT | | | 0.056 | |

TABLE 7-4

Association analysis on SNP:rs11227447

| SNP:rs11227447 | Allele type | | Genotype | | |
|---|---|---|---|---|---|
| | C | G | CC | CG | GG |
| Curly hair trait | 17.4% | 82.6% | 0.0% | 34.9% | 65.1% |
| Straight hair trait (control) | 29.4% | 70.6% | 7.8% | 43.1% | 49.0% |
| p value ($\chi^2$ test) | Allele type | | | 0.055 | |
| | Genotype | | | 0.089 | |
| | CC vs CG, GG | | | 0.061 | |

TABLE 7-5

Association analysis on SNP:rs2282568

| SNP:rs2282568 | Allele type | | Genotype | | |
|---|---|---|---|---|---|
| | C | G | CC | CC | GG |
| Curly hair trait | 82.6% | 17.4% | 65.1% | 34.9% | 0.0% |
| Straight hair trait (control) | 70.6% | 29.4% | 49.0% | 43.1% | 7.8% |
| p value ($\chi^2$ test) | Allele type | | | 0.055 | |
| | Genotype | | | 0.089 | |
| | CC, CG vs GG | | | 0.061 | |

TABLE 7-6

Association analysis on SNP:rs3741367

| SNP:rs3741367 | Allele type | | Genotype | | |
|---|---|---|---|---|---|
| | T | C | TT | TC | CC |
| Curly hair trait | 70.9% | 29.1% | 48.8% | 44.2% | 7.0% |
| Straight hair trait (control) | 82.4% | 17.6% | 68.6% | 27.5% | 3.9% |
| p value ($\chi^2$ test) | Allele type | | | 0.036 | |
| | Genotype | | | 0.149 | |
| | TT vs TC, CC | | | 0.051 | |

TABLE 7-7

Association analysis on SNP:rs1789165

| SNP:rs1789165 | Allele type | | Genotype | | |
|---|---|---|---|---|---|
| | G | A | GG | GA | AA |
| Curly hair trait | 21.1% | 78.9% | 0.0% | 42.1% | 57.9% |
| Straight hair trait (control) | 12.7% | 87.3% | 2.0% | 21.6% | 76.5% |

TABLE 7-7-continued

Association analysis on SNP:rs1789165

| SNP:rs1789165 | Allele type | | Genotype | | |
|---|---|---|---|---|---|
| | G | A | GG | GA | AA |
| p value ($\chi^2$ test) | Allele type | | | 0.138 | |
| | Genotype | | | 0.088 | |
| | GG, GA vs AA | | | 0.062 | |

Example 5

Haplotype Analysis

As a result of the analyses in Example 4, seven hair shape susceptibility SNPs were found. Further, a haplotype analysis was carried out in order to found a correlation between hair shape and polymorphisms that are present in the surrounding regions of the SNPs, particularly those that have not been typed, and to identify hair shape susceptibility genes.

In the analysis, the linkage disequilibrium coefficient D' (pair-wise LD coefficient) based on the EM algorithm was calculated using Haploview 4.1 Software (Barrett, J C, et al., Bioinformatics, 21(2), 263-265, 2005), and the analysis was carried out. A linkage disequilibrium analysis was carried out on the SNPs found above and the SNPs present in the surrounding regions, using the HapMap PHASE data of the International HapMap Project Database (HapMap Data Rel 21/PhaseII July 06, on NCBI Build 35 assembly, dbSNP b125). Meanwhile, the analysis panel consisted of JPT+CHB (Japanese people in Tokyo, Japan, and Chinese people of Han race in Beijing, China).

The method for inferring the haplotype block used the confidence interval (Gabriel, S B, et al., Science, 296 (5576), p. 2225-2229, 2002). That is, it can be considered that the haplotype blocks to be determined are mostly in the genome range where historical recombination has not been recognized, and strong linkage disequilibrium exists within the regions. Usually, when the upper limit of the 95% confidence interval of the linkage disequilibrium coefficient D' is lower than 0.9, the region is considered as a region having an evidence of historical recombination. On the other hand, when the upper limit of the 95% confidence interval of D' is higher than 0.98 and the lower limit is higher than 0.7, the region can be considered as a region where strong linkage disequilibrium exists.

As a result, haplotype blocks of the following items (1) to (5) containing the seven hair shape susceptibility SNPs shown below were found.

Figure 5:
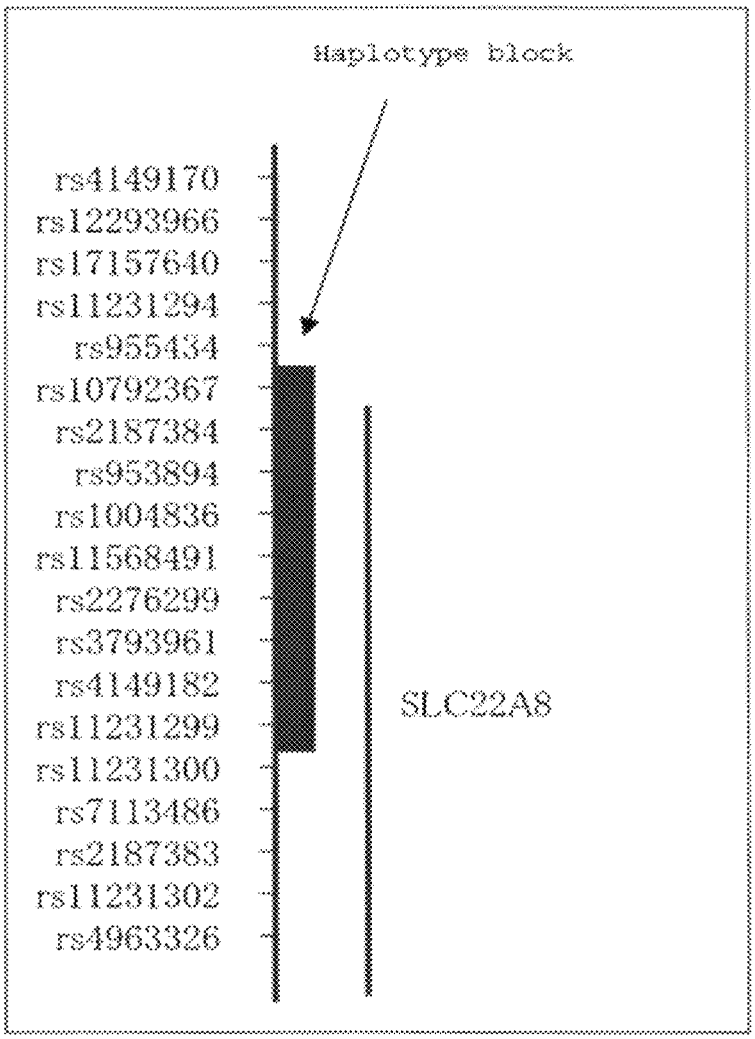
FIG. 5 is a conceptual diagram of a 12,590-bp haplotype block represented by a base sequence set forth in SEQ ID NO:1, which contains SNP: rs2276299 and extends from SNP: rs10792367 to SNP: rs11231299.

(1) A 12,590-bp haplotype block ranging from SNP:rs10792367 to SNP:rs11231299 and containing SNP:rs2276299, and represented by the base sequence set forth in SEQ ID NO:1 (FIG. 5). This haplotype block was a region containing SLC22A8 gene. From this result, SLC22A8 gene was identified as a hair shape susceptibility gene.

Figure 6:
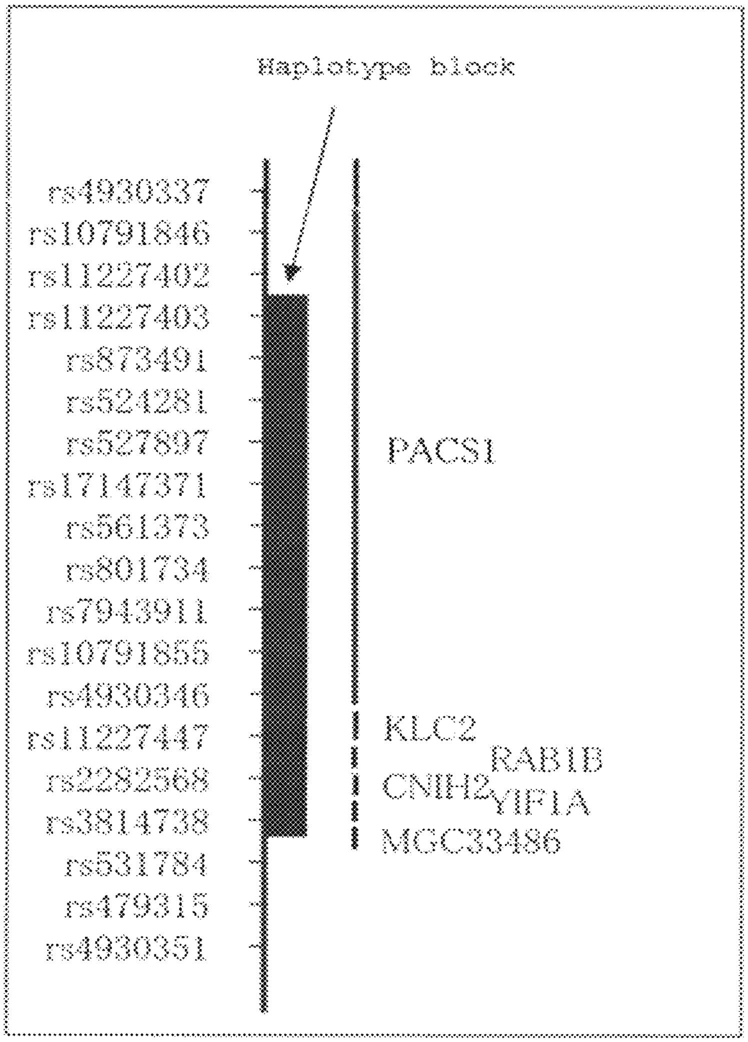
FIG. 6 is a conceptual diagram of a 202,111-bp haplotype block represented by a base sequence set forth in SEQ ID NO:2, which contains SNP:rs11227447 and SNP:rs2282568, and extends from SNP:rs11227403 to SNP:rs3814738.

(2) A 202,111-bp haplotype block ranging from SNP:rs11227403 to SNP:rs3814738 containing SNP:rs11227447, and SNP:rs2282568, and represented by the base sequence set forth in SEQ ID NO:2 (FIG. 6). This haplotype block was a region containing PACS1 gene, KLC2 gene, RAB1B gene, CNIH2 gene, YIF1A gene, and MGC33486 gene. From this result, PACS1 gene, KLC2 gene, RAB1B gene, CNIH2 gene, YIF1A gene, and MGC33486 gene were identified as hair shape susceptibility genes.

Figure 7:
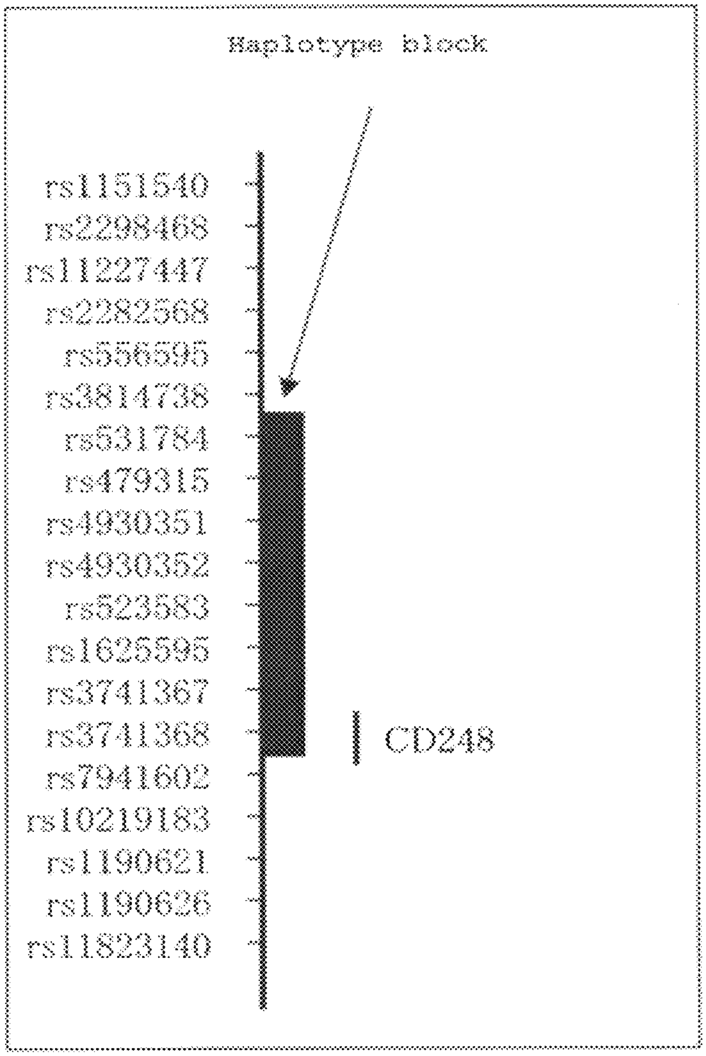
FIG. 7 is a conceptual diagram of a 18,933-bp haplotype block represented by a base sequence set forth in SEQ ID NO:3, which contains SNP:rs3741367 and SNP:rs3741368, and extends from SNP:rs531784 to SNP:rs3741368.

(3) A 18, 933-bp haplotype block ranging from SNP:rs531784 to SNP:rs3741368 containing SNP:rs3741367 and SNP:rs3741368, and represented by the base sequence set forth in SEQ ID NO:3 (FIG. 7). This haplotype block was a region containing CD248 gene. From this result, CD248 gene was identified as a hair shape susceptibility gene.

Figure 8:
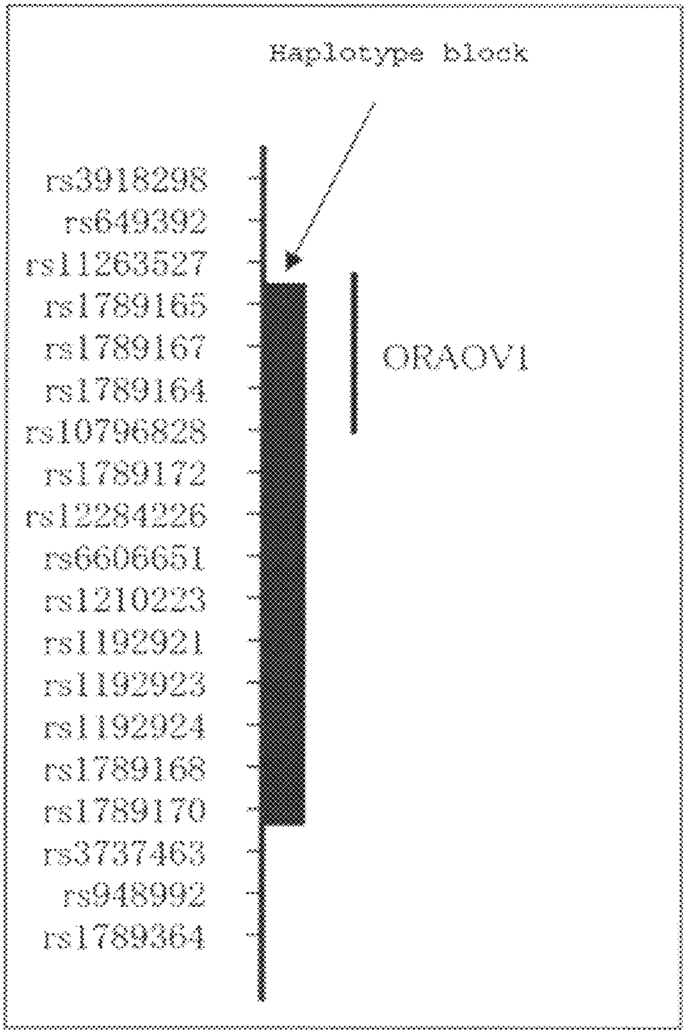
FIG. 8 is a conceptual diagram of a 27,375-bp haplotype block represented by a base sequence set forth in SEQ ID NO:4, which contains SNP:SNP:rs1789165 and extends from SNP:rs1789165 to SNP:rs1789170.

(4) A 27,375-bp haplotype block ranging from SNP: rs1789165 to SNP:rs1789170 containing SNP:rs1789165, and represented by the base sequence set forth in SEQ ID NO:4 (FIG. 8). This haplotype block was a region containing ORAOV1 gene. From this result, ORAOV1 gene was identified as a hair shape susceptibility gene.

Figure 9:
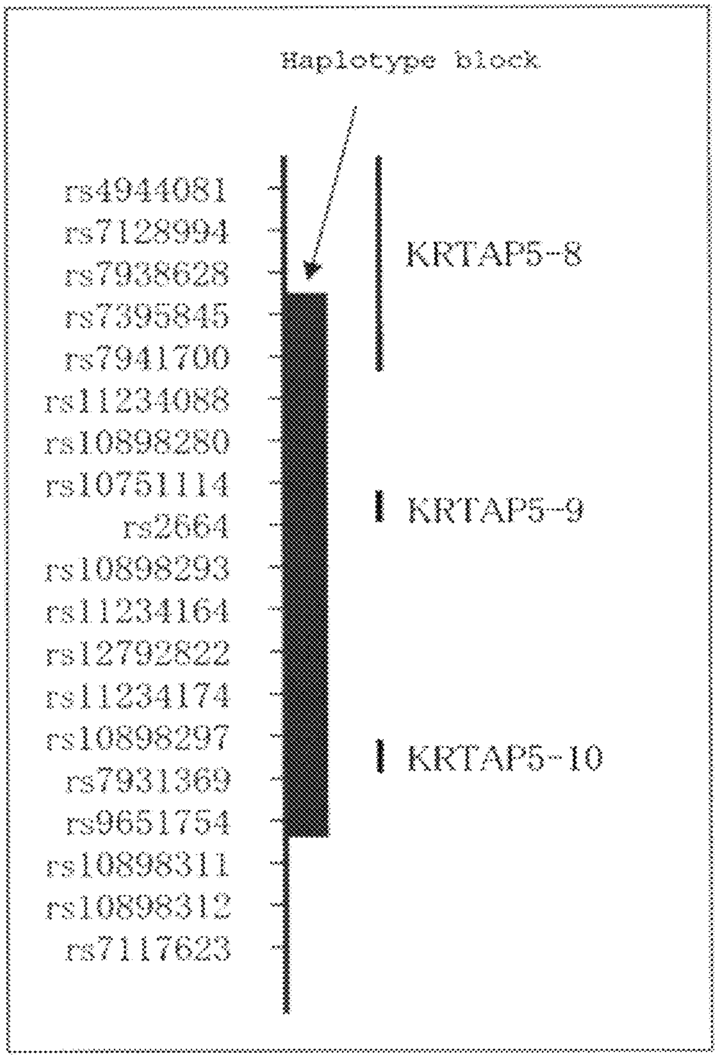
FIG. 9 is a conceptual diagram of a 35,979-bp haplotype block represented by a base sequence set forth in SEQ ID NO:5, which contains SNP: rs2664, and extends from SNP: rs7395845 to SNP: rs9651754.
Figures 1, 10:
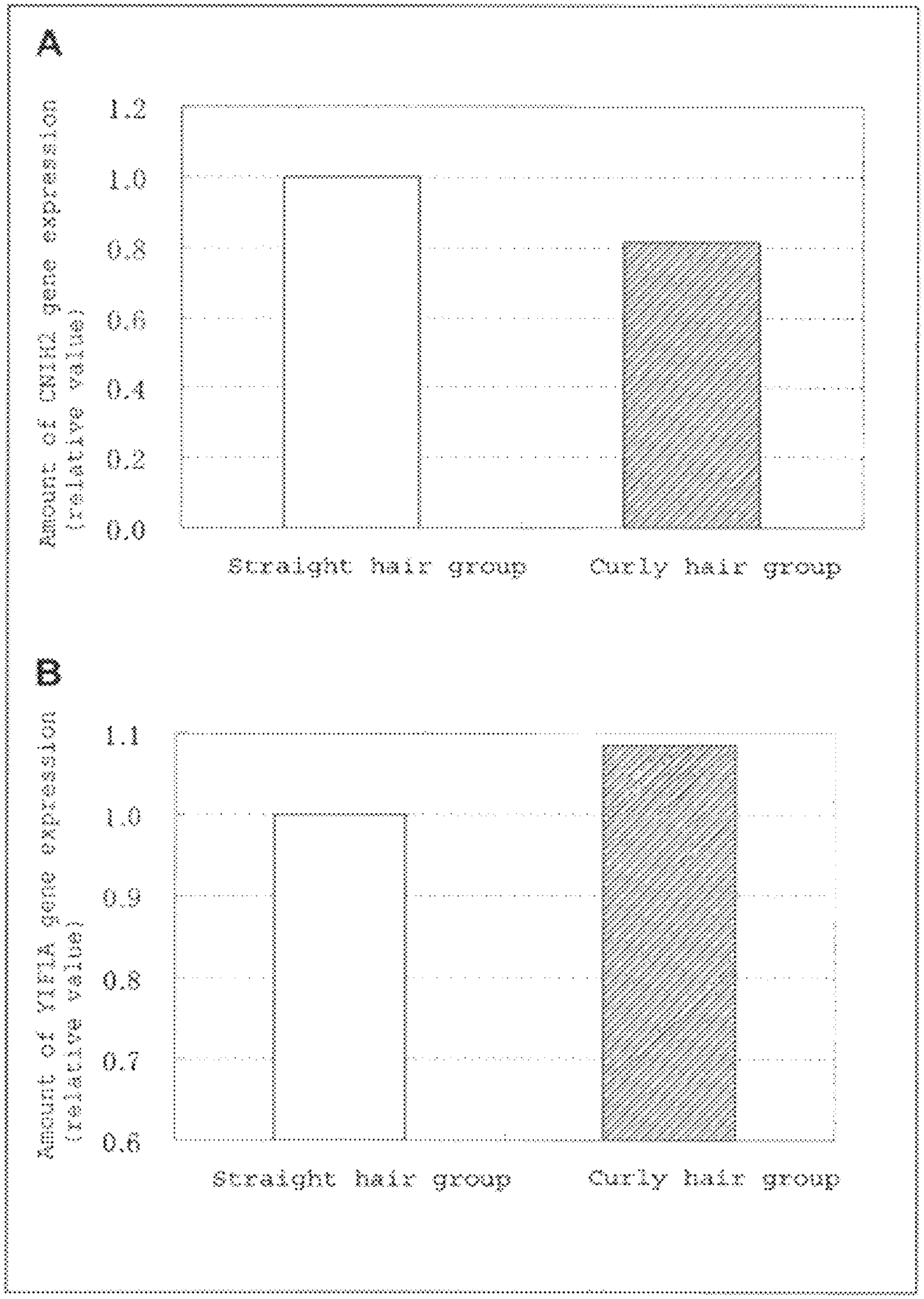
Figures 2, 10:
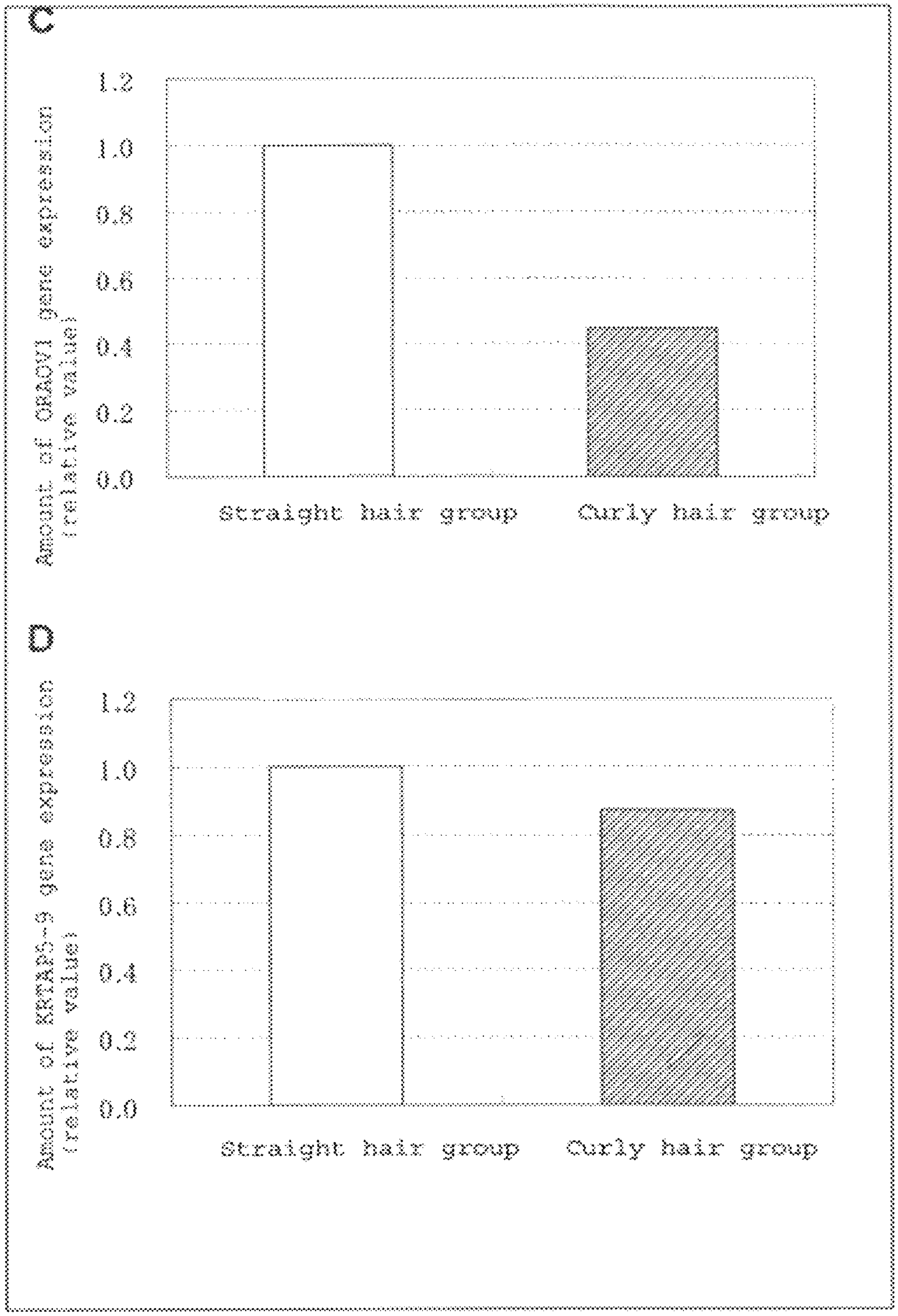

(5) A 35,979-bp haplotype block ranging from SNP: rs7395845 to SNP:rs9651754 containing SNP:rs2664, and represented by the base sequence set forth in SEQ ID NO:5 (FIG. 9). This haplotype block was a region containing KRTAP5-8 gene, KRTAP5-9 gene, and KRTAP5-10 gene. From this result, KRTAP5-8 gene, KRTAP5-9 gene, and KRTAP5-10 gene were identified as hair shape susceptibility genes.

Example 6

Identification of Hair Shape Susceptibility SNP Marker

While haplotype blocks were found in the haplotype analysis in Example 5, a haplotype was extracted from each of the haplotype blocks using the same Haploview 4.1 Software (Barrett, J C et al., Bioinformatics, 21 (2), 263-265, 2005). By comparing the respective nucleotide combinations of the extracted haplotypes, that is, the SNP marker groups, SNP loci that were linked to the hair shape susceptibility SNP marker loci were identified. The SNP loci thus identified can be identified as additional hair shape susceptibility SNP markers.

As a result, additional hair shape susceptibility SNP markers shown below were respectively found in the haplotype blocks of (1) to (5) shown in Example 4.

(1) 12,590-bp haplotype block represented by the base sequence set forth in SEQ ID NO:1: There were six principal haplotypes in this haplotype block (Table 8). As the SNP loci that are linked to a hair shape susceptibility SNP marker, SNP:rs2276299, additional two hair shape susceptibility SNP markers shown below were identified.

SNP:rs10792367 (single nucleotide polymorphism represented by Nucleotide Number 1 in the base sequence set forth in SEQ ID NO:1), and SNP:rs4149182 (single nucleotide polymorphism represented by Nucleotide Number 9315).

TABLE 8

| SNP marker | Nucleotide number in base sequence set forth in SEQ ID NO: 1 | Haplotype 1 | 2 | 3 | 4 | 5 | 6 | Hair shape susceptibility SNP |
|---|---|---|---|---|---|---|---|---|
| rs10792367 | 1 | C | C | G | G | G | G | ○ |
| rs2187384 | 2363 | C | C | T | C | C | C | |
| rs953894 | 3624 | C | C | T | C | T | T | |
| rs1004836 | 3670 | T | T | T | T | T | C | |
| rs11568491 | 4746 | | | | | | | |
| rs2276299 | 7633 | T | A | A | A | A | A | ○ (Example 4) |
| rs3793961 | 7872 | | | | | | | |
| rs4149182 | 9315 | C | C | G | C | G | G | ○ |
| rs11231299 | 12590 | G | G | A | G | G | G | |

(2) 202,111-bp haplotype block represented by the base sequence set forth in SEQ ID NO: 2: There were fourteen principal haplotypes in this haplotype block (Table 9-1 to Table 9-3). As SNP loci that are linked to a hair shape susceptibility SNP marker, SNP:rs11227447 and SNP: rs2282568, which is additional 34 hair shape susceptibility SNP markers shown below were identified.

SNP:rs11227403 (single nucleotide polymorphism represented by Nucleotide Number 1 in the base sequence set forth in SEQ ID NO:2), SNP:rs11607393 (single nucleotide polymorphism represented by Nucleotide Number 16722), SNP: rs3825067 (single nucleotide polymorphism represented by Nucleotide Number 19992), SNP:rs11227411 (single nucleotide polymorphism represented by Nucleotide Number 21051), SNP:rs10896081 (single nucleotide polymorphism represented by Nucleotide Number 21927), SNP:rs11227413 (single nucleotide polymorphism represented by Nucleotide Number 25269), SNP:rs11227415 (single nucleotide polymorphism represented by Nucleotide Number 27032), SNP: rs3862386 (single nucleotide polymorphism represented by Nucleotide Number 35997), SNP:rs9645684 (single nucleotide polymorphism represented by Nucleotide Number 49537), SNP:rs10896085 (single nucleotide polymorphism represented by Nucleotide Number 55405), SNP:rs918299 (single nucleotide polymorphism represented by Nucleotide Number 69180), SNP:rs7943911 (single nucleotide polymorphism represented by Nucleotide Number 84627), SNP: rs2177054 (single nucleotide polymorphism represented by Nucleotide Number 86185), SNP:rs10750778 (single nucleotide polymorphism represented by Nucleotide Number 90221), SNP:rs6591207 (single nucleotide polymorphism represented by Nucleotide Number 91247), SNP:rs10896091 (single nucleotide polymorphism represented by Nucleotide Number 92398), SNP:rs7946917 (single nucleotide polymorphism represented by Nucleotide Number 98150), SNP: rs10896094 (single nucleotide polymorphism represented by Nucleotide Number 100779), SNP:rs7941431 (single nucleotide polymorphism represented by Nucleotide Number 101730), SNP:rs2293121 (single nucleotide polymorphism represented by Nucleotide Number 102920), SNP: rs10791855 (single nucleotide polymorphism represented by Nucleotide Number 105310), SNP:rs512421 (single nucleotide polymorphism represented by Nucleotide Number 126741), SNP:rs2155201 (single nucleotide polymorphism represented by Nucleotide Number 133917), SNP:rs7925123 (single nucleotide polymorphism represented by Nucleotide Number 134786), SNP:rs2236651 (single nucleotide polymorphism represented by Nucleotide Number 142991), SNP: rs2236652 (single nucleotide polymorphism represented by Nucleotide Number 144254), SNP:rs476551 (single nucleotide polymorphism represented by Nucleotide Number 147896), SNP:rs10791861 (single nucleotide polymorphism represented by Nucleotide Number 150043), SNP:rs2298466 (single nucleotide polymorphism represented by Nucleotide Number 152853), SNP:rs10791863 (single nucleotide polymorphism represented by Nucleotide Number 168931), SNP: rs2155031 (single nucleotide polymorphism represented by Nucleotide Number 172500), SNP:rs2276036 (single nucleotide polymorphism represented by Nucleotide Number 175003), SNP:rs2298468 (single nucleotide polymorphism represented by Nucleotide Number 184535), and SNP: rs3814738 (single nucleotide polymorphism represented by Nucleotide Number 202111).

| SNP marker | Nucleotide number in base sequence set forth in SEQ ID NO: 2 | Haplotype 1 | 2 | 3 | 4 | 5 | 6 | 7 | 8 | 9 | 10 | 11 | 12 | 13 | 14 | Hair shape susceptibility SNP |
|---|---|---|---|---|---|---|---|---|---|---|---|---|---|---|---|---|
| Table 9-1 | | | | | | | | | | | | | | | | |
| rs11227403 | 1 | T | C | T | T | T | T | T | T | T | T | T | T | T | T | ○ |
| rs537497 | 7760 | A | G | G | G | A | G | G | A | G | A | G | G | G | G | |
| rs4930340 | 10763 | T | T | T | A | T | A | T | T | T | T | T | A | A | A | |
| rs17147325 | 14667 | A | A | A | G | A | G | A | A | A | A | A | G | G | G | |
| rs471203 | 16334 | G | G | A | G | G | G | A | G | A | G | G | G | G | G | |
| rs11607393 | 16722 | C | A | C | C | C | C | C | C | C | C | C | C | C | C | ○ |
| rs873491 | 18143 | G | G | G | A | G | A | G | G | G | G | G | A | G | A | |
| rs3825067 | 19992 | C | T | C | C | C | C | C | C | C | C | C | C | C | C | ○ |
| rs11227411 | 21051 | C | T | C | C | C | C | C | C | C | C | C | C | C | C | ○ |
| rs6591205 | 21066 | | | | | | | | | | | | | | | |
| rs10896081 | 21927 | A | T | A | A | A | A | A | A | A | A | A | A | A | A | ○ |
| rs11227413 | 25269 | G | A | G | G | G | G | G | G | G | G | G | G | G | G | ○ |
| rs11227415 | 27032 | T | C | T | T | T | T | T | T | T | T | T | T | T | T | ○ |
| rs1211863 | 27747 | | | | | | | | | | | | | | | |
| rs524281 | 28235 | A | C | C | A | A | A | C | A | C | A | C | A | A | A | |
| rs526852 | 33005 | A | G | G | G | A | G | G | A | G | A | G | G | G | G | |
| rs3862386 | 35997 | G | C | G | G | G | G | G | G | G | G | G | G | G | G | ○ |
| rs7121996 | 39216 | | | | | | | | | | | | | | | |
| rs549187 | 40204 | G | A | A | G | G | G | A | G | A | G | A | G | G | G | |
| rs7941469 | 41725 | C | T | T | C | C | C | T | C | T | C | C | C | C | C | |
| rs527897 | 42350 | G | A | A | G | G | G | A | G | A | G | A | G | G | G | |
| rs535395 | 48107 | G | A | A | G | G | G | A | G | A | G | G | G | G | G | |
| rs486311 | 48815 | A | T | T | T | A | T | T | A | T | A | T | T | A | T | |
| rs9645684 | 49537 | G | A | G | G | G | G | G | G | G | G | G | G | G | G | ○ |
| rs471709 | 50433 | | | | | | | | | | | | | | | |
| rs540943 | 51702 | | | | | | | | | | | | | | | |
| rs7109823 | 51946 | | | | | | | | | | | | | | | |
| rs17147371 | 54097 | A | A | A | C | A | C | A | A | A | C | A | C | A | C | |
| rs565198 | 55081 | T | A | A | T | T | T | A | T | A | T | T | T | T | T | |
| Table 9-2 | | | | | | | | | | | | | | | | |
| rs10896085 | 55405 | A | T | A | A | A | A | A | A | A | A | A | A | A | A | ○ |
| rs801741 | 58657 | T | T | T | C | C | C | T | T | T | T | T | C | C | C | |
| rs561373 | 63637 | A | T | T | T | T | T | T | A | T | A | A | T | T | T | |
| rs801739 | 64162 | A | A | G | G | G | G | G | A | G | G | A | G | G | G | |
| rs1115508 | 64722 | T | T | T | C | C | C | T | T | T | C | T | C | C | C | |
| rs918299 | 69180 | C | T | C | C | C | C | C | C | C | C | C | C | C | C | ○ |
| rs526200 | 69346 | G | T | T | T | T | T | T | G | T | T | G | T | T | T | |
| rs801736 | 70003 | A | A | A | T | T | T | A | A | A | T | A | T | T | T | |
| rs534489 | 72240 | A | G | G | G | G | G | G | A | G | G | A | G | G | G | |
| rs708472 | 72563 | A | A | A | G | G | G | A | A | A | G | A | G | G | G | |
| rs801734 | 72789 | T | T | T | C | C | C | T | T | T | C | T | C | C | C | |
| rs541954 | 75941 | | | | | | | | | | | | | | | |
| rs7943911 | 84627 | G | A | G | G | G | G | G | G | G | G | G | G | G | G | ○ |
| rs7123153 | 85220 | A | G | G | G | G | G | G | A | G | A | A | G | G | G | |
| rs2177054 | 86185 | C | A | C | C | C | C | C | C | C | C | C | C | C | C | ○ |
| rs6591206 | 88001 | | | | | | | | | | | | | | | |
| rs10750778 | 90221 | T | C | T | T | T | T | T | T | T | T | T | T | T | T | ○ |
| rs6591207 | 91247 | T | A | T | T | T | T | T | T | T | T | T | T | T | T | ○ |
| rs10896091 | 92398 | T | C | T | T | T | T | T | T | T | T | T | T | T | T | ○ |
| rs580891 | 96254 | T | G | G | T | T | T | G | T | G | T | T | G | T | T | |
| rs7946917 | 98150 | A | G | A | A | A | A | A | A | A | A | A | A | A | A | ○ |
| rs17307346 | 98576 | A | A | A | C | A | A | A | A | A | A | A | A | A | C | |
| rs10896094 | 100779 | C | T | C | C | C | C | C | C | C | C | C | C | C | C | ○ |
| rs7941431 | 101730 | G | A | G | G | G | G | G | G | G | G | G | G | G | G | ○ |
| rs2293121 | 102920 | T | C | T | T | T | T | T | T | T | T | T | T | T | T | ○ |
| rs10791854 | 105116 | | | | | | | | | | | | | | | |
| rs10791855 | 105310 | A | G | A | A | A | A | A | A | A | A | A | A | A | A | ○ |
| rs7942894 | 118098 | T | C | C | T | T | T | C | T | C | T | T | T | T | T | |
| rs3016319 | 123419 | C | C | C | T | T | T | C | T | C | C | C | T | T | T | |
| rs512421 | 126741 | G | A | G | G | G | G | G | G | G | G | G | G | G | G | ○ |
| Table 9-3 | | | | | | | | | | | | | | | | |
| rs3741370 | 131331 | G | G | G | T | G | T | G | T | G | G | G | T | G | T | |
| rs9326370 | 133581 | T | T | C | C | C | C | C | C | C | T | T | C | C | C | |
| rs2155201 | 133917 | T | C | T | T | T | T | T | T | T | T | T | T | T | T | ○ |
| rs7925123 | 134786 | G | C | G | G | G | G | G | G | G | G | G | G | G | G | ○ |
| rs4930346 | 135252 | G | A | A | A | A | A | A | A | A | G | G | A | A | A | |
| rs559298 | 140330 | | | | | | | | | | | | | | | |
| rs3782081 | 140505 | C | C | C | T | C | T | C | T | C | C | C | T | C | T | |
| rs2236651 | 142991 | C | T | C | C | C | C | C | C | C | C | C | C | C | C | ○ |

-continued

| SNP marker | Nucleotide number in base sequence set forth in SEQ ID NO: 2 | Haplotype 1 | 2 | 3 | 4 | 5 | 6 | 7 | 8 | 9 | 10 | 11 | 12 | 13 | 14 | Hair shape susceptibility SNP |
|---|---|---|---|---|---|---|---|---|---|---|---|---|---|---|---|---|
| rs10896104 | 143442 | C | C | C | T | T | T | C | T | C | C | C | T | T | T | |
| rs2236652 | 144254 | G | A | G | G | G | G | G | G | G | G | G | G | G | G | ○ |
| rs476551 | 147896 | G | C | G | G | G | G | G | G | G | G | G | G | G | G | ○ |
| rs10791861 | 150043 | G | A | G | G | G | G | G | G | G | G | G | G | G | G | ○ |
| rs2298466 | 152853 | T | C | T | T | T | T | T | T | T | T | T | T | T | T | ○ |
| rs2155198 | 155873 | C | T | C | C | C | C | T | C | T | C | C | C | C | C | |
| rs10791863 | 168931 | C | T | C | C | C | C | C | C | C | C | C | C | C | C | ○ |
| rs2155031 | 172500 | C | T | C | C | C | C | C | C | C | C | C | C | C | C | ○ |
| rs474005 | 174874 | C | C | C | T | T | T | C | T | C | C | C | T | T | T | |
| rs2276036 | 175003 | C | T | C | C | C | C | C | C | C | C | C | C | C | C | ○ |
| rs3814739 | 177552 | C | T | T | T | T | T | T | T | T | C | C | T | T | T | |
| rs524859 | 182652 | G | G | G | G | A | G | G | G | G | G | G | G | A | G | |
| rs1151540 | 183380 | A | A | A | C | C | C | A | C | A | A | A | C | C | C | |
| rs2298468 | 184535 | G | A | G | G | G | G | G | G | G | G | G | G | G | G | ○ |
| rs11227447 | 189853 | G | C | G | G | G | G | G | G | G | G | G | G | G | G | ○ (Example 4) |
| rs2282568 | 194405 | C | G | C | C | C | C | C | C | C | C | C | C | C | G | ○ (Example 4) |
| rs556595 | 199655 | T | T | G | G | G | G | T | G | G | T | T | G | G | G | |
| rs3814738 | 202111 | G | T | G | G | G | G | G | G | G | G | G | G | G | G | ○ |

(3) 18,933-bp haplotype block represented by the base sequence set forth in SEQ ID NO:3: There were six principal haplotypes in this haplotype block (Table 10). As a SNP locus that is linked to hair shape susceptibility SNP markers, SNP: rs3741367 and SNP:rs3741368, additional one hair shape susceptibility SNP marker shown below was identified.

SNP:rs523583 (single nucleotide polymorphism represented by Nucleotide Number 5297 in the base sequence set forth in SEQ ID NO:3).

TABLE 10

| SNP marker | Nucleotide number in base sequence set forth in SEQ ID NO: 3 | Haplotype 1 | 2 | 3 | 4 | 5 | 6 | Hair shape susceptibility SNP |
|---|---|---|---|---|---|---|---|---|
| rs531784 | 1 | C | T | T | T | T | C | |
| rs479315 | 142 | C | G | G | G | G | C | |
| rs4930351 | 1815 | A | A | G | G | G | A | |
| rs4930352 | 2144 | G | G | T | T | T | G | |
| rs523583 | 5297 | A | A | C | A | A | A | ○ |
| rs1625595 | 13280 | T | T | C | C | T | C | |
| rs3741367 | 18280 | T | T | C | T | T | T | ○ (Example 4) |
| rs3741368 | 18933 | G | G | A | G | G | G | ○ (Example 4) |

(4) 27,375-bp haplotype block represented by the base sequence set forth in SEQ ID NO:4: There were four principal haplotypes in this haplotype block (Table 11). As SNP loci that are linked to a hair shape susceptibility SNP marker SNP:rs1789165, additional six hair shape susceptibility SNP markers shown below were identified.

SNP:rs10796828 (single nucleotide polymorphism represented by Nucleotide Number 8378 in the base sequence set forth in SEQ ID NO:4), SNP:rs1789172 (single nucleotide polymorphism represented by Nucleotide Number 12624 in the base sequence set forth in SEQ ID NO:4), SNP:rs1192921 (single nucleotide polymorphism represented by Nucleotide Number 20147 in the base sequence set forth in SEQ ID NO:4), SNP:rs1192923 (single nucleotide polymorphism represented by Nucleotide Number 22309 in the base sequence set forth in SEQ ID NO:4), SNP:rs1192924 (single nucleotide polymorphism represented by Nucleotide Number 24512 in the base sequence set forth in SEQ ID NO:4), and SNP:rs1789168 (single nucleotide polymorphism represented by Nucleotide Number 26599 in the base sequence set forth in SEQ ID NO:4).

TABLE 11

| SNP marker | Nucleotide number in base sequence set forth in SEQ ID NO: 4 | Haplotype 1 | 2 | 3 | 4 | Hair shape susceptibility SNP |
|---|---|---|---|---|---|---|
| rs1789165 | 1 | A | G | A | G | ○ (Example 4) |
| rs1789167 | 4276 | G | A | G | G | |
| rs1789164 | 7195 | G | C | G | G | |
| rs10796828 | 8378 | G | T | G | T | ○ |
| rs1789172 | 12624 | T | C | T | C | ○ |
| rs12284226 | 14644 | | | | | |
| rs6606651 | 16324 | | | | | |
| rs12278346 | 16388 | | | | | |
| rs4441044 | 18395 | A | G | A | A | |
| rs1210223 | 19530 | C | G | G | C | |
| rs1192921 | 20147 | G | C | G | C | ○ |
| rs1192923 | 22309 | A | T | A | T | ○ |
| rs1192924 | 24512 | T | C | T | C | ○ |
| rs1789168 | 26599 | T | C | T | C | ○ |
| rs1789170 | 27375 | G | A | G | G | |

(5) 35,979-bp haplotype block represented by base sequence set forth in SEQ ID NO:5: There were six principal haplotypes in this haplotype block (Table 12). As SNP loci that are linked to a hair shape susceptibility SNP marker SNP:rs2664, additional six hair shape susceptibility SNP markers shown below were identified.

SNP:rs7934055 (single nucleotide polymorphism represented by Nucleotide Number 18895 in the base sequence set forth in SEQ ID NO:5), SNP:rs17363723 (single nucleotide polymorphism represented by Nucleotide Number 26143 in the base sequence set forth in SEQ ID NO:5), SNP: rs11234174 (single nucleotide polymorphism represented by Nucleotide Number 26545 in the base sequence set forth in SEQ ID NO:5), SNP:rs10792781 (single nucleotide polymorphism represented by Nucleotide Number 27090 in the base sequence set forth in SEQ ID NO:5), SNP:rs7107678 (single nucleotide polymorphism represented by Nucleotide Number 27751 in the base sequence set forth in SEQ ID NO:5), and SNP:rs7106362 (single nucleotide polymorphism represented by Nucleotide Number 30274 in the base sequence set forth in SEQ ID NO:5).

| SNP marker | Nucleotide number in base sequence set forth in SEQ ID NO: 5 | Haplotype 1 | 2 | 3 | 4 | 5 | 6 | Hair shape susceptibility SNP |
|---|---|---|---|---|---|---|---|---|
| Table 12-1 | | | | | | | | |
| rs7395845 | 1 | C | A | A | A | A | A | |
| rs11600364 | 329 | T | C | C | C | C | C | |
| rs7941700 | 3851 | G | A | A | A | A | A | |
| rs7926544 | 4100 | A | G | G | G | G | G | |
| rs11234079 | 5311 | G | G | T | G | G | G | |
| rs11234088 | 7947 | G | G | T | G | G | G | |
| rs11234092 | 8532 | C | C | A | A | C | C | |
| rs7940512 | 8632 | C | T | C | C | C | T | |
| rs10736764 | 9720 | G | A | G | G | G | A | |
| rs10898276 | 9941 | A | G | G | G | A | G | |
| rs7951558 | 10846 | C | T | C | C | C | T | |
| rs7933199 | 10978 | C | G | C | C | C | G | |
| rs11234102 | 11882 | A | C | C | C | A | C | |
| rs10898280 | 11898 | C | A | C | C | C | A | |
| rs10792768 | 13485 | T | T | A | A | T | T | |
| rs10898282 | 14329 | A | G | G | G | A | A | |
| rs10751114 | 15755 | G | A | A | A | G | G | |
| rs760420 | 16259 | C | C | T | C | C | C | |
| rs10792769 | 16579 | A | A | G | G | A | A | |
| rs2664 | 17000 | C | T | C | C | C | C | ○ (Example 4) |
| rs2663 | 17053 | A | G | G | G | A | A | |
| rs2665 | 17105 | T | T | A | A | T | T | |
| rs10792770 | 17605 | T | C | C | C | T | T | |
| rs7358341 | 17835 | G | T | T | T | G | G | |
| rs10792774 | 18020 | G | G | T | T | G | G | |
| rs11604725 | 18407 | T | C | C | C | T | T | |
| rs10898286 | 18762 | C | G | G | G | C | C | |
| rs7934055 | 18895 | G | T | G | G | G | G | ○ |
| rs4129754 | 19446 | C | A | A | A | C | C | |
| rs4129753 | 19708 | G | A | A | A | G | G | |
| rs7949169 | 20135 | T | C | C | C | T | T | |
| rs10792777 | 20858 | C | T | T | T | C | C | |
| rs10898288 | 21495 | A | G | G | G | A | A | |
| rs10898289 | 21527 | T | C | C | C | T | T | |
| rs10898290 | 21678 | C | T | T | T | C | C | |
| rs11234149 | 21845 | G | T | T | T | G | G | |
| rs11234150 | 21894 | C | C | T | T | C | C | |
| rs10898293 | 22901 | T | C | C | C | T | T | |
| rs10792779 | 24300 | G | T | T | T | G | G | |
| rs11234164 | 25011 | T | C | C | T | T | T | |
| rs17363672 | 25026 | C | G | G | C | C | C | |
| rs12790712 | 25260 | A | G | G | G | A | A | |
| rs12792822 | 25276 | G | A | A | A | G | G | |
| Table 12-2 | | | | | | | | |
| rs12798817 | 25612 | C | T | C | T | C | C | |
| rs17363723 | 26143 | A | G | A | A | A | A | ○ |
| rs11234174 | 26545 | G | A | G | G | G | G | ○ |
| rs10792781 | 27090 | T | C | T | T | T | T | ○ |
| rs7107678 | 27751 | A | G | A | A | A | A | ○ |
| rs10898297 | 28001 | A | A | T | A | A | A | |
| rs7106362 | 30274 | C | T | C | C | C | C | ○ |
| rs7931369 | 35218 | T | C | T | C | T | T | |
| rs9651754 | 35979 | A | T | A | T | A | A | |

Example 7

Analysis of Gene Expression in Scalp Hair Roots in Curly Hair People and Straight Hair People Ten curly hair people and ten straight hair people were collected according to the classifications of Example 1, and an analysis was carried out on the expression of the hair shape susceptibility gene in the scalp hair roots of each test subject. In regard to the collection of specimens from the test subjects, an approval was granted in advance by the ethics committee, subsequently the person in charge of the implementation of informed consent explained the contents of the study to the objects using a written explanation, and written consent was obtained.

About 60 scalp hair strands per person were pulled out from all over the whole head of each test subject, and only those scalp hair root parts that were determined to be in the growth period from the shape of the hair root part, were collected in a petri dish filled with ice-cooled PBS (manufactured by Invitrogen, Inc.). Under a stereoscopic microscope and using forceps and a needle teeth, the outer hair root sheath and the inner hair root sheath were removed from the hair root part as much as possible, and the hair root of the hair shaft only (hair shaft keratinized region) was separated and prepared. The hair shaft keratinized region was introduced in a 1.5-mL tube containing 0.5 mL of an RNA extraction solution, ISOGEN (manufactured by Nippon Gene Co., Ltd.), and the tissue was sufficiently crushed with a mini codeless grinder and a homogenization pestle. 0.5 mL of ISOGEN and 200 μl of chloroform were added thereto, and the mixture was sufficiently stirred in a vortex mixer and then was centrifuged (15000 rpm, for 15 minutes) using a small-sized microcentrifuge. Thus, about 500 μL of an aqueous phase containing RNA was collected. 50 μL of 3 M sodium acetate and 1 μL of Ethachinmate (manufactured by Nippon Gene Co., Ltd.) were added to the collected solution, and the mixture was sufficiently stirred. Furthermore, 1 mL of isopropanol was added and stirred, and the mixture was centrifuged (15000 rpm, for 20 minutes) with a small-sized microcentrifuge to precipitate total RNA. The supernatant was discarded, and then 75% ethanol was added to the precipitate. The mixture was centrifuged again (15000 rpm, for 10 minutes) with a small-sized microcentrifuge. The supernatant was discarded, and the precipitate was dried in air and was dissolved in 20 μL of Nuclease-free Water (manufactured by Invitrogen, Inc.). A portion of this was used to measure the RNA concentration using an absorption spectrometer (GeneQuant: manufactured by Pharmacia AB, or NonoDrop: manufactured by Nanodrop Technologies, Inc.), or RiboGreen RNA Reagent and Kit (manufactured by Invitrogen, Inc.). cDNA was synthesized from 1 μg of the total RNA thus obtained using QuantiTect Reverse Transcription Kit (manufactured by Qiagen N.V.) according to the attached protocol, and the cDNA was used in the quantification of the amount of gene expression by PCR.

The quantification of the amount of gene expression was carried out using TaqMan (registered trademark) Gene Expression Assays manufactured by Applied Biosystems, Inc. (ABI). According to the attached protocol, the synthesized cDNA, a primer & probe set specific to the gene to be detected and quantified, a real-time PCR reagent and the like (manufactured by ABI) were mixed, and fragments of the gene to be detected and quantified were amplified with Applied Biosystems 7500 Real-Time PCR System (manufactured by ABI). At this time, real-time PCR was carried out in the same manner using a known cDNA derived from a standard hair shaft keratinized region sample, and a calibration curve was produced. Thus, standardization of the amount of gene expression was carried out. Furthermore, standardization of the amount of expression of the gene to be detected and quantified was carried out using GAPDH gene as an internal standard, and also employing KRT31 gene and KRT85 gene, which is recognized to be uniformly expressed in the sample hair shaft keratinized region, as internal standards.

In order to detect and quantify the amount of expression of CNIH2 gene, Assay Number Hs00704421_s1 of TaqMan Gene Expression Assays (manufactured by ABI) was used as a specific primer & probe set.

In order to detect and quantify the amount of expression of YIF1A gene, Assay Number Hs00610969_g1 of TaqMan Gene Expression Assays (manufactured by ABI) was used as a specific primer & probe set.

In order to detect and quantify the amount of expression of ORAOV1 gene, Assay Number Hs00411598_m1 of TaqMan Gene Expression Assays (manufactured by ABI) was used as a specific primer & probe set.

In order to detect and quantify the amount of expression of KRTAP5-91 gene, Assay Number Hs00534357_s1 of TaqMan Gene Expression Assays (manufactured by ABI) was used as a specific primer & probe set.

The amounts of expression of the hair shape susceptibility genes in the scalp hair roots of the curly hair group and the straight hair group are presented in FIG. 10A to FIG. 10D. From the results shown in FIG. 10, decreases in the amount of expression of CNIH2 gene, ORAOV1 gene and KRTAP5-9 gene were observed and an increase in the amount of expression of YIF1A gene was observed in the curly hair group, as compared with the straight hair group. Therefore, it was made clear that CNIH2 gene, YIF1A gene, ORAOV1 gene and KRTAP5-9 gene are hair shape susceptibility genes serving as indicators for the evaluation of hair shape, and the measurement of the amounts of expression of these genes in the hair root area is valuable.

Example 8

Screening of Substance Regulating Amount of Expression of Hair Shape Susceptibility Gene Normal human neonatal foreskin epidermal keratinocytes (KK-4009, manufactured by Kurabo Industries, Ltd.) were used in the screening. Normal human neonatal foreskin epidermal keratinocytes in a frozen state were melted, and then the cells were seeded in a 75-$cm^2$ flask or a 25-$cm^2$ flask at a density of 2500 cells/$cm^2$. The cells were cultured in a serum-free medium for human keratinocyte culture (Defined Keratinocyte-SFM, manufactured by Invitrogen, Inc.) containing added supplements, under the conditions of 37° C. and a $CO_2$ concentration of 5%. The cells were subcultured at the time point at which the cells reached a sub-confluent state, and the cells were seeded in a 6-well plate at a cell density of 2500 cells/$cm^2$. At the time point at which the cells had reached a sub-confluent state (Day 0), the medium was exchanged to a serum-free medium for human keratinocyte culture containing no supplements, and the cells on Day 1 were used as the cells for screening.

To the medium (serum-free medium for human keratinocyte culture containing no supplements) for the cells for screening prepared as described above, a plant extract was added to a final concentration of 0.1% or 1%, and the cells were cultured for 24 hours under the conditions of 37° C. and a $CO_2$ concentration of 5%. Furthermore, as control, 50% ethanol (control) was similarly added to a final concentration of 0.1% or 1%, and the cells were cultured.

After completion of the culture (Day 2), the medium was removed by suction, the cells were washed two times with PBS (manufactured by Invitrogen, Inc.), and then 1 mL per well of ISOGEN (manufactured by Nippon Gene Co., Ltd.) was added to the cells. The cells were sufficiently lysed and mixed through pipetting, and the solution was collected in a 1.5-mL tube. Total RNA was extracted by the same method as the method described in Example 7, and cDNA for use in the quantification of the amount of gene expression by PCR was obtained. The quantification of the amount of expression of the hair shape susceptibility gene was also carried out by the method described in Example 7.

In regard to the determination criteria for a substance that regulates the amount of expression of a gene, for example, if the amount of gene expression is higher by 10%, preferably 30%, and more preferably 50% or more, as compared with the control, the amount of expression is then said to be significantly high, and the test substance can be selected as an expression promoting agent for the hair shape susceptibility gene. Furthermore, for example, if the amount of gene expression is lower by 10%, preferably 30%, and more preferably 50% or more, as compared with the control, the amount of expression is then said to be significantly low, and the test substance can be selected as an expression suppressant for the hair shape susceptibility gene.

Approximately 700 kinds of plant extracts were evaluated by the screening system described above, and a search was made for substances that regulate the amount of expression of the hair shape susceptibility gene. As a result, expression promoting agents and expressing agents for the genes were respectively found as indicated in Table 13.

TABLE 13

Substances that regulate the amounts of expression of the hair shape susceptibility genes

| | Name of plant extract | |
|---|---|---|
| | | Amount of CNIH2 gene expression (relative to control as 1) |
| Expression promoting agent | *Aristolochia manshuriensis* Kom. (stem extract) | 3.08 |
| | *Asclepias curassavica* (root extract) | 2.31 |
| | *Ipomoea purpurea* (morning glory) (seed extract | 1.81 |
| Expression suppressing agent | *Raphanus sativus* (seed extract) | 0.48 |
| | *Aster tataricus* (root extract) | 0.33 |
| | *Agastache rugosa* (whole plant extract) | 0.20 |
| | | Amount of YIF1A gene expression (relative to control as 1) |
| Expression promoting agent | *Hydnocarpus anthelmintica* (seed extract) | 2.80 |
| | *Rosa rugosa* (flower extract) | 2.36 |
| | *Sassafras albidum* (bark extract)) | 1.92 |
| Expression suppressing agent | *Amomum cardamomum* (round cardamom) (seed extract) | 0.70 |
| | *Forsythia suspensa* (fruit extract) | 0.52 |
| | *Ligustrum robustum* (leaf extract) | 0.45 |

TABLE 13-continued

| Substances that regulate the amounts of expression of the hair shape susceptibility genes | | |
|---|---|---|
| | Name of plant extract | Amount of ORAOV1 gene expression (relative to control as 1) |
| Expression promoting agent | *Benthamidia florida* (bark extract) | 2.66 |
| | *Solidago virgaurea* (whole plant extract) | 1.86 |
| | *Amomum cardamomum* (round cardamom) (seed extract) | 1.41 |
| Expression suppressing agent | *Hibiscus rosa-sinensis* (flower extract) | 0.53 |
| | *Thamnolia vermicularis* (thallus extract) | 0.39 |
| | *Stellera chamaejasme* (root extract) | 0.25 |

Reference Example

Relations Between Hair Shape and Form of Hair Follicle

In general, the hair shape varies with the human races, and the people of the Asian race relatively more frequently have straight hair, while the people of the African race mainly have kinky hair (or curled hair). A large proportion of the people of the Indo-European race have a trait of wavy hair (wave hair) which is intermediate of the two. As a feature related to such variation of hair shape, the form of the hair follicle at the hair root part may be mentioned. That is, if the form of the hair follicle is curved, the hair is curved, and if the form of the hair follicle is straight, the hair is straight (Thibaut, S. at al., Br. J. Dermatol., 152(4), p. 632-638, 2005).

In order to investigate the relations between the hair shape and the form of the hair follicle in more detail, tissue specimens of hair follicle were produced from the human scalp tissues of various races, and the form of the hair follicle was observed. Meanwhile, in regard to the collection of specimens from the test subjects, an approval was granted in advance by the ethics committee, subsequently the person in charge of the implementation of informed consent explained the contents of the study to the objects using a written explanation, and written consent was obtained. The collected hair follicles were frozen after being embedded in Tissue-Tek OCT Compound (manufactured by Miles Laboratories, Inc.), which is an embedding medium for frozen tissue section preparation, and frozen section specimens were produced according to a standard method. Subsequently, the specimens were subjected to HE staining, and were observed with a microscope.

Figure 11:
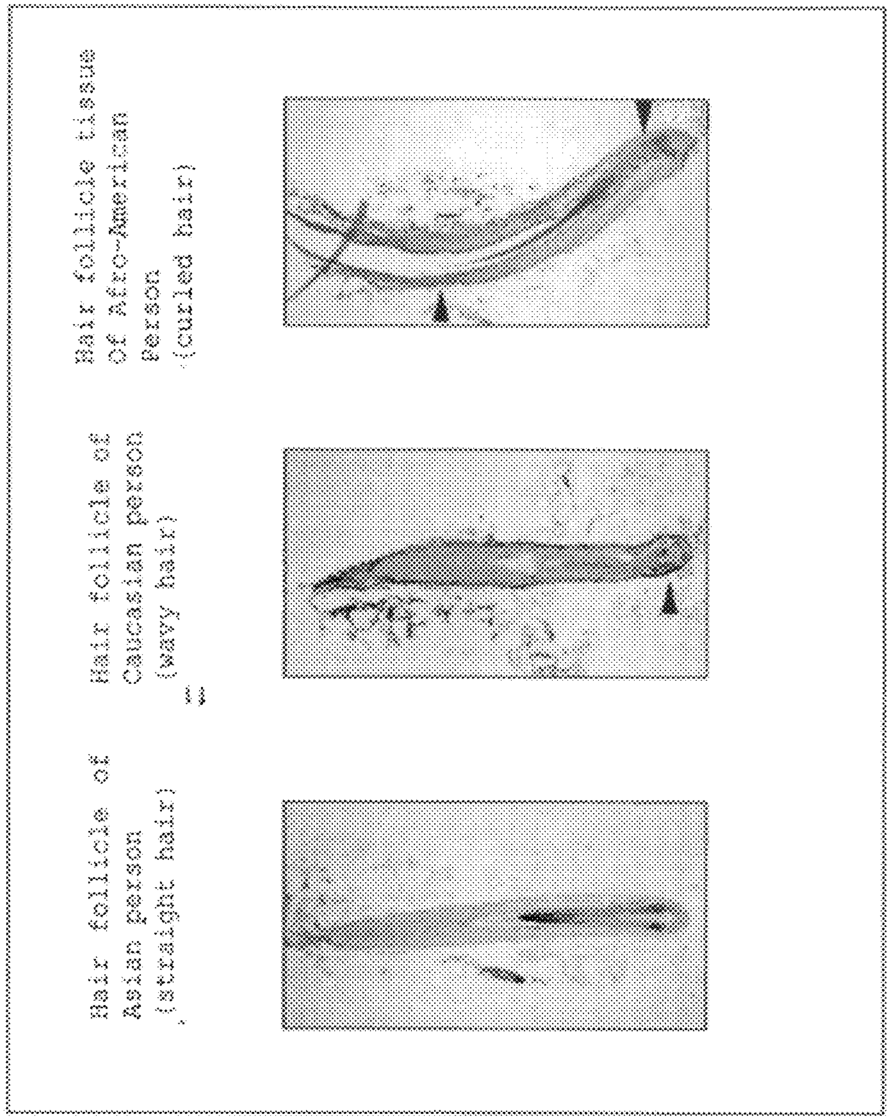
FIG. 11 is a set of photographs showing the images of hair follicle tissue of various human races, while the arrows indicate curved regions.

FIG. 11 presents images of the hair follicle tissue of various human races. As can be seen from the results shown in FIG. 11, the hair follicle of an Asian person having straight hair was straight, while the hair follicle of a Caucasian person having wavy hair was bent only at the lowermost part of the hair root. Furthermore, in the case of an Afro-American having curled hair, it was found that the entire hair follicle tissue was curved. Therefore, it could be confirmed that the hair shape and the form of the hair follicle were closely related to each other.

Example 9

Evaluation of Form of Hair Follicle Through Culture of Human Hair Follicle Organ As a method for evaluating the hair shape and the form of the hair follicle, an investigation was conducted on an evaluation method based on the culture of the human hair follicle organ. The scalp tissues of the temporal region or the occipital region of men and women in the age of 30's to 80's, which had been excised by cosmetic plastic surgery and became unnecessary, were obtained and used in the experiment. Meanwhile, in regard to the collection of specimens, an approval was granted in advance by the ethics committee, subsequently the surgeon explained the contents of the study to the objects using a written explanation, and written consent was obtained.

The human scalp tissue thus obtained was recovered in a petri dish filled with Williams' E medium (manufactured by Sigma-Aldrich Company) containing 1% of antibiotic/antifungal agents (manufactured by Invitrogen, Inc.). The hair follicles were aseptically isolated one by one under a stereoscopic microscope and using forceps and a scalpel or a needle teeth. The isolated hair follicles were separated from the epidermal tissue at the position of the lower part of the sebaceous gland, and any extra connective tissue, adipocytes and the like attached to the lower part of the hair follicle, were removed as much as possible. The isolated hair follicles thus prepared were transferred, one hair follicle per well, onto a 24-well plate to which Williams' E medium (manufactured by Sigma-Aldrich Company) containing 400 μL of 10 μg/mL insulin (manufactured by Invitrogen, Inc.), 40 ng/mL of hydrocortisone (manufactured by Sigma-Aldrich Company), 2 mM L-glutamine (manufactured by Invitrogen, Inc.), and 1% antibiotic/antifungal agents (manufactured by Invitrogen, Inc.) had been added, and culture was initiated. The culture was carried out in the manner of suspension culture, under the conditions of 37° C. and a $CO_2$ concentration of 5%. Thereafter, the medium was exchanged at an interval of 2 to 3 days, and at the same time, photographs of the hair follicles were taken.

Figure 12:
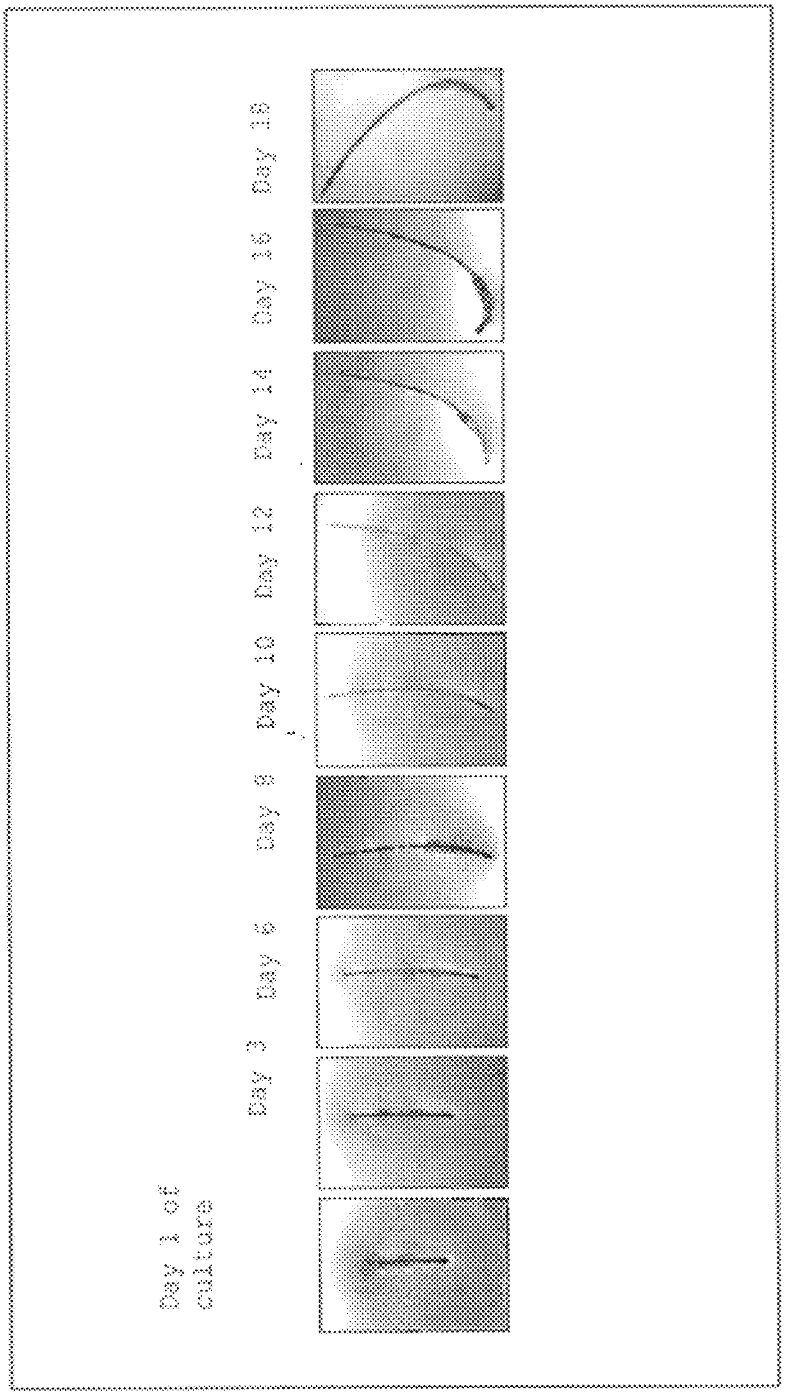
FIG. 12 is a set of photographs showing the changes in the shape of a hair follicle during culturing in a human hair follicle organ culture system.

The photographs of the change in the form of the hair follicle during culturing days are presented in FIG. 12. The hair shaft in the hair follicle grew with the progress of the culture, and thereby elongated. Furthermore, along with the progress of the culture, it was observed that the hair follicle was straight (straight hair) after one day from the initiation of culture (Day 1), but the hair follicle (hair shaft) was gradually curved with the culturing days.

In order to quantify the degree of curvature of the hair follicle (hair shaft), the ratio of end-to-end distance was calculated. The ratio of end-to-end distance is one of the indices representing the degree of curl, and can be determined by the following calculation (Hrdy, D., Am. J. Phys. Anthropol., 39(1), p. 7-17, 1973).

Straight length between the ends of the object (hair, hair follicle)/curve length along the axis of the object (hair or hair follicle)

That is, according to the formula shown above, the ratio of end-to-end distance represents a value between 0 and 1, so that a straight object gives a value close to 1, and an object with a large degree of curvature gives a value close to zero (0).

The photographs of the hair follicles shown in FIG. 12 were analyzed using an image analyzing software (Nexus NewQube Ver. 4.23, manufactured by IMAX Systems, Inc.), and the length of the hair follicle (hair shaft) and the ratio of end-to-end distance were determined (Table 14).

As a result, it could be confirmed that the hair follicle (hair shaft) elongated with the culturing days, and at the same time, the hair follicle was gradually being curved. Therefore, it was found that when this evaluation system is used, search for an agent for curling of hair, or a curly hair ameliorating agent (hair straightening agent) can be conducted. That is, a test substance is added to the evaluation system of human hair follicle organ culture, the hair follicle organ is cultured, and the ratio of end-to-end distance of the hair follicle (hair shaft) which has elongated to a certain length is measured. When the hair follicle is cultured in the presence of a test substance, if the ratio of end-to-end distance becomes smaller as compared with a control cultured without adding the test substance, the test substance can be selected as a hair curling agent. When the hair follicle is cultured in the presence of a test substance, if the ratio of end-to-end distance becomes larger as compared with a control cultured without adding the test substance, the test substance can be selected as a curly hair ameliorating agent (hair straightening agent).

TABLE 14

Changes in the length of hair follicle (hair shaft) and the ratio of end-to-end distance in the hair follicle during culturing

| Culturing days (day) | Length of hair follicle (mm) | Ratio of end-to-end distance |
|---|---|---|
| 1 | 3.465 | 1.005 |
| 3 | 4.419 | 1.002 |
| 6 | 5.732 | 0.997 |
| 8 | 6.748 | 0.988 |
| 10 | 7.571 | 0.973 |
| 12 | 8.131 | 0.958 |
| 14 | 8.758 | 0.901 |
| 16 | 9.433 | 0.825 |
| 18 | 9.720 | 0.818 |

Example 10

Evaluation of an Agent of Regulating the Expression of Hair Shape Susceptibility Gene Regulating Agent Based on Human Hair Follicle Organ Culture For the purpose of verifying the effect of an agent of regulating the expression of hair shape susceptibility gene on the form of the hair follicle, an evaluation was conducted using the evaluation system of human hair follicle organ culture.

The human hair follicle was prepared according to Example 9. The isolated hair follicles were divided into two groups, with 12 hair strands in each group, so that there was no fluctuation in the size. One of the groups was suspension cultured for 15 days in a medium for organ culture (400 μL) to which a morning glory extract, which is an expression promoting agent for CNIH2 gene as described in Table 13, was added at a final concentration of 0.2%. The other group was suspension cultured for 15 days in a medium for organ culture (400 μL) to which 50% EtOH (a final concentration of 0.831) was added, as a control. According to the same procedure, a group added with an round cardamom extract (final concentration 0.2%), which is a YIF1A gene expression suppressant and an expression promoting agent for ORAOV1 gene as described in Table 13, and a control group (50% EtOH, final concentration 0.83%) were prepared (n=12 for each group).

After the initiation of culture, the medium was exchanged at an interval of 2 to 3 days, and at the same time, photographs of the hair follicles were taken. From the images of hair follicles thus taken, the degree of elongation and the degree of curvature (ratio of end-to-end distance) of the hair follicles were respectively measured.

Figure 13:
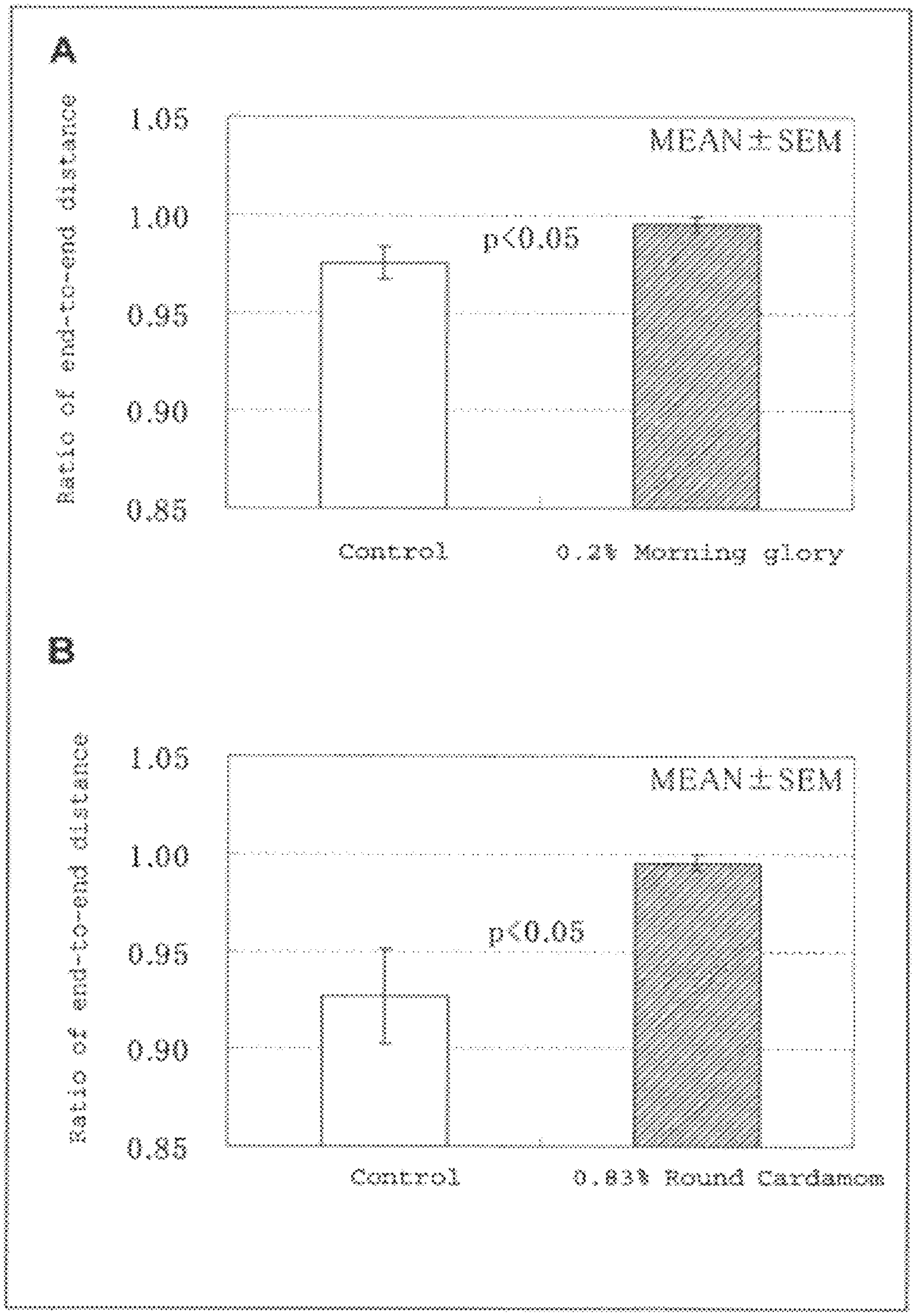
FIG. 13 is a graph showing the effect of a hair shape susceptibility gene expression regulating agent on the hair follicle shape, A: Morning glory, B: Round cardamom.

At the time point at which the length of the hair follicle (hair shaft) elongated by 1.5 mm or more as compared with the length at the initiation of culture, the ratio of end-to-end distance of the hair follicle (hair shaft) was measured. As a result, it was found that the morning glory extract and the round cardamom extract significantly increase the ratio of end-to-end distance, which indicates the degree of curvature of the hair follicle (hair shaft), as compared with the 50% EtOH-added control (FIG. 13). From these results, it could be seen that an agent of regulating the expression of hair shape susceptibility gene expression can be selected as a curly hair ameliorating agent (hair straightening agent) for the hair.

What is claimed is:

1. A method for evaluating or selecting a hair shape regulating agent, comprising the following steps (a) to (c):

(a) culturing cells in the presence of a test substance, wherein the cells are capable of expressing a human ORAOV1 gene or a protein encoded by the gene, and wherein the cells are selected from the group consisting of human hair follicle tissue cells or hair root area-derived cells;

(b) measuring the amount of expression of the ORAOV1 gene or the protein in the cells that were cultured in the presence of the test substance in step (a); and (c) selecting, based on the results of step (b), a test substance that decreases or increases the amount of expression of the gene or the protein as compared to that in control cells cultured in the absence of the test substance;

(d) culturing a human hair follicle in organ culture in the presence of the test substance that is selected in step (c);

(e) determining the degree of curl of the hair follicle's hair shaft that occurs as a result of the culturing as compared to that of a control hair follicle that is cultured in the absence of the test substance; and (f) selecting a test substance from step (e) that both (i) increases or decreases the amount of expression of the gene or the protein in step (c), and (ii) alters the degree of curl of the hair follicle's hair shaft in step (e) as a hair shape regulating agent wherein a test substance that decreases the amount of expression and increases the degree of curl is selected as a hair curling agent and a substance that increases the amount of expression and decreases the degree of curl is selected as a hair straightening agent.

2. The method of claim 1, wherein the test substance increases the amount of expression of the gene or the protein.

3. The method of claim 1, wherein the test substance decreases the amount of expression of the gene or the protein.

4. The method of claim 1, wherein the gene encodes an ORAOV1 protein having the amino acid sequence of SEQ ID NO: 39.

5. The method of claim 4, wherein the sequence of the ORAOV1 gene is that of SEQ ID NO: 38.

6. The method of claim 1, wherein the cells in step (a) are human hair follicle tissue cells.

7. The method of claim 1, wherein the cells in step (a) are hair root area-derived cells.

8. The method according to claim 1, wherein step (f) is selecting a test substance that decreases the amount of expression of the ORAOV1 gene or ORAOV1 protein and increases the amount of curl as a hair curling agent.

9. The method according to claim 1, wherein step (f) is selecting a test substance that increases the amount of expression of the ORAOV1 gene or ORAOV1 protein and decreases the amount of curl as a hair straightening agent.

10. A method for evaluating or selecting a hair shape regulating agent, comprising the following steps (a) to (d):

(a) introducing a fusion gene to cells, wherein, in the fusion gene, a human ORAOV1 gene's regulatory region is linked to and controls expression of a reporter gene, wherein the cells are capable of expressing an expression product of the reporter gene and are selected from the group consisting of human hair follicle tissue cells and hair root area-derived cells;

(b) culturing the cells that contain the fusion gene of step (a) in the presence of a test substance;

(c) measuring the amount of expression of the expression product of the reporter gene in the cells cultured in the presence of the test substance; and (d) selecting, based on the results of step (c), a test substance that increases or decreases the amount of the expression product of the reporter gene as compared to that in control cells cultured in the absence of the test substance;

(e) culturing a human hair follicle in organ culture in the presence of the test substance that is selected in step (d);

(f) determining the degree of curl of the hair follicle's hair shaft that occurs as a result of the culturing as compared to that of the hair shaft of a control hair follicle that is cultured in the absence of the test substance; and (g) selecting a test substance from step (f) that both (i) increases or decreases the amount of expression of the protein encoded by the reporter gene in step (d) and (ii) alters the degree of curl of the hair follicle's hair shaft in step (f) as a hair shape regulating agent wherein a test substance that decreases the amount of expression and increases the degree of curl is selected as a hair curling agent and a substance that increases the amount of expression and decreases the degree of curl is selected as a hair straightening agent.

11. The method of claim 10, wherein the test substance increases the amount of expression of the reporter gene.

12. The method of claim 10, wherein the test substance decreases the amount of expression of the reporter gene.

13. The method of claim 10, wherein the sequence of the regulatory region of the ORAOV1 gene is that of SEQ ID NO. 44.

14. The method of claim 10, wherein the cells in step (a) are human hair follicle tissue cells.

15. The method of claim 10, wherein the cells in step (a) are hair root area-derived cells.

16. The method according to claim 10, wherein step (g) is selecting a test substance that decreases the amount of the expression product of the reporter gene, and increases the amount of curl as a hair curling agent.

17. The method according to claim 10, wherein step (g) is selecting a test substance that increases the amount of the expression product of the reporter gene, and decreases the amount of curl as a hair straightening agent.

* * * * *

SEQUENCE LISTING

<160> NUMBER OF SEQ ID NOS: 45

<210> SEQ ID NO 1
<211> LENGTH: 12590
<212> TYPE: DNA
<213> ORGANISM: Homo sapiens

<400> SEQUENCE: 1
ctttggttac aaggagcagc ccatcaagtt agcttaaaca gaaaggggaa tttatttgga 60
gaattcaggg atatttaata gaaccccggg gtaaaaagcg catccagggc tgatgaggaa 120
ccgagacctg gaattcatta agaaccagtg gaagtcgcct caccagctct ttttatctgg 180
gcccatgtgg tctcttgttc tctttttctc tgtgtgtctg ccttattctc ttgctgcaac 240
tggctttctc tgctctatct gcatctgggc cagcctagcc tcatgctaac ctgccttccc 300
agggcaagga caaagagatg gataagaacc tcttaagatc tcaaatccta gcccaggaga 360
gagtatgtga taaatgagat ttggatctgg agtgccctgt ggtctagttg gtcaccacca 420
gagatggcag attatggaac tgttcagttg gcagattccg gggatgcaga tccttagaaa 480

-continued

```
aggggtgggg gcaggatagg caaagtgaac actgcagcat ttataggata ccgcagaggg    540
gcctgagaag gagtagccag tgtgtggggg ggagctgcaa acacgtggcc tctcagaaac    600
taaggaagaa gagagtgacc agtaggacca aatttgccaa aaggccagta agaggagggc    660
tgaagagtga cttatggatc cagcacaggg aggggatgag cgtccttggt gaaagcggtt    720
ccagggaggg aaggggtagg agccggagtg cagtgggga gatgtatgag gctagaaggt     780
ggatacaggg gaggcagaca gctcctttat gaagtctggc ttcgaagggg agaaagagcc    840
agtgtggccc ttggaaggag atacaacatc ctggcatgtg tttgtgttga tttttgttaa    900
gttgggagaa gcctaagctt gtttaactgg tgatgggcgg cagccaagac agagggaatg    960
ggcagagacc ccagagggaa agggatggct gctggtggag ggattggctg ttctgctgtg   1020
gctggaggga accgggaaca tggcagcaga tattgacagc ggtcagctac cattgcagtt   1080
ttctgatatt gacagcggtc agctaccatt gcagttttct cagttaacac gagaaaaact   1140
atctgctggg catggggctg agacatagat cagagatttg gggtgatcag gggaaagaaa   1200
tcaggattgg aggggctctg gcttctgtct gcagccactc tgggcttggt cagtcatctg   1260
ctcatatgca tgctgggacg tgtagacaca cacatgtatt ttcatgcaca ggcgtggtgt   1320
acacacctca gagcactcac atgtgcttgc tcatgttcac atcagtccag cttgcatgta   1380
cctgtggtgc ctgtacacag gcctgtcgta catgaagtgt ggatggacag atgtgcatgc   1440
tcacgtgtcc acacggtggc cagctcccat cccaccccca ttcctgaaca tcatggctag   1500
agttcttatc gctgtttatt gaaacctccc atcaaagaaa agtgtgggag gcaagaaggg   1560
gaggacttct catcttgtta agactcagtc ttgttaggac tgagccaggg gatatcaggg   1620
gacctcaggg gaagaggacc gggacagtgg gggaaggtgg ccagtgggga agggctagac   1680
agaagaatgg cagggcctgg gttgcaggga gaacaagggc agggatggct gaacctttga   1740
actggccagg gctgggcagg aggctctggt ggtggtgatg gagacacctt caccaagctc   1800
tcagaaggct tcatcctagg aggatggacc tatatggggc ctccctatac tcctaaggtg   1860
cctggctagg atcagtctct ggagggcagg gaaagggggt tccgttgtcc tcagctggag   1920
cccaggcctg gtccgtgagg ctgtagaggg atcctctggg aggccttttc cacctctggc   1980
tcctgctttg gcttctttgc ccgcagggac ctagggacag agagctaagg aaaagccctg   2040
ggcccagacc tgcttcccca gggaggagca ctgatggggc cagaggcagt gactgaccag   2100
ttttccaggt cttcgatagt ctctggcaag ggctgattca gggtctcagg caggaagagg   2160
gcagcactgc ccccgaggag ggcggtgatc ccgtagatga tattggggat gaagggctgt   2220
acctcacccg tgattttcac cagcggggac accatgcttc ccacgcgggt ccacaggtta   2280
cttacgccca tacctgtttg cctgcgaggg ttcagagtag ggattggtag cctgtgtgtg   2340
gggttcataa aggatggctc ccctgggtag aggacaggac aatgccacag tcccacctga   2400
cctgtgtcct ctggctgggc ctggccccag gtccagcacc tacctgatga ctgtggggta   2460
taattcactt gtgtagagga agaggcagct gaaggagctg gataggcatc ccttcccaaa   2520
cacagccaat actgtcctca cggtctgcaa gtctgcagag ggaagaaaat gtggtgggcc   2580
ttggagttca ggagcaccta agagttctca ctccttagct gatcttgtct ccctttttgc   2640
tttggcttcc aagaagctca gatccaaact taaagctgag taatgctttg catgcctgtg   2700
tcctgctatg tttgtgtttt cccctgcctc tgatcctcta tttccattta tattttgttg   2760
tatatgttct tgttcttgtc ttaaaatacc tcaagttctt ttggaagggt ataggtgtta   2820
tcaaccaact aacacccata taaaataaac gtagcttttc caaggtcatg atggagtagg   2880
```

-continued

```
ttgtggggtc tttcttgagc atgagctctg tcgttttacc atctcagctt atctctacag   2940
tgatgtcact caggacactc tcaatacctc aaaaattttc acactatcca gataccacca   3000
tactttttgc ccagtccaag tcagatctgg aaaggagctt tcatgtcatc tagcccaatt   3060
gcgttatttt ctagaagaga gaccctgagc cccagagagt gcagggacct gctcaaggta   3120
acacagtgac ttagaggcag agccagcagt gaagtccctg gcacccaacc tggcagcctc   3180
ttccagaggg ttctggggta gccccagtct ctcacccaag ggcacaaagg tgagagccaa   3240
gatggcccct cctgccagga gcagggcagc ggcctgagtg gtatgccggc ccaggtagct   3300
taaggagagg atggtgatga acttggctgg gacatcgacc ccaccaaaga tgatctggag   3360
gatgtagagg ttgactccaa attcttccac acccatagcc aaactatagt aggcaaaacc   3420
ggtagcaaac ctgagaggca gagaaggatt ggttagcacc tgcagccagg cagaggccac   3480
tccccatgct ggtcattggg tcaccaggat gatgaatagc ttcacttctt gtgccaactg   3540
caactgatga taggggctgc ttgagtgtcc ttttgaggtt tctgagatcg tgtctgggct   3600
cagggagaaa gtgctgtgat tgactggtca tgtctgacgt gggcatggtc cagggtgtgg   3660
tggcaaaggt gccaataact gactctagag aagatcagga ctggagggaa tctcggagac   3720
caaaggaggc agtaaatgat ctctcctggt tgggcagcag tttaacatcc agactggcga   3780
ggtgagcatt gagctgtatg cctgggtcag atgtttccct tcctctctct gaactgtggg   3840
atccctttga agggttcctg gacaaattga atcctattca caaagaaatg gccaggatgg   3900
gaagcagaaa ccaggtcaca gaaagggctt tcagggagca ggagaaagtc agacagagga   3960
gaaaacttga gataaacata atttttgtct tcgagtctga aacccattgg tctagccttg   4020
ctctgtgggg ttccagaggg cagagctgac ccagaggggg gcagtgacag agagggagag   4080
catggggaca ctgagcggca gggatgtgag ctggggaagg ggcctggaac atttgtcctg   4140
tgggtgaggg gtggggcatt gtgaccccag agggaagcag accctgatgg ctggacctgg   4200
gtgtggggca ggaatgcagc agatttctgg ggttggggct gggctgtggt ggcccaggag   4260
aggggattct ctgacttctc tttcagatgc cctaggcctt gcccttaagt gagcctactg   4320
gaggccttgt ctatcacccc ttccttggca gggtgtgggc agggagaggg gggttaccag   4380
gccagggaaa gacagaaggt catgcggcgc agcatgggta tccggaacag gtcacttgcg   4440
gtgtacttgg ccttggccaa ggagatctcc ttctgcaggt tgagtttgag ctccttcggg   4500
cagaggaggg ggaggggtgc cattaatgac cagctagtgg gcaggacgaa gagagggaga   4560
tgcaggcgtg gtgcctctag aggagctcag ggaatcagat gtggtatagg ctgtgagcca   4620
ggggaacaga ggcaagggga ggggccagcc caagagtgga gcacaggggt tctgctccca   4680
gactatagtc ctcagcccct acctccaagc tgagcctttc tccctcttcc ttcttgccat   4740
tgaagacagc cacccgccgg agtatcttca gggccttcga ggactttcca gacaagacca   4800
accagcgtat ggactctggt gtccacctgg gggccagaga ccagtcacag tggctcctcc   4860
cactccagag ccccttttga gaggctggaa gaacatcaac agccagggcc aaggggtagg   4920
aggaccagaa acctgagcta tctcactgca gatttcatgg aatttaaact tggacaaact   4980
ctgcccctgg gctgcctgca gccagcacaa attccagtgt tctcttcttc cccttccaga   5040
agacactttc ctctgccccc gacctgggcc acttgttatt gttgggtgtc ttccttaact   5100
aggagcccca ggctctaggc caaggcaggt ggggctgggg gaggggatgg catgttcaag   5160
gctggactgc tgctggaggg tcctgcacat ccacctcccc agccttcctt gggctgcatt   5220
```

-continued cccagtctct ctggagaaga aagggcaggg ctgcagccac agggcagctt gggaggggga 5280
tggaggctaa ggtgaggtca gggactaggc tttgggacct tcagattctc cctgcaaagg 5340
actaactctg ctgggggagt tgtggggagg gagtgagcac agcatggggt cttgggattg 5400
gcaaataggc agtcaccccc actctccctt gcccccaggc tatgcttttg agattggctc 5460
attctgagca gttcctgagg gtcaccagga taagaggaaa ggaagaggtt gagatgtggg 5520
gagaaaggag tggtgtttgg agaagtctgg tccaaggcag gatcagcttt agctgtagcc 5580
cctgtgggtg acctggatcc ggtgaggccc tcagggagtg gacattggtt gcctggcctc 5640
aggccactgc cccagctgat ggtggcagct tcctgggccc atcactcctc ctgccctgat 5700
ggtcttctga gcctgctctt accaagatta tcagtgactt cctcccaaaa ccatggcaag 5760
ggcctggcac tctatcctcc tcttcccgag aattatggca ggaatggctt acagttagtg 5820
agccttcctg tgtaccaggc ccatgaaact ctgggtgaca ggcaacatta tcttcatttt 5880
acctagaaaa atatttttct tttttttcct gtttttgaaa tggagcctcg cactatcgcc 5940
tgggctggag tgcaatggca tgatctctgc tcactgcaac ctccacctcc cgggttcaag 6000
tgattttcct gcctcagcct cccaagtagc tgggattaca ggcacgcatc accacacccg 6060
gctaattttt tgtgttttta gtagagacgg ggtttcactg tgttggccag gctggtctga 6120
aactcctgac cccgcgatcc gcccctcagc ctcccaaagt gctgggatta cagccgtgag 6180
ccactgcacc cagccaccta gaaaaatctt gatgctcaga gggcatgaga cttgccccaa 6240
gtcacacagt gaactggccc aagctctcaa ctgtgctctg ctgatcgccc acccttattt 6300
tgcctcctga ctctgagtgc tctcacgcct aggttgccca tcccctctgg gagctgctat 6360
tctcatttcc gagctgaggt tccatcccag ctttgcatct ttttgtgtaa ctttgaggaa 6420
ctgcttcaca tctctgagcc tcagtttcct catctgcaaa atggggacaa taatgtctcc 6480
ctcacacaga gaagccatga ggatcagaga cgacgtaggt tgatgcccaa aacgggctgt 6540
gcacatagca gatgctcaat aaaaggtcgc tccaagactt cacttctttt cctgagcgcc 6600
tgtgggattt cctgctcttt ggctctgact accttttttt ttgagacgaa gttttgcttt 6660
tgttgcccag gctggagtgc agtggcgtga ccttggctcc ctgcaacctt cacctctcag 6720
gttcaagtga ttctcctgcc tcggcctcct gagtagctgg gattacaggc atgcgccacc 6780
atgcacggct aatttttgta tttttagtag agatggggtt tcaccatgtt ggccaggctg 6840
gtctcaaact cctgacctca agtgatctcc ctgccttggc ctcccaaagt gctaggatta 6900
caggtgtgag ccaccgtgcc cggccagctc tgactacctt ctaaagaccc atttcctgtc 6960
tttcagtgtg gcctcgggtt caacatgttg gtaatgagct ctctgcccac tctgggtctc 7020
tgacccaggc acctccattt tcccaggttc ccaggctcag gcttctcttt aaactttcct 7080
ttgtacttcg actccagcag tccccaattc tccagattct tccttcaaga tatatcccag 7140
attagtctcc ccgaatcttc ctcccagcac catcccctcc catctgtcta ttgtccccac 7200
tcagttgggt ctgtccttct gggctattat ttcacaaatg gaaacttgat caggcctgta 7260
gcaccataga ctctttctgt ggctttctac ctccctccat atgaagtcca ggccccccag 7320
ctttctgtgc tctcccagcc agtctccatc ccgtccacct ccacttaccc tcttcttcag 7380
ctgcaggcag gccctccttc cccacgtgcc cccatccctg ctctctcctg cagcatgcat 7440
ttgtttatgt agttcctcct ccctggagtg cccttccctg actctgggac tgggtgcccg 7500
gggacacaga gttggccagc ctgggcaggt atgggctccc ctgtttggcc ctggggcacc 7560
taaggaaaca gatgaagagg agagggccac ataccaggat gataggaaga agacgaagaa 7620

-continued

```
gggaatggac acagttaact gcagccaacg ccactggggg atggcgtagg ccaggccggg   7680
cagaatgaac tggccaaagg tgtagcagta cccgagtgct gtcgacatga tggcccgcat   7740
ccgggtaggc acccattcca catctgtggg aggagtccaa gcaccagatt agtgttctgc   7800
taggtcccag gcacctccgc gtgaaggggc accagcttct gcatccccac ggctactgac   7860
atcctcccca cggatgctgt tgatatcgcc ctccgttggg tcttcctgct gttctgatgc   7920
tgaccctaag ttcatcatcc ccattttaca gatgccacag ctgaggctca aggcgatagg   7980
actcaaacct aggtgtgtct gtttccaaac tcatgctctt aaccactgct tctccagtgg   8040
caagtgactt tccttgttct gcctcagttt cctgatctgt aaaatgggaa taatagtgtc   8100
acttacttgc aagtggtatt gaatgagatt gtgtacctag cagagtgtca ggtccagggt   8160
aagtcctcag tattgacagc tgctattact atgcttgttg tcatttttaa atttaagtga   8220
ggcctctgag gtcctgagag ggggtggcac cttgaccaag gtcacaggga gcctgtggtt   8280
gagccagacc cagaccccat tctcttttgg cttctggatg gtgctcccca aagcccagct   8340
ccatgcccca ctgcagctca ctcaagatga cggtgctcag ggtaatgcct gagatgccaa   8400
agccacacag gaagcggaag accatgtaga tggggaaggt ggggctgaag gctgcaccgg   8460
agccgctggc tgccagcagc aggtagctgc aggtcaggat gggcctgcgg ccaaacctgt   8520
agctcgaagg agaggagggg ccaggttagc cacagtgtgc ctgccaagag gagtgactct   8580
gcatgctgtg gggcaaaggg ctgaatccga cccccaacct ttccctgttg ggcacataaa   8640
gctccctccc cagacacagc tttcttggta attgctattt ttgacaagtt tgcaattaga   8700
ggtttgagtt aatgagtgat ctcctctaca tccgcctcag cttagctgac tgagcagggg   8760
tcaaaggacc gcccatctct aagcagtcca tctcctctgc ctccactgct acacagccac   8820
tacgctgtgt cccaaaacct ggaggttttt tcccctggaa gaagggaagg ctggaggcca   8880
gacacggtgg ttcatgcctg taatcccggc actttgggag gccaagatgg gagggtcact   8940
tgaggtcagg agtttgagac cagcctgacc aacatggtga aacctcgtct ctactaaaaa   9000
tacaaaaatt agccaggcgt ggtgacacac gcctgtaatc ccagctactc gggtggctga   9060
ggcaggagaa tcacttgaat ccgggaggtg gaggttgcag tgagctgaga ttgtgccatc   9120
gcactccagc ctgggcaata agagtgagac tccgtcttaa gagaaaaaaa aaaaaaaaaa   9180
aaaggaaggc tggaagattc cagttgtaag ggctttgggg tggagagaag gctgtggtcc   9240
agaaaggtag tgaggtttgc ccaaggccac acagcaagag ccatcccacc ctcccccagc   9300
tctttgcctc tttgcgggtg cacgggtgga gcagagtagg gaagggttgt ccccatgggt   9360
catgcttcca tgggctgtgc ccccatgtct cacctgtcag acaggtctcc aagcacgagc   9420
cctccaatca gtatacctgc catgaagata gactgggcca tctccttcag tttgttggag   9480
ttgcacacca agtcccactg cacaagagaa aggtagggct agcctaactc agtgtagaca   9540
gcctgctcag ccatgctcag cctgtggcct catacatgtg ggcttcctct cccagcgccc   9600
tgactttgcc cctacctccc aaggaccgtt tcctttttca gcccggctcg gagctccttg   9660
ggtttgtctg tggctcttcg gcccctgacc tgcatccctc aggcatgtgt ggcctgtcat   9720
atggctctca aagtccactc agctaccaca tccaggtctg gcctcaactg cttcctcctc   9780
tccaagttgc ctgcttccct gtttgcctcc tccctgcccc tcacatagcc caggccagtc   9840
cctctgcgta ccccccttgac cttgccttct ctcctctaca gggacgttcc tctatccttg   9900
ccacctctct tcatcctgca gatccagtct ctctctctct ctgctcctcc tcatcagtat   9960
```

-continued

```
ttaggtgtgt ccaaatctct ccatcttaaa acctctttcc tttcctcatt cactccattt  10020
ctctcttccc ttcaaagcca aatcctttga acgaggagct gtacttgctg tcactccatc  10080
ctcatctcct tttcatgtct cacttctgcc cccaacccat ccactgaatc tgtgcttatc  10140
aaggtcactg aagtttcatt tttacggcgc acaatggaac gtccctaatc ctggcctggc  10200
ttgccctctg gcagatgtgg atgctgctga tctcgccctc cgtcaggctt cctgctgttc  10260
tgcactcctc gtctccttca cagctcgttt ctctctgcct agtccttgaa gctttcccag  10320
ggctcttcct gaatcctcct ctctctccac tttccccagg cgatgccatc tgttcctgcg  10380
gcttcaattc ctattttata ctgaagattc caaatctaca actccagccc aacctatctt  10440
ctgacccaca gaggagtaga ttcagtggtc ccacttgaga actctgcctg gatagagtca  10500
caggcacatc ccagattcaa tgggacttat caccccactt ctcattaaag tcccaatctc  10560
agggactggt aaccttctct ttttaattaa ttaattaatt aaattaattt ttttttgaga  10620
cagggtctca ctctgtcacc caggctgact acagtggcat gatcatggct caatgaagcc  10680
tcagtctcct gggctaaagc catcctccta agtaactggg actacaggtg tgcatgacca  10740
cacctggcta attttggatt ttgtatatag acaggagctc actatgttgc ccaggctggt  10800
ctctaactcc tggcctcaag tgatctgcct gtcttggcct cccaaaatac tggaattaca  10860
gatgtgagtc accacatcca gcctcttttt tatttttatt taaaaaaaat tatatcattt  10920
ttaattggca aatcataatt atattacata tatgaaaaca atgtggtgtt ttgatatatg  10980
tatgcaatgt gaagtgatta aatcaagcta attaacatca cttcatttac ttgacatttt  11040
ttgtggtgat acttttgaaa gtcacccttc tagttatggt gaaataaaca atacatcatt  11100
attcttgact gtagccatca tgctgtgaaa cagatctcaa aacgtattcc acccatctag  11160
ctgaaacttt gtaccctttg atcagtaact ccccattcct ttccccagcc ccttcccccc  11220
gagcttttgg taaccatcat tctactctct acttctgtga attggacttt tttttaaaga  11280
taccatatat aaatgagatc atgctgataa ccctcttgat tccttcctcc ctctcctact  11340
ccacaatcac ttgatcttca agattctagc tttttgatat ttcttgaatc tggattcttc  11400
tatttccaat actactgcct tagtgtaggc ctcatcatct tgcacttaga ttaataatga  11460
caactgatat ttattgaggg tgttctaggt actgggcact gttctaagct ctttccatgt  11520
tttaacttta atcttcacaa taaccttatt atgtaggtgc taatatcatg ctattttaca  11580
gataaagaac ctgaggccca gatgaggctg ctgcagcaac ctcttgacag gtctactgga  11640
cttcggcctc atcccttcct agccattctt tccctgataa cctgaagggc taaaacgcca  11700
ctcaaatcag gtgcctgtct tgcctaaagt gctcactggc ttctccttgc cctttcggta  11760
aagataatgc cccattaaca tggggtttatg aggccctcca tgctctggcc cctgcctacc  11820
tgtctggtct aatctgctaa tccccaacat gcaccctttg ctccagccat ctgaattact  11880
tgtgcgatga agtggagaat ttaattcaat agaaatgcct cacaagaatg ttttggaagc  11940
aaaacattcc aaaaggtgaa gaaccaaaca ttccagggag ctctttctca ctttcctcag  12000
ttggaagtga gggagaatgg tggtggatgg aatctccggg tcctacagct gtctcagagt  12060
ggcccagcat ggccagcaag cctggtggtc cgttttagtt gggaaggggg cctgcatggt  12120
atgtgtgttg ggaggagatg gaggagggac aaaggtaaag gaagaagcaa gggggtgtga  12180
ggtggaggaa tgtgcaaggg gccatctaga gagacttctg gtactttgtg gcatgctgtg  12240
taaagtccct ttaggaaaat ctaaaggaga gacctactgt tcacctaaat tcattcaccc  12300
cttcttccat agtaaatagc acatttccct gatgaccttg tactgagtgg ggccatgtag  12360
```

ttcttgacaa tggaatgtga gtagaagaga tgtatgttac ttccacctca tttgcttaag 12420
agggattccc tagtctggac ttgcatgctt tcttcccctc ctgttggtgg gaatggtgac 12480
aactagaaca actctggaga gttgctgtca gtctgggtcc ctgaatgact ctgtgaagca 12540
gaaccaccca ttggcctaaa atgctactca ccttggaact gttacatgag 12590

<210> SEQ ID NO 2
<211> LENGTH: 202111
<212> TYPE: DNA
<213> ORGANISM: Homo sapiens

<400> SEQUENCE: 2
tggaatatgc ctaatactaa taaaatattg aatttcaata tgatttctcc accccagtaa 60
atcttagtct ctttaattag cattacattt agcatacaga ttcttagaaa agacaaatgc 120
tccttttaat tgtgtttttg tttcatttga agtttcagca tttgattact ttcctccctg 180
gtttgtttta cttatttatt tttttgagac agactctcac tccagcccag gctggagtgc 240
agtagtggat ctcagatcac tgcaacctcc gcctcccaag ttaaagtgat tctcaggcct 300
caacctcccg agtctctagg attacaggtg tgtgccacca caccaagcta atttttgtat 360
ttttagtgga gacgaggttt caccaagttg tccagtctgg tcttgaactt ctgagctcaa 420
gcagtccacc cacctcggcc tcccaaagtg ctaggattac aggcatgagc caccacgccc 480
agcctggttt tattttttgg tagtccaaat tccccagtag ttttttttct cattgttgtt 540
gttgttgttt tttttctttt ttttttcttt tattattatt atactttaaa ttttagggta 600
catgtgcaca atgtgcaggt tagttacata tgtatacatg tgccatgctg gtgtgctgca 660
cccattaact catcatttag cattaggtat atctcctaaa gctatccctc ccccctcctc 720
ccaccccaca acagtcccca gagtgtgatg ttccccttcc tgtgtccatg tgttctcatt 780
gttcagttcc cacctatgag cgagaatatg cagtgtttgg ttttttgttg ttgcgatagt 840
ttactgagaa tgatgatttc caatttcatc catgtcccta caaaggacat gaactcatca 900
tttttatggg ctgcatagta ttccatggtg tatatgtgcc acattttctt aatccagtct 960
atcattgttg gacatttggg ttggttccaa ctctttgcta ttgtgaatag tgctgcaata 1020
aacatacgtg tgcatatgtt gttatagcag catgatttat agtcctttgg gtgtataccc 1080
agtaatggga tggctgggtc aaatggtatt tctagttcta gatccctgag gaatcgccac 1140
attgacttcc acagtggttg aactagttta cagtcccacc aacagtgtaa aagtgttcct 1200
atttctccac atcctctcca gcacctgttg tttcttgact ttttaatgat tgccattcta 1260
actggtgtga gatggtatct cattgtggtt ttgatttgca tttctctgat ggccagtgat 1320
ggtgagcatt ttttcatgtc ttttttggct gcataaatgt cttcttttga gaagtgtctg 1380
ttcatgtcct tcgcccactt tttgatgggg ttgttggttt ttttcttgta aatttgtttg 1440
agttcactgt agattctgga tattagccct ttgtcagatg agtaggttgc gaaaattctc 1500
tcccattttg taggttgcct gttcactctg atggtagttt cttttgctgt gcagaagctc 1560
ttgagtttaa ttagatccca tttgtcaatt ttggcttttg ttgccattgc ttttggtgtt 1620
ttagacatga agtccttgcc catgcctatg tcctgaatgg taatgcctag gttttcttct 1680
aaggttttta tggttttagg tctaacgttt aagtctttaa tccatcttga attaattttt 1740
gtataaggtg taaggaaggg atccagtttc agctttctac atatggctag ccagttttcc 1800
cagcaccatt tattaaatag agaatccttt ccccattgct tgtttttctc aggtttgtca 1860

-continued

```
aagatcagat agttgtagat atgcggcgtt atttctgagg gctctgttct gttccattga   1920
tctatatctc tgtttggtac catgctgttt cggttactgt agccttatag tatagtttga   1980
agtcaggtag cgtgatgcct ccagctttgt tcttttggct taggattgac ttggtgatgc   2040
gggccctttt ttggttccat atgaacttta aagtagtttt ttccaattct gtgaagaaag   2100
tcattggtag cttgatgggg atggcattga atctataaat taccttgggc agtatggcca   2160
ttttcacgat attgattctt cctacccatg agcatggaat gttcttctat ttgtttgtat   2220
cctcttttat ttcattgagc agtggtttgt agttctcctt gaagaggtcc ttcacgtccc   2280
gtgtaagttg gattcctagg tataaagagt caagacccat cagtgtgctg tattcaggaa   2340
acccatctca cgtgcagaga cacacatagg ctcaaaataa aaggatggag gaagatctac   2400
caagcaaatg gaaaacaaaa aaaggcaggg gttgcaatcc tagtctctga taaaacagac   2460
tttaaaccaa caaagatcaa aagagacaaa gaaggccatt acataatggt aaagggatca   2520
attcaacaag aagagctaac tatcctaaat atatatgcac ccaatacagg agcacccaga   2580
ttcataaagc aagtcctgag tgacctacaa agagacttag actcccacac aataataatg   2640
ggagacttta acaccccact gtcaacatta gacagatcaa caagatagaa agttaacaag   2700
gatacccagg aattgaactc acctctgcac caagcggacc taatagacat ctacagaact   2760
ctccacccca aatcaacaga atatacattt ttttcagcac cacaccacac ctattccaaa   2820
attgaccaca tagttggaag taaagctctc ctcagcaaat gtaaaagatc agacattata   2880
acaaactgtc tctcagacca cattgcaatc aaactagaac tcaggattaa gaatctcact   2940
caaaaccact caactacatg gaaactgaac aacctgctcc tgaatgacta ctgggtacat   3000
aacaaaatga aggcagaaat aaagatgttc tttgaaacca acgagaacaa agacacaaca   3060
taccagaatc tctgggacgc attcaaagca gtgtgtagag ggaaatttat agcactaaat   3120
gcccacaaga gaaagcaggg aagatccaaa attgacaccc taacatcaca attaaaagaa   3180
ctagaaaagc aagagcaaac acattcaaaa gctagcagaa ggcaagaaat aactaaaatc   3240
agagcagaac tgaaggaaat agagacacaa aaaacccttc aaaaaattaat gaatccagga   3300
gctggttttt tgaaaggatc aacaaaattg atagaccgct agcaagacta ataaagaaaa   3360
aaagagagaa gaatcaaata gacgcaataa aaaatgataa aggggatatc accaccgatc   3420
ccacagaaat acaaactacc atcagagaat actacaaaca cctctacgca aataaactag   3480
aaaatctaga agaaatggat aaattcctcg acacatacac cctcccaaga ctaaaccagg   3540
aagaagttga atctctgaat agaccaataa caggctctga aattgtggca ataatcaata   3600
gcttaccaac caaaaagagt ccagtaccag atggattcac agctgaattc taccagaggt   3660
acaaggagga actggtacca ttccttctga aactattcca atcaacagaa aaggagggaa   3720
tcctccctaa ctcattttat gaggccagca tcatcctgat accaaagccg ggcagagaca   3780
caaccaaaaa agagaatttt agaccaatat ccttgatgaa catcgatgca aaaatcctca   3840
ataaaatact ggcaaaccga atccagcagc acatccaaaa gcttatccac catgatcaag   3900
tgggcttcat ccctgggatg caaggctggt tcaatataca caaatcaata aatgtaatcc   3960
agcatataaa cagaaccaaa gacaaaaacc acatgattat ctcaatagat gcagaaaagg   4020
cctttgacaa aattcaacaa cccttcatgc taaaaactct caataaatta ggtattgatg   4080
ggacgtatct caaaataata agagctatct atgacaaacc cacagccaat atcatactga   4140
atgggcaaaa actggaagca ttccctttga aaactggcat aagacaggga tgccctctct   4200
caccactcct attcaacata gtgttggaag ttctggccag ggcaattagg caggagaagg   4260
```

-continued

```
aaataaaggg tattcagtta ggaaaagagg aagtcaaatt gtccctgttt gcagatgaca   4320
tgattgtata tctagaaaac cccattgtct cagcccaaaa tctccttaag ctgataagca   4380
acttcagcaa agtctcagga tacaaaatca atgtacaaaa atcacaagca ttcttacaca   4440
ccaataacag acaaacagag agccaaatca tgagtgaact cccattcaca attgcttcaa   4500
agagaattgt tgttgttttg agacggagac ttactctgtt gcccagtctg gagtgcagtg   4560
atgtgatctc cactcactac gaactcaatc tcctggattc aagtgattct cctgcctcag   4620
cctcctgaac agcaggggtt acaggcacat gctaccatgc ctggctaatt tttgtatttt   4680
tagtagagac ggagtttcac catgttggcc aggatggtct cgaactcctg acctcaagtg   4740
atccacccgc cttggcctcc caaagtgctg ggattacagg cgtgagccac cacgcccggc   4800
ctcattattg cttttatttt taatcaaagt tatacatata ttttagagag tcacgtagtt   4860
ttacagactt atttagaaaa caatctttag gtattatctg gtgaattcca gctgtcgaaa   4920
actgtttggc tttttcatca gcacccacat tttcccaata agtttgtaat ttcttctttt   4980
tttttttaa atttttgaga tagagtctca ctctgttgcc caggctgaaa tgcaatggcg   5040
tgatctgagt tcactgcaac ctccacctcc caggttgaag gaattcttct gcctcagcct   5100
tctaagcaac tgggattaca ggcatgcact accatgctca gctaattttt ttattttagt   5160
agagacgggg ttttgccaat tgcccaggct ggtcttgaac tcctgccctc aagtgagcca   5220
ccatgcctgg ttttcttttt atctttttct ttcttttttt tttttttttt tttttttgat   5280
gtagggtgtt tcgctgtgtc accaaggctg gagtacagtg atggctcact gcagccttaa   5340
cttcccaagc tcaagtgatc cacctgcctc agcctcccga agtgctggaa ttagaggtgt   5400
gagccactgc gcccagctag tagttcattc tttttttattt ccaagtattt cattgaaaca   5460
tgatataatt tgcatatcca ttctcctgtt gatggacata taggttcttt acagctttta   5520
gcttttatga ataaagttgc tatgaatttt tttttttttt tttgagacgg gagtttcact   5580
cttgttgccc aggctggagt gcaatggcgt gatcttggct cactgcaacc tctgcctccc   5640
gggttcaagc gattctcctg cctcaacctc ccttgtagct gggattacag gcatgcgcca   5700
ccatgcctgg ctaatttttt ttattttgtg gagacggggt ttctccatgt tggtcaggct   5760
ggtctcaaac tcctgacctc agatgatctg cccacctcgg cctcccaaag tgctgggatt   5820
acaggcctga gcaccgcgcc cagccgctgt gaacattctt acacaggtgt ttttacagac   5880
atacatttc atttctccct ctctctctct tttttttttt tttaatgtag agacagtctc   5940
gctttgttgc ccatgccagt tttgaactcc tggctttgtg gaatcctatt gcctcacact   6000
cccaaagtgc tgggattaca ggcatgagcc accacgccca gccccatttt catttctttg   6060
ggggtacata tgttggagtg gaatggtgtg tcttagagta ggtgtatgtt taaactttgt   6120
aagaaactgc caattttttc aaagtgattg tatcagtttg cattcccact aactgaggca   6180
gacagattct gaagtggccc ccatgataaa taccccctgg tatttatggc ctagtagtcc   6240
tgtgcccttg ggtgcaggtg ggacctgtga ttgactcctc actgatagaa tatggcagag   6300
gtgacaggat gtgtatggtc atgcatacct gattattccc agtcagatcg taatgctcat   6360
cttgtgagga gactctctcc cttgctggct ttggtgctgt gttgtgagct gcctatggag   6420
acggccctgt ggcagggagc tcagggcagc ttcaaaccca cagccagcaa gagactgtgg   6480
ccctcagtcc agcagcccac aaggaattga gtgttgccaa caaccatgtg tgtttggaaa   6540
cagatcctat cccactcagt tctcagatga gaccatagtc tcagccagta ccttggtggc   6600
```

-continued

```
accttataga ggacccagct aaactgtgcc tgggcttttg acctatagaa tctgtgagat   6660
aataaacatg cattagttta agctgctgct aagctttgct agtattatta tgctacagtg   6720
gataactaat acgagcaata tagttcctgt tgccctgtat ctccaccgac atttagtgcc   6780
tgtcttttag attttagcca tgttagtggg catgaaatgg aaactctgag gctttaattt   6840
gcatttccct aatgacattg aatacctgct aattggacat ttggatacct tcttttgcga   6900
agtatctgtt caagtctttt tcttatttta aaaataggta ggttgggcat ggtggtttac   6960
acctgtaatc ccggcacttt gggggccaag gtgggtggat cgcctgagct caggagtttg   7020
agaccaccct ggcaacatgg tgaaacctcg tctctactaa gatacaaaaa attagctggg   7080
catggtggtg ggcgcctgta gtcccagcta ctcaggaggc tgaggcgcaa gaatcacttg   7140
agctcgggag atggaagttt cagtgagccc agatcatgcc accacactcc agcttgggct   7200
acagagtgag attccgtctc aaaaataata aaaataataa gagtaagaat aatcaatatg   7260
tttgtctttt tataatttat ttgtagaagt tctttatata tgacgggtta agttctttat   7320
cagatgtgtg tgtgtgtgtc tctgcatgaa tgtgtgttgt atgtttgtgt gtgtatctga   7380
tagagttttc ttctagtctg tgatggggag gaacttgcac attcctctca cctcatgcag   7440
atttccaaac tgttcacgtt ttactgcatt tactctattg tactatttct ctctctaaat   7500
cagtttttc tgggtcattt gagaccatgt tatgcacatg ctatcctagc acccttaaat    7560
atttcagtgt ttattttccg ccagttaagg gcactcccaa ataaccacta catactcctt   7620
taagtcagac aatttgcagt gataaaaccc tattgtccaa tctattgacc ccattcacag   7680
tttgctgccc caactatatc tcatttctgt tttgtcccag aatcccaggg aggagtgtgc   7740
attgcaccta gctgtcagcg tctcttcaca ccctccagtc tgggatcatc ctttgtcatc   7800
ccggttgttc ttgtccacaa ccgttagata tcctgtaggg tgattggcaa ggcggatctt   7860
atagtatttc cttatgacca aattcaggtc atgatttctt ggcaaaagta tcacaaaaat   7920
gatgctgtaa tagtctcagc acatcacatc aaggggcaca ttctgttaac cagccctgtt   7980
actgctgttg ttggccctca tcacctgctc atgttggtgt cttccaggta tctctgtttt   8040
tcttactgta atgccattgt ttttctttc ttttcctttt cttttttccc ttttcccttc    8100
ccttttcaat ggagtctcac tctgtagccc aagctggaat gcagtggcac aatctcagct   8160
cactgcaacc tccgcctcca gggctcaagc agttctcctg cctcagcctc caaagtagct   8220
ggtactacag gtgcatgaca ccacaccggg ctaatagtta ttgatttatt tatttattta   8280
tttttgagac agagtgtcgc tctgtcgccc aggctgcagt gcattggcac aatctctggt   8340
cactacaagc tccgcctccc aggttcactc cattctcctg cctcagcctc ccgagtagct   8400
gggactacag gcgcccacca ccacactcgg ctaatttttt tgtattttta gtagagatgg   8460
ggtttcactg tgttagccag gatgttctca atctcctgac ctcgtgatcc accctcctcg   8520
gcctcccaaa gtgctgggag tacaggcata agccaccgtg cccagcctat cactttctat   8580
atcattttct tttttggggg ggttttgagg gcagggtctg gctctgtctc ctaggctgga   8640
gtacagtcgc tcgatatcag ctcactgcaa cctccgcctc ctgggctcaa gtcatcctcc   8700
cacctcagcc tcccgagtag ctgggaccac agacatgtgc caccataccc agctaatttt   8760
tgtatttttt gtagagttgg gattttgcca tgttattcag gctggtcttg aactcctgag   8820
ctcaagtggt ctacccacct tggcctccca aaatgctggg attataggca tgagccacca   8880
tgcctggcct atatctgttt ttgtttttg agatggaatt ttgctcttgt tgcccaggct    8940
ggagtgcaat ggcgcaatct cggttcacca caaccttggc ttgctgcaac ctcggctcac   9000
```

tgcaacctcc gcctcctggg ttcaagcagt tctcctccct cagccccctg agtagctggg 9060
attacagaca tccgccagca cacccagcta attttgtatt tttagtagag acgtggtctc 9120
gccatgttgg tcaggctggt ctcgaactcc tgacctcagg tgatctgccc gcctcggcct 9180
cccaaagtgc tgggattaca ggcgtgggcc accacgcctg cctttttctt tatatatctt 9240
aaaaaccatg tattcagact gatctcttaa attccaatgt aacattttag ggttctctcc 9300
agcctaagcc ctttgcatgt ttgtaagtac ctcttccaag aggtacttgg aagaaacctg 9360
gctttcacta ttctcagtat atttacttat ttgctccttg taactggtct ttcacctacc 9420
ctgaccttgc cttctgtcta ccacatctgc acgtgccctc acacccctgc ctcagcaccc 9480
tgcgtccttg agcactagta ggtggaagca ggaaaacaga cgtgtaaact tcataacagt 9540
gactcataag acaatagagg tggaaagcga gaagccgatt tactctgcaa aatcataagt 9600
agtatttgtt ccattatcta ctgttgtgta aaaaagtctc tccaaaagtt atcacttaaa 9660
ataagggaag aactattttg catacaaact gcactttggg cagagttcag caataatact 9720
caattctctc tgcggcactc aagtgaggtg ggctggttca aagttggagc atccaggggc 9780
ggaggctaga atcttgtgca gtctccctca ccgtgtgatg tctggcagct gatgccagct 9840
attagctggg acctccatga gaactgtggc tggaacacct gttatggcct ttccacgtgg 9900
ctgcttggct tcctcacggt acggtggctg ggttccaagg gcaggcatca cacaagcaag 9960
agcgagctgg cggaagcctc agtgcctgtc ctcctccagc gtggagagtc acatggcctc 10020
atttctactg cattctgctg gttagaagga agtcactaaa gccagccata ttcaggggga 10080
gggtaatttg tttccacttt ttcatgagag gactgttaaa gaatttatag atatgtttta 10140
agactggcac agaatttaaa aatatactat tttctggaag aatggaagat tcatttgtac 10200
agttgcattc gttcagtatt tttaattcat ttttttaaa agttttaaac acttacatct 10260
actggtatat aggtatgctt gccccatttc cttttctttt cactttctct ttttacagaa 10320
ccctgctgca agctaactca tgtatgcgtc cgttcatgct tttgttcatt cttgtgtgat 10380
acagaaatgt atatacacat acatacagtg ggttgggaat cttgttttta aaaaatagaa 10440
tcacattgaa actaattttt gcatcctgtt tttctgaaca ccttggagaa atccctataa 10500
atcaagaggt ttcattctaa tttgttcttt ttagatgctg cacatactct gttttctgat 10560
ttggttattt gatcatgacg gggtaggaat agagagggac aggcttcaaa gaaagggtag 10620
tcaggaaaga gaaagaggag gagtgctagg tattcctggg gtcttcaacc tgatgtgtca 10680
tcgaagtggg tgggaagttg ggaaaatggt ggtggggagg tgtgttggtt ggttttagcg 10740
gggaaatgag tattttttta tatgcactaa aattacctac caggcagttg aatacatagg 10800
agcagggagt gagtccaagg ataggactgg agttgataga caaagctata aagggagacg 10860
gttactgggg ggagagctct gtctcgctta gcatcacttg ctgttagtgg tgggcccaga 10920
cagtgactga aatattttca ttccagacca gggtccagtg tatttatact tgatgcatta 10980
agttctgatc tttaaaaagc tgccagtttt ttagaaggag agtttttatt ttcattttat 11040
atggtgtggg ctgaaggaat cttttgctaa atataacaat gtgagtttgc tagtctttct 11100
gaggcattga aggcatttaa aatttgaaac cagagctacc tgatgggaac atccttgatc 11160
tcttctccaa gtcaaaccaa cctaggccac gtgtaataat tagttcaatt gaatggctga 11220
agaaggattt atttgcccct tttatgttac agaggagatc cacagtacag ctagaaaagg 11280
gatgcagaat gaacaggaca gacacgtgat tctgaccctg ataaccactc tgcatccatc 11340

-continued

```
ggatttacta ttattattat tattattatt attttatttt ttattttgag acgggtctca  11400
ctctctcacc caggctggag ggcagtggtg cgatctcggc tcactgcaac ctccgcctcc  11460
caggttcaag cgagtctcct gtctcagcct cccaagcagc tgggactaca ggtgcatacc  11520
accacgccag gctaattttt ctgtttttag tacagaaggg gtttcaccat gttggccagg  11580
ctggtctggg attcctgacc tcaagtgatc tgtctacctt ggcctcctaa aatgctgaga  11640
ttacaggcct gaatcactgt gcccagccaa gtttactatt attattaaaa atactggtgg  11700
ccttgaaatc agtgtaaaat aataatgtca tctttttagg aataaaaata ctgctctccc  11760
catgccccac tggctgtagg aaaattgagg gaaatggttg ttatttctc tttgtaggtt  11820
ggattactga acctcggagt gagatgacct gtgagtttta tttattttta tttatttcat  11880
tttatttatt ttggagacag atcttactct gtgtcccagg ctggagtaca gtggcacgat  11940
ctcagctcac tgcaacctcc acctcccagg ttcaagccat tctcctgcct cagcttcccg  12000
agtagctggg attaaaggca cgtgccacca cgcccagcta atttttgtat ttttagtaga  12060
gaatgggttt taccatgttg gccaggctgc tctggaactc ctgacctgaa gtgatccatc  12120
tgccttggcc tctgaaagtg ctgggattac aggcatgagc caccaagcct ggccaacctg  12180
tgagttttat ataaatggca cagttgaaat gataaacgtc cttaagattt aattttgatt  12240
aggggaagtg agtgaaaggt attcctcttg ttggttttcc ctgtattctg tttggtttgg  12300
tctttttca gataagttca acagtggggt gtcaattata tgtaaagtac atggagaaag  12360
ctgcaaggat gtgggtggct caggcctgtc cttagagagc tccccatctt ggtatctaca  12420
gctcactgca agacagagca gattgaaata agtaacaact agagttacat gtggggtaat  12480
ttaggagaaa agggcattag tccctttgga atctggcatt tgacctggaa tttttctttt  12540
cagtttttg tttggaattt tttttttttt tttttttttt ttttgaggcg gaatctgggg  12600
ctggagtgca gtggcacaat ctcatctcac tgcagcctcc acctcctgag ttcaagtgtt  12660
tctcttacct cagcctcccc agtagctggg attacaggtg tgcaccacca cgcccagctg  12720
atttttgtat tttttttagt ggagacgggg tttcaccatg ttggccaggc tggtctcaaa  12780
ctcttgactt caagtgatcc atccgcttca gcctcccaaa gtgctgggat tacaggcatg  12840
agccagtgtg cccagctgga aaattttta aatatacaaa aatagagaaa ggtgtgtgat  12900
gaatccctgt gtactcacca ccctgcttta ttatcagctc aggggcagtg ctgttttatc  12960
tgtgcccccca tcccctcccc ccactcccac ccccagatta tcttgaagca aatcccagtc  13020
atcatcacat ttcttttgta ataatttcaa tatgtatctt caaaagatag ggacacttta  13080
aaaaatacat aaccacaata ccattatctc tcctaaaata atagtaagtc cttaatttta  13140
tctgatttgc agtcacttta gttggaattt acaaagagaa gattttaata gatggtgaat  13200
gggaggaagg gaattcagat agagggaata acacatggaa aatcagggac cgtgtgtaag  13260
tgaaaggtaa taaaagtctg atttagggct gtggcattgg gcggaaagga aattgcaaat  13320
gtcagtcacg gcagaggtaa acttaatgga attttccagt tgaggacagc acgtgtgtct  13380
tccttctatt tctggttaat agtagtcatt ttgaacccta tagaacaggg ttgacaaacc  13440
atggtttgta gcccaaatcc tgttctcagt ctgtgtttgt aaataaagtt ttactggaat  13500
acaaccacac ccatttgttg atgtattgtt gtgtatggct gctttcatga accccacaat  13560
gggcagagtc aagcagttgc agcagagact ctatgaactg taaaacccca aatacttact  13620
actatctggc cctttataga aaaagtttgc caacctctga tctagaagaa actgggccct  13680
ggatttagtg cttgctctca gaggagttga gtagagtata tggattagaa acagccatgt  13740
```

```
ctttgtgata tacaggggta tacaggagtc agaaacagtg gattttgttt tgctctgtct  13800
ttatcattca ttttatagcc tgagaaagta agtctaagaa tctttctgcc tctgtttatt  13860
atttgatttt atattgtgaa ctaagctctg tgaaatcaga ggtttttgtc ttttcctcac  13920
tactctattg gcagggcctg gatcagtgcc agacatttag taggcattca gtaagtaatt  13980
gttgaataag taagcaaata ttttagtctt tttgcttctc ttctgtatta cacacatttg  14040
gagtttcttg gggaacaag gatgatatat ttgtaggtgg caattatgtt actatgtaaa  14100
tctgttataa tttttcccaa aagttcagaa aattgtttca ttagtacaat ggagtattaa  14160
gcagcagtta aaactagtaa ttatgggctg ggcacggtgg ctcactcctg taatcccaac  14220
actttgggag gccgaggcgg gcagatcacc tgaggtaggg agtttgagat cagccttacc  14280
aacatggaga aaccccatct ctactaaaaa tacaaaatta gccaggcgag gtggtgcatg  14340
cccataatcc cagctactcc agaggctgag gagggaaaat cgcttgaacc ggggaggcag  14400
aggttgcagt gagctgagac tgcgccattg cactccatcc tgggcaacaa gagtgaaact  14460
ctgtttcaaa acaaacaaac aaactggtaa ttatgataac tatagaaatg aggagaaatg  14520
tttatggtag gtcaaaatcg taggcacact gcctccctaa aatatgaatg aatatggaca  14580
aagactggaa gataatgtga aaatgaaatc attttaagac agtggaattt ttggtggttt  14640
ttctctccaa aattttcttt aatactattg cttactcatc ttttcagaaa tgattttaaa  14700
tatgtataaa ctttccatgc ccttccctgc actatgtaca gaaatagaat ctttaatgtg  14760
gatcacaaat aacacaataa tcagaaatta gagatggtgt tgaatctcag cattggtaat  14820
gagaataggc tttatggata gatattccac tttatcctga gatacacagc tacagtatac  14880
tttctgggag gagtatgcct ataagcatcc ttggctggaa cctgaattgg gtttacaagc  14940
ttacatttag ataaaagcct ttttatttga gatgaaaccc atacaggcag ggtagaaagg  15000
agtggcctgg gtgagaatgt ctaatgtttg ggttttctca aagcgtcatt cctcctttcc  15060
tcttattctg gctagctttt ccacagtgtc atgtaaagag gcagcatttt ctagaagatg  15120
caagtcattt gaagtagtca tttggttttc ttctcatttc actttcagcc tgcctttaaa  15180
aatgtagctg aggcccaccg ctgtggctca cacctgtaat cccagcactt tgggaggctg  15240
aggcggaagg agcacatgag cccaggagtt caagaccaac ctgggcgaca gagggagaac  15300
ctacaaaaaa tgaaaaataa aaaatacaaa aatggccgag tgcagtggct cacgcctgta  15360
atcgcagcac tttgggaggc tgaggtgggc agatcacttg aggccaggag ttcaagacca  15420
acctggccaa catggtgaaa ccccatttct actaaaaata caaaaattag ccgggcgtgg  15480
tgacacgtac ctgtaatccc agctacctgg aaggctgaga catgagaatc acttgaaccc  15540
ggggaggttg cagtgagctg agatcgtgcc actgcactcc agcctgggtg acagaatgag  15600
actccatctc aaaaaataaa aaaaaatata aaaaaattag ccaggcgtgg tggtgcatgc  15660
ctgtaatccc agctactggg tggaggtgaa gaggtaggct gaggtgggag gatcgcttga  15720
gcccaagagg ttgaggctgc agtaagccag gatcacacca ctgcactgca tgcaacctgg  15780
atgacaaagc gagaccctgt ctcagagaaa aaaaaaaaag ataaatcttg tctttgtacc  15840
ttagtttctc cacatgcaaa actggttctt tataccttc cgaaggttgt gtggtgagtt  15900
tgctgctaaa taggttttg tgtttcttct accaaactac ctttccagga tatctacagt  15960
tggtgttcaa gccattgcct ctgggcttca tgtgagcatt cttgccccgg gcaggaattc  16020
tgcagcacaa aacaaagtac taaagatttt accctttgag aagcctactc cttaaggaaa  16080
```

-continued

```
tattacctcc caggtttagc agttgggaag acatgaagta cctgttctca tttcattcaa  16140
atgccattca gtggtctgtg agtctacatg aaatgactcc ctgcggacag caccctcccc  16200
cagtctgacc acctactact tcctcccagg tcactccctt gcagccacgc aggcttcttt  16260
gctctttcct gaaaatgtca attatgatct gccttggtct ctgcactgcc tctgccacat  16320
agagtcatgg ttcattttca ctcctcctca aagtgtttgc tcatgtgtca tccatcccag  16380
tgaggcctgt cctgtgctcc cctcccccca cattattcct gcttcccttt ctccatagca  16440
cttgtcaact gctaacacac tatatccttt tcctgtatac tatgctgatt gtttactgtc  16500
tccctgtttc caggtagaat gaaagctcca tgagggccat gatttgtact gattttgttc  16560
actgttctat ccccagtggt tagattaggg tcaaccacat agtaagtgct tggtaaatat  16620
ttgttgaatg aatgaaatgg ctgggacact gagtttcacc ctctgcttgg aattctttta  16680
cttatatgat tgttaccact ataccacgtt ggccagggat gctctgttcc ccctttaatg  16740
aacaaggaca aaaacatctt ctcttgattc tttcttagca taactgagat aggctggaga  16800
gttcaaggaa gtgttttgag tactaagaac aatagagaaa ccagcataga gaatgcaaca  16860
agtattacaa cagtctggct taacagtgtt tcactcttgg agctgccata tctagcttgt  16920
tctcatattt tgcaggcccc atcctaatct acccacttag gagaaatcta attccagctt  16980
cataggacta gtcctgacct tgccttgatg ccctgcatgt ggcaccatct cataatctgt  17040
tactaaggag ctccctttg tacatcatga cagctgccaa caaggccaag agaacccagc  17100
aaggctcatt ttctagtttg agtgttgtgt tagtctgcat gggctaccat aacaaaatac  17160
catagaatga gtggcttaaa aagcaaacat tttctcacag ttctggagac tggaagtcca  17220
agattaaggt gccagtaggg gttggtttct ggtgaggcct ttcttcttgg ctgcagacgg  17280
gcacattcta ggtgtgtctt catgtggcct ttcctctgtg cacagagagc atatgtaagc  17340
ccttgtgtct tcctttaata aggatgccag ccctatcaga ttagggcccc acccttctga  17400
cctcatttaa ccatattaca tccttagggc actatctcca aatgcagtca ctttagggat  17460
tagggctcca gtataggaat ttagggccag gtatggcagc ccacacctgc aatctcagag  17520
ctttgagagg ccaaagtggg aggatcgctt gagcccagga gtttgaaacc agcctgggca  17580
tcatagcaag accccctgtc tctacaaaag ctggcagcct gagtattaag atcttatctc  17640
tacaaagaaa aaaagaaaat taaccagaca gggtggtatg tacctgtagt ccaagctact  17700
tgggaggctg aagtgggagg atcactagag cctgggtaat tgaggctgca gtgagccatg  17760
attgtgccac tgcactctag cctgagtgac agagagaggc cttgtctcaa aaagaaagag  17820
agaaagagag aagagagaga aagagaaaga aagaaagaat gaatgagtta gctgggtgtg  17880
ctgatgtgtc tgtagtccta gctacttggg gctgaggtag gagaattgct tgagcccaag  17940
agttcagggc tgcaatgagc tatgtttgtg ccactgtact ccagcctgga tgacagagca  18000
gcaagaccct gtctctaaaa acaaaacaaa actaagaatt ttaggatgac acaactcagt  18060
ccatagcaag tgatacctct ttgactggaa caaataacct tatgcttcag gtgcaatatc  18120
tcacacagac actatggcct tcgttcactt tttaaactag catttattga agacaaaact  18180
atgtgccaag ttttatgcca gctgcagggg atatcccgta ccctccacca gtagaggaga  18240
cagagccagt ttcagagaag ggtggtgagt acctggggat ggatggatgt gtcaggaaaa  18300
gtttcattga gaaggtcgca tatggccagg cgtggtggct cacgcatgta atcccagtac  18360
tttgagaggc tgaggtggat cacttgagcc aaggagtttg agaccagcat gggcaacata  18420
gtgagacccc atctctattt taacaaaaag taaaagaaaa agagaaggtc gcatatggtc  18480
```

tttcaggtct gtgaagaagt gtgtgcatag tttaccacac aacagcatat gagtcatgtc 18540
accatcatta ttgtcatcac ccatctttat agtaacaaga aggtagttcc ttcacactct 18600
aacctaagcc ctttttcttc atcttcacct ggctttggtt cttttgctac agttactcca 18660
gcctctctcc ccagccttta tcttccacat tttctgctgt gttgtttcaa cagccagtga 18720
cttttctgtt catactctat tgatgatgaa gtaaaaattg attttgattt gtttctgatt 18780
tcttttcctt agtaagtttg agttgaacct ttagttctct ctcctcatct cctcgctttc 18840
tacaaaggca attcctggtg ttaagtgaaa gctgttcctg ttagagccta ctgtttgcca 18900
ttaataagtg ataagggagg ttgtcagcca gcattaatac tctgtttatg aaattacagt 18960
tactgatgca gtattttgtg aagttcttaa gatataaacg gcacaagtga tttgataagt 19020
tatagctcca gagacttcct tacatagtat gccagtattt ctttttcccc tctcaacggg 19080
acacacataa cattaaatta agtttgtctt ggttgccatt tactttaaac ggatctggtg 19140
cctgtgctca gatatgttta tgagagtata attgacttct ctgaaagcat tgagattgag 19200
ggagtagtta tatcttacct tagtctcatt gatgattcat ggaattgaaa taattaaaaa 19260
gtacttatta catgcctgat tgcttcatga ccctttgata aactaccaac actcatatca 19320
aatgtctcct gatttaaaaa aaaaaatttt ttttatacat atatagacaa gttctcactg 19380
tgtcaccgag gctggagtat ggtggctttc acaggcatga tcatagctca ctgcagcctc 19440
gccctcctgg gctcaaggga tcctcctgcc tcagcttctc gagtagctgg gaccacaggc 19500
acctgcgtct agctaaatgc ctcttgattt taatggcatg tcttgtcttc atagcatatt 19560
ccacaaaaaa ctctaaagtc tgatagaaat gatccttctc tttcctgtag tttttttttg 19620
tttgttttgt tttgagaaag ggtctcactc tggttgccca ggccggagtg cagtgatgcg 19680
atctcggctc actactacag cctctgcctc ctgggttcaa gtgatcctcc cacctcctga 19740
gtacctgaga ctccaggtgt gcaccaccat gcccagctaa tttttgtatt ttagtagaga 19800
cggggttttg ccatgttggc caggctggtc atgaactcct gacctcaagt gatcctcccg 19860
cctcagcctc ccaaggtgct ggcgttacag gcatgagccg tagcacccag ccaacatttt 19920
actctttata cgtgtgttca gctacaaaac tttcttccct accaaccctc ccaagtctaa 19980
gtaaaattga tctcggagtc acttgaccta tttatctggt attatcctgg tacgctgcta 20040
gaggtatata tacagggtca tgtgtcactt aaggatgaga atgtgttctg agaaacatgt 20100
catcattgag tgtacttaca caaacccaga tggcatagcc cactacgcac ctaggctgtg 20160
tggtatggcc tgttgctcct aagctacaaa cctgtacagc actgattcaa ctttaggcaa 20220
ttgtaacaca gtggtatttg tggatctaaa catagaaaag gtacagtaaa aatacagtat 20280
aaaaaatgtt gcatctgtat agaacaactc cattataatc ttatgggacc cctgttgtat 20340
atgtggttta ttgttgactg catgttgttc tgcggtgcat gactgtacta gttttaaaag 20400
cagaactgtc tctataatcc acttcttagc ttcaggtact atttcctaat atcagacacg 20460
tggcactgac ttttcttctt aactccagac ttatgtatcc aagtgcctat ttgacatctg 20520
catttggata ttggatcagc atcacaaatt taatacaagg acctaactct tgattctctc 20580
cacaacgcca aacctgtttt tcctctaatt gtccccacct cagtcaacta tattatccac 20640
ctagctgcct aagccagaaa cctaggaatt atcccagatt attattcttt tttttgtttt 20700
gttttgtttt ttgtttttga ctcactcact ctgctcaggc tggagtgcag tagcgtgatc 20760
tctgctcact gcaacctcca cctcccgggt tcaagtgatt ctcctgcctc agcctcccta 20820

-continued

```
ggtgctggga tcacaggcat gcgccaccac gcccagctaa tttttgtatt atagagatgg  20880
ggtttcacca tgttggccag gctggtcttg aactcctggc ctcaagtgat ccgcctgcct  20940
tggcctctca aagtgctgga attacaggtg tgagccactg cacccagctc agattcttct  21000
ttataatgcc tgcctcatgt agtccctcag caggagctat tgattctgaa cccttcccat  21060
cccccgtggt tcccttgctc tcctgtcgtt cacaccaccc tgtctcacct gcatcacgca  21120
gtagccacca gactgatctg tttcactgcc tgtgcagttc ttctctacac tgccggcaga  21180
gtggtctctt tgaaatgcag atctgattgt tgcactcacc tgcctaatcc cctccagtaa  21240
aacccagact tcttctcctg gcctacaaga tcctgtttgg cttggcctct gcctgctctc  21300
cagcctgttt cttaccctct tcgcctagtt tgctgcatgc ctgccacatg gcctgccttc  21360
tgctgctgct tggataggag aggctcagtc tctccttagg gcctttgtgc ttgcagttct  21420
tggaaatgct tggatgtcag aaggttacat ggctgtcccg ttggtgtcat tcaggtctca  21480
ctcagcgcag acaggccttc cctcgctgcg cagttagtca catgcctctc gttgctttct  21540
taatatttta ctttaaactt tttttctatt acatacctta tccgacatga ttttgtttgt  21600
gtgttttaca ggagaggggt tatatctgtc tcgttcatga ctgagttctc agtgcctgaa  21660
cagttcctga catccagtag accctttata tctatttgtt gaataagtga ctgcttttcc  21720
cgttgtgcat gggccagtgc caggggtcga gttgtagtga actgagagta catggacagt  21780
gctgaatggg gaaatgaaag ttatcaaaag cctctggtgc cttgcttatt catagcagat  21840
ttgttcataa taacaaaagc tggaaagaac ccaaatgccc atcaacacat gaatgaataa  21900
actgtggcta tgatttggct ataaaaagaa tgatacatgg tggaatatgg atgaatcttg  21960
aaagcattat gctgcatgaa aggaagcctt acacagaaga gcacatactt aggattccat  22020
tgatatgaaa ttctaggaag ggcatttaat ttatagtaag agaaaagtgg ctaaccagaa  22080
cccaggatgg gagagggttg actgggatgg aacacagaac ttttagggta atggaaatgt  22140
tctgtatctt aaatatggtg gtgattacac aggtataaat ttgtcagaac ttatcaaaat  22200
gtacaattaa atcagtccac tttattgtat ataaactatt tctcaaagtt gaactggtgt  22260
ctgacattta aatgtacttt ggatttcttt tgtttaccta cccacttctt gggcagatga  22320
cttttctttt aatttccagt tctcctagct acctgctgac tcatcccaga cgtacttaca  22380
ttcctgtttc tgaatcagtt ccaacatcct ttgggtctct tgtcctcaat ctctagttgg  22440
caaaacatct ttctaattgc agggttattg gttatcttca gatatgctat tggaacttac  22500
ttaccatcaa ggctagttgg gtctccacct caaagactaa gtatctccaa acagatactt  22560
ttacaacgta acaagcaagg aaaaaaaatg tttgcagcac atgtagtttg acaagaagac  22620
ataagagtat attttaaact ctcagttcct ttcggtatga tgacttgtat actttgatca  22680
gacttcctct tcagaagttg tagtctttat gtttaggatt cctcctgttc ctgttaatac  22740
agcagctgaa ctgaaagctg tatagagatt tgatgaatag ttgactgtct cgtgatcaaa  22800
ctcttgctct gacattaata tactttattt agtatcaagt ctaattttca tcttttattt  22860
ttcctccctt tagttcacag aatcacccag tcctttcttc ctttattaat acattatttt  22920
gcaagtgata tatgaccaca gcctcataaa gtactcaagc aaacacatag ggtatgatgt  22980
gaaagtgcca ctgaagctct tttgcatctc tccacctccc cagacaaaaa tacgattaag  23040
agttcggcag acattcttcc agatcttttc ctaagcattg acataggaca tgtgtacaga  23100
tacatagaca ttgtttacgt aagcagaatc actatgagtt gttcagcttg tttttttttc  23160
acataaaaac gtatcttggg ggctgggtgc ggtgtctcac gcctgtaatc ccagcacttt  23220
```

-continued

```
gggaggccga ggcgggcgga tcacaaggtc aagagatcga gaccatcctg gctaacacgg  23280
tgaaaccccg tctctactaa aaatacaaaa aattagccgg gagtagtggc ggacgcctat  23340
agtcacagct actcgggagg ctgaggcagg gaaatggcat gaacccagga ggcagaggtt  23400
gcagtgagct gagatcccac cactgcactc cagcctgggc gacagagcaa gactccgcct  23460
caaaaaaaaa aaaaaaagta ccttggggat ttttctgttt ttgtacttac aggcctatct  23520
catacttttt aatggctgct tagtatgcca tagaatagag aaaacacagt ttatttaact  23580
aatcctacta aatggacatt tatttctaat tttcactcta atagtcaaaa aatgaattta  23640
gaaaatgcaa ataatttgtg tttttagggt ctttcatttc ttatttagtt atataattat  23700
tctagctttt aaaaaagctt attagggtgg gaagtgcctc actgatactg taatgttaga  23760
actacactga aaactttgtt tcagaagaaa aagttgaatg taagttctct gtgactgcgg  23820
acttcattag cattgtgtct tcagggcttt ctttttaggt atgattataa accaaaagca  23880
ctataagtgg ttacataatt ttcttacagt ttgtatacct cattcaaaag aagcatacat  23940
ctctaaggat tagaactaga accataagcc aggtgtggtg gctcacactt gtaatcccag  24000
cactttagta ggctgaggtg ggaggatcat ttgcacccag gagtcagaga ccagcctggg  24060
taacataggg agaccccatc tctacaaaaa aaaaatacaa aaattagccg ggcatgctgg  24120
ctcatggctg tggtcccagc tacttgggag gctgcggtgg gaggattgct tgagcctggg  24180
aggtcaaggc tgcagtgagc tgtgattgtg ccactgcact ccagcccagg taatagagcg  24240
agaccctatc tcaaaaaaaa aaaaaaaaaa aaactagaac agtgaccttt ggttgtaaca  24300
tgatcagcag ttggttataa tgagtgcttt aaattaatgt tttcccatgg agctggagcc  24360
aagcatttgt gaaaaatgtt ttttctctct cccttttca gtttgaaatc ctgctaatac  24420
actaatttct gtggaacttt ctaccagcct ctactggtga ccagcagttg ctggtttatt  24480
agcactcaaa atatttaaaa caagcaagaa acctgtcttt ccatctcctt gccctgtata  24540
tggagatgca caaatatgga aaattctgat gtttaagcag aattagttat atttcaggta  24600
gatggatttg aatctttcaa aaccccacat gaggtaagta tatttcttca gccctgcttt  24660
tcagcaaata gtgggactgc agagcaggct gacatttgtc ttagctaccc aagaaggacc  24720
aaaattgcct tcctgttagg ttttgcctgc atgtttagtt atgagacagc ctgagaccct  24780
gtttttcttt cgtattagct gacctcggta ttaacctcac cttccctcct ccccttcttt  24840
ttttggtttc tggttttcct tttcaatttg ttacaagtac gcttaaagca cgaaggcgtt  24900
gcagttgtta gagattattt tgttctctgg cggtttcagt tatcttgact ttaagctttc  24960
ttcctcttag acaaataata taggcagctg tcatatctga gggttttaaa ttcttgttaa  25020
ccttttaact tattgtgatt aagatgaatt tgaaaagaaa gccatttcct ctatttaaga  25080
attgccttgg caagaagttg gaaatcctag aaccttgttg caaaggaatg tgtcgctatt  25140
tgttatgaat gagtctggtt gggtccagtg aaaccttcct attgctaatg tgcaattagg  25200
tatcttcagt gagggagaga ctgtcctcta agcaaagcag ctaaagctcc aggggcaaag  25260
ggcagagcga ataagcaggg gcctgggtca tctattttgt tctctggcct gaaagcattt  25320
gactgctcat ctcacatccc ttctttgccc tcagtcgtta gatattaggt ctactgtggt  25380
tgaatgagac tgtctacaaa agggttccag tgctcaccaa aagctgtttg taaatacgaa  25440
gtattacata ttatctttcc taaggttgtg agaacctaga agaactgcct ttgattaatg  25500
ctagaaaaca gctcttatga gacataaagt tcatttaata atcccacaaa tgcttacgag  25560
```

-continued caactattct ataccaggca gttttctagc tttttggaaa tagagtggtg aacaaaatag 25620
atgaacatct ctgccttcat agaacttaga ttctagctgg gcacagtggc tcacgcctgt 25680
aatcccagca ctttggctga ggcaggtgga ttacttgagc tcaggagttc aagaccagcc 25740
tgggcaacat gttgaaatca catctctacc aaaaatacaa gatattagcc aggcgtggtg 25800
gtgtgtgtct gtggtcccag ctactcataa gactggggtg agaggatcac ttgagcctgg 25860
gaggtggagt ttgcagtgag ctaagatcgt gcaactgcac tccagcctgg gtgaccaagt 25920
gagactccat ctcaaaaaca aaaaaaaaaa caactcagat tctagttggg gagacatata 25980
ctaaataaga taacacaaat aaagggcagt atatagtgaa ttcagtaggg acaaatgctg 26040
ggtagaaaaa actaagcagg ggaagaagac aggaagtgtc aggagtagta ctgtggcttt 26100
attattataa attgtttcct tttaaaaacg atgtgtatta tgcattaaag cattgctctg 26160
agaaggggtc ctctgacttc tccagactgc caaagggacc ctggcattga aagggttaag 26220
gaggctgggc gcagtggttc acacctgtaa tcccagcact ttgggaggcc taggtggata 26280
gatcacttga ggtcaggagt ttgaagccag cctagccaac atggtgaaat cgtgtctctc 26340
ctaaaaatac aaacattagc tgggcatggt ggcgggcacc tgtaatccca gctactcagg 26400
aggctgagtc aagagaatcg cttgaaccca ggaggagagg ttgcagtgag ccgagatcgc 26460
accactgcac tctagactgg gcaataagag gaaaactcca tctcaaaaaa aaaaaaaaga 26520
gagaaaagaa agaaaaagaa aaggttaagg accoctcatt agagttacaa gaccagccct 26580
caacatgtga ttaaaagatg tttgttatgg ccgggcgtgg tggcccatgc ctgtaatccc 26640
agcactttgg gaggccgagg caggcggatc acctgaggtc gggagttcgc gaccagcctg 26700
accaacatgg agaaacccca tctctactaa aaatacaaaa ttagctgggc atagtggcgc 26760
atgcctgtaa ttccagctac ttgggaggct gaggcaggag aattgcttga acccaggagg 26820
tgaggttgca gtgagccgag attgcgccat tgcactccag cctgggcaac aagagtgaaa 26880
tgccatctca aaaaaaaaga aaaaaaaaag atgtttgttt cctctttgat gctttatgtg 26940
ataatgatgc ggtagacttt ccacatatct ccctattata tctggtaatt gtggctttaa 27000
attatttgaa gctgtcattc acttttgaga ctagtgtttg taggatgttt tttccatttg 27060
tgttctgtag aaccccaggg taccctgaag cctttttggc acatgtgggg gtcattttaa 27120
acgtatgttt ggattattca tctacgttag tctaaacaag taatcagatg cctggctttg 27180
aggtaggtat aagtaaagag aatagactaa ggggttggtg catatttatg gaacataaac 27240
agcatagatg gttaacagat gctacacaca ggtgaaccac tgatttaacc tgttatgtgt 27300
atgccattga gccactatca agaccttgag ctgctaccta gtgtctgtat aaagataaga 27360
atttccagcc aggggccggg cgctgtggct catgcctata atccgggcac tttgggaggc 27420
tgaggcagta ggattgcttg agcccaggag ctcaagacca ccctaggcaa cataaggaga 27480
ccttgtctct gcaaaaaatg aaaatatcag ccagatgtgg ttgtgtgcac tggtagtccc 27540
agctccttgg gaggctgagg tgggaggatc acttgagcct gggaagtcaa ggctgcagtg 27600
agccatgatt gtgccactgt actccagcct gagtgacaga gtgagatctt gtctctaaaa 27660
tataaataaa taaaaaggat attttctagg ccaggcgtgg tagctcacgc ctgtaatccc 27720
agcactttgg gaggctgaag tggaccaatc acctgagctc aggagtttaa gaccagcctg 27780
ggcttaggca acatggcgaa accccatgtc tacaaaaaaa aaaaaaaaaa aaaaaagaaa 27840
gaaaaagaaa aaaagatatt ctgagcttat tttctcgtta tttccttctc tcccttccca 27900
aatatttttt tgagcatctg tgtcagctag gaatacagaa actaaaaaac attgcttgcc 27960

```
cttgtgactg gggagatata gacaattgaa taatcaacca caacatgtta tagtaagtgc  28020
taagataaag gtaggcacaa gtgtcaggga aaacacagaa gtgggatgcc tgagctgagt  28080
gggagtgggg gtggcccaag aaggcttcct gaaccagtgg caccagatgg acaagggaga  28140
ggccccctac tccctgcttg tcctctgctc tcttctgacc ggtagcgtta atacttcttt  28200
ggtttaatgc aggatcacca gactctgtgg cccacgacct gtttttgtgt agcccataag  28260
acataccttt ctaagtacta tagctgaaaa acatcaaaag agtagtaata ttttgtgaca  28320
tgtgaaaatt atatgaaatt caaatttctg tctgtaaacc tcactggaac acagccatgc  28380
tcattcgttt gtatatggtc tgtggctgct ttctccctac aacggtagaa ttgaacagtt  28440
gcatcagaga ccttatggcc tgctaggcca gaaatgttaa gccctttaca gagaaagctt  28500
gctggctcct gtttaatgct ttaactgccc tactgaaagg caggaggttg aaaaaatgat  28560
ggtagtcaaa aggaatgcat gaaatcctgt tgtcttctgt tagctgattg caagtagtac  28620
acaggatata tttgagacat ctcttttcct atctcccacc aaaggataat tcaggcggat  28680
ctcagtgcac aggcacaggc atttgcctca ttcttgtttt gtctgttttg aatttagtta  28740
tgggaatatt ttaatatctc tcaaaaatag ggtatctggt gtgagtcaga atgattatag  28800
aacatgcttg cctggagaac aggaaatgcg ggatccactc ctggtgtgct gttagctgaa  28860
ggacgtcaga actgtccttt aacctccctg caggtctcta aatggtagga ttgtttgggg  28920
attacactag atcatctcta ggcaccgttc agctcagtag agacattgct gcatggtgga  28980
aggagtgacc tcagtgtgaa tcctggttct gtccctttct gcccaggaga ccttgagcag  29040
cttatctaaa tgctgtgtgc ctttgttagc tcatctgaaa atgtggctgt aagaatgacc  29100
tcatgagaat ggactgagat catattctta aaactcttgg cactaatagg tatttaatct  29160
actataactg tgaaaattat gtctgtgaac tctttttttt tttttttttg agacagagtc  29220
tcgctctgtt gcccaggctg gagtgcagtg gcacgatctc ggctcactgc aacctctgcc  29280
ccctgtgtgc caccactctc ggctaatttt tgtattttta gtagagatgg ggtttcacca  29340
ttattggcca ggctgttctt gaactcctga cctcaagtga tccacctgtc ttggcctccc  29400
aaagtgctag ggttacaggc gtgagccact ggacccagcc tgaatactaa ttatatactt  29460
cattttaatc aaactcaatt tgtgaaatag ctggatttag gatttgctta atgaaagaga  29520
tatgacgttc ctttaaaagc cagcttttct actagaatca acattatttg aattacatgc  29580
aattatatga gatcatatca atgcatagga agctagacat gtattagatt gtggttaagg  29640
gcatacgctt tggagccata taatatagct gtggttcaaa gcctggcttt gccatttact  29700
tactagctgt gtatgatctt ggccttccat ttcctcctgg gaatgataat aatacttgct  29760
gtgaagatta aatgaaatta cccatgtgaa atgcttagca tggtacctaa gtagtgccac  29820
tctaaagttt catggcctcc tactctctgg acacatacct atcctctgtc tgctagaact  29880
cctcacttcc ctgttctcct aacttactta tccttcagag cccagttcaa gggacgtctt  29940
catgaagtcc ccccttgcccc agccctgtgc ttccacaggg cctgtgcacg cctctctctg  30000
cttcccactg tgtgcgggcc ctacctcctc cttttattgt gcttcacttt cttgtgcttc  30060
acagatgctg catttttttac agattgaaga tttgtggcaa ccctacgttg agtaagtctg  30120
tcggcactgt ttttctaata gcatgtgctt actttgtatc tctgtgtcac attttggtaa  30180
ttcttgcagt atttaaaatt tttttattat tgtgttggtt acggtgatca gtggtctttg  30240
atgctgctgt cgtgattgtt ttggggtgcc atgaaccgca tccgtgcgag acgttagacg  30300
```

-continued

```
taattgataa tgttggcatg tgctctgact gccccactga ctggccattc ccccatctct  30360
cttcctctcc tcaggcctcc ctatttcatg agatacagta ttgaaattag gtcaattaat  30420
aaccctacaa tggcttttaa atgttcaagt gaaaggaaga gttacgtgtc tctcacttta  30480
aatcaaaagc taggaatgat taagcttagt aaggaaggaa tattgaaagc caagacaggc  30540
taaaaaccag gcatattgaa agccaagaca ggctaaaaac caggcgtctt gcagcagtta  30600
actaagttgt gaatgtaaaa gaaaagttcc tgaaggaaat taaaagtgct actccagtga  30660
actccggaat gctaagaaag caaaacaacc ttattgctga tgtggagaaa gtttcagtga  30720
tctggacaga agatcaaacc agccacaaca ttcccttaag cctaagcttg attcagtgca  30780
agatcctgac tctcttcaat tttatgaagg ctcagagagg tgaggaagct gcaggagaaa  30840
agtttgaagc tagcagaggt tggttcatga gttttaagta aaaaagcaac ataaaaatgc  30900
agggtgaagc agcaagtgct gatgcagaag ctgtagcaag taatccagaa gatatagcta  30960
aggtggctag atgatgaaat gaaggtggct acactaaaca acagattttc agtggagatg  31020
aaagagtgtt ctgttggaag aagatgccat ctaggacttt catagctaga gaggagaagt  31080
tagtgtctgg cttcaacatt tcagaggaca ggctgactct cttgttaggg gtgaatgcag  31140
ctggtgactt taagttgaag ccaatgctca ttgactattc tgaaaattct agagccctta  31200
aaaattatgc tcaatctact ctgcctgtgc tctataaatg gaacaaaaaa gcctggatga  31260
cagcatatct atttagagca tggtttactg aatatttaag cccactgttg agacctgctc  31320
agaagaaaag attcttttca aaatattact gctcattgac agtgcacctg gtcacccaaa  31380
attcagatgg agatgtacaa agaaattaat gttgttttca tgcctgttaa ccacaacatc  31440
catgcagcag cccatggata aaggaatatt ttcagttttc aagtgttatt agttaagaaa  31500
cattttgtaa ggttatagct gccataggta gtgattcctt tcatggatct gggcaaagta  31560
aatttaaaac cttctggaag ggattcacca ttttagatgc cattaagaac atttgtggtt  31620
catgggagga ggtcaaagta tcaacatcaa caggagtttg aaagaagtcg atttcgactc  31680
atggatgatt tcaaggtgct cacgacttca gtggaggaaa taactgcaaa agtgggggaa  31740
atggcaagag aactagaatt agaagtgggg tctgaggata tgactgaatt gctgtaatct  31800
cgagataaaa tttgaacaga tgtttcttgt ggatgagcag agaaagtggt ttcttgagat  31860
gggacctact cctggtaaag atgctgtgaa cactgttgaa atgataatgt attacaataa  31920
tttataacaa taactatgta ttacataaac ttagtgataa agcagcagta aggtttgaga  31980
gaactgaatc caattttgcg agaaattctg ctgtgggtag catgctatca aatgtattgc  32040
atactttaga gaaatcttta atgaaaggaa gagtcagtgt gacaaacttc attgtcttat  32100
tttaagaaat tgtcacagat accccaacct ttagcagtca ccatcctgat cagtcagcag  32160
ccatcaacat tgaggcaaga ccctccacca ggagaaagat tgcaacttgc agagggctca  32220
gaaaattgtt agcttttttt tttttttttt aatgagacgg agtcttgctt ggttgcccgg  32280
gctagagtgc agtagcatgg tcttggctca ctgcaacctc cgccttctgg gttcaagcaa  32340
ttctcctgtc tcagcctccc aagtagctag gattataggc acgtgccacc atgtccagct  32400
aatttttgta tttttagtag agacagggtt ttgccatgtt ggccaggcta gtcttgaact  32460
cctgacctaa ggtgatccac ctgcctcggc ctcccaaaat gctgggatta taggcgtgag  32520
ccaccacgcc tggctcaata agccattttt attttttat tttatttatt tatttatttt  32580
tttgggacag agtttcgctc tgtcgcccag gctagagtgc tgtggcgtga tctcggctca  32640
ctgcaagctc cacctaccgg gttcatgcca ttctcctgcc tcagcctccc aagtagctgg  32700
```

-continued

```
gactataggc acctgccacc gcgcccggct aatttttgtt gtttttagta gaggtggggt  32760
ttcaccgtgt tagccaggat gatctcgatc tcctgacctc gtgatccacc cacctcagcc  32820
tcccaaagtg ctgggattac aggcgtgagc caccgcaccc agcccatttt taaattaaag  32880
tatatacttt ttttttttt aagacaatgc tattgcacag ttgatagact actgtatagt  32940
gtaaacataa cttttatatg caccgggaaa taaataattt catgtcactt gcgttattgc  33000
agtggtctgg aactaaagcc acaatatctc caaggaactg tttacttgct gtctcgctat  33060
cagactgtga gactgtcaag ggcaggcatt ctgcgcagct ttggcaatac cgtctagttg  33120
taaaaaagac ggaactgttt caggccatgg gcattctagt gggaagacaa atatttaatc  33180
tcaagtgtgc aaaatgctgc catagaacag gagtgcagtg gagcataata ggagctctgg  33240
accttgtctg aacacataaa agaagccttt ttcctaagga gtgattgctt aagttgaaac  33300
ctgaaggatg tgtgggaatt agctaagtga agagaaggaa gagttccagg cagagaaaac  33360
tgtggacata atggctttgg gcaagttact cagcttcttc tctgcttcag tgtcttcatc  33420
tataaaatgg gaataatata acctagagtt atatagttag ggttgttgtg atcataaaga  33480
cagtatttta agtcatcatc ttctaatatt tctgaagtgg ggcataattg gttcattcag  33540
gataacttct gggtccacgt ttatgtattg aatggctaaa tgtatggatc tgcttactgc  33600
actttaacct tgttctttac ctgctctgaa gcctttcttg cattttaatg acaagaacgg  33660
tgtattttgc ctttcagtga gtttgttaat tatggagatc aaactctgcc tttcattact  33720
gcataagtct catggtgtgt cagacatctt aggtcagtgt gtgtcatcag ttagaatgct  33780
ttcaccttca agaaacagaa aagccagctc aatgacttaa acacacagat gtttatcatt  33840
tcagaaaaca aaagtctggg gcaagggtga gtccagtgct ggttaactga gcagcctggc  33900
aaaggcatca aggagccaag ttcattttgc cctcctgctt tgtcatcctc agtacaggct  33960
tgcccgctgg ctccccatgg tctcaggtgg cctgtcgcag ttccaggtgc cacagggaga  34020
caccagaaca tcccattgag gaggaggaac tgtttctttc catgtctgtc tctttattga  34080
tgaacatttg ggtggcttcc accttttgtc cattgtgaat aatgctgcta tgaacattgg  34140
tgaacaataa attcttttta aaaatacagc atctaggggc taagctatga ggatgcagag  34200
gcataagaat gatacaatgg actttgggga ctcgggtgaa agggcaggag gcaggtgagg  34260
gataaaatac tgcaaattgg gtacagtgta tactgcttgg gtgttgggtg caccaaaatc  34320
tcaaaaacct acggaaataa aaaattaaag taccacatca attaatgcgt agaccaaatc  34380
ttattgcaat taaatttcta cttttagcat catttgctac aatgaagttc tagtatttga  34440
aatattttga gccactgact tgctgtttaa tgggatttga tcccatagta aagaagatat  34500
aaaccaagta agtcaaaagg atcttagaag caattttatt ccatcctcta ttttgaagat  34560
gttctggatt cagagtgatt ttccagggtc agagagctaa gtcatgttaa ataattcaaa  34620
gtgtatgaaa atacacatta ctcacagatt caagtagagt aaccaggggt gtcttttgcc  34680
tctagtctta ctctaaccag tgtctaacta tgcctgtgta gataaaataa aatagaaaac  34740
tgggataatt caggtattca agtaattgaa gaaaatcagt cctgtttaaa atatctgggc  34800
aggccgggca tggtggctca tgcctgtaat cccagcactt tgggaggccg aggcaggcag  34860
attacttgag gtcgggagtt caagaccagc ctggccaaca tggtgaaacc tcgtctctac  34920
taaaaataca aaaattagtc atgcatggcg gcgcatgcct gtaatcccag ctactcggga  34980
ggctgaggca ggagaattgc ttgagtccag ggagcagagg ttacagtgag ccgagattgt  35040
```

accattgcac tctagcctgg gtgacagagc aagactctgc ctcaaaaaaa aaaaaaaaaa 35100
aatgtgggca actctaatac ttagctttta ggtatttgct tcagtagtcc actttatgtg 35160
ttagtgttcg acattactag tgggattttg cttctcatgc tctattttct gatttctatc 35220
accagtggtt tcatagttgt atacagtaat ctctggttag agacagaggc agtggcctgc 35280
tggggaacac accagacgga aagtgagagt tccttgtttt gggctttact ttgcccttga 35340
cttccagtaa tcagggtgtt tccttgttct gaaacacgct tgtgttagtc acaacaggtt 35400
cacaactggc agacaggtaa tccctgaaca agtaaatccc agtggaacca gaaaactggg 35460
tcttgttttc cttaattgga acctgactta gaatcagcta ttgaactggg aaacaaacaa 35520
aaaataagtg ttagccatta gaaaatgaat ttaaattact ggtctgtccc tatttagaat 35580
ttcttgcaat catttccact gtatgtaaca ctgaaatcct ttgtggttgt ctgctgcaaa 35640
agtgaatctt tgacccagca actttaaatg cttttgacac cattgggaat tttgagaatt 35700
gttaatttaa tctgcacttg tcctaggtgg gggtggggat gagggagaag tgatgtcctt 35760
ttgcattggc agttatgctg tttgtaagca gaggcttgtg cttctggaac ttatgtttac 35820
tagggagtga ttattagcat aataagtatc atattctagc ttttatttct ggaggcagta 35880
aagagccagc caagcagaga gaagagtggg aggtgactgg cagcaagggc ctcgtcgcta 35940
ttagtgcaac actgctgcgg gtggaggagc ttttcatcaa agcaggaaga aggggaggcc 36000
ttttctgcct atgactccaa cttccctgca tgccacgtct ttgcaggcct gcagtgaggt 36060
taggatgtaa acgactttct tttctttccc atcccaagct catcatgggt tctctctaac 36120
tgattcttgt tctcttagta attatttagc tgtcaagcag ggacttgtcc tgacaaggag 36180
aacgggaagg ccctctggtt cctgtctaca caatgtctgt agtcccttct ctcaaagact 36240
cagtgttgag actcacatgt ctccccgaag ggaaggagga ggcattcaag tagaaacaca 36300
tttacgtcaa caggttttct gaacccccgg tgaattttga gttcttagtg caaccttccc 36360
ctgcttcacc gttcctgttt cttctctgtg cctctgtttt ccggttgggg aagtggaaag 36420
gatcctgact ctggaggaaa gtggagaaga accagtgggc ccgactgcat caagagcctc 36480
cccttagcag agaaccgcct ggtcctcctc actcatacgt gctgtctgtg tgcagggtgc 36540
tcatgggaga tgttgaagag gtgtaagaag gcttcttctc tgtgtaactg gggagcaaga 36600
catgcacaca aagacaagtg catcagggta cgttcagtgt gtaacttaaa ataagcgaca 36660
gacatagtgt ggtgggcaga actgtgtgta tttcagacag cggctcaagg actgcttgtc 36720
tctttgtagg aacactgtag gccagaatca gtctgttaaa tgggagttga tgtcctgtga 36780
cacttttcta gattaaatcg tcctaatact ctacaataaa tgcttttgtt tttagttact 36840
tgagggaaaa gatggtattt ttcaaaaagt gagacagaaa aaggcatatg ggacattgta 36900
tgtatgtcct ggtatgtgtg cacaccacca cctgtgaagc agccttgctg ctaaagtaga 36960
ccccgagttt gataaaacgc ctagatctta ctgtgtattt ataggaaata cgagggatgg 37020
agaaacattg taaatggctt tttggggata gaatcagcaa attccaaact gcattatagg 37080
ataaacagaa cagtttttc aacaaataaa tcataagggg aaaaggtgag aaaaaagcct 37140
ctatagataa aaagagattg aagagatgaa tgaaccaata gtcatatatg attgattcag 37200
acaaaatgaa gaaaatgtga ggcaatctgg gaaatgtgga cactgactga ttatttgatg 37260
gtattaatgg tattaagaag tttattttat aaaacaaacc aaaaaagaca agaggaaatt 37320
tatcttatat tgaatattga caacaaataa ttaaatttaa aaaatttgtt agttaagtgt 37380
gaaaattgtg gatacatttt aaaagaatat cctttaaaga gacatacata ttgaaatatt 37440

```
tacatatgaa aagaaatgct gtctgtgatt tgcttcagaa tagcccaggc aagggagtag  37500
gtgggagaat cactgacaca ggactggtta tgcattaaac atcgttgaag ctgggtgttg  37560
ggcaaactag gctcattcta ctgttctact gtgtatatgt ttgaaaattt tagaattaaa  37620
ttttaaaatt taacaagtga gtgagggctg ggcacagtgg ctcatgcctg taatcccagc  37680
actttgggag gctgaggagg gtggatcacc tgaggttagg agttcgagac cagcctggcc  37740
aacatgggga aaccctgtct gtactaaaat tacaaaaatt agccaggcgt agtgacatgc  37800
gcctgtaatc tcagctactt aagaggctga ggcaggagaa tcacttgaac ccgtgaggcg  37860
gaggttgcag tgagccgaga tcgtgccact gtactccatc ctgggcaaca gagccggact  37920
ccatctcaaa aaaaaaaaaa aatgtgagtg agatatcttg acaaaagacg gagtagtggt  37980
tgcctggagc ctgggtaaag gggtggcgtg gctgcagagg ggcacaaggg atcttttggg  38040
gtgatgggaa tgatctgcgt cttggctatg atggtgattt catgggtacg tacatttaaa  38100
ctaatcaaac tgttcattta aatgtgtgta ttttattgta tgtaaattat actgtaatgt  38160
caatttaaaa attgattaaa gttagtaaga aggggccagg tgtggtggct catgcctgta  38220
atcccagcac ttggggaggc cgaggtggac agatcacctg aagtcaggag ttcaaaacca  38280
gcctgaccaa gatggtgaaa ccctgtctct actgaaaata caacaattag ccaggtgtgg  38340
tggcgcgcac ttgtaatccc agctacttag gaagttgagg caggagaatc acttgtacct  38400
ggaaggtgga ggtggcagtg agctgagatc gcaccactgc actccaggct gggtgacaga  38460
gcaagactcc atatcaaaaa aaaaaaaggg tttaaaaaat attattatta ttattattat  38520
tattattatt attaaaatag agacggggcc taactatatt gcccaggctg gtctcgaact  38580
cctgggctca agtgatccac cctcagcctc ccaaagtgtt gggataatgg tgtgagccac  38640
tgtgcttggc cagtaagaag ggtttttgtg tattatacac atagtgtgga atcagtagtg  38700
tcagaagtgt gaggcaccca gcactgccag gcagcaggga ttacctggct tgtgctgcat  38760
ctttattttt cccttcacct caagttaact ttatcgttca tatttctgat tttgcagtag  38820
tgtctctaat ttctccttgc agctgtagag tcagcttgaa ttttgtgatg tttgtccatg  38880
tgtctgccat ccaaaaggac atgcattttt atgctagaat aaatgatgtt aggaggacat  38940
ctacccattt atgataattc tttaaacatt caattggcta cattataata gtcaagcact  39000
aagggtacac ctgagctgaa aacaattcag ctggattata attttgattt attttccatc  39060
cagtctacca accaaccaac cagtcagcca gtcagcattt attgaatgta ttctttgcac  39120
catcccccga gttgggtttt gggtgcatga ggatgaatat gatacagtcc tgcccttaag  39180
gatgtaactt tcagggtgag aagatagctg tgtatatgta taatttcagc agcatgacaa  39240
atgccatggt caaagtgggt gcaagatgca atatagtagg ccgcatttat acatgttggc  39300
ctcctccctc cctcccctct agccccccttc cttacctggt aagtcaaatg aaccaaatgt  39360
caaacagttt ggaaaggaga gttgaagcag aaggaaactt ccttctgccc ctttgaattt  39420
gttacttttt cttccaatta aaaatgtgtt atttttacaa taccattata ttgacattgc  39480
aagggtccct gatgttttta ttgttttctg ttgtcacttt gtatctcttc tcccattccc  39540
atcccactcc cattagcatc ttctctgatg tgtttaatat gtatccttgg atatatatgt  39600
attcttacat ggtgttttct gtaaatttat ataaatagta ttacatgata attctcattc  39660
tgatcctttc ttcatttaaa actatgtttt tcagttctgt tggtgttgtg tttatatggt  39720
gcttttagcc actgcattgt atttttattg ctctgtctac tgcgttttat ttgcctgttc  39780
```

-continued

```
ccctaagtga cagacacctt atttgttctc cctgtaccac aaacaatgct ctgtgggtat  39840
agtggctcac acttatagtc tcagaacttt ggggaggctg aggcagaagg atcgcttgag  39900
cccaggagtt cgagaccaac ccgggcaatg tgacaaaaac ctcatctctg ccagaaatta  39960
aaaacttagt tgagcacagt ggcatgtgcc tgtggtccca gctacttgag agactggggt  40020
gggaggatcg cttgagccca ggacgttcag gctgcagtga gccttgattg tgccaccact  40080
gcactccagc ctgggcaaca gagtgagact gtctcaaaaa aaaagataaa actaaataaa  40140
ttaataagaa gatcctcata tatgtcttct tacgaacttg tacaagagtt tctctggcta  40200
aataccaaca agtatcattg ttgggtcaca gagtataatc atatttaatt tcactaagta  40260
atgcatgatt gcttaatttg tatttccact actaagtgca gtccttagta tttgacttta  40320
aaacttttgt gagtttggca ggtttcacat gttattaata tctttttaaa ctcacatttc  40380
tctgattact aatgagcatg gctagatttc tgtatatact gggtagtctt tggattttcc  40440
ttttatgaat gacctggtca tatcattttc ccatttttcc agtagagttt cttatatatt  40500
gtagctatta atcctaaggc agttataaat gtttcagatg tcttcttctg tccctcatct  40560
acctgctaac tttgtttgtg gtgtccttta ttcagcagaa atcttttgtt ttaatttaga  40620
catttccttt ggtttttcca tttataaaga tttgtgcttt ttgatgtctt acttaagaaa  40680
tcttttctgg gccaggcgtg gtggctcatg actgtaatcc cagcactttg ggaggccaag  40740
gtggaaggat tgcttgaagc caggagttcg agaccagcct gggcaacata gcaagactcc  40800
atctctatgt aaaaaaaaaa ggcattatcc tgtattttct tctaattagg tttatatgtg  40860
tctcaaattt acatctccag tttgattttt tctctgatct ctaaatttgt atactcactg  40920
tctacctgat agccccacct aaatatctaa cagatatctc aaacttagca ttgctaaaac  40980
ttattttatc ccttcctcat taaaaaaaaa aaatctgttc ctctcccaat ctttattcat  41040
ctaagtacac ttgtcccttg gtatctctgg gggattggtt ccacgagcag ccctccacaa  41100
tggatactga tataggttag ctgtgtgtcc ccactcaaat ctcatcttga attgtaatcc  41160
ctgagtgtta agggaggaac ctgatggcaa gtgactggat tatgggggcg gtttcttcca  41220
tgctgttctt gtgacagtga atgaattctc acaagatctg atggttttat aaatggtgct  41280
tttttcctgc gctctcacac acctctgtct cctgccacca tgtgagacag tccatgcttg  41340
cttccccttc acgatgattg tgagtttcct gaggcctccc ctaccttgtg gaactgcgag  41400
tcaattaaaa ccctttcctt tataaattac ccagtctcat gtagtatctt tatagcagtg  41460
tgaaaacgga ttaatacaga taccaaaatc cacagatgct taagttcctt atatagtgac  41520
actgtatttg catataacct acacacatcc tccctcgtac tttaatctct tgaatactta  41580
taatagttaa tacaatgtaa atgctatgta aattgttgtt atactgtatt atttagggaa  41640
taaacaagaa aaaaaaagtc tgtacatgtt cagtatagat gcaaccagcc ttttttttccc  41700
cctaaatata catataggta catacttctt gagatggagt tttactctct tgcccaggct  41760
agagtgcagt ggtgggatct ctgctcactg caacctccgc ctcccaggtt caagcaattc  41820
tcatgcctta gtctgctgat tagctgggat tacaggcaca tgccaccacg cccagctaat  41880
tttgtatttt tagtagagac ggagtttcac catgttggcc aggctggtct cgaactcgtg  41940
acctcaagtg atctccctgc cttggcctcc caaagtgctg ggattacaga agtgagccat  42000
ggcacctggc ttttttccta aatatttttg atccatggat atggaacctg tgggtacaga  42060
gggccgactg taaatggtgc tgccttccac cctgttgctc aagccaaaaa ccccggagtc  42120
atctttgctt ctttttcatg ctctgtgtgt gcaatctatc agcaagttct atacattctg  42180
```

actccagaaa atttctggaa tctgtcctgg gcactttatg gcctcctgct gctactctaa 42240
cccgtgtcac ctgtcttcgt atagccatta ttactctgct ttgcagagtt tatttgttgc 42300
atttattcat taaagactct cacctcagct ttatagctag ttttgcaaga tagagcacta 42360
ggtctggcta gccatatgct gccagatgga ggagctgagt ttttttccta tgttctgctc 42420
cttggcttca ctagtggctg ctggaggcat cactgtgcac agatgcttgg ggcaaaggat 42480
cttgccaacc tcgatgcagg tcactggaac agctgataat gtccgtggtt tataacctga 42540
tgtagatcca gagatgtcat tgaaagattt ttgcctgcca gcaggtctga gtctgaagac 42600
catgcccagg ctggggtggc gctatcatag ctcactgcag cctccgattc ctgtgttcaa 42660
gctgtcctcc agggtagcag gaactatagg cacacaccac tacacccagc taacttttca 42720
attttttgt agagatggag ttccacatct gtcggtcaga ctggtctgaa acttctggcc 42780
tcaagcgatc ctcctatctc aaccccccaa agtgctggga ttacaggtgt gagccactgc 42840
gcccagccag actttttgt taaatgtacc ttaaagcaat gctttcttct tttttttccc 42900
atcacaaatt taattattta taaaaatatc taatggaaag aaactggatt agcaagccag 42960
acagatactt gtcctggcta agtgtgatac tgggcaagtt gttgacttcc ttcttcagat 43020
gcctgtgata tataccccat gtttattcta atttcttaaa gatatgagaa cctagctcta 43080
acataagcat gaaatgccta ttcctgaggc attgatcaca ttgtcattgt tccaggttcc 43140
tctctgtgct ccctgaaatc cccattagcg taattcccca ccatcccctt gtgcggagtc 43200
cactgcccca ctgtgctgct gccctcgact gttgtgaggc cggctgagtt tcagtaacag 43260
ggactcggtg attaaatttc tttttctttt tctttttctt ttttttttt ttttttttt 43320
tttgagacgg agtctcgctc tgtcccccaa gctggagtgc agtggagcaa tctcgctcgg 43380
ctcactgcaa cctctgcctc ccaggttcaa gtgattcttg tgcctcagcc tccctagtag 43440
ctgggaccta caggtgcctg ccactacacc tggctaggtg atgaaatttc ttcagctttc 43500
tctggccctc cctacttcta ggatccaaat gacacgctac gtatcgttgc catttctgat 43560
ttggatgtac aaatataggg acagatgggt ttgtgtttgt ttttgatgta ttttttttc 43620
tctcttaatc tggctgtaaa agcatttcca atggcttata gtttagtatg tgttcccaaa 43680
gtgggagcag cctgtacata tggaagtcca gttgggtagg gctccctgta ccctggcgcc 43740
agggcgttgt tctgaccgat ggtgcccccct gatggccagt gtagaaactt ggtcacggtg 43800
tcatcttttt ctcactatca ctggggattc ccttcactcc ccagcaatta ctcactttta 43860
ttctgtcttg aatcttagat aattatgccg gagataatcc ttcttatctc ctctttgggt 43920
ttcttgtttc ttccttattt attgctctct tacctcaaaa atatcttatt tcagccaagt 43980
gcagtggctc acgcctgtaa tcccagcatt ttgggaggct gaggtaggtg gatcacctga 44040
ggtcaggagt tcgagaccag cctggccatc atggtgaaac cctgtctcta ctaaaaatac 44100
aaaaattagc caggtgtggt gctactccag ctacttggga gtctgaggca ggaggatggc 44160
ttgaacccgg gatgtggagg ttgcagtgag ctgaggtcac atcgctgcac tccagcctgg 44220
gcaatagaga tagactccat ctcaaaaaaa aaaatcttat ttcttctcac cactcattct 44280
tttcattata ttttgaacta aaagcttgtc ctggtaatgg ctaaagagta cttagtggtg 44340
tgtccatatc aaaaagaaag gaagcccttg attttgaaga gaaattagaa gccacgctaa 44400
ggactcatgg ttgccatctt cacgagctct gagataggta aggcacgccc ttcagaatct 44460
ttatgggttt ttgttagctc ctcagctttc tccaactaaa attgctttgg cttaagcttt 44520

-continued agaactcaag ataaatgaaa gttcttcatt ttaactttag ttgataaatt actagtatta 44580
cagagcgatt ttctgtgtgg aaaacatgcc agcactgtca cccagacaca ctgtgcacag 44640
gttcagcatg taccatggct gcctgaggcc tgccctcatc cctgctggcc tcctctcctg 44700
cgcttttttt ttttttttga gacagagcct tgctctgtca cccaggctag agtgcagtgg 44760
tgcaatctca actcagtgca acctccacct cctgggttca agcaattctt ctgtctcagc 44820
ctcccgagta gctgggatta caggtgccta ccaccatgcc tggctaattt ttgtattttt 44880
agtagagacg gggtttcacc atgttggcca ggctggtctc gaactcctga cctcaagtga 44940
tccaccccac ttggcctccc aaagtgctgg gattacaggc gtgagccact acacccagcc 45000
tcctgcgctc ctcttaacgt ggtttcagat tctgcccacg tgccttccag actagcttct 45060
gaaacactgt ccacctgtca gttgaattat tgagctactg atttgtctgt gacttttagc 45120
tcataattgg actgtcgtaa atgacgtaga tacgtaagta cgtcctacgg gttatgtggc 45180
tatgctgctg agacctcaca ctcaaccctc cagcactaat tcactctctt tcaaaattgt 45240
gctgttgctt tcagtgtttg gggagcccag gagaggaatg tgaaacagga ctgcccaatc 45300
ccgctaacac acacacacac acacacacac gccaagaatg tgaaacagga ctgcccaatc 45360
ccactgtcac acacacacac acacacacac acacacacca aaaaccaaaa caaaccaaaa 45420
tattcctgag tgcaggagtt atgatttaac aaaaccttca tatcctctaa catccccact 45480
ccagagaaca ccctacttag aataaaaagc taggagtgat gagcaccatg gctttcagtc 45540
tttatggagc tgtgatagcc catcattatt tgatttattc tcctatcttt tccagagcgg 45600
atgtagtctt tgaatagaat tgcataattt tagggtttta agcaccctca gtaatcgtgc 45660
agtttagttt cccatctcat gccttccaaa aaacttcata caagttgacc ctcatctagc 45720
cttggcccga gtgcttccac tgaacaagaa ttcagcagtt ttttaagcag gcccattcca 45780
ttgtatggac tgcccgaatt attaataagt tctctatgtt cggctaaaac ttaactcatg 45840
ggaatttcca ccctaagtcc tgatttaacc atttgtagaa atgaatgact cagtttttc 45900 actcccacag aagtggtctt cagctattgg aggacagtgc ccggcctccg taggctctcc 45960
agcctcagca ttgcccactt ttctcttggc ttgttgggct tttttcttct tgatttttgg 46020
ggatttttga aaatagccct atgtcttgga tatgagtcac aaattgcccc cccccccacc 46080
atttcgtcat ttgtctccaa gctctgttta cattggtgtt tgccgtgcag aagtttttct 46140
ttaatgtaat aaaatgtagc catctttttt aaaatgacct ctggacttca tgtgtttgga 46200
gtttattcat acttagaaag gccttgtcca cttgaggctg tttaaaaaat acccatattt 46260
tctgctagta cttaaatgga tttgtgtgag tgtgtgtgtt tgtgtttgtg tgtgtgtgtg 46320
tgtacttaaa tcttttatgc atctagaatt tattttaaga taagatgtga ggtaggggtt 46380
caaattaatt tttttccagc tagctgtcta gttactccaa cattattgaa ttactcattt 46440
tttcctgttt tgaaatgcca ttatattaaa ttcatgacac acttttggat ttattcctag 46500
agtgtttcat atgttttatt tccaagcaaa ccaccacaca catcttatac cttcattact 46560
gaaattttta acctaaatgt aaaacttgtt atgtgcttac ctggcatcca gccggtcagg 46620
atggtctgac tctgctcctt cctgcctcag cagcctcctc ttttgtgcca cctgcaggtt 46680
aataagcatc tcttatgtca ttatccaggc cattgaccaa ggggtgacaa taatattggc 46740
cattgtaggg ctgtcctttg gactccagtg gagagccatt actcactgtt tcctatttta 46800
gaaatgcagc atgataggtt aaaaagtgct tagggttttg gtttcagttg cagaactaaa 46860
tttgagcatc ccttctattc attgtttctc agactttaat gtgaacagga ataacctgag 46920
aatcttgtta aaatgcaaat tctttttttta tttttagtag agacggggtt tcaccatgtt 46980
ggccaggctg gtcttgaact cctgacctca ggtgatccac ctgccttggg cttctagaat 47040
gctggtatta cagacatgag ccacagcacc cagcataaaa tgcaaattct gattcagtag 47100
gtctggggta ggccaagatt ttgccccgtt tatttattta tttatttatt tattggacag 47160
tatcacactc tgtcactcag gctagagtgc agtggcctga tcatggctca ctgcagcctc 47220
aaactcatgg actgaagtga tgctcctgcc tcagccttct tagtagatag gactgtagac 47280
ttctgccacc atgcccaggt aattaaaaaa aatttttttta cagagatggg agtcttgcca 47340
tattacctgg gctggtattg aaatcctgtc cccaagcaac cacccaaagt gggattacag 47400
ggtgagctat ggtgcccaga cggcttttgc atttttaata agtccccagg ccatgctgat 47460
gctgatggtc catggactac cctatacttt gcaggaccaa gactagagtg agtcaagtga 47520
catgccccac gaagtgtgtg aggaggcact tactgtcttg gcacttgcac aaacctgaga 47580
gcaagcactt ctttaagttt tgtaccctgg gtcccttgct tgcctcaccc taatcccagc 47640
cctgatattg tgtttcttat tattgttagg cttactgctg atgaagctac taaataggac 47700
tcttgagagg tgagctcttg ctgtctgcac tttttttttt tttcgagaca aagtcttgct 47760
ctgtcgccca agctggagtg cagtggcgcg atcttggctc actgcaacct ccgcctcccg 47820
ggttcaagtg attctcctgc ctcagcctcc cgagtagctg ggactacaga catgcgccac 47880
cacgcccagc taatttttgt atttttagta gagacagggt ttcaccatgt tggccaggat 47940
ggtctcgata tcttgacctc atgatccgcc cgcctcagcc tcccaaagtg ctgggattac 48000
aggtgtgagc cactgtgcct ggccgctgtc tgtattttta aacaggttcc ccaggcgacc 48060
cttaggcaca ccaaagtttg agaaccactg aaaaagagaa gttctgactt ttaggattaa 48120
tttacagcct gttatgaaac cagtgcttgc aacctgaaaa catcatgcta ctgtttacct 48180
ttagttttca tgatgtgctt gagatagtgg tggctaagcc cgaaatatat aaatttttaa 48240
ttttcatgtt tgtgggtaca tagtgggtgt atatatttat gggttgcatt tgttttgata 48300
caggcaggca atgcataata atcacatgag ggtaagtggg gtgtccaact caagcattta 48360
tcctttgtgt tacagacaat ccagttatac tttttagtta ctttaaaatg tataattaaa 48420
ttattttgta ctatagtcac cctgttgtgc tagcaaatat taggtcttat tcatgctttg 48480
taactttttt ttttaatcca ttagccctcc ccacttccct cccatccacc cccctaaccc 48540
caccactacc cttcccagcc tgtggtaacc atccttctac tctttgtctc catgagttta 48600
attgtattaa tttttagctc tcacaagtaa gtgagaacat gtgaagtttg tcttgctgtg 48660
cctggcttat tttatttaac ataatgatct agttccatcc atgtttcatc catccatcca 48720
aaggatcaca ttcttttttg tggccaaata gtactccatt gtatatatat gtactgcatt 48780
tatttatcca ttcatctgtt gatagacact tgctttcaaa tcttgcctac tgtgaatagt 48840
gctgcagtaa acatgggaat gcagagacct cttttctata ctgatttcct ttatttgggg 48900
tatataccta gcaatgggat tgctggattg taaggtagct ctgtttttat ttttggagga 48960
acctccaaac tgttctccat agtggttgta aagttgcaaa tattgacagt agttactcaa 49020
gtggtgccaa actacaggag aaggcctact tgtatttggc aaaaccaacc tttacccacg 49080
tactgaatct gataacgtgg cttttgctca aaatccaact ctgatgtggt aaaaacctta 49140
attgaaagtg gaccatagct cagtgcttct caaactctaa tgcgggtaag aatgttctgg 49200
gtgtctcgtt aaaatgcaga ttctgattca gctggcctgg ggtgggacct ataagtctgc 49260
atttctgaca agcttttaga gggtgctgaa gctttagctc tacagctgtg cttgcaaacc 49320
gaggagattt ttgactgagc tctagttcgg aactttttcc taacatatga gagttttggt 49380
taggaatgtt tggagaagtt attcatggat tttacttcag cagacaggga aagatgcttt 49440
gtatccgcgt gacctgcctt gctcacaaaa gccagtgatg gattcccaac cgtggacctc 49500
ccagactcag gcatgacttg taacttgtac tctgccgtca cggtgcatgg ctgagagagg 49560
gatgcccact gggtagaaca ctttgtttcg tttttttaaa tgtgtgaata ggcaatacat 49620
ttacaaggtt caaaattcaa aagatataga aggagataca cagcgagtag tgtcctcccc 49680
ttaattcccc atctgctcag ttcccaattt tcctcacccc tccaaccctg ccaaattagt 49740
aaaagtactt tattagtttc ttgtgcatct ttccaactat ttttatgtaa tacaagcaaa 49800
cataaattta tttatatata attatatata gtgtctcttt ctcaccttaa aacaaattaa 49860
tgttaacata ctatggacat tgttctgcac cttgattttg ttttttcatg aaaaaattaa 49920
tcttggagat ctttccacat gtccacatga agagcttttt ttggttttct ttcttattgg 49980
tatcttattg tatggatcta ccatacatat cgtggtatct tattgtatgg ttctaccata 50040
atttaactag aaacttattt actgatggac ttcagattgt ttccaatttc ttgctgttaa 50100
aatgcaaaga ataaattcac atttgtatat tttatgtaca ttacacattt tgttttcttt 50160
tattcagcaa tgttctattt tatgaagtct taaaatttta tgtatcttga actttttgta 50220
tgtttaatga aatattactt ttatatcttt aagttctcct ttgatgagtt tggaatgctt 50280
tttcacattc ctaatgttat taacacagaa cagattaaat atatttatat gcatttttcc 50340
tttttttttcc ccagagacag ggtctcgccg tgtggcccag gctagagtgc agtggtgcaa 50400
tgaaagctca ttgtaggcca ggcactgttg cttacccctg taatcccagc agtttcagat 50460
accaaggcgg gcggatcacc tgagatcagg agtttgaggc cagcctgacc aacatggtag 50520
aaccccatct ctactaaaaa tataaaaatt aggcgggcat ggtggtgggt gcctgtagtc 50580
ctggccactc aggtagctga ggcaggagaa tcacttgaac ccaggaggcg gaggctacag 50640
tgagccgaga tcacaccact gtactctagc ctgggcaaca gaatgagact ccatctcaaa 50700
aaaaaaaaaa aaatgctcat tgtaacctca gacttctggg ctccagtgat cctggtgcct 50760
cagcctccta cgtaatgggc cctacaggta tgtgccacca cacctagcta tttttgttg 50820
tttttgtag agatgcagtt gttttttgtt tgttttgttt tgttttttga gacggaatct 50880
cactttgtca cccagaatgg agtgcagtgg cacatctcag ctcacggcag cctctgtctc 50940
ccgggttcaa gcgattctcc tgcctcagcc tcctgagtag ctgggattat aggcgcccac 51000
caccacaccc agctaatttt tgtattttta gtagagacgg ggtttcacca ttgttggcct 51060
ctgggctggt ctcaaactcc tgacctcaag agatctgcct gccttagcct ccgaaagtgc 51120
tgggattaca ggcatgagtc accgctcccg gccagagatg cagttttgat atgttgtcca 51180
ggctgctctc ctgggctcaa ctgatcctct tgccccggct cccagagtgc tgggattatg 51240
gacattgttc tgtaccaatg tgtgctgggt gtgcagtcac tgcccagctg ggctgcatat 51300
attttttcca aaacccaggt aaaatgtgtt catcgcttaa gaatcagcat tttttaattt 51360
taatttttat ttttttgggt gagacaaggt ctcacactgt cgcccaggct ggagtgcaat 51420
gccgcaatct cggctcactg caaccgccac ctgatcctca cgcctgatcc ttctgagtag 51480
ctgggaccat gggcacttgc caccacgccc agctaatttt ttgtattttt tagtagggat 51540
ggggtttcgc catggtgccc aggctggtct tgaactcctg agctcaggca atcctcccac 51600
cttggcctcc caaggtgctg ggactacagg cgtgaggcac tgcgtctggc ttatcagcat 51660

-continued

```
tttattaaaa aaaaaaaaaa aaaaagagga aggagataat tacgttgaaa cctgatagtt  51720
agaactttca atttaagctg aatgggagtg gggctcctga aaaagaaggt ttgtgaccag  51780
catgggcaat gtctctacta agagaaaaaa aaagagggaa gaaggttcaa cctgctgcca  51840
tttaacactg cttctcccag gagagcagcc ctgtgaggct tgggtttctc tgaatgatgt  51900
cttgggtttc aacattgtcc ccttacttgt tagccacttt catggaaaaa acccgcaatc  51960
catgaatatt tgtcatctcg catgccatta ctggtcaaac aaaatgaatc acaagctggg  52020
gcttgaatag aaattccatt atttacagac aggtcagatt aatctatcta ggagggacag  52080
tgaaagaggc tatttttcct gatggtactt tttaaactgc agtaaggtgg tgctgttaat  52140
gaaaatgcca aagagaaaga gtgatttcct tcctaagcag tattagatta tagtgttgtc  52200
aggagtcttg caattgaatt accttttttgt aatcaattcc gccttatcag ttaactctac  52260
ttgtaatgga ctgctggctt caagagactg agtctggatt atttaaaact tcttgctgta  52320
aaggagacat cacctgtagc atctcccctt ccccaggtgg agcatcccct gttggagcac  52380
tttggaggct gcagtgttat gagctctgcc ctgtctggga agggttctgg aacaggtctg  52440
aagccctcag agcaaaggct catttgtctg cttgatgcca acgtgctgtg ggttctccag  52500
aggctggggc tggttgcttc tgagtccttg ttagtattgt taccgcactt cccattcgca  52560
tctgcctgtc atgttctacc actaaccccc aggaagaaat gaatgggaaa tttagtttgc  52620
catgattttt gccctgattt aacatacggt acttagtttg ggaagccatt tgctgttgaa  52680
gaccttcttt cttgtttttt taagacagag tcttactctg ttgcccaggc tggagtgcag  52740
tggcacaatc tcggctcatt gcaacctctg cctcctgggt tcaggcgatc ttcatgtctc  52800
agcctcccaa gaacctgggt ttacaggctc acaccaccat gcctggctaa ttattgtatt  52860
tttagtagaa atggggtttt gctatgttgg ccaggctggt ttccaactcc tgacctcaag  52920
tgatctgccc gccttggcct cccaaagtgc tgagattaca gaggtgaacc actgcacctg  52980
gcccctgttg aagacttttg tgaaacaaag catttttttaa agtttcttaa gtaatattgg  53040
aattaactta gagtggactg tgtgaagtaa atgtgttgtc acaaacttaa cggtgtcaac  53100
atggtaacaa tattgaaaaa tgcttttaat tttgtgagat gcgtattcat agaactaaga  53160
gtcagaagtt cttgaacctt gattcctgtt tgcctcttac tgataatgga ctatatttag  53220
ccttttcttg ggttgggtcc ttatcaaaga atgagaagac taactaatag taacaataat  53280
atgtgtttgc tgtatgacaa gagctagcca ggtgatttgc agttttagta gggtaaggta  53340
cagcactatg aaccatttct ataacaaaaa ggaaatgtat catgtcaaaa gagtaaacaa  53400
agttttttag agaagaggaa aacaaatctt gaatttgtta tttgtacaaa tatacataga  53460
aggctatcag ggctgtctga gtttttcttc atgtgtgaga atgaaggtaa aacttgctcc  53520
aggtgcttag ataagacttg aaggaaacac aggcatttat ttggtttatt gttagatcaa  53580
tatagagttg tacggcaatc ttttacattt tccactctca agacctagaa atgcatggta  53640
taatagctta gaaagacaac tggtgtgaag tatgttcatt attctttttt ttctttgaga  53700
tggatctcgc tctgtggccg agggtggagt gcagtggcac aatctcggct cgctgcaacc  53760
tctgcctccc gggttcaagc aattctcttg ccttggcctc ccaagtagct gagattacag  53820
gcatgcacca cgacgcccag ctaatttttt gtatttttag tagagatagg gtttcaccat  53880
gttggccagg ctggtctcga actcctgacc tcaggtgatc cacccacttt ggcctcccaa  53940
agtgctggga tcacagatgt gagccatcac gccaggcctg ttcattattc ttgatgatct  54000
```

-continued cacatttgac ttacagtgca cttttatgtc atgtgatgag gtgatacgtt tgaagatgaa 54060
agagggcatt taaaagtagc tgaggacaga atcagaactt tagtagttac agtgaggaag 54120
tcaaaatctc tccccacaaa acaacaataa taccagacaa aattgttaaa agcaactgtt 54180
tcagggctct agaaatggaa taaatgcaag aaagaaatgg agaagcattt atccaagaga 54240
aactgccaaa cttcaggtaa gaacaatggg agtctttgac tccttgccta aatggtaggg 54300
ggttactccc atcccttcct gccattggtg tggtaattct gttagggtac agcaggccgt 54360
gaaaactaac agcttggctg ccagaggtaa tgcgcttgat ttggagcagg tgaaaagccc 54420
ctgtccggtg gcattgacag tgaaagtaat gaccctcagt agcaagagaa caaggaaggc 54480
caacagttct ggtagtgaga gagctatccc aagtgggtca agcaacagac tggcaaacta 54540
gcccaaaact taattaacag agatcctgga aatgagacag ttacagaggg gtctgaaggg 54600
ctgtccacac atttctggct gacttagaag cctctgcaca catgcaggta aaactagaga 54660
gatcccatgg tacccatttg tccctggttg gctgggaatc tgcatgaacg tatgaaggaa 54720
atgtgacagg gctgatccga aaggaaaagt gggatagacc tgaaaactgc ttgaactttt 54780
gctccctaac cctgcacaga cccatgggca gaggttggaa gcctagtagg ctcaagagat 54840
gcaaacacaa cctgtaacca atcattgcct gatcactaag ctgtgtgtca gcaagtcagg 54900
cttaaaaata aaaacaagaa tttgaaaaga aaaactggaa aaaagaagaa aagaaactga 54960
gtagagacat caaatagcca cacatcacag gggagacaga ttttgtagat ttagtcaggg 55020
caaattacta aagaaataac acacgtgaaa aattacagtt gagagttgct acaatatatt 55080
atctaaaaca tctagttttt taaaattatg attatgtctg taatttatta tggttatgtc 55140
tgtaaggaat ggctacagaa aacaaacaga aaaacaaaca ctaatgggac aaaaaaaaca 55200
ggaaagggtg gttcatattc agggaagata atcagtcaat agaaactgtc tctgagagag 55260
cctagatgtt aggtttagta aacaaagact tcaacacagc tattatacat gtgttcagga 55320
aatacaggaa actatgcatg tcatgtttaa atatttaaag aaatgtatga tgacagtgac 55380
tcaataaatc tcaataaaac agaaactgta aaaaagaacc aaatgcaaat tctggagatg 55440
aaaaatacag taactaaaat taaaaattca ctacaggaat tcaacagcag atttgagaca 55500
cagaagaaag aatcagtgaa cttaaagata gatcaataga aactgccaat ctgaagaacc 55560
tgagagaaaa aaatgaacag agcctcagag atctgtggga caacatcagg cataccaaca 55620
cacatgtcac agactcctac aaggaaagga gaagaaaggg cagaaaaaaa atgtatgaag 55680
taacagccag aaacttccta catttgatga aaatcatgaa tctatgaaaa cttcaaatcg 55740
gataaatatt aagggatcca cacctaggca tatcctggtc aaataattga caggcaaaga 55800
caaaaagagg ctgggtgtag tggctcacgc ctgtaacccc agcaccccag cactttggga 55860
ggctgaggtg ggcagatcac ttgaggtcag gagttcgaga ccagcctggc caacatggtg 55920
aaacccccgt ctctactaaa aatacaaaaa attagctagg catgatggca catgcctgta 55980
atcccagcta ctcaggaggc tgaggcagga gaatcgcttg aacctggaaa gtggagcttg 56040
cagtgagccg acatcatgcc tgccactgca ctccagcttg ggcgaccaag taagacactg 56100
tctaaaaaca gacaaagaca aaaagaataa gaatgtcttg aaagcagcaa gaaaaagata 56160
actcctcaag ttttttattg taacagtatg aatgtttgct gacttctcag cagaaacagt 56220
gtagggtaga aggcaatgga atgacatatt caaagtactg aaagaaaaaa cgaaacaaaa 56280
caaaattttt atatctagca aaagtattct tcaaaaatga aggcaaaata aagacattcc 56340
tagataaaca aagactagga attgcttgct acgagatcta cctgaaagaa gttttttga 56400

-continued

```
ctgagaggaa aattctacca atggacagta atttagatcc acaagactaa aggaagaaca  56460
ccaaaattgc caaatatttg ggtaaatgta agataatata taaaaatagc tgaggcttaa  56520
agtagtaaag aacattctcc tggtaagagg aaaatgataa caatggaaac ttgagtcaat  56580
ttaaaggaat aaagaatgct aaaaatagta agtatgtagg taaacataag aaattttcta  56640
atgttgtaat ttttctaaat ggtaattgac agtaaaaagc aaaaataata acaatgtatt  56700
atggagttaa aacatgtaga atagagagta aaggggtgat tcctggaggc tgggaaggtt  56760
agggggtagt gggagggaag tgggttagtt aattggtaca aaaagaaaga atgaataaga  56820
gctagtattt gctagcacaa cagtgtgact gtaatcagaa ataattgtga tataaaaata  56880
actaattatt gtctgtgaca caaatgataa atgcttaaga tgatggatac cccatttacc  56940
ctgatgtgat tattaggtat tgcatgccta tatcaaagca tctcaaataa cctataaata  57000
tatacacctt ctatataccc acaaaaatta aaaataaatt tttaaaattt agaaatgaaa  57060
tatacggcca taataacaaa agacataagg aaaaaaaaat acctgagact ctcttgtagt  57120
ttgttgagtg taattggcat aatccttttg aaagctagtt gggcagtagc cattaaaaat  57180
gtactttttta aaaattaatt attattatta tttttgaga cagagtctca ctctattgcc  57240
caggctagag tgcagtggtg tgatcacagc ttactgcagc cttgacctcc tgggctcaag  57300
tgatcctctc agcttagctt cccaggtagc tgggactaca ggcacacacc agcatgcctg  57360
gctaattttt gtattttttta tagagatggg tgtctcgtga ggctgtactc acactccagg  57420
cctcaaatga tcctcttgcc tcggcctccc agagtgctgg cattacaggt gtgagcacca  57480
tgcctggcct gccattaaaa atttaaatgt ttagtccttt tgacttagca ctttcagttt  57540
taagaacaca tatcatagaa acactacaat aactttgtaa taactaagaa ctataaaaaa  57600
gtcaaatgcc catcagaaag ggactgatta agtaagtagt atatttattt tgactaacta  57660
ttataaccat taaaaggaat gaagtcaggc cgggtgcggt ggctcacgcc tgtaatctca  57720
gcactttggg aggccaagga gggcggatca cttgaggtca ggagttcaag accagcctgg  57780
ccaacatggt gaaacccctt ctctactaaa aatacaaaaa ttagctgggc atgttggcgt  57840
gcatctgtta tcccagctac ttgggaggct gaggtgtgag aattgcttga accagggagg  57900
tggaggttgc agtgagccga gattgcacca ctgcacttca gcccaggtga cagagtgagg  57960
ctccatctca aaacaaaaca aaacaaaaaa gaatgaagtc actatatatg ttttaacatg  58020
gaaaggtgtc cacttaacag ctgctaaatg tgatgcattt ggtcgaaaag agattgagca  58080
gcacagaagt atatgctcaa aggtatgtgt gagcatgtgc acatgcacac gcactttttt  58140
ttttttttt ttttttgaga tagagtctcc ctctgtcacc cattctggag tgtaatggtg  58200
tgatcttggc tcattgcaac ctctgcctcc tggattcaag caagtctgcc tcagcctccc  58260
gagtagctgg gattacaggc gtgcgccacc acacatgact aatttttgta tttttagtag  58320
agacaggttt tcaccacgtt ggtcaggctg gtctcgaacc cctgacctca ggtgatgcgc  58380
ctgcctcggc ctcccaaagt gctgggatta caggtgtgag ccaccatccc cagccaacac  58440
gcactttttt ttcttcagcc ttttaatagt gatcttctct ggcgatttat aggattgttc  58500
cactttatta tatatttcca aaataagagg tttttttcct actgtgtgtt tctacttttt  58560
ctacttttca aactattact ttaaaaacaa atattttata aacatacaca ttttaaaaag  58620
tagctcatag cataacatta actttgtatt tgaaattgtg agatgaaatc aagtacccgg  58680
tctataaaca gcactttcta catccattcc acatcttgtg ttcgtgtgtg tgtgtgtgtg  58740
```

tgtgtgtgtg ttttacatgt ctgttcagta cattataaga tctttggggg gcaaaactga 58800
tcttttttttt gagacggagt ttcgctcttg ttgcccagac tggagtgcag tggcatgatc 58860
tcggctcact gcaacctctg cctcccaggt tcaagcaatt ctcctgcctc agcctcctga 58920
gtagctggga ttacaggcat gcaccaccac acctggctaa ttttgtattt ttagtagaga 58980
tggggtttct ccatgttagt caggctggtc tcgaacttgc cacctcaggc gatccacccg 59040
tctcggcctc ccaaagtgct gggattacag gcttgagcca ccacgctcgg ccaaaactga 59100
tcttattcat atttgttcaa tttctccccc acatcccctc tctctattcc tatcatatag 59160
tgctttgcac ataacagacc atctgtgaat atttatactt tattaaagac atataaaata 59220
gtaattattc tctacagcaa ttggaatcca atacagtaat ctatatacag ttatttgatc 59280
cactgacata cgttctttct ctttctccca aaaataacca ttgagactaa caaaaccaaa 59340
acaaaaccga aacaaagagc tctagctttt cccatcttct ccagttacta aatgtagaac 59400
agactgggtt ttgctgactt ctaggcagga aacagattct atttctagga acagaattcc 59460
tatatctaac tgagctattc tttttctttt atgttgtttc cttttcacta aaatagaaaa 59520
aaaaaagaaa cattttaagc ctttctacct ttgctatatg actttatcac atgcaacatt 59580
tggaatattt gatctaataa atttctaaag acaattagga ctttgccact gaagtgttat 59640
tgttcattac ttgaaaacgt gttactttta aatgttttgt ttatagcact atgcctttaa 59700
aagtaaggtg ttatatttaa aaatccaaaa agtaaattac tttctgttgg attagaggaa 59760
atttccatta agggagattg aagtggttgc ataaaccctc ctacagataa caattgaaag 59820
atctgggtaa aatataagaa acaactaaaa gcatccaaaa gctgtcccta gaacctgagg 59880
agaattgact cctgaaacac tataatagaa ggagcaagaa ttgcaagttt gtgacttttt 59940
tgccagaggt tatgcatcag tacccatggt ggtttcagta gaaagaaatg atagtggaaa 60000
gctgcagcct tacagatgag aggtgccaaa gaagagaagt cagggatgga agacaagctg 60060
gaaagttcag gggggaatcc tggaaacaag agaggactac agaaaggggg aggccccaca 60120
tctgagtgaa aactgcccaa attcctggtt gactattaaa ctctaaatgt atagtgaaat 60180
cccagggagc ccagcaagac aaaaacaaaa ataaaaacca gccaaccaat gaaacaaagc 60240
aagcaggcag aggctagaga ggaatctacc cttaaaagac agacctatac tagatgagat 60300
ctgtgaggtt catgcttttt aaaacagtat atccctaaac tgtgagcagc gaagcagtgg 60360
aaagctgaag ccttactggc ttggggttca gaggaaagac cctaatattg cccaagcagc 60420
tgaaaactta ggaggaaatc acaagaacac aaaagtcaca gagtgtgagc ccctaaatct 60480
gagtatgatc agcctaaatc cctggctgtc tgccagatta cacagaagca tgggagaccc 60540
cagggagcta ggctagacgt tgtaagagct gagcagagat agcagctgct tcatacgaca 60600
ggagagacag ttcgcagttt gaatccaggc aagttaactg cctactagaa tataaaaaga 60660
gaaagttctc agaagaacac agtagaatcc agagttgcta taacatctta tctacaatgc 60720
caagttttca atctacaatt actagacatg taaataaaat ggaaagtcta actcatactc 60780
aggaagaaaa gcagtcagta gagactgact ctgagcatct aagtgggtac agtgttggat 60840
tttgcaggca gactgcaaag ccactgtgct atgatcaaag aattaaagga aaaataagtg 60900
aacagataga gaaattgtaa caaagaaatg gaaagtgaaa aaatggaagt tgtagagctc 60960
aaataagtaa tagctgaaat aaaaactcac tggaggccgg gtgcagtggc ttacacctat 61020
aatcccacaa ctttgggagg tcaaggcagc aggatcactt gagctcagga gtttgagacc 61080
agcccgggca acatagtgag accccacctc tacaaagcaa ttttaaaatg agccaggcat 61140

-continued

```
gatggtatgt gcctgtagtg ccagctactt gggaggctga ggtgggagga tcgtttgagc  61200
ccaagagatc gaggctgcag tgagctgtga tcgtgccact gcactccagc ctggctgaca  61260
acatgtctca aaagaaaaaa aaagttcact agatgtgctc aacagcagtt ttgaaatgac  61320
agagaaaaga atctgtgccg ttgaagatag atcaatagaa attatcccat ccaatgaaga  61380
gaggagcaaa gattgaagaa aagtgagtag agcctcagag acttgtagga cgatatcagg  61440
tagcctaaca taagtgtact tggagtctta gaaagggaag agaaaaatag gcaaaaaaca  61500
atatttgaag aaataatatc cccaaacttc ttaaatatgg tagaaaacac tatagattca  61560
agaagttcag tggagtctga gcacaaagga aaagcactca taggcatatc atagtcaaat  61620
tgctgaaacc aaagataaaa agaaaatctt aaaagcagat agagatcctt ttgcagctca  61680
tgagtgtgac gattgggtgt tcatgcatgt gtgtgaggtg tgccaccctc tgaaccttgt  61740
tacaacatca gcacattacg tctctgaact tgcatgggga ggggaagcag gtagagaaaa  61800
gtgacacatt acataaaagg gatcagtgtt acaaatgtga ctgacttttc atcagaaatg  61860
aaggaggcca gaagacactg gaacagtata gtcaaatact gagagaaaaa ccctgtcaac  61920
caagaatcca gtatccagag aaacacattt tcaaaaatga gggctaaaga cattttcaga  61980
aaaacaaaaa ttgagagaat tcatcaccag cagacttcca ctaaaagaag ttttcagaat  62040
gaagggaaat gataccaggt ggtaactcat ctacaggaag aaataaaggg cattggaaat  62100
agtaaatatg taggtaaata taaaagacta tgattttttt ccttctctaa tttctttaag  62160
atacatatgt gttttttttt gagatggggg tctcactatg ttgcccaggc ttgagtgtgt  62220
tggctattca caaggacaat tatggtgcac tatagccttg aactcctggg ctcaagctat  62280
catcctgctt cagcctcctg agtagcagag actacaggca tgtgccactg tgcctgctgg  62340
tgacataaga aacaagattt taaagatttt ataacactct agtgctgggt ttataatgta  62400
catataggtt ggtcacagtg gctcacacct gtaatctcag ccctttggga ggccaaggtg  62460
ggaggattgc ttgagcccag aagtttgagg ccagcttggg caacatggtg agaccttttc  62520
tctacctaaa aaataaaaaa cctggccagg cgcggtggct cacgcctgta atcccagcac  62580
tttgggaggc tcaggtgggc ggatcacgaa attgggagat cgagaccatc ctggctaaca  62640
cggtgaaacc ccgtctctac caaaaataca aaaaaattgc ccggcatggt ggtgggcacc  62700
tgtagtccca gctactctgg gggctgaggc aggagaatgg cgtgaacccg ggagacggag  62760
cttgcagtga gccgagatgg tgccactgca ctccagcctg ggtgacagag cgagactgtc  62820
tcaaaacaaa caaacaaaaa aaacctttta aacataatat gtatataggt gtaattatga  62880
caacagtagc actaagatgg ggcagggcaa atggaaattt actgttgtaa gatttgtaca  62940
ttttacctgc ttagaagaga cacactttaa acacagagac acaggttaaa agtgaaagga  63000
tggaaaaaga ttataccatg aaaagaatac acataagaaa gctgaagtgg cgatattaac  63060
atcaaatgaa ataaatttta agatgaggaa tattgctaga gattaaggat actttataat  63120
gataaaaggg tcagtatctt acagagctat aaaaatcttc aatgtgtatg tccctgataa  63180
cagagcttca aaatactgaa ccaggtgcag tggctcacgt cagtaatccc agtgctttgg  63240
gagtccaagg caagagtatt gcttgaggcc aggaattcaa gaccagcctg ggcaacatag  63300
tgagatccca tctctgcaaa aaagttttaa aaattagctt attgtagtgg tgcacacctg  63360
tagtcctagc tgctctagag gctgaggcag gagaattgct tgagcctggg aattcaaggc  63420
tgcagtgagc tatgatagca ccactgccct ccagcctggg caacagagtg agaccctgtc  63480
```

```
tctaaaaaat aaaaatagag aggctactag gactggtaag tgagtttagc gagatacagt  63540
aggatctcac tactgtaaga atacaaggtc agtatatcaa gaaaaccatt tatgttttgg  63600
tcagaatacc aaaataacag ataactggaa aaaaaatttt aagtatagta ttccacttgc  63660
catatcatcc aaatacatga agtactaggg ataaatttaa caaaatgtat gtaaaactta  63720
catactgaaa actacaaaat attagtataa ataggctcgt ggattggaaa tctcagtatc  63780
ataaacataa tcaattttct acaaattcat ctgtagattc aatacattct caatcaaaat  63840
ttctgcgtat ttttgttgta gaaattgaaa agctggttct agaatgtgta tggaatgcaa  63900
agtacttaaa actggcaaag ccagcaaaaa ttgaggactg acttctacag caccgcaagg  63960
ctgtgatact ggcaaaataa tagacatgta cataaatgag aagatggaat ccagaaagag  64020
atccacacgt aaatagacaa ttgatttgca gcaaaggtcc tgaggcaatt caatggggaa  64080
aggaacatct tttcaacaca tggtacagca gcaactaaat atctgtgtgg aagaaaacaa  64140
acattaaccc ataccttata cactgcccag aaagctcaaa acggaccaaa gtcctaaacg  64200
agttaaaact ataaagcttc tggaaaaatt ataggggaaa acgttcatgt gacttctggg  64260
tgtgaaaaga ttttctaagt aggatacaaa aagcacatac cataaaataa atgaatgcta  64320
aattggactt tatcaaaatt gaaatgtgct ttttcagaaa ggaatgaaga aaatgtacaa  64380
tatgggataa aatgtttaca atagataaat ctgacaaagg attgtaaaga actcttacag  64440
ttcagtaata gtaaccccat tttttaaatg cacaaaagat ttcaaagtat acttcacaag  64500
gtaagataaa acagtggcca ggagctacat aaaatacttc atattattaa ttatcagaga  64560
aaagcaattt ccagccataa tgaactaccg ctctttaccc tctacgtatg gctaaaattt  64620
aagagactga tagctccagg tgttggcaag gatgtggcac aagcagaact ttcatatcct  64680
ctgttgagaa tgtaaagtag tactagttta gagaacagta gtttgtttta aagttaaaca  64740
acagttactc aaggatacag taattccatg cctagatatt tatctgagag gaatgaaaac  64800
gcagaggctt ctccatgagt gtttgtagca gcgtattcat gacggccaaa ggctggaaac  64860
aatccggggg ctcatcaggt gaatggatga acaaactgtg ctgtcccagt ccaatgagag  64920
ctctgagcag gaaaaaggag ctctagacag catggatctg gctcaaaaac atgctttgtg  64980
aaagaagcca gacccagagg tgtacatgct gtatatttat ataaaagtct caaaggtgca  65040
aaccagtgga tagtgacaat aaaataaagg agtgattgcc tggggcttgg gtggagggaa  65100
gattgcaaag aggcgtaaag gaactttcaa gggtgatgga aatgctcagt gtctttattg  65160
tgggggtgtt tccactggta tattgtatgt aaattttgtt tattgtctgt aaattatatc  65220
ctccacaaag ttgtttcatt ttttaaatta tatatatata tatatatata tatatatata  65280
tatatatata tatatatagt tttttttttt ttaagacaga gtcttgctct gtcccccagg  65340
ctggagtgca gtggtgtgtg atctcggctc actgcaactt ctgccccccg ggttcaagcc  65400
attctcctgc tttccgcagc tgggattaca ggcatgtacc accacgccca gctaattttt  65460
gtgtttttag tagagatggg gtttcaccat gttggccagg ctggtcttga actcctggcc  65520
ttaagtgatc catccgtctt ggcctctcaa agtgctggga ttgcaggcgt gagccactgc  65580
acctggccta aagttgtttt ttaaaaaaat ctttccggct gggcatggtg gctcatgtct  65640
gtaatcccag cactttggga ggccgaggca ggcggatcac aaggtcagga gatcgagacc  65700
atcctggcta acacggtgaa accctgtttc tactaaagat acaaaaaatt acccgggcgt  65760
ggtggtgggc acctataatc ccagctactc gggaggctga ggcaggagaa tggcgtgaac  65820
ctgggaggcg gagcttgcgc gagccgagat ggcgccactg cactccagcc tgggcgacag  65880
```

-continued

```
agcgagactc tgtctcgaaa aaaaaaaaaa aatctttcca tggtttaata aaggcagcta  65940
ttcagtattc actctctagg tgatgattat actttaggtt gtttattctc tttcccagaa  66000
cctctttctt gttcaggtat cagattcttc tttgtggtga tgttcttcta ggaagaatgt  66060
tctgacccca agttctggtc attttgcttt gtttgataat tttgtctccc ctcaattacg  66120
taggatggta catgttacca agttgtgacc aatgacaaat gaacagatgt cttcagggtc  66180
aggagagact tttagaaaag atggagaaat gagatggatt atatttcctc cctccccaac  66240
cccactaaaa tgacagtaaa ggaattttct tttaaaaaag ttacaaatct ataaggatga  66300
agagattggg agaggagatc acagtgggcc agaatttttc cctacaaaat tttgaaaact  66360
gaaatgtagg tgcatatatg atgagtcatt taggtttcaa cttcatctgc tccactaagt  66420
atttgcagtg gaggaagcta acaggaagca atcctgtttt cagccacatg tgggccatgt  66480
tctgagataa gttttaggta cctgtgaata taggatatac actggggctg aaaacaggaa  66540
aatgagttga aagtctgaat gtggaagagt tagcacccca gatccccatc cccaaagaat  66600
atgtgtgtca aagtctaacc tggggaaacc ctgttataaa tgagggtggg aggcaggttt  66660
cttacccaaa atagtagatc aagttgaagt ctgcatattc agccagatct ttccacctac  66720
cttcctgtct tggctgtggg acttgttatc acagacacca tctctgccca ccaagacatt  66780
gaaagacctc agagcaactg acccatcctt ggctcctaga atactcattt ataagcccct  66840
cagccaggac attatcacat ttctgtctgg ggaaattgac tagcctatgg gaaaaaaaaa  66900
aaacctaaca tggtatttag aatttcctta tcccatcaca tgctgtgagg tcccacagga  66960
agcaagcggt gcttatccac atagaatttc tagttagctc tttagcacct cttttgtttt  67020
ttgagacagg gtctggctct gttgcccagg ctggagtgca gtggcatgat cacagtcttg  67080
gctcactgca gcctccttcc cctggactca agtgatcttc tcacctcagc ctcccgagta  67140
actgagacta cagatacgcg ccaccacact tggctaattt ttttgtattt tttgtagaga  67200
caaggttttg ccatgttgcc cagactagtc tcgagctcct gagctcaagt gatccactgg  67260
ctttggcttc ccaaagtgct gggactacac gtgtgagcca ctgtgcccgg cctgcacttt  67320
gaaaaacaaa ttccttagag ataagatgtt acatcaagga aacaagagca ggatgccatg  67380
taaaggaact attcaagaat gttcttgaga attgaaaaat ctcactaagt gaagattgca  67440
gtaaagcagt tggaagatag gccgggcgtg gtggcttaca actgtaattc caacactttg  67500
ggaggccagt gttgatggct cacttgagac caggacttta agaccagcct gtgcaatatg  67560
gtgatgatac cctgtctcta caaaaacaga aaaaactaac tgggtatggt ggggcacacc  67620
cctagttcta agtacttggg tggctgaggt gggagtattg cgtgagccca ggagttctag  67680
gctgcagtga gctatgacca caccaccaca ctccaacctg ggtggcagag agagtaaagt  67740
aaagcagttg gtcaaagata atagacaata agtggaagaa aaaagaaaat taaaggacat  67800
ctaggaggtc caacatctga ctattggagt tctagaaaga tgaaggacaa ggcattattt  67860
aaaaagcaac acaagaggtt ttccccaaaa atgtctcaga tggataagag ctcacccagt  67920
gtccagaatg aaaaaagtga tgaaaaagac cctcaacaga gtacattgtc atgaaatttt  67980
gtgacactga tgacaaattt taaaagcatc agagagaaaa gtcacataaa aatgatctaa  68040
aacaagtgac attagaccag ttaacaatag cactgggatc tataagataa tagatgaatg  68100
ccatctaaag cctgatggaa aaattttcag tctataattc tacacctagt caaactgtca  68160
aatcaagagt gaaaaatgtt ttcagaaatg cagggtctcg gccgggcgtg gtggctcacg  68220
```

-continued cctataatcc cagcactttg ggaggccaag gcaggtggat cacctgaagt cgggagttcg 68280
agaccagcct gaccaacatg gggaaacccc atctctacta aaaatacaaa attagctggg 68340
cgtggtggca catgcctgta atcccagata ctcaggaagc tgaggcagga gaatcacttg 68400
aacccgggag acggaggttg ccgtgaccca agatcacgcc attgccctcc agcctgggca 68460
acaagagcaa aactcagtct caaaaaaaaa aaagaaatat tgagtcaaag agtatgtgca 68520
tatgcaaggt ggggagacat taccaaactg ccctccatag gggtgtgcca gttacattcc 68580
cacaagctag gtaccagtgc ctgcttcccc acagcctggc caagagattg tcgtaggttt 68640
ttcagttttg ggggtggggg agcgggtggt atttgctgat ctggtaaatg taggatggca 68700
gctgtttagt gttgatcaat ccacccttat gagactgaca tggaaggtta ctccactttc 68760
acagaaacag tggaaaaagt ccagctatct ttacatttaa caagctgtaa ggaaatgcta 68820
atggattaag aaattaacca caggacctaa ttagaaaaag atctggcaac atgcccagct 68880
catccagcgg gagagggaga aaatattctg cattcgtgac actgtttaga aaggggtaat 68940
ttaaatgccc tttaatctgg gctagtattg tccaattaag aagtctgtta ggatgataac 69000
acttgggttt tttaatactt agtgtggtga agcagattta ttttctcccc ttagtatatt 69060
tatattgaat ggtaaaggtt atagtttaat taaataagct acacatttcc tgttttcttt 69120
taaaccactg tgctaggagt tagattcatt aagagttgga catggtctct gttcttcaac 69180
acattagcgc aatgtgactg taattcaaat tggagtttga cacccaagtt ttatatctaa 69240
tttaggcagc ctaacctagt taacacagat tggtgctaga tcctggctga cacctactag 69300
ctgcgtgacc tcaggtaaac tactgaagtt ttctgcacct cagttttctc aaatataaaa 69360
taaagattat aattgttttg aagattaaat tatatacatt gcacataaca gtatctggct 69420
tatagtgtta tatgtttgcc agtatgatgt tacaccccca caaattgtga aagttttgtt 69480
taaaaatata ttttcctgat taaaaaaatt aatgcatgat ctttatagga aatgtgggat 69540
atatagaaaa gcttattttt ttttgagatg aggtcccttg gccaagatgg tgtacggtag 69600
ccctaacatg actcactgta tcctcaatct cctgggctcg agtgattctc ccacctcagc 69660
ctcccaagta gctaggacta caggcatgtg ccaccatgcc tggctgattt tttttttttt 69720
tttttttttt ggcaggggag tgagggtggg gatgacgtct cactatgttt cccaggctgg 69780
tcttgaactc cttaggctca agcgatcctc ctgcctcggc ctcccaaagt gctgggatta 69840
taggtgtgag ccactgcacc tgaccaaaaa gcatttttta aaaactcatc tatcacctca 69900
ccactaatag aacagtgtta gcatctgggc acatcctcag aggcagtctt gcttgcattg 69960
tggttaagaa catggactct gaagccacct acctgggttc atattcaggt cccgctgttt 70020
actaatctct gttcatctct ctcagtttcc tcatctgtaa gatgtggcta atagtacccc 70080
tcacttagtg aggataaaag atgctaatat atgtagagca tctagaatag gcgaggcaga 70140
ggtaagtgta tgtgtttgtg ttgttgttgt tattctgtgt gtatggccaa agtttaaaga 70200
aatttcatca gcctctgaaa tagagaatat atatatggca ctcatgagtg gtgccggcag 70260
gcaagaagtg ctacagggga taaacaaaca tacacaaata tgtaatttcc gtgactggca 70320
gatggctgaa aggcactaaa aaaaaattag ccgggcgtgg tggcatgtac ctgtcatttc 70380
agctactcag gaggctgagg gagttaggat cataagagcc caggagttca aagcttcagt 70440
gagccgagat cacactgctg tactctagcc tgagggacag agcaagaatc tatctctaaa 70500
acgaaaataa aaacaccaaa taaataaaaa taaagaaggc actagagtgg agaaaggaaa 70560
ctgaagtaga gcggatggaa tcttagttcc ccctagctaa ctggaaaata atttcttcct 70620

-continued gggcaattag aaaaaaaagt gaataaatct gtggtttaaa actcaagtaa aagataagaa 70680
tgtctatatt gtgggtaata aaaaaagatc ctattactct aatttcattg ggacaatgaa 70740
taaattccca ctttaaatct cagccagaaa agtaagtaga aattcaattg gctacatttt 70800
tttttcctac ggaaaaaccc ttactctgat ttgcaaaaca gataaattag agaatgagca 70860
ttcacagcct cgagagattc cctattgact tcctataaat aatagctttt ccacagtcag 70920
gttggattcc aggaggaatg tgatgattgc catgagaggc aaacacacat tattttagga 70980
gcccaacctg atggatatta attggtgtag tgggttgaat attggccctc aagtaacccc 71040
tggtacttag gaatgtgacc ttatttggat cgagagtctt tgaagatgag ataatcttgg 71100
attgaagaca gacctgaaat ccaatgactg atgttttctg ttggtggtgg tggtggtttt 71160
tttttttttt tttttttttt tttttttgag acagtgtctc tgtcgcccaa gctggcatgc 71220
agtggtgtga tctcagctca ccgcaacctc tgcctcccag gttcaagtga ttctcctgcc 71280
acagtcttcc cagtagctgg gattacaggc acccgccacc acgccaggct aatttttgta 71340
tttttagtag agacagggtt tctccatgtt gaccaggctg gtctagaact cctgacctta 71400
ggtgatctgc ccacctcggc ctcccaaagt gctgggatta caggcctgag ccaccgcgcc 71460
tggcctgatg ttcttataag aggaaggaga gagagtttta agacatagaa atgggagaaa 71520
ggctatgtga agacagaggc caaggttgga gtgacagggc caagaatgcc caggattccc 71580
agcagccact gggggctgga aggggccagg cgggatgctc ccttagagcc tttacaggcc 71640
gcacagccct gcctacacct tggtgttgct cttctggtct ccagagctat gagagaataa 71700
attatggttg tcttaaacca ccaagtttgt ggtaatttgt tgtggcagct ttaggagatg 71760
aaaacaaggc ataatttgaa gttgtcaatg ggaaaattat tttatgtaca tatgcaaaaa 71820
tatatttgct aagactaatg cgtctattat gtgaaaccaa gtaagcaatg ttaaaatttt 71880
atccgcagta aatgtggggt tggagaagtc aaagatacca ttttagatat cagcaatcct 71940
gatgggtata ataaaatgac cctttttatt tggaaaattt gaagactgaa tatggttatt 72000
aaatttgcca ttggagaata actagaaatc taaaagtgat acaagtaagt ctcatttcct 72060
attaatacaa aaaagtttat tgcagtttct ccttaaaaat agttactggt ggccgggtgt 72120
ggtggctcac acctgtaatc ccagaacttt gggagaccga ggtggttgga tcacttgagg 72180
tcaggagttt gagaccagcc tggccaacat ggtgaaatgc catctctacc aaacaatacg 72240
gaaattagtt gggtgtggtg gtgcgtgcct gtagtcttag ctgctcaggg aggctaaggt 72300
gagagaactg cttgaacgag gtgagcagag gttgcagtga gctgagattg ctccactgca 72360
ctccagcatg ggcgacagag tgagaccctg tctcaaaaaa aaaaaaaaaa aaaaaagtta 72420
ttggtagtct gacctgatgc tgtcctatcc cagtatctca gtcacaccca gcatttataa 72480
ttacctggaa accatgcttt gtttttgtat tgctgctaac atttctgata caaagctaga 72540
tgattattca gatcttaggt ctaaaattta tacttcctgt attgaggtct caacagtaga 72600
cttaaagatg ctcattcata tcccagaatt cttctttaca aggtggaaga tctttgaata 72660
ggtagctatg atgtgacgtg tattgttatt tgaatcaaag tcttctggtt tcaaacagta 72720
agataatggt attttctgtc tgtgaagtcc tttatcagga atgtctaagg attattttgt 72780
tttctctttc tgagtgcagc tgtttgtttc taaagcaaaa tataggtctt gccttgaggt 72840
gggatagata gggagatcag agaaagatgg aattatctct ggtcaaaaaa ccccagctga 72900
ttatacaatg ctttaaaatg taccatttaa aggtaaaata gcaagttgtt tcggcctctg 72960

-continued

```
tgacctattt ttaaaaaatg ttaattgtct ttgtagataa agacatcttg agtccaaatt  73020
gcagttttct tactctgttt aagcattgta agactgtcag aagctgaact ttgtgggagg  73080
ggagtcaagt gaggagagaa tgcaagtaag aaaggaaaaa gagtgaaatc acaagttggt  73140
gtttcccgtc ctggcttttc ggttcatggg aagtggcaga atctggattt aatgcctcca  73200
taattgggaa aaagagcaga aatcttcata tttagtctct gggtattact gtgcagcttt  73260
cgaactctac agagttaatg atttcttcca tgtgcgtttt tcagttcatc actcaagtct  73320
cgttacagag gagatacaga tcaactcctg atctatatga tttcaaaaat agcacagtga  73380
ccctggggta atgatatggt aggacataat tgaacctttc tgggcacttg tgtgctatgt  73440
catttgtcct gtatgtagtt ctagagtgac atcagatcta ttaaaaaaaa aatttttttc  73500
atttgtgagt atagtcccag ctactgggga ggctgaggca ggaggatcct ttaagcccag  73560
gagttcaaat ccagcctggg caacatagtg agatcactgt ctcttaatac atatatatat  73620
tttatatatg tattatataa tatataatac atatatatat gtattttttt tttgtaaaga  73680
cgaagtctca ttatgttgcc caggctggtc ttgaactcct gagctcaagt gatcctcctg  73740
cctcagcctc ccaaagtgca ggaattacag gtgtgagcca ccgcacctgg ccttctaaaa  73800
ttttttttaa ataacagttt taaaacattg tttatagttt gttgacatta cattcaggtc  73860
ccccttcaca tctcttccct atattctcag gtgaaacttc acttctctct taacagggaa  73920
tcctcagaac cacaagagat cttagagaac atgtggtccc aacatcttaa caagctgtgc  73980
tagaaattga gttggtggcc ttactgctgg ccagtgtgga gaccaagctg caggtacagg  74040
ttccttctgc tgtacagcat gccctttatt gcagcttgaa atcttgtcct ctgtcctcac  74100
tttcatctgc aactgattgt cttcctaaga aggaaagatc ctttagtcaa atgtttttcc  74160
tgctccactg aaatgtctac tattgtagtc accagtattc ttcattctgc cagatccggt  74220
gatgagtttt ctgttctcag cttattccac tcttcggcag catctgacac atcttctgga  74280
ccactttctt ctctaagttg tgaaggcgtg tccttccggt tttcctccct catcggcagc  74340
tcctcagttt cctttgctga acttttctcc tctgccagac ttctaagcct tggaataccc  74400
agggtcccat tcttggccta ttctcttttc tacctgaact ctcctctgga agatcttagc  74460
caatcccatt gctttaaata ccatctctat gcctcgactc ctaaatctgt ctctctaggc  74520
tgatctttcc gttgagatca aaactcataa gcagctggcc taatagtaat tcagttttct  74580
actcagatat ttaagatgtg tcaaacttgc atgtcctgac ttttctgccc tatttacccc  74640
aaaacttctc ccagtctcct ttgtctgatt aaacagcacc accatccatc caccctgttg  74700
ctcaagccaa aagcccagaa acatattgga gtttttctat ttgccccata ccctgtgggt  74760
atttatatat atatgtatta agggtaaaat atatatatgt attaagagac agtgatctca  74820
ctatgttgcc caggctggat ttgaactcct gggcttaaag gatcctcctg cttcagttca  74880
tcatcagcaa gacccgtcag ttctatcagt gttcctgagt tccacactta aatccagctt  74940
tactactgct tcagaacaaa cttcttcctg cctttcctgg gccacgccac agcctcctaa  75000
ctggttttcc tgtttccact ctcccctttc tttgtccatt attcacctag cagcagggcg  75060
atcttgcaca aatcattttc tatcacccct ttgtttataa ttcttcagtg gctttccatc  75120
ataaacaaaa taaaggtccc tactgcatag tccaggctcc gtttgcctct gacctcacat  75180
ctttttgttt gtttgtttgt tttgtttttg agacagagtc ttactctgtc acccaggctg  75240
cagtgcaatg gcatggtctc ggctcactgc aacctctgcc tcccgggttc aagcaattct  75300
catgcctcag cctcccgagt agctgggact acaggtgccc gccactacac ccagctaatt  75360
```

-continued

```
tttgtatttt ttgtagagat ggggtttcac catgttggcc aggctctctc gaactcctga  75420
cctcaggtga tccacctgcc ttggcctccc aaggtgctgg gatcacaggc gtgagccacc  75480
atgcacagcc tgatgtcaca tcttacagct gtcgtcattt gccatgcact agacatcctt  75540
gccttgtttc cttcaaatat cccagcctca ctttatttag gtttcatctt ctttttaaa  75600
gttttactct atatgtattt ccctgcacaa ttaatcgttt atttttgctt ggttttgaat  75660
ttgatatagt acaatattat aggtagtctt ctgcagctta agcttagttc attcactttc  75720
attgctggat cgcttttgat tgtgtgaatt tacaggtttg tctactcctc tgacagtgta  75780
cacttgggtt ctgatgagaa cagtgcaaat attgtctagt atataaggaa cttataatgg  75840
gccaggcagt gttctcagtg cttttatata tatgggcact aagagcaacc ctatgagttg  75900
gtattattac gatgctcatt tttcagatga gggagcagag acataggaag atgagtaact  75960
tacccttgtc atctggtaat gagtgaaatt gctggatcat ggacttcaca tatgtttagc  76020
ctcaaaagat gatgcctaat agtttctgaa gtgattgtac cagttgatac tcccaccagc  76080
agcatatgag ttcccatcgt gccgcatctt cacacacacc tagttttgcc aaatttgtgg  76140
gtgtaaaatg gtattttgat ttcaatttgc atttccccga ttcctaatga tttgagcata  76200
tttttgtata tttattatcc attagtgttt cctcttccgg aaacatggag cgtctgttca  76260
tgtcttttgc ccacttttcc attgatttgt cagtcttttt cttactgact tatagttctt  76320
tccctttgtc agtattagga gtttcagtct tctctgggtt catggctttg gcttgtcttt  76380
ttttttttt tttttgttga gacagggtct tactctgtga tccaggctgg agtgcagtca  76440
tagctcactg caacctcgaa cttgaactcc cggcctcaac tgatcctccc acctctgcct  76500
cccaaagtac tggaattaca ggcatgagct accacagctg cctttggctt gtcctttgag  76560
tctcttttg gtgtctcttg atgaatagaa attcctaatt ttaatatagt tggatttctc  76620
attgttttca atgtcttatt tttagaaatc tactcttacc tcagagtcat aaaaatattg  76680
tccaatattc taaaatttg cctttcacat ataagtattt aagctacatg aagactattt  76740
ttatgtatgg tgtgaggtgt ggatccaact ttcctttttt gcatttcata gtttattttt  76800
tttcccagtt attgaaatac tgcctttttc ttatattgtt tctgcatgat tgtgggatta  76860
tttctgggca ctctattctg tttcattgat ctttttgttg ttccttcact aataccatag  76920
tgcttcaact actgtttctt tacagtaaat ctagatacct gatagcctaa tttccccacc  76980
ttgtttcttt tcttcaggag tgtcttacag tggtgtgatc atggctcatt gcaacctcaa  77040
cttcccagac tcaagcagtc ttcccacctc agcatcccaa gtaactggat gccaccacca  77100
tgcctggcta ctttttaaaa attttttgta gagatggggt ctcgccatgt tgcccaggct  77160
gatcttgaac tctgggctta actgatctgc ccaccctggc ctcccaaagt gttgggatga  77220
caggcatgag ccaccatgcc tggcctgctc ctccttataa attttagaat tagcatctgt  77280
ggaaaatcct gttggaattt tgatcggtgt tgtattaatt ttttatatca atttggagga  77340
gaatcaacgt atcaatgcta gagtgtctct tgtgcatgaa catggcatct cttttgtctt  77400
acaatgacat ttgtatacgt acagtataac ttacaactcc atgcaggtct tgcacatctt  77460
atggagcgag acagtgtaga gacagcgtag agtagtggtt ttaagagcaa aggcttcgga  77520
accaggctgc ctggtttcag tcctcactta gctgcttacg gtgtcatctt gggtttcaat  77580
cctgttggtt tcaatcctca cctagctgct tacaatgtca tcttgggcaa gtcagcctct  77640
ctgtgcctca ttttcctcat ctgtaaaata ggcgctaata tttctacttc atagggggcat  77700
```

-continued atagtaaatg ctcagttgtt ggtagctgtt gctattattt tgttttatcc ctaggtgtct 77760
tattttttgt tgcttcctaa atagtatata tatatatgtg tgtgtgtgtg tgtgtgtgtg 77820
tgtatacatt tacacacatt tacatttttt aattttacat ttttaaattc tttgttgctg 77880
gtgtttagaa atgcatttga gtttcagaaa tctagcaacc tggttaatct ctcattaatc 77940
ctaataatga gaattcttct ggatttccca aatgggctat cataaatcaa cctgcagata 78000
atggcttttg tttcttccat ttcaaacttc atatttttat gtcttttttg ttcttttact 78060
gagctggtct ttttttgctt ttagctgaac agccttctca aatagctagt cttgacaaca 78120
gtataacctt gaataaaagt gggactggtg aacaccttgt cttattccta gtttttaaga 78180
gaacattcta atgtttcact attaaagtgt ttgctgtaga tttctgatgt gtatctttta 78240
tgtcaaggaa tgtattctat tccaagtttg ctaagaggac ttatcataaa tggatgttga 78300
gttttaccaa atgcttgata taaatctgtt gaaatgataa tatattttgt cctttaatct 78360
gttaatgatg aagattacag gcattggttt tctaatgtta aagcatcttt acattcctga 78420
aataaatcta aatctaactg gttcattact tttttttttt ggagacagag tctcaccctg 78480
ccacccaggc tggaatgcag tggctcaatc ttggctcgct gcaacctctg cctcccaggt 78540
tcaagcgatt ctcctacctc agcctcctga gtagctggga ttacaggtgt gtgccaccac 78600
gcccggctaa tttttttttt tttttttgt atctttagta gagatggggt ttcattcacc 78660
atgttggcca ggctggtctc gaactcctga ccttgtgatc cacctgcctt ggcctcccaa 78720
agtgctggga ttacaggtgt gagtcactgt gcccggctat tttttaaata cattatttgt 78780
tttgctaata ttttgtttta aaatttttca ttactgatca taaaagagat tggctaatta 78840
tttttctttc ttgggtactg aggttatgtt aattttatga aatgaattgg aaagtgtttc 78900
ctccttttga tcctctggaa gaatgtatat aagattaaaa tgatattttc tttgaacgtt 78960
tggtagaatt tgcctgtgaa gataatctgg acttggtgtt ctcattttca gaagagttta 79020
aactactgac cactgtcttt aatagttgta gaaactttca ggtattctct agcttcctta 79080
ataatttctg ttaaattata tgtttctaga aatctacctt tttcatctaa gtttccagct 79140
ttacttgcat aaagtggttt gtggcatagt gtagtcttat gaatcttcgc ttaatctgga 79200
gtatgctcct tgaaaaacaa ttctaggttt ctagatttta ttagcctctt aagactaata 79260
tatatatgct ttctattctg tgaaatttgc ttttatcctg ctttctttta gatttttagg 79320
cttatttggc tgtcccttta ttttttactt cttaatggct gcttaattca ttaatttcag 79380
catttcttct tttctcatat aactacttaa agctgttgtt tcctttaaaa aataataaaa 79440
taaagtttcc cctaatacct gctttaatgg catagcaaag ttttgatacg tcatatttta 79500
gtgtttggtt ctgaatattg tctgatttat attataactt cttctttgac ccatgagttc 79560
tttacagggt tgtttttata ctttcaaatg cattatcttt aaagttatct tcttattact 79620
gatttctaat ttaattgcat tttaatgaga aaaagtagtt ctcatattac tgattctttg 79680
aaatttattg gtaaaggctg ggtgggcatg gtaactcatg cctgtaatcc tggcactttg 79740
ggaggctgag gcaggtggat agcttgagtc aaagagttcg agaccagcct gggcaacatg 79800
atgaaacctc atctctggaa aaaaaaaaaa aaaaaaattt gcagggtgtg gtggcatgca 79860
cgttagtcct agctacttgg gaggcagaga ttgcagtgag ccgagattgt gctactgcac 79920
tccagcctgg ttgacagaaa aaaaccctgt ctcaaaaaaa aaaaaaaaag gaaatttgtt 79980
ggtaacttac tttataccta aatacaagat cagtttttga aaacattcta tgtatgtttg 80040
aaaagattgt gtattctctt gttgtggggt tccggatttc atgtgttcgt ttgaatattg 80100
gtaatgttag cattttttc tgtttaatta tcaattacta agagaggtat gttaaaatat 80160
gcccctctga taagtaagct tgtcactgtc ttatactttt gtcagttttt gtggtattta 80220
tttttaagac attttattaa gtttatatag gtctagaatt ttcttcctga tgattctctc 80280
tctagtaatt ctattttgtc taatattatc tattccagct ttcttttgat tattatatat 80340
ctggtataac tttctagtct tattctaggt gaatcttatg aagaacatat aagtaggttt 80400
tgttttataa atctaatcta tatcttttac cttaggagtt taatatattt atacttactg 80460
tggctattga tatccatagg tgtttttttc tgccatctta acttatgctt tctatttgtt 80520
cttttttggg gggggcggtg tctctatttc tggatgactc tttagccttc tttgtctcct 80580
tttgaattcg ttggtggttt ttctctcatt ccatttttct tttcttttct tttctttttt 80640
tgaaacggag tctcgctctg tcgcccaggc tggagtgcag tggcgcaatc tcggctcact 80700
gcaagctccg cctcccaggt tcacgctatt ctcctgcctc agcctcccga gtagctggga 80760
ctataggcgc ccaccaccac gccccgctaa tttttgtat ttttagtaga gacggggttt 80820
caccatgtta gccaggatgg tctcgatctc ctgaccttgt gatccgcccg cctcggcctc 80880
ccaaagtgct gggattacag gcttgagcca ccgcgcccgg cctcattcca tttttctaaa 80940
ctatgcattc gaaagataga cattcaactt ttattttctt agtttactct caagctttga 81000
atgtgaatac ttaagagttt aaagttagtc aatttccatt ctcttctgaa acaattaaag 81060
gccctaaaaa atgctttaat tcagtcagtt cctcccacca cgcttgccgt accgtttact 81120
gtgcgtaaat cagacattgc cattcttgtt ttataaaagc aatgtttgtt taaatttccc 81180
tatattttta cagttttctt tgtccatcat ttatttttct atccttgatc ttctttctgg 81240
gacctttcct tacttttacg gtatatcctt aagacacttc atgaaatgtg tgagccagcc 81300
tccacggtct cccttatgac tgtggctctc tgtgactcac acgcccacac cgaagagggc 81360
tgacctgtgt aagcattgga acgttgcagc agtgatggag cgtgacttct gaggctgggt 81420
cataaaatac gttgcacctt tttgccttgc tctttcttgg gccactcact gtgggatgcc 81480
ggctgccatg tcatgaggtt atcaagcagt cctgggaaga ttccatgtgg agaggaactg 81540
aggctccctg tcaactgcca gtacaaactt gccagccttg caaggcagcc acacgggcag 81600
cagatcctgc agccccctca agtgactgta gccccagcca ccaactggat ggcaacctca 81660
caagagatcc tgagctagga ccacctagcc cagctgcttc tgaatctctg acacacagaa 81720
actgtgagat aataaatgtg ttttgcagcc aggtgcggtg gctcacatct cagcactttg 81780
ggaggccgag gcagccagat cacaaggtca agagatcgag accatcctgg ccaacatggt 81840
gaaaccccgt ctctactaaa catacaaaaa ttagctgggc gtggtggcgc gtgcctgtag 81900
tcccagctac tcagaaggct gaggcaggag aatcgcttga acccgggagg cggaggttgt 81960
agtgagctga gatcacacca ctgcacgcca gcctggtgac acagcgagac tctgtctcaa 82020
aaaaaaaaaa aaaaaagtgt tatcagtatt gttacacagc agtaattaat atacattagt 82080
gagagtattc tggtagtaaa ctctgttttt atcttaaaat gtttttttgat tttggttttt 82140 ttttttgtt tttttttgta gagacagggt cctgctatgt tgctcagtct ggtcttaaac 82200
tcctgggctc aagcaatcct cccacttcac cctcccaagg tgctgacatt acaggcataa 82260
gccaccacat ccagccatct gaaaatgtct ttaattaatg cccattccta aaatatattt 82320
tatctatata tacaattctg tattcacaat tattttcttt cagcatattg aagacatttt 82380
ttattttctt ctgagttcca ttattgctgt taaaagtcca ttgtcaaata aaagacttgt 82440

-continued

```
atctagacta tgtaaaaaac ctaacactca gccgggcgca gtggctcacg cctgtaatcc  82500
tagcactttg ggaggccgag gcaagcggat cacttgagct caggagttcg aaaccagctt  82560
ggccatcatg gtgaaaccct gtctctacta aaaaatacaa aaaattagct gggcatggtg  82620
gtgtgtgcct gtaatcccag ctacttggga ggctgaggca ggagaatcgc ttgaacccgg  82680
gaggcagaag ttgtagagag ccaagatcat gccaccgcac tccagcctgg gcgacagagc  82740
gaaactccat ctcaaaaaga aaaagaacct aacactcaac aaacacctca gtttaaaaat  82800
gggcaaaaga ttcgggccag gcgtggtggc tcacacctgt aatcccagca ctttgggatg  82860
ccaaggtggg cagaacacct aaggtcagga gttcgagacc aacttggcca acatggcgaa  82920
accctgtctc tactaaaaat acaaaaatta gctggcctgg tggcacgcgc ctgtaatccc  82980
agctactcag gaagctgagg catgagaatc acttgaacct gggaggtgga ggttgcagtg  83040
agtcgagatc gtgccattgc actccagctg ggcaacggag caagactctg tctcaaaaaa  83100
aaaaaggcaa aagatttgaa tagagatttt accaaagaag atatgccaaa taaacacttg  83160
aaatgatgct caaaatcatt agtcgcttga gaaaggcaaa ttagtcacga gggaaatcca  83220
aattaaaacc acattaaata aaataacaaa aaaatcaaaa aaccgtaata agataacact  83280
tactgaatga ccttaatcag aaaagcagac aataataaat ggtggtgagg atatagagaa  83340
acaagaaccc tcatacattg ctggtaggaa tgtaaaatgg catagccact ttggaaaata  83400
cttttgacag tttcataaga agttaaacat aaatttacca tatgaccctg caattccagt  83460
ggtaaatata cacccaggag aaatgaaagc tgggtccaaa acattcaaag acttgtatgt  83520
tcataacatc attattcatt aaaactaaaa agtggaaacc actcaagtgt ccaccaactt  83580
gtaaatggat aaataaatat tattcaccaa taaaatgaat aaaatactga tgcatgctac  83640
aaatgggtca gtttcaaaac atgttaaatg aaagaagcca gacatgttgt attgtccctt  83700
ttgtatgcag tatccagaaa agacagacct atagagatgg agacatgatt ggcttcctgg  83760
gagggaatgg aaatagggat taactataaa tgggcacaag gggtcgtatt ttgatgatga  83820
aaatatccta gtactgtatt ggggtgatgg ttgcactatc taacaaattt attgaagagc  83880
attgaattgt acgtttaaaa taggtgaatt ttggccaggg gcagtggctc acacctgtaa  83940
tcccatcact ttgggaggcc taggcgggtg gatcacctga ggtcaggagt tcaagaccag  84000
cctcaccaac atggtgaaat cctgtctcta ctaaaactac aaaaatgagc tgggcgtggt  84060
cgcagacgcc tgtaattcca gctactcggg aggctgaggc agggtaatcg cttgaaccca  84120
ggaggcagag gttgcagtga gccaagattg caccattgta ttggtgcaac tggtctgcct  84180
gggcgacaga gcaaaactct gtctgaaaaa aaaagaaaaa aaaatggtga attttataat  84240
atgtaaatta aaccaatacg gttttgtttt tgttttgttt tgttttgttt taagtcgtca  84300
gtctgggtgc ttctgtcttt ttctcaggca gcttttaagt cttctttgtc tttggtattc  84360
tacagattca cagtaatatg tttgattgtg gattcatttt tctttaccct ccctttgaat  84420
ttgttgggct ttctaaaatg tgacagtggg tggctttggt aaattctgga aattttttttg  84480
ccattggccc tttgaataat gcccctcacc tgttctgtct atttccttgg agactcattg  84540
catctagatt agatttcagc tctaacttct ctgttttcta ggtctaactt ttcttttaca  84600
ctttcactgt cactttgcta cgttttgtgt aagttgtgat ctgtcttcca ctgtacaaac  84660
tccatcagtc ccagtggcct ttaggggaca tggagtgtgc ttatcgcttc ccatacatag  84720
gtcacgggct ttacttctgg agccagggtg gtgtcacctt ctccaggacc aagtggattt  84780
ccacaaacca tgttggggag gggtgtgaat ggcaatcaca tatactgatc attcaaccca  84840
```

gaaacctgag cgtcgtctct gatttttcct tctctactct tggcatcctg taggttgaaa 84900
tatcacaggg ttgattccgc tttctaaatg tttctcagat tgaatttttt tccttttgat 84960
ctcagtgacc acattccagg ttcaggaatt catcatttct cacctggaca gttacagtaa 85020
cttcctaact cttcttgtct ttatactcac cagttccaat ctactccaca cactttgacc 85080
aaagtggact ttccaaaaat atagacatta tttccttcat ttttaaaaat ttcaactttt 85140
cttttagata tagtggatac atgtgcagat ttgttgcatg ggaacattgt gtgatgcaga 85200
gttttgtagt acaaatcccg tcacccaggt agttatcata gtacccaata ggtagtgttt 85260
taaacaaacc accccaccta gctccatctc tggtagtctg caatgtctgt tgttcccata 85320
tttatgtaca tttgtgctca gtatttagcg ctcacttatg tgagaacatg cattttagtt 85380
aaagagagta tatctgcatt ttaatgttac tcccctgtct aaaatccttt aatttctatg 85440
tcccagcata agatccagat tttttttttt ttttgagatg gagtttcact cttgttgccc 85500
aagctggagt gcagtggcgt gatctcggct cactgcaacg tctgcctcct gagttcaaag 85560
gattctcctg cctcagcctc ccgaatagct gggtttacag gcatgtgcta ccacgcctgg 85620
ctaatttttg tattttttat aaagatgggg tttcatcacg ttggtcaggc tggtctcaga 85680
ctcctgatag caagtgatcc gcctgcctcc gcctcccaaa atgctgggat tacatgcgtg 85740
aaccatcatg cccggtccat atacactctt aatttccacc tacttacctg ctttcttaaa 85800
gaaccagttc tgtggctttg aacatgatgt tctctctgac tggaatgatc ttccccctcc 85860
ctgccaggtg agctccgact catccttatt ttctgtgaag cctcctctta ctccccagga 85920
aagacgtcag acactccttt gcattccata gtaacttgca tatgtctcag gtaaagcact 85980
tataagttag gctgttgttt gcatgccatt ctcactagac tgaggatgct ctgaggtcag 86040
ggatcgttct tgatttactt agctccatcc ctgttccttc atttgtcttt ttcaacagtg 86100
gctgtctatc ccagggctac tggtagttct ttttcaagtc tgttttgggc aatgcaagga 86160
tagcaaaaag gaaaaggaag atttcttaga aaggggaaag gatctccagg tttaaaaata 86220
ctttcagaaa tgttctgaga ggagaaattt gtgttaattt ttgtgagagc atattactaa 86280
acagcagcct cctctcccca aattgaaagt ggtgcatcca ccacctcccg ggttcaagcg 86340
attctcctgc ctcagcctcc caagcagctg ggattacacc atgcgccacc atgcctggct 86400
aattttgtat ttttagtaga gacggggttt ctccatgtcg gtcaagctgg tctcgaactc 86460
ctgacctcag gtgatctacc cgtcttggcc tcccatagtg ctgggattac aggtgtgagc 86520
cactgcaccc ggccaaaata gataatttct gtatttcagc tagacttttc agttgttctt 86580
ggcaggtgtg ctgatttgct gcacctactc tatccttcta ttaaaagtcc accttctctt 86640
cctgtaaggt ttttttgttt ttgttttgtt tttgagactg gtcttgctct gtcatccagg 86700
cccaactgta atggtgcgat catagctcac tgtagccttg acctcctggg ttcaagcaat 86760
cctcccatct cagccctgca agtagctggg cccacagctc tcacaccacc atgcccagct 86820
aatttttaat tttttttgt agacacgggg tctcacattg ctgtccaggc tgcagtaagc 86880
attttaagag tgggaacttt gcgtattttg tatcaacatt tagcacattt gtatttgtag 86940
cataatagta tttgtattca acaattagca caatagtcca taatggatgc ttaagaaaaa 87000
tgtagtgaat taatgcatcc aggtgtctag gttccatttt taatatttag atctgcttca 87060
tcttttccag agagttgaac caatatgata tctagttata ttaaatatca agtgttttac 87120
taagtattga gtagatatat aggaatattt agtatatata tcatgtaaag aatcacatta 87180

-continued

```
caacaaacac ccaataacct accacccaat ttaagaaaat taatttaatt atcaggagtt  87240
ccttgtatga ccttttttct cattcctttc ccttcttctc agaagtaact gctatcctaa  87300
attctgttgt tatcattccc ttgagtgttg ccttcttgaa cagtatattg ttagtgttgc  87360
atgttttgag cttcatgtac atggaaccgt actggatgtg ttctattttc ttatttctgt  87420
gtatagcagt aattctttcc ttttcactgc tatgtagtat tccattgtat tactacatgt  87480
gcatgcgtgt gtgatagaca ttcacagtat taagcagttt tttgattttt tgctttttcc  87540
aaagagcagt gctaaaaaat tcttgttcct gttttatggt ggattatatc tatcagtatt  87600
tactgtatta aaattgaaat agaaatgttt taaatgttta cttagtaact catttagaat  87660
aacaatttaa aataataaaa ttaaaataaa aatggatgtt tttatgaaaa aactgtttta  87720
aaacaaaaaa acagaagtgt ggcattattt tatatttttt tcagatctct ttactgtgtg  87780
gcttaataga aaatagctaa gttctcacat ctctttctgc attcaatctg ttacagtatc  87840
aacaatagtc agaaacctca ctatacttga gagagaatga ggttgaaata ggaaataaaa  87900
tatataatta ttttgaaaat agctttgacc ttgcacatct tctgaaaggg tttcaggaac  87960
tcccacaggt cccagatcac actatcacac ttaaagaacc actgccccag ggtgtgtcca  88020
ttctccccct ttgctggtaa ggccagaccc ctccaaagtg aatgaatgta ttaagttgtc  88080
ccctgccacc caccagcagt gtttaattgt tttagtcact cttatcacag cacttgatgt  88140
tgtcagattt ataattttg ccagtctggt aaaaatgaaa tactgtctcc ctgtggtttg  88200
atttgcattt tctttgttac taatgaactt aaccatcttt ttatatttta ttgaccactt  88260
gctctccttt tctgttaagt acctatccag tatttttcag ccataactca agtttcattc  88320
taccttgtaa agtaatttaa aatgtttctt tttaaagtac acattcgagg gtcaaatgga  88380
ctgttcccag ttttatttaa gcagtaattt aaacattaag gaaaatgttt aagattaaga  88440
atattgttta gacctcgggt gatcggcccg ccccaggctt ccaaagctgg gattacagac  88500
gtgagccact gtgccaggcc tagaggtttc ctagatttct ttgggagcta ttaactggca  88560
cttttgcagg gggaaacttg tgtaatgttt gggtcagtat aacattcagt attaacatat  88620
atacccattc taatcagagg aaatgtatct tgacttaaaa ggtttctgtt atctctttgg  88680
acctcagttt ccatcagtaa actggaaata gtactttcag ctccagtact ctgggttcta  88740
attgactttg tttaatcttt acttcagttg tataaagggg cttgaaatta acttgaacca  88800
taggtacttt ttctttaagt gccctttaac agttaattgt ggccctctga attctgttca  88860
gcctgttcct tttgctctca ttgtttgttt gtttattttt atgtatttat tttgagacag  88920
agtctccctc ttttgcccag gctggagtgc agtggcatga tctcagctca ctgcaacctc  88980
cgcctgccag gttcaagtga ttctcatgcc ttagcctcct gaacagctag gattcaccac  89040
cacatctggc taatttttgt attttagtag agatggggtt tcaccatgtt ggccaagctg  89100
gtctcaaact cctgatctca ggtgatccgc ctgcctcagc ctcccaaagt gctgggatta  89160
caggcatgag ccactgtgcc cagcagattt tttatatttt aatttgatat tatcttggct  89220
gagcacaaat gctccactgc actccagcct gggcaacagt gagaaacttt gtctcaaaaa  89280
aacaaaaaac aagatattaa tgctgccacc agctttttg gttgattctc ttgagatcca  89340
ataaatacaca gtcatacatt tacaaataag gattgtattg tctctttctt tcagcttttt  89400
tttttgtgtg tgtgtgtgaa acggagtctc actctgttgc caggctggag tgcagtggcg  89460
tgatctcagc tcactgcaac ctcccactcc ctgattcaag caattctcct gcctcagctt  89520
cctgagtagc tgggattaca ggcacgcacc accacgccta gctaattttt gtatttttag  89580
```

-continued tagagacagg gtttcaccat gttggccaaa atggtctcga tctcctgacc tcatgatccg 89640
cctacctcag cctcccaaag tgctggaatt acaggcgtgc gccaccgcac ccagccttat 89700
ttttttactt acttaatttt gagataggat gttgctctct caaccaggct ggattgcagt 89760
ggtatgatca tagcccactg cagccttgac ctcctgggct caagtgatcc tcctacctca 89820
gcctccctag tagctgggac tacaggcatg agccaccata cttaacagat tttttaattt 89880
tttgtagaaa tgtggtttca ccatgttgcc caggctggtc tcaaacccct gggctcaagt 89940
gatccaccct ccttggcctc ccaaagtgct gggattgcag gtgtgagcca ccatgctcag 90000
ccctttcaac cattatccct tttatttcta attacttcag ccagctttcc agagttttat 90060
gtaagtaaca cagataagcc cttccttata ttgttcttgt ctgcagaagg aatgttctgg 90120
tctctcattg ttaatcctga tgctaattat acacaaatat gtagctgtat atatttatgg 90180
aaggtatata ttttttaaat tatgttaagg aagtattttt tctgttgctt ttttttttat 90240
tttaatttta atttttttatt ttttattttt tttgagatag agtctcactc tgtctcccag 90300
gctggagtgc agtgtcggga tctcagctca ctgcaacctc cacctcccag ggttcaaacg 90360
attcttctgc ctcagtctcc tgagtagctg ggattacagg tgtccaccac cacacccagc 90420
taattttttt tattttcagt agagacggga tttcaccatg ttggccaggc tggtcttgaa 90480
ctcctgacct caggtgatcc acccacctca gcttcccaaa gtgctggggt tatagacgta 90540
agccacccca cccggcccta ttgctctttt aaaattagta gtgtatgttg aattttatta 90600
agtgcctttt ttagcatcta ataaaataat tatgcttatt tgttcttttg agcttattaa 90660
tgtgataatg tattaagttt ctaatatttc ttgtcttagg agtctccctt agatataata 90720
tatttttgtt tgattagttc ttgcccaaat tagttttggc tggaacctgg atggtttttt 90780
gtttgttctt tttttcccca cacaccctgg acagtttctg tttgtttttg ttcctcccac 90840
atacctgctt tacctcagtc actgagacac atgtactaat gggttgtcat gaatgaagaa 90900
ctggaattta agtgactagg attcgtcaaa tgctgatgac gtgtaaggtt ctctttagca 90960
aagtttaagg aaggcagttc acctttttga gcacttctgt atgccagagt ctatgctagg 91020
aacttttcac atttgctagt tcacacagca attctatttt atagatgaga aagcttacat 91080
ttaagtctct tctgcaatac tagaggagct actttggacc tgagactttt tgtatctggt 91140
tttaataagc aaaagtccac accctacctc tgaggcctgt ttcccaatcc agaaaattat 91200
catcaaggag attgcagaga gagatagaaa atgtcataca ttgtgttggt ctgtgcaagt 91260
aattggcatt cataacccaa agataaacat accctgagta actgaaaatt ttcttagaat 91320
cttatgtccc tctacttcat agaaagccac atcttatggc tatggagtaa aatatcccta 91380
aggatgttcc ttagttctgt ttattgttta ggcttaagtt ttttctcatt cgctgatatt 91440
ctcccatctg agtgatttca ggatgaaatt gccccattca aacattttcg ggaagaaaat 91500
ttagttgctt tgcttttttt ttttcttgag acatggtctt gctgtcaccc aggctggagt 91560
acagttgcgt gatcatagct cactgcagtc tcatctccca ggttcatgtg agcctctcac 91620
cttagcctcc tgagtagctg gaactatagg catgtaggca catgggcgcg tgtgccacca 91680
ccctgggcta gtattttttta atgtttttat tttttgtaga aacaaggcct cacttatgtg 91740
ctcaggctgg tcttgaactc ctgagctcaa gcaatgctcc tgcctcagcc ctccaaagtt 91800
ctgggattat aggcatgggg caccatacct ggtctagttg ctttgctttt gaaaaatctg 91860
ctttaaggtt actggtttaa aaataatgcc ttaagctggg tgtggttgct cacacctgtg 91920

-continued

```
atcccaacac ttcaggaggt tgaggcgggc agatcgcttg aactggagtt tgagaccagc  91980
ctgggcaaca tggtgaaacc tcgtctctac taaaaataca aaaattatct gggtgtggtg  92040
gtgtgcacct gtggtcccag ctacttggga ggctgaggtg ggagaatcac atgagcccag  92100
gagatggagg ccgcagtgag ctgagatcat cccactgcac tccagcctgg gtgacagagt  92160
gagaccctgt ctcaaaaata aatagataaa taaataaata atgccttagt tcattgtttc  92220
acaatcaaaa ttatgctatt tcatatgaaa taataggttc agtatctaca tatatttggg  92280
taacttcttc agcagtaaga atatagtgct cagaaattta cttgttggtg ttattgaagc  92340
ttgttgagac ttccacaggt gcctgtaaaa tagaaacaat tttagaaatg tttttactct  92400
cacaaaggaa aaccttttc acaatttttt tctcttggtt tactctttat gtgaataaat  92460
gctgttaagg gaagaggcag ggcttattct tcccatcttc tgattaaaga actcacacag  92520
agaggaaaat gccttgctca tatgacacag ccatttcttg gtaggacaaa ggagtaatcc  92580
aggtcacttg tcttctgttc cttgcattta tctgctctgg tcacaaaggg accagtgtag  92640
gacaggcaag ccccagaatt ggggcttagc ccaggaaggt tctttgcttt gctcaggaaa  92700
gaattcaaga gtgagccagt ggtagaagaa accagcttta ttgaggtggc agtgttacag  92760
caccgtgact gctctgcaga gcagggatag acctggtagg cagcctcaag agcagcactc  92820
agtggcagtt ctgcagtcgt atttataccc actcttaatt acatgcaaat taagaggcag  92880
attattcaga attttctaga aaaggggtgg taacctgcag gttgttgcca tggaaaggag  92940
tagtgacatc tgggtgttgc catggcaatg gtaaactaac atacaccagt gggtgtgtct  93000
tagggagtgg tggtgttgcc tcttctgtta cagccagtct tcaatctggt ccagagttct  93060
gcctcctacc tcacgaccat cattttgatt tggggtctaa ctagtcaggt ttttatttca  93120
tccagatctt tgtttctcct ttcttcccct ttttctgtgc aaaatttgac cactttgctg  93180
tttattgata tcttattaga agggtattag ccgggtggta gtggcatgca cctgtaatcc  93240
cagctacttg ggaggctgag gcaggagaat cgcttgagcc tgagaggcgg aggctgcggt  93300
gagccgagat cgcaccactg cactccagtc tgggtgacag agtgagaccc tgtctcaaaa  93360
aaaaaaaaaa aaaaaaaaaa aagagatgag aggggaatgg aatatgacca tttctctctt  93420
agtgagcctc tcaagtttgc atgagagtag gttagaaaca gctgttaaat gcaagttgag  93480
gatcatttgt agaaattatt caaggctgtt tctcctttat cctacagtca cgtataaact  93540
agaattattt agaaggtttc aaaagattct tgtcactata ttttgttctt ttctgtaccc  93600
agttatcaag tagacagcct tattctttca gacttagtct aatgagagct aaataatttc  93660
ttgagagaat ttgcttgtgc tcaaatatgt cctcactgaa gccttagccc agttactcag  93720
tgatctcctt ttgtgtaatt cagaacttaa ttatgcactg tcacgtttgt tggttaattg  93780
tttgatatac ttaaatcctg tcctttcaac taggttatga attgctcaaa agcagagatt  93840
atgcccattt ttttcttttt cagctcctag cacagagcta agtacagaga atatgtacag  93900
taaaaggctg atggaggtct ttctgggaac actctatcag cggtactctg tccttcctgc  93960
tggtggcaat gggaatgttc tctgcaaggg ctcacgaggg cttgcatgcc tatgaagtgg  94020
aagagaaatg gcttgaggtg cagggaatga ggggacaggc caggaactct cggcctaatt  94080
ataatagcta ttgcctcgct gcttttattg gactgctctt attggaagga aattgatccc  94140
aaagagagtc aaagacaggc taaaacactg aactcataaa aatatgaaaa gtaagcggtg  94200
agagcagatc aagggaccaa gattcgttgt tttgttattg ttttattaat gatggtctag  94260
gacttccaaa tggagtttta aaagttgaaa ataaatgacc tgttactaat atattttcag  94320
```

aatgcctatg tagagaggaa gattatttct cagctgagta acgtgggatc ctcctttaaa 94380
agtcctttgg actctaatca tctttgtaat actctgtttt actttgaagg cagactcaac 94440
ttcttagagt tccagcacat tgagccctgt ttgtctcatc catcttttca ctgaccttcc 94500
aaaggtggac tggctggaga accccagctg tccattgtgt ttgaaatccc tttaagtagg 94560
gactcggcta gaggtgttct tctgcctgat ccccagatga aaaggacggg aggggagtga 94620
cagaggagtc ttcagccagc tgccatatcc ccatgccgga ccatggaacc tgacttccag 94680
cgcactgtag cagagaggta gctagagagc agaaagtaga gatttggctc tcctagggat 94740
cttggagaga actttgttat ttcagctttt gagatatctt ctcttccttc ataaggatga 94800
gacccagggt ttcctgatag ggcactgccc tttaaaatgg actttgggaa taatttggcc 94860
aactggttct ttttgaaagt attaatgttt gggggttgta actaaagtcc taacaccttg 94920
ggaatctgtt cctggtgaac attacttaaa gataggttca cctgcataca caacagaaaa 94980
accacaaaga agaggtttct ttctttctca cgtaaaaatg aaaaaatcag ctggcagcag 95040
tggctcacac ctgtgatttc agcactttgg gaggccgagg caggaggatc gcttgagccc 95100
aggagttaca gaccagcctg ggcagtgtaa tgagacccca tcgctgcaaa aaaaattttt 95160
tttttctaat tagctgggtg cggtagaatg cacctgtagt ctcagctact taggaggttg 95220
agatgggaag attgcttgag tcccagaagt tcaagattgc agtgagcttt gatcatgcca 95280
ttgcattcca gtctgggtga cagagcaaga ccctgtctct taaaaaaaaa aaaagccaca 95340
tcttgcgtat ggtttacaga ggcctgcatg tgaagcagcc ccacataggc tccctggcct 95400
tgctgtttca caggcagacc aagcatgcag ccagcttaag gcctatgtac ttcttcccct 95460
caacctagaa cttctcaagg aggcccaccc tggccaccta actcagaatt tcagccctcc 95520
ccgctctcct ctgcctcttg ctcgcaatac ctagctctat tttcacacaa tctgacctac 95580
tacataattt acctaattat tatgtttatt gcttattgac tgtgtccttt cactagagtg 95640
tgaactcaag gacaagacat tttgtctgct ttgtttactg atgtatcaca agtgaccaga 95700
acagcatgtg cctcattata aggctgacag atgagtgaca gagtaacgtg acagagctgc 95760
agttcaaacc agagtgtatc tgactctaca gccttcattc aggcattttt tttgttttaa 95820
atcaatgtgc agattgcata cagtggagtg catgggtttt ggatataagc cctgtgggtt 95880
tctgctggtg tgtaggcccg taacgttgcc gttgttggcc agagggctcc ctcatatccc 95940
ttccaatcag tgcctccacc tgccttggtc actgtactgg catcaccaca tgttggtctt 96000
acctgttctt gaacttcacg tggatggtaa gacagtacgt ggtcttttgg gtctggctct 96060
tccggctcag tgtagtggtt ttgaatcatc catgttgaca catgtatcat agcttggtct 96120
tttttgtgta ctacatttg tttgttcatt cttctgttgg tgggtgtgtt gtttccagta 96180
taggaccatt gtgagtggag ctgctttgaa ccttattttt taattttta tttaatttta 96240
aaattgaccg atcttacata ttcatggggt acgtagagat gttttgatac atgcaatgta 96300
tgatgaacag aacaggggga ttagcatacc catcatctca aacgctgatc atttctttgt 96360
gttgagaaca ttgactctcc tcctcctagc tatctgtaat taatattatt attaactgta 96420
gtcatctttc tgaacactag agcttattcc tcctatctag ctgtaatttt gtacccttta 96480
agaaatctct ccattttcct ccctttcccc tgctattctc agcctctggt atcatctgtt 96540
ctacttttta cttctatgag attaactttt ttagcttcca tgtgtgagtg agatcatgca 96600
gtgttttact ttctattccc agcttatttc acttaacaca atattctcag ttccatccat 96660

-continued gttgctgcaa atgacaggat ctcacacttt tttatggctg aatagtactc catggtatgt 96720
gcacaccaca ttttctttat ctgttcctct gttgtcggac ccctaggttg attccttctc 96780
ttggctattg tgaacggtgc tcggtaaaca tgggggtctg cattgtctcc ctgatacaat 96840
aatttccttt cctttgaacc gattcccagt agtgggattg ctggatcatg tggtagtttt 96900
atttgtagtt ttttgaagga acctccatgc tgttctccat agtggctgca ctagttcaca 96960
ttcactagtt acaacagtgt agaagagttc gcttttctct gcatcctctc cagcatttgt 97020
tatttttgt ctttttgata gtagccagcc caactgggga atatgatacc tcattgtggt 97080
ttcgatttgc gtttccctga tgattaggga tgttgaattt ttttttata tgttcgttgg 97140
ctatttgtat gttttctttt gagaaatgtc tgttcagatc gtttggcgat ttttttaatc 97200
ggattttttt tttttttttt tggccgttga gatatttcag ttctttgtat attctgggta 97260
ttaatccccc catcagatga gtagtttaca aatattttgt cttattcttt tcactctgta 97320
gattgtttcc tttgctgtgc agaagctttg aacgttcttg tacctgtctt gttgtggtgt 97380
gccttccttt ctcttgggtt cccttgggag ctggttatag gagtagacac acacaaacac 97440
acacacatat atgtaaaatc taatcaacta ccaaatggtt ttctcgagta actgtaccat 97500
tttccactgt ccccagccat gagtgtaagt tctggttacc ctacatcttc accagcactt 97560
ggaattatca gcctttataa ttttgctgta aaattatttt ctgctgtaga aaaaccaatt 97620
aaagcaggag tgtcatcagg gaaagactct tctcttcagg ccttgtatcc tacattttca 97680
ctgcatgaga agcgcccacc agtgaaacac agggtagcag gaaacctggg gtgggcagct 97740
aactaaccca gcttcctaat cactgagact acttcgttac aatgtcttgc cagacacagt 97800
cagcatgagt catcctcaca actatatcta ggagtctttc catcaaatgt gtgcaaatgc 97860
gggtttatgg agaaatttat cttacttcct tagtgttctc tgttatatta aggtatatgt 97920
taaaaagttc atttataatt aaaataattc ttctaatttg ctaataaaat gctttatacc 97980
aacttcaatt ggtctctgga ctgtgatagg cctaagtgtg catcatgtct tgactacttc 98040
ctatgtgacc tggggacatt ttcttaactt ccagcatccg tatctgtaaa ataggtataa 98100
tacccacctc ttagcattac tgtgaaactt aaaagagata atgaaatgca tgtcaggcaa 98160
ctagtacctg atagatactg aatgagggat aaacattttc ttgtactttg aagaattaga 98220
atacatttga gtccccaagt acccttgagt catgccattg aaaacaaaca aaaaaaaatc 98280
ctgttgaact gattgccaca ggtttcaaaa tcagtgtgtt gtgtggcatt tctgtgaaaa 98340
catggaacat atccagtctt gctgttgctt tacctaaggt actaaatctt tcttggccat 98400
cttgttaaca tgaggtgccg tggcataaag gtctgtcttg tctatttatt caacaaatat 98460
ttattggtct gtgatgtttt ttcctcctaa cataattctg ccatattatc ctatgatgtt 98520
ttatatgtta tgtaagagcc ttctggggca taatagagca gcagcacaga acgtaacgtg 98580
attgtttgct tttcccgctg cgctgtgtag cccacatcct tctacaactc caacaactgg 98640
ttcagtacca ggcgcagagt gaatgttctc taaatgtggg cagtgttgat gagtgaagaa 98700
tcttaagcag agaagaaact catgtccctg actgactcct gtgagacgtt tatcttgcag 98760
tgagtttatt cagcagccac aaatcaattt gaaggtggaa aatgtttgct ttgaaaacaa 98820
ggaaaaacct aacccatcag aagcgttcat gattagcagt ctgcaaaagt tgatcataca 98880
cattgagtta tcctcgtcat acccaaccaa aacagagccg agaaactagg ggaaaggcac 98940
tcaaggcatt gctccagaaa tggaattctc tgcaaacctg gctgctgaaa ctgcctgcta 99000
taacctgaaa cctgttttat ctgatgtcta ctgtgacgac gtgctgcagc tctaagacta 99060

-continued

```
gctttgccca ccactctcac tcacctatca gagattgcca gtttcccaaa acctttcttg  99120
tgccgatgaa ctttctcaaa gagcaatagt aacatttctc ttttttataa aacatctaag  99180
cttctctttg ttctttggac atactgaaga ctacctgatc tacaggtatg ctcccaattg  99240
cagcagtttt tttcttctca aataaaacat ttgaatttca gagatttgtt tctattttat  99300
ttgattttgg caagcctcag atgaggacga acgttgggca tattcagtct tttccattgg  99360
ctcatcccag tcatgtccca tttcattttg agccatcatt ttttgccttg atgaaggcac  99420
aaaattcagt taaacaatgt acgtagttaa ctacatttgt ttttgtttgt ttgtttgttt  99480
gtttttgag atggagtctc cctctgtcac ccaggctgga gtgcaatggc gcaatcttgg  99540
ctcactgcag cctccacctc ccgggttcaa gcgattctcc tgcctcagcc tcccacattt  99600
ctttttattt ttaagagaat gggatctttc tatgttgccc aggctggcct cgaactactg  99660
ggctcaagca gtcctcccac ctcagcctcc tgagtagctg ggactgcagg agttaactac  99720
atttctgaat agccatttgt gaactgtaat aatccctttg atatcagtag aaccagagtt  99780
ccctgtggga cagcacatct ctgctctgaa gggaagggag aaacaggcgg tactgtgggc  99840
agtcattgaa ggggggattt tggaggaaac agcatgaacc cagatggctc cagagcaaca  99900
gatgtcagga gagtgtttta ggacatcaga gttgagggca cccaggtcac aggctgagga  99960
ggcggtgacg tgatggggaa gggccaggcc ctgggatgag gggtggttca cttcctactg 100020
ctgctgtgac gagtggccac aaacttcgtg acttcacaca acacacgttt attatcttgc 100080
atttctgcag gtcagaagtc caaaataggt ttcactgggc agcacggaag gtgtggacag 100140
ggtggtgctc cttctggagg ctgcaaggaa ggactgtttt cttgcctttt cctgcttctt 100200
gaggctgcat attccttggc tcctgacccc ctccctccat cttcaaggcc atcagccata 100260
tctccagtcc ctgcttcctc ctttgactct ttcctccctg gccccctctt ttaaaggctc 100320
ttgtgatcat attgggtcca cccagataat ccaggataat ctccccatct caggagcctt 100380
aacttaatca catctgcaca gtccctttg ccatgggact ttgccaaggt accatattca 100440
caggttttgg ggattaggag atgacatctg ggtggtgggg gctgggtatt tggtccacca 100500
caaagagatt agttagaatc cagctctgtc atttactggc tgtaagtgaa tttgggcagg 100560
tcactactcc acttgaaatg tttttctgtt gcatgcgtag aacagtgagc cccccaacac 100620
acatccacac agtcctgttt ttgaggtcta ggtaaaatga tatagatgaa gagacctgat 100680
aagctttcat acattttatt tgattttgat tctagcttaa agcaaagaaa gagatttatt 100740
tgtttttctt tgtgttagtc agcagatctt tgaaagtact tgggtgactg ggcgtggtgg 100800
ctcacgcctg taatcctagc actttgccag gccgaggcag gcggatcacc tgaggtcagg 100860
agttcgagac cagcctggcc aacatggtga aaccggtctc tactaaaaat acaaaaatta 100920
gccagacatg atagtgggtg cctgtaatcc cagctaccca ggaggctgag gcagcagaat 100980
tgctggaaca cgggaggtgg aggctgcagt gagccaaaat catgccactg cactccagcc 101040
tgggagacag agtgagactc tgtctcaaaa aaaaaagaaa gaaagttctt gagtgaggtt 101100
aattcaaaac cagaatttag ttctgttgac ctggatttgt cctcctttaa aaaaaaaaca 101160
aaacatgaat tatattaatt tcttcacata ctcttgttaa tctgatttta gctagaagcc 101220
attttaggaa acttaatgta acaaatattt gctgagcaac tatatactgt gcccagcatt 101280
tgggcagatg ttggggagag agcggtggag aggcaagcct gctgcctgcc cgccggaagt 101340
tacactccag tggcatgata ggaattgtgc tggggacaca tcacagactt tgcaaggcat 101400
```

-continued

```
cgggggaagt tctcctggca aaaatgcata acccaaggct gaggaggcgt taggtggcag 101460
ggtggtgcca acagaaggaa cagcagcctc caaaggccct gaggcgagag agggtggcac 101520
tgccacggag ccaaaggaaa gttagtgtgg ctggagctga gggagggctg tggagatgca 101580
agacaggggc ctgagcaggg cctagagggc ctcagcacgg aggaaaaaag aggtatgaaa 101640
tccagccgga ttctctggac ttgtcatgac tctggtaagc aacatccctc atgtgtaccg 101700
ttccccagaa cctctcccag gagaagaatg tgtaaagact ttgaccaccc aggcagccat 101760
agaaaggcag cttccagagt ctccctccca ctcctgctgg aagtccaggg tggccctgct 101820
gtggtaaggc caaggtaaag tcagagcaga gttactgaga ctccacagtg agggacaatc 101880
ctgtcacttt tgagttgcgg ggaatttctt gatttgtggc actgaagatt ttctgcatat 101940
ttggagcaaa atgcagctga aatagaattt gtgaccattt aactatttcc tgccaaatga 102000
tgtatgtttt gtttgtgtgg attatctcct cttgctaaag atttacatct gtacatctgt 102060
caggtgtgat caggtggaaa gtagaagagg aactgtgtga ttctcctccc ttggtctcct 102120
cttccccctc agaaatggct ccaacatact aggcatggag aatattttgc ctttggcttg 102180
agatgaatga tatccatgga agttcatgca ataatgtacc ttttgacact taactttaga 102240
agctgggcat ggtggcatgt gcctgtggtc ccagctactc aggaggccaa gacggggagg 102300
atccttgggc ccagggctcc agtctgggca acatagtgag acccatctct taaaagtata 102360
aacattaagt aagaggggat gctcttctac tgagagaggg gaccccctggg actgaggaca 102420
gcgttctcac attcttactt caggtaaggc agattgccta accaattgtt catcactttt 102480
ctcgcaagtt cctcgcatat gacagcatct tccttctctg tttttctagg ctattcagct 102540
tgaccctgaa gaaactcgtc atgctaaaag aaatggacaa agatcttaac tcagtggtca 102600
tcgctgtgaa gctgcaggtg agtggggcag gactgtttgt tcagggccca gggaagctgg 102660
ataaccattt gcccactgct gcggcttcag aaacactact gggaccacct ctgtcttcct 102720
cctctcagca cagcaaggtg cacagtggaa agataacaga gctcacagga ccttctgagc 102780
ccagctctgc ctcttggtta gggcactcag tttcttcaaa cctatctttg tctgaagaac 102840
agaaatggtt tttcctacac atactgtgag gatcaagtga tatagatcct aaagtgttta 102900
ttgtaaacta ctcagaaatt actaggctgg ctagctttgg tttcagtctt agtcccagga 102960
ttgctagatc caggtagatg cacgggtatg ggaagcactt tggaggtttt cttttatttt 103020
cttttgagac agagtctcgc tctgtcaccc aggctggagt gcagtggcgc gatctcggct 103080
cactgcaagc tccgcctccc gggttcacgc cattctcctg cctcagcctc ccttgtagtt 103140
gggactacag gcgcctgcca ccacgcccgg ctaatttttt tgtattttta gtagagacag 103200
ggtttcactg tgttagccag gatggtctcg atctcatgac ctcatgatcc gcttgcctca 103260
gcctcccaaa gtgctgggat tacaggcgtg agccaccgcg cccagcctgc acttcagagg 103320
ttttctatag ggtggaagaa acttacagat tgttatttca gacttggcaa tttaaagttt 103380
actgggatat tttatctcta tataaatccc acttataact ccttacattt ggtatattca 103440
agggacccaa aatatttcac aaacatttgt attcttaagt attcctgaat ttaaggaaaa 103500
gagaagggaa aagctgaatt atagaagggc tcaggaattt acctgttgcc agctaattac 103560
caagcgacag aacttggacc agaaactaaa gagtgggtaa tttgtgtgct cattaaatcc 103620
catcaccaga cctcccttaa ctgattaatc ctttctgctg atgactccct ggagtagagt 103680
gagattctgc agtgcctctg gagtcactaa ataatgactg gagtcttcag cttaaggatg 103740
gtgtatttac tgaattctta ttcattgaaa aatagcaaac tgtatgataa ctccctacta 103800
```

accagaatat tttattagct agttcaccta ctatgctgca gtttattgta ctatatcacc 103860
ttcattaaaa tccacttcta tatcactctc agtgtgtgaa tcatatattg aggtgcctcg 103920
gcctctttct gggataaaga cgttagtccc aaatacataa tttagttctc aaaacttaaa 103980
atgttgggcc gggcactgtg gctcacacct gtaatcccag cactttggga ggctgaggtg 104040
gtggatcact caaggtcagg agttcgagac cagcctggcc aacatggtga aaccccatct 104100
ctactaaaaa tacaaaaatt agccaggcgt gcatgtagtt ccagctactc agggggctga 104160
ggcaggagaa ttgcttgagc ctgggaggga gaggttgcag tgagctgaga ttgtgccact 104220
gcactccagc ctgggtgaca gaatgagact ccatctcaaa acaacaacaa caaaaactta 104280
aaatgtttta attactcatg aattcctgtg tgtcccacct tatattctaa ttccctgttc 104340
attttatgca taattccttc caaatctatg aaatgttccc agacactgtg ttgggaaagc 104400
aagtgtggga cagcaatgtg aactattagt gtcttgtcct cctctcccga ttttggtccc 104460
catttctagg tcacaggcag tgttcccgtt ttcaggaatt gcttcctttg ctaaagaatg 104520
ttgctgtcct gtgccgacac cattggggtg gttttgaaag ttccccactg cgtttgccat 104580
ccctgcagct aaatgctttt gccaaagaaa taatttattt cctgattaaa tatttaagat 104640
tctataattc taaattatac caaaactaca aatattttga atttttaaat tgttctactt 104700
ccaagcagct gaaagtaatt acagatgtca ccacattcat ttattcagtc acttatttat 104760
gcattcatat aataaatact tattgagcat ctattatgtg ccaaacattg ttctaggcac 104820
aggggataca gcagtgatca aaacagacaa aaatccctgc ctttaagaag cgttgagcag 104880
taattcccca aaggagatct gcagaccctg aggtctctaa gacacttcca gggggtacag 104940
gaggccacaa ctattttcat gataatactg tggcattatt tgccttttc agcatgttga 105000 cttttgcact gaaagtacaa gagcaacagt ggataaagct gctggtgcct cagcacaaat 105060
gcccccaatg tcccagaggt cattgtgttg tttaccatct catgagtgaa ataagaagat 105120
aaaagggctg ggcacagtgg cacacccctg tagtcccagc tacttaagag gctggggcat 105180
gcgggtcact tgagcctagg agctggctgg aatgagctgt ttgtgccagt gcactccagc 105240
ctgggtgaca gagcaagact ccgacccaaa caagggagag aaagccagtt ttgcttaaga 105300
atgttcttaa gaaagcagta aaacgtgtta atttattata tctcaacctt gagtctgcat 105360
ctttttcata ttttgtgtga tgagatggga cgtgtacact gagcacttct gccttgcagc 105420
aaagttcgat gtctgtctct aagactagag cctgtgtgag gtggagctac tgagttgtga 105480
accacagtag ctgcttttt catgaacacc atttttactt caaagaggga cttccagaca 105540
aacaggttat ttagactcag gtatttggaa ggtgtttcct taaaattgaa cagagttacc 105600
ctatcaattc agggaaaaca acttaatatt ggttgccaat gataaataaa atttgacctt 105660
tttttttgtt tgagacagag tctcgccctg ttattcaatg gcgtgatctc ggctcactgc 105720
aatctccatc tcctgggttc aagtgattct cctgcgtcag cctcctgagt agctgggact 105780
acaggcaccc accaccatgc ctggctaatt tgtgtatttt tagtagagac ggggttttac 105840
catgttggcc aggttggtct cgaacccctg acctcaggta atctgcccac cttggcctcc 105900
caaagtgctg ggattacagg catgagctac cacacctggc caaaatttga gcttttaagt 105960
aaaaattaga attttggaaa acttgcttct gtcactgaaa gcttaacagc ttcccagttc 106020
ttaaagactt ttctgaagaa gtcagaagtg atattaaaca tttttagttt tttatattgt 106080
ataatatgta acatttgaat attttctaaa tgactaatgc atgagtttac aaaatcatgc 106140

-continued tggataaaag atcctttcaa agaacaaaat agaccagtgg attgggtttt taactttcta 106200
ttttaaaata cttttaaatg tatccaagag atgcagggtt agtctaaaga gttcctgtat 106260
accccaccca gcttctccca acactaatat ctctcttaac catggtacat ttatcaaaac 106320
taagaaatta tcattggtat gatactatta attaaattcg acttcagatt tcctagtttt 106380
ttcattaacg ttctttttct gttaattgga ttttaacata taagagcaca aaagtcttat 106440
tgatattatt taaaattcta ctttggaaaa aaaattttta ctttgcaact aatctttagg 106500
aaactaccac ttagagagtt aatggtgtag tatcaaagga aaatagtcca caactggctg 106560
gtcacaatgg ctcatacctg taatcccagc actttaggag gccaaggtga gaggattgtt 106620
caagcccaag agttcaagac catcctgggc aacacagcaa gaccccatct ttaccaaaaa 106680
taaaaactat ctgggcatgg tggcatatgc ctgcagtccc agctatttgg gaggctgagg 106740
caggaggatt gcctaagccc aggagttcaa gtttacaatg agttatgatc acaccactgc 106800
actctaccct gggcaacaga acgagacctt gtctctaaaa ataaaaaata aaaaataaat 106860
aaaaaattcc acagttgtct gaaaaggctg ttaaaatgct cctctgtttt ccaactgtat 106920
atcactttgc gtctggattt ttttcatata ctcaaccaaa gtaatgtttt gcaacacatt 106980
gagtccaaaa taggaatgag aatctagttg ttttctatta agtcattcat taaaaagatt 107040
tacagaaatg taaaactatg ccatctccct catacactgc tgttgggaat gtaaaataat 107100
gcagccactg tgttgttttg ttttgctttt gtttttattt tagagacaag gtcttgctgt 107160
gttgcccagg ctgctctcaa actcctggcc tcaagcaatc ctctcgcctt gacctcccag 107220
tgctgggatt ataggcttgt gccaccatgc ccggttctca aaaggttaaa gactgagtaa 107280
ccatatgact tagcaattct actcctaggt atgtccacaa gagaaatgaa aacacacaaa 107340
atctaacatg caaatgttca taacagaatt attcacgagc taaaaagtag aaacaatcca 107400
agtccatcaa ctgatcaatg gataaataaa atgtggtcta gtcatacagc ttcggaatac 107460
tatttggcaa taaaaaagaa tgaagtacct ccatgctcca ggtggatgaa ccttgaaaac 107520
atgatgctaa gtgaaagaag caagacacaa aaaaccacat attgtatgat tccatttata 107580
tgaaataggc agatccctag ggtcaggaaa tagattgtag ttgccagggg ttaggggtgg 107640
gggtgggcag actgcagagg gtgataatta aagaatatga ggtttctttg ttgaatgatg 107700
agaatgttct gacactgact gtggtgatgg ttgcacagcg ctgaacatag tgaaagccat 107760
tgaattgtac actttaaatg ggtgaattgt gtggtatttg aattatatcc cagtaaagct 107820
gtaatttttt taaaaaacta tgtcttctca ctaaattatt tttgtttggg gaacatatat 107880
ttttcatttt aaaactttgt atgtaaacac ataataggtt tattgttaat tttaaatgga 107940
ttaataaata ttttaaaata tctgttttaa ttcataatat ggtgactatt gatagataaa 108000
cctacataaa caaaatattg atagatatac ctacatacac aaaagctatt tgggattctt 108060
tctaaaagtg taaaaagggc cgggcgtggt ggctcacgcc tataatccca ggactttggg 108120
aggccaaggc aggtggatca tgaggtcagg agatcgagac catcctggct aacatggtga 108180
aaccccatct ctactaataa tacaaaaaat tagccaagcg tggtggcggg cacctgtagt 108240
cccagctact tgggaggcta aggcaggaga atggcgtgaa cccaggagtc ggagcttgca 108300
gtgagccgag atcgcaccac tgcactccag cctgggcaac agagcgagac tccatctcaa 108360
aaaaaaaaaa aaaagaggga ggggggatga agttgaacta tagagttttt attggttttc 108420
tctttgcttc tttgtttttt gtttttgcaa tcagagttaa cttaccattc agtttaaaat 108480
aatgttttat aagatgttat ttgcaagcct catggtaact gcaaatcaaa aaaccctaaa 108540

-continued acagatacac aaaaaataaa aagcaagaaa ttaaaaacat accatcagag aaaatgactt 108600
tcacaaaaag aaagacaaga aggaaagaag gaaggaagat aagaccacaa aacaaccaga 108660
aaacaaataa caaaatggca atagtaaggc cttacttatc aataataaca ttgaatgtaa 108720
atggacaaaa ttctgcaatc aaaagacgtg gagtagttga atgcattaaa aaacaagacc 108780
cagctgggca cggtggctca tgcctgtaat cccagcactt tgggagccca aggcgggcaa 108840
atcatgaggt caggagttcg agaccagcct ggccaacaca gtgaaacccc atctctacta 108900
aaaatacaaa aaattagctg ggtgtagtgg cgtacacctg taatcccagc tactcgggag 108960
gctgaggcag gagaatcgct ggaatctggg aggtggaggt tgcagtgagc ccagattgca 109020
ccactgcact ccaacccagg caactgtgcg agactctgtc tcaaaaaaac aaaaacaaaa 109080
acaaaacaaa acaaaaaaaa aaacaagacc cagctaggca cagtggctca tgcctataat 109140
cccagcactt tgggaggctg aggtgagagt attgcttgag ctcaggggtt tgagaccagc 109200
ttgggcaaca tagtaggacc ttgggtctac aaataatttg aaaaattagc tggatgtggt 109260
ggtgtgcacc tgtagagtca tctactcagg agtctgaggt agaaggatca cttgagctca 109320
ggaggttaag gctaaagtga gctatgattg tgccagtaca ctccaccttg ggcaacagag 109380
tgagacgctg tctcagaaaa acaaaaacga aaacatgatc caaacatcta tcgcctacga 109440
gaatcacact tgacctgtaa agacacatag agactaaaaa taaagggttg gaaaaatata 109500
ctctatgcaa atggaaacaa acaaaaaaaa aaagagtagg aatagctata cttatatcag 109560
acaaaataga tttcaagaca aaaattgtaa aaattgataa gttcattata taatgataaa 109620
ggggtcaact cagcaagaag atataacaat tgtaaatata tatgcaccta acactggagc 109680
acccagatat ataaagcaaa tattactaga gctaaagaga gtgttagacc ccattacaac 109740
aatagctaga gactttaaca ccccactttc agcattggaa agatcatcca gacaaaataa 109800
agaaacatca gacttaaccg cactatagac caaatggacc gaatagatat ttacagaaca 109860
tttcttccaa tggctgcaga atacactttt ttttttcatt agcatgtgga tcattctcaa 109920
ggataggcca tatgttaggt tacaaaacaa gtcttaaaac attcaaaaaa aaaaaaagtt 109980
gaggccaggt gtggtgactc acgcctgtaa tcccagcact ttgggaggcc aaggtgggtg 110040
gatcatgaga tcaggagatc catagcatcc tggccaaaat ggtgacagcc cgtctgccct 110100
aaaaatacaa aaattagctg ggcgtggtgg caggcgcctg tagtctcagc tactcaggag 110160
gctgaggcag gagaattgct tgaaccctgg aggtggaggt tacagtgagc ggagattgcg 110220
ccactgcact ccaacctggg tgacagagtg agcctctgtc tcaaaaaaaa aaaaagttga 110280
aataatatca ggcatcttcc ctgaccataa tggaataaaa ctagaaatca atagcaagga 110340
attttgaaag caataggcac acatggaatt aaacagtatg ctcctaaatg accagtgggt 110400
caatgaataa attaaaaagg aaaattgaaa ttttcttgaa gcaaatgata atggaaacac 110460
aacatatcaa aacctatggg atacagcaaa agcagtacca agagggaaat tcgtagctat 110520
aagtgcctac atcaaaaaag aagaaagact tcaaataaac aacttaatga tgcttcttaa 110580
agaactagaa aagcaagagc aaaccaaacc caaaattagt agaagaaaag aaataatgaa 110640
catcatagca gaaataaatg aaattgaaaa aaaaaagtca acaaaacaaa atgttttggg 110700
tttttgtttt tttttttct gagacggagt tttactcttg ttgcccatgc tggagtacag 110760
tggtgcaatc tcagctcatt gcaacctctg cctcccaggt tcaagtgatt ctcctgcctc 110820
agtctcctga gtagttggga ttacaggcgc gcaccaccat cgcggctaat ttttgtattt 110880

-continued

```
ttagtagaga cgaggtttca ccttattggc caggctggtc ttgaactccc agcctcaggt 110940
gatctgcttg ccttggcctt cggtgctggg attacaggtg tgagccatca cacccggcca 111000
aagagttgtt ttttgagaag acaaaatgga taaaccttta gccagaccaa ataagaaaaa 111060
aagagagaag acacaaataa atcagagatg aaaaaagagg tgactgacac tgcagaaatt 111120
caaaggatca ttagtggctg ctatgagcag ctatataccg ataaactgga gaacctagaa 111180
gaaatggata aattcctgga aagatacaac cttccaagat tgaaccatga agaaattcaa 111240
aacctgaata gaccaataac aaaaaatgag ctagatgcca ttaacaaagt cttccagcaa 111300
agaaaagccc aggccttgat agcttcacta ctgaatttta ccaaacattt aagaagaact 111360
gtttcaaaaa atagagaata attccagact caatctatga aaccaatatt cctctgatac 111420
caaaaccaaa gaaagtgaca gggcagtatc tctgatgacc actgatacaa aaatcatcaa 111480
gaaaatacta gcagagttca gcaacacatt aaaaacatca ttcatcatga ccaagtgaga 111540
tcccagggat gtgcaaggat ggttcagcat acacaaatca attaatgtga tacatcatat 111600
caacagaatg aaggacaaaa cccatgtgat aatctcaatt gatgccaaat ggctgggtgt 111660
tgtggctccc acctgtaatc ccagcacttt gggaggccaa ggtagatgga tcgcttgagg 111720
ccaagaattt gagaccagcc tgggcaacat ggcaaaacct catctctagg aaaaaaaaaa 111780
aaaaaaatat atatatatat atatatatat atatatatat atatattctg aaaaagcatt 111840
tgataaaatt caacaaggct tcatgataaa aatcctcaaa aaatgggtat aaaagaaaca 111900
tacctcaaca caataaaagc catatatgac agacctatca cttgtatcag actgaacgga 111960
gaaaaactga aagcctttcc tttaagatct ggaacaagac aaggatcatc actttcacca 112020
ctgttattca gtatagtact ggaagtccta actagagcag tcaggcaaga gaaagaaata 112080
aaggcatcca gattggaaag gaagaaatca aattatcctt gtttgcaaat gatatgctct 112140
tctatgtgga aaaacctaca cttcacaaaa taactattag aactgataaa atcagtgaag 112200
ttgcaggata caaaatcaac atacagaaaa taggtagcat ttctatatgt caacagtgaa 112260
caatctgaaa aagaaatcaa gaaagtaatc ccatttacaa gagctacaaa taagatacct 112320
aggaataaac ttaaccaaag aagtgaaata tctctatatt aaaaactgta aaacattgat 112380
gcaagaaatc taaatagaca cacaaaaaat ggaaagatat tccatattca tggattggaa 112440
gaatcaatat tgttaaaatg tccataccac ccaaagcaat ctacagattc aatgcaatcc 112500
ctatcaaaat accaatgaca ttcttcacag aaatagaaaa aaaaaatcct aaaatgtata 112560
tggaaccaca gaagacccag aatagccaaa gccatcctga gcacaaagaa caaaattaga 112620
gaaatcacat tatctgactt caaattatac tacagaacta tagtaaccaa aacagcatgg 112680
tgctggcata aaaacaaaca cctacaccaa tggaagagaa tagataatct agcaataaat 112740
ccatacatct acagtgaact aattttcaac aaaggtgcca agaacataca ctggggaaag 112800
gacaatctct tcaataaatg atgctgggaa aactggatat ctatatgcag aggaattaaa 112860
ctagactgtt gtctctcact atatacaaaa atcagataaa aattgactgg agacttaact 112920
ctaatacctg aaactatgac actactaaaa gaaaacattt ttccaactgc tttggccact 112980
aaaataataa aaataaaaga aaacattggg gaaactctcc aggaaattga tctgggcaga 113040
gatttcttgt gtaatacctg gcactggcaa ccaaagcaaa aatggacaaa tgggatcaca 113100
tcaagttaaa aagcttctgg gccaggcacg gtggctcatg cctgtaatcc cagcactttg 113160
agaggccaac aagggatccc ttgtccatct gacaagggat taataaccag actatataag 113220
gagctcaaac aactcaggaa aatatctaat aatccgatta agaaatgggc aaacgatctg 113280
```

aatagacatc tctcaaaaga agacctacaa gtggcaaaca ggcatatgaa agggtatgta 113340
acatcattaa ttgtcagaga aatgctaatc aaaactacaa tgagatatca tctcacccca 113400
gttaaaatgg cttttatcca aaagacaggc aatagtgaat cctggtgagg atgtagagaa 113460
aagggaaccc tcgtacactg ttggtaggaa tgtaagttag tatagcgaat atggaaaata 113520
gtatggagtt tcctcaaaaa accaaaatag tcccatgtag cactattcac aatagccaag 113580
atttggaagc acctaagtgt ccatcaacag acaaactgat aaagaaaatg tggtacatat 113640
acacaatgga gtactatgca gccataaaaa agaatgagtt cctgtcattt gcaataacat 113700
ggatggaact ggaggacatt atgttaaatg aaataagcca ggtacagaaa gacatacttt 113760
gaatgttctc acttacttct gggagttaaa aattaaagtc atggagatag tctaatgatg 113820
gttaccacag gctcatatgg gcagtcgggc agtgatgata gttaatggat acaaaaacat 113880
agaatgaata agacctggta tttggccaag catggtggct cacgcctgta atcctagcac 113940
tttgggaggc tgaggtagga agattccttg agtccagtag tttgagacca gcctgagcac 114000
catagtgaaa ccccatctct attttttaaa aacttttttt tttttgaaac ggagtttcac 114060
tcttgttgcc taggctgcag tgcaatggcg caatctcagc tcactgcaac ctccacctcc 114120
caggttcaag cgattctcct acctcagcct cccaagtagc tgggattaca ggtgtgcacc 114180
atcatgccca gctaaatttt gtatttttag tagagactgg gtttcaccat gttgcccagg 114240
ctggtcttga actcctgacc tcaggtgatc tgcccgcctc agcgtcccaa agtgctggga 114300
ttacaggcat gagccaccac gcccagccaa aacaattatt ttaattataa aaattttttt 114360
aatgttttaa agatctgata tttgatagtg caacaggacg attacagtca atgataattt 114420
atagtacatt taaaaataac taaaagtata attggaatat ttgtaacata aataaatgat 114480
aaatgcttga ggcgatggat acccaatata acctgatgtg attattacat gttgtatgcc 114540
tgtaccaaaa tgtcttatgt accccataaa tatatatgcc atgtacccat aaaaattatt 114600
agttaaaaat tgaaataaag aataaatgaa aaataacagc ttattttcag acatccaaga 114660
aaccccaaca aatttcctca aatatcacta caatactctt aatttttttt tttttttttt 114720
gagaatggga tctcactatg ttgcccaggc agctcttata ctcctgggct caagctatcc 114780
ttccacctct gcctccttaa gtgctgggat tacaggcatg agccaccaca ttcagcaata 114840
atactgttaa atatctatat gataagaatt tttggtttaa ataagaagca tttaaaacag 114900
cagtaacctg gccggtcacg gtggttcatg tctgtaaatc ccagcacttg ggaggccaag 114960
gcaggtggat cacctgaggt caggagttca agaccagcct gggcgacatg gtcaaacccc 115020
atctctacta aaaatacaaa aattagcccg gcattttggc acatgcctgt agtgccagcc 115080
actggggagg ctgaggcagg agaatcgctt gagcctggga ggcggaggtt gcaatgagtt 115140
aagattgcac cactgcactc cagcctgtgc aacagagtga gactctgtct caaaataata 115200
ataataaaac accagtaacc taatttttaa aataatatta atattggata ttttaatgtg 115260
ctatgttact ttagtattaa atataaatgg ttttgcttct atactgcaaa agaagatata 115320
ctgttatata gataaacaaa tgatacaaaa gtatattaaa aataattttg aaattggacc 115380
ctggttggta gtgccccagg cacctggaag aagcaaatac tggaacccat gaaagctaaa 115440
cccctgggga agggtagtaa agatgaggac agtagtgcac catgcttgaa agggctgggc 115500
tgggctgggc ctggctgcga tcccgtgaca cactgcactc cgcatcctgc tacctgcaca 115560
cgcagattac ttctagcgaa tttgaaattc agatagtgaa tttgggatac aaagttttac 115620

-continued aggtatttag agcacatact tgggtggtga gagttcatat aatcatataa tgaggctact 115680
gctgttggaa ggtgatgtcc tatagtgaca ataactaaga taaaggggac cgagagggct 115740
ggggtggagg aagttaacgg attccctacg gtggtcacgg tagacctggt tgagaagatg 115800
acatttaccc aaagactttg agggaggtga gggccatgca ggtatctgga ggaagagcct 115860
tccaggcaga gggaagaccc aggaccaggc cctcaggcct tcatattctg tgaatatatg 115920
ctctgagctg agaaatctta aaagaaccct aagcactgat tacttttttc aacttttatt 115980
ttggaaaaat ctcaaacgtg caaaagtaga cgaagtagtt tacaattccc tcgaacccct 116040
tactaagctg cagttgttat caacttatgg ccagtctcgt ttcgtctgtg tccccactgt 116100
ttcccttcac cagtgttatt ttgaggcaat ccgtacatca taacatttca cccacaaata 116160
tgtcgatatg tatttcaaaa atgtaggcag tatatttaaa caaaacctcg ataccattat 116220
cacaccttgg ccagacgcgg tggctcatgc ctgtaatacc agcactttgg gaggccaagg 116280
ggagcggata acttgagatc aggagttcaa ggccagcctg gccaacatga taaaacctca 116340
tctctactaa aaatacaaaa attagctggg cgtgatggca ctcacctgta atcccagcta 116400
ctcaagaggc taaggcaaga gagtcgcttg aacctgggag gcggagattg cagtgagccg 116460
agatcacact actgtactcc agcctagtcg acagagcaag actctatcta aaataacaaa 116520
aaccttaata tcacaaaatc agtgttcaaa tttccagttg tggcatgaat ctcataaatg 116580
tgtgggtctt gtgggagaga gtggctgttg gttttgcttt ttatagttta tttgatgcat 116640
tcggtcttca gttgccacta tagcactcga gcttccgggt gtcctgaggc cctggcctgt 116700
gtgcgggctg gctgtgtgct tctgctgatg ttattttatt tttgctgttt tttgagacag 116760
agtctcgttc tgttgcccag gctggagtgc agtgatataa tcttggcttt tgttttgttt 116820 tgttttttt tgagacggag tctcgctctg ttgcccaggc tggagtgcaa tgatatgatc 116880
ttggcttatt ccaacatctg cctcctaggc tgaaatgatt ctcccacaca gcctcctgag 116940
tagctgggat tacaagtgca cgccactatg cctggctaat ttttgtattt ttcgtagaga 117000
cgaggtttcc cagtgttgcc caggctggtc ttgaagtcct gagctcaggt gatccgccca 117060
cctcagcctc ccaaagtgcc gggattacag gtgccaccac acccaggctt ctgctgattt 117120
tatacccagc cttcccccta tggccattac ccataggcag catcgctata taatgacata 117180
accatcaggg ctccacttcc ttggtctcat tttggcctca tgagtggctg aggcgttttt 117240
ccatgtgtgg agttttcccc taagggtcag caccgcggca tagtaccatt tcaacagaaa 117300
cagctcccag agtaatcaca gctttgctga agacacgtga gagatgagca gctcaaaaat 117360
ttgtcattaa ttataaacag ggatgagtgt ggggctcaaa tctgtaatcc cagcactttg 117420
ggaggcagtg gcaggaagat tacttgagcc gaggagttca agaccaacct gggcaatgta 117480
gcgatacccc atctctacaa ataaaaaata aaaacggtaa aaataatgtt tcaatgaaca 117540
gctccttgtt tacagatttg cttcttttta aaactcattc ctggcccagc ctggtggcct 117600
ataatcctag cactttggga ggctgaagtg gaaagatcgt ttgagctcag aagttaaaga 117660
ccagcctggg caacatagtg agacctcgtc tctcttttta ttaaaaaaaa aaaaaaagaa 117720
gaagaaaaag aaagaaagga aggaaggaaa gaaagaaaaa aatcattccc tccaagttca 117780
tgggatcaag ggagaaaaaa gaaaataata tataaaaatc atgcccttag aatttatttt 117840
tttggattac aatttttgaa tagaaatgtt tctttattgc caggctactt tctaaaaggg 117900
ttattgtaat ttactttgct tcaacaatga atgaatttgg aaattctacc acatccttac 117960
caactttgga tgttgtgggg ttttttttat tggtattaat tttaaaactg attttttttt 118020
agacaaattt attcaacact gtttatttgt gtgctgggaa tcatactgaa caagacatat 118080
ctttgtctca tggatcttga agtttagtga gattcagtaa ctggcagtaa gagggctgtc 118140
taacccaaat acaaggtttg gaggcgggga ggttacagag gaagttcctg ggaaaaaaaa 118200
attcagctga gacctgaaag atgagttggt tacttgtgtt cagaagccaa aaaaagcatc 118260
caagaagaga agaaaagcac atgaaaaggc ccagagacaa gacagtatgc ctggggagtc 118320
agagggagga tcacttgaag tcaggagttc gaggccagcc cggccaacat ggcagtaaga 118380
gggctgtcta acccaaatat taggtttgga gagcagggag gttaaagagg aagttcctgg 118440
gaaaaaaaag gaacagtggg cagggagggt cttacacacc ctggggactg acactaccgg 118500
cctcttcccc aggagtgctg ggaactcaca gacgttaaca aatcattttg ctgtgataac 118560
cttttatgca ccctacagca tcatatatgt aaaatcagac ttatggtaga ggcttgattc 118620
aaataagtac aataaagact catgaaatat ttggactggt aagaatgttt gggccgggct 118680
cagtgactca cacctgtaat cccagcactt tgggaggctg aagcaagctg atcatctgag 118740
gtcaggagtt caaggccagc acatggtgaa accctgtctc tactaaaaat acaaaaaaat 118800
tagccgggca ttgtggcagg tgcctgtagt cccagctact caggaggctg aggcagggta 118860
atcgcttgaa cctgggaggc ggaggttgca gtgcgccgag atcacgccac tgcagtccag 118920
cctgggtgac agaatgagac tcgtctcaaa aaaaataaaa tttaattttt ttttttaaa 118980
gaatgcttgt agagtttaga agttgtttgc aaacatagta tttcttttgg tctgattttt 119040
ggtgacacag ctttgacaga ttttttttt ctttttatta ttgatattat ttgagacagg 119100
gtctctctct gtcacccagg ctggagtgca gtggcaggat catgactcac tgcaggcttg 119160
aactcctggg ctcaagtgat cctcgcacct cagcctcctg agttgctggg actacaggca 119220
tgtgtaccac cacacccagc caattttttt tattttttgt agaaacagga gtctcactat 119280
gttgccccag gctggtctca aactcctgag tccaagcagt ccttctgcct cagcctccca 119340
aactgctggg attactggca caagccactg cacctggcca aacagacttt tcttcttggt 119400
ttcagggttc aaaaagaatt cttcgctcca acgagatcgt ccttccagct agtggactgg 119460
tggaaacaga gctccaatta accttctccc ttcaggtgag actctcctaa tcttaggccc 119520
ctaacatgct atatcctggc tagtccccag acagtcctct aacccagaga ctgttttatc 119580
ccagagcccc cattccccaa cttgggcagg aatgaataaa agtcacctgg aggtttatgg 119640
ctggcctgga gggccaaagc aaccctttag ccagtgacgg taagggtgtg gagacctggg 119700
taggcaccgt ggccccttcc cttcctctgc cttggctaac actgttagcc atctgctgca 119760
ccacatcaca tctccttagt gatcctcgca caccccgtgg actgtgccac catcagcctc 119820
cacgtcggga tctccgtcct tcccctctac tccgtatccc tcctagtcgg tgtccctctc 119880
atcgtaattc cagtaattca atgcccaaat tgaaacacat ggagaaaaca cctgataaag 119940
tggcaaggga agagacagtt ctctgaatag gtgtggaccc cagagctgtg gcgtagaagc 120000
caggcatcaa gccgaatcag ctccaccagc agcaacttca tggctctcct ttcaaccctg 120060
actgcccccct tttagagaca ggaagaattg aagcacagaa agactgtgtg tcctccagaa 120120
cccctcaagg acccagctgc ccattaacca cgctcgactc tgttttgtat ttcgtagtac 120180
cctcatttcc ttaagcgaga tgccaacaag ctgcagatca tgctgcaaag gagaaaacgt 120240
tacaagaatc ggaccatctt gggctataag accttggccg tgggactcat caacatggca 120300
gaggtgagag gaacacagtc tccagactgt tggcctttga gtcacagagc ccaaggga ca 120360

-continued

```
ccccagccca gccagttgag ccttccagat gattttccca gcctgctggc taggtgctta 120420
attctgtttt acgagttaat tatttgctgg aaattcagag tatacttgtt tttatcaaat 120480
actgtctcct tcatgaaaag ttttaatttt taaacaggta aaactcaaaa aattacataa 120540
aatttcaaac tttcagaaaa gttacaagaa tagtacaaag agttcccata tgtggattca 120600
tccaagttct ttaacatatc accacatttc atatgctctc ctcatagata tattgatagg 120660
tattattttc tgagccatcc gagagtaagt tgctggcacg atgccccatt acacgttaat 120720
actgcaccac gttaatttcc ttaacatgag aatactctgc tgtctaaact ccctgccacc 120780
atcaagatca ggacactaac gttgagataa gattgccgtc taacccacag tccctattcg 120840
gattgtgctg agtgtctcag tgataccctt tatgggcctg ggatccgatc taggattatg 120900
tgccgcatat cactgtgtcc ttcgtcccct tcggtctgca gcagcccctc ggttttcctt 120960
acctttcatg accttgacat tttttaagcg cacaggctgg ttactttttt gaatactcct 121020
cagtccaggt tcgcctgatg ttgcctcaag attagattcc acctgtgtgt ttctggcagc 121080
attaccacag aagtgctctg ttctcagtgc agcttaggca gcacctgatg gcaattggtt 121140
cctttcctgg ggatattaac ttttaatttt ttttattttt actttttttt ttttgagatg 121200
gagtcttgct ctgtcgccag gctggagtgc agtggcatga tcttggctca ctgaaacccc 121260
cgcctcccgg gttcaagtga ttctcctacc ttagcctcct gagtagctgg gactacaggc 121320
gtgcaccacc atgcccagct aatttttttt tttttttagt agagacgggg tttcaccatg 121380
ttggccagga tggtctcatt ctcctgacct tgtgatccgc ccgccttggc ctcccaaagt 121440
gctgagatta caggcatgag ccactgcgcc tggccttaac tttttttttt tttttttaga 121500
gacgaggtct tgctctgttg tccaggctgg tctcaaactc ccaggctcaa gcaatcctcc 121560
ctccttggcc tcccaaagtg ctgggattat aggcatcagc ctctgtgccc ggcctgatat 121620
tatcacttgg ttaacatgga gtctgcaggg tttttccacc acaaagttaa ttaataagca 121680
ttttgtactt actggaaaaa atattttacg aggaggtaaa tatattaagg ggagaagaag 121740
aaaggcaact atctttttcc ttatcacatt tcacccacta gttttagcat ctattcatga 121800
ttcttgcctg aattggtcat cactatactt ggatgcttac cagacagtga atttctaatc 121860
ccaccattcc ttacatattt attaattggc tttatttatt tatttatttt cgagacagag 121920
tctcacttca tcacccaggc tggagtgcgc tggcacaatc tcggctcact gcaacctcta 121980
cctcccgggt tccagcagtt ctcctgcctc aacctccaga gtagctggga ttacagggac 122040
ccgccaccat gcccggctaa tttttttat atttttagta gagatggggt ttcaccatgt 122100
tgtctgggct ggtcttgaac tcctggcctc aagtgatccg ctgctttggc ctcccagagt 122160
gctgggatta caggcgtgag ccactgctcc cggcctcatt aattggcttt ctgtagtaag 122220
atagtgcttt tcctttgctc tcatttattt gtatcagtta tggaccgtgg gttcctgttt 122280
tatttgatgg ggctgaatct gctactatca ttttttttatt ttgatgcaca aacttatcag 122340
atttggccca tgggagcccc ttcatgccag ctttgagtcc ttagtaatat gtctcatcat 122400
tcgttacatc ctaccgtact ttctggtaca aaacatttca ggctcatctt gtactttccc 122460
tgacccagct cccagaatga gcagattctc tgaggagccc tggttctttt cagtagagga 122520
tggtgttcag aaaccaagat ctgggtacca ggagtgccca tgtccccaac tgggtgtcat 122580
gcactcccac tgagcagaca gagctgagaa agatctgtct gtatgcacac atgtgctcgt 122640
gtctacacac gtcacagctc ctttcaggtc taggtccaga tctatctaac cgtgagcaca 122700
catcgataat ttcagttcca acccaatgcc tttttatagc ttttctttct ccatgtttct 122760
```

aattcccttt tggaatggta agaagtcagg ctgtgggctg ggcgcagtgg cttacgcctg 122820
taattccagc actttgggag gctgtggcag gcggatcacg aggtcaggag atcgaaacca 122880
tcctggctaa cacggtgaaa ccccatctct actaaaaata caaaaaatta gccgggcatg 122940
gtggcgggcg cctgtagtcc cagctactcg ggaggctgag gcaggagaat ggcgtgaacc 123000
caggaggtgg agctttcagt gagccgagat tgcgccactg cactccagcc tgggcgacag 123060
cgcgagactc catctcaaaa aaaaaaaaaa aaaaaaaaaa aggctgtgat tattctcaat 123120
acatgtactc attggtgcag ctccctgtgt gccaggcagt tcctctcaat cctaacagga 123180
agaagaaagc agccgctaat ctgtttttaa aattatttct gtactttagt aaattaaata 123240
ggaacaattt tgtggccatg atagaaaatt tgagatagtt ccagcccgtc tttctgtcct 123300
gctcagtcag tgtttgtgtc agtgtggaga cggggcagtg aattcccgcc agcacccact 123360
gcccctgcta cgccaggctc tgccattccc tgtagactgg gctccttttc ctcattgcca 123420
gtgacaggcg accaccacct ataggcctgg cctcacccag actcaagagc aagtttctct 123480
gtgaaggact tacactaaaa ttagtcttag agattagcaa ccatttcttt ccttccttcc 123540
ttccttcctt tttcttcctt tctttccttt ccttcctttc ctttccctcc ctccctccct 123600
ccatcttcct tccttccttc tctctctcgc tcccattctt tcttcctttc ttctttttct 123660
tttctttttt tttttttttt cctgagatag agtctcactc tgtcacccag gctggaatgc 123720
agtggtgcaa tcacagctca ctacagcctc gacttcctgg gctcaggtga ttctcccacc 123780
tcagcctcct gagtagctgc aactacaggc atgcgccacc acacccagct gatttttttta 123840 tttttagtag agacggggtt ccaccatgtt gctcaggctg gtctcaaact cctggactca 123900
agcaatctgc ccgcctcagc ctcccaaagt gctgggattg caggaacagg ctactgtgcc 123960
cggccaagca accattttct tttcttttct tttttagatg gagtgttgct ctgtgaccca 124020
ggctggagtg caatggcaca atcacgactc actgcaacct ctgccgcctg ggttcaagtg 124080
attctcctgc ctcagcctcc tgagtagctg ggactacagg cgcccaccac cacacctggc 124140
taattttttg tatttttagt agagacgggg tttcactatg ttagccagga tggtcttgat 124200
ctcctgacct catgatccgc ctgctttggc ctcccaaagt gctgggatta caggtgtgag 124260
ccaccacacc tggcccgagc agccattttc aatctttgat tgttatcttt aagcacatgg 124320
ccctgaccag cacttctggg gataatttta aagttaagac cttaggccaa atgcagtggc 124380
tcacgcctgt aatcccagca ctttgggagg ccaaggcagg aggattgctt gagcccaaga 124440
tttcgagatc agactgggca acatagtgag accccatctc tacataaaat ttaaaaatta 124500
gccaggcatg gtggtgtgtg cctgtggtcc cagctactga ggctgaggcg ggaggatcac 124560
ttgagcctgg gaggtcgaga ctgtagtgag ctgtgatcac accagtgcgt gccagcctgg 124620
gtgacagagt gagaccctgc ctttaataat aataaaaaac aggctgggtg cagtggctca 124680
cacttgttat cccagcactt gggaggccga ggcgggcaga tcatgaggtc aggagtttga 124740
gaccagcctg gccaacatag tgaaaccctg tctctactaa aaatgcaaaa aatattagct 124800
gagcgtggtg gcagacgcct gtaatcccag ctacttggga gcctgaggca ggagaatcgc 124860
ttgaacctgg gaggcagagg ttgcagtgag ccgagatcac gccactgcac tccagcctgg 124920
gcgacagtga gagactccgt ctcaaaaata ataataataa taataataat aataataata 124980
ataataataa taataaacaa agtaagaccg tgaagcagta ggacagtagg catggatttg 125040
aaagtaagga agaaaacgta tcagcagaat gctgttgccc ctggggtctt gtgcattcct 125100

-continued tggctgtgtt tctccaggtg cctctgtagt aacacgcctc caccacctcc cctggctcct 125160
aggtgatgca gcatcctaat gaaggcgcac tggtgcttgg cctacacagc aacgtgaagg 125220
atgtctctgt gcctgtggca gaaataaaga tctactccct gtccagccaa cccattgacc 125280
atgaaggaat caaatccaag ctttctggta agaagcatgc agcatctgga gaccctacga 125340
agagggagcc catcctggga aaggtgaaca agacagtgcc tgagatgttc ctgggcaaga 125400
gacctttaga gacccctgaa agtaaaatgt ggcttcggcc ctggccctcc cctccaccct 125460
ggctgtgttt ccacccaaag agaaccattg attccagccc atcgaagttt cttaggccag 125520
atcttcccat tgcaaggtta tcttactcag gtgtctgttg cagatcgttc tcctgatatt 125580
gacaattatt ctgaggaaga ggaagagagt ttctcatcag aacaggaagg cagtgatgat 125640
ccattgcatg ggcaggtaac tttctgtggt ccctcacatg gcgtgtccaa gaagctcctg 125700
gggtttccca ccctcattct gtccctgtac ccacttagga cttgttctac gaagacgaag 125760
atctccggaa agtgaagaag acccggagga aactaacctc aacctctgcc atcacaaggg 125820
tgagcctcaa aggtctgggg agtggttggc taagattttc agtctggggg taggttggca 125880
gcagcatatt caggcctagt ggagacttct taaaatcaac acagggtcat cccttcaacg 125940
attccaatga acgctctata tcctcaccac cgcccaatta gactcactgt tgttgggaac 126000
cacaattact gataagagtg ttatatcctt caggttatcg tcagatagaa aaaaggagga 126060
gaacccttct tgtagaattc agaacagata gtggtccatc agggaacaga ccgcctccca 126120
cccactccag tggctgcttc atgtcacatg ctgtcctctg cagcgagaaa gccagctccc 126180
tctaggagta gcactagttt taatcatgtg ctgaacttag gcagagataa taggctagtc 126240
atggggtgct cctatgaccc tgggcttgct aagctttaat tacatcagat atcgttcctg 126300
ccttaacgga tccataacct tggagaccag gtgccttttg atacttttcc tccataagac 126360
ttcctcaaga gtcactgttt tgatgacatt tgagtcctga actaagaagc taaaaacctg 126420
aattcctagg tggtctttga cagattctgg agtgcctgca tgaagtgtgg gagggccaga 126480
agtgctggga gcatttccga aggggaattc acagctccat ttacccagag gcatcctgat 126540
tctccccagt gcagagctag cctagggacc aaacccctga gagccgagat gcccacccct 126600
tcagggatga aacggaggcc agatcactct cccatcacaa tgaggtgtca ctggacttca 126660
ggtaaatccg tgagactgtg acctggattt cccatccagt cagcaactag ggagcgggag 126720
gactgtttcc ttgtcctcag gtatccacct ctcaattggt gctccaaatg gtccccatga 126780
ggtgtgtcac cagtacccca aatgcttgac ctccattgca ctctggaaat agggagtggc 126840
tgtaggatct ctctctagtc agcccctact gctgaggctt tctttttcct gctctgtaac 126900
cagaaagcgg ccctatttc ttcccaacgg gtgcccccag agcttcataa gtcacctctt 126960
cctacgtggg gtctcttcct tggcatgacc ctggcacatg actggagttc agtgctcctg 127020
ctaatgtata ctcccccaga ggtgtttctt tttaagctgc aggcactttc cagttctatc 127080
ccagagactc agtgacctcc cttagtgcct gtctcctctg tgcatgcgca ttcttctctc 127140
ccaccaagaa cacagatgta cttgaccttc tgtgaacatg tctcatgctg ctctgtcact 127200
gggagctcga cttttttct ctgctgtgaa tgccctttct gccctttctc tgaagaccta 127260
tcagcctcgc aagttcattg ttttcatccc cagatggcga gtctgtcatt caggcaggaa 127320
gtacatacaa ccacaggcta agcatcgtgc ccagagacaa agagataggg cccagtccat 127380
gccatcaagc gcacagtgtc tagtgacacc acacatttca acaaataatt acagcccagt 127440
aggacaggtg ccataagaca gagctttgca atgacaccag gggactgtgg ccacctgtcc 127500

-continued caggagtgcc aggacagctt cccagatgag atgctgagag atgggttttt taaaataaaa 127560
cttcaccaag tggatttggg gaaaattttt attcaaggca gaagataccc tatataaaga 127620
cccagtacag tgctgtggct cacgcctgta atcccagcac tttgggaggc cgaggcaggc 127680
gcatcacaag gtcaggagat cgagaccgtc ctggccaaca tggtgaaacc ccgtctctac 127740
taaaaataca aaaattagct tggtgtggtg gcacgtgcct gtaatcccag ctactcagga 127800
ggctgaggca ggagagtcac ttgaaccagg gaggcagagg ttgcagtgat ccgagatcac 127860
ctcactgcac tccagcctgg caacagagca agactccatc tctaaaaaaa aaaaaaaagg 127920
cccagtacaa cagcatgcag tttttcccag gaactcaaag cagtgagttt ccacttgact 127980
atggggtgtg aagggtcaaa tagagagata aggctagaaa caggcagacc caggcttcgg 128040
acacgtacag gcctgactgc tgagctctgt tcaagtagtg gaggccaatg aagacttcta 128100
gtcggagggt agcatgagca ggtttgcact cggaaggacc actgtgggct gtggagggag 128160
aaagaccaga agcaggtggg cagggtatga gatgtcagct gaaggctgtt gctatgatcc 128220
cagagaggca aggagaaagg cctgactgga aacagtggtg tcacagatgg aaaagggagg 128280
atctggggta gctagaatgg gcctgcgggg agaacgagaa ggagagactc caggcgtaga 128340
tgttggttca ggtgtgttgg cgacatcagt aagaggatcg gggtgcaagg agaagacggg 128400
acgctgcgtt ccaccgtgga ggtggtaagg ctgaggtgcc cgcgctgtgc atgcgcaggt 128460
aggagtcagc agtgggcact gtgaatccga agggcaagag aaagggatga gctggagacc 128520
cacatttggg aggtgttggg gcacaggggg gtggaggacc tggggataga cattccttct 128580
ccccgcagct gcacccaagg cccaggagct acactggaat ttggcctgtc ttcctgacag 128640
gctttgagtg ccaagggcag agaccaagtc ctccagtctt cgtgtcttcc cacagctcgt 128700
catgaaagtg ggctctggtg ggtgtttatt gacttgaatt gaccccaagt ggacgttgct 128760
gagaactgtc atgcgatttg tccctacagc aacctaacat caaacagaag tttgtggccc 128820
tcctgaagcg gtttaaagtt tcagatgagg tatggcctct tactcccaag gttaatggtg 128880
agtagaattc cccgggtttc acccagcatc cctggagtac actctgtatt gccactgaga 128940
gtcaggattc taggattaat attcctgctc cccgtggcat acctggtaga gccctaaggg 129000
agagggtggc taagaaggac ttaagcaagc agaggagaga gaggctatgc acacaacgca 129060
gggcagcaca gctacgcccg acccttggtg atgcgcaagc ctctggcatg cgatacaggg 129120
acagacccag cggatgctgc tgcggttgtc acttaatttc ccctcttatc ccacgggaac 129180
atcagtgagc agcagcttgt gaggtggaaa tgtccttgtt ggtcagccct ggaataacca 129240
ggaatggggc tgctgagaga gaagcagtct tttccctggg ctccgggagg ggcccgtttc 129300
cacaggcctc tcagtgggct aacagaggga taaagatgaa aattgttgag agcgattgct 129360
tcgccttcct gtgagctgta aggagggtag gaagaaccca catgggcgat gggcctcggg 129420
attcctcagc tgtccctcct ggcacagctt cacagtgtgg agcggtggca ggaactgggg 129480
ggaaggtggc ctcaccatgt ccccgccctc aggctggatc atggaaatga cgtgaaggtt 129540
actccagcca gtgtgaagct ctggcatgtc ccttaagcag gactataagg gcagcccagg 129600
agaaaggagc tgctcatcaa ccaaaattgt taatagggat gaccctaaat tcagagactc 129660
ctttttccct gcaggtgggc tttgggctgg agcatgtgtc ccgcgagcag atccgggaag 129720
tggaagagga cttggatgaa ttgtatgaca gtctggagat gtacaacccc agcgacagtg 129780
gccctgagat ggaggagaca gaaagcatcc tcagcacgcc aaagcccaag ctcaagtgag 129840

-continued

```
ccccctctc tgtagctggc ctccagactc tccttcctgg ccatagcagt ctcctgaccc 129900
ctccctcgct gtcccctcta ttaccagaga atcttggtcc ttcatccttt ctgaacctct 129960
ggctgtcttg gagaaggtca ctgttttgcc tctcactgac agaagtccta taggactctc 130020
aggaagtacc ccctctcctg acccgcccct cctcttcacc ctgcacttcc ctgctcaccg 130080
ggcgttctgg acacctgtag cttgttgacc caccctgaat gccagctcca ttcaactctc 130140
ccagcatgct gttctgagcc ctggcagcac tgaccctggc tgtgctcttc accacaggcc 130200
tttctttgag gggatgtcgc agtccagctc ccagacggag attggcagcc tcaacagcaa 130260
aggcagcctc ggaaaagaca ccaccagccc tgtgagcgca accgcgactg cggggcgggg 130320
tgggaccgtg gcatgtcagg gctcgacgct ctggccctct gcatctctga tcagggctca 130380
tgttgtgacc ttagaaaagt ggccccattg gctgggcatg gtggatcaca actgtaatcc 130440
tggcactttg ggaggtggag tcgggcagat catgaggtca agagattgag agcattctgg 130500
ccaacatggt gacaccccat ctctactaaa aatacaaaaa ttacctgggc gtgatggtgt 130560
gcacctgtag tcccagctac tcaggaggat gaggcaggag aatcacttga agccgggagg 130620
cggaggttgc agtgagccaa gattgagcca ctgcactcca gcctggcgac agagcgagat 130680
tccctcaaaa aaaaaaaaaa aagaaaagaa aaaagaaaat ggcctcatct tgtttcagcc 130740
tcagttttcc tcccctcagt ctggctggga gcttagctct ttggggtcat tgctgtgtca 130800
ggctgggttg ttccttttgg tctgtttctg ccatggccca gcgccttccc tctcagaata 130860
catacaatct ccccctctgc tgggcgtggt gactcatgtc tataatccca gctctttggg 130920
aggccagggc gggtggatca cttgagccta ggagttcgaa accagcctga gcaacatggt 130980
gaaagcccat ctctacgaaa aatgcaaaag ttagccaggc atggtggtgc acgtctgtag 131040
acccagctac ttgggaggct gaggcaggag gatcccttga gcccaggagg cagaagctgc 131100
agtgagctgt gatcgcacca ctgctctcca gcctaggtga cagaacaaga ccttatctca 131160
acaaacaaaa acctctccct tcgtgtctgt tctgtggtag ctgagagtgt ggcatggagt 131220
gggcgtttgg ccagtagtga gtggccctgc accagactgg ggaaggagca ggtatggaga 131280
ggaggggagc cactgagacg tgctcaggag gccctagtag gctttattgg gccaagaatc 131340
catagagggg agcagtgccc cgagaaaatt tataatttag tcaagaggtt tccatttttt 131400
ctggtgagca aggggaaaag ggggcatgta ctgtagcagc cggagccacg acctgggcct 131460
tgctccgccc ctcctagaaa ggccctgctc cctcagcaga tcacaggcag gggtgggtgt 131520
gagcctgaag tgacctcagg ccctaggaag ctgctcttcc ttcgtttaca atggaaggca 131580
agtgagtgtt gtcgcgatgt gagtgcccag cttaggattt gccctccaaa gcccagtgtc 131640
ttttctgtag atcaaagaaa caaatccttt aagtcctcct gttcacctgc tttactggca 131700
gatgaagcct actcatggtt caccaggggg aataccaaac tcgccctgca gatcggtagt 131760
aattgtgcgg agatgatagg aaacaggaga ggcctctacc gctgaaaagc acgggtctga 131820
aagggcaggt gcctgtcctg gaaaccacct tctcttgggg catcccctgg ctgcccttct 131880
gcctgttgcc accaggtggg gctctctccc agctcaccgt tcttcctgct taggacagcg 131940
ccccacgtga cgttagtgag gcaatgcatg ggaaactgca gcccaaacag actcctccct 132000
gggagaaacc ccagccctgc ccctgcagac cctgcaccct agacgccgtt ccaggccggg 132060
ttcatgggga tccaagaact gaggagacct cgatttacaa aaaaaaaaaa aaaaaaaaaa 132120
aactctttct aaatttattt tttattttta ttggagtcgg agttttgctc ttatcgccca 132180
ggcaggagtg caatggagcg atctcggctc actgcaactt tcacctcccg ggtgccagcg 132240
```

attctcctgc ctcagcctcc cgagtagctg ggactgcagg cacgtgccac ccacacccgg 132300
ctaatttttg tatttttagt agagatgggg tttctccatg ttggccaggc tggtctcaaa 132360
ctcctgacct caggtgatcc gcccgcctca gcttcccaaa gtgctgggat tagaggcttg 132420
agccgctgtg cccggcctat tttttttttt ttgagatagg gtctcgctgt actccccagg 132480
ctggagtgca gtgtgtaccc agccacctca ctttctttgg tattagtgtt taggatgtgg 132540
cttggagatg catttcctca catggaactg ctgaatggcc ctgctgaatt gacagcatcc 132600
acatgggcaa accctactgg gcaaacccta cccctggcca tgagagctaa attccctctt 132660
aactatatgg gatgactcta gaaagatacc tgggagctgg ctgagggagg actctttctt 132720
agtgttctag gaatgtagag caagtgccct aatataacaa aatgtaacta aatcactaac 132780
tgagacagtg ccccaaaagc agtaagcaga acacctaaca ctgtggatgt tcaataaatg 132840
ttagttacct gacttataaa acttacagaa aaaattactt agacactctg agcctcggtg 132900
cctcatctgt agggttgtgg tgtcggtata ggagcccatt tggctcaaaa gccagttgag 132960
ggcggacacg gtggctcaaa cctgtaatcc cagcactttg ggaggccgag gtgggtggac 133020
cacttgaggt caggagttcg agaccagcct ggccaacatg gcaaaaccct gtttctacta 133080
aaaatacaaa attagccagg catggtgatg cacacctgta atcccagcta ctcgcgtggc 133140
tgaggcagag aattgcttga acctgggaag cagaggttgc attgagccaa gatcccgcca 133200
ctgcactcca gcctgggtaa cagagcaaga ctccatctca aaaaaaaaaa aaaaaaaaaa 133260
gccaggtgag tgtcagcctt tataatatga tggcctaagg gcctctgtca gggcaaaaac 133320
acatttggga cagggtagag cttctgagtt tgagtcttga ctccaccact ccactgactg 133380
tgtgatcttg ggcatgttac cacgcctttg cttcctcatc tacaaggtac gtgttaaagc 133440
tcgtgcctcc caaggtagtg aggagatgga acaggatcat gcacatcaga ctgctgcgtg 133500
gggtgtgcct gattgactta ctgcacacag agcactgctc attgctcacc gactactatt 133560
gcttttatta ttataattcc ttagtgccat ttcagttgtg gactcctaaa attgatagaa 133620
tctagatgtc tttttagtga gtccttcaaa ttctggttcc cttggccacg tttcagactc 133680
actttgctgg ttctgtgctg atatttctat tttgaagagc cccatatgtc tggatgtggg 133740
tgtgaaactt tggaatcctt tggtatgaaa ggcgctttgg gaacagcaga accagactgc 133800
gctcttaaat ggagaacttc tgaatggatt aggaaaaacc acgagattgt gcacctgtag 133860
gcaggtgtgc acgcaccacc tcaacttgtg tcctctcttc cctggtttcc tagcactgtt 133920
atttatttat ttttcttaat cttgcttttt gttccccaca ttttagagga ttcagtttat 133980
cgctagaacc agaaagaatt tctcctgata cgaattattc cagttgttga attttcccaa 134040
ggcttgagca cacaatggca acataatttg gttctccaag ctgataacaa tgagccctga 134100
cagtgcgtca gggcagccac agatgcagac ttccagccag gactgcctgc tgctaagtcg 134160
ctatttccac agcactataa ataatggcat tagagcctag tccttcatga aatgatagcc 134220
tacacattac ccactcttgc ccccttctct ctgacacggg cctacactct tacccttcag 134280
cagctgacat tgtccatgag cacagtggtg cagacttctg ggacctctag tgatacctca 134340
tccatatccc atgccaaaca cttggtcaga cacagctgga gtcctgctgg tgttccaaca 134400
tcttttgggg gaaaaagccc tttagtgttt atagaagcag gaacagaaat gtgatgaaat 134460
tgggaatttg tccccaggag gattgtctgg gacatctgga agagccagta aatagccagc 134520
aggtgtcctc taagcccaat ccaagttaaa gatattatca ggagatggat atgctaatta 134580

-continued ccttgattta atcatttcac agtgtatcca tacatcaaaa catgttgtat actgtaaata 134640
tatacaattt ttatttgtca attatagctt aataaagctg ggaggaataa agatcttaat 134700
aaatgttgca gctttgacat ggaagcaatg ctgtagctgt catagggctt aacaacaagg 134760
cgtgctactt caaaacctcc cagcagacct gtgttatcac ccagttcatt ctctttaaaa 134820
cgcgtttaat taatttgtca tattgagatc gaaaatggag tgaaattatc tctagtctca 134880
ggtctaacca gagcttttcc atgattctag attctattaa tgttggccga ggctgggcgt 134940
ggtggctcac acctgtaatc ccagcacttt gggaggctga ggcaggtgga tcacttgagg 135000
tcaggagttc aagaccagcc tggtcaatca acatggtaaa agctgtctct accaaaaata 135060
caaaaattag gcaggcatgg tggcagacgc ttgtaatcct agctaatcag gaagctgagg 135120
caggaaaatc acttgaaccc gggaggcaga ggttgcagtg agccaagatt gcaccactac 135180
accccagcct gggcaataga gtgagattca gtctcaaaaa aacaacagca acaacaacat 135240
tggctgatca tatagagaag gtgtaaatga gctagctctg caatctggaa gcaacctgtt 135300
ctgtggctgt gagccattac acaagccaaa ccatctgaag atctggggtc ccagagtctg 135360
gctcaggcat gctgagttag tcctgcaaat ggcctggagc aggggttctc aactggggat 135420
gattttgcct cccagacata tggcaatgat tggagacatt tttgtttgtc acaaatgagg 135480
gagtggagag ttgccactac cagcacctag tgagtagagg ccagggatgc tgccagacat 135540
cccacagtac acaggacagg cccccacaat aagaatgagc cagccccaaa tgtcaatcgt 135600
gccaaggtgg aggaaccctg gtttagagtg tgacataggg agcctgctgt ggtgatcctt 135660
gttccatagt ttactaggtg accctgaact tactagcctg atgcttctca gtattatatg 135720
attgactcag agaaaggact ttgagtcatt gggaggaagt gggatatcat ttatattttt 135780
ctgcctccta tggttcccta caagaaacaa aaagattcac taaagccagt accttccctg 135840
catctaagac ctacaaccca cacgtcactg ctggtgactt tgagttgctg tctgcacagc 135900
aagaagcaat attaacaaat acgaaaatct ggttatgtgt ctatatttgc aaaggaaatt 135960
tttaatattt atgagaaatg ctaataagag ttggggacaa atggagaatt aatttacacc 136020
taaatggctt aacattgggt gtctttctgc ttagtatatc ctgttagagg gttttctgga 136080
tgttcccacc aagcaaaaag catttggcta ccatggatgt ctttagtctc aaaatcaaag 136140
acctgaacct agcatactcc tttctctggc aagcaaagga ggcctcccct ctatgtcctt 136200
cctgggcaag tgtattcact ggatccaggg tcaaagactt catggatgca atagcaaagc 136260
catctaaatt ttgagcttct cttgcctagt gacacctcgt ggagtcagaa tttctgggtt 136320
ctgaatctcc gtgttattga cttgatgaca aagataactg atccctccaa aacctggttt 136380
tcacagaaat gtacccgcct ccccggccca cataagaaaa aagccctgaa gattttatga 136440
ggtttgagat taaatgaaag tattttaagc ttcataggga cctagtaaaa caaattaaag 136500
tggtagttat ttggatcagt gataactaat tcttataatt tttgcagatg gaattggctg 136560
ctctagaaaa aattaaatct acttggatta aaaaccaaga tgacagcttg actgaaacag 136620
acactctggt atgtatgggt cagtttcctg tttcagctgt ttcaaatagt gtttgtccct 136680
ttagaaataa cggcagaagg accctcagga ccaccataga aatttcacct aaatctgcag 136740
gcttatgaat gtcctgcact ctctttctcc tgaaatcctt acccgtggaa tgcaacctac 136800
tacctggtgt agacaccagg ttgctctcaa acttagtata ccagaaatgt cctcattctg 136860
ccctttaata agagctgacc aaatgctagc tggggaaact tctcaccatc tgtcaccagc 136920
gttctccctg gaaaatcatc ccttcctcat tggatgttgc tgtttccgtg gccaggcaac 136980
ccacaacatt cagtctctga ctggtactgg tccgtgttct aagaggtgct ggagctgccc 137040
aggagtgcag gcctaagccc cagtgaagtg gaattgagtt ggttgggatg cccagttttt 137100
ttacaggtcg aattgcacaa acatttactg tgcccctgct tgtgctgggc actgaagatg 137160
caaacatgag tgagccacag tttgcatccc ctgtacctcc ggcccaggga ggtacagggg 137220
atgcaaactg gagaagcgac atctgagctg ggctttgcag gttacgtcaa agttcatccc 137280
gtgggaccag aggcaggacc cttgtgggga aggagcagag aactttacag aatgccatct 137340
agggatgagc ctcacggtgg gacctgctgg gagttgacta gaatctgtga aagaattatt 137400
ttagccttat gttttctata gtaaataaga ctacattaaa gatcttatgt atttaggctt 137460
gattcaagat taatttgaaa ctcactaccc taacttacat tttctagttc accagtaatc 137520
tgaataatcc tacttccacc gtggccccac tgtagtccgt actgcacgtg gcaagtacag 137580
tgtggccttt tcaaaattaa attccaattg tgtcacttcc tgattaaaac tcttcagtga 137640
ttggccaaat ctcagcaatt taatgttgag tgagtaaaaa gaagccgaat gccaaaaaat 137700
gcacgccata ggattccagt tctgtgaaac tcacaaacag gcaaaactaa tccatgaggg 137760
tgacgtcagc atacctgtta cccaggggag agggaggggc atcgggaggc ctcaggaatg 137820
ctggaacgtt ctgtcttgat ctggttaatg gtcacctggg ggcatatttg cataaaaatt 137880
caagttgact attctagatt tgtgcttctt actttataga agttatgccc tcagtaaaca 137940
ttttgaaaac ataaagacca ggcagaggca gggaagtagg caggtgtgcg gcctgtattg 138000
gtagcagagt cctccctgag ggctggatca ttagggaggt agtgggccca gggaggaggc 138060
acgggaggtt aatttagaaa ggtggcccag gctgggtcat ggtgggcctc agaggcccca 138120
ctaaagaatc agacttggcc aggtgtggtg gctcacacct gtaatcccag tacttttggg 138180
aggctgaggc aggcacattg tttgagcctg gggattcaag accagcccgg gcaacatgga 138240
aaaacccgtc tctacaaaaa aaaaaaaaaa aaaaaaatag taatacaaaa aaattagcca 138300
ggcatgctga catgcacctg tacttggaag gctgaggtaa gataaccact tgagcccagg 138360
agttcaaggc tgcagtgagc tgagaccatg ccactgcact ccaggctgtg caagagagca 138420
agaccctgtc taaaaaaaat ttaaaaggat gtcaggaatt aggctggggg cggtggttca 138480
tgcctgtaat cccagcactt tgggaggccg aggcgggcgg atcacgaggt caggagatcg 138540
agaccatcct ggctaacacg tctctactaa aaataagccg ggcgtggtgg tgggcgcctg 138600
tagtcccagc aactcgggag gctgaggcag gagaatggca tgaacccagg aggcagagct 138660
tgcagtgagc cgagatcgcg ccactgcact ccagcttggg cgacagagca agactccgtc 138720
tcaaaaataa ataaataaat aaaataagta aataaaataa ataaaaaagg atgtcaggaa 138780
ttcgagacct gcctgaccaa catggagaaa ccccgtctct actaaaaaag aaatacaaaa 138840
ttagccaggc atgatggcac atgcttgtaa tcccagctag tcgggaggct gaagcaggag 138900
aattgcttga acttgggagg cggaggttgc ggtgagccaa ggttgcgcca agattgtgcc 138960
actgcgctcc aacctaggca ataagagcga aagtccatcc caaaaaaaaa aaaagtgatc 139020
tgaggaaagg caaaggcctg ggctcagaag gtgggataga gagggtggat gtgagagtgt 139080
ggccagagcg ggacacacag cagtggcttg gggatgagga aggaagggag aatctcaacg 139140
gagatgcagg tggctttggc caaggtaagg aatggggcta aaaaaaaaaa aaaaaaagaa 139200
aaaaaaaaaa ggaatggggc tatggccctc cctgctctcc tagaccagat aaggtccggt 139260
cagggcacca gggagatgca tctaggggtc ccctcttcac tcctggagac agcagatcat 139320

-continued cagtccactc ttcttgtgcc agcaggtcgt ttgtaactgg atatttactg gattgcagca 139380
tatggtgccc acacggggtg tactcagtca cccgtgaaca gtggcgattt tccttcggct 139440
gaggcaggag ctttaggacc acttgctttc aggaaaagaa aatgagtaac tctctcttca 139500
ggatggtgat ggggcctggc cagtccaagg aggctcctgg gtggtcactg agtgggaggt 139560
catcttcact gtttcctctc ctccatggta ggaaatcact gaccaggaca tgtttggaga 139620
tgccagcacg agtctggttg tgccggagaa agtcaaaact cccatgaagt ccagtaaaac 139680
ggatctccag ggctctgcct cccccaggta ctgcagatgg aaaggaagca gggggtacag 139740
cctgcagctg tgcttagcat gggcttcagg gctgagggaa agcggggctg gcagcagctt 139800
tggggttgga ggggctattt caccagcctt tttccacctc cctggcagca aagtggaggg 139860
ggtgcacaca ccccggcaga agaggagcac gcccctgaag gagcggcagc tctccaagcc 139920
cctaagtgag aggaccaaca gttccgacag cgagcgctcc ccagatctgg gccacagcac 139980
gcaggtactt ctgggtgccc ccaaaacacc aggaccctct gagattccct gaacttcagg 140040
ctctgttttg ttggcttcct tggacagtta gttggagaga agaggaatac ttggaaatgc 140100
tctgaacaaa aactcttgaa gaaagactaa attagagagg tctcctatat tccttgctta 140160
ctgccagtgt ggaactggct tccacgctga cctctagggc gcaggcaggg gagccaaaaa 140220
cgctgtgtgg tcgtggcctg ccacggctgc gagtgtcgat tccacaccac cggtgtctct 140280
gcctccatca gacgtcagtc tggagattgt gccgtgaatc cactgttgca gaggacagca 140340
gcctctggat ctcatgggac atcctgaccc gagctcccaa cctgagtatt gctgtgggcg 140400
gtcatcgtgc tttcaagccg ggaagccaac aatattaaac tgtttcaatg gaaggacccg 140460
agagtgggct ggagaagaag tcagaagaac tgggcctcag gaatcgtgtt ctccttttga 140520
aggcctgtgg tgtcagagat ctgggacagg gattttcccg gcacacctta cacagttcca 140580
gttctgctag ggttaaacag ccagcctgtt cattcccctg ataacttacc aagtgcattg 140640
tcagtgtggc ctcctgagct ccatgctatt acatggctga aaatgaactt gagactagaa 140700
tagcccagtg cctggggtga ggtattgtcc ttcttgttaa tcactgttcc tgaaatacct 140760
tttgttccct cagacagcag gtacccacac agcactcatt gccactctca ttatttctct 140820
ccccactgcc ctcgtttctg tttctctgag cacctgctgg ccgccctctg cctctccctt 140880
cctggttctt acgctgctgc ccctcctgcc acccacaccg tttcccatcc gcgaggcttg 140940
ctgcacctcc atcctctcca cctgccctgg caggacaacc gctgtggctt tgttcctcat 141000
ctccatgtgt cctctaagga ctcgctttgc tgcttctttc tcctcctttc catcgtggtc 141060
tggccagtgg gagactgagt ctccctccca aagtcctgat atctgttctc tctaacaccc 141120
ctgctccaga gactccccat gcaccagtcc agcagccctg tcctcaggct ccccagggac 141180
tccctaacaa gagacacttt cttttgttcc tgcagattcc aagaaaggtg gtgtatgacc 141240
agctcaatca gatcctggtg tcagatgcag ccctcccaga aaatgtcatt ctggtgaaca 141300
ccactgactg gcagggccag gtaagtgctg aaactgcgag gccatgtggg gtcctggagg 141360
gcaggcaatg cccggttgca ttgtcagtgt ggcctccata ctattgcgtg gggaggtggg 141420
gaactcaccc ctccatcagc ccccacctgc tctgaactga gcccagaact ctgagttcta 141480
gtccaacttc tgtcattatc caacttgtgg gatcttaaat cactaagttt gctctacctc 141540
agcttcctca tacgttaaaa aacaaacaaa caaaaagcaa cagtaattcc tccagggcgc 141600
cacatgcgtc aggcagcata gtggaacgga ggcctgtaga gaagcacccg gctgtaacct 141660
ccagggctgc cccatgaagg caggtcagca aggcagagca tccctgcctg ctccctcacc 141720

```
gctgtccacc tggcttagac actggtgccg gggacacctg gagtgtccta gcatgtgaaa 141780
ccccctaagg cttcccatct ctcacactct gcgtgtctcg tgggtcggcc ccaccccctc 141840
cttactggca gtccggagac ctggctgcct ttgcccagct tcggtctgaa ctgcagagga 141900
caggggccct gcagctcggt ctgggtctca cttgcctctt ggcccttgtg aaggagtgat 141960
gtgttctcac ctgtgtccct gctctcctcc ctccctatcc cagtatgtgg ctgagctgct 142020
ccaggaccag cggaagcctg tggtgtgcac ctgctccacc gtggaggtcc aggccgtgct 142080
gtccgccctg ctcacccgga tccagcgcta gtaagggctc tggcctccct tctcctgccc 142140
ttagagattc cctctgacct catcttccaa ccctgacttc taagcaatga tagaccctcc 142200
tggcctcatc agaccaagaa tttgcagagg ggcgtatgtt tagggggggtg gcggcagcag 142260
gctgtagggc ttgaggcccc ggcagacccc agaggatcgg gggtggaaat atcaattcct 142320
gtgctccctg cctccctgcc tggacccccg ccatgccttg acttgcttta tcctcttaaa 142380
cccatgatga aggagaggac acactggttt taaaaagatc ttttattcct tccatctgca 142440
acatgctgct agacactcag gagtcagtgc ttcccctacc ctcagggcct tcttaaaagg 142500
cccaagtccc ttgcccttgt gaaagagaac tatggattcc aggcctgggg gcacacaccc 142560
tgcgggcatc ccaggcacac tgccgagtcc tacgttagcc tcagctgttc cgtctgcttc 142620
atgggcaatg ccctctgacc ctggattttt ctcttggttg tgaaagcact gtggcttatt 142680
ccctgtatga tcctctctgt tttattttgt ggattggttt gcttttcccc tgtgggttgt 142740
tgagatcaca gaaagtcagc tctgggcctc ccccgggcag gatcctggca cccctgagca 142800
ctgctatgac gctccccttc ctccccagct gcaactgcaa ctcttccatg ccgaggccag 142860
tgaaggtggc tgctgtggga ggccagagct acctgagctc catcctcagg ttctttgtca 142920
agtccctggc caacaagacc tccgactggc ttggctacat gcgcttcctc atcatccccc 142980
tcggtaaaga cgggaggcac caggagggcg tcgggcatga gggttccata gacagatgcc 143040
tcatctggaa caggacggtg gggttggggc ctaggaaggg acagtcaagg agaccaaggc 143100
cgtggccagg gacagctgct cccacactgt ctcatctcct gacgaattca ccacctctgg 143160
ttttccatct accaggttct caccctgtgg ccaaatactt ggggtcagtc gacagtaaat 143220
acagtagttc cttcctggat tctggttgga gagatctgtt cagtcgctcg gagccaccag 143280
tgtcaggtaa tggccccgtg taaggagctt actcccaccc ccggggtcca caggtgccag 143340
cctggctgca gaaggaggct gaggtcatgc tgctttcctc cctgcagctc tcaccttccc 143400
ggtcactctg tccattcatt tttccataag tgtttattaa gcggaggctc actgtgcaca 143460
gcccctccac tctgccagtt ttcatcctct gctatttgct ctgctcctgt tcatctggaa 143520
ggaacaaggg ccatgctggc atagtggcca gggcgtctct agttgtagag atgaaataca 143580
aggagcagag aatagcagtc aagtgacaaa gcagtcactt gataaatgaa tagcacccca 143640
ccaaccaggt gctttcttga atatcaaata aaggtggcag aggtcaaggg cacggtggat 143700
cacttgaacc caggagttca agaccagcct gggcaacata gcaagaccct gtctctacaa 143760
aaatacaaaa attagctggg tatgttggtg tgcacctgta gtcccagcta ctcgggaggc 143820
tgaggtggga gaattgcttg agaccagaag gttgaggctg cagtgtgatc atgccactgc 143880
actccagctg ggcagcagag gtgaaactcc gtctcaaaag taaaataaaa taaaaataaa 143940
aaaataaagg tggcagggat cagaaagagg ttgagctctt ccaggctgag aggtagtgag 144000
ggcctggcgc aactgagaag gaggtgatgg caaaagtctg tggggtgagg ctcctccagg 144060
```

ccaccggatg ggtatgtgca aggacaggca ggagcaagtg gacatgagaa gaagggtgtg 144120
cgtggcccaa gaaagagcag ggctttgagg aactgcaaag attggaaggg agaggaccat 144180
ccttgggctc atgattcctt caaaccagaa ggaccgtaga gccccatcct tcactcaact 144240
cctagagtct gacgggtctc aggaagggat ccctctccga gagggtctgc aggtttgcca 144300
gctgaagtca gtaggcagtt agtgatctct tggcttttct gcagagcaac tggacgtggc 144360
agggcgggtg atgcagtacg tcaacggggc agccacgaca caccagcttc ccgtggccga 144420
agccatgctg acttgccggc ataagttgta agtttgactt tgaggggttt cttaaaaata 144480
ggttgggtgg gttagaggaa tcttgagtct tccttgcttt ctcacatttt ccttctccac 144540
atgctatatt ccttcatagg aacccaaaag gatatgagtg gtttttacca ccacctcccc 144600
agcactcctt ccttgcccaa ggcctcccac ccataggagc ctgagttcat cagtttcctt 144660
tcctgccctt cagtataaag cagcccatcc tcatagctgg aactcagacg tgggaagcag 144720
ggagcgtagc ttgcatgatc aggtcatttg ccctcatttt gtgagctcca catgcacagc 144780
aagtcccaga ccttccccat gccaccccag gatgtgatgg gcagaggcag cccagcatcc 144840
tggactctgc tgcagccaca gtgagatagg aaaggccaat tccccagcac tcctccctgt 144900
ctctcctact aactatgaag ctctcctgtg tctcccaaca gccctgatga agactcctat 144960
cagaagttta ttcccttcat tggcgtgagt actgactccc tctgcttggc accccacccg 145020
ttctcctggt cttcctgttc cccccttacac aggaaaacaa aagattcatc tagaacagtg 145080
gttctccaga cactggagat tttgcctcca gggactacct ggcagtgtct ggagacgtgt 145140
ttggttgtta tacgggggggt acccagtggg tggaggccag ggatgcagct ggtcatcctc 145200
cagtgcacag gaggtcccgc agcagagaat ggcttggccc caagtgtcag tagtgcagag 145260
gtggagaaac cctgggccgg acatggattg ggctgtccct tttagtgtcc gccttttcca 145320
aatcacgaac tgttcctggg tccatcactg atgtctcctg tttattacac caggccctga 145380
cctcgctgcc ttcacccggg gagtgatgtc cagacgtggc tcacgggaaa gggagctgct 145440
ttggtagtag tggaaggcag cattcagaaa agtctgaaaa cagatacttc tgtcttcatg 145500
gttggatagg ccactgagag gaaggctttc ttctttcctt ttctatttaa ccaaggagaa 145560
atctctatac tagtaaactt tgaaagtcaa ggaagaaccc cgtggatgtc tcatggcagg 145620
tgcattgccg gctgtctgtt catcagcagc tgggccacag gctcagcctg acctagggag 145680
gggtccgggg gagctgtgca gtcctgccag aggccagagc atggcaccgg agcaggactg 145740
aaaactccga tttccactta aaagagcttt acatttccct tcgaaaccag cttctatctt 145800
tttttattat ttttttttt tatgagatgg agtctgactc tgttgcccat gctggagtgc 145860
aatggcacaa tctcagctca ctgcaacctc tgcctcctgg gttcaagtga tcctcctgcc 145920
tcagcctcct gagtagctgg gaccataggt acatgccacc acgcctggct aattttttttt 145980 tgagacagag tctcactctg ttgccaggcg ggagtgcagt ggcgcgatct cgactcactg 146040
caacctccgc ctcccaggtt caagtgattc tcctgcctca gcctcccgag tagctgggat 146100
tacaggcacg tgccaccaca cccagctaat ttttgtattt ttagtagaga cggggtttca 146160
ccatgttggc caggatggtc tcgatctctt gacctcgtga tccggctgcc ttggcctccc 146220
aaagtgctgg gattacaggc ttgagcccct gtgcacggca tgcccggcta atttttgtat 146280
ttttctgctg agatggcatt tcgccatggt gcccaggctg gtctcaaact cttggactca 146340
ggagatccac ctgcctcagc ctcccaaagt gctgggatta caggcgtgag ccaccatgcc 146400
ccaccagctt gtatcttttt ttgtaatttc cttgaggctc cctcgtagct tctagacagg 146460
gaggggctca tgtggatgag ggggcctagc tccctgctct ccctgctttc tgcgcatcca 146520
agatgtgggt gtcttgagtg atctcaggag atacctgagc tggggaaatc cagcagccct 146580
ttctcgtgcc ttgcagagcc tcctgtcctg cagtctagcc agtccccggt tagcccctgg 146640
gctgctccca tagccacatt acaggcccca agaccatggc ccatagctgt ggctggtggt 146700
ttgacacatc ttcgtggagc tgtgagttgc tgctcactca ggcctcgcaa ccgagagaga 146760
cagagagata acaaatttaa aacaaattaa aaaccaaaag agctagcaac ctcaccaaat 146820
gccaggcaaa caaggagaga aggggagttg tatccaggaa gccccagagt ggcaatttgt 146880
tcctctctgg gaatcaaaag aagggcgcat agagaatcgg gacagacttc agcaaacaca 146940
gccttgctgt cgcggcagcc tccaggcaac cacctgcagg cctgtgcggt agatttcgcc 147000
ccatcagggt ccagccctct ggactcccag cccagctgcc tctttgccta ggcctgggcc 147060
caggtgatag ggcccaggac tttacctgtc acttcagacc acagcctgga tgctcaccta 147120
gtctgtggct gtgttctttt ctagccactg gagggcccag gctgtccttt ccagaattct 147180
ctatggagaa ttgaaaattc ctaaagaacc cccccacccc cattcagtac acttccagat 147240
tccaggaaga ccagagagga gaaggctggt gtccacacct tagcacgtcc acttggcttt 147300
agactctccc acctggcaga gacagagcca tcttcctagg ccctctgccc acaggacctt 147360
agagaaacaa catcaggaca tcacagtgat tcctgccttc agccctttat ccccagagaa 147420
gagctgcaaa gtctcgcatg ccccatctca ttgttgcaac taggttttgt tgttttttgt 147480
ttgtttgttt ctacagctgg gctgctccag atttgcaaag attttttat ttacttattt 147540 atttgatgta tttatttatt ttgagatgga gtctcgctct gtcgcccagg ctggagtgca 147600
gtggcgccat ctcagctcac tgaaacctcc gcctctcagg ttcaagcgat tctcctatct 147660
cagcctccca aagtgctggg attacaggca taagccacca cgcccagccc agatttgcaa 147720
agattttaaa gtcggcaata aaataatgtg tagtgatggc tcttgtgcca ccaatgtgtt 147780
tctggttgga tcagaacatg cctgctttaa caggaggatc taatgagtgc ctcttctctc 147840
cttgcaggtg gtgaaggtgg gtctggttga agactctccc tccacagcag gtgaggctgg 147900
ggctcccttg ttctgtggag tgaggctggt gccctccctg tcttccctct agtccagcag 147960
gccagaagtt aagctctgga tgccctgagg gaagtcagag cttgagcagg aagcctatgg 148020
gcgccctcac tcccctgctg cggtggtggc tgggggaggt ggaaggagcc tggggccaaa 148080
ggaggaaagc aggccacagg atgggaggaa ccccggctcc ttgccaccac caagtcagag 148140
atagcttcct ctggccaact gtgtttgtcg tttgtcccct gacaggcgat ggggacgatt 148200
ctcctgtggt cagccttact gtgccctcca catcaccacc ctccagctcg ggcctgagcc 148260
gagacgccac ggccacccct ccctcctccc catctatgag cagcgccctg gccatcgtgg 148320
ggtaaggctc ctgcccgtac ctgtcctgcc atgccctcca tcaggcccac ccggctgatt 148380
ccagtgacag gcgcatgggc ttagaaggta gccacaggaa gccgggcgtg gtagtgcaca 148440
cctgtggtcc tagctactca ggctgaggca ggaggattgc ttgagcccag gaatttgagg 148500
ctgcagtgag ccatgactgc gccactgcac tgtagcctgt gtgacagcaa gaccctgtct 148560
ctcaaaaaaa aacccaaaac actaaagtta gaattcagag acatatcact agccggcctg 148620
gtcatgggag gacactttct gccctgtttc acagtattgg gttgaatgag acaatgttgg 148680
cagaggcctg tgaagtgctg tgcaagtgtc ttgttatggg acctcccagg tgttgttatg 148740
ggacctccca ggtgcaagaa agagcatggc acttgggaaa taaaacacac gtgggtttga 148800
gtggttctgt cttgtctctg cactgcctta gcttagacaa gttactgaac ttcaatttca 148860
tctaatgaaa agaggtgaag tggccacctt gcaggactgt ggagcaggtt acataagaac 148920
gtggaaacca ggcctcatcc tgtagttcca gccactccgg aggccaaggc cggaggatcg 148980
cttgagccca ggagttcaaa gctaggcctg ggccacgtag tgacgtggat tgggctgttc 149040
tttctagtgt cttcctttt tcttcttttt tagggacgtg gattgtctcc tttggtgaca 149100
gtcagagggc ctctctaaag gaaacaatcc acgtctctaa aaaagagaaa aagaacatgc 149160
gtgtcagtgc ctggcacagt gaggcagccc tgctgaggcg ctagagctgg agccggcgcg 149220
ggagcaagcg gcggagctcg ggttcaggct gaatctctga gaccactgga agcagtgata 149280
tagcaggagg ccgtgtcttt aggatctcaa gtatctacag tttagatcaa gggtccagca 149340
gcagggggca gagagagggt ggaggggtgg gctcctgaca agaaggccga ggtgaggaga 149400
gcaggcgtgg tcagcgctgg gaaggagcag cctgccttcc cttcccccat ttcgctgcct 149460
tccgccttcg cctcttccct ttccttgtag caacagcgag gatggcattg gccggtggct 149520
tcccccaaag tgctagtaat gtgttgggtg gcacgaagcc tgccccggag ctagaatccc 149580
agtccctggt ctccctcagc ctctgctcct cggggcactt cccttcaggg tcttctggag 149640
ggaacagtag aggaaaggag gaagtaccca cgcagccaag ttctgccctg gggacctcag 149700
gttcctggcc tcctggaggc gttttctctc atctcacccc acagcggaag ggtttctgtc 149760
cagcatgggt ttggggagcc ttggcaccaa ccctttcctc tacctccttt cccttccaag 149820
ttaatcttgt tttttaatgg aacctccaaa atgaggcaga aagagaaaag tcagatgact 149880
ttcctagcct gtgtacctat tgtgtctgac acctcctttc aagacatacc agcccttctc 149940
ccgggagcta aaattatcgc tgagctaaga gtgccatgaa aaggagaaag ctgcaggtcg 150000
ggtggcacca gctgctgtcc tgaggctgca ctggagccgc ccgcaggggc ttctgccggg 150060
ctcaggcctt ctctccagct cgaggctcag tttggcccag gctttgcctg ctgggcgtgt 150120
atgtgtgtgt gtgtgtgtta tatgtgtgta tatgtgtgtg cacgcatgca cttatgtaca 150180
cacacacttt cttccttcat aaagcttcct tctctgctgc ccttgtcatc ctgtgaagat 150240
tttatttggt ttccttttcg tgacttgggc ctttattctc cccagctttg ttctcagatc 150300
agcctgattc tcctctccta catgagctgc tctgtgtggc tggagggaac agagctgcag 150360
ccttcctcag cctgccctcc cggggactgg catggcccct accccatcag gcctatgtag 150420
ttgggagctg aaggcagagc tgacctctcc tctttgttcc ctttcctcag gagccctaat 150480
agcccatatg gggacgtgat tggcctccag gtggactact ggctgggcca ccccggggag 150540
cggaggaggg aaggcgacaa gagggacgcc agctcgaaga acaccctcaa gagtgtcttc 150600
cgctcagtgc aggtgtcccg cctgccccat agtggggagg cccagctttc tggcaccatg 150660
gccatgactg tggtcaccaa agaaaagaac aagaaaggta agtacccccca aggccgggga 150720 agaccatggg ccaccaggcc tcccgtctcg tctctcaggg cctgggaata aatctgcttt 150780
tgggatattt gggatgaaga agcatcccat ggtctggcat ggggtgcaga gggggcagtc 150840
ccacctcccc tcgagggaca aggccattcc ttctgtcatg caggaaaccg aggctgcaga 150900
gagtcgcttg gtcactctct gctgagctcc agtactttag gggctgaggc agctgccact 150960
gtgtaatgaa gggggccttt ctggccactg ctgtccggga tggactgcag acagggagag 151020
gcctctctat atcacagctc caggtccctg tgacgcagga gtagagaact tgcacccagc 151080
cctggaggcc tctccaaaga ggcctcatga gcaaaaggac gtggttgtgt tttcaggatt 151140
aaggggcata cagtccattc tggatagcag gggtagctta aggagctgga ggggagttgg 151200
agctggcccg gctcctgtgc gtgggagtga ggcaggaacc cccatggctg ggccagtgct 151260
gcggcagcgc ctgccaccgt tggtgccagc tggggacccg caactggtag tgcacctgca 151320
gcactggcat gaccccaacc ccgcctcctt tgggtgctgc aaagcagctg tgcctatttc 151380
tgtgtgtgac tcccctctgc agagttcccc tgggggtca ggcatggggc tgtgccaggc 151440
ccacagccaa aacccacggc ctgcagcaca gaaacttgca aggggaagct gcctgctcag 151500
cagtgacctc cctgcccttg cttcctttct ggagtgggag tggaacaggg agcactcccc 151560
ggcatcccca ggacagcgtg aggacaaact catgctgcac tggctcctgc atagagcatg 151620
cgcctgatag ggaggcaggc ccctgcccca caggctgcct agaacgttcc agctggaaag 151680
gacttcagag accatctgga ccaaggtctt cactgaacag gcgaagatat cgagccccag 151740
ggggagaagt gggaccttag ccaaagtcac cagcccagtg ctgggactga gtcaggaacc 151800
tgaagatcct gacccacagc ccagtgccag ggaggagggg ttggtttgca gatcacctcc 151860
cctcgccaca ggaagaaggg gacagtcggc tggggaggag aggggtggcg gcttccccag 151920
gggctgggac acaggtggcc ttgcttgctt tccagttccc accatcttcc tgagcaagaa 151980
accccgagaa aaggaggtgg attctaagag ccaggtcatt gaaggcatca gccgcctcat 152040
ctgctcagcc aagcagcagc agactatgct gagaggtgcg agggcaggca gggccgggag 152100
gagggcaaga aagggactgg agagggaggc aggcaatggc ctttcccaag gggccctggg 152160
gagatggcct gagcagtctg gtcacccctc ctctcctgtc accccctagtg tccatcgatg 152220
gggtcgagtg gagtgacatc aagttcttcc agctggcagc ccagtggccc acccatgtca 152280
agcactttcc agtgggactc ttcagtggca gcaaggccac ctgaggccct gtctcccagc 152340
cactttccct cctggcactg ccaccagcct caccgcctgc gggcaggggg aggccagcag 152400
gcccgggccc agcacccctt ccctggcacc agggtctgcc tctcactcgc ccaggtcccg 152460
aaggacactg ccacagggac gccttccctc ccctcccctc cagcccaccc ctgcacagcc 152520
cctcctcctt cccgcttttc cccttctccc tcctgctcca ggcccaaggc gtgttggttt 152580
tgccttctgg tgcccatagt cccctggact gagtccccca ggccttcctt cacccgactt 152640
ccaaactctt ccttgtggta tcagtttcct tctcggaaat gagaaagctg gaatcctggt 152700
ccccagcagg agagcctagt cctcccccag cccctccagc caccagggtg tcctctagga 152760
tgcagctgcc agatccactc actctgctgc ctccagcagg acccaaggcc actttcaact 152820
cttatggggt tctccacctg ccccagagct tctcaaggga gggtaagggg gcaccctgag 152880
cccacaggac ccctacttca cagctcacag gggcaggagg cagctcccct gcctccagga 152940
ccctgttgct atggtgacac agcgtttcta ggacagaggg gcctcccagt ctcccccccac 153000
cacccgtgca cgacttcctc accacccccca ggttccctgc agatgtcgtg tgtgtcctga 153060
gtgtttcttt ggttctttgc acgccaagtc tcttggttgt accatgtgac acaccctgtg 153120
cactggtcgc tgtcttcgtg gcttccaccc ttgttaatga tgctcctgcc tctgcctccc 153180
agcccctcac ccagcacagc tctgcctgga cttggagaga tgggaggcag acccccacca 153240
ccatacatgc tgtctgtggc ccctcagaca ttctgtttca tctcccattc atctccctcc 153300
tcccaccgtg tcagtttttc tgcctttccc tgctctgttc ttccccctcc ttaggcccca 153360
gcctgggccc agacccatcc tcccagccag gtttccctcc agcaggctcc ttccctccct 153420
gtcacctccc tctcaccaac ccggggtctg agcccctcat tcctgaccgt ccgtgttctc 153480
aggagtggtt gaggacacag ggccccagcc cagccctctg caccccccag cccggccatc 153540
tgcgccccac agcccctttg gagcttttct cttgtcctct cactccttcc cagaagtttt 153600
tgcacagaac ttcattttga aagtgttttt ctcattctcc atacctcccc caagctctcc 153660
tccagccctt cccagggctc agccctgctg tcctgagcgt ctcctgggcc agagagagga 153720
gatgggggtg ggagggactg agttgatgtt gggtttttca ttcaataaat tggtgatttc 153780
ttaccgactg ccttgggctt ctatgccccc tcactgtgcc acaggagctg cccaacccct 153840
tttccacagt gcagcccaac tccagtgaaa atccaccagg aacgtaggtg gaaagaagcg 153900
tactcccatg ttctcaatca tggaaacagg catgaaggtg tctcacctgg catgaggcag 153960
gcagaggtcg gaaacaggaa agatgtcatt tccacaccaa aagcccgttt ttccccagga 154020
cccaccatcc ccaaatccac ctcccaaggc agtgacgtgt tgagtgtggc ttccccatct 154080
tctgatcaaa ggtcagaact tagcttctct cccctgctcc aggttggtga agtccgagcc 154140
agtggggtct ttgcctctgc aggtggaggg aatagggctg agggacatct gtggagttcc 154200
ttttcctgcc cgcccttgac ttagagatgg aaagcagtgg tagccactgt cccctgggtg 154260
cccggttttt ccactagctt ccaagacagg cctgcacaca cgaagaagtg tgtgccttcc 154320
ccatgaagaa gtgcccagag gtggccaggc acagtggctc acgcctgtaa tcccagcact 154380
ttgggaggcc aaggcaggcg ttttgcccga actcaggagt ttgagaccag cctgggcaat 154440
gtggcgaaac cccgtctcta ctaaaaaata taaaaaattg gctgggtgcg gtggctcaca 154500
cctgtaatcc cagcactttg ggaggctgag gtgggtggat catgaggtca ggagattaag 154560
accatcctgg ccaacatggt gaaaccccgt ccctactaaa aatacaaaga ttagctgggt 154620
gtggtggcac gtgcctgtaa tcccagctac tcaggaggct gaggcaggag aatcacttga 154680
actcaggagg tggaggttgc agtgagccga gatcgcgcca ctgtactcca gcctggcgac 154740
acagcgagac tccgtctcaa aaaaaaaaaa aaaatttttg ccgggcgtgg tggtatgtgc 154800
ctgtaatctc agctactcag gaggctgagg cacgagaatc acttgaaccc gggaggcgga 154860
ggttgcagtg agctgagatc gtgccaccgc actccagcct ggacgacaga atgagactct 154920
gtctcaaaaa agagaagtgt ccagaggtga aggcttgcag gagaggcagc gcttggcatc 154980
cttgccctac aggtatagcc ccagaggagt ggatggccat ccagagcttg ctgtcactgg 155040
cctcagtctt gggttcccca agccctgtgc ccagacgacc tcacatagag aggcttgggg 155100
acccagctgt gtggccctgc gcaaactctc tgagcctaga aaatgaaaat catacctgcc 155160
ttctaaatga ggtgatagcg gggctggtga gaggaaaggc caggagaagc aaatcatacc 155220
tagtgtgacc tggatctagg gtgtgagtgt ggctgcagag cagggtgaag tgcccacgag 155280
gacttcccgg agcacagcca ggcgagggct gcagggcagg agctgtgcag agctgggggc 155340
cagggagttc cagtggaggg ggtgggacaa gtagacttgg atcccagctt ctggccccct 155400
taggttctgg cttagagcta ggagagaggg tgaagggtga actctcagcc cgtctgcatc 155460
tgacaccata tcctcagcct ccccttctgt ggcaataaat gccccaccct gctcccatcc 155520
tcggggccca tccctcttca ctccttgagg gcttttctcc tacagtcgcc ctctctcctg 155580
cactgcgggt tctcccctct gccaggactt tccacccact tacatgcatc ccaagtgggt 155640
atagctcaat atcaaagacc agagacttcc agattctctt cagctgccat gccttgtctc 155700
tgctccccttagagcaaaac tcttccaaag agctgtgtgt gttccccgtc tccacttctg 155760
cccactccct tccagttttt tcctcacaat cccaccaaaa gtttcctttc cacagttgcc 155820
agtgacctgg gttgcccagt cctatcagta gcattggatg caaataatca cccgcttgag 155880
tctttccacc tggcctgtgg acagctctgt gctctcctct cacctccctg gcctctcctt 155940
tttggcctcc cttgctatgg tgtcctcagc ttcccagcct caaaaccctg gaggactcgg 156000
ggctccagcc tctaatatag cctcctctct ccccacactc agccctaaag ggagctcact 156060
cggccccatg gtgtgaaatg tgctcccctg gggagacttc cctcctagta aatgcaaact 156120
cggttcttca gttccgaggc cgaaaactgg ggaatcctcc tcgattcctg tttctcttgt 156180
acccaccatc taatccatga gcaaatcctc caggcttatc ctgacagtgc cttgcccctt 156240
cctctactgc gattatctct tgtctggata ttgcaatagg ctcctaatta tccctgctcc 156300
caccctcttc tccctgtagc ctgttctcca ctcaatagcc agagattttt cagagctgag 156360
cagatcgtgt tggattgctg atccaaactg tgcagagtgt cccacctacc taggtgtgta 156420
agctgaagcc ttacctgtga ggggcccaca tggtctgatc tcccaggagc tgctggatct 156480
taattcctct tacgcttccc ctcctcactg gcctctcaac attcctcaaa caccactcag 156540
cctcagggcc tttgcacgga cctttggtcc tgtccatcct gctgctgccc tcaggcccgt 156600
gtggcttgct ccatcattca ggtcttggct gaaatgtcac ctcaggaggc cttcccttct 156660
ccaacccctc ttttttttt ttcttactca tatttcccac tccttggcat taattattca 156720
tttgtctctc ccacaagaat gcaagctcca agaaaagagg aaatgttttt ccctgttgta 156780
tccttggcac ccaaaatact gcttggccca tcacaggtgc acaataaata ctcgtttgca 156840
gaatgaagtt ccctcttgct gctggaattg ggttccaaat ccagatgtgc tactcaagac 156900
attttaactg atgccttagc ccaaaagaca cctgggtttt ctcataggct cagaagtaag 156960
aagatagact cctaccccgg gcaaagaaga ggaaatcagc tgtgtaggga cagtttggag 157020
cacaaggcaa ctcaggtgga aggtgctgac tcagaccctg aagcagctgt gcccagtcac 157080
caggagttaa ggctggacca gagcagagct gcccaaggtc cgccagagac taaaggcttt 157140
ttgatgcaga aagtggaaga gcctctatct aacctgcacg ccaactccag actggtttta 157200
tttttaagta aactatttta gaataccttt agatttatgg aaaagttgca aaaatagtag 157260
aaagagtggc tatataccgc cctgccagtt tcccttactg ttaacatgtt acattcatgt 157320
gcatttgtca taactagtga gtcaatcgtg atgcacgatt attaactaaa gtccctattt 157380
tggccgggca cggtggttca ctcccataat cacagcactt ggggaggctg aagcaggtgg 157440
atcatctgag gtcaggagtt caagaccagc ctagccaatg tggtgaaacc ccatctctac 157500
taaaaataca aaaattagcc aggcgtggtg ggcacctgta atcgcagcta ctcgggaggc 157560
tgaggcaaga aaatcgcttg aacccgggag gcgtaggttg cagtgagcca agattgcacc 157620
actgcactcc aacctgggcg acagagtgag actctttctc aaataaataa ataaatgtcc 157680
ctattttatg catgtcctta gtttttccct aatgtccttt ctccatttca gactcccacc 157740
cagaatgcca cactacgttt ggtcattctg tcttcttttt tgttgttgat tttagagacc 157800
aggtcttgct ctgttgccca ggctggagtg cagtggtgcc aacctagttc actgcagcct 157860
ggaactcctg ggctcaagcc attctcctac ctcagccttc tgggtatctg ggactacagg 157920
catgtgtcat tacacctggc tctttgtttt gttttgtttt ctttcgtttt ttttggtaga 157980
gatagggtct tgaactgacc tcagttatcg atcctcctac cttgcctccc aaagtgctag 158040
gattacaggc gtgaaccaac acatccagcc cattctgcct tcttaggatc ctttgggctg 158100
tgacattttc ttagactttt tgatctctat ttttgatgac cttgacagtt ttgaggagta 158160
ttggtcaggc attttgtaga atgtccctca gttggggatt gtctgatgtt cttctcgtgg 158220
ctggatggag gttataggtt gtggggagga agacctcaaa ggtgaatgcc cttctcagcg 158280
cagcctgtga agggcacatg ccgtcaacat gacatcatgg atgaggttga cctgggctcc 158340
tcactgtaaa gtcccacaca cctgctccca tgctgttctc tttggaagga agttgctggt 158400
gcagcccaca ctcgggtgag gtgttgatta tccctacatg catcatctgg gattctgctg 158460
tacaggaggt ttcagactaa tctttaaact gcttctttcg ccaccccttt cacctgccgt 158520
gtccaaggac tgacagcatt aatagctgtc accgtcacct acagggcatt gcctttgagc 158580
caggctgctg ctgagtgcct tatatggttt atttcatcga gtccttaaag cagccctccc 158640
tgtgaaatca attctgctga tgcttccttt tgcaaaggag gaaaccaaag gtcagagcct 158700
cccctcccaa ctctagagcc tcccatctaa ccacttatgt tgcgacctga acactcacag 158760
tcatcccaga cttcacatgg ccaaagcaag actcctgatt tcccttgatc ttccccagtc 158820
ggcaatggca ccagcctcca tcctgttact ccagccagaa acccggactc atcctgcgcc 158880
gcccctccca atccatcagc aactcttgtc catgctgcct cccaaacgct gtttccaact 158940
ataagccagg gtaccttcct cgcatagagt atcctttgtc gtcctatcct cccagtgccc 159000
tctgaataga ggccaaccac cgtccaccag gcccgtggtc tggctcacta ccttcacttc 159060
tagttgcttt ccccctgcca tgctcaccac cctcgagcca cacctgacct ttcagtgctc 159120
acatccctct tccaacccca gagtaagctc cttttccttt aagatgtggc ctttgtatca 159180
cctcctccaa gagccttccc caaccacccc acccaaagcc tggttgttag cctctgtctc 159240
ttcagtcata gagttcacta ttacctgcag caaatgtctc tgtaccacat tcgaatgaga 159300
gctccaggag gacaaagacc cgagccgccg gactcattgt tgcagtatcc agcaccctgg 159360
catgcggcgg accctcgata aaggttggtt cagtgcatga gtgagggtta agtcactcgt 159420
ccaatgcaca catatcggct gagaagaggt caggtttcta aaccccatca tctgactcag 159480
gccatatctc agggccctac tcagatccca tcttcccaac catccataca tctggctttt 159540
attaacttcc tactagttcg tgtcctaggt acagcatgaa cctaggttgg gtcccaacct 159600
atacaggaac gctaaggcca gtaggggaga caagcagacc atcgccacac agcatgacag 159660
gttgcactgg tgcacacagg agggatgtcc accctgcagg aagaggtgtc caagaagatg 159720
tcccaaaggg aatgacacct gagtggcata ctgaagacat ctgacaagga tggatgttct 159780
gggcatagga agtagcatga gataagggag ataagagaga taagggagaa tgtggctgat 159840
gccaagaacc acacagggct cagtgcagct ggagaccatg gggatggtga gtgccagtgg 159900
gagcggagga agagtctagg ccctgaggaa cctcgtagct gttactgtta ccactgtgag 159960
ccagagcaag gactgcacac tctgtcctga gagacagggg agctggcgaa gggacctagg 160020
cagagaagtg agacgacata tttcagaaag atctccttaa tacaacacac cgggagaaac 160080
aagacctgct ctgcagacca gcagatgagc ttgaagggtg cagcagccat ttagaaaaga 160140
tgtgatgagg acattgtaaa ggtggaaggg ttagagggaa atagataaat ctgagagcga 160200
cttaagaggt tgaattaata ggttttggta gctggttaga aaacgagagt tgaggccggg 160260
catggcggct catgcctgta atcccagcac tctgggagac caaggcagac agatcacttg 160320
aggtcaggag tttgagacca gtctggccaa catggtgaaa ccctgtctct actaaaaata 160380
caaaaattaa ccgggcatag tggcgggcac ctgtaatccc agctacttgg gaagctgagc 160440
cacaagaatc gcttgaacct gagaggcaga ggttgcggtg tgccaagatc gcgccactgc 160500
actccagcct gggcaggcga cagagtgaga ctccgtctca aaaaaagagg cctggcatgg 160560
tggctcagca ccttgggagg ccgaggcggg cagatcacct gaggtcagga gttcgaaacc 160620
agcctgacca acatggtgaa accccgtctc tactaaaaat acaaaattag ccaggcatgg 160680
tggcgcatgc ctgtaatccc agctactcag gaggctgaag caggaaaatc acttgaaccc 160740
tggtagcaga ggttacagtg agccgagaca atgccattgc actccagcct gggcaacaag 160800
agtgaaactc catctcaaaa aaaagaaaac agagttgaaa gagagtccag gacagactga 160860
ctgtcctgtg tgaacatccc tgcaggagat ttggacagga cttagtgcta ttccaactgg 160920
aagtggaata tatgggtctg ggtagagctc aggggactga tctgggccag agatggagat 160980
gtgggcctcc ccaccgtgtg ggagagctga cgctggggag aggtgagctc atccctcgct 161040
gggctcatct ccttcctgat cacatgggca cctacggtcc acactacaca gctcacgctt 161100
gcttctattc agtctctgcc gcctcatttg tggctcacct tcattctgag tgcatctctg 161160
tccaacaaca ctgcaggcag aagctgcccc gtatttctca ttcttttccc acaccttgca 161220
ctcagggtct gttgactact aagcttgatg gtgatgagaa taaacaacca ctaggaatag 161280
tgtctgttat gtacaaggcc taatgttaag cctttatgcc ttttttgttt gtttgttttt 161340
ggtttttgag acagagtctc gctctgtccc ccaggctgga gtgcagtggc gcgatctcgg 161400
ctcaccgcaa gctccgcctc ccgggttcgc gccattctcc tgcctcagcc tcccgagcca 161460
ccatgcccgg ctaatttttt gtatttttag tagagacggg gtttcaccat gttagccagg 161520
atggtctcga tttcctgacc tcgtgatccc cccgcctcgg cctcccaaag tgctgggatt 161580
acaggcgtga gccaccgtgc ccagcccctt tatgccattt tattgcattc tctggatgtc 161640
ccaacaaagt aggtaatagg aaccctgctt tacagatgag gaagcaggta aaataacaga 161700
ccatgcctaa aaagcgacac cactagcaaa tggagaaacg cggctttgaa cttagctgag 161760
tctgacccca aggcctgcgg tccctccact gagcagggca ggaccggtct accctggctg 161820
ggaggtcaca aggaagagag ggtgcagatt tgccataagg ccacaggaca ggaaccagga 161880
gcctctgggg acagctttga gtagactgat tcttggctca gtggcagaaa gaaccaacaa 161940
ctagtggtgt ccaaggtaga caagggcccc tcaggaagct caggaagctg gggagacatg 162000
gtctttaagg agcctcccat cttgagcact tatgggtgaa tgtgctgact tttttttttt 162060
tttttttttt gagacagagt ctcactctgt cgcccaggcc tctcaggttc aagcaattct 162120
cctgcctcag cctcccaagt agctgggact acaggcaaga gctaccacac ctggctaatt 162180
tgttgtattt ttagtagaga cagggtttca ccatgttggc caggctagtc tcaaactcct 162240
gacctcaagt gatccgccca tctcggcctc ccaaagtgct gggattacag acgtgggcca 162300
ctgtgcccgg ccatatctgc tgacatttca agtgggacga cagccttggc aaaagtgccc 162360
cagccacttc agagaaaggg agggaatcta gccaaaagaa aaagaataat ttaagaaagc 162420
agatttcagt gggacgaggg cttctgagga tctaaaggga tgcagtagga gaagtgggag 162480
tgattttcag ggaggaaaca gtaatattaa aagtagcaag aacaacttcc caggcatggg 162540
atggcagggg gctgctgagc actgtggaaa gagcataagg agctgaatca ccactgggca 162600
tggatttctt cctttattct ccatttactg agtgcccatc agcagcctgg catgagatca 162660
gcagctgctg gaggagcaca ggacagtgca ggatgaagta acagtctctt cctttgggag 162720
acacacagtg caatcctcag agacaagata aaaagccaag tggctgaaag ggccgaacac 162780
atgcgaggct aagcgacaag agaatgagaa ccagcaggga aggcccagcc ttcccccacc 162840
agcacaccgg gcggagcagc cagcgcctaa ggagaatccc aaaggaacca ctgaagccca 162900
cagatggtga gcagaacaat tggagccagg aacctgcaca agtcacaaag ggagattgag 162960
aagtgttctc tccatttacc gggaaaaagg tgataaaata aatgtgctcc ttggccgggc 163020
gcagtggctc acgcctgtaa tcccaacact tggggaggct gaggcgagtg gatcacctga 163080
ggtcaggagt ttgagaccag cctggccaac aaaaaattag ccaggtgtgg tggcaggcgc 163140
ctgtaatccc agctactcgg gaggctgagg caggagaatg gcgtgaacct gggaggcaga 163200
ggttgcagtg agctgaaatt gcaccactgc gctcctgcct ggggaacaca gcaaggctct 163260
gtctcaaaac aaacaaacaa acaaaaaagc ccattgagcc cggtgcagcc gcctttcact 163320
tctctgagcc tcagtttctt cacctgcaaa acagagacac tgaaacagca ctttcaatcc 163380
agggcgcaca gcacaggcac cacttaagct ttaaagccac aagaggcggc cgggctccgt 163440
ggctcacacc tgtaatccca gcactttggg aggccgaggt gggatgatcg cttgatccca 163500
gtagttcaag aacagcctgg gcaacatatg gacagcccat ctctacaaaa aataaaaatt 163560
agctgggcat ggtgagcacc tgcctgtagt cccagctact caagaggctg aggcgggagg 163620
atcacttgag cccaggagtt caaggctgca gtgaactatg attgtggcac tgcactgcac 163680
cctgggtgac agtgggacct cggctcttaa aaaaaaaaaa aaaaaaaagt ccactttggg 163740
aggccaaggt gggcggatca tggtaaatgg taaatggtaa aaataatggt aaaaccctat 163800
ctctactaaa aacacaaaaa ttagccagtg tggtggcatg cgcctgtagt cccagctact 163860
tggaaggctg aggcagaaga atcgcttgaa cccaggaggc agaggttgca gtgagccaag 163920
attgcaccac tgcactccag cctgggcgac agagcatgac tccatctcaa aaaaaaaaaa 163980
gtcccaagag gtgcccagga ttcaccctgg caccaccaaa tctcaatctc tagagggaaa 164040
gccttctaag aaagttattt ctcaaaagat tttgaaaccc agtgtcatga agaacaaaag 164100
tgccttgtgc tccatattct gtttcctccc tgtgaacaga acatgctggg caggtgggag 164160
tccagtcatg gtcggatgta gtctctatgc acagaggcag acttaccaaa atgcaatcag 164220
tgcaacatat atgtaggtat atattttgag acagggtctg gctttgccgc ccaggctgga 164280
gttcagtggc atgatgttat ttctgctcac tgcaacctcc acctcctggc ttgagccatc 164340
ctcccacctc agcctcctga gttgctagga ctacaggtac acaccaccat gcctagctag 164400
tttttgtatt tttgtagaga tggggtttca ccatgttgcc caggctagtc ttgaacttct 164460
gagctcaagc aatctgcccg ccttggcctg acaaagtgct gggattacag gtgtgagcca 164520
ctgagcccag cccaaccagt ggcaatatat ctggaaaata aggccaatgt gagggctgaa 164580
ggatcacaga tcccaaacgc aacagacccc aacctcaggg gccctggagg aaaattgacc 164640
agctgaaatg gacaaggata aacacaagct cagcactgat gcaaataaca taatcaatgg 164700
acataagaaa caacagaagt tgcttccgga gaggggggct ggatggctga ggacagcagt 164760
cacagagata actacatttc attgtaactt gcttgtttgc cttttttttt tttagttttt 164820
ttttttgag acagagtctg tctctgtcac ccaggctgga gtgcagtggt gccatctcag 164880
ctcactgcaa cctccgcctc ccgggttcaa gcgattctct tgcctcagcc tctccagtag 164940
ctgggactac aggcgtgcgc caccacgcac agctaatttt tgtattttta gtagagacag 165000
ggtttcacta tattggtcaa gctggtctca aactcctgac ctcagatgat ccacctgcct 165060
cagcctccca aagtgttggg attacaggtg tgagccactg agcccagtct ttgtatgtct 165120
tttgaatgtt gcacaaatga aagtatctgc tatccggaaa aaaatcattc cagtcacggt 165180
gtctcatgcc tgtaatccca gcactttggg aggccgagat ggaggactac ttgagaccag 165240
cctgggcaac atattgagac cctgtctcta agaaaataaa ttggaaaaaa aaaaaagcca 165300
ggtgtagtgg catgcacttg tagtcctagc ttcttgggag gctatgatgg gaagattttg 165360
tgagcccaag agtttgaggt tacaggctgg gccgaggcca aggtgagtgg atcacctgag 165420

-continued gtcaggaatt tgagaccatc ctggccaaca tggtgaaacc cgtatctact aaaaatacaa 165480
aaaattagct aggtgtggtg gtgggtgcta taatctcagc tactggagag gttgaggcag 165540
gagaattgct tgaaccctgg aggcagaggt tgcagtgagc caagatcgtg ccactgcact 165600
ccagcctggg agacagactc catctcaaaa agaaaaaaag gagtttaagg tcacagtgag 165660
ctatgatcac accagtgcac accagcttgg atgataaagt aagaacctgt cacttaaaaa 165720
aaaccattgg cagagcacag gtttgagaag aacctggttg gatgtaactg agatgtgtaa 165780
aatagagggt cttcacttgt gtcaaaggca gcctgattta cagcttttttt tttgtggaca 165840 ggtggcatcc ttattatggg gggacgtccc tctgatcttt gcagttcatt ccttgtctct 165900
ggtcactggg ccctgggctg atcaccacct tctgagcagg acccagacgg acaagctaga 165960
ctacacccag aaaggagaaa ttgggatggg gaagggtcag gaaactgcgg taggactgag 166020
tgaagggacc aggggcagcc cagggaagag atgagaccac gcggggcacc atcgctgtct 166080
ccaaatacct taactgacac aagggagcag ccttctttct gaagacagag ctagggctgt 166140
ggatgagcac tgcaggaagg cacttcgggg tctatcagag gaaatttttg ctaaccttcc 166200
gagttgtctc agagccaaac gtagtaagct acctgtcacc ggatgtgctt gagctaaggg 166260
cgctgaacca cctctgtcag agacggtgca tcccccaccg gatgtgaccc cgggatgcgg 166320
agcctggggt cagatctgcg agccagataa cagcggcact cacttctcgg gtcttcgtga 166380
gcattaagtc aatgaaccca gggcaccaaa gcgcgcaaca cgcagtaggc gctcagttag 166440
tggcgcctcg ctctgtactc caggaagccc aaccttctcc ctgcgcctca gtttctcccg 166500
acgtcctcga tggcgccatg gcgccacact aggtaccttc gggttcgacc tcccgagcag 166560
ctccacacgc tgaggccccg cggcattttg cggccgaggg cacccctcgg ggctggcggg 166620
ccctgggaac tgcgccccgg gcgggtcctc gcaccgcccc cgcctcgatg gccccgcccc 166680
gtccccctcc cgctggagcc ggcccggccc gcgctccttt aaggcagcga acgggccaag 166740
agaagcgtgt ttcgccccct ccgacgccac cgaggtagcg gcttcacctt taaggcggcg 166800
cgggggctgc tgggaaggcc ggcgggatgg aggcggcggg accggctcgc gggtgcgggt 166860
ccgggtgaag cgggaggcag ccagagtcgg agccgggccc gagcaccagg cgcaggtcgg 166920
cgcgggccga ttgggccggg agacggggtc aggccctaaa gcgggggagg agactccggg 166980
tcggcctagg ggaggggggtc gtcatgggcg cggcctgtgg gaggatcggg ccagccctgg 167040
tagggggcgc ggtcccgggt ggcccggggc gggggcgcgg ccttttcagg gaaggcctca 167100
gggcgttgcg ctggcctagg ggaggggtcg tcgtgggcgt agcctggaag gactgggggc 167160
cgcgtactca gcccctctag tgggagcgcc tccgcagggt cggctcgtcg ggaggatggg 167220
ctccgcggct tggcctgcct tttggggatg gggctgtccg aggggctggg cccggatcgc 167280
cggaggggcc agggtctcct gcacaggagt gagcccccac gttccccata cctgtcctgg 167340
ttagggggtc cccggggaaa cccggacact gagccgccta agtcggcctg agccggtggt 167400
ctggggccga agcaggatcc ggctgcaccg cattgcgtct cccaggccta gacaagctag 167460
gcgcgccctc tgtaggccaa gcgcgggcac ggtgcgggct gccggctggg ggacctgggc 167520
acacgggaga ctcaggcgtc cggggaccgc ctgtttacct aatccggggc ggacggcggt 167580
gtggccccag gcccggcgcc cgcctgcccg caccctcgtc ctcacagacg ccacagccat 167640
ggccatgatg gtgtttccgc gggaggagaa gctgagccag gatgagatcg tgctgggcac 167700
caaggctgtc atccagggac tggagactct gcgtggggag catcgtgccc tgctggctcc 167760
tctggttgca cctgaggccg gcgaagccga gcctggctcg caggagcgct gcatcctcct 167820
gcgtcgctcc ctggaagcca ttgagcttgg gctgggggag gcccaggtag gtcagtctgg 167880
ggcactgagg tgggaggtca ctggagggat cgagccttca agaggaatcc ggtaatgtag 167940
gagaagaatc tgagcaggga accgtctgtt tcctggagcc ccatgttagg accccagtaa 168000
atacctttg aagaaataaa tgcactttgg cgaccccagc cctgccctaa gagaccatga 168060
tcacccttgc ccccacgcag agccccattt ccggctcccc tctacctaag ggagactgga 168120
tggcatatga gaacagaaag aaaatcctta aggaaacata gcctcccacc aattaattct 168180
tctattcact cgttaacaga tgagttattg agggccagcc agggtgttag gtggatacag 168240
ggcccaacaa aatagacaag attcctgccc tattagagac aaaaacacac atacagaaat 168300
aattggttgt tacaaattgt gatgagttct gcagagaaaa gaacaagatt ttatgatagc 168360
tcgcagcagc gagtcttgtc tactggtcag gcaggacttc tgtgaggaaa tgacaaactg 168420
aaacctgagg gaagaaatga accagcctcc aggaaaggga ggcaggggag aagttgcatg 168480
tgcaaaggtc ctggggtagg aaagagcttg tggtggagga actcagggaa gaactgtgtg 168540
actggagctt catggaaggg agacagggac agaagaggcc tggggagaag ccaagaacca 168600
gatcatggcc tggttggttt gggttttatt ctcaggaaat cagaaagcct ctggagggct 168660
ttaagcaggc aggcaacaca gtctgacttg agtttctaaa aactctctct ggctgagatg 168720
tggagaataa acctcagtgg gtcgaggatg gaatcactct ccaatgagtg gttaggaagc 168780
cactgctgga attcaaatga gagctggtgc ttggaattaa ggggtggcta tgacggtgga 168840
gaaaagggac cagttctgga tgttctggag gtaggtccag caagacctgg gggtggaata 168900
agggagagag agaggaaggc agcatcactc ccaagtttgt gatttaagca aattaaggga 168960
ggagagggcc ttggtggatc agaactctgt tttggcctcc tttaattgag gctgccagga 169020
tgatatgcag ttggagatgt ccaggagcca ttgggatgta caaggagtta gacttgtttt 169080
attcccctca gagcttggct gagcccctgc ctggcacgtg aaccctgggg aagttgtatc 169140
attttggttt ccttgtcttt aaaataggga tcatgccatc tgctgtgtac acttccaggc 169200
tgttggggga attttttttt ttttttaaag ctagtggtta tggaaacacc tgtcacttag 169260
gcatttgcta accaacaaca aagtacaggg tctcagacag cctggccctc tgcaaggaca 169320
ttcactccct gccagttggc cgtcagaggt agagaggacc actcaggggc cgcacacctg 169380
gtggagcacg tgcactctca cagaggggga acaatctgca cggagggcat gggcatcaag 169440
gccatgtgtg aagctggagc aaagtgggag gtgtgactag ctggagacac aactgcagaa 169500
atgatcctga accgggaagg actgggaaag ggtggaggcc gggtgtggtg gctcacgcct 169560
gtaattccag cactttggga ggcccaggtg ggaagactgc ttaaatcccg gacttcatga 169620
gaccctgtat ctacaaaaaa taatttttct tttttttttt gagacagtct tgctctgttg 169680
cccaggctgg agtatagtgg cacgatctca gctcactgca gcctctgcct ctcaggttca 169740
agtgattctc ctgcctcagc ctcctgagta gctgggacta caggcacgcg ccaccacacc 169800
cagctaattt ttgtattttt ggtagagatg gggtttcacc atgttggcca ggatggtctt 169860
gaaatcctga cctcgtgatc tgtccgcctc agcctcctga agtgctagga ttacaggcgt 169920
gagccaccgt gcctggccaa aaaatttttt aaattagcca gctgtggtgg tgtgcacccg 169980
tagtcccagt tactcaggag gctgaggggg aaggaccact tgagcctgga aggtagaggc 170040
tgcagtgagc tgtgacggtg ccatagccct tcggcccagg tgacagagtg agacattgtc 170100
ttaaattaaa aaaaaaaaaa aaaaagagag agcaagaagg gaggttggac cctaggcagg 170160

-continued aaggcaggaa gagactggaa actaaggaaa ggagttgcag aggctgggga gaggggtggg 170220
ggttgaggcc aaggcctttg gatacttttc ctgcccctgt ggctcctcat gccaactgag 170280
catttgggac acatgcccct tccctacctg ggagctgcag aaaggcaggg gatgctgtgg 170340
cccctcagca gaagtgggga tggagtcttt gggtggtcct tcagccatct agcagagttc 170400
tgtgggcaag cgctagccct gaggcaggga gcagtaacct actggctgtg gcagcagagg 170460
cttgagtaca acccagggag agacgaagga aggggctagt agctcaggga aagcacagca 170520
ccccaactag cccttttggg gttctcctga tcctagaagg aaggaactgg ggactcccaa 170580
gcctcctggg tttgggcttt gcattatggt gtgtcggggg ccttgaggag attctccctt 170640
gacaagcaga gaaaagacct gcagctcctc actgtagggc caggcctggc ccttcactgg 170700
gtgccagagc ccaactaggc ccaggctaca gtcataggcg agggggtcga caggcctccg 170760
acccttacct gggctggttg cacaggtgat cttggcattg tcgagccacc tgggggctgt 170820
agaatcagag aagcagaagc tgcgggcgca ggtgcggcgt ctggtgcagg agaaccagtg 170880
gctgcgtgag gagctggcgg ggacacagca gaagctgcag cgcagtgagc aggccgtggc 170940
ccagctcgag gaggagaagc agcacttgct gttcatgagc cagatccgca agttggatga 171000
agacgcctcc cctaacgtga gctcctacca tggtcactgt tgcccagcaa ggaggcctgg 171060
gagcagggag gggcagcatg gagcagattc ggctccaccc cagcccatgg acaccccggc 171120
tgccctgtgc ctccttccct gatgctcatc ctgtcttcct tcccaggagg agaaggggga 171180
cgtccccaaa gacacactgg atgacctgtt ccccaatgag gatgagcaga gcccaggtgc 171240
ggatgggcag ttctggagtg ggggaaggaa aggttgtgtg aactcttggt ccttgggacc 171300
gagtggctgc catgttcctt cctgcctcac ttctgatcat gacatcctag tgtgttagag 171360
cttcaagaac agttgtacgt gctgctgctt ctcacatccc cccagctctg tggtgagcag 171420
acatcacaat tagctgtgga gtcaccagcc tggcttccag tgctgctctg ccactagctt 171480
ccctgaccct tgggagagtt ctcttcctct ccgaatcacc tctgaaggag gcacatgcag 171540
acagccacaa tggggccagt gcctgctttg ctgatggtac tggttatgca tcggggcctc 171600
cactctgtac acagggacac aggctcagag gttaggcagc ttgccccagg acacagagcc 171660
tgaagtactg gagctgggcc tctacccccct ctttctatgg ggtaactaga cccattctat 171720
aaatggggaa actgagaaag agtggttagt gacttgccca gggccatgtg tcaagtggct 171780
caaaggcaca gctggcatgt gccatcccag tccagtgggc agatggtaca tctgacctcc 171840
tgcccttggc cctgcagccc ctagcccagg aggaggggat gtgtctggtc agcatggggg 171900
ctacgagatc ccggcccggc tccgcaccct gcacaacctg gtgatccaat acgcctcaca 171960
gggccgctac gaggtagctg tgccactctg caagcaggca ctcgaagacc tggagaagac 172020
gtcaggccac gaccaccctg acgttgccac catgctgaac atcctggcac tggtctatcg 172080
gtgaggactc tctgggggtg cccaaattct tctggaaggc tccagccctg gatcactaac 172140
ccttggtgcc tgctgtgggc caggactcgt ggcccacctg cgtggagctg ggctacagat 172200
gcaagtaaaa ctgtctagtg taagagagag gcttggccag aactggggag ggactgcaca 172260
tgaggactcc aggggtcctg gggagtccac acagcttctc caggcaccaa ggctggagga 172320
ggggctttgc cagaaagtga gtttgcccaa acacaagagg gctagaaaag gttcccatgg 172380
caaaaagcca gcatgagcaa aggcactggg acctggagag caggacacgc taaaggggca 172440
gcaggagagc catgtggcgc ccaggaatgc taggcaccag gcagtcggtg ggaccccagc 172500
actgcgcacc ccagccaatt gtgagaaaac tgcctacagc ccttggagct tggagagcag 172560
gagctgagca ggtctcccca cactctgggt ctcactctgt catacacact cagtgagtac 172620
aggagtgacc acagggattg cagaccattg gggagggcct tgagctggag gacagccctg 172680
accatgctcc tacctgctcc cagggatcag aacaagtaca aggaggctgc ccacctgctc 172740
aatgatgctc tggccatccg ggagaaaaca ctgggcaagg accacccagc cgtgagtgag 172800
ggttgggtgg gaggtggggg ctgtgcccca tcccctgcag gtcccagagt cctgcagggc 172860
ctgagtcaag aagcttccgt tctcccacct ccaggtggct gcgacactaa acaacctggc 172920
agtcctgtat ggcaagaggg gcaagtacaa ggaggctgag ccattgtgca agcgggcact 172980
ggagatccgg gagaaggtgg gaacaggcag ggctgggcag gctgggggtc tgggaggcag 173040
gggcccgggc agccctgagc ccaacccctg gctccctctc ccatcccagg tcctgggcaa 173100
gtttcaccca gatgtggcca agcagctcag caacctggcc ctgctgtgcc agaaccaggg 173160
caaagctgag gaggtggaat attactatcg gcgggcactg gagatctatg ctacacgcct 173220
cgggcccgat gaccccaatg tggccaagac caagaacaac ctggtacctt ggggctgaga 173280
ggagctggag gatgggaagg agggaggcag ggatgaggtt ggggaagaag gagagaaaaa 173340
ggcttggctg catgcatccc gctcactctc tgggtctccc gcttccaggc ttcctgctac 173400
ctgaagcagg gcaagtacca ggatgcggag accttgtaca aggagatcct cacccgcgct 173460
catgagaaag agtttggctc tgtcaatggt gagtgcgtgg tcaccaggtg cctctagccc 173520
atccatccca ggcccactct gccatcagca cccaggacaa atccctcagc agggcaggcc 173580
ctcaggcttt ggcctggctg gtcaccagcc tcaccctcag atggtgccca gccacctgtg 173640
ctcacgtttg cacacatgag cacacaccca actcacgcag ccccccttggc ctgctagggc 173700 ctcacacgcc tttgcatccc ccttctccac tggcgattct tgctcacctt gagggcctgc 173760
cccagtgtct cccactctgg gaaaccacct ctggccccgg atggtcagtc atctgctcct 173820
gagtccctcg gagcctggcc catcattcag gcctagcaca tgtcttgggc tgtggcctga 173880
ggtgcaaggg tctgttctgc tcatctctgt ccagaagagg gtcagcagtg ttttgggtct 173940
tactcttgtt catgcattca acgaagccca accgtggtct cccctcccct gaccccagtc 174000
ctgtgtccag cccaaccagg tgagacctat atggtaggct ggtgacagtc ccctttctct 174060
ccccagggga caacaagccc atctggatgc acgcagagga gcgggaggaa agcaaggtag 174120
ctctgtgggg caggctgggc ggttgtcagg ggaggctggg atgtgcagag gggggcctgc 174180
tctcacttct tgtgaccatt ctttcctcca ggataagcgc cgggacagcg cccccctatgg 174240 ggaatacggc agctggtaca aggcctgtaa agtagacagg tgagtggggc ggggctgggc 174300
tggggagcag ggcacggcag ggcgggctcc acattccata ctctcacccc caacacaccc 174360
ctcctctgct gctcatctgg caaggcccaa ctcacaggtc acctgtccca agaaggctct 174420
gtctcccaat tctcagccta attctctggc tctgggtctc ccagcttttg gtcctggtga 174480
caacatccca tgagggccct ggggccaggt ccccagccct ggggtgattt ccccaggaca 174540
gaagaggctg ggtgggccca gcacagggct tgacatggga aggaatggat tctggctacc 174600
ccggaggtcc atgcttcctc agggcccact gtgggctggg tgccaggatg ggccctgggt 174660
ctgggggaac atggagtttg agactgtccc atccacagcc ccacagtcaa caccaccctg 174720
cgcagcttgg gggccctata ccggcgccag ggcaagctgg aagccgcgca cacactagag 174780
gactgtgcca gccgtaaccg caagcaggtg gggctccatg caggaggggg tgggcagaca 174840
cctgtgtggc cctgggtgtg gtccattcac tgcctgatgc ccctgcccct ccctcagggt 174900
ttggaccccg caagccagac caaggtggta gaactgctga aagatggcag tggcaggcgg 174960
ggagaccgcc gcagcagccg agacatggct gggggtgccg ggcctcggtc tgagtctgac 175020
ctcgaggacg tgggacctac agctgagtgg aatggggtga gtccggggcc tgggccgggt 175080
cgggctggga gcctaggtgg ccagcggggc ctagaggcaa gcctgtccac ctgcaggatg 175140
gcagtggctc cttgaggcgc agcggttcct ttgggaaact ccgggatgcc ctgaggcgca 175200
gcagtgagat gctggtaaag aagctgcagg ggggcacccc ccaggagccc cctaacccca 175260
ggtgagcccc ccaccaaggt gagcctcaag aaccacccag caaccccgga tgagctcctg 175320
acccagagtg tgccccactg accccaggca acctccccat ccctctcagg ctccaccacc 175380
caccagtctg ttccctcccc agccccaccc ttctccctgc cccatctcc cgtgagttcc 175440 tccttgggca aatcccaggc tgtccttttc cctcaggatg aagcgggcca gttccctcaa 175500
cttcctcaac aagagcgtgg aagagccgac ccaggtaggg gcaggcgggt gtctgggcac 175560
tgggcagctg cggccggggc tgcatgcgtg ctgccaagct tccctccagc atgcctcttc 175620
atccagcaac agttcctggc tctgtctcag gcctactttg ggctggacaa cggggagaca 175680
cgaggggaac ccagcctctc ctgggggtgg acgtgtaaac ggccagtgct aacaccgtca 175740
ctgtggagat ggacgggagt gtcagggcac cagggtgtgg ccttgggtca gaactgccat 175800
tgcctctgcc cagctcaggg attccggctg cctctgccag gtcagacccc ttcaggccag 175860
ggaggcacag actggcagca gcacagggct gagccacctg ccccctctgc ccacagcctg 175920
gaggcacagg tctctctgac agccgcactc tcagctccag ctccatggac ctctcccgac 175980
gaagctccct ggtgggctaa tgctgaaggg gcagccagtc accagagcgc ccacctggca 176040 caccccccctc accccagccc tgcgcatggg cctgctgctt gtcccgcctg tctctcccac 176100
agcccctgtc ttttctgttc aatctcaggg taaccttctc ccttgtcatc tcagcctgag 176160
ccctggaggc tgggcctgcc cactccagct ccatccctta tttattcctt ccagcagggc 176220
cctcttccct aggttcgggc cagcaggagg tgccggctgg agtctccacc atagactcag 176280
tggcctggcc tccccagacc ccagagccaa gaacactaag cactcgccgg cccttcggca 176340
ccctcgccct ccctcccgac tcaacccggc cgttgcttct gtatatagag aaataagtta 176400
ttggccgcgc gcctcccttc agtccacggt actacccggg cctcccctcg tccctcttct 176460
agtggtaccg cccaggcctt aatcaccccc attccgtgcg gtggtatctc ccaggctcta 176520
cattctcggg agcggcgcct cccaaggggg tcctgggacc ttctcgcgct cctcctggcc 176580
tctgagggat gcgtcctacc cgcgccatcg ccccgtggcc caggacgggg acctcccctt 176640
agtccgtcct cccaccgccg ggccctgccc cgcatcccgg ccttatgcac tgcccctccc 176700
acccggcccc gcccaggcac ggccgacccc gccccgggca ccgcccaccg agccatcctg 176760
cctcgcctcc ccccacgcct gcagcttctc gcgaggggcg gcgacggtcc cctggtggca 176820
ggaggggctc cccctgttgc gggtgaggcg gctgctctca tattttcaga tgttgctgta 176880
gaaataaaga cggtttaaat ctgagctggg cttgttttga gacggaggtc gggggccccc 176940
agcgtctcta gactggggtg gagccgggaa gggtcgtgcg tgagtggggg acagtgtgtc 177000
tcgctcaacc gctgtccgcg cagctgggcc cagatattgt gccccacccc ggaattgcgt 177060
gaggggccca caagtcaggc tttccctaaa acactcactt gtggggttct ggagaccgcg 177120
ggctcttatg agctctgctc ctcacaaagt ttttgacctt gagtgagttt cccgagactc 177180
agttttttca tctatgaaat gcgggtgatg acgcgcggct gcgagttagg actgcccagt 177240

-continued acacgaagaa ccctggacaa atgtactttt attagtctta ctagaaccca cattctcatt 177300
taatgttcac aacgtgggta ttgggagggc aaggatgact acctccgtca gacagatgtg 177360
aaacgtgcca agcccagccc taaattgagc tttctaaaca ccgagtcgcg gtcaggcttt 177420
ccagcactgt cctcaagcct gagtgcgtcc ggagtgcaaa ctacaagccc cagaaggcaa 177480
tgcgccagca gtgatgggag tgggcgcgga ggcgcgggct ccccgactac gcctgcgcag 177540
cggggctgag ttggagaacg tcttagacta caagttccgg gaatcagcgc ggcgaggcct 177600
gagaagaaga cgtttgcgcc tgcgcgtcgc gggcggggcc tctggggcgg agcggccacc 177660
atcttggaac gggaggcgga gcagagtcga ctgggagcga ccgagcgggc cgccgccgcc 177720
gccatgaacc ccgaatagtg agtgagcccc gcccgcgccg tccagcgcag cctcgatccc 177780
gaatacaggg ctgtacgctt accggggttg tctggcccgg gtcaggactg tgcggcgccc 177840
ccacatccgg gtccctcttc cgctgacccc cccccacatc cgggttctgc ccctcccccc 177900
aggggcccca ggaccccggc tcaaaacccc gagccctcgc acccggggcc cagacgtggc 177960
gacccccagg ggcagctctt ggagctcgag acatcggtcc taccaggcct tatcggtcag 178020
atgaccccgc agtcccggtc acttcaggcc tcagtttccc cacctgctgc ttgacaactg 178080
tcccggagtt ttggagcccg tcttgatagt ttctggtctc gggttcaggc ttgggccctt 178140
taggtcgggc agtgaatccc tctacccttc tctttctcct gaagcccggc tcctggggcc 178200
ggcccagaag ctagccaact acgcgggagg ccccgaagcg ccgcttgggt cgcgtctccc 178260
gcaggtcctc tcttccgggg ctgcctccta ccctttgcct gggtcgcgct gtcctgtcgc 178320
tcccgccggt ccgtcctttc ccgccctctc ctcgcttttg ctcaggcccc caacgccacc 178380
gtcacacccc ttcccttggc tgtcacactg cctgtgaagt ttagatgaat atggaatttg 178440
ctctccccct tcctgtggga ttctctggtc ctcaaactct cctcactctt ggtcactccc 178500
cctgcgggta ggtggcccac atctcatgcc caggactaat agttttcccc aagtatcagt 178560
tatcttcttc cttttctgcc acttcctttt tctactccac atccaggtct cagatttcct 178620
tggggaaggg tgaagctctg agctggattg ggaggggaac agagaaggga accagcaggc 178680
tctcgaaggg actttggagt ctgagaaacc tggtttgagt cttaaagcga taaactgtgt 178740
aagttagggc aagtcacttc ccttctctgg cctctggttt cctcattagt tgacaatgac 178800
aaaactgact tcattgaact gttgtgaaga ttaaatgaga tgatgcattt aaagtacttc 178860
acacagggtc cgtccacagg ttggaactca agtatattaa atgtgattac cttttgcctt 178920
tttttttttt tattttgaga cagggtctct ctctgtcacc caggctggag tgcagtggcg 178980
tgacgatggc tcactgcagt ctccaactct tgggctgaag cagtcctcct gccttgtcct 179040
cctgagtagc tgggaataca gaggcacacc accacacctg gcacattttt taatttttttg 179100
taaagacagg gtctcgatat gtttcccagc ctgatctcaa actcctgggc ttaaatgatt 179160
ctcgtgcctc gggcttccaa agtgttggga ttacaggtgt cagtcactgc acccagcctt 179220
aagtgcaatt ttcactgcaa cttgaccacc tcttcctggt gacttcataa caggtttttg 179280
ttgttgttgt tgttgttgtt gttgttgttg ttgttgttgt tgtctccaaa gagatggggt 179340
tagccgggtg cggtggctca ggcctgtaat cccaggactt tgggaggccg aggtgggtgg 179400
atcacgaggt caggagatcg agaccatcct ggccaacatg gtgaaatccc gtctctacta 179460
aaaatacaaa aattagctag tcatggtggc gcatgcctgt aatcccagcc actctggagg 179520
gtgagacagg agaatcactt gaaccaggga gtcggacgtt gcagtgagcc gagatcgtgc 179580
cactgcactc cagcctggtg agagagcgag actctgtctc gaaaaaacaa aagaaaagag 179640
agacggggtt gtgctgcatc acccaggctg gtcatacact cctaggctcc aaggatcctc 179700
ctcctgtttc agcctcccca gtagctggaa ccacaggcac acgccacagc acccagccat 179760
cagtctctct acgtgggttt tcaacttaat aggttctagg ctgggccctg gcttctactt 179820
ctggggcctt ctctgccaag ctaggcacac gcagggcatg tactggggat tccctaaata 179880
gctcctactg gaccaaacca tgaagtttca gaaatcaggt taggataccc agctctgttg 179940
ccttggcagg tcacgtgtct tgatttcttt ctccataaag tgagaattta gactcagcaa 180000
gctgagagcc ctttgggcta gctgtttgtg gagggaggca tcagccctcc ctgaccggga 180060
ctgttgggaa gatctggtga gcaccatagt attctaaacc aagggatggc caggcgcagt 180120
ggctcacccc tgtaatccca gcactttcag aggccaaggc aggtgaatca attgaacccg 180180
ggagtttgag accagcctgg gcaacatagt gagaccccat ctctacaaaa aatgaaaaga 180240
ttagccaggg gccgggtgtg gtggctcaca cctgtaatcc cagcactttg ggaggccaag 180300
gcaggtggat cacctgaggt caggagttcg agaccagcct ggccaacatg gtgaaaccct 180360
gtctctacta aaaatacaaa acttagacaa gcatggtggc aggtgcctgt aatcccagct 180420
actcgggagg ccgaggcagg agaattgctt gaacccggca gacagaggtt gcagtgagcc 180480
aagatcgcgc cattgcactc cagcctgggc aacaagagca aaactcagtc tcaaaaaaaa 180540
aaaaaaaaaa aaaaaaaatt agctagaagt ggtggtggtg gtggacacct gaagtcccag 180600
ctacgcagga agctgaggtg ggaagatcac tttgagcccg caaggtagag gctgcaatga 180660
gccgtgatca cttcagtgca ctgtagcctg ggtgacagag tgagacctta ttgctaaaaa 180720
aaaaataaaa ataaaccaag ggatgcctca tggggtgggg gaatcctgta attgtgactc 180780
caggatgatg gtaggtgggc tccctgcctc ccttcacgcc ttcccatctt ctctctccag 180840
tgactacctg tttaagctgc ttttgattgg cgactcaggc gtgggcaagt catgcctgct 180900
cctgcggttt gctgtgagta agaagcctcc cataccatcc acctggggtc ctgactggca 180960
gctgggggga gaagggacaa cacagagcac agtagttgca agatctggga accaggggtg 181020
aagctgtaag acctgccacc agcacatctg ccctgaacaa gacagggctg gccagctgag 181080
tgctgggaat tggggcttgg tggttcggag acccagctgg ggcagggaac tggagggagg 181140
ctctccaagt gggcctcacc tcattaactc ccatgatttc attggcccct gaactttcag 181200
gatgacacgt acacagagag ctacatcagc accatcgggg tggacttcaa gatccgaacc 181260
atcgagctgg atggcaaaac tatcaaactt cagatcgtga gtgtcgctct tcccaaaatc 181320
cccagtacag aggtatccac cttgggaggg aagggactct gggactctgg acctcagctg 181380
acctgctcct ctgcctactg tctcctagtg ggacacagcg ggccaggaac ggttccggac 181440
catcacttcc agctactacc ggggggctca tggcatcatc gtggtgtatg acgtcactga 181500
ccaggtactc ctggactagc catcctcagc ttggcctcct tagccttagg tctttgactc 181560
ttctttttcc tccttccatc ctctctttcc tgatgcttcc tggaaaggac actatttgtc 181620
tgcttacagg aactaactag gaaaaagaaa aaaaataggt gactgtactt ggactcattt 181680
cacaaggagg gaaacagcca cagaaatgga tcctctgaag gccctgctgc aggttctggc 181740
aggacaaggc ctcacacctt ccctccccac caagccaaac ttgccacctt attgtagacc 181800
ttctgggcac ctttgtgttg tgggagttta gtcaggcggt tggctgctat gctgggcctg 181860
tggcttcctg tgtgaagaca cagtgcaggg ggacaattag agggccttag acaaagaagc 181920
agggaagctt gagctctggg cccaatgtga gcagagatcc agaagctctg cctccagcag 181980

-continued cagcgttagt cccatgtgac tagcagtggt ggtagcaagg gctggaaatg gttccatgaa 182040
accttatagt ttacagaacc tggcccagcc ctcagattgc ctctgatgct cagaagaggt 182100
ctgtgttccc atcgcacagg taaggagctg ggctcaggat ggtgaggtga cttgccgagg 182160
gtccttcagc tagtccggtg gcagaggcag aaagcctgga tggctcattc cacctgcttt 182220 gtttttttcta ccaaatgttg ttgcttaaca gggccaatcc ctgaagataa ggagaagctt 182280
aaatcagccg tgggccggga agagtccctg tctgaggagc agccgggctc tttagctcac 182340
cagggactca tgatgtcccc agctctggac gagctgtggg gaagctacat accacccaga 182400
caagttacca gggcccacct gactgccata tatccagtga tcttatttca gcacattgac 182460
ctctcgtggc tttggacact gctctcttct ctctccttga aaagtggacc atccccccgct 182520 cctcagtctc ctgcagcact cgattctcta ttgtcagtgt ctatttgctg gtctgtccag 182580
tgctgcctcc catcaccctg tgtttggtgc ttccccactg ccctggactc tcctccttac 182640
tcttgtgcat ggctgcggcc actctgtggt ttgcttctgc cttgtgttct gtgattcctg 182700
catctaacag ccgtggctgt ggcttccctc ctctgtccat gtctacactg gcactttgtg 182760
tctgtattaa tcctgatctt catgatcttc tctagtaaac taaatggtga ggtttgtgtt 182820
ttctagatga ggaaacttgc ttggagaggt gttaagtaac ttgccaccgg tctcacggga 182880
agggcaaagc cagttttgga gggctcttgg cttttgagca caccctttcc caccctcaag 182940
cagcctctgc agaactcaga tgtccagcgc tggcctcact gtctctcccc aaaccagcgc 183000
ctctatcccc atttttaata tttttattta ttttaagaca tggggtctca ctctgtcacc 183060
cagactgcag tgcagtggtg tgatcatagc tcattgtaac ctcaacctcc tgggcttaag 183120
ggatcctcct gcttcagtct cctaagtcac tgggactata gacacacacc accatgcccc 183180
agctgcatcc ccatctttgt gacacaatcc ttgtcagcct gaccagaaaa ctcttccctc 183240
ccccatccag tcagtctcga gtcccctcta ttctctcccc atcatctttc tgaaatctgt 183300
cccctcataa taatagcagt gatgaggata atagcagctc ttgccaatta agcacttgtt 183360
atgagacaag cctgtgttca ttctcttcat gctcacaatc agcccttcta ggaggtactg 183420
tttatagaaa tgaggaaact gaggctcaga gtggtcaggt aacatacctg gggtcacaca 183480
gtaaatggct gagccaggcc ttcagcagca gtggtctgac taaatcctgt gtgcttccct 183540
ggctcagtgc acgttctctt ccctgagtta ttccagccat tcccagttgg tctctatctt 183600
gctattctga tctgggctct gcctcctgtc aggactagca taggtgtgat cctgttgctt 183660
ctggcctaag aaacgcccac tggctcctgg tctaagtcca agacttagcc atgctaagac 183720
agtctgtgct ctggcctctc cccaatcccc cctctttcct cccctcttcc ccctctcccc 183780
tcttgccttt ctcctcccca ctccccccatt ccccctccct gtccccccctc cctgttgagt 183840 gtctgcatcc cagcaacatt ccatttcctc ccattcccca gacacaccat gcccctcccg 183900
ttcagtgacc tggcacatgc tggctcccca gctggcacct ctcctgcaca aggccagttc 183960
ccacctgcag gcttaggtcc actgttgctc ccacctcaag cagaggtggt ctgggggctc 184020
cccagcccct gccttctaac ctgttttgcc cttgtgtgtg gcctggtcta ttcatctact 184080
gtcccgtgaa tgtgttaggg cagggcccaa gtatgatttc cccctttgtc cccagcactt 184140
agcacaggac ccaacttgga acatggcaag aggtctaagt ttgagccagt gtgatatgac 184200
caggcttctg gctcctaagg agtataagtg gccctagctt gagcactttc ctgaaagtcc 184260
tgtcctttgt gtgtggggta ggggcgcaag tgctgggaga gtctgaagcc aagtaatgag 184320
gctgttggtg ccaaaagtag gatgaatttt aggctgttcc caggattcct gtctccccac 184380
aggccagggc cacctctgag aggaccctcg aactcctgtg ctccaaggct tcaaacctta 184440
aagggatttt caggccacgg tgggaactgt ggctcttgcg gacccgttac tctctgttcc 184500
tatctcccgt ccgctctctc tttgcttctc acatgtggtt agggcctgca agtgtctcag 184560
ggagagagac agctgcaggg agcagagctg gcaggcccaa gttggggcag ctgttgaggt 184620
gttggggcag ctggcaggct gctggggctg ttctgggtct cggatggaag agggcaggga 184680
ggaaggttca gcctggagca gagggcttcc tctgcatctc tgcatcgctg agcccaggac 184740
ttaaggggcc cggagctgta ctgttcccct cagagaaggt cttctccagg cctggggtag 184800
gggtgacagt tgggagcaaa ataactttgg cccctggccc cctttaggaa tcctacgcca 184860
acgtgaagca gtggctgcag gagattgacc gctatgccag cgagaacgtc aataagctcc 184920
tggtgggcaa caagagcgac ctcaccacca agaaggtggt ggacaacacc acagccaagg 184980
tagcagacgg gccggtctgc ccggggtcgg ggcgctgggg cctgctgccc ctcacctgct 185040
ctcccctcct cttctctccc ctcctcttct ctcctctccc ttgtcaggag tttgcagact 185100
ctctgggcat ccccttcttg gagacgagcg ccaagaatgc caccaatgtc gagcaggcgt 185160
tcatgaccat ggctgctgaa atcaaaaagc ggatggggcc tggagcagcc tctgggggcg 185220
agcggcccaa tctcaagatc gacagcaccc ctgtaaagcc ggctggcggt ggctgttgct 185280
aggaggggca catggagtgg gacaggaggg ggcaccttct ccagatgatg tccctggagg 185340
gggcaggagg tacctccctc tccctctcct ggggcatttg agtctgtggc tttggggtgt 185400
cctgggctcc ccatctcctt ctggcccatc tgcctgctgc cctgagcccc ggttctgtca 185460
gggtccctaa gggaggacac tcagggcctg tggccaggca gggcggaggc ctgctgtgct 185520
gttgcctcta ggtgactttc caagatgccc ccctacacac ctttctttgg aacgagggct 185580
cttctgtcgg tgtccctccc acccccatgt atgctgcact gggttctctc cttcttcttc 185640
ctgctgtcct gcccaagaac tgagggtctc cccggcctct actgccctgg ctgcagtcag 185700
tgcccagggc gaggaatgtg gccaggggat ccaggacctg ggatccaggg ccctgggctg 185760
gacctcagga caggcatgga ggccacaggg gcccagcagc ccaccctttc ctctccccac 185820
tgcctcctct cccttcctac actcccagct cgagccgtcc agctgcggtg ggatctgagt 185880
atatctaggg cgggtgggcg ggtagcagtg ctgggcctgt gtcttgagcc tggagggagt 185940
ctgctcctgc cgccctctgc cctgccagag acagacccat gcgctgcctg cccaccgtgc 186000
ccctttgtcc ccatgtcagg cggaggcgga aggcccaccg tgccagaggc tgggcaccag 186060
ccttaaccct cactctgcta gcacctcctc cctttcccca aggtagcaca tctggctcac 186120
tccccactcc gtctctggag cccaccaggg aaggccctca tcccctgccg ctacttctct 186180
ggggaatgtg ggttccatcc aggattgggg gcctctctgc tcacccactc tgcacccagg 186240
atcctagtcc cctgccctct ggcacagctg cttcctgcaa gaaagcaagt ctttggtctc 186300
cctgagaagc catgtccctc gtgctgtctc ttgcctgtcc cacctgtgcc ctgccctcca 186360
gcttgtattt aagtccctgg gctgccccct tggggtgccc cccgctccca ggttcccctc 186420
tggtgtcatg tcaggcattt tgcaaggaaa agccacttgg ggaaagatgg aaaaggacaa 186480
aaaaaattaa taaatttcca ttggccctcg ggtgagctga gggtttttgc aaggaagttg 186540
tggtggccaa gtgtggtctg tggtctaagc ccagccttgg ggtgggggga tggaactgga 186600
accctgggct tggtggggtg cacgggggtc ctggcttggt ttctgtgtcc taaggctgct 186660
ggcaaaagcc cttgaccccg tttcctgagg ccaggaaagc tgcttgtgct tctgtggtct 186720
gtccccaagg gcccagcacc gttctgtcag ggaaagaggc aggcggccat cagctcatac 186780
ctggcgtgcc gccgccaact cccgcggggc acacggcaga ggtgtggggt cgcgcagccg 186840
ctgagagggc ccccactgca cctggcccaa cctccttcag cgccccccaa aaccccactg 186900
ctcccattca gcccctgtcc tggcgtcatt gtgtgtccca gccaggtgct tctgccgtct 186960
ccgacagtga caagtgcctc gcacttcagc ctttgccctg agcgcccgcc cgagggggcc 187020
gagtgcggct gtgccggtgg ctggagtgcc gaggggtgcg gggtgccggg ggcggccgcg 187080
tctacgctgt ccggagggtg aacggccgcg ggcttgtcgg ggctgggggt ggcgcccgag 187140
ccgggcgggc agacgagggg cccgcggaga cccagccccg cccgaggccg ctcgcgcggc 187200
ggccccgccc ccggctccgc cccgccggct tcgcgggctg gagagcgagg gagccgcggg 187260
cgagggatcg caggatgagc gatcggggcc cgggcagccg gcagcggacg cgccccccga 187320
gcccaccggc ccgcgccccg cgccccccac ggccccgcgg tcccggtccc ggccgcatca 187380
cccacgtccc ccgagcccca cgggccatgc ccggccggcc ctaagcgcgg gccgggggc 187440 gtccccttgc gcccgggccc cgcgctggcg ccccccgggc cgccgcccgg cgcgggggcc 187500
atggcgttca ccttcgccgc gttctgctac atgctcaccc tggtgctgtg cgcctccctc 187560
atcttctttg tcatctggca cgtaaggccg ggctggggct ggggctgggg gcggggtggg 187620
gggcaggggc cacgcggagc tggagggacc cagggcgggt ggtctcagag cccaggggaa 187680
acttgctatc ccccagccgt cggcttgtcg gcttcgcccc cattaacacc ccccgtggtc 187740
ggctttcttc ccggggcccc ccttcctccg ccgcccccgc ctgtctgtgt gtatgtcagt 187800
cggtctctga cccccctcctc tgccctcgtc ctctgctccc atgcagcccg tgaggtgggg 187860
ggtggaattc tggcattttt gttgctttat cttctatgtc cccccccacc accatccagc 187920
cgcctccatt agtccgtcgg gcagtttgtc tgtctgctgc cccccccccc ccgcctttgt 187980
gggtttttcc agccagagtg atggagctgg ttgctatggc aactgcatct gtttacagga 188040
cccacagatc tcagagtcca ttaacccttt gccttcccag ccccctccct gaccaagcag 188100
cagttggctc tcatcagccc ccagagacct agcccccacc accggctcac cttgggtttc 188160
cctacccctc ctgttggggg cttcccagcc ccccaggttt cctctccatt ttccagcttc 188220
cctcctcttc ctgtccccct tccccttttgt ctctcacata ccccttggtc tgtccctcgc 188280
cctggcctag cctcacacct ggttcttcaa aatgtccatt cctcatcctg catccgaccc 188340
atcgcttccc ccaggctccc tcctcctccc ctcccgctcc tctcctccag ggcctcctct 188400
gcctggctcc cgtcccctca ctacagaact atcaatcagc ctccagctgg ttgttggggg 188460
cccctggccc cactttactg ccctccgtcc ccaccccccac ccaaaccccg tgcctgtttc 188520
tgtaacagcc tgcccagctc ggccctggct ggctcagctc agcatcctct gctcacacct 188580
cccgcgcaca cctccctgat tgtcattccc tttcaggggt cctcttatcc ctccctcaat 188640
cccatttccc atagcccttc cctccttcct cccggtgcct cacctgcttc tttcccgggc 188700
tctccacttc ctctctcctt tctcttcctg ggacctgccg cctgctccat ggttcccccct 188760 gcgctccctt tgccatcccc tgccaccttg ctctttgaca tcgggaatcc atagactgaa 188820
cccctactgt gtgaagagtg agcccccaaa ggcacctcag cacacacccc agctccagcc 188880
ctgtcactcc ttggcctggc tctgctctct ctctgggtct tggttgcttt gtctttcccc 188940
ctctcccccg caccccgagt tactctattt ttctttctgt ggggtagggg caggagggct 189000
agggttctaa ggactggagg gagctggggg ccacaggcta gggaatgcag agctgaccag 189060
ctcctgggag aagggctcct ggaattcaag aagcctcttt ttggggcctt ccccacccag 189120
ggccttccca cagcccctgt ggggtccctg tcctcagggg atcctcagca gtttatccac 189180
cacgcctgca ttgatgcttc ccaaagatca ggctctgggt ggctttgagg gggtcaagga 189240
tgaataaaac ccagactttg cccttgtgga gtgcccaggc tgggaggaaa ggcccaagct 189300
ttgaagaaat gtctttgttc attcaacaga tattgattga gcacctgtgt gaggtactct 189360
gtccactcag ccatttagct ggacaatctt agcaagtcat ttgtcccaag tctggttcct 189420
cgccggcaaa gtggacctgt gcacatcaga gtgcctagtg cggcctgctg ggtggtaggg 189480
gataggaggc gtggtcctca gtccacagct gctaagaact agactcttaa cagggcggga 189540
ccccagatcc cactccagac cctcagccca ggccccagtg gttcctaggc aaccctggcg 189600
gtgagtgacg cgtgtcagct gtcaccatgg gggattgttt gttccggggg gctgagtcag 189660
cgccaggcag cctggggggt gggaggggtg acgcccgccg cctgctggtg gtgccagctc 189720
tggggtacag acggcaccct tctgctccct gtggaccctg ttgctgtgcg tgccaagtgg 189780
cgctgcccag agtcaatggg gagctgggcg gggagggggg atgatccaga tggcctcagc 189840
tccctccagg aagcccatgt tctttctctc tgagccgtct ggggcctggg atgcctgggg 189900
gtggtgggcc tgctgcctca tcctagggct ggagccgaca ggaggggacc ccagcaggct 189960
cctctgccag cccatttccc ccaagtcacc tgtcagctcc ttcccatccc atcatcccct 190020
caaacacttg ctcccctgga gagtttccac ccgtgaggac actgccgtct gccagacacc 190080
ccaacacctg aagccacctt agatttctgc cttcacttct cagccatttg aaccctctgg 190140
agtctggctc ctaaagagct gtagaatccc atgcacgcct tccgtctcca ctacaactct 190200
cctcactcag accaccatca gccctgcccc taaccctcca aaccgtcccc ttgctggtct 190260
ggcctgagta tgacacagtg gttaggaatt ttaactctgg agtcacactg ggttagaatc 190320
cactaaccag ccgtgtggcc ctggacaagt cacttaacct gcctcagctt cctcatctgc 190380
aaaacagaca tgaaaataaa actagtacct aagtcataag gttgttaaga attaaatgag 190440
tgaatccaca taccggccag gagaagcacc acttagatct cagctgtgac tgtcagtgag 190500
ctcggatttc ctgccccacc aatcctgaga catggaccaa tcctaagaca tggacctgac 190560
caccccactc tgctgctgtg tactcttcaa tgcctccccc caaaattttt gtgttaaagt 190620
aagtccaaac tcctgctctg gcctcacagg gcgcccatgt ctggctctgc tgaattctcc 190680
agctcctctt ccaccactct ctcttttctt cctgctcgct gcgctgtcac gccagcccca 190740
tgaaacccgc agcctcctga atgtctcctg acctttcacc cctctgccat tgcaccttct 190800
actgcttgga ctgcatttcc cccatttgct caccaacacc tactccgagt ccagcctgaa 190860
ctccctcacc ccccacacag ggttaagcgc ccactccagg tcctccctgt accccaaacc 190920
ctgatcacct ggaaggcaga gtgatcatcc ctctgggcct gggttcctcc tgggcagggg 190980
ctgcatccca ggcctctgga gccccagtgc tcagcacagg gcctgagact tggcagggca 191040
gacacgaagc catgtcttgg gatgttttgg aagggggtgt agtggacatg ggcctgaact 191100
gggcatccag acgctagggt tcccttctgg actgttgtaa tgaccttgga ccaggccctg 191160
ctcctccctg gacctcggtt tctccacctt tgcaacaagc tccacctggc tggtcctctt 191220
cagtaaacta tcccacagaa ggacttgggg gaaggccata agctgctgcc ccaaccctga 191280
cgggcacacg cccctccccc agatcatagc ctttgatgag ctgcggaccg acttcaagaa 191340
ccccatcgac caggggaacc ctgcgcgggc agtaagtgat acatgtgctg tgccgaggtg 191400
tgtccgtccg tctgtctttc catctgtcgt gggctggggg tgggagacgg gaagacgggg 191460

-continued gtggggtggg gggcctacgg ccatgccccc ttcctctctg tctccgcccc cagcaaacac 191520
ctggcgcggg ctcagggctg agttcctctt ggcggggcgg tggttgccag gctctgggcc 191580
gttgccatgg agacgcgggt gaaggccctt ccatggtgac ggtcgccatg gggacggcgc 191640
ggctgcttcc cggccgtgcc gacagtgccg cagagatcgc tctggcgccc cctggcggcc 191700
acatgtggag cggtgggagc tgctccagta cctgcttctc cgccacccca tcgcggcctt 191760
ttccttcccc caacagcgcg agcgtttaaa aaacatcgaa cgcatctgct gcctcctgag 191820
gaaggtcagt gtcagggctg gggcaggag gctcctagcc cagcgctgcc cccactgtct 191880
gtggcccaga accaggcctt cccctgcttt gggcctgttt gatccactct acttgggagg 191940
gagtgggaag ccagaggcct tttaatcccc agaggtcacg gtgggtgggc acctcccaaa 192000
ccccagctcc tctctgtccc cttgaaggct ggtctgtcat agcaccaggc cgctgacctc 192060
tcaccctcac tcccccagct ggtggtccca gaatactcca tccacggcct cttctgtctg 192120
atgtttctgt gtgcagcaga gtgggtgacc ctgggcctca acatcccccct cctcttctac 192180 cacctctgga ggtgagggta gcagctgcct tggggaggct gagatgggga acaggggcag 192240
gatgggggtg ggagtcctga tggcagacac tcaggcccct gtctgcccca ggtacttcca 192300
ccgtcctgca gatggctctg aggtcatgta tgatgcggtc tccatcatga atgctgacat 192360
tctcaactac tgccagaagg agtcctggtg caaacttgcc ttctacctgc tctccttctt 192420
ctattacctg tacaggtgag gccttgccca cagcagtcag aactcaggga agggatgtcc 192480
cagcatcacg cttccaatcc caagttcctg ccttttgccc ctgaggactg agggcagccc 192540
agggtgtgac caggtgggca tctgggtggc tgtgtgtgtg cagggctagg ctcactggct 192600
catcttccta cagtatggtt tatacgttgg tgagtttcta aggggaagc cggccaggga 192660 gcgagcccag aacggaccgg acgcctgtgc acccccagcc ctgccccttg gccgcagagg 192720
cctcagccct ggggagggag ggggcactgg tgcccccagc ctctccaacc cccaaactgc 192780
tgctgcgggg aacccccccc accccgcctt cagagccctc cccttggac tagagcggct 192840 gggcagagct ctaaacaggg gcaggggctc ctctgccagc ctgtgggcat ggcagtcatt 192900
cctggaaggg gcaggacctc cggccttgtc catttcgggg gaaacttggg ccctgccaag 192960
gggcagagct tgaccctgga aattctgggc catccccctc cacccccacc ctgaggctcc 193020
ccctgcaggt gggggggtac ccgcaccggg aatgagcagg ctcagcaggg gggcagcccc 193080
acccctagtc tgccctcccc tctcccccag gctctttctc cagccctgtc tccatctgcc 193140
ccaacctcag cccaccttgt ctcttggacc tattttctat gtcgcctgga ggagtccggc 193200 acccccctccc cggccatttg tgacaaaata tgaataaact actgcaaata tgtgggcccc 193260
ggttctgctc ctggaaagct tgaagaggag atgggggccg attacaggga ctgtataggg 193320
ggcagcccta agctgaatcc ccagcctggc ttgtctcacc ccactagccc acagaccctg 193380
ctggagcccc ccagagggat cagacgcctt ccaggtcccc tcagcagcct ccttccatct 193440
tctctttccc agctgaggct gctgaaaccc ttacaaggca gtatcaaggt caccaaagtc 193500
atgaagccct ccctgggtcc accttcttcc tagacggccc caagcccgat cccctgggca 193560
atgcagaggc gcagaggtat ctgtagctcc ccatcaggcc ccaggaacaa gggtcagaca 193620
aagtcaagga aatcaaatct tcaatgaatg aaaaactcag tgccatctgg ggccaggggg 193680
tcaccggacc aggtggaaag tcagccagta tatgatgagg ggctggaagg ctgcagctcc 193740
cagagtcagg tagagctgga gacgctgccg ggggacgggg ccccccatgc tgtcggggcc 193800
cagggctgct gtccgcaaag agcgcacctg gaagaaagga gaactgaagc ctggccagga 193860
gggggaggtt tgccctcaag tgaaggcagg ggaatggggg ggtgcaccag actcacaatg 193920
aagtacatga gcgccgatga ggtccaggcc agcgccacgt agtagccatc gctgccgaac 193980
agcagccccg tgagcacact gaggatcatt ctgggggtgg gaggaggaaa gggttggtga 194040
cccccagggg tctaggcctg agattggccc taccccaac gcccagagcc cagctagacc 194100
ccacctccca cagcaccttt tactctcaat ctgtccccac agggacccag accccaaagg 194160
gatatggaag gcccaggact cagccccagg acctggatct gagacccct tctctcccca 194220
agactcgcag agtgactctc aacacctccc caacctctgc atggcacgca gatcctcagg 194280
agactgctgg agacagctgc tccctcttaa cagagcagtg ctagaggtca ctaggggccg 194340
agacatgtcc agggtcacag ttcgaggcta cagctatgca ggcccagatc caaggccacc 194400
tccccctggc ccacaagtgc tcaccccacg tatttgtagc cactgtaggc cagcaggtga 194460
aaggtgctca ggtcactgcg cacggtggcc aggtagaggc ccaggagcag ggccagcacc 194520
tccatcacca cccacaccag cgctgtgctt gcacacaggc ccagcacctc cggggagaac 194580
ctgcgccaaa gcaggggtgg ctcagagcca ggcatcctga ggcaggggtg aggaagagag 194640
actggggcaa cagagggtga gctggggacc accacatatg ccctagggag gttgggagaa 194700
gagctcacag ggaggggagg gtaagggagg ggcttggcac tgaccttttc tgaatgccca 194760
gtgccatccc agccaggagc acgtaagtaa tgaaggccat cgctgccaag tgccagagag 194820
atgccatcag cttggcttcc tccatcagag ctgccttact aggcattcgg gttcaccgac 194880
atgtcccata cttccttctc tgaatagccc agcatggcct gacctccaca ttctgcttcc 194940
aaatgccctg cctggaatgc ctgtctccga tcagccctct cccactgtgt aaatgccacc 195000
tgacccttct tccagaacca caagccacct ttcctgtccc tgtgctggga agctcatcag 195060
tgttctgctg catctcagaa actgtatcat gggccaaggc cattgttccg cctatacagg 195120
gaccaaactg gtttctggca agaccagaag ccaggttcag tggacaccca tgctgtcctg 195180
agtctggggt catggagatg acctcaccgc agtcagcaat tctaagtctc agcactggct 195240
agggctctgg ctgcccaaca atgcagggaa ctccaagttt aactttgggc agtattcata 195300
aaagctcaga gccagtggga gccgggcatt agcagcagtt ttaactctgt cttctgcccc 195360
gcttaaagca ctagaattgg ctgggcgcag tagctcacgc ctgtaatccc agcactttgg 195420
gaggctgagg caggcagctc acttgagccc aggagttcaa gaccagcctg ggcaacatgg 195480
caaaaccctg tctctactaa aaatacaaaa attagctggg cctggtggca ggcgcctgta 195540
gcctgcagtc ccagctgctc aggagactga ggcaggagga tcaccacctg agcctgagag 195600
gcagaggctg cagtgagcca agatcacacc actgtactcc agactgggtg acagagtgag 195660
accctgtctc aaaagaagaa gaaaaaaaaa gcactgacat gaccaccagc ggggagtgtc 195720
tggagttctg gagtcaggaa atcagctgta ccacctgtca actttgaggc ctcaatgata 195780
ctgaagctcc tctgaggctt ggcttcaaca tgtaaaatgg ggatgccagt tccagcctta 195840
cacggtggct acgatgggca cacgggatga aggatggaag cccctgtgct gcccagcaca 195900
cctaggctgg ctgcctgccc tcagtcccac tggctgccct cactggaagc tcatctgcgg 195960
gctggtccct gcacactcac tcaccctggg tgtccacgat gggcctggcc ctgtgcagcc 196020
aacaggacag agaagagtca gctgtatgtg tgggcagcct gaaaaatgcc atgtggacag 196080
gcagttgtgg gaacccagaa gggagccacc acttgctcag gggtcagga aaggcttctt 196140
ggaagaaggg ataacagagc acgccttgga ggacaagcaa taacgatgat aagagttaat 196200

-continued gtttcctacg tccttcctgt gtgccaggtg aggtgctgag caaacatcac cttgctgaat 196260
ctctccaaca gtcctttggg gtagggacta cattagtcct gttttactga aaagtacaaa 196320
taaccagcct gaaatcccat agctggagtc tgcaaagcca ggtctaaacc cagagctcca 196380
ggctggggag ggatacagtc caaatcaaga aacaggaagg tctcaaaagg gtgtcctggg 196440
gacactgaag gcgcattcag gaagctcctt actggtcacc ctgcactgcc tgcctggtgt 196500
cttgcaactg ccacacatac acaaagcacc aagaacagat gctgactcag tagctgcgcc 196560
tctcttccca ttcatccctc aaggcacaag tccccccga ccccacccca ccacgttccc 196620
cagcccaggt tggagactca ctggggatat agaggtcagg ggcgttgagg tcttgccggg 196680
ggggcagagg agcatcacga ctgtactgca cttcccagtt ctggcagtgg cagtggcagc 196740
agcggccaca tcaggagggg aagaagagaa aagaggagag aagggggttg aggtctgggg 196800
gccagactcg ggcagaatga ggaaggccca ccagctccct tggtaggaag ctcacctggt 196860
gtgtgtaggg gaagaccagc agccctagct tcttggccac gtaggctgtg tccacagcaa 196920
aaaaatactt gagtttgctc acagacacaa aacggtgcag ctgggagggg agagaggaag 196980
ctgtgggcaa gccgcacccc aggcctcagg gtgcccctct gtgtgctcca tccctgaggg 197040
cactgtgagg aatcgggtgg aatcccatga tgccccagcc ctagccaaaa attctgccac 197100
ccgtgccccg ggggcaggcc acacctcctt gtgcaccatg tccttcccat gggatgcgat 197160
ggagctgcca taggccatag ccacattggc cattgggtcc ccaagcaagt ggttgacact 197220
gaaggccacg tctgctcctg tggctgggta tcccccgggc tggctggaat aaccaccgct 197280
tgtgtcatcg aagaggggag ggggatccgg ggctgcccgg gccctgtgct tggagcctgt 197340
gggtttggag gtatcagagt agatgacaga aataccaagc atgagcccaa accaccgccc 197400
cttccctggc tggacagccc tgcacgggtc ctggaggcac cgatcagtga ggggacccca 197460
agctgggtga gggggagcta actgagaaaa aactgtgatg agggatcctt tgcgagaaat 197520
ccgttgctaa atgtaggcaa agaaagagct gaggcagcgc ctagaactgg ttgcccactt 197580
ggggtttctg aaggcctctc actggaagtg acctctgaac tgagccacag tgagtagaag 197640
tgtgctaggt gaaaataact gggagggcat ccttccgtga acaaagctgg gagaggcgac 197700
agctggctac ctggaggccc tggacagtga tcagggacct catcaggttc acaacagtca 197760
aaggagtttc tggaggagga ggcggacccc gtttttgccc gactccggca tgggattccc 197820
aggactgggc cgagagggcg aagtccggga cgtgttggag tgttacgagg ggcaggaacc 197880
cgagtgacac ccccgccctg ggcggcggtc ccagtcgcta tctccctcgg ggtgagcggg 197940
ccacgccgcc gactctcccc ccgccggccg cgccgcgccc cgcccgcgcc ccacgcaccg 198000
tgggctccgt agcccgagtg ataagccatg gccgcgacgc tcgctgtccc cgagggcccg 198060
ctgcgccgcc tcgtgggtac gaatactaat gaggcagctg ctccgcgccc agggtaccga 198120
ccgaggccac ccggccgcgc gacacgtccc ccacccccgcc ggtctcggcc accatgtccg 198180
tggcgtcatc ccccgcgcct gccattggct cttcggcggc gccggctcgc ccctcccctc 198240
tcccaattgg ccactgacga gctctggcct gagcggattc ggcagaaggc aacatccggg 198300
tgagggacag gcggagcgac ttgcggtgcc tgggattgga tcacgggctt gccagttcac 198360
ggtgggaaca gccaatagaa gagttaagaa agaaggtggg cgagaattat ttgcgcgcct 198420
gcgcggtgag gcacttgacg caccctgcca cgactacacc agggagtcga gaggtaacct 198480
gcagccggag tcaggagcaa agcttccttg gtgggacgta ctccaggagg gaacggggcg 198540
gtcgagttcc aaccaagccc tgcccttcgg ggcgcctgtt tctccctctc tgggcttgtt 198600
ttcctccccc gtcacctaca cttcacccaa tcttggaacg gagccccggc agacccggag 198660
gtggtggtgg gaggccggac ctatcagtga cagagctgcc aagcaagccc caggatgctg 198720
actccacccg cctcccactc ctcttctccg cgcgggtgct gtccgtcgtc cggtgctgaa 198780
aatgtcctcc cgcctcagcc gccatcctgt agactcccgg gggcctgcgt atgggaagat 198840
ttggggtctc gaaccacacg ctcctagcga gcgcgtggcc gcacgcacac atacacgcat 198900
actgcaaaac tggggcccag aggatccgaa gtctgagaga ttgggtggta taggtggggc 198960
aggatcctgc cccgggcctg tcccatagac tctcccgtag tccagcagat ttgggggcag 199020
aggtgtgctg atttgcgtcc tgaagctgca gcctaaactc ctgagtcatc gccgggcctg 199080
tggtcttctt gaagtgaggc ccctaagcct cacttgtagt cccgggggtt cctttctctc 199140
cacccaggtt ctgatcactc ccaaccccgc ggagacagtc ttcaggggcc tccctctcac 199200
agaccttcag ccaccgcttt ctagagagca tgagcaggtt ctctgcgacc tctctaatta 199260
gctaccaggt atccagttac accagatgac cttcctgctc cccaaactca gcccacgtgg 199320
tctgattgca gtgccattgc ccagaggtcc cctccacctg ggatgccctt ccccctcata 199380
tccacttgtc cataagccta gttatcttta agagttagtt catctcgtgc ctctcagagg 199440
gacaaagggg acagagacct gacccggtca ggggtggagg tcataggttg ggttctaggc 199500
cccctctggg tgcacccaat ttgccctgca tgtaagttcc atgaggacag gccctgttgt 199560
cattctccac ttccaccctt gtcttcccag tgccaagcac aatacttgca tatggaagac 199620
acccaataaa catctgtgtc caagaaattc ataataaata gataaaaccc tggaccagtc 199680
ctttcctgtg tccacatctc aattacctaa tctttaagtg ggtaaggatg tttaattgaa 199740
tggtctttga gttgctcttt gcctgaacac acgcacatac aaaaatgaat taacccacca 199800
gtattgcagc tcattttctg cccatattgt ctagtttggg agcaaagcca gacccagaca 199860
cagatgtgaa gatctgaggc cctggagggc taggaggtag cactggggcc acgtgtacct 199920
gggagggggt catctaatgc aagtcagttc ccatgtcact gcagggcaca atggatactt 199980
gtaaactgaa tccaaaacct ttctatgtct tttcttttcc ttctttcttt ctttatttct 200040
ttttctccct ttctttctgt cttcttcttc ttctccttct ccttctcatt cttcttctcc 200100
ttctaggcag ggtctcactt tatcacgcag ctggagaaca gtggtgcaaa cacagctcac 200160
tgcagcctct tactcccaga ctcaattgat cctcctgtct tagcctccca agtagctggg 200220
aatacaggtg cacaccacac catcatgccc agctcatttt ttaatttttt gtataggcag 200280
ggtttcgcca tgtttccaag gctgctggaa ttcctggact ccagtgatcc tcccacctcg 200340
gtctcccaaa gtgctgggat tacaggcatg agccactcag tccagctttt atccccattt 200400
ttcagatggg aaaactgagg ttgagagtgg agcatgctgg cccaaggtca cgcagcctag 200460
ggtcccttgt gtcctggccc cagcctgcct gtcctaagct gagcccagca cccctgccca 200520
gccagtgaga ctcgtcacgc ttttctcagc tgtaactacc ctcttctcca agtgaggctt 200580
cagggatggg atctgggtgg gcttaactct gggcctactc cttagagatg ggaccccgcg 200640
agcgcccacc caccttggag attctccttc ctcgagggtt ttacagcccg ggaagctcag 200700
gcgccagagg gttagaccag ctcaaggtcg cgagcgcgag cgcggccgga ggagaaccca 200760
ggggtccagc cgcccagcgg gggcttctcg gggacgggcg gagcgcccgc ggtgccaggc 200820
gctgccggcg gcgccgccgg tgccgcgggg gcggggtcag cggagggcgg ggcgcctggc 200880
acccgggccg ccaacgccgc cgccgccgct gccgccgcgc tcgggctcga gctccgcgca 200940
ctccctccgc ggccgctgag ccgagcggac gcccccgggg gccgcgtcgc agccctccgt 201000
gctcccccct atcatgcccg gtgcccaggc tggggccgcc caagcagcca ggacaccatg 201060
cccgaggacg gcgctggcga cggcggggag gtgcccgcgc tcatcccgga cggcgagccg 201120
ctgcgggaag aggtaccggc gctgggggg ccggagccgg gcctggggcg gcgtgagagg 201180
gaccagtgca aaaggcgacc ccaagagagg ggctgaggag ggaagtccca gagcccctac 201240
ggccaatgac gtcattgggg tcacctgcgc cctgccaagg gtccaggggc ccgcgttggg 201300
ggtaggggtg gggcggctgg acagcaatat gcggggcgac ttccgccccc ggcgtcccct 201360
catccagcct cgcccgtcct gtgacgtcag tgcctggccc ccacgcgtcc cagtgccgca 201420
gcgcagcggg ggatgctgcc cccaccccca gggccgcggg gtcaggtccc cagcccggcc 201480
cagccgctca cgaggtgtcc gggcagcgcc tgcaatgcag cagcagtcgc agagcctaga 201540
ggggaggagg ggaagaggaa gggaggcgcc tgggtacccc ttctccttgt cctcgaggtg 201600
aggattgagg gcccattctg ctggctggga cccccgacgg cccctcctca gccctagcca 201660
ggaaggtctg caggacctgg ggccccgagt gatgtgtggg gtgatagggt ggtgagtggg 201720
gctgtgcatg catttgggtg aatgtagcct gcttctgtgt gtgtgttgtg tgggtgtgtg 201780
aattgggtgt gtgcgccctg tagtcaggtg aggggcgagt gggtgcctgg ctcgggttgt 201840
cacccagtgg tctaggtgtg cgcatgtgag tgagtccctt tgtgggcagg tctctccctg 201900
tggagtctga ggagcctggg ggtcagtttg cagtgggggg tggggagatg tgcactgtgg 201960
tcaggtgaag gtctggtatg tctctgggct tcactgcacg tgcaacgtgt atgtgcacgt 202020
gtgtgtcctg tggtggatgg gtatgtggtg tgtgcgtgtg tgtgtgtatg tgtgtgtacc 202080
atgctacggt tctgggagtc tgtgccctgg g 202111

<210> SEQ ID NO 3
<211> LENGTH: 18933
<212> TYPE: DNA
<213> ORGANISM: Homo sapiens

<400> SEQUENCE: 3
tttcacgcaa aggtggctta agggctagtg gtggcccggg aagtgtgctg agaatgggtg 60
gatttcacta agcaaagaca tggcaagcaa tgtcttggac agccgatgct gcccagacaa 120
aggcctggtt gtcgggcatg agctgaggtg tgacaaggag atagaagcaa gaagccatgg 180
aaggctttgc tgcagcttcc atgccaaacc ctagaatttg tccttaaact ggagcaaact 240
gggcaatctg gaaccatgga agggggttgg gcagggacgt gatacagtca aggctgcatt 300
ttaggatatt tagcaaaagt ccagcgacct gctggctctg tcgggagggt ggagtgaaag 360
accagagttc tccctgtgcg ttaacccaca gcctctcttc tttgggtgtg aaatcagttc 420
ctcgttcaga agcaaattag gtggaaaacc ctgtggtgcc caaacattca acaaggctgc 480
agggggtggc caggcacagt ggctcatgcc tgtaattcca gcactttcgg aggccggggc 540
agacagatca tttgaggtca ggagtttgag atcagcctgg ccaacatggt gagacacccc 600
ccacccccgt ctttacaaaa aatacaaaaa ttagctgggt gtggtggcgg gcacctgtga 660
cagctactca ggaggctgag gcaggagaat cgcttgaacc cgagaggcag aggatgcagt 720
gagctgaaat tgcgccactg cactccacct gagactgtca aaaaaaaaaa aaaaaaaaaa 780
ggctccagca ggtagggagg ccagcatgct ggtttcagct ccttgccatg ggaaagaccc 840
tttttccacc attctgctct aacaccatag ccaacaactg cccactggcc actcactgtc 900
cattctcctc ccttccccaa taacagaacc ccagttttgc tgcagaaggc aatgtgccca 960
gctaaagggc aacatttcca gcctccctgg catatatggt atgactgtgt ggctgaattc 1020
taggatatta gatataaaca gaaggtgctg gaagggatct ccaagaatgc cccttgaata 1080
gaagcagtat tgatgaaggc catttttgtc ctctctgctt cagcctgcat tcagccttgg 1140
atgcatatgt gatagctgga acgccagcag ccatcttgga gcaggaaatg accttgaaaa 1200
ttgtagccac aggctgggcg cggtggctca tgtctgtaat cccagcactt tgggaggcca 1260
aggcgggcgg atctcgaggt caggagatcg agaccatcct ggctaacacg gtgaaaccct 1320
gtctctacta aaaatacaaa aaattagcca ggcgaggtgg caggcgcctg tagtcccagc 1380
tacttgggag gctgaggcag gagaatggca tgaacccggg aggcggagct tgcagtgagc 1440
cgagactgcg ccactgcact ccagcctggg cgacagagca agactccgtc tcaaaaaaag 1500
aaaagaaaaa gaaaattgta gccacatgct gaagacagca gagcaacaag ggaaaagatc 1560
ctgggcttct gatgacacca tgcaagtttc catgtcatcc cttgggtcgc ctacctccag 1620
acttcaatga gaaagagaaa taaactgtaa gtctgcttaa gcccattgct tttttttttt 1680
gtctctgtta ccagcagctt ttaccaatta tctactgcca cataacaaat tatcctaacc 1740
ctagtggctt aaaagagcaa taattattat gctctctcct ggcttctgtg ggtcaagaac 1800
tcagatagga cacaatgggg atggcttcta tgctccacga catccagggc ctctgctgga 1860
agactcaaaa gctggggctt gaatcatctg aatgctcatt cactcacatg tctggcagtt 1920
gatgctggct gagggctgag ggctgagagc ctaactaggg ctgttggtgg gaacacccac 1980
acaggtcctc tccaagcggc ttgaccttcc tcataacatg gtggctaggt tccaagaaca 2040
agtatactga gagggtgaaa gctgtattgc actttgtgat ctagcctcct aagtcacatg 2100
gcatcacttc tgcccctttc catcggtcaa ggctactatg aaggtccact cagtttcaag 2160
gggagggaat ataggatctc atctctctgt ggaggcttgt caatgtcaca ttgttagaaa 2220
agcatgcggg atgggagata tattagtggt catcttcaaa aatgcaatca actgctgagc 2280
caaatgccat ttgccattcc taactgattg atacctgtaa agtgatctgc aaaatgaaca 2340
ccaagctctt tatagtgctg gtttaaggaa ggaaggtggt ggcatgtcag atatgggcct 2400
gctcagggca aagtgagctg ctcagatcat ttatggggac cttcaggcct atggtagatt 2460
aaatatggcc acaaattctt tgccactcct ctcctcaaga ggtggaatca ggccgggcac 2520
ggtggctcac gcctgtaatc ccagcacttt gggaggccaa ggcaggtgga tcacttgagg 2580
tcaggagttc aagaccagcc tggccagcat ggtgaaaccc caactctact aaaaatacaa 2640
aaattagctg ggcgtggtgg tgtgcacctg tagtcccagc tacctaggaa gctgagacag 2700
gagaatcact tgaacccagg aggcagaggt tgcagtgagc tgagatcacg ccactgcact 2760
ccaggctggg caacagagca aggctccatc tcacaaaaaa aaaaaaaaaa aagaaaagaa 2820
aagaagtgga atctgttcgc cctttaaatc tgggctggac ttgtgatttg ctgtgactga 2880
ttggatgtga gggaagagat gttggcccac ttctgaggct aggcctcaag gactctcgca 2940
gcttccacct ttgccctctt gcaatcctga gaccaccatc tgtaaagatg tccagccaag 3000
cctcctgaca gatttgaggc tgcgtggaga actgaggccc ccagccaaga gccagcatca 3060
gctccagata tgggatgaca gaggccatct tagacactgt agccccactt gagccgcaga 3120
tgacaggagc ctcaggagtg acccaaggtg agaccagcag atgaactacc aagctgatcc 3180
cagcccagac tgctgtccta tagaatgagg ggaaataaat ccttgtttta atccactaca 3240
ttttggagtg atttgttaca tgttacatga tcactgtcac aaggctctaa acccacctgc 3300

-continued

```
acctcatgag ggagggcact gggcctgcac agccaggaag aggagggacc cagaagcccc   3360
attgtttgat ggacagctct cagctcacaa tctcctgatg ggagatgggg tggccacgtg   3420
ttcagactct cttggagtca acatcaagcc aaggtgttct gttctaaacc gttctcaaga   3480
gaagaattca tgcctgagaa ggggtgcaaa gcctggctcc caaaccccag cggcctctgc   3540
ctctgctctc tcctgacata ggctacccac agcatggcag gaacagaacc tgtaatttcc   3600
acccctacca ccatctgctc ctctctgtct tccatctcag gaaatagagc taccattcag   3660
ccagttgcct aagccaggca ccagcacggc aagcctcttc tttttttttt ttttttttga   3720
gatggagtct cactctgtcg cccaggctgg agtgcagtgg ccaatctcag ctcactgcaa   3780
gctccgcctc ccgggttcat gttcatgcca ttctcctgcc tcagcctccc gaatagctgg   3840
gactatgggt gcccgccacc atgcccggct aatttttttgt atttttagtg agacagggtt   3900
tcactgtgtt agtgttagcc aggatagtct cgatctcctg accttgtgat ctgcccgcct   3960
tggcctccca aagtgctggg attacaggca tgagccaccg cgcccagccg cctctttttt   4020
tttttttttt gagatggagt ctcgctgtca cccgggctgg agtgcagagg cgtgatctca   4080
gctcactgca acctccgcct cccgggttca agtgattctc ctgcctcagc ctcctgagta   4140
gctgagatta caggcacatg ccaccatgcc tggctaattt ttgtattttt agtagagacg   4200
aggtttcacc atgttggtca ggctggtctc aaactgctga cctcgtgatc cgcccacctc   4260
agcccctcaa agtgctgaga ttacaggcgt gagccacccc gcccggctgt ctcttctttt   4320
tttgagaccg agcctcgctc tgttgcccag gctggagtgc tgtggcgcaa tctccgttca   4380
ctgcagcaac ctccgcctcc agggttcaag cgattctcca gcctcagcct cccgagtagc   4440
tgggattaca ggcacccgct gccacgccca tctaattttt gtatttttag tagagatgag   4500
gtttctgcat gtcggccagg ctggtcttga actcctaacc tcaggtgatc tgcctgcctc   4560
agcctcccaa agtgctggga ttacaggcat gagccaccac gcctggcctg ttctttcttt   4620
aaaactttgt attatgtaaa atttcagctt gtaatcccag cactttggga ggctgaggtg   4680
agaggatcac ttgagcttgg gagtttgaaa ccagcctggg caagatagtg agagcccatc   4740
tctaccaaaa agttaacaat tggccaggtg tgttggagct cacctgtagt tccagctact   4800
cagaaggctg aggtgggagg atcgcttgag ctgggaggtc aagaggtcaa ggctgcagtg   4860
agccgtgatt gtgccactgc actccaactt gggtgacaca gcaagactct agtctcaaaa   4920
ataaaataaa atatctttct ttcttttttt ttttgttttt tgtttttaga cagagtctcg   4980
ctctgtcacc caggctggag tgcaatggtg cagtcttggc tcattgcaac ctctgcctcc   5040
tgggttcaag tgactctcct gcctcagcct cccgagtagc taggattaca ggtgtgtacg   5100
accacacctg gctaattttt ctaaaaaata aaataaaatt tcaaacatca caaaagcaga   5160
aagattggtg cagtgaggcc ccttctactc agcacccagt gctgtgatga tcatccacct   5220
gcaaccactc tgggctccat ccacactcag ccccacttat ttgagctcca actggattat   5280
ttgaagaaga cctagaagct gtagcatttc gtcagctccc ctcacccgcc ccaccacgcg   5340
tgatatcgac cacccaagat tctactcaga acacaacaca ccccacctcc tctccacccc   5400
aagccacctt gctccaagtg cccaggattc ctcccccatg actccgacag gcctcccacg   5460
cccacttact cctgcggcct atgcagagac ctcatgtaaa tcaaatcacg tccccattgg   5520
tttctgtcta aagttctctc ccaccaactc tcagctcgct ttgcatttcc tttcggccac   5580
tcaccataag ttacaattat tttcatttat ttatgcacga gtttctttat ctgtttcttc   5640
tattagaatt aaggccatgg ggctggtcat ggtggctcac gcctgtaatc ctagcctttg   5700
```

ggaggccgag gcgggcggat catgaggtca ggagatcgag actatcctgg ctaacacggt 5760
gataccctgt ctctactaaa aaaaaaaata caaaaaatta gctggggcgt ggtggcgggt 5820
gtctgttgtc ccagctactt aggaggctga ggcaggagaa tggtgtgaac ctgggaggcg 5880
gagcttgcag tgagccgaga tggcgccact gcactccagc ctgggcgaca gagcaagact 5940
ctgtctcaaa aaaaaaaaaa aaaaaaaaaa agaatcaagg ccatgggagg cgaatagtta 6000
cacggccaga cccttgagtt ggttggaata attccaactc tccactacaa cctgagaagc 6060
cctgggcaag tcacttattc tctctcttct tcagtcttct catctgcaga atgagagatg 6120
acaatagaac ctatttactt caggccgggc gcggtggctg acacctgtaa tcccagcagt 6180
ttgggaggct gaggcgggag gatcacgagt tcaggagatc gagaccatcc tggccaacat 6240
ggtgaaaccc catctctact aaaaatacaa aaattatcca ggtgtggcgg tgtgtgccta 6300
tagtcccagg tacttgggag gctgaggcag gagaattgtt tgaacctggg aggtggagac 6360
tgcagtaagc caagatcacg ccactgcact ccagcctgag tgacagaatg agactccatt 6420
tcaaaaaaga tagatagaca gatagataga tgatagatag atagatagat agatagatag 6480
atagatagat agagatatat actttttttt aaattcatag acagggtttt gccatgttgc 6540
ctaggctagt ctcaaactcc tgggctcaca agatcctcct gcctcagcct ctgcagtagc 6600
tgggaccaga ggtgtacgcc accatgccca gctatatatg tttatatttt gtagcgatgg 6660
gatctcccta tgttgcccag gctggtctca aactcctgat ctcaagcaat cctcccacct 6720
cggcctccca aagtgctggg attacaggtg tgagccactg tgtgcccagt caaatttttt 6780
tttttttttt tgaggcagag tctcgctctg tcacagaggc tggagtgcaa tggtgagatc 6840
ttggctcact gcaacctcca cctcccaagt tcaagagatt ctcctgcctc agcctcctaa 6900
gtaactggga ttacaggcat gagccacgat ggccagcaat tttttgtatt tttagtacag 6960
acagagtttc accatgttgg ccaggctggt cttgaactcc tgacctcaag tgatccacct 7020
gccttggcct cccaaagtgc tgggatgact gatgtgagcc actgcacccg gcctataaat 7080
aaatatatat ttttaaatat ttatttattc cccatctaat cttatagacg gccttatcta 7140
aggctctctt atttatttat ttatttttga gacggagtct tgctctgtct cccgggctgc 7200
agtgcagtgg catgatcttg ggtcactaca acctctgcct cctgggtcca agcgattctc 7260
ctgcctcagc ctcccaagga gctgggacta caggcatgtg ccaccatgcc tggctaattt 7320
ttgtattttt agtggggatg gggtttcacc atgttggcca ggctggtctc aaactcctga 7380
cctcaggcga tccacctgca tcggcctccc aaaatgctag gattacaggc agaagccact 7440
gcactcggcc aataaatatt ttcttaaaag atactatgtg accgtgctta aatcagggtc 7500
tcaagcatag gaagtgctca ataaagattg ctatcatcat catttgcatt attataaatt 7560
acaagtggac gctccctctt acaacatacg cacacttcac cagcagccag cgcagtgcct 7620
ggcacacata atggatgtct agtcaatctg tgttaagtga atgattcccg atctcctacc 7680
aacacttcca acttcctggg gttagctggg tcctgagggc caagtggacc acggcccaga 7740
ccagccaaag ttttcattgc ttggccacac ttgcagtgga gcttttctga tctttggtta 7800
gtgggcttga gaacttaggg cacccaggga agcatttgcc aactacctaa tccagcaaac 7860
catggcattc tatgtttcct ccttggatcc agaccccaga ccactagacc cctagagctt 7920
ccccgaggtg gcaggcccag gtgcattcat tttttgtgag tttcatcttc cctcttacat 7980
cacacctgct gccttctgtt cttcagagcc cgtgagtatg aagtcactgc tgagatggcc 8040

-continued

```
tgggatgtat ctggaaaggg caaggaggat caggcatcca gccaaaagtt ggatacaccc   8100
tgagtgagga tggggaaggt gcgctgctgc ccttctgggt aaaggtcaaa gctcctggaa   8160
gtcagattca acagagacca agacagacag attggttaaa ctgatgacta catatcaaat   8220
gtagctgtgc cacatctgct ccaaggaggc atttctgtcc agaatatcag ctgagactga   8280
aattggctag ttctcagtaa cccatggtca cagtccaaaa gatagatgta tttttctttt   8340
ttcttttttt cttttttttt tttgagacgg agtcgcgctc tgtcacccag gctggaatcc   8400
agtgccgcaa tctcggctca ctgcagcctc cgtcttctgg gttcaagtga ttcttctgcc   8460
tcagcctccc gagtagctgg gattacaggt gtgtgccacc acgccccact actttttgt   8520
atttttggta gagacggagt tccactgtgt tagccaggat ggtctcgatc tcctgacctt   8580
gtgagccacc cacctcggcc tcccaaagtg ctgggattac aggcatgagc cactgcgctt   8640
ggccatagat gtatttttct tctcttttta aaaaacatat aaaataaaac ggaccaaaat   8700
acgaatactt ttttcagtag aatagtttca atttatgtgt tataaaagca caatacaggc   8760
tgggcgcagt ggctcatgcc tataatccta gcactttggg aggccaaggt aggcagatca   8820
cttgaggtca ggagctcaag accagcctgg ccaacagggc aaaaccttgt ctgtacaaaa   8880
aatacacgcc tgtagtccca gctacttggg aggctgaggt gggaggatcg cctgagtttg   8940
ggaggttgag gctgcagtga gccatgattg taccactaca ctccaacctg ggtgacagag   9000
tgagaccctg tctcaaaaga aaaaagcaca atacattata aaagacaata acattgtgct   9060
ataaaagact gcaaaagtgg gccgggcgtg gtgactcaca cctgtaatcc tagcactttg   9120
ggaggccaag gtgggcagat cacctgaggt caggggtctg agaccagtct agccaacatg   9180
gtgaaacact gtctctacta aaaatacaaa aattagtcgg gggtcgtggt acgtgcctgt   9240
aatcccagct accgggaggc cgaggcagga gaattgctgg aacccaggag gcagaggctg   9300
ccgtgagccg agatcgtgcc actgcactcc agcctgggca acagagcgag cccgtctcaa   9360
aaagaaaaaa aaaagaaaag agaaaaaaag actgcaaaaa gtatagagac tattttaata   9420
aagatcaaat tcctgttggg catggtggca caaggctata atcccagcat ctggggaggc   9480
caaggccaga ggattgcttg aggccaggat ttccagacca gtcccggcag cataccgaaa   9540
cccctatctt tagttaaatt aagtttaaaa aaaatgtttt ttgagacagg atctcactct   9600
gtcacccagg ctggagttca gtgctgtgat cacggctcac tgcagccttg acctcccggg   9660
cccaagtgat cctccttcct cagcctcctg agtagctggg actacaggca tgcaccacca   9720
catttttcat ttgttttatt ttaagagaca gggtctcact atgttaccca ggctggtctc   9780
aaattcctgc gctcaaacga ttctcttgcc tcagcctccc aaagtgcagt gctgggatta   9840
taggtgtgag ccacctcgcc cagcctaatt ttaaaaagat caagttcaaa cctccataat   9900
taacttctga gatgaaaaca taatcatgta gaaactcaaa caatgtggac atacatgaag   9960
tcaggagtag gagtgccctc tgttgctttc caaagccaaa ctgggaaacc acgggtagga  10020
gtgctaggac tcctcgtcat gcttaaggtg gtggtgctgg tggtttctgg gactctccca  10080
gcagtggggt ataatggaaa ctcaaatctg accttgaacc tggacctcgg ttttgagccc  10140
cagattcggg tagccaggtg tcttaccaag cagtccactt agataacttc ccaacacctc  10200
aaactcaaca tagcccaagc tgaccatacc atctatcttc ccaaagcacc tttttcacct  10260
atgtctccat ctccgtgcgt ggcattaccc aggagaggac ctttcttctc cttcaattca  10320
gccagtcact gggtcctgtt caaatcttcc tgccggccac ccctcaatgt tgccgtcttc  10380
tcctgttcca actctgcctc tgcctaaggt ctcttcttgc ctgggcagtg ccctaagtgg  10440
```

-continued tcttatcata agtatacttg ctgttctcct atctagttac tttagtatcc ctcatcccta 10500
gtggagtctc tgaggcatag cagggtctca attaatattg aataaatgaa tgcacagttt 10560
attatcttag tgtgcagggg gctccagtgg cctctacctg taatagccct tgggtcagaa 10620
ggcaatatgg gaactctgag tgtaagttac cctcttagga accaggaaaa tagcctaggt 10680
gctctgtggg caagtcctgc agtaaaacac ttgggaggga aaaacacctg ggagggcaaa 10740
acacctggga gggcagaaaa tgaaatctac actttattat ttgcctatta gtgagagaaa 10800
ctgccacata aaagttgccc atcacttttt atctagctgg tattaagaca caagtggctg 10860
agcgcggtgg ctcacgcctg taatcccaac actttgggag gccaaggcag gaggttcacc 10920
tgaggtcagg agttcaagac cagcctgccc aacatggcga aacccccgt ctctactaaa 10980
atacaaaaat tagccaggta tgggggcagg tgcctgtaat cccagctact cgggaggttg 11040
aggcaggaga attgcttgaa cccaggaggt ggaggttgca gtgtactgag atcagaggtg 11100
gagtttgcag tgagccaaga tcatgccatt acactccagc ctgggcgata agagtgaaaa 11160
ttcatctcaa aaaaaagcca aaacacaagt acctcttttc tgtacaaata ctttttttatt 11220
taattaatta attttttaga cacgaagtct tgctgtattg cttaggctgg cctcaaactc 11280
ctggatcaag cgatcctcct gtctcagctt cctaaagttc tgagatcaca agtgtgtgcc 11340
actgtgcctg gccaacaagt atttcttttt ttttcttttc tttttttttt tgagagagag 11400
tctcactctg tcgcccaggc tggagtgcag tggcgcaatc ttgtctcact gcaacttcgc 11460
ctcccgggtt caagaaattc tctcgcctca gcctcccaag cagctgggac tacaggcgcg 11520
tgccaccgtg cctggataat tttttgtatt tttagtagag agggggtttc accgtgttag 11580
ccaggatggt ctcgatctct tgacctcgtg ttccgcctgc ctcagcctcc caaagtgctg 11640
ggattatagg cgtgagccac cgcgccaggc cgccaacaag tatttcttat gttgtttgga 11700
cctaactttt tttttttttt tttaaagcag ggtctctctc tctctctctc tgttacccag 11760
gctggaatgc agaggcatga tctcgactca ctacaacctc cacttcctgg gctcatgtga 11820
tcctcccacc tcagcctcct gagtagttag aaccacagat acatgccacc acactccgct 11880
agtatttttg tattttttgt ttgtttgttt ttagagacag gactttgcca tgttgcctgg 11940
actggtctcg aacttctgag ctcaagtgat ctgcccgtct cggcctccca aattgcaggc 12000
gtgagccact gcattatgaa atggaactgt ggagtaattc tttcatgaca ttcataggcc 12060
aaaaaatacc taacagcagt tcgatagtgt catgaaaaaa ttactatgtt gttggaccta 12120
tttatgaaat gaaattgtta ggtatttttt ggccaatggt gtcaggaaaa aattactgag 12180
acacccaaga caagtgaagg agagtgttcg aagcctctac ctcagggatg tggtgggctt 12240
cagacgtcag tttctgctga ttcagctctc cccgtgatca gtttctggac tctgtcttca 12300
gggatcccca gagccagcta aagcagatgg tgtctttgat agcagcttcc tgcaccatcc 12360
tgaagatact catagggcttc aagcaggaaa ccttagtttt cctcatatag aatccttcct 12420
cctctatagt atctctgctt ttcaaatgag gaggcaaaca tagagcaata aaggaatgtc 12480
cctgagctcc cccagccatt aagcagtgga gctggcatgc aaacaaggct gatgcagagt 12540
gctagctctt accactgtgc tagttggcct cccagaaaaa tcactggact cactgaaacc 12600
aggctaacac atgagccaac agatgcccca aggccgcacc tcgcctgggc acatggtcca 12660
gatcccacga tcccagcaaa tgctttattt accagcatca cctgccaaag ccacagacga 12720
caaactctcc ttgggggaag aaggcttcaa tctctctggt caatctcagt gccgtcagcc 12780

-continued

```
tctctgagag tctgcgtctt gcagcctcac ccttaaaagt gagtttccca gggtgtgggc  12840
attttctttt cttttctttt tttaaacaga gtttcactcg tcacccaggc tggagtgcag  12900
ctcactgcaa cctccacctt ctgggttcaa gcgattctcc tgcctcagcc tcctgagtag  12960
ctgggattac aggtaccctc accatgcctg gctaattttt gtatttttag tagagacatg  13020
gtttcgccat gttggccagg ctggcctcga actcctgacc ttaagtcatt ccccacgcct  13080
cagcctcccg aagtgctggg attacaggcg tgagtcaccg cgtctggcca ggtgtgggca  13140
ttttctgatt agagacttgg ctatcacata tggactggct ttgctgtagg gggtaaagat  13200
cacaggatct gcctgggttc aaaccccccac ttactagttg gtcaactagg gcagatggct  13260
taatgcagtt aggcaagtgc cttcagcttc ctactctgta aattgtggta agaacggcac  13320
ttacttcttg gaggttgtta tgaatcttac atggattaag ccaagtaaag cccttaaaaa  13380
aggaccgggc atgtaagaag tgcttcaagg ctgggcatgg tggctcatgc ctgtaatccc  13440
agcacttcgg gaggctgagg tgggtggatc acctgaggcg aagagttcga aaccagcctg  13500
accaacatag tgaaaccccg tctgtattaa aaatacaaaa attagccggg cgtggttgtg  13560
ggtgcctgta atcccagcta cttgggaggc tgcggcagga gaatcgcttg aacctgggag  13620
gcggaggttg cagtgagccg agatggcgct attgcactcc agcctgagca acaagagaga  13680
aactccgtct cgaaaaaaca aaaacaaaaa caaaaaacaa aaacaaaaac aaaacagaag  13740
tgcttcaagc attcactatt attatcgtca gtatttagcg ctaaacccta tttacatttg  13800
taatggctag tgcacgagca ttggaacctg gtctggaaag tatccctctc cccaggcctg  13860
atttgcccgg aggtgggtaa gggcaaggtt ggcagctaag gcaggaagca aagggcccaa  13920
ctggagctca gtggtgtcaa ctcccttcct cctcaagggt tgctccctgt ctgtcccact  13980
aatgtttgaa aaatatttta ctgggttcct agccctgaac ttcagcgtct cctgccctcc  14040
aggctgttat tttcagaggt agagatgaga gctgagatag ggtctccctt gagacactgt  14100
ccctaaaaac tacgaccttc agctcctaat tgagggcttc cccgcccaaa cccacccctt  14160
cgcaacacag cccccaggga aggtgtctag cctttggagc actaggtggg ggcgggggaa  14220
acctggtcct aggaattcta ggccgccaga tgagaggcga tgctttcgcc ctccaggcga  14280
aaggatttgt cggggagaga cagcaagagt tcgaccagcc agccacttta gagattgtca  14340
ggggcgctca gctcataggg tggctcgagg gccagtgcga agctccctta gggacgaatt  14400
tccacatacg acgaaaggca tctgcgaaag gatgggctgt cccgtggggg gagtcggcag  14460
atatttaagt aacactaaca tttaacgaat taagcagcta tttctattta ctgagcaatt  14520
agtacgcttt gagagagagg ccctaccgag gcctcgcggt ggctgtaagt ccgtggggcc  14580
gaggccaggt ggcgccaaag gcccatcgac gccatctgcc cggctgtccg ggcccagtct  14640
ccgggctcgc ccagagaacc cgaaatctgg acaaacggaa accgtaggtg gaggaagaag  14700
agggctccag ggccaggttc aagggcatcg tggtgagaga tgaggggttc ggaggactgg  14760
tggatctggg catatcgcga aggtggtaag ggacccaggg gtggagtggg cggtgcttgc  14820
gccaagaggg tgagcctgag tgtgggcggg gcgtgcgata agaggctcgc tcggtagcgc  14880
tcttcgcaga gccgtatttg tgcgctacgc cgcagccagg gcgctctggg tgggcgggac  14940
tccagggccc ccaggggcgt ggcttgcatc tttcgtgggc ggccccgggg gcggggctcc  15000
gtgtaggtga accgctacct ccgctcgatg tgtgaggtgt gacagtccta cgagggcgca  15060
gttcttccac ttttgtgagc ttgagagggg gcggagcttg tagctgggga cggagcctga  15120
agaggaggtt gaggggaact tcacacgttt ccctggaggg cggagtttac atcatccccc  15180
```

aacagagtta agacctctga gggattccct gcagtgtcca gggctctgtg aggcgaagct 15240
tgcagttgtg ttgggcgggg cctgtagcgc cgcgtgaaga gaatgtgtaa actcggggcg 15300
aagttcatac ctcctagaag ccgagactaa tagttccgcc aatctgcgcg cgccgagcgg 15360
aggaggtggg gcttgtaggt tgtgggcggg ggactgggcg gggccaagag ggcagggggc 15420
gggcacaatc gctgctggaa tctttgagtt ggcaggggcg gggcttgtgg ctttgtgggc 15480
ggggcctctg gagagctccc gggggctctc ttctgttctg cagcgagtag gcgtggctcg 15540
tagctcccag gtccgggctg ataccgctgg agtatgcagt tcgccgccgc gcccgaatga 15600
ggcggggcct gcgagtaagt gggctgagcc cgggctgggc gcaggccggg gctctgccct 15660
gggaggccgt ctgtttaggc ccgcacgcag ctccgcatct ggtgctcatt accagatgac 15720
aaagagccgg ctctgggccc ccttccccac tcccatcccc cgcctccgac tgcagtgtat 15780
ttaactgttt cctgccctcg aggcgctcta gatccctacc cgaggtcacg gaggggactc 15840
cagaccatcc cgtctctgca ggccttgtcg ctccccaggc ttcctcacct ccttcccaga 15900
ctcagccgtc tgggccgcct cgcaaccctc attggcatcc agcaaacctg cccgacggcg 15960
tctccgaggt taaagctgtg caggatctgg cggggacgtc tggtttgagt taggggaacg 16020
tgagagcggg gaccgggggc ggtgcgtagc gttccctccg ccccctccgc gaccccctgg 16080
ttcatcccca gctccggccc ctcctttcct ggttccctgg ggcccagctc agccttccag 16140
ctcaggtcca ggcccgaagg gggcgctggg ccactcctcc tcgcctgccc gggtggtcgt 16200
ggcggctctg ccccgtccta attagaggcc cccaagaggc tgtaactgaa aaattacaga 16260
ggcggtggga actggcgcct cccctcccca ggtctcaccc ccgccccccca aggcagtgag 16320 cacgaaatga gggaggtcac tcccaccagg ctgtgatctt tgaccaggcc ctccagttcc 16380
tgggacactt cagtcctgag cagccggagc cctcgctcaa gctcaggtct gctgagctct 16440
gtctgtcccc caccaccccc agccaacatg gacaagagca acgtgcggcc ctggcaaaag 16500
gaggccttgc tcctgcggct gtccaagcag ttagcatggg atctctccca ggttcccggc 16560
ctttcccatc ccagcctcct ccccggagca agcggaggaa tgcctccaag agcacccaca 16620
aaccaggggt tggcagtccc cttgagttac cctgagcccc agcccccaac ttccgcgaag 16680
cttacaggga tgggaaggga agtgtctgaa gaaaggagca actcacccac tagacccctc 16740
cttcactcct ctgaatcacc agccccagag cctactttga cccctaaacc ccagtccggt 16800
tcagcagatg ccctaattcc acaaccgtcc cccagattca gccccacctt cttggagctt 16860
tggtaaaata aggaataaat atgaaattct ccccatgcca aacctcccac tgctgggctc 16920
aactgtgtga ccttgggcaa ggctctgccc tctctgggct cctgcttccc tgagaatctc 16980
tgaggcatac cctcccttaa agggatctta ccttatctct ttgaggactc agacaaactg 17040
aaggaagatc ccctcctttt tgctgagtcc tcccagaacc tcccttaagc accagtgggg 17100
gtcagaagcc ttgggtaagg ttgacacccc atttattgga gaagacccca gcacccgccc 17160
cctgaggtct taagggcttt ggtgtatcct tggtcacgag cgctgggcca ggaagcagag 17220
ttcctgagag ccaagtctag tggttgagag aggaccctgg ctgggcctgg ggagcaggaa 17280
gccatctgtc cagctgggca gcccccatgg gtccctggtg cagccccggc catgtgtcca 17340
gcgccccata ctccatgagg ggggtctgca ccccatcaca cgctggttct gcaggtctgc 17400
acccctgtga ggctgcccct ggggggcatg ggttctgttg ggctcttgct cccagcatgg 17460
atgacccagc gatagcagtc agtgatgcgc ttgttgggtg catgggggcc acagcgggtg 17520

```
cagtacacga tgcccagtgc aagcaggacc accaaaaaga cacacgttgg caccaggagt  17580
gccaccagca gccaccggtc atccctctgg ctgtgctcgg caagaccagc ctcccccagg  17640
gctgttgggg ctgctgtggg agctggtgag ggcagccaca gggccaactt gggactgggg  17700
ccatcttccc ttgggatttg gggggctttg gaatggggat gtgtagggct gatgggtgag  17760
gtctggttag tggggctctg agagggcagg agggtgggga gggctgcggg ctgggtggca  17820
gcaggcacag agatttgatg ggcaggagac acaggggacc tggaggtggt ggtcagagag  17880
ggctgggcag ttgggataat gggaagctgg gtggcctggg ttctgaggac aagggcatct  17940
ggggcttgag ggggtagctg ggcaccgagg gtggtgacca gaggggcatg gttaggtggg  18000
attccaggca aatgagtggt ggtctgggtg ccagcgaccc gggtgtctgg aaacatgggg  18060
gactggtggg cagggaagag ctccggatat ttggttgaga tcataggggg ctggtgggca  18120
ggaggctgtg ctgaatgaga gacagagaga ataccgggtt ggtaggcaga aggcagatct  18180
ggatagttgg ctgcgatcac ggggatctgg tggtcacggg acaaagctgg gtgtgtggca  18240
gggatcacag gaggctggtg ggcagaaggc agtgtgggat gcgtggcaga gaccaccaca  18300
ggccgggtga cggagagcac tgaggagtgg taggggaccc tgggggcact gagcgggggt  18360
ggccaggtgg gctccgggta gggtatctgt ggctctctgt cctctgggaa gctcggtcta  18420
taggccaggg caaagtcagg cggctgcgta ggctccatcc acaggatccc aggcatctcc  18480
gtccagccac cgttgaaggc cttccaggcc tcgtcttcat cttcctcatc ctccccgtca  18540
tccagcaact catctccgag gtcctgggaa gcctgggcac ccatggcccc tgcagggctg  18600
cagctgatgc catcagcctc cagctcatgt ccctcgctac aataacactc gaagccacca  18660
acgtagttga cacacatctg ctggcacaca ccggcaatct ggcactcatc tgtgtccaca  18720
cagcggtgcg gatcatcctc cgctggccgg aaacccaggc gacagtggca gctgtagcct  18780
tgtggcccac cgggctcaca ctgctgctcg cacggagcct gggcacaggg gtcctcgcaa  18840
ctgcgcccgt ctgctgccag ccggaagccc tcagtgcagc ggcaggacac gtgaccatcc  18900
acctcctcca cacattcgtg ttcgcagccc ccg                                18933
```

<210> SEQ ID NO 4
<211> LENGTH: 27375
<212> TYPE: DNA
<213> ORGANISM: Homo sapiens

<400> SEQUENCE: 4

```
gaccctatcc agagccaact ccaacccaga accagctagg cctgtgctgc cggagaggct     60
gtcaagtcaa tgcacgaggg ctctgccagg gacggcttca gcccaacaaa gggcatgtgt    120
ggcgaggccc caagacgggc accaaggtga cacaggcaga aaaccccagg gaaggaagcc    180
ctcccacggc cgaaccggaa ccctcaccct cccaatgaac aactgccttc ccagcaccgt    240
ctggcccttc accgcatttc taaacacgtc acacacacat ctgttcctcg acgttcggtc    300
tctgttcatc catcctcctc aaaatgaaag tccggaacct tctgcactaa ttttaaagtc    360
tggctgaaca ttgagtaacg aacaaaactg aaaacacaaa agagatggta tttttaatct    420
tgtgcatttt tactgaaaaa tgagaagata actctatctc tagctatagc ttttcctgtc    480
tatgtggcca gcccataaat gagttctaac tccttttctc tggactgtct tcagttttcc    540
tgcactgcga ctcaaggatg aggcgcctct acggacagtt ccgcggcgca cgcagcccca    600
ggccattgcc gcagcggccc cgggagtgcg ctgccccgcc tgggaaaggc gcaatcaggt    660
gctcctagca ggaggaaaca cacagtgcac gcacctgttt aaattttcct ctgatcttgt    720
```

-continued

```
ctaagtcttc atggagttta tcgtaagtag ggtcatcata agggaatttc tggatcattc    780
caatcaatga ttctaagacc ttcatctttc tgctgtaaag cacagaaata cagactctca    840
gtcatgtgca cacaacaggc tcaacttaca caacagctat gctgctggct tcctgaaacc    900
cagcaggtgc gctaagaatg ccttcgttca aaagctggat gattattttc tcattacacg    960
aaatcatatt tatttaccta gcaacgagct taggcccata cccagtgcct cgacagcaag   1020
tgtgtgccta gcttacagac acgcctccat tccgaccacg gggccaaggg gctgaggcag   1080
ccagaagccc tgctgactct cgaggtcaca catgcagaaa cagacagaac tgggcaagag   1140
ggactggggc tgggcacgag caggcctgct ctgggtctgg ggatttttcca ggatctggat   1200
tctttgtgct caaagccttc caaagttcag ctgcaggtaa accagcaaac ccctccctcc   1260
aaaggcggaa atcagtactg tcccctcccc agggaggaaa cagctttgct ggggaggcaa   1320
ggaggttctg cagaaaggct gtgcactcag gagacagcag ccctgggcat gacatctccc   1380
caacacctct ctacctgctt tcaaccctgc tggcctcatc tgtaaaatgg ggggcatccc   1440
agcctccaga tggtgagaaa ttaatttctg ttttgttttt ttttttttaa tggggagagt   1500
aacagcaacc tcacagactt tcaagaggat taaataactg acatgggccg ggctcggtgg   1560
ctcacgcctg taatcccagc actttgggag gccgaggagg gtggatcacc tgaggtcagg   1620
agttcgagac cagcctgacc aatatggtga aaccctgtct ccactaaaaa tacaaaaatt   1680
agatgggcgt gatagtgtgt gcctgtagtc ccagctactc gggaggctga gacaggagaa   1740
ttgctggaac ctgggaggtg gaggttgcag tgagctaaga ttgtgccact gcactccagc   1800
ctaggggaca gagtgagaat ccgtctcaaa aaaaaaaaaa aaaaaaattg acatgaagct   1860
tggactccag cacagagtag gtgctcaata aatgttagtc tcttggtctc ttggtttcct   1920
ctggatccta gagatcaggg ctctcacctg caggggttta aaaataatcc acacatgtgt   1980
acatctcgtg gggccaggtc ttttcaatga accacaggtg gtcctgagaa gcatgctgcc   2040
tctatgccgc attggaccat gtgagtggcc agagtaggca agatactcga ttaacgggca   2100
ttttaaagaa ctgacagtta ggatgaatca acagcaattc aaagcaacca agacctcctg   2160
tgtacttgca aacagctggt gctcctggat acagagaaga gcaagtttgc cagcagcatc   2220
cagtttacaa gagctaacca tggctacctc tctgagaaaa tacaaaactg tgaaaggtca   2280
aagcaagtca gttttagcaa caaagcacct ggtttccagg gaaaccaaag ggagatgcca   2340
aaacgtggga ggtggctgta tgctaacccg atgcagagga ccacgcactt tccacttggc   2400
aagcggttac ttttctggtc agcgatgctg ctcagacaca cccagccggg cgcaccatca   2460
gaggcggcac acgtcaggca ggtgtgagca gctcagggct aatgaaagaa aagtgatggt   2520
gccagagccc ccgtgctcag ccccggtgcg cgctggtctg caggagggtt tcaccagact   2580
gctgaagccg gggacagaag tgtcacgcag tttaccggaa agctagttac tcaacggaaa   2640
gcaccatctt ttggcctgag atgccgctct ccgtggtttc tttggtgtta caatgcccag   2700
cattttgctg aatgacaatg cggtggcagg tgtttttctc ttaacatcct tatttggaaa   2760
aatttacagg taaaacatgc aatatcagcc cttcaccatt taaaaaaaaa caaaaaaacaa   2820
aaaaaaaaac ctgacatgta agatctaaac atccatgaac cactgctcta caataaagcc   2880
ttaggttcca aagagacctc tgggtactac tggatgggat gagggcggct gcgagggggg   2940
tctggcaggg cttccaccag cccctcgtca accaaagcgg ttcttctctg ttagctagac   3000
tgagtgtgct gctttcagac gtcagcaaac ccctgctctg ggtaagggc tggcaacctc   3060
```

-continued

```
ctgggatggg accactggca cacagcggag cacttctcca ggagccggca gattctgccg   3120
ctgtgggaga agggagacag gcggagaact ccaagaacac acatcctttt gtggcctgga   3180
gttgagagcc aggctcagct ttgactgcca cctagtggta gcacaggctg ccaacagcga   3240
ttcccctggg atccccagct gccggccgct gcctgagaac caggaggaaa atgtcctcaa   3300
gtgcccctct gctaacccag aatcccatcg actcccaact gctggtacaa acggagcaga   3360
aagaactacc cgtatcagtt gcaagcatcc tcattcttaa acatttgaat attcaagata   3420
ttcaaggtat ttctagaaat tcaagatatt tcaaataaaa gcacaagtca cgtagtcagg   3480
gagagagtta cccactctcc ttgtgcccct cccacgctag gcaaggccac caggtgtcag   3540
aatgacgcag agcaccagct caggtcccgc gcttgctgct gcccatgaac agcagagtat   3600
ccaaaccatc tcaagggttc atttccagct tcagaatgaa gatagataaa gcagggtcac   3660
atggggcttc agtaagtaca atgcaggaag aagagttttt gtttgtttgt ttgtttttga   3720
gaaggagttt tgctctgtcg cccaggctgg agcgcagtgg cattatctca gctcactgca   3780
acctctgcct cctgggttca ggcaattctt caacctcagc ctcccgagta gctggcacta   3840
cagacacatg gcaccacgcc cggctaattt ttgtattttt agtagagaca gggtttcacc   3900
atattggcca ggctggtctc gaactcttga tctcgtgatc tgcccgcctc ggcctcccaa   3960
agtgctggga ttataggagt gagccactgc gcccggccga gaagagtttt taaaggctaa   4020
aaacaattca aatgacagct aacacttact gagtgttgac aagttccaga aaggagttaa   4080
acacatttaa aggcattttc ttgttaacag acttagttgg ctacattaaa aaactgatga   4140
cactggtgtc ctcatctctg agcccaagtg atacaaaact gttataattt gtttattaga   4200
agctcagggg aaaggtgaat gagaaaatac aatcaatgtc aacattattt tattggtagg   4260
gtatctaaaa gccacatggt gcactaatga ctccaggtaa aaggcaggag catagaactc   4320
ttgagaagca acaacagcca gtgttcacca aacacctaaa atgtgcctgg cactttctat   4380
ttagtatttc cgttaaatct cctaacaaca ctcaagcttg acactgataa ttttctccat   4440
tttacagatg aggaacagac agattgatta ctcaagggca tgctggtaac ccatggaact   4500
agaactcctg gttcctacgc tgagaaagaa agacatctcc acctttacct gtccttctca   4560
gtggtgcaac tgtgcagtag acatttccat gcaaaagcaa aaccttggta gcacccgatc   4620
tgtgaatgtg aaaaatattt aagagtgaaa ttaataagca actagctaca ctttcattac   4680
caagatctca aaacaaaagg tgggggcaga aggcagcggt gcttctcaca ctattgttct   4740
ggaagcacct gttgagcatt aggcaatgga aattaggaaa ttaggtcatc ggtggggcag   4800
ccagcctccc agatgcccca gtcctcatct cctggtaccc atgccctgtg caggtccctc   4860
gacactccac cagggtggct ttcgtaacca acagaatgtg gaggaacagc acaaagctcc   4920
tgagtctagg gataaaagcc agtgtcactt gcctcaccag ctctcttgga ccactcgctc   4980
ttgaatgtca cgaggacaca caagcagccc catggagacg tccatgccca cagtcaggtg   5040
acagcaccac cttggaggca gatcctccaa gcccagtcaa gccttcaggt gacacggctc   5100
tggctgacac cctgagccag gaccacccag caaagctgct cctgagttcc caaccctcag   5160
aaacatgtga gatcatccat atttgctgtg ttaagcccat gaattttgtg gtgatctgtt   5220
tcacagcatc gaacatccaa tatagtcata actgcctcaa ctcagacttt gccactaagg   5280
gccacttatc tgtaagggcc aatctaggac aaagggcaag aagagaaaaa aaaaaatcat   5340
aaagttaatg aaatttcaac gtaaacataa atggaatatg ttcacatgac agagggcacc   5400
cattctttgg cttagtacat gagccagcac catgacactc ccaagtaaac taaggagacc   5460
```

-continued agggacttgt tttcttttat ccagcatgca taatttaatt gtatctacct acagcaaaat 5520
gcactcttgg ttctgtacta agaatatttc tccagcaaca gtccatctag tccattaact 5580
cccatgcaaa ggcactgtga tttttttgt ttattttttg gagatggagt ttcatcctgt 5640
cgcccaggct gcagtgcaat ggcacggtcc cggcttacca caacctctgc ctcccaggtt 5700
caagcgagtc tcatacctca gcctcccaag tggctgggat tacaggcatg caccaccatg 5760
cccagctaat tcagtatttt tagtagagac agggtttcac catgttggtc aggctggtct 5820
ccaactcctg acctcaaggc gatccaccca cctcagactc ccaaagtgct gggattacag 5880
gtgtgagtca ccgcgcccat ccggcactgt gattttaaaa ggcctgacaa ttcttactcc 5940
atcacactga atatcgaaat aaattataaa ttgtaaatga agaggcttca tctccagatg 6000
ggggttccca cttacctcag acccgatttt ggctccatgc agcgtgccat gctgccttcc 6060
ctccatcaca cccaaactac tgccttcttc atagccttcc cgataccctt ccccatgaaa 6120
cctgtgaaga agaagcatgc ttcatcaaat caacaggaga aagaatactt tctccagaaa 6180
aacttctctc tcttgtatta cccggaccca gtaagacaaa ccagagtaaa ggaggaaaag 6240
cctaaaattc aagtcagaag acacagattc cagtcccaga tctaccactt cctatttgcc 6300
tctggaagtc actgtacctc ttgtagccca gtttcttcat ctacaacaaa gggctaaatt 6360
agggattccc aaacctgata gggtactaga aacacacaag gaaaattcaa agatattaac 6420
tcaaaagcct cacccccaga gattcagtac gtctggagca aggccctgga atctactttt 6480
ctttcttcct tttttttttt tttttttttg agacagggtc tctgttgccc tgcctggagt 6540
gcagtggtat gatcacagct cactatagcc tcaaactcct gggctcaagc gatcctccag 6600
ctttggccgc tccaagtgtt gggattacaa gtgagggcca ccgcacctgg cctgcaatcc 6660
acttttcttt tcttgagatg gagtctcgct ttgtcgccca ggctggagtg cagtggtgcg 6720
atctcggctc actgcaagct ctgcttcccg ggttcacgct ctcctgcctc agcctcccaa 6780
gtagctgaga ctacaggcgc ccaccaccac atccggctaa tttttgtat ttttagtaga 6840
gacggggttt caccatgtta gctaggatgg tctggatctc ctgacctcgt gatccgcccg 6900
cctcggcctc ccaaagtgct gggattacag gcgtcagcca ccgcatctgg cccggaatct 6960
acttttcaaa gtctcctaga taagtctggt ttgcagccag agttaggggg ccaaagttct 7020
gtgagtgttc aagtagcact agcccaagtc aaccgcttcc aaaaaactgc aacatacaca 7080
gggtttgaca tcacatgggt agggcaacag agagaaatgg catcagatca ccacaaaatg 7140
ttctccgact ggtacccgga gtagcactga ccctgaggcc caacagtgga actgccacta 7200
tcttaacctg cagtcaccaa acatgcaagg agtgggctgc agcgccccat gaagcagggt 7260
gcatagctcc ccacttaata gttgtgtgac cctggaaagt gactgtgcct cctagtctgt 7320
aaattccgaa gaataatagg atccacttac taagtagggc tgaagtagat aaccagggtg 7380
gaacgtttag ctcagtgtct gactcacagc gcgagctaaa taaacgtcag cgcctgactg 7440
ctaaatgttc ggccgctttc ttaactaaca tctatggacg cgtcctctgg gccgggcact 7500
ggaagtcagc caggaggcaa ctcacagctc ccccactgtc gcagcacgag gggctcccca 7560
ggggctctgg agggaaaagg ggtgtggtcg ggtacatcta tcagcacatc catgaatact 7620
gccgtatgtc ctatgattaa ggaaccagaa aaaaaggcag ctcccagatg gcaaaggtct 7680
gtcctcccag aggacgaggc ggcctcggag gaggggaacc accaggctga gcagatgttt 7740
ggggcagccc tgacagggaa ggcgggtctg gaagagcagc tgggcacgtg ccccgccgga 7800

-continued

```
gcgggccagg agaagaggac cagagcatca ggcccacact tgtccctgcg tccacggcca   7860
ccaggcgctc cccaatgcgc acgcccaagg gacgccaggc tccagcagcc gccctgggcc   7920
gcagccggcg gcgaagccgc tgggagacga ccagacaggg cggggtgcgg gcccggcctc   7980
accacccacc tctcatccgc catcacgatg gcatcgaata tgtcctgact gccagccata   8040
gcggcaagca gcccgccctt ggcccccggg tttctgcagc cccgcggtgc cgtagcagac   8100
ccggcagctt caggcacaaa tgctccgctt gggaggagac gagacccact tccggaagcg   8160
gcggcgcggg gcaggccggg taagaacggc acgcgggagg gcccaaagca gcctgtacat   8220
ggcgcatgcg cggctgcagc ggtgggcggg gccggcctcg actgaagccc cgccctgggg   8280
tcctttcgcc ctgcccagct ccagcaaagg gcctgtctgt ccgcgctggg agcgtccatt   8340
ggccgcgcgc gtggagagcc gacctgtatt ttaccactgc agatagaacc gaatttccca   8400
aagtggctcc gaaagaacca aggaagaaat gggaagtcat cagctggcgc ggtggctcac   8460
gcctgtcatc ccagcacttt gggaggccga ggcgcgcgga tcacctgagt tcgggagttc   8520
gagaccagcc tggccaacat ggtgaaacct cgtctttact gaaaatacaa aaattagccg   8580
ggcatggtgg caggcgcctg taatcccagc tactcgggag gctgaggcag gagaatcact   8640
ggaagctggg aggcggaggt tgcagtgagc cgagatcgca ccactgcact ccagactggc   8700
gacagagcca gactccgtca aaaaaaaaaa aaaaaaggga aaagaaatgg gaagtcatca   8760
aagaaccgac gcctcaggag gctccaggcc aggaggctct gcatgtggga ttttgggcag   8820
aaatttgtcg gttttagttc tcatatttgt catttccatg agatgtgctt tctgaacacg   8880
atttttaaaa agggatttca aagtctaagc gacaacggaa ctcagatgag aaacaccaga   8940
agcattccta ataaagtcag tagtaaaacc tcacgtgacc actgaacatc tttctaccag   9000
ccctggccaa tgcagtaaaa catgaagcaa gaagtggaaa taccaaaaaa aaaaaaaaaa   9060
aaaaaaaaag gcagaaatac tactatttgc agatatgatg gcccacgtgg aaaacccaaa   9120
tagtcaccta agacgttctc agaatccata atcgcagcaa gtagctatgt gtatgatgaa   9180
tagggaaaaa aacactttct gttattccaa caataattgg tagtaacctg agcaggggtg   9240
gtgatgggaa aatcgcctta tgatagtcat aatacatttc ttagaaataa gaatttctaa   9300
caatttgagc aggacccata taaggaaaac tacagctcta ccatgattga ggattgggga   9360
actgaacaag tgcagtacca aagaaaattc catgagatct ggtaaaatgt gtcaaaatcc   9420
taaacttttt catccgtatg aataaactaa taaaaataac taagatgttt tagaaaaaaa   9480
tgattttcat atcagatatg aaaagataaa gtgtcaatat aaatattgtg gtatgttggt   9540
tcaagaagtg gcagaccagt gaaataaagt aaatggccca gacaatggac tctcatagat   9600
gtaaagcctt ctcatgtggt aaaaagaaga attacaaatt aattggagaa aggaaatatt   9660
aactaataac tataatggaa aattggttgt ttgggaaaag cttggttcca tttatgcctc   9720
acaccattca tcaaaataat tccagatgag ttaaagagtt aacttaaaaa aattaagcac   9780
attggctggg cacggtggct cacgcctgta atcccagcac tttgggaggc ccaggcaggt   9840
ggataaccag agttagggag ttcgagacca gcctgaccaa catggagaaa ccccgtctgt   9900
actaaaacta caaaattagc ctggcgtggt ggtgcatgcc tgtaagccca gctactcggg   9960
aggctgaggc aggagaaccc aggagacaga ggttgcagtg agccgagatc acaccattgc  10020
accccagcct gggcaacaag agcaaaactc catctctaaa taaataaatg aataaagcac  10080
attttgcctg taatcccagc actttgggag gccgaggcgg gcggatcatg aggtcaggag  10140
atcgagacca tcctggctaa catggtgaaa ccccgtctct accaaaaaat acaaaaaaaa  10200
```

```
aaaattagtg gggcatggtg acgtgtacct gtagtcccag ctacttggga ggctgaggca  10260
ggagaatggc atgaacctgg gaagtggagc ttgcaatgag ccgagatcgc gctactctac  10320
tccagcctgg gtgacagagc gagactctat ctcaaaaaaa ataaaataaa ataaaaataa  10380
ataaataaat aaataaaata aagtacatta aaaaatctag gtggaacatt cagacaagta  10440
tgaagatgct cttttaacac ataaaagcca tgaaggaatt ctcagcaagc aaaaccaaca  10500
ttttaccatg taaaaatgca aacttgtgtg taccaaaagt gataagaaac aaaatttaaa  10560
gttaaagaac aatatgggga aatatttgtc ataaatattg taactaaaga aataataatt  10620
ctggtaaaga gtttatttaa atacatgtat ttatttaaat aaatacatcc taacggggaa  10680
aaaaaaggac ttgaaacatt attcacagaa agagcaacag ctggccaatc aggaaaagca  10740
gacgcagcct cactagtaac caaagcaatg ctgagaaaga ataatgagat gcatttttta  10800
tcttttaaaa tagcttaagt tctttttctc ctttttttaga attaaaagat actcttaatg  10860
agcacaagtg catacattga agacacctct tggtcaggca gttcaaaaac ataggaaggg  10920
cattatatat atatatattt tgtttgtttg tttgtttgtt tgtttgtttg tttttactag  10980
ctaggcgtgg tgggtcacgc ctgtaatccc agcactttgg gaagtcaagg tgggtggatc  11040
acctgaggtc accagttcca gatcagcctg gccaaacagt gaaacttcgt ctctactaaa  11100
aacaaaaatt agccgggtgt ggtggcacgc tcctgtagtc ccagctattc tagaggctga  11160
ggcaggagaa ttgcttgaac ctgggaggtg gaggttgcag tgagccgaga ttgtgccact  11220
gcactccaga ctgggcgaca gaatgagact ctgcctcaaa aatagaataa aaaagttttt  11280
ttttgcccct ggacctagtc atttcacttc taagacttca tctctaggaa ataatcaaag  11340
acaagtcaaa atattatgta cagtgttgtt cagtgcaaca cgatttgtaa aaggcaaggc  11400
aaggaaagca gctacattga caaaatggtg gaattatgac atgtattgta ggctattcat  11460
gttgaagact cctaagcaac cattacaaat aatatttcaa caaaagtaac atcatggaaa  11520
atgcccatga tatttcaaga aaaagaaaaa aaaatcctct atgtgaggct gcagtgagct  11580
atgaccatac cactccactg cagccaggcc agggcaacag agtgaaatct catctcaaaa  11640
acataaaaag aaagaaaaag aaaaagaaaa aaaaacactc tacatatact cgaattgcaa  11700
tcacactaaa cactatttca aaagaatgag agtagccagg tgaggtgact cacacgtata  11760
atccaacact ttgggaggcc aaggtggaaa gattgcttga acccagagtt caagaccaag  11820
ctaggtaaca tagtgagact tcatctctac aaaaaaatag aaaaaattag ccaggcacgg  11880
tagtgtgctc ctgtagtccc agctacttgg gaggctaagg cgagaggatt gcttgttctc  11940
aggaaattga ggctgcagta aaccgtgatc gtgccactgc actccagcct gggcaacaga  12000
acgagaccct atctcaaaca aaacaaacaa acaaacaaac aaacaaaaaa ccagaaaaga  12060
aaaaaggaag agaaaaaaga gtgaaagcaa gtacagcaaa atgttcatag agaatatagc  12120
tagattttgg aatgacagtg attttttttaa tgtcctcatt tatatttttt ggaacatctc  12180
atgtttgttt gcacaatgaa cataagttat gttataagca taaaaaaatg tttttggtgg  12240
atgaaattaa atagacttcg tattattttg ttctgaagat gtctttaatt tttaggtttt  12300
ttaaataagc aaatgaaatc acacaacact tggaatatag gaaaaaggga aagacagcaa  12360
gccaaaaaaa acagttcacc ctgtccacca actgattttt gctaatttta ttatttttcc  12420
cttgaatttt catataaaca taatttaata tataaacaat gtaatatcct tctccctgcc  12480
cacttaacat tagattacaa acacctccca aataagggaa ctgttctctt atcagtacat  12540
```

```
atttaaaaca catttttgag cataaatttc attagctgaa ataaaataaa ataaatatat 12600
cttttggata ggaaaataga taacgcggtg agaaaaataa atgaccactt acagaataaa 12660
gcccgtggac atggaggctt atacagaaga gcgtaggttt taatttctaa cttcaaaaat 12720
atttgcaaag ccttgaacaa ttatatgtgc tacaaaaatc aacactattg atacaaatta 12780
ttaatctgaa ataaagcttt ggggagattt tctgtcccca atcatcaatt tgttcatctg 12840
gtttgttctt aaaatattta ttttgaagcc agactgtctt agcattaaag acaaagaagg 12900
gccgggtgtg gtggctcacg cctgtaatcc cagcacttta ggaggccgag gtgggtggat 12960
catctgaggt caggagttca aaaccaacct ggccaacatg gtgaaaccct gtctctacta 13020
aaaatacaaa attatctggg catggtggct catgcctgta atcccagcta gttaggaggc 13080
tgaggcagga gaattgcttg aacctgggag gtggaggttg tagtgagcca aaatcgtgcc 13140
attgcactcc agcctgggca tcaagagtga aactctgtct caaataaaaa ataaataaat 13200
aaaataaaaa ataaaggcaa agagcctgat tccattatcc tggatttcca atagtttatt 13260
tacaaattgc tttattttca aataaggacc agattgttaa agcagggcct ttggggctgc 13320
atgcagtggc acactcttgt aatcccagca ctttgggaag ccgaggcagg aggattgctt 13380
gaggctagga atttgaaacc agcctgggca acatagtgag accccgtctc tacaaaacat 13440
ttaaaaatta gctgggtatg gtggctcaca cctgcagtct tagctacttg ggaggctgag 13500
gcttcattga gctatgattg tgccactgct ctttagcctg agcaacaaag gggagatgct 13560
gtttaaaaac acatgcacac acacacacac accccgacac acaccgacac acacacagac 13620
acacacacat gcacacacga cacacacacc aacacacaca catgcacaca cagacacaca 13680
cactgacaca cacagacaca caccgaccca cacacatgca cacacagaca cacacatgca 13740
tacacagaca cacacaaaca gacatacatg cacacacaga cacacacaga gacacacaca 13800
ctgacacaca catgcacaca cacatgcctt tgaaagtaga aaaagtttta aagttcaaat 13860
atttacgtca acatccttaa ataagttgca aattttatgt tttagcaact gaacacataa 13920
aaagcatagg aagaatctga attaatatcc ccccttggct gggcgtggtg gctcactaat 13980
tgtatttatt tcagtggttt caaaacacta ttagtaaata tttaacttat aacaaaaggt 14040
ataaaggaga taatataatc acctcccagg aatctaccac attaagaaaa aaagcatttt 14100
taaaatagaa atgttggccg ggcacggtgg ctcatgccta taatcccagc actttgggag 14160
gccaagacgg gtggatcacc ggaggtcagg agttcgagac cagcctggcc aacatggtga 14220
aactccgtct ctcctaaaaa tacaaaaatt acccaggcat ggtggtgggc gcctgtaatc 14280
ccagctactt gggaggctga ggcaggagga tcgcttgaac ccaggaggtg gaggttgcag 14340
tgagccaaga cttcgccatt gcactctagc ctgagcaaca aaagcaaaac tctgtctcaa 14400
aaaaataaat aaataagtaa acaaagtata aatattgctt acattcttgt gagagttcaa 14460
agaaaaacca ggtcaatata actaaagtga aaaacaagtt catcgaagtt taatactaaa 14520
cagtgtttac ttaccagaat actttttttt aaattttata tttaaatttt tagcctgtag 14580
tcccatgctc caaaaaaaaa aaatgaggac attaaaaaaa ttacgacaat tccaaaatct 14640
atttggtgga cttcttctag cagcaaaata ctaagtagtt ttcaaaccaa accaaaccaa 14700
acctgacaat atagatctat agttgttaac ctggaaacac atccatttta ttagaaaaaa 14760
aaaagttaaa aacaaaatat catttgttct tattttggtt caagaaaaag gccctcgagc 14820
atagcaacag gtttttatct atgtagagaa taatctgcaa ggaccacaac ccctgatgtt 14880
gcagtggtca cgtttgggtg atggattatg tgtcatctta attattttcc tttgtatgtt 14940
```

```
tctgtatttt gtgatttggg tttatttttt ttacagcatg aagctgctgg atgtggtggc  15000
tcatgcctgt aatcccagca ccttgggagg aggccgaggc gagtggatca cctgaggtca  15060
agagtttgag accagcctgg ccaacatggt gaaacccatg tttttgtctc tacaaaaaat  15120
acaaaactta gccaggcgtt gtggcatgcg cctgtagtcc cagctactca ggagactgac  15180
ttgggaggat cacttgtgcc caggaggtcc aggctgcagt gagtcacgat catgtcactg  15240
cactccagcc tgggtgacag agcaagaccc tgtttcaaaa aaaaagcatg aagcaagtgc  15300
ggctttcaca gtccagaaga aaaagaagca gttttaaatt ctgaaaagga agtcattaaa  15360
tgacagttca cttcaaggaa ctaaagtttc atctcatgct ctattcatca taaataaata  15420
acacattcgg aaaaggaggc aagttgcagg caggcctcaa atccaagttt gaccccatgg  15480
ggtaggcagg aggaggagaa tgcgaggctt gagttacact cgatctttcc agctgcgcct  15540
cctctctgct ccttctctaa taggtgtgct tgggtttggg agcctgtcaa atgccatttt  15600
ctacctgctt ccctggtggc cctagcgcag gagacctggg ttggggtgga ggtctggtgc  15660
tgtgagcagt aactgagaac agggctcctc tgggcaccca cctgcctgcg gaagggctct  15720
ggccagcagg gctcagcctc tgcccatccc taaggctccc aggggagtct tcttcaggct  15780
tctagagaag agataacatt ttgggaaagt gacacaaaga tgtggcaaca gtacctgtat  15840
tgggagcgga ctgaaagtct gagaggaggc ctacttttca ctgtctaact tgcattagtc  15900
aggttaggcc aggctgtgct gcaataagaa ataagccctg acatctcagt ggcttaacca  15960
ggaagggcta tttcccactt ccacgaagtc cactatgggt ggggcagctc tcctccacct  16020
tgcaggaacc aaggccccct cattgcccca gcaggggaag agacagagga agcaggctag  16080
ctcctagctg ccttgtccca ggagaacact ttatttccat tccattgacc agaaccagtc  16140
ccaaggccct aaccaaactg taggggagcc tgggaaatgg agatgagccc acggacgttt  16200
ggtcaactct gtctctgcca caatgcttta atgctgttag gattttattt tgaaccctgt  16260
aaatatgtgg cttctccaat gtaaaaagaa agaagggaga gttgttatct aatgtgtata  16320
ttatatatta tgttatatat tctatgtatg taacaggtgg aatatatcag tcacctctcc  16380
tcacccagtt gaacaaaatg caaaacacaa tagatgctgt caaagagata tgtcatatcc  16440
acattttact ggaaataata atttctccaa aattgtggtt cctgaagtaa ataaagattt  16500
aaaataaatg atgaaagttt gaatcttagc agataccgaa agtgtagatc ttactttgca  16560
cagggtgtag cacataacag gtgctcagta aatggttgct gagtgaataa gtgagaatgt  16620
agtgtggcag tgggaggaga aggcccctct gagccatggg agggggacag gccatgtttg  16680
ctgtggtgtt tgcccatggc ttttgggtca tctcagtaga gagggtgcct ggataaacag  16740
ttttctttcc agagctcaaa gaccgtttac caaaactggg cccagcccct tagggctagc  16800
tgtatttccc tgtttgtgtc gaggaaaggg ggaatgaggg atccaacctg ggcttgggct  16860
gccacctgct ggatgcagtg gctcatgcct gtaatcccag caccttggga ggccgaggca  16920
ggtggatcac ctgaggtcaa gagtttgaga ccagcctggc cagcatggcg aaaccctgga  16980
gagggaagtg aggcagccga ggacgcatag tggctaccgg ggacccagcc ctgccatggc  17040
ctgaggcatt gtccctctag gtgggagcgt gtaggactca tgcacccccc cgggaggctc  17100
caagagagtc ccccatttga cctacacccc ttatttctta gaaggcccta gcgcggctgg  17160
gcgtgatggc tcacacctgt aatcccagca ctttgggagg ccgaggcggg tggatcacct  17220
gaggtcagga gttcaagacc tgcctggggc caacatggtg aaactccgtc tctactaaaa  17280
```

-continued

```
atacaaaaat tagctgggtg tggtggcggg tgcttgtagt cccagctact caggaggttg  17340
aggcaggagg atcagttgaa cccaggaggc ggaggttgca gtgagccaag attgtgccat  17400
tgcactccag cctgggcaac agagcgagag tcttaaaaaa aaaaaaaaaa aaaaaaaaaa  17460
agaagaagaa gaagaagaag aaagaaggcc ctagcaagaa gaagaagaaa gaaagcccta  17520
gccctggggc tccagtgtcc gtcttcgaag ggctgtggcc ttcatccggc ctccccttca  17580
tccggcctca agctcctccc tggcttttcc tctcctctgc cctccacctc ccgaggctca  17640
tccccgcagc ctgggggagc ttcctccttt ccgcccttgg tggagcagaa attcttgctg  17700
ggctccttcc cccgcaccgg gagagctgtg aggagtggcc ttgctgtttc catcttcttt  17760
cttctgcact gaccgttccc ccttcccaac tggacagcag catcccagag gcaggacggt  17820
ggctccttct aaaccttggt gcccccagct atgcccagta tggggtctct ggcatgaagt  17880
ccggtgcaat aaagggtgag cagttctcct tacccgcctt cccatgtcca cctctggtca  17940
gtgggctgtg ctggtccagg aagccaggga tttttggctt ctgagatgca gtctccacca  18000
ctccacatgt ttttttggt ttttggtttg ttttaagaca gagtcgcgtt ctgtcgccca  18060
ggctggaagg cagtggcacg atcacggctt actgcaacct ctgcctccta ggctcaagcg  18120
atcctcccac ctcagcctcc caagtatctg ggactacagg tgcatgccac cacacctgga  18180
taatttttat attttttggt aaagatgggg tttcgaattc ctgggctcaa gtgatccacc  18240
caccttggcc tcccaaagtg ctagggctac aggcgtgagc cactgtgccc tgccaaattc  18300
caaacgtttc ttgacagcgt tagtgaaatt cacgttcctg cacctcagtt tgctcatctg  18360
taaaatggga gtgatgttgg taccccgttt tcaggatcga catgaggatg aatacttgca  18420
tataggaaac agaagaaatg tattgataga taaatatagt gaacataaat tcgaatacag  18480
gaacaggaag ttgtggaggt gatggagcct gcctctccct tgccctttgc tgaggtccag  18540
gcacacacag taggggcttt gttgatgttt gtgtgtagcc gatgttcttt tgcttcctgg  18600
gggcttgtct gcaaaagttg caggggggcag ggtggagggc agctagtcaa ccatcagatc  18660
agactgcggg aggggcgagc gtgagcgagc agctgctggg tgctctcagg gcaacctcgc  18720
ggcttccgag tccccggccc cgcgcgggta aaggggcacc gaaggcacct tgcagaccgc  18780
gccctgcact ccctgaccct cggccttgcg cggggcccat tccagtcacc gccaccgggg  18840
gccgccattg cgccgcggac ggccccgctc ctccggggag ccgcagagcc gcctccctcc  18900
cgggccctct cttcgccgct ctgggacggt gtccctgcgg ccgctagaat tctcttctga  18960
atctccactg ccccagccag atgtcatcct gataatcaga cctacgggag atcggaccgt  19020
ttactttttc tttttctttt cttttctttt tttttgaga ccgagttttg ctcttattgc  19080
ccaggctgga gtgcagtggc gtgatcttgg ctcactgcaa cctccacctc ccgggttcaa  19140
gcgattctcc tgcctcagtc tcccgagtag ctggaattac aggtgcatac cacaactcct  19200
ggctaatttt tgtattttta gtagagatag gggtttcat gatgttggcc agctggtctc  19260
gaactcctga cctcaggtga tccgcccttc tcggcctccc aaagtgctgg gattacaggg  19320
atgagccacc gtgcccggcc cggactgttt tcttagatcc tcacttgaag atcctagcag  19380
tctgctttgg agatggacat cgcgggcctc actggggaag acactgcgct ctgggagaca  19440
cagctcctag gggcaggtgc ccctcccacc ttagtcccca ccagacccgc ccctgcctcc  19500
tccaccccat taggctgagg ctgatcagag gggccctggc ccactgcccg ggtccctgct  19560
cagaggcccc acacaactca tggggagaag gagacatggg cccagtgaca ggttacccgg  19620
ctctgatggg aaaagcgagg tcttggagcc ctgcctgttc tgggtgcttc tgtttgtcag  19680
```

cctgcttggg cctgggctgt cccccgagtc tcaggctcct catctgggct ggcattgggg 19740
cccaggcttc agccaggtct agactcccca ccagccactc aggcaacagt cactccactt 19800
gggaccccag gaaccacagg gcaggacagc tgacaaggaa gggggccccc acttcacccc 19860
gaacctgcct tgagcctccc atgcctggtg gggaccccac caaccccagt gtctggggaa 19920
ggcaggactc tgagacaggt ggggctccca gccccggcag gtgtcggtgg cagggaaaac 19980
tcaaggcctg gcaccgatac catcattctc ggtcttcccc aaagtaaggt gagtatacgt 20040
ggtgccgatg agtcaggtcc atgcccaggt atgcattaaa atttccctgg gaaaaaatag 20100
agagtgtaat ttggcaggct ctggggagat tttagaggtg cctgcacttc acttacgtct 20160
ttccactgcc tggtcaacat agtgaaaccc cgtctctagc aaaaatacaa aaattagcag 20220
ggtgtggtgg tggatgcctt taatcccagc tacttgggag gctgaggcag cagaatcact 20280
tgaacccagg gggcagaggt tgcagtgagc caagactgca ccattgccct ccagcctggg 20340
ctacacagtg agactccatc tcaaaaaaaa aaaacaaggc ttaaaaaaat ttttttaaac 20400
agcctcaccc atatgacttc ttttaacctt aatcacctct tcaaaggtca tatctttaag 20460
tacagttata ctttgaggta cactggaggt taagttttta acatataaat tttagggaca 20520
caattcaggc acatatgact gtgtatacag acacctatac acacacacac atatatatac 20580
acatacacgg tttttgaaaa aaagaaactc aaactgaaga aaaggttata gtagaagttc 20640
tccttcctac cccgtcccca gtcctctaat tcctgtcccc agaactaccc acagttttat 20700
tgttttctat acttctttcc agagaggttc tctgcatata taagcatgca tatatatata 20760
tatctttttt aaattattat tttgagatgg ggcctcactc tgtcacccag actggaatgc 20820
agtggcactg tcatagctca ctgcagcctt gaactcctgg actcaaggaa tcctcccact 20880
tcacttccca agaagctaga actacaggca tgagtcacca cacctggctg atgtttacat 20940
ttttttgtag agatgacatc ttgctgtatt gcccaggctg gtctcaaact cctggcctca 21000
agtgatcctc ccacctcggc ctcccaaagt ggtacatgct cttttaaatg acaaattata 21060
ttatactata gactgtgtcc tgaatttact tcttctactc cacaatatac cttcaataac 21120
aaaccaactg tgaaattgcc aagactcaat ataacaaagg tttatttatc cactgttctc 21180
ctccaagtcc agcacaggtc actgggggtt ctgctccacg tggtcacgca gggacccagg 21240
cctagaaggt tcaccaggtt gtgacacagt cattgcaacc tcttccacgt ggcttggtag 21300
agaaacagag agtgtgaaga attcacaact ggtttttggt tcccttttta catagacatt 21360
tcaaacatac ccaagtgtag atagtgtaaa cagaccccca tataccaata cccagcctca 21420
gcaaggatca atatttcact gttcttgttc caacaatgac ctcattcccc acgcccacca 21480
tttttgctga gtcatttcac ctgtacatac ttcagtgcat atctaacaga tacagagttt 21540
ttttacataa ccataataca tgatcccacc tagccaatta acaatataat tcagtttcca 21600
gaccatttcc atttgtttca acagttaaaa actgtctttt taaagtgttt ttttttaaac 21660
agcctcactc ataagacttc atttaacttt aatcaccttt caaaggtaat atcttcaagc 21720
acagtcatac tctgaggtgt actagaggtc aagtttttaa catgtgattt ttgggtacac 21780
aattcagtcg tgtgtgtata cacacacaca cacacacaca cacacacggt tttggaaaaa 21840
acaaactcaa actgaagaaa aaggttatag taaaagttct ccttcctacc ctgtctccag 21900
tcctctaatt cctgtcccca gaagcaccca cagttttatc gttttctata cttgcttcca 21960
gagaggttat ctgcatatat aagcatacat atgtatatgc cttttttttc tttttttttt 22020

-continued

```
tgagatgggg cctcactctg tcacccagac tggaatgcag tggcactgtc atagctcact  22080
gcagccttga actcctggac tcaaggaatc ctcccacttc acttcccaag aagctagaac  22140
tacaggcatg cgccaccaca cctggctgat atttacattt tttgtagaga tgacatctcg  22200
ctatattgcc caggctggtc tcgaactcct ggcctcaagt gatcctccca tctcagcttc  22260
ccaaaatggt acacaccctt ttaaatgaca aattatatta cattatagtt ggtgtcctga  22320
atttacttct tctactccac aatatacctt caataacaaa ccaactgtga aattgccaag  22380
actcaatata acaaaggttt gttaatccac tgttctcctc caagtccagc acaggtcact  22440
ggaggttctg ctccatgtgg tcatgcaggg acccaagcct agaaggttca ccaggttgtg  22500
acacagtcac tgcaacctct tccacatggc ttggtagaga aagagggagt gtgaagaatc  22560
cacatttggc ttttggtttt cttttcagtt tctattatag acatttcaaa catacccaag  22620
tgtaggtagt gtaaacagac ccccatatac caatacccag cctcagcaag gatcaatatt  22680
tcactgttct tgttccaaca atgacctcat tccccacccc caccttttct tgctgaatca  22740
tttcacctgc agatacttca gtgcatatct aacagataca gatttttttac gtaaccataa  22800
tacatgatcc ccctagcaaa ttaacgatat aattcagtac ccagaccatt tccgtttatt  22860
tcaatagtta aaaactgtct ttttaaagtt ttttttaaca gcctcaccca tatgacctca  22920
tttaacctta atcaactctt caaaggtcat atctccaagt acagtcatac tttgaggtgc  22980
actggaggtt tttttttttt ttgagacgga gttttactct tgttgcccag gctggagtgc  23040
aatggcggga ttttagctca ctgcaacttc tgcctcctgg gttcaagtgg ttctcctgcc  23100
tcagcctccc aagcagctgg gattacaggc atgcgccatt atgctgggtt aatttttttg  23160
tatttagtag agacgggctt ttaccatgtt agtcagggtg gtctcgaact cctgacctta  23220
ggtgatccac ccgccttggc ctcccaaagt gctgggatta cagacatgag ccacagtgcc  23280
tggctaagtt tttaacatat gagttttggg gccacaattc agtcacttat gtgtgtgtat  23340
acacacctat acacacacac acacacacat atggtttttg aaaaaagaaa ttcatactga  23400
agaaaagggt tacaactaag agagaaggtt ttgcacctat tttgttgagc tgaaaaccaa  23460
acaaggccca tgtgttgagt tgctggctct gtctcctggg tctctttatt ttcgacttca  23520
gtgatgagaa tgcacaggag gagagtggct cagagaggac acgaagggga aacctgaact  23580
gtgagaggtt tacagggaag aatgaaagtg ggtgacgctt tgccttaagc cataaatgaa  23640
ggcaagggag atcaagcagg cagtcttgac gttagcgggg aagtgaaaaa gaagatggaa  23700
gaaagaaagg aagggccagg gaggaaggga aggtgggagg gacagtgggt aggatggggt  23760
agaaggaagg tatcaacttt cacacatcat tatcaagaac aaggaaaatt tcaacttcag  23820
tgtgaataaa caatcatcga caaatgcgga gattaatgag atgacagaat gattaataaa  23880
ttgttggata agggttttaa agcagccatc ataaaaatgc ttcaactgca attatgaatt  23940
cccttgaaac aaacgaacgc attaaaaatc tcagctgtcg gccaggcacg gtggctcaca  24000
cctgtaatcc cagcactttg tgaggctgag gcaggtggat cacttgagct caggagttcg  24060
agatcagcct gggcagaata gtgagaccct gtctctacaa aaaatacaaa aattagccag  24120
gcatagtggc atgtgcctgt agttccagct actcgtacta gagaggctga ggtgggagga  24180
taccttgagc ccaggaggca gaggttgcag tgagctgtga tcagccactg cactccagcc  24240
tgggtgacag agctaggccc tatctcaaaa aaaaaaaaaa aatcttagct gtgaaaactg  24300
atcttacaaa ctggattatt cttgtcatac ccaactaaac aaagtccaga agcccggggg  24360
gaaaagcact cctgatacat aacagtattt caaaaatgta attctctgca agcctggttg  24420
```

ctgaaactgc ctgctataac ctgaaatcag ttttacccaa tagctgctga tgcaacctgc 24480
tgcaacccta agactaggtt tactcaccgc ccttgctcac caatcagagc ttgccagctc 24540
cccaaaacct ccttcatgcc aatgaacttt cttgaagagc aataggtaat atttctcctt 24600
tttacaaaac ctttaacctt ccctttgttt tctggacata ttgaagactc cctagtctgt 24660
atgtgtgccc caaattgcaa ttctttcttc ctaaataaaa tgttttaatt tcagagattt 24720
ttctctatgt tttactggat tttgacacag caaagaaatg gaagttatgg aaaagaacca 24780
aatggagaat ttaggattga aaaatacagc caggcatggt ggcccatgct tgtaatccca 24840
gcactttggg aggctgaggt gggtggatca tgaggtcagg agatcaagac caccctggcc 24900
aacatggtga aaccctgtct ctactaaaaa tacaacaatt agccgggcat ggtggtgcac 24960
acctgtagtc ccagctactc gggatgctga ggcagaagaa tcacttgaat ctgggaggtg 25020
gaggttgcag tgagccgaga tcgtggcact gcactccagc ctggtgacaa agcaagactc 25080
cgtctcaaaa acaacaacaa tcacacacac acacaaaaac ccaataacaa taacaacaac 25140
aaaacctttc tggatgggct caacagtcaa gtagagatga gggggatgaa gtcagtgaac 25200
ttgagaacag agtgatcaaa aaaaatgcag cagtgcagaa gttgtggtaa tgaaccacag 25260
ggagaaagca gaccagaaag aaaatgagca gtcccagggc ctatggaaca acagcaaaac 25320
agtgaaaatt cctatcatgg gagtctcaga aggagaagat agaagagtgg ggctgaaaaa 25380
gtagccagaa aaatagaggc tgaaaacttc cccaatttgg tgaaagacat aaacctacaa 25440
attcaagaag ctgaaccaac cccaaatagg aacaaaacaa agaaatacat ggcaagacac 25500
atcatagtta aacttatgaa aacttaagac aaactctcaa aaatgctcag agagaaatga 25560
ccctttactc atagggaaca ccagttggaa caacagtgga tttctcattg gaaatcatgg 25620
aagctagagg aagtggcaca tctttcaaat acgtagaaag cagggaaggg ggaagaactt 25680
tctgaaaata tccttcaggg ttgaagagaa aattcagata ttctcagatg aaggaaaact 25740
aagagaagtt gttgctagca aacttattgt ttaaaaaatg gttgaagggg gctgggcatg 25800
gtggctcacg cctgtaatcc cagcactctg ggaggccgag ggaggtggat cacgaggtca 25860
ggagttcaag accagcctgg ccaagatagt gaaacctcat ctgtacaaaa aaaatacaaa 25920
aattagccaa gctcagtggc aggcacttgt aatcccagct actcaggagg ctgaggcagg 25980
agaatcgctt gaacccaggg agcggaggtt gcagtgaact gagatcacgc catcgcactc 26040
cagcctgaag ggttgggtgc agtggctcat gcctgcaatc ccagtagttt aggaggtcaa 26100
ggtggaagga tcgcttgatt ccaggagttc aagaccagct tgggaaacat agggaaacct 26160
catctctgaa caaaattagc caggcatggt agtatgtgcc tgtggcccca gctactctgg 26220
aggataaggt gggaggatct cttgagccca ggaatgcaga gactgtagtg agctgagatt 26280
gtgccactgc actccagcct gggtgacaca gtgagactcc atcttaaaaa aaaaaaaaaa 26340
aaaaagaaaa gaaaagaaaa gaaaatgttc aaaggaagtt ctctaaatag gctttgaagt 26400
tcagaaagga aagaagaata tcggactgat taaaaatagg ggtaaaaata caagattgtc 26460
cttcttacgc attttaacaa tcatctttga tgcctgacac caaaaatcat ggcatctgat 26520
gtggtgccca atataggcag aggaaagact taatgataat ttaaaagtgg agagagaaag 26580
agacctaagt aaaggtaacg ctcttgcatt tcactcaaaa tgttgagctg ttgatagcct 26640
cagaccgtgg tgccttatgc aggcagtcat gtatgtacac aaccatgcaa tgctaacaat 26700
ggggtacgtc ctcagaaatg catcgctggg tgatttcacc attgtgcgaa cattatagag 26760

-continued

```
tgtgctcgca caaccctaga tggtgtcgcc tgctgcacac ctgggctatg tggtacagct  26820

gattgctcct aggctataca cctgcacagc acggtactgc tctgaacact gcaggcaaag  26880

gttgcacaat ggtaagtatt tgtgtatcta aacatatcta aaaacataga aaaggcatag  26940

taaaaatatg gagttttaat gttatgggac caccattgta tatgtggtcc accgttaact  27000

gaaacatcat tatggggcgc atggctgtat tgtaaaactc agtgtctgtc tgtctgtctc  27060

tctttctttg cctctagtgg caaaaggtac accttctctc ctcgctcccc taattgaggt  27120

tcctttttgg tcaccttgac agtgggggag ggagtatgag actaaggcag gcaggatgct  27180

gtctcatgtc ctccataact gaatggacaa tttctgcatc tgggtggccc tgccccaccc  27240

actccctctc ctctttggtc ttgtagaaca tttttggctg tcatttccca atccaaagag  27300

ggaaggtcgc ccagtggata gtgaactgta ggaacctggg ggaatacctg tgccgtgggt  27360

tttcctctgg ggaaa                                                    27375
```

<210> SEQ ID NO 5
<211> LENGTH: 35979
<212> TYPE: DNA
<213> ORGANISM: Homo sapiens

<400> SEQUENCE: 5

```
ccaactgagc tccttctcat ccttcacgaa cgcctctctt cgaggtcaac tcaccccatt     60

gggaagtccc tatcttgtct ccttggccag cttctctttt agggtgaacc gcctgatctt    120

cactgcagtg gccttgcctg gctcccagca gatgttctcc aatgtcactt tcagtgacat    180

cacagaatcc tacatttctt tctttttgc aagcattgca attttactta aaatttgcac    240

tgtaaatatg actgtggaaa atgtatttaa gagagctggt tctgcaaaga cagggaagag    300

atttgggagg caggggtgtg ggaataagcg atattcttaa gtaagtgagc tgcttgagtg    360

gaggacactt ttagaagtgg tcagcttggg cttggcatgg tggcttactc ctgtaagccc    420

agtattttgg gaggttaagg aagaaggaac actttagctc aggagttcaa gaccagcctg    480

ggtgacatag caagaccccg tctctacaga aaaataaaat aattagctgg gctaaattat    540

tagctgggct aataattttt ttattttttt tctacagaaa aataaaaaaa attagctgtg    600

gtggtgcaca cctgcagtcc cagctaatgg ggaggctgag gtggaagaat ctcttgagcc    660

tgggaagttg aggctacagt gagttatgat tgcaccacta tactcccgcc cgggtgacag    720

agtgagaccc tgtcttaaat aaataaataa ataaataaaa gacatggtca gcttgtttac    780

ttgtttgtga ttattttctt tttttccttc ttcttcctct tttcttttct tttttttttt    840

tcaatagagg tagagtctca ctgtgttgcc caggctagtc ttcaactcct aggctcaaag    900

gatcctcctg cctcagtctc tcgagtagct ggtactacag gcatgcacca ctgccgctag    960

tgaatatttt caagaccaga tggtcccccc aacccaagga atcttggata atgagtgaag   1020

ggagaccctg tatggggcct ggagaagctg gctatgtgtg gagtggtcac tgagggagca   1080

tcttagcatg aatcttggtc agagtgatcg gggaaccaga ctcagtctgg aaacaagcag   1140

ggtacacctt cagcttacag acagcagatt gtggagctgc tcagcctcca taattacata   1200

gttcaattct tcagaatcat ctgtgtatct ctctatctat ctatccatcc atctatcatc   1260

tatgtgcctc catatccatt tatgtttttg ttgttgagat gatcaagttg gttctaaaat   1320

ttcgttggaa aagcaaagga attgaaaaaa agaaaacaat ctttaaaaag aagaatgagg   1380

ttgaagtctc acaatacttg acttcaaaat ctcccataat gtcacagtga cgctgtgttt   1440

gcattaggaa gcagcataca gacctgcgga gcaggacaca ggaacaaact cgccatagtg   1500
```

-continued

```
tcggctgatt ctcattaaaa acatcagcga tttcagtggg ataaggatgg ttggtttatt   1560
tatttgttta tatagtcatt tatttattca tttttcagat ggaattttgc tcttgttgcc   1620
caggctggag tgcaatggga tgatctcggc tcactgcaac ctccacttcc cgggtccaag   1680
caattctcct gcctcagctt cccgagtagc tgggattaca ggcctgtgcc accacaccca   1740
cctaattttg catttttagt agagacaggg tttctctatg ttggtcaggc tggtcttgaa   1800
ctcatgacct caggtgatct gcccatatag gcctcccaaa gtgctgggat tacaggcaaa   1860
ccacctttgt ttgtttgttt gttttgagac ggagtctcac tttgtcgccc aggctggagt   1920
gcagtgccac aatcttggct cactgcaacc tctgcctcct gggttcaagc gattctcctg   1980
cctcagcctc ctgagtagct acgattacag gcgcccacca ccacgcccag ctaatttttg   2040
tatttttagt agagatggag tttcgccacg ttggccaggc tggtgttgaa ctccttacct   2100
caggttatct tacctcgtcg gcctcccaaa gtgcctggat tacaggcgtg agccactgcg   2160
cctggccacg atagtctttt tatcaaatgc tgctgaaaca attggatgaa aatgtgaaaa   2220
aatggatctc aactcctacc tcacattaca cacaaaaatt agcttgagat ccagcataga   2280
actaaatata gaaacaaaaa ctctaatgct tctagaggaa aagctaggaa agagagtttt   2340
caaaaaggtc acaagaaagc actagctgtc aaagaaacaa atgttaaatt gcacttcaaa   2400
atcaaaaacg tttccctata aaaataagat aataataagg caaatcaaat actgaaaaat   2460
tatatattat gtattataca tacatatata ttatatatac acatatgtag ggaaaagaaa   2520
gagagatcag actgttactg tgtctatgta gaaaacgaag acatcagaaa ctccattttg   2580
acctgtaccc tgaacaattg ctttgccctg agatcctgtt aatctgtaac tttgccccaa   2640
ccttgagctc acaaaaacat gtgttgtatg gaatcaaggt ttaagagatc tagggctgtg   2700
caggacgtgc cttgttaaca aaatgtttac aggcagtatg cttggtaaaa gtcatcgcca   2760
ttctccagtc tcgagtaacc aggggcacaa tgcactgctg aaagccgcag ggacctctgc   2820
cctgcaaacc tgggtatggt ccaaggtttc cccccaggtg atagcctgag atatggcctc   2880
gtgggatggg aaagaccgtc ccccagcccg acacccatga agggtctgtg ctgaggagga   2940
ttagtaaaag aggaaggcca cttgcagttg agataagagg aaggcctctg tctcctgcct   3000
gtccctggga actgaatgtc tcagtgtaaa acccgattgt acatttgttc tattctgaga   3060
taacagaaaa acccccctgt ggcaggaggc gagacatgtc ggcagcaatg ctgctctgtt   3120
attctttact ccactgagat gtttgggtgg agagaagcat aaatctggcc tacgtgcaca   3180
tccaggcata gtacctcccc ttgaacttaa ttgtgacacg gattgctttg ctcacatgtt   3240
ttcttgctga ccttctcccc actatcaccc tgctctcctg cctcattcct ctcgctgaga   3300
tagtgaaaat agtaatcaat aaatactgag ggaactcaga ggcctgtgcc ggcacaggtc   3360
ctccgtatac tgagtgccgg tcccctgggc ccacttttct ttctctatac tttgtctctg   3420
tgtcttattt cttttctcag tctgtcgtcc cacctgatga gaaataccca caggtgtgga   3480
ggggctggcc cccttcacac atatatgcat gtatataaaa tacatgtgta aatatatata   3540
tatatacata catatggcaa agcatttcat tcatatattc ttgatattga atttatgaag   3600
agttccaaca actcaataac cctacaataa agtgggcaaa caattttaac aaaacctttt   3660
aacaagaaag atgtgaaaat gaccagtaag tgcaagaaaa gaccctcaca aacattagtc   3720
atcagagaaa cgcagatcaa aatccacatg agaggcaatt ttacacccat ccgacgcctc   3780
acatttgaaa acccaatggc ggtactgaca ggcctggggc agcggacgct ctcaggcatt   3840
```

-continued

```
gctgaggaga agggaaagca gcttgagcgt ttggaaagct gtctgtttct tagaaagtta   3900
agcatacact actctatggt ctagcaaggc cagtcctcaa tatttaacca aaaaattaaa   3960
accaaaaaca tgaatacgga aggactggaa ggcatgatta tgtgttattt atcatcgccc   4020
caaactgcga acaattcaaa tatctatgaa caggagaatg gaggaacgcc gtggagagta   4080
tttttacacg aaacactacg cgatgattaa aaaagaagaa taaggccaga cgtggtggct   4140
catgcctgta gtcccagcac gttgggaggc tgaggcaggt ggattgcctc agcccaggag   4200
gtcgaggctg cggtgagcca tgagcgcacc actctgcact ccagcctggg tgacagagca   4260
agaccctgtc tcaaaaaaaa aaaaaagaag aagaagaaga agggcaaatc attgacacac   4320
acaataacat cgtgagggaa agaaaccaga gtacattttt aatgatttca tttccgcgac   4380
attcaatagc aggcaaaact agtcagcaaa gctgtgcctg tagtgatggg caggaaggga   4440
aggccgtgaa agtgaacctt ctggggttga agcagttggt catggttggg gtgatgggca   4500
cacgagtaca tgtttagcgg aactcatgga attgtacact taaagtatgt gcagaggctg   4560
gtaggccaag gctgcagtga gctaggatcg caccactgcc ctccagcctg ggcgacagaa   4620
tgagacactg cctcaaaaaa aaaaaaaaaa aaaaaaaaaa aaaaaaaaaa atgcagtccg   4680
ggtgtggtgg ctcatgcctg taatcccaac actttgggag gccgaggcag gtggattact   4740
tgaggtcagg agttcgagac cagacaggcc aacgtggtga aaccccctct ctactaaaaa   4800
tacaaaaatt agctaggcat ggtggcacac gcctgtaatc ccagctactc agggggctga   4860
ggcaggagaa ttgcttgaac tcgggaggca gaggttgtag tgagccgaga tcatgccact   4920
gcactccagc ctgggcaaca cagtgagatt tagtctcaaa aaaaaagcat ttcactgcat   4980
gtaaatttta cctcaatata aaattaaaat taatcttcgg aaaataaaag tacattagag   5040
aggatggcta atcaaaattt ttgtagcctt caaggagaat aaatttgaag catatctgtt   5100
gatttgtgga atttttacaa agacttaatt gaggaaaact tgaaagcatt agaaagggtc   5160
ccgttcctct gttccctctg tgagcccagc ttgcctgaag ggaacgtggg tctaatccgt   5220
gtctggagga gtgagccgaa ccacaggaag aagaggtaag aaagacaaag gagaaccagg   5280
gccacactca aatccacgct cttcaaaact gtgttttaca aatttgacaa aatatttatc   5340
ctggaaattt ttaagcggtg gaacctatag acagcctttt ctttcagctt attttgttag   5400
ttttaatttt atttaatttt tttacaaaat gaccaccgtt gatataaaca ccaatgccag   5460
ggggtggagg gtctgcatcg ctgaggagag ccctgagcgc caaggaaaat ggtccacccg   5520
ctggccaagc caccaccgtc tcccaggctc ccgggacacc tgctggagag ggagcccagt   5580
gtcttctaac aaagggaaac acctatgagg aagaggccaa atttagaaac caaggaaagg   5640
agagcttggc tggagctgat ggcggctcat gggattgtga agagattaaa aataacactc   5700
gtgcatgtga aatagcagaa acaacaacag aagtattcat gtgttcagta taaacacctg   5760
ggcagggata taaagggccc aggctcaggg agttccacac ctgcacacct ccctctcacc   5820
tgctcctcta cctgctccac cctcaaccca ccagaaccat gggctgctgt ggctgctctg   5880
gaggctgtgg ctccggctgt gggggctgcg gctctggctg tgggggatgt ggctctagct   5940
gctgtgtgcc catctgctgc tgcaagcccg tgtgctgctg tgtgccagcc tgttcctgct   6000
ccagctgtgg ctcctgtggg ggctccaagg ggggccgtgg ctcctgtggg ggctccaagg   6060
gggactgtgg ctcctgtggg ggctccaagg gaggctgtgg ttcttgtggc tgctcccagt   6120
gcagctgcta taagccctgc tgttgctcct caggctgtgg gtcatcctgc tgccagtcca   6180
gctgctgcaa accctgctgt tcccagtcca gctgttgtaa gccctgcagc tgctcttcag   6240
```

-continued

```
gctgtgggtc atcctgctgc cagtccagct gctgcaagcc ctgctgttcc cagtccagct   6300
gctgtaagcc ctgctgctgc tcttcaggct gtgggtcatc ctgctgccag tccagctgct   6360
gcaagccctg ctgttcccag tccagctgct gtgtcccaat ttgctgccag tgcaagatct   6420
gaggctctgc ctacaaatct cagctggtcc cacagatctg ggctctccag gaatgactgt   6480
agctgtgtcc tgaattcctg aagcacatct ctgagtctgt cctcctctgg actaaggcag   6540
cctagcgtcc agggctcagt actcagctgc tcagcctctg aggtcatgag ggcttctggc   6600
atgctgggtg ctgcccatca accctcccag aatcccctct tcctttcctg acctcatcac   6660
ttcaaccttc tcagggcttc aagatcccac atccctgggc ccctcctgtg agcctgctgg   6720
aaacacactg aaactggaat cctccgacct gctgccgcct ctccccggtc cctgcaacct   6780
cctggctcct ccacccttca tcttcatcct gcctgagctg ccacagctcc gattgttttt   6840
ggagttgacc tagaggactc agaattatta gagaccccag gatcctctcc tgaggaggag   6900
gggcgcccag tctcctcttc tacctctgac ctggccttgt ttctttcccc agggcttcgc   6960
cttgtaagtg cctaggctga atcttctaaa taaatacgat ccacacctcc cacgagtttg   7020
cgttgtgatt cttttgtttc aacttctgtg tgattagata aatgtacaat tttcacagag   7080
tcgcactccc aggcatttgg gaaccccccg ttccctgctg tgtgagtttg ctagggctgc   7140
cccacaaacc atgtggctta tgcaacggga gtggatcgtc tcacagtttg gaggccagaa   7200
tctgccatcg aggtgcctca gggccgggtc ctcctgagac ctccctccgt ggcttactga   7260
tgccgccatc cctatatcct catgtgcttg tccctctgtg tgtgtctgcg tcctcatctc   7320
tttgtataag gacacagatt agattagggc ctaccctact ccattatgtc cacgttttaa   7380
ctaatcaccc ctgtaaagat ctatctccaa ataaggtgcc attctgagat actgcagtga   7440
ggactccaac gtatgtacca gggggcacaa ctcagccgtg gtatccactt ggcttggggc   7500
atcaccatct ttcccatctt ccaggataca gaattgggag gccccttggg cttctctccc   7560
ctacaagtcg ccaaatccca cagcatctcc tggaagacat cctaagacac ctccttcctg   7620
ccttcttgtg acacctccct acctagacct ctgcttcagg cccccaactg tcccttccct   7680
gctgcctctg tcagctcggg ctgccagaac aaaacccaca gagtaagcct ggaagacgga   7740
acaacagaca ccatttctcc cagttccgga ggctggaggg cctagaccaa agtccggcat   7800
gttcgactca tggggaggga aggcaggagc tggcggagga ggaggtgggc tgcaaggctg   7860
gagcccccag acccaggcgt ctgtaacagc agagcacggg aggctgctcg ggaagccacc   7920
ttctcacagg atggcaggcc gtgagtgtct gatggaactg tgacaagaaa gtgaaaactc   7980
aacaacacgg aatttttaga atgtgcttct gagtttctgt tttagtaagt aaggttgact   8040
agacactatt cacaacctgg aacttctcaa aggacatggt gaaaccccgt ctccactaaa   8100
aatacaaaaa tgagccgggc atggtggtgg gcgcctgtat cccagctact caggaggctg   8160
aggcaggaga atcgcttgaa accgggaagc agagggtgca gtgagcccag actgcaccac   8220
tgcactccag cctgggtgac agaatgagat tccatctcta aataaataaa taaagtttta   8280
aagtgctgta tttaaaacat atatttttta agtcactgag ctgttgaaaa aataaaataa   8340
tcctcagagc caacaagcaa gagagagctg gacccacaga ggaaggtgaa agtcaaaaac   8400
ggcctccacc ctgtggctgg accagaaaga ggccctctct gttttcttcc acctgtggta   8460
ttgcttctgt tgtcagcatg aatctgagaa aaacgtagtt tctctacact ctcacacaga   8520
acactctcat tcctgatgtg cgggttttcc ccacactact caattttctg cctctttcca   8580
```

-continued

```
cactgaccaa ttctctgaca ccagctgggt gtcctgcaat tcactcccat cttgaaacag   8640
agttcatttc agatcccaca ggcgaagggc tcagtcccac aagactgtcc ccacttcaga   8700
ggctgacatg gttttcctct gtccccaccc aaatctcatc ttgaactgta gctctcacaa   8760
ttcccctgtg ttgtgggagg gacccagtgg gaggtaattg aatcacgggg gtgggtgttt   8820
cctgtgctgt tctcatgata gtgaataagt ctcacgagat ctgatgattt tatgaatggg   8880
agtttccctg cacaagttct cttatcttgt ctgccaccat gtgagatgtg cctttcacct   8940
tccaccatga ttgtgaggcc tccccagcca ggtagaactg tgagtccatt aaacttcttt   9000
cttttgtaaa ttgcccagtc tcaggtatgt ctttatcggc agtgtgaaaa tggactaata   9060
cagatgccaa tcacgagtcc agcctcccaa gcttctaacc gatgggctat aaatcagggt   9120
ttacactgat acctgaaatg agtggctgag gcaaagctct ctgtccatca aggtttacta   9180
agcctgcttt aaggcgcacc tgagaaaaat gcaagatgca ggcacatctg tggctgtttt   9240
cccagagaga tttttgggaa gtttggtatt tatacatttc cttaaagggg ggcaggcagg   9300
taggaagagg caggtaagca ttaggcaaat gattgcattc ctgtgagact ttagttagtg   9360
cccagtaaat ctacatttta catgaggtaa ggtgaacgtt tgaagagaaa aagggactaa   9420
aggaagagtc ggttgtgcag acctctctgg gtagatggag gagggactgg tgtcatcttg   9480
tttttgttct gcttctggga agataaactc ataatctata tgatcagtgt ggaatggaac   9540
actttcgttt taggagctgg acttggattg caggcctgaa gtcacaacgg gcacatcctt   9600
gttgatggca ggacgcactt cttgagaggt tttgcaacca gcatagcgca tatttatgag   9660
tgatttgtgg aggaagtgtc ctgagacacc tgaagccttt gccgtttcct gggcctggca   9720
agcgaaacac acagcaacac aggctgtgga ggaacagtgc tgcttttgcg agagggcttg   9780
gggttctgag atttttattt ttctttactc aacaccaccc tccttgggtt tgataatctg   9840
ctagaacagc acccagaaca cagggaaaca ctagcttatg tttactggtt tattatagag   9900
gatgagacac agacgaaccc ctaggtgaag aggcaccaag ggtgaggtcc aggatggtcc   9960
tgagtgtggg agctttgtcc cgtggagccg gagtcatcgc tctcccggcg gggggatgtg  10020
tgcaccaact ggaagctgat gggatctcac tattcagttt tgcagagctc tcacctgcag  10080
ccctccctgt cctggagctg agttcccagg ctcttctcac tgggtctttc tgaccaccag  10140
tctcatcctg aggccatcta ggggccccac cctaagtcac ctcattaaca taaacacaag  10200
tgtgatctaa gggagcttat taggaataac aaaaaacaaa caaaccaaca cataattaaa  10260
aaacccaaga aaacaatatc cctcagagaa attgcaaggg cttgaggagc tctgtgccgg  10320
gagccaagaa ggaaggtcaa gaccgtctct tctcacacag tgaaagctcc aggtcagtgt  10380
gctttgcgca tgtccatgag tcctttccat catttggttc tgtgcaactg ctgcaggagg  10440
aagctattac gaatcaggga agaaaacagc cgagctttta aaaaggcttt gagactgggc  10500
gcagtggttc acacctgtaa tcccagcact ttgggaggct gaggtgggtg ggtcatgagg  10560
tcaggagttc gaggctagcc tggccaatat ggcaaaaccc tgtgtctact aaaaatacaa  10620
aaattaattg ggcttggtgg cacatgcctg taatcccagc tactcaggag gctgaggcag  10680
gaggatcact tgaaccggga ggcagaggtt gcagtgagct gagatggcac cactgcactc  10740
cagcctaggc aatagagcga gactccatct caaaaaaataa aaaaaggctt tgaaaggccc  10800
aatgtggatg ggtacgagca tgtaaatccc cagaggtccc tgccttggtg agtcactaac  10860
agcctgccag ctctatttcc ccacggctcc tgagaaagac tgcatacatc gggtaagaga  10920
ggcatcaggg ccgctgcagg agtgggatgg agaggagagc caggccaccc tgagagcgag  10980
```

gccacagcag ctgcaggtgg aggagggcca gggagcccag ggtcgtctgg aggacagaca 11040
caggggctgc tgacgtctga ggaaggcagg agaatggaca gacgccctgt aagcaagatc 11100
ccagatctgc tccagagaag ggtcccttcc tgacctctag cacttgagcc ggtagaactt 11160
aatctagcta acgaagccat gagcctggaa ctgcccaagg gggttcacct tgcccgctgc 11220
ctggacagag ctgattcatc aagacagggg aactgcaata gagaaagagt cattcacaca 11280
gagctggctg tgcctgagac cggagtttta ttattactca gatcagtctc cctgagcatt 11340
tggggagcag agtttttaag ggcaacttgg tgggtgggga gaagccagtg atccaggagt 11400
gctgattggt cagggatgaa atcacaagga gtcgaagcca tcttcttgca ctgagtcagt 11460
tcctgggtgg gggccacaag atcagatgag ccagtttatt gatctgggtg gtgctacctg 11520
atccatcaag tgcagggagg gtcagaatct tgtaaatgac ctctggctac atgactccta 11580
aactgtaatt tctaatcttg tggctaatgt tagtctagtc cccaggcaag aaggtggtct 11640
gctttgggaa agggttgtta ctgtctttgt ttaaactata aactaccaac taaatttctc 11700
ccaaagttag ttcagccaac acccaggaat gaacaaggac agcttggaga ttagaagcaa 11760
ggtggagtgg gctaagttag atctctcact gtctcagtca taactttgca aaggcggttt 11820
caagcccagc tgccaaccag aggaactcac tcaacacgtg agcagcaggc agaagcaaga 11880
gccttcccct gagaaatagg aaggaaatcc tagcctcgcc cccgcaacca ctgactgaac 11940
gggacccctc ttggccaagg gggtgtcgac aaaaagtgtc aaactctgta aaatatttta 12000
aaagattctg agccgaacat gactgacaaa tggcccgtga cacagccctc aggaggtcct 12060
gagagcaggt gcccaagagg tttggggtgc agcttggttt tatatatttt agggagacat 12120
gagactttaa tcaaatacat ttaagaaata ctaaggccta aactctgttg ttgttttttt 12180
taatcttgct caaattccta tctaaggggt ctgcgcatgc cctacaaatc ataaactctc 12240
aacagacagg ttttgtttag ccctaaatat tgtgacttac tttccaaccc gactctggca 12300
taacattatg agacaaggaa gaaaatcaaa atactttacc ccaaaacatg tttctttgct 12360
gtattttgaa atggccctgc agagcgtcct ttgtggggga aaatttggat ctgcaaagaa 12420
tctctattaa catagctaga tctttttctt ccagaccctc ccagtcctaa agagattaac 12480
taaggtctga ataggaaaca tttgtcatct attgtctcta agggcagcca ctatcagact 12540
tcaaaagaac tttggtctcc acaatcttta tcttaacttg aactttccct tcctatccat 12600
cccaggtctt tagacaaact caaccaaccg tgaaccagaa aatgtttaaa tttacctata 12660
gcctggaacc ccctcacccc ccatccccca ccacccgctt tgagttgtcc cgcctttctg 12720
gaccaaacca atgtaatttt gaaatgtatt tgattgatgt ctcctgcctc cctaaaatgt 12780
gtaaaaccaa gctgtaccat gaccaccttg ggcccatgtt ctcaggacct cctgagggtt 12840
gtgtctcagg ccatggtcac tcatattggg cccagaataa atctctcttc aaatatttta 12900
cagagtttga ctctttttgt cgacattaca ttggtttggt ccagaaaagt gggacaactt 12960
gaagggtggg gagtgcttcc aggctatagg tagatgtaaa aattttccgg ttgacagttg 13020
gttgagcttg tctaaagacc tgggatcaac agaaaggaat gtctgggtta ggataaagga 13080
tcatggagac ccaggttgtt atttgcagag gaagccttta ggtagcaggc ttcagagaga 13140
agaggttgtg agacgtttgt tatcggactt aaagtctgtg tggatgttaa tgccagagag 13200
gtagaatgag gcatgtctga cccccactgc ccatcatagt gtctcaggtt aaattttaaa 13260
acagccctgg ctgaggagga agtccattca gatggtcggg gaggaggtct tagaatgtta 13320

-continued

```
tgtttggtta accgggaaac cttggaagct gagttcctgg ctacgggggg atgggaagct  13380
ggacttgcgc ccttctccta ctccctggcc agccatgacc cagctccctc ccctcaggga  13440
aaacagaaac caattctgtg gagactgcac tgaggagatc agtgtacccc tgacattgcc  13500
ccctccttct tgataggaga tccaccacgg agaggccctg gccattctac ggaagaggcg  13560
caaggaagtc ttctgagtcc gctgcttcac cttttgacat cagagggcca aaagctccac  13620
cctcagatca ggctaacacc tctggttttt gcacatagag agggggtgaa gctggattgc  13680
gcatatgcct ggttttgggt ctgcagttgg ttcctgctgg tgggttcgtg gtctcgctga  13740
cttcaagaat gcacccatgg actttcacgg accttcgcag tgagtgttac agctcttaaa  13800
gatggcacag acccaaagag tcagtggcag caaggtttat tgtttattcg cgaaaggaca  13860
aagcttccac agcgtggaag tagacccgag tgggttgccg ctgctggctg tgtggccagc  13920
ttttattccc ctattggccc cgcccatgtt ccgtttctgt cctatcagag tgcctttttt  13980
tcaatcctcc ctgcgattgg ctactttcag aatcctgtgc agattggtgt gttttacaat  14040
cctcttgcaa gacaggaaag ttcctgattg gtgcatttta caatcctctt gtaagacaga  14100
aaagttcccc aagtccccac gggacccaag aagtccagct ggcctcatgt ctcagtttct  14160
cctcttatca atattcatgt ccctcccaca gcttattgaa tatgcatatt cagccacccc  14220
cactcagtgt agatctctgc tttattcttc cctccctcca agtgtctgtt tccagcttcc  14280
taccagaggc tgcgcctccc aaccagtcag aacagccaca ctcagcccgc agcactttat  14340
gagaagtaaa gcgctccttt ccaaattgac gacctcgtcc ttcttcagtt aacacctccc  14400
tctctcaatg acgatgatgg agcatgtcca ggtgttggtg acacagctac atggctgcgt  14460
gtgggataaa gtcgctgccc cttcagaact cacacccccc tggagtggga cacacacctc  14520
taagaacaaa caaggatgag agcagagcca gcttggcatc gtgggaatca ataaatgaaa  14580
cagaaagtgc aaggtggtgg gggtagctat ctcgggacgg ggtgtcagag gtggatctga  14640
gttgggcaga caggagggac gcagtccagg gcggtcctgg gtgagtctgt tccatgtaag  14700
gaactgccag cacacaggtc gtaaggagga gtgcggtgtg gccccggcac caatccaggg  14760
ctggatgaag aatgattgag gcagtctgaa gatgacacca agtcattctc ctcccacgga  14820
gaggtggact ttctcttctc tctgcaatct gggctggcct cagtgacttg aggagggaga  14880
aatactctag gattcctagg ctgggtcata aggcaccttc tagcctctgc tcgagtgacc  14940
tcctaggaag tacagctgcc ctgagcccac catgctgtga ggaagcccaa gccagccgtg  15000
ggaagaggcc gtgaggtggg ggaggggagg gagatctgtc cggcctcacc tgttgtagcc  15060
atcccatagg tgtgtgaaca cagcatcttg gacaagccag ccccagctga cataatttac  15120
agaaaaacca aggaaccctg cagacagccg gaactgaggt cccaaaatac agcccagcca  15180
agccatgctg ccatcgttag ccattggtac cttcccaatt gagaccccac aaatcatgcg  15240
gcctgtgcca ccatccagtg ccggatctga actactgatc cactgagctt tgggctgatt  15300
ggttctgcaa cgatgggtgg ccaaggccac ggtcaaatcc agctggagag gtggatgggg  15360
ccagtgtcag gggtttggat ttcaccccaa gtcagctgag gcacactgga atgtcgtaag  15420
cctgcacatc cactcatcac acattttaac cgcatctgag tgtggaccgt accgatgggt  15480
tcctgcacct gcagcctcca caccattgct ggtgccctgc ctcctagctg gagtatcctt  15540
cctgtctctt ggctgctctt tgtacccatc atggtccccc taccaccctc caagttctgc  15600
tccaagcttt gttttcctcc aagagaagaa cctgtccaga caatagtttc aaagcagcgg  15660
gaagctctgc tcacgtgtcc ccaaggacca tgctgtgtga aattcccttc tgtaatcaca  15720
```

-continued gagcccattg ccctggccta ttcctggtcc aggaataggg aggaggtaga cagaggatgc 15780
ctccttcccc actgctgaga accctgccat cctcagccac agttgccaca gagaagatac 15840
cacatccctg ggggaatcag caggaatcag gtagagagtg gcactgctct ggggagggag 15900
ggcgtctcac agcatcaaac gtcaaaaacc cacaacattg acccagtcct gccaagacgg 15960
aaccctgcat gagcatgggg gatggggagt tggggtgttg caaaagacgc aatacatgaa 16020
tgatctcagg taattctcag gcaacccccg gaggctggtg ttgctagcac ccctctgcag 16080
gagaagaagc tggggctcgg gagctgactg gatctgctca aaggcccagg aagaataaga 16140
gttaggaact gggacagacc ttgaggaagc tgcacttcct cctgaggtga gccagcgttg 16200
gagctgtttt tcctttcagt atgaattcca caaggaaatc atctcaggag gaagggctca 16260
tacttggatc cagaaaatat caacatagcc aaagaaaaac aatcaagaca tacctccagg 16320
agctgtgtaa cagcaaccgg aaagagaaac aatggtgtgt tcctatgtgg gatataaaga 16380
gccggggctc agggggctcc acacctgcac ctccttctca cctgctcctc tacctgctcc 16440
accctcaatc caccagaacc atgggctgct gtggctgctc cggaggctgt ggctccagct 16500
gtggaggctg tgactccagc tgtgggagct gtggctctgg ctgcaggggc tgtggcccca 16560
gctgctgtgc acccgtctac tgctgcaagc ccgtgtgctg ctgtgttcca gcctgttcct 16620
gctctagctg tggcaagcgg ggctgtggct cctgtggggg ctccaaggga ggctgtggtt 16680
cttgtggctg ctcccagtgc agttgctgca agccctgctg ttgctcttca ggctgtgggt 16740
catcctgctg ccagtgcagc tgctgcaagc cctactgctc ccagtgcagc tgctgtaagc 16800
cctgttgctc ctcctcgggt cgtgggtcat cctgctgcca atccagctgc tgcaagccct 16860
gctgctcatc ctcaggctgt gggtcatcct gctgccagtc cagctgctgc aagccctgct 16920
gctcccagtc cagatgctgt gtccctgtgt gctaccagtg caagatctga ggctctagtg 16980
ggaaacctca ggtagctcct gaagatctgt gctttccaac aagtgactac ccttgaagca 17040
catccccttc tggatctgaa aagagccctt ggctcagggc gtctttttcc agcccctgag 17100
gaaatggaat gaaccactcc ctgcccattc cctataagaa tatcccaaga cccaggcaat 17160
tttgcccctc tttcccacat gcccccatat gtctgagcca aactgcactg ggggctgccc 17220
tcatgccaag caagagcctg gaattcccct tcttgataat tccatgggag acagcaaacc 17280
cttctttcct ttgcctgcca ggagcttcac gacatttgca gatggatgtc ctgcaaccca 17340
aatgatcaca tgtatctatg gaaatccaaa atgcatctgg gtgcagcact aaataaattc 17400
tccatccctc agccttggtc tcactgactc ttttcttcca gcctctgtct cattggcaaa 17460
ctggccacat gtccttcccc tcctccctga tagcttattg ctcccactgc tgtaacagtg 17520
tgccaggccc agctcccatt ccagaaacag ttgttgaact gattaatgaa ggaaccacta 17580
gcagtatgta tgaatgaatg aagacgagga atgaatgagt gaatgagtga gtatctctca 17640
ttagtacaca gggagtccca gctgtatctc agtgggattc agtctgtctt ggttggaatt 17700
tggactccta cttcttcccc atgggaggat atgtttggga gagaaggaga actttgccct 17760
cagtgcctag gaagggatgt aatgggtgct ctctgggtcc agccagtccc cagtttgtgg 17820
gtcaagccag gagatgggga agcgagacta gaatgagctg tgtccctgag atgctctgta 17880
ggacaacact ggaaactgtg ctgcttcaag gatccaagac ggtgtggctg aacacaggct 17940
gaagtgcacc ctccatctct gggctcagag tgaggaggaa tccaagtgtc cacaggcttc 18000
ccagctttgg tttggcacag ggaggaacag aagggacttt tctcagcctg ataaaggcca 18060

-continued

```
tctacccaca gtgaacacgg tgcttaacta tgaaaacctg gatgttttcc cctaggatca  18120
ggaacaggaa aagaatgtcc acacccacca cttctatgca acatttcact gaagctatag  18180
ccagaataac ataacaggaa aagaaaataa agccatccag gtaagaaaaa aggaagcaaa  18240
actatctcta ttcacagaaa acctcatctt gtatacagaa gatgctgagg gacacacaca  18300
cacacacaca cacacacaca cacacaacta ttagagccaa taaccgagct cagcagagtg  18360
cagaacacaa ggactataca caatagtcag ctgtgtttct ttacaacagc aaaaagcaag  18420
caaaaaggtt gtaaggaaac aataaaattc ctgggaacaa atgcaaccaa aaaagtacaa  18480
gacttggaca cttaacacta caaaacacca ttggaagaag ttaaggagga ccaaagtaat  18540
gggggaaaaa atcctatgtt catgtattgg aagacctaat attgtgaaga ttgaaacact  18600
ccaaaaaaaa attgttctac caatttaatg caattccgat caacatctca gatttctttt  18660
ttcaaaaatt gacaagttga tcctaaaatt tatgtggaca ttcaagggac cctaaatagc  18720
taaaacaatc ttgaaaaaga aaagcaaagt ttgaggactc aggttttcca atttctaaat  18780
gggctgcaaa gctacagtca tcaaggcagc atggctcttg cataaggata gaaagatgga  18840
tcaatggggt aggtttgaga ctcttgaaat aaagcctcac agttgtggtc aatgtatttt  18900
cacaggtact atacaattcc atgggaaaag aggaatgttt tcaacaaaca atgctgctaa  18960
gacaactgga tgtccacatg caaaagagtg aatttgaatc ttgacctcat accatatacc  19020
aaacaaacaa aaaaaaaata gaaaaaatag atcaatgacc taattgtaaa agccaaaact  19080
agaggattac tagaagcaaa acaggttaag ttttcatgac cttggagtat gaaatggttc  19140
ttagataatg acaccaaaac cacagggaaa aactagatta actaactaca tcaaaacgaa  19200
tagtttttgt gcttctgagg gcactatgaa gaaaatgaag atacaccaac agagtggaag  19260
aaactacttt gaaatcatat atttgataag aacttgcatc tagacatata aagaattctt  19320
actactcaaa cacacaatcc aattaaagac ccagcagagg atttaaatag gcattttcca  19380
aagaagatat acaaatggct aataagcaca tgaaaaggag ctcaacattg ttagacatca  19440
gggaaaatca gggaaatgca aatcaaaacc acaataagat agcagttcac atcctctggg  19500
atggctatta tcaaaaagac aataagaagc actgatgaga atgtggagaa atgggagccc  19560
ttgtgcattg gatgaaaata aaaaaatcat gccactactt tgaaaaatag ttcctcaaat  19620
gttccatgta gagttaccat atgactcagc aattccactc ttaggtaact actgaaggga  19680
actgaaatgt atatcacata aaaactcata tgatgatatt catagcagcc ttattctcat  19740
ttgccaacaa gtggaaccat ctaaatgtcc atgaactgat gagtcggtaa acaaaatgtg  19800
gtatagtcat acatggacat attcatattc tggatgttat ccccatatca tttttaaatt  19860
ttagtgtttt aatgttaaaa atgatagaca attgtagaag acaacaaatt actcataacc  19920
ccaatctcta gagtgctaac attttggttg ctcccatgta atttgtgtat tcgggcatct  19980
catgacctct ctattaccca aggtcaccac ggtgttctgc ttgccaaggc acaggctctt  20040
cactggcccc ataacaatga cccgagcccc cattgtaggc agagggttgc atgtcccacc  20100
tgagtgagtt tatgtgggaa tccccagggc ctttcgtgtt ctccacgcgt tggtggagcg  20160
gcccctgctt ctcccccagg gtgtgcctgc agccccttcc ctgcctcctg ccattcccat  20220
gggtggtgcc aagagaagct ttagggcagc caagctcctc cttccttctt ggcatcagct  20280
agaggttcct acgaatgcta atggttgggg gcatggtggg gagaattcat tatttcttcc  20340
agcactgctc tcttaaaaat ttgtattatc aatagtttag aaaggttgtt tttagtttca  20400
tagctcacta tcaataacta tgttaatttt taggattatc aaatttgggg agatgtcatc  20460
```

```
gaattgcttt cctatatgag atatagtatt tggaagacat ttctgaaaac cagctctgcc  20520
tctgtacctt tccttttttt tttttttttt tttttttttt ttttttttttg agacggagtc  20580
tcactctgtc acccaggctg gagtgcagtg gtgcaatctt ggctcactgc aaactccacc  20640
tcccgggttc aagtgattct cctgcctcag cctccggagt agctgggact acaggtgccc  20700
cccaccatgc ctggctaatt tttttttgta tttttagtag agacggggtt tcaccgtgtt  20760
agccaggatg gtctcgatct cctgacctcg tgatccgccc gcctcggcct cccaaagtgc  20820
tgggattaca ggtgtgagcc accacgcctg gccacctttc tacctttcaa accttgattc  20880
tcttctgctg cccacaggta gccactgaag gatgcatggt atcatgacat aatctacaat  20940
ctctggccat tcatctttgt gtcaccttac tggggcaaat tgtcacagtg gatggtagga  21000
gtagtcctgg aagtcattca tcctctaaag gataagaaat tattggaata cagttggaaa  21060
ggactctgaa ttcataaatg tatcccactg aaccaacccc aaaatgacta acgccccagc  21120
aatattactt tacacaaagc ctgctttggg ctaaaaccct aaccctggta catgcacttg  21180
aatagataca cttagcttga ctttctctca tttcttatcc ttctcacact ctggactatg  21240
agacgggtga catcctgtgc ctgggctggc gtgtaggccg tctcctccag gacaagctcg  21300
cctgtttctg cttatgctgt tctgggagcc acctctcttg tggaactggg gatgatggtg  21360
ggtccttgag tggcgactgc ttcagatgaa gtccctgaag gggtctttct aatggagatg  21420
ggactacctt agctgggggt gggtgggtgt gagggggtga ctagggtggg ccaggacagg  21480
ctgcttagag ttcagggaaa tttggggatt ccaagttttt ggctcaccta tgtccacccg  21540
gatgatttca tcccaagagt ttcagcaaat gccctcctcg ccagttgtgt ccctacctta  21600
taattagcac ctgattgcag ggctgtgcat tttaattgcc attccagctt tgcagccccc  21660
acggtcaggt gtgggtgtga tccccagcca gggctgctca caataaaaga taccgacacc  21720
ccagggtgct ctgactgtag ttatggtgtt tttttttttt aatttttcat tctaccagtt  21780
tttatttctt gcacaatgac atcgtgacag ccacaaacaa aataattctg aaaataaggg  21840
aaacttgccc ataatccctt tactctaaag catcaagttc ttatattcca tgtcctcatg  21900
aaaattcatt tgtttttctg cttttttttt tttttttttt ttttttttga gacggagtct  21960
cgctctgtcg cccaggctgg agtgcagtgg cgggatctcg gctcactgca agctccgcct  22020
cccgggttca cgccattctc ctgcctcagc ctcccaagta gctgggacta caggcgcccg  22080
ccactacgcc cggctaattt tttgtatttt tagtagagac ggggtttcac cgttttagcc  22140
gggatggtct cgatctcctg acctcgtgat ccgcccgcct cggcctccca aagtgctggg  22200
attacaggcg tgagccactg cgcccggcct gtttttctgc tttttacag aattgcggaa  22260
aaaacatttg acaaagaaat atacaccaaa cccagctctt ttgtttaaaa gccaattgca  22320
aaaacacaga acgaatgacc tggtttaatg gtggctaaga acaatagaaa aagggcctgg  22380
tttatttgag ttaaatttga gctcaggatg aggctagggt gtggtgttgc tgtcaaaacc  22440
cactctgtgg tctgagggtg gattcgtagc cacacagtgt ccaactgagg ggtgaatgag  22500
cccctccgca tcagcccatg ctagttcctt taatggactt ttttttaag agcagtttta  22560
ggttcacagc aaaattgaga ggagtgggcc acgacatccc ctgtgctcta aaatgagagt  22620
gcttcctcag agtccatggc agtgggtcac tctctggggg tccccaggga ctcagggtgt  22680
ggctggcctg tccccaactc aggagagacc aggagttgtc cagtgtttcc ttcattggaa  22740
gtctctgtgg atgcctccca cggacctgga tgttgagggc ccatgatttc cacagtacat  22800
```

-continued

```
ttaggagcca ggatgcaggg cccccatttc ctctatgtgt gccctggaca ccccaggccc  22860
atgggacagg cctggccctg caaccttatc agggtcctga caccaggctt gacctggcct  22920
tgtgataagc aagagaagag gcaggtccag agacacctcc tgcatgggat cgcctgcatc  22980
cgacccccat gacaggcagt ggccagcacg gtgtggaagg ggccaggatg gcacccggca  23040
ggctgccctg taccccagat ggctcctggc ctcaggaaat taatatccac ggggaaactg  23100
gtcacttgga ggctgccaga gggaagggtg agtgtcacat tccctcagcc atggccagcc  23160
agcagcatgc cgtatggcct ctggcccaac ctgtgggaca gggaccccag acagggcaca  23220
agtccctgtc ccagagggtc ctggcctggt gctcacccaa gccctgtaaa gggaggggca  23280
ccaggggtgc catgggcacc cagcagcagc caggatgatc acacagggga ctgagacttc  23340
tgtggcagtg gccagaccca gaacttggcc aaaagcaggg caagccacct gggacagagt  23400
ggatgctgtg cctgtgcgtg cccagcaagg ctgagccagt gacgctacca gggtccatga  23460
ggcaagggtg gggcaggagc aggctgagca gccgccaacc tcgtccgctc caggaggcag  23520
ggatggccga gctcccacac cctagtggcc gccacctgcc caccgatggg gcagaggcct  23580
gaggtcaagc agtcagtgct ggggccctgc ttccagggtc tacaaactgc tccagtccgg  23640
aaggccaacg ataactgggc atgtgagggc ccaggaggtc aggtccctac gtctgccaac  23700
cttggcagat gcatttcaca gtccgaaaaa gtcaagaaag gtgacacctc tcaggtgtta  23760
ttatgaagga ctctcccaag acacgtattt tttacattta tttttattgt atatattcat  23820
ggtggacaac atggtgttgt ggtaaatatg tacacaactg aaatgatggc tacaattaat  23880
atctccaaaa ctttccatgg ttccctttttg tatgtgtgtg tatgagtgtg tgtgcatgag  23940
tgtgtttgta taagtgtgtt tatgagtccg tatgcatatg tatgtgtgtg tttgtatgat  24000
tatgtgtgta tgagtgtgtg taaggtgtgt tttaattgtg tgtgtgtgag actgagtgtg  24060
tgtatttatg tgtgtgtatg agtgtgagtg tgtgtgtgta tgatgcgtgt gtgtgtatgt  24120
gtgtgtggta agagtacctg gagtcttctc tcagcacact tgcagcacac agcacctgtc  24180
accggtagtc cttgcactgt gcacttgact gctcggctcc ctctcctaca caactgcaag  24240
cccttgacct cctcctcccc ctttccttct tcctccagac cctggtaacc actgttctat  24300
tctatgtttc tatgtatttg actttttcaa aatgtggaat atatacatac atctatatat  24360
gtatatatgg aatattcctc agctttcaaa agaaggagat ctggttactt acaacaacat  24420
ggacgaatct ggagaacatt acacagggtg aaaagaggca gacacagaaa gacagacacc  24480
acatgctctc cctcacacat ggagtataca ggagtgaaac tcacagaagc acagagtgca  24540
agcacgggaa ccacaggcag ggaaagggga aatgaggagg tgctagtcca gggatccaaa  24600
gcttcagttc tacaagatga ataaggcttg gagacccaat acatagcaaa gtgaccacag  24660
gtaacaacac ggtgtttagt gtgtacttaa aatgtactga gagggtagat cctaaatgtt  24720
ctcaccacca agaaaagaga gagagagagc tatgtgaagt ggcggatatc ttaattatct  24780
tgactgtggt gattatttca caatgtagac atatatgaga tcatcgaatt gtatgtctta  24840
cattatacac aataaaaaat aataaaaaca acccccagtg ccaggcccta caggcacgcc  24900
cacccaaccc tcttgcttgc acatacaatg tataaaagaa tagatgcaca tacatgattg  24960
ggtattgtta ccaattagaa ttttattatc cacatttctt tgcaacttaa cttttttcac  25020
taaaagctgt aacatggttg cctctcctag gaagtagatc tgggtataag tctatgtttc  25080
tttatgcata tgcatattca tatatatgaa atttttccat aagtaagatc acacatactg  25140
gtctcacttt tcattgccat tttctttttg ttgattccta cacaccttcc ccactccacc  25200
```

cagccactgt cctatgtacc tccaggcaca cactcaacat atgtgtaaga gatatttttg 25260
ttgtttgcta ctaaaataag atcctgctgt gctcatttcc ctgcatctac atttcacatt 25320
agccagagcc ttgaggctcc aagtccactg gtacagctgc aatctaatat tttactgggc 25380
attactttca gtattcattt tcaatttgct aggattcttt ttctgacact gcaaacaatg 25440
tatcatacac atatatgtat acataaatat gtttacattt aatcttattt tcagtaattt 25500
caagactaat agtattgata ttacctaatt ttattagata ttgttttcaa aaaatactat 25560
aataaattat atcccctgaa caatgtaaaa cagtgccttt tccccgcaat ttcactagca 25620
ataggtgtta ttattcttgt taatttttgc cagtctagta gatataaaat gttgcaggta 25680
accactaact ggggccactg gcgtgggcag taaaggaatt taccaagaca attgtaggta 25740
aggaaaggca gatttattag agaatgtagg aaaatacgtt gcaagaatgg aaagggcagg 25800
tcagcaaggg aggagctggc tgccaggaga caaaggcttg ctggggattt tataggatgg 25860
tgcttgtgcc ggagagggtt acatgcagtg ctgataatgc caaggtttca gtgagctaac 25920
ctgcattttt ctgtcaactg aggtcataag ttgagtgcag gaagattgtg agttatgtga 25980
gttatttgcg caggagggct aagtcctgca ccatgaagaa aggcagactt gtagttcatc 26040
taccttctct ttttgctttc ccttggtcca accaacctgg ctccttttcc atcattagga 26100
ctccacagaa aattcccatg tatctgacca ccagggagtt tggtttactt tttatatttt 26160
taattgcaca tttccatttg tttatcagag agtcatcttt ttaaaaactt ggttgtttgt 26220
cttctacttg tcaatttgtc agagctacta atgttttata gatttttat tttgagacag 26280
gttcttactc tgttgctgga gtacagaggc aaaatgtcag ctcactgcaa cctctgcctc 26340
ctgggttcaa gcaattctcc agtctcagcc tcccaagtag ctgtaattac aggcatgccc 26400
caccaccatg cccagctagt ttttgtattt ttagtagaga tgaggtttca ccatgttggc 26460
ctggctggtc tcgaactcct ggcctcatgt gatctgcctg gttcgaactc ccaaagtgct 26520
gggattatag gcatgagcca tcatattcag ccaatgtttt atagattata gaactaataa 26580
atgaatccag caagttttta gaatacagga ccaatatata aaaatcaatt gtatttctac 26640
tcacttgcaa atctgaaagt gacaaaacac tgttgaaaga aactgaagaa gatctaaaac 26700
atcccagatt tgttgtggac tgaatattta tgttctttca aattcatatg ttgaatccat 26760
cactcctatt gtggctgtgt atggagacga gttctctaag gaagaaatta aggttacata 26820
aggtcataag ggcttccata gaatttgcat cttcataaga agagacacca gggagcatgt 26880
gcctctgtct ctctctctct ttctctctct ctctcttcct ccctccatct ctttctctct 26940
ccacacacaa aggaaaggcc atgtgagcaa agagtgggaa agcagccatc tgcaacccaa 27000
ggagagagca ctcaccagaa actaaatttg ctggcacccg atcttggact tctgatctcc 27060
agaattgtga gaaaataaat gcctgttgtc tgagccacca aatctgtggt attttgttat 27120
ggcagcccaa gcagactgat gttcatgtat cagaagactt aacattttc agatggcaat 27180
atccccaaaa ttgatctaca gagtctataa tctctatcag gaaagcagct ggcttctttg 27240
cagatattca caggctgatt ctaaagttcg tgtggaatct caagggaccc tgaatagcta 27300
aaacaatgtt aaaaagaaga acaggcgggg tgtggtggct cacgcctgta atcccagcac 27360
tttgggaggc caaggcgggc agatcacgag gtcaggagat ggagaccatc ctggctagca 27420
tagtgaaacc ccatctctac taaaaataac aaaattagcc aggcgtagtg gcaggtacct 27480
gtagtcccag ctactcggga ggctgaggca ggagaacggt gtgaacccgg gagatggagc 27540

```
ttgcagtgag ccaaggttgt gccactgcac tccagcctgg gctacagagt gagacttcgt   27600

caaaaaaaaa aaaaaaaaaa agaaagaaag aaagaacaca gaagaacaat gttggagggc   27660

tcacacttgc caatttgaaa acttactaca aagctgcaat catcaaggca gtttagtact   27720

ggcattagaa tagatgtatt aaaccagtgg gatagaattg agagccagaa ataaaccctc   27780

gtgtagatga ccaactgatt tttgacagag tgccagatta ttcaatggag gaagagcagt   27840

acttcaacaa atggtgctgg gaaactagac atccacatgc acaggaatga gctgaacccc   27900

tacctcacac cacaataatt aattcaaaat cggtccaaag gcctacatgt aagagtcaaa   27960

tctataaaac tatttaaaga aaacatgacc tggatttagc atggattgat agataggaca   28020

ccaaaagggc cagcaacaaa agaaaaatac aaatacattg gatgtcatca aaagttaaat   28080

atttttgaat caaaggatac tatcaacaaa gtgaaagaac aatctacata aaggaagaaa   28140

agatttacaa atcagatatc tgataagcgt ctagcatcta gagtatataa agaacttttt   28200

cttcaacttt tatttgagaa tcaagcagta catgtgcaga tttgtcacat ggatatattg   28260

tgtgatgctg aggtttggag tagtgactgt agtacccaat agttttttcag cccttgcccc   28320

ctccctcctt tcctccctcc tcttgttccc cagtgtctat ggttttcatc tttatgtcca   28380

tgtggactca atgtttagct ctcacctata agtgagaata tgtgggattt ggttttctgc   28440

ttctgcatta gttctcttag gataatggcc tccagctgca tattgccgca aaagatatta   28500

cttcattctt ttttatagct gtgtagtatt ccatggtgtg tatgtaccac attttcttta   28560

tccaatccac cattgatggg cacctgggtt gattccacat ctgtgcttct gtgaatagca   28620

ctgcaatgaa catatggatg catgtgtctt tttggtagat tgatttattt tcctttgggt   28680

atatacccaa taatgagatt gctgggtcaa atagtagttc aattcttagc tctttgagga   28740

atctccaaac tgctctccat ggtggctgaa atcatttaca ctcccaccaa cagtgtacaa   28800

ctgttccctt ttctcccaag ctttgccagc atctgatttt tggtttgttt tgttttgtgt   28860

tgtttcattt tttatttttt atcaaaagcc attctgactg atatgagatg gtatctcatg   28920

gtggttttga tttacattcc cctaatagtt agtgatgtgg agcatttttt catatagttg   28980

ttggccatgt gcatgtcttc ttttgagaag tgtctgttca tatcctttac tcacttcgta   29040

atgaagttat ttgttttttg cttgttgatt taagttcctt gtagattgca gatattagac   29100

ttttgtcaga tgcacagtgt gtgaatattt tcacccattt tgtaggttga gtgttgactc   29160

cctgatagtt tctcttgctg tgcagaagct cttccgttta attacgtccc gcttgtcaat   29220

ttttgttttt gtagcaattg cttgtgagga tttagccgta attcttttttt aacaaggctg   29280

atatcaagaa ggtgatttcc taggtcttct tctaggattt ttatagtttg aggtcttaca   29340

tttcggtctt taatccatct tgaattaatg tttgtatatg gtgatctggt tagcggccca   29400

gttttattct tctggatgtg gaactcagta ataaaaagac aaataaccca attaaaaagt   29460

gggcaaagaa tcttaattag acattttctg aagaagatac ccaaatgaca acaagcatat   29520

aaaaagactc tgagcatcat gattcaacag ggagatgcaa attgaaatca caatgagata   29580

ccatttcaca aacactagga tgaatataat gtaaaaggtc agacattaac aagtattggg   29640

gcagggtgtg cttgtacctg taatcccagt gactcaggag gctggaaggg aggatccctt   29700

ggggccacga gtttgagtct agtatgggta tcatggcaag accttgtctc tacaaaaaat   29760

taaaaattta gctgggtgtg atgaggcaca actgtagtcc cagctactgg ggagtttgag   29820

acaaggattg cttgggtcca ggaggttgag gctgcagtga gctatgatca tgacactgca   29880

cttcagcttt gtcaacacag taaaaccctg tctctaaaaa ataaataaat aaaaataaaa   29940
```

taaaataaca actgttgaca aggatgcaga aacactggaa cctccatgca ctgctgtggg 30000
aatgtaaatt gctcagccac tgtggaaaac agtctgcagt tcctcaaaaa cttaagcaga 30060
gagttaccat agggcccagc aattctgctc ataaggatgt tcccaaggga aatgaaaaca 30120
cattccatgc aaaaactggc acacccatgt tcacagcagc attactcaca acagccaaaa 30180
ggtggaaaca gtctaatgtc tgccaactga ggaatgaatg gtgtattcat acaaaggaag 30240
attagtgtaa ataatttatc atagtaatga agttctgttt caggctgcaa catggatgaa 30300
ccacaaaaca ttacactaag tgaaagaagg aaattataaa agaccacata tcatataatt 30360
tcacaggtat gaaatttcaa gaatagaaaa atagagagag acaaaaagta aattagtagt 30420
agcctctggc tactactaat gttacccatt tatcagactc aggtgagaca ctcacatatg 30480
tcacaggaag tgggtatacc agttacagac aggcagcaag ggagaacagg agcctcggat 30540
tcattgggag ccctctagcc tcagcaaagc ttcccaggtg agctgagtct tatccatgtg 30600
tgccccactc acaccacagc tgagggatcc cagaaagccg cctgccctcg gtcttatgtc 30660
ccagggctac aggattcact gcactaaagc acgaaagaat atcctgtttc taggaactgg 30720
gacaaagccc gactcttctg gccagtccct ccctaactca ggatgttgca ttcccagcat 30780
attctacagt tattcttttt ctttctttat taatatttta attgaagcat gatcattgta 30840
catgtttatg gggaccagtg agatatcaac ttctttagct tgcacctgtg agtgagatca 30900
tgcagttcat ctttctgtgc ctggcttatt tcatttagca taatgtcctc caagctcacc 30960
tgtattgtca catagggcag aattttgttc tgctctaggg ttaaatagaa ttccattgtg 31020
tgtatacacc atcttttcct tttcattact tttccatgtt ttccattcat ctgttgacaa 31080
gcacttaggt gctttcatat catggctatc gtgagcagtg ctgtgataaa catggggtgc 31140
agatatctct tcaacacact gatttctttt cctttggata cacaccccat agtgggattg 31200
ctgggttagc tctattttta gctttttgag gaatctccat acagttttcc ttagtggttg 31260
tacaacttcc cactaacagc atacgagttc cctttcttca cttcctctgc aggatttatt 31320
tttgcctttt tgataatggc cattctgtgg gatgagagga cacctcattg tggttttgac 31380
ttgcgtgtcc ctgatgatga atgatgctga gcattccttc aagctcttgt tggtcatttg 31440
tacgtcttct ttcagaaatg tcggttcagc tccctctgca gtcacgcctg agaaccacaa 31500
gtgagacacg gggagaattg cattggtctg aagccgcctg gagaaccgtc ctgtggggta 31560
gtgagtgggg ggtactaaag ggcatgaggt tatgaaattt tctacaactg attatggtga 31620
taggtacacg gctctgtgaa tatactaaaa gcattgaatt gtatacctta aatgggagaa 31680
ttgtgtggta tatgaacgat atgtcaataa agctgttaac aaaacaagaa gaggtatcag 31740
agaggttggg gatcagtgaa gccgtggttg tatcaatgca ccaagagttc tggtggaatg 31800
aaagcactgg agaaagtgag ctagaaagag gagggtggct ggaagcgggt gcatgggaca 31860
caccccactg gggtgccctg tgaagaacaa gggcacagat atcaccacag gggtgagggg 31920
tggggaagga tcttttactt gtgtaaatga tccccacagg ggcactgctt aactgagcag 31980
tgggaaggag gacaccatcc tccagccccc agaatggtag agcaactgac agcttgcatc 32040
ttgagcatgg agaagctgca ggcacccaac tccaacccat gagagcagct gcagggggtg 32100
aaccctgcaa agtcacgagg gtggagttcc ccaaggcctt aggagtccac ccctcactcc 32160
agtgtaccct ggatgtggga ctgggagtcc aaggacatta ttttggagct ttaagattta 32220
atggctgccc tgctggattt cagacatgca tggggtccgt agccccttcc tttgggctga 32280

-continued

```
cttctccctt ttggaatggg aatgtttacc caatgcttct accctcattg catcttgtaa  32340
gtaaataatg tattttgatt ttcacaggtt cataggtaga aggaacttgg acttgggact  32400
tcagacttga tgttggaatg agtcaagaca ttgagaggac tgttgagaag agatgatcct  32460
attttgtgat gtaaggacat gagatttgag gggtcagggg gataatgaca tagttgggct  32520
gtcccctcca aatctcttgt cgaaatgtaa tccccagtgt tgaaggaggg gcctgcaagg  32580
aggtgtttag gtcatggggg cggatccctc ataactggct tagcgccatc tccttggcga  32640
tgagtgtgtt cactcagatc tggttgttcg caagtgtgtg gcccctcctc accccttgct  32700
cccattctca ccatgtggcg tgcctactcc tgcttcgcct tccaccatga ggaaaacctc  32760
cctgagggcc tccccagaag ctgagcagag gtgggtgcca tgcttgtgca gcctgcagaa  32820
ccatgagcca ttctaacctc tttcctttat aaattaccca gcctcaagta tttctttaga  32880
gcaatgcaaa gaatggtcta acacacccag aaagctgaga ctggtatgag taaaatataa  32940
agaccatgga taacttttga aatctgaaaa tgtaaaatta atattactgg gggagttaac  33000
acaggaaaga tgagagcatg tgggcagagg ctgttgccca ttggtcacat gtggtcagca  33060
gagagcaggt gaccagcacc ctggagcttt gcaagaagta ccagacagcc tggagttgag  33120
gttttaatta taggggccaa aacaaacggg gaaaaagaca aatttagcat acaaagaaag  33180
tagatgctca actgagccag gaggaagtca ctagcaaaaa ggaaaaaaac agagctctgg  33240
aaaaataatg taaacagtca caagaaaggg accctgtgtc ctgcctgaca tctggacagg  33300
tatataaaga gcccgggctc agggagctcc acacctgcac ctccctctca cctgctcctc  33360
tacctgatcc accctcaatc taccagaatc atggctgct gtggctgctc cggaggctgt  33420
ggctccggct gtgggggttg tggctccggc tgtgggggct gtggctccgg ctgtgggggc  33480
tatggctctg gctgtggggg ctgtggctcc agctgctgtg tgcccgtctg ctgctgcaag  33540
cccgtgtgct gctgtgtgcc agcctgttcc tgctccagct gtggctcctg tgggggctcc  33600
aagggggact gtggctcttg tgggggctcc aaagggggct gtggttcctg tgggggctcc  33660
aagggggggct gtggctcctg tgggggctcc aagggggggct gtggttcttg tgggggctcc  33720
aagggggggct gtggctcctg tgggggctcc aaaggtggct gtggttcctg tgggggctcc  33780
aagggggggct gtggttcttg tggctgctcc cagtgcaatt gctgtaagcc ctgctgctgc  33840
tcctcaggct gtggatcctg ctgccagtcc agctgctgca atccctgctg ctgccagtcc  33900
agctgctgtg tccccgtgtg ctgccagtct agctgctgca agccctgctg ctgtcagtcc  33960
agctgctgtg tccccgtgtg ctgccagtgt aagatctgag gctctgaacc cagaccttca  34020
ggtttcacct gtttggtgaa agcatttgtt atgatttccc tgaattaatt catcccacgc  34080
atcctccctg aggcacctgc cccttctcca gctcatcatc catgcacgca cctccttcca  34140
tggctcagct ctccactggg ccctgccttc agcctcctca ctccggaaat gcatgtttcc  34200
ttgatgcagg aggtggcctt gcctggacgc gggcacccag ccaactgcca tggtgttccc  34260
tgcacttggg tgtggaccat cttcttcttc tccctcggct gactgagatg caaggtctga  34320
ccccacaagg ccaggccaat gttgctcagt gatcactaag aaccagcttc tcaaccacca  34380
ttgggaccct ggatcctcca gggccgctcg ctgcctgttc tccagtggcc acctgtgacc  34440
aggaaggtct ccttccttcc tgttgtctcc atctatttaa aaacaataac aaagtaatga  34500
atgaatttcc ttacaataaa gcctctcatg tctgtaaatc agctgcatgc ttggtgcaat  34560
tctgtccaac ccctttcctg tgcagtgact gattctgcgt tctgatctgt cagctaagct  34620
gggaaacgcc tgccagcagg cctggtacat tcacaaaaaa acctgccatt cccttctgtc  34680
```

ctcctctcag cctcaaatat cttcagtctc tgctcgcagg agaagagggc aaagcccggg 34740
aggattcagc attcaatgcc cgccctagag gcgcagaggg gcaggcaggc cctgagtcct 34800
gacgaccagc caagcagggc tttgcacaag acccatggct tccagcttcc cgctctcctc 34860
tggggcctcg gaaggacccc aggcagggca aggtcggagg agggaggagt gaagcaccgc 34920
tgagctccaa cgcactctga ttcaaacatt caattagcct tttacaatta tgaggtcaac 34980
ggctttccat aactaaaggt aaccaggaag ttacagaatg gcccaaggtg tcctcggagc 35040
tcagtctccc ggcaggaaag gagagttcct gggaagtgac acatttgggg accctgagcc 35100
aagtccatct gtttcatggt gacatgccac cacgctgagc ctgttctctg accagtgtca 35160
caggcaaggc tttagaaatc acgcactggg gaggaggaga caagagtgat ctgaggacaa 35220
tctccagcca agcgaacccg gagggaaaag gtggagggaa gacagcacac agggagtgct 35280
ggtgagaaat gagctcccac agaacactca cagatctaag cgactgctga tactgccggg 35340
gaagagcaga gtgggaattt ccaagacaaa tttctgagag aaaagagatg caatgtaagg 35400
aaaaatgaaa taatctagaa ataaaggctt agattaattc agccacattt aggaaaggga 35460
ataaaagtgt gtcaaaggtg catcttgcta ggggacatgg ctatcgttag tttcacgacg 35520
ttaaaaggaa atgctgctta agacagttca ctcaaaaatc caaactggga aactccagaa 35580
ggtgacagca gacatgaacg cagagttcat tacatatggg ccctgtacat tcccacaacc 35640
cacaggacac cgagcaacta ggtaacaaaa ccgaaaatgc atgctggaga cataacaaaa 35700
ccaggtaagc tgggcatggt ggctcacacc tgtagcctca gctacgtgga aggctgaggt 35760
gggaggatgg cttgagcctg ggagtttgag gctgcagtga gctgtgatcg cacccctggg 35820
atccagcctc agcaacctaa agtgagatag tgtctcaaga aaaaaaacaa gtgaacctca 35880
aagtccaaga aggtggggat aaatttacaa gagccacagt cccccagggt ttcagtgtct 35940
gtgtaggaga aagcaaagaa acatctaaca gagccgaat 35979

<210> SEQ ID NO 6
<211> LENGTH: 16
<212> TYPE: DNA
<213> ORGANISM: Artificial sequence
<220> FEATURE:
<223> OTHER INFORMATION: Oligonucleotide as PCR primer

<400> SEQUENCE: 6
agtggtgtgc cgacaa 16

<210> SEQ ID NO 7
<211> LENGTH: 18
<212> TYPE: DNA
<213> ORGANISM: Artificial sequence
<220> FEATURE:
<223> OTHER INFORMATION: Oligonucleotide as PCR primer

<400> SEQUENCE: 7
tccaaatcag ggctttct 18

<210> SEQ ID NO 8
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 8
ggacagatgc ttccagaaaa 20

<210> SEQ ID NO 9
<211> LENGTH: 23
<212> TYPE: DNA
<213> ORGANISM: Artificial sequence
<220> FEATURE:
<223> OTHER INFORMATION: Oligonucleotide as PCR primer

<400> SEQUENCE: 9
agattatgca tgtgtaaaga gcc 23

<210> SEQ ID NO 10
<211> LENGTH: 17
<212> TYPE: DNA
<213> ORGANISM: Artificial sequence
<220> FEATURE:
<223> OTHER INFORMATION: Oligonucleotide as PCR primer

<400> SEQUENCE: 10
gaaggactcg gctccag 17

<210> SEQ ID NO 11
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 11
gtaagaggat ggtaggaggg 20

<210> SEQ ID NO 12
<211> LENGTH: 20
<212> TYPE: DNA
<213> ORGANISM: Artificial sequence
<220> FEATURE:
<223> OTHER INFORMATION: Oligonucleotide as PCR primer
<220> FEATURE:
<221> NAME/KEY: misc_feature
<222> LOCATION: (11)..(11)
<223> OTHER INFORMATION: n

<400> SEQUENCE: 12
ctaagcatga ngccaagtta 20

<210> SEQ ID NO 13
<211> LENGTH: 23
<212> TYPE: DNA
<213> ORGANISM: Artificial sequence
<220> FEATURE:
<223> OTHER INFORMATION: Oligonucleotide as PCR primer

<400> SEQUENCE: 13
agtttgacat tagggaattt tga 23

<210> SEQ ID NO 14
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 14
cagaaatgcc acccagagag 20

-continued

<210> SEQ ID NO 15
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 15
ttccggagtt tgcacaatct 20

<210> SEQ ID NO 16
<211> LENGTH: 18
<212> TYPE: DNA
<213> ORGANISM: Artificial sequence
<220> FEATURE:
<223> OTHER INFORMATION: Oligonucleotide as PCR primer

<400> SEQUENCE: 16
catgaatgct cttgtccc 18

<210> SEQ ID NO 17
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 17
aaccccctgg aaaatagact 20

<210> SEQ ID NO 18
<211> LENGTH: 22
<212> TYPE: DNA
<213> ORGANISM: Artificial sequence
<220> FEATURE:
<223> OTHER INFORMATION: Oligonucleotide as PCR primer

<400> SEQUENCE: 18
ttcagtaaca ggagacaaaa gg 22

<210> SEQ ID NO 19
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 19
tggtttcgga tctcttctca 20

<210> SEQ ID NO 20
<211> LENGTH: 18
<212> TYPE: DNA
<213> ORGANISM: Artificial sequence
<220> FEATURE:
<223> OTHER INFORMATION: Oligonucleotide as PCR primer

<400> SEQUENCE: 20
acctcacggt gtaatccc 18

<210> SEQ ID NO 21
<211> LENGTH: 18
<212> TYPE: DNA
<213> ORGANISM: Artificial sequence
<220> FEATURE:
<223> OTHER INFORMATION: Oligonucleotide as PCR primer

<400> SEQUENCE: 21
cttgaagccc atctttgc 18

<210> SEQ ID NO 22
<211> LENGTH: 19
<212> TYPE: DNA
<213> ORGANISM: Artificial sequence
<220> FEATURE:
<223> OTHER INFORMATION: Oligonucleotide as PCR primer

<400> SEQUENCE: 22
aaggtgtgag gatcactgg 19

<210> SEQ ID NO 23
<211> LENGTH: 17
<212> TYPE: DNA
<213> ORGANISM: Artificial sequence
<220> FEATURE:
<223> OTHER INFORMATION: Oligonucleotide as PCR primer

<400> SEQUENCE: 23
agctcatggg ggctatt 17

<210> SEQ ID NO 24
<211> LENGTH: 17
<212> TYPE: DNA
<213> ORGANISM: Artificial sequence
<220> FEATURE:
<223> OTHER INFORMATION: Oligonucleotide as PCR primer

<400> SEQUENCE: 24
gaatcgcttg aacccag 17

<210> SEQ ID NO 25
<211> LENGTH: 17
<212> TYPE: DNA
<213> ORGANISM: Artificial sequence
<220> FEATURE:
<223> OTHER INFORMATION: Oligonucleotide as PCR primer

<400> SEQUENCE: 25
ccaggtggtc ttaacgg 17

<210> SEQ ID NO 26
<211> LENGTH: 18
<212> TYPE: DNA
<213> ORGANISM: Artificial sequence
<220> FEATURE:
<223> OTHER INFORMATION: Oligonucleotide as PCR primer

<400> SEQUENCE: 26
cccagcctta catattcc 18

<210> SEQ ID NO 27
<211> LENGTH: 18
<212> TYPE: DNA
<213> ORGANISM: Artificial sequence
<220> FEATURE:
<223> OTHER INFORMATION: Oligonucleotide as PCR primer

<400> SEQUENCE: 27
gctgatgagc agaggtag 18

<210> SEQ ID NO 28
<211> LENGTH: 16

<212> TYPE: DNA
<213> ORGANISM: Artificial sequence
<220> FEATURE:
<223> OTHER INFORMATION: Oligonucleotide as PCR primer

<400> SEQUENCE: 28
aagttgcagt gagccg 16

<210> SEQ ID NO 29
<211> LENGTH: 17
<212> TYPE: DNA
<213> ORGANISM: Artificial sequence
<220> FEATURE:
<223> OTHER INFORMATION: Oligonucleotide as PCR primer

<400> SEQUENCE: 29
ttccagccca ttaacct 17

<210> SEQ ID NO 30
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 30
ggaaggcacc atgatacttg 20

<210> SEQ ID NO 31
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 31
gtgaagtctg ggatttcagc 20

<210> SEQ ID NO 32
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 32
ccagctcaaa tgctcatcag 20

<210> SEQ ID NO 33
<211> LENGTH: 23
<212> TYPE: DNA
<213> ORGANISM: Artificial sequence
<220> FEATURE:
<223> OTHER INFORMATION: Oligonucleotide as PCR primer

<400> SEQUENCE: 33
ttatcagcaa catgaaaatg gac 23

<210> SEQ ID NO 34
<211> LENGTH: 1330
<212> TYPE: DNA
<213> ORGANISM: Homo sapiens
<220> FEATURE:
<221> NAME/KEY: CDS
<222> LOCATION: (233)..(715)
<223> OTHER INFORMATION: CDS

<400> SEQUENCE: 34
cgcaggatga gcgatcgggg cccgggcagc cggcagcgga cgcgcccccc gagcccaccg 60
gcccgcgccc cgcgcccccc acggccccgc ggtcccggtc ccggccgcat cacccacgtc 120
ccccgagccc cacgggccat gcccggccgg ccctaagcgc gggccggggg gcgtccccctt 180 gcgcccgggc cccgcgctgg cgccccccgg gccgccgccc ggcgcggggg cc atg gcg 238
Met Ala
1 ttc acc ttc gcc gcg ttc tgc tac atg ctc acc ctg gtg ctg tgc gcc 286
Phe Thr Phe Ala Ala Phe Cys Tyr Met Leu Thr Leu Val Leu Cys Ala
5 10 15 tcc ctc atc ttc ttt gtc atc tgg cac atc ata gcc ttt gat gag ctg 334
Ser Leu Ile Phe Phe Val Ile Trp His Ile Ile Ala Phe Asp Glu Leu
20 25 30 cgg acc gac ttc aag aac ccc atc gac cag ggg aac cct gcg cgg gca 382
Arg Thr Asp Phe Lys Asn Pro Ile Asp Gln Gly Asn Pro Ala Arg Ala
35 40 45 50 cgc gag cgt tta aaa aac atc gaa cgc atc tgc tgc ctc ctg agg aag 430
Arg Glu Arg Leu Lys Asn Ile Glu Arg Ile Cys Cys Leu Leu Arg Lys
55 60 65 ctg gtg gtc cca gaa tac tcc atc cac ggc ctc ttc tgt ctg atg ttt 478
Leu Val Val Pro Glu Tyr Ser Ile His Gly Leu Phe Cys Leu Met Phe
70 75 80 ctg tgt gca gca gag tgg gtg acc ctg ggc ctc aac atc ccc ctc ctc 526
Leu Cys Ala Ala Glu Trp Val Thr Leu Gly Leu Asn Ile Pro Leu Leu
85 90 95 ttc tac cac ctc tgg agg tac ttc cac cgt cct gca gat ggc tct gag 574
Phe Tyr His Leu Trp Arg Tyr Phe His Arg Pro Ala Asp Gly Ser Glu
100 105 110 gtc atg tat gat gcg gtc tcc atc atg aat gct gac att ctc aac tac 622
Val Met Tyr Asp Ala Val Ser Ile Met Asn Ala Asp Ile Leu Asn Tyr
115 120 125 130 tgc cag aag gag tcc tgg tgc aaa ctt gcc ttc tac ctg ctc tcc ttc 670
Cys Gln Lys Glu Ser Trp Cys Lys Leu Ala Phe Tyr Leu Leu Ser Phe
135 140 145 ttc tat tac ctg tac agt atg gtt tat acg ttg gtg agt ttc taa 715
Phe Tyr Tyr Leu Tyr Ser Met Val Tyr Thr Leu Val Ser Phe
150 155 160 gggggaagcc ggccagggag cgagcccaga acggaccgga cgcctgtgca cccccagccc 775 tgccccttgg ccgcagaggc ctcagccctg gggagggagg gggcactggt gcccccagcc 835 tctccaaccc ccaaactgct gctgcgggga acccccccca ccccgccttc agagccctcc 895 cccttggact agagcggctg ggcagagctc taaacagggg caggggctcc tctgccagcc 955 tgtgggcatg gcagtcattc ctggaagggg caggacctcc ggccttgtcc atttcggggg 1015 aaacttgggc cctgccaagg ggcagagctt gaccctggaa attctgggcc atccccctcc 1075 acccccaccc tgaggctccc cctgcaggtg ggggggtacc cgcaccggga atgagcaggc 1135 tcagcagggg ggcagcccca cccctagtct gccctcccct ctcccccagg ctctttctcc 1195 agccctgtct ccatctgccc caacctcagc ccaccttgtc tcttggacct attttctatg 1255 tcgcctggag gagtccggca ccccctcccc ggccatttgt gacaaaatat gaataaacta 1315 ctgcaaatat gtggg 1330

<210> SEQ ID NO 35
<211> LENGTH: 160
<212> TYPE: PRT
<213> ORGANISM: Homo sapiens

<400> SEQUENCE: 35

Met Ala Phe Thr Phe Ala Ala Phe Cys Tyr Met Leu Thr Leu Val Leu
1 5 10 15

Cys Ala Ser Leu Ile Phe Phe Val Ile Trp His Ile Ile Ala Phe Asp
20 25 30

Glu Leu Arg Thr Asp Phe Lys Asn Pro Ile Asp Gln Gly Asn Pro Ala
35 40 45

Arg Ala Arg Glu Arg Leu Lys Asn Ile Glu Arg Ile Cys Cys Leu Leu
50 55 60

Arg Lys Leu Val Val Pro Glu Tyr Ser Ile His Gly Leu Phe Cys Leu
65 70 75 80

Met Phe Leu Cys Ala Ala Glu Trp Val Thr Leu Gly Leu Asn Ile Pro
85 90 95

Leu Leu Phe Tyr His Leu Trp Arg Tyr Phe His Arg Pro Ala Asp Gly
100 105 110

Ser Glu Val Met Tyr Asp Ala Val Ser Ile Met Asn Ala Asp Ile Leu
115 120 125

Asn Tyr Cys Gln Lys Glu Ser Trp Cys Lys Leu Ala Phe Tyr Leu Leu
130 135 140

Ser Phe Phe Tyr Tyr Leu Tyr Ser Met Val Tyr Thr Leu Val Ser Phe
145 150 155 160

<210> SEQ ID NO 36
<211> LENGTH: 947
<212> TYPE: DNA
<213> ORGANISM: Homo sapiens
<220> FEATURE:
<221> NAME/KEY: CDS
<222> LOCATION: (165)..(890)
<223> OTHER INFORMATION: CDS

<400> SEQUENCE: 36
ggggatgacg ccacggacat ggtggccgag accggcgggg tgggggacgt gtcgcgcggc 60
cgggtggcct cggtcggtac cctgggcgcg gagcagctgc ctcattagta ttcgtaccca 120
cgaggcggcg cagcgggccc tcggggacag cgagcgtcgc ggcc atg gct tat cac 176
Met Ala Tyr His
1 tcg ggc tac gga gcc cac ggc tcc aag cac agg gcc cgg gca gcc ccg 224
Ser Gly Tyr Gly Ala His Gly Ser Lys His Arg Ala Arg Ala Ala Pro
5 10 15 20 gat ccc cct ccc ctc ttc gat gac aca agc ggt ggt tat tcc agc cag 272
Asp Pro Pro Pro Leu Phe Asp Asp Thr Ser Gly Gly Tyr Ser Ser Gln
25 30 35 ccc ggg gga tac cca gcc aca gga gca gac gtg gcc ttc agt gtc aac 320
Pro Gly Gly Tyr Pro Ala Thr Gly Ala Asp Val Ala Phe Ser Val Asn
40 45 50 cac ttg ctt ggg gac cca atg gcc aat gtg gct atg gcc tat ggc agc 368
His Leu Leu Gly Asp Pro Met Ala Asn Val Ala Met Ala Tyr Gly Ser
55 60 65 tcc atc gca tcc cat ggg aag gac atg gtg cac aag gag ctg cac cgt 416
Ser Ile Ala Ser His Gly Lys Asp Met Val His Lys Glu Leu His Arg
70 75 80 ttt gtg tct gtg agc aaa ctc aag tat ttt ttt gct gtg gac aca gcc 464
Phe Val Ser Val Ser Lys Leu Lys Tyr Phe Phe Ala Val Asp Thr Ala
85 90 95 100 tac gtg gcc aag aag cta ggg ctg ctg gtc ttc ccc tac aca cac cag 512
Tyr Val Ala Lys Lys Leu Gly Leu Leu Val Phe Pro Tyr Thr His Gln -continued

```
                105                 110                 115

aac tgg gaa gtg cag tac agt cgt gat gct cct ctg ccc ccc cgg caa      560
Asn Trp Glu Val Gln Tyr Ser Arg Asp Ala Pro Leu Pro Pro Arg Gln
            120                 125                 130

gac ctc aac gcc cct gac ctc tat atc ccc acg atg gcc ttc att act      608
Asp Leu Asn Ala Pro Asp Leu Tyr Ile Pro Thr Met Ala Phe Ile Thr
        135                 140                 145

tac gtg ctc ctg gct ggg atg gca ctg ggc att cag aaa aga atg atc      656
Tyr Val Leu Leu Ala Gly Met Ala Leu Gly Ile Gln Lys Arg Met Ile
    150                 155                 160

ctc agt gtg ctc acg ggg ctg ctg ttc ggc agc gat ggc tac tac gtg      704
Leu Ser Val Leu Thr Gly Leu Leu Phe Gly Ser Asp Gly Tyr Tyr Val
165                 170                 175                 180

gcg ctg gcc tgg acc tca tcg gcg ctc atg tac ttc att gtg cgc tct      752
Ala Leu Ala Trp Thr Ser Ser Ala Leu Met Tyr Phe Ile Val Arg Ser
            185                 190                 195

ttg cgg aca gca gcc ctg ggc ccc gac agc atg ggg ggc ccc gtc ccc      800
Leu Arg Thr Ala Ala Leu Gly Pro Asp Ser Met Gly Gly Pro Val Pro
            200                 205                 210

cgg cag cgt ctc cag ctc tac ctg act ctg gga gct gca gcc ttc cag      848
Arg Gln Arg Leu Gln Leu Tyr Leu Thr Leu Gly Ala Ala Ala Phe Gln
        215                 220                 225

ccc ctc atc ata tac tgg ctg act ttc cac ctg gtc cgg tga              890
Pro Leu Ile Ile Tyr Trp Leu Thr Phe His Leu Val Arg
    230                 235                 240

cccoctggcc ccagatggca ctgagttttt cattcattga agatttgatt tccttga       947


<210> SEQ ID NO 37
<211> LENGTH: 241
<212> TYPE: PRT
<213> ORGANISM: Homo sapiens

<400> SEQUENCE: 37

Met Ala Tyr His Ser Gly Tyr Gly Ala His Gly Ser Lys His Arg Ala
1               5                   10                  15

Arg Ala Ala Pro Asp Pro Pro Pro Leu Phe Asp Asp Thr Ser Gly Gly
            20                  25                  30

Tyr Ser Ser Gln Pro Gly Gly Tyr Pro Ala Thr Gly Ala Asp Val Ala
        35                  40                  45

Phe Ser Val Asn His Leu Leu Gly Asp Pro Met Ala Asn Val Ala Met
    50                  55                  60

Ala Tyr Gly Ser Ser Ile Ala Ser His Gly Lys Asp Met Val His Lys
65                  70                  75                  80

Glu Leu His Arg Phe Val Ser Val Ser Lys Leu Lys Tyr Phe Phe Ala
                85                  90                  95

Val Asp Thr Ala Tyr Val Ala Lys Lys Leu Gly Leu Leu Val Phe Pro
            100                 105                 110

Tyr Thr His Gln Asn Trp Glu Val Gln Tyr Ser Arg Asp Ala Pro Leu
        115                 120                 125

Pro Pro Arg Gln Asp Leu Asn Ala Pro Asp Leu Tyr Ile Pro Thr Met
    130                 135                 140

Ala Phe Ile Thr Tyr Val Leu Leu Ala Gly Met Ala Leu Gly Ile Gln
145                 150                 155                 160

Lys Arg Met Ile Leu Ser Val Leu Thr Gly Leu Leu Phe Gly Ser Asp
                165                 170                 175

Gly Tyr Tyr Val Ala Leu Ala Trp Thr Ser Ser Ala Leu Met Tyr Phe
            180                 185                 190
```

```
Ile Val Arg Ser Leu Arg Thr Ala Ala Leu Gly Pro Asp Ser Met Gly
        195                 200                 205

Gly Pro Val Pro Arg Gln Arg Leu Gln Leu Tyr Leu Thr Leu Gly Ala
    210                 215                 220

Ala Ala Phe Gln Pro Leu Ile Ile Tyr Trp Leu Thr Phe His Leu Val
225                 230                 235                 240

Arg


<210> SEQ ID NO 38
<211> LENGTH: 2525
<212> TYPE: DNA
<213> ORGANISM: Homo sapiens
<220> FEATURE:
<221> NAME/KEY: CDS
<222> LOCATION: (159)..(572)
<223> OTHER INFORMATION: CDS

<400> SEQUENCE: 38

cccgcgtgcc gttcttaccc ggcctgcccc gcgccgccgc ttccggaagt gggtctcgtc      60

tcctcccaag cggagcattt gtgcctgaag ctgccgggtc tgctacggca ccgcggggct     120

gcagaaaccc gggggccaag ggcgggctgc ttgccgct atg gct ggc agt cag gac     176
                                          Met Ala Gly Ser Gln Asp
                                          1               5

ata ttc gat gcc atc gtg atg gcg gat gag agg ttt cat ggg gaa ggg       224
Ile Phe Asp Ala Ile Val Met Ala Asp Glu Arg Phe His Gly Glu Gly
            10                  15                  20

tat cgg gaa ggc tat gaa gaa ggc agt agt ttg ggt gtg atg gag gga       272
Tyr Arg Glu Gly Tyr Glu Glu Gly Ser Ser Leu Gly Val Met Glu Gly
        25                  30                  35

agg cag cat ggc acg ctg cat gga gcc aaa atc ggg tct gag atc ggg       320
Arg Gln His Gly Thr Leu His Gly Ala Lys Ile Gly Ser Glu Ile Gly
    40                  45                  50

tgc tac caa ggt ttt gct ttt gca tgg aaa tgt cta ctg cac agt tgc       368
Cys Tyr Gln Gly Phe Ala Phe Ala Trp Lys Cys Leu Leu His Ser Cys
55                  60                  65                  70

acc act gag aag gac agc aga aag atg aag gtc tta gaa tca ttg att       416
Thr Thr Glu Lys Asp Ser Arg Lys Met Lys Val Leu Glu Ser Leu Ile
                75                  80                  85

gga atg atc cag aaa ttc cct tat gat gac cct act tac gat aaa ctc       464
Gly Met Ile Gln Lys Phe Pro Tyr Asp Asp Pro Thr Tyr Asp Lys Leu
            90                  95                  100

cat gaa gac tta gac aag atc aga gga aaa ttt aaa cag ttt tgt tcg       512
His Glu Asp Leu Asp Lys Ile Arg Gly Lys Phe Lys Gln Phe Cys Ser
        105                 110                 115

tta ctc aat gtt cag cca gac ttt aaa att agt gca gaa ggt tcc gga       560
Leu Leu Asn Val Gln Pro Asp Phe Lys Ile Ser Ala Glu Gly Ser Gly
    120                 125                 130

ctt tca ttt tga ggaggatgga tgaacagaga ccgaacgtcg aggaacagat           612
Leu Ser Phe
135

gtgtgtgtga cgtgtttaga aatgcggtga agggccagac ggtgctggga aggcagttgt     672

tcattgggag ggtgagggtt ccggttcggc cgtgggaggg cttccttccc tggggttttc     732

tgcctgtgtc accttggtgc ccgtcttggg gcctcgccac acatgccctt tgttgggctg     792

aagccgtccc tggcagagcc ctcgtgcatt gacttgacag cctctccggc agcacaggcc     852

tagctggttc tgggttggag ttggctctgg atagggtcag tcaccaggcc tggactgaag     912

gcagttattt ttattattat tattatttgc aatgagagag atggttggcc ccgaatgagg     972
```

-continued

```
ctcatgggag gtttggacgg gtgctgtgcc gcatgtcgag gccgattgtg tgccaggcgg   1032

tgcgggacgt gcctcccgtg tgttatttaa tcccttcagg agcccacaag atgggtgtta   1092

ttctcatttt acagaggagg gaggggagac gcgaagggat tgcctggtct aagggcaccc   1152

agcagcagag ctaggacttc cgccctaagg ctgtgcctca ctgccaccag gcacagccgc   1212

ctccggaatg cacaggcgag tccctgccct ccctcccagg ccgcacaggt cctgccaagc   1272

ctcacggagc acgggggagt ctgtggtggc cagtttacct gggcatctgg ctgagaggaa   1332

gaaaggccaa cctgatcctg aggggaccca gacatatcct ttgcactgtc cctagagggg   1392

cgatgagctt tgcagcatta aaaaatggtg aagggggggaa atattttgaa ccaaagacca   1452

aatgttaggc cgccgttata tttgcagaag ctttgagaac catgcgtata gcctcctgca   1512

ttctcccctc tcctaggagc tcttttgtct ctgtccttac gaggcgtcat acagaggcag   1572

tggggtgggc acagatgagc agagtggatg gttcggtggg tccccacgag gcgagtggtg   1632

gtcatatgtg atggcacgtg ttcacacacc ctcctgtgta cccccccagg gtcaccgaag   1692

tccccacacg ctggctctcc acacccctcc tgttccagaa agcatgtccg aaagcagtcc   1752

aggagattat taaggggtcg ccatgaatcc actttggttt taaaaccatt cccgaatgtc   1812

ctagtggatt gtgttgtgct gcctaagctg ccggctgcag gagccagaga agtgaccccc   1872

gcgggagcag cggcaggtgg atctccacgg tggctcgctt tgtttttgtt ttgtttttc   1932

ttttaagacg gagtctcact ctgtcgccga gtttggagtg tattggcgcg atctcggctc   1992

actgtaacct ccgcctcctg aattcaagtg attctcctgc ctcagcctcc ctagtagctg   2052

ggattatagg cgccccccac cacgcccaag taacttttgt atttttagta gagatggggt   2112

tttgccttgt tggccaggct ggtcttgaac tcccagcctg aaatgatcca cccacgtcca   2172

cctaccaaag tgctggaatt gcaggcatga gccaccactc ccggcctgct ttttgttttt   2232

gaagacagga cttaggtctc ctcctcccga actctaaacc tgcgtgtgtg gctgtgcacc   2292

gctcgtttgt agcgtcacct caggtctggg gaagtctgtg ctggcatctc ctcattgtgc   2352

cttcatcaga gctggtgcct tcgggccaga aagactctcg ttctttctag atggtgggat   2412

caggggcctt tgctgtgttt ccccttggtgg atttttgtgt tttgtaagtt gtctattttg   2472

ataatgtatt atttttataa ctgtaaaaaa agtaaatagc atattttaaa gtg          2525
```

```
<210> SEQ ID NO 39
<211> LENGTH: 137
<212> TYPE: PRT
<213> ORGANISM: Homo sapiens

<400> SEQUENCE: 39

Met Ala Gly Ser Gln Asp Ile Phe Asp Ala Ile Val Met Ala Asp Glu
1               5                   10                  15

Arg Phe His Gly Glu Gly Tyr Arg Glu Gly Tyr Glu Glu Gly Ser Ser
            20                  25                  30

Leu Gly Val Met Glu Gly Arg Gln His Gly Thr Leu His Gly Ala Lys
        35                  40                  45

Ile Gly Ser Glu Ile Gly Cys Tyr Gln Gly Phe Ala Phe Ala Trp Lys
    50                  55                  60

Cys Leu Leu His Ser Cys Thr Thr Glu Lys Asp Ser Arg Lys Met Lys
65                  70                  75                  80

Val Leu Glu Ser Leu Ile Gly Met Ile Gln Lys Phe Pro Tyr Asp Asp
                85                  90                  95
```

-continued

```
Pro Thr Tyr Asp Lys Leu His Glu Asp Leu Asp Lys Ile Arg Gly Lys
            100                 105                 110

Phe Lys Gln Phe Cys Ser Leu Leu Asn Val Gln Pro Asp Phe Lys Ile
        115                 120                 125

Ser Ala Glu Gly Ser Gly Leu Ser Phe
    130                 135


<210> SEQ ID NO 40
<211> LENGTH: 734
<212> TYPE: DNA
<213> ORGANISM: Homo sapiens
<220> FEATURE:
<221> NAME/KEY: CDS
<222> LOCATION: (47)..(652)
<223> OTHER INFORMATION: CDS

<400> SEQUENCE: 40

ggagctgtgt aacagcaacc ggaaagagaa acaatggtgt gttcct atg tgg gat        55
                                                   Met Trp Asp
                                                   1

ata aag agc cgg ggc tca ggg ggc tcc aca cct gca cct cct tct cac      103
Ile Lys Ser Arg Gly Ser Gly Gly Ser Thr Pro Ala Pro Pro Ser His
    5                   10                  15

ctg ctc ctc tac ctg ctc cac cct caa tcc acc aga acc atg ggc tgc      151
Leu Leu Leu Tyr Leu Leu His Pro Gln Ser Thr Arg Thr Met Gly Cys
20                  25                  30                  35

tgt ggc tgc tcc gga ggc tgt ggc tcc agc tgt gga ggc tgt gac tcc      199
Cys Gly Cys Ser Gly Gly Cys Gly Ser Ser Cys Gly Gly Cys Asp Ser
                40                  45                  50

agc tgt ggg agc tgt ggc tct ggc tgc agg ggc tgt ggc ccc agc tgc      247
Ser Cys Gly Ser Cys Gly Ser Gly Cys Arg Gly Cys Gly Pro Ser Cys
            55                  60                  65

tgt gca ccc gtc tac tgc tgc aag ccc gtg tgc tgc tgt gtt cca gcc      295
Cys Ala Pro Val Tyr Cys Cys Lys Pro Val Cys Cys Cys Val Pro Ala
        70                  75                  80

tgt tcc tgc tct agc tgt ggc aag cgg ggc tgt ggc tcc tgt ggg ggc      343
Cys Ser Cys Ser Ser Cys Gly Lys Arg Gly Cys Gly Ser Cys Gly Gly
    85                  90                  95

tcc aag gga ggc tgt ggt tct tgt ggc tgc tcc cag tgc agt tgc tgc      391
Ser Lys Gly Gly Cys Gly Ser Cys Gly Cys Ser Gln Cys Ser Cys Cys
100                 105                 110                 115

aag ccc tgc tgt tgc tct tca ggc tgt ggg tca tcc tgc tgc cag tgc      439
Lys Pro Cys Cys Cys Ser Ser Gly Cys Gly Ser Ser Cys Cys Gln Cys
                120                 125                 130

agc tgc tgc aag ccc tac tgc tcc cag tgc agc tgc tgt aag ccc tgt      487
Ser Cys Cys Lys Pro Tyr Cys Ser Gln Cys Ser Cys Cys Lys Pro Cys
            135                 140                 145

tgc tcc tcc tcg ggt cgt ggg tca tcc tgc tgc caa tcc agc tgc tgc      535
Cys Ser Ser Ser Gly Arg Gly Ser Ser Cys Cys Gln Ser Ser Cys Cys
        150                 155                 160

aag ccc tgc tgc tca tcc tca ggc tgt ggg tca tcc tgc tgc cag tcc      583
Lys Pro Cys Cys Ser Ser Ser Gly Cys Gly Ser Ser Cys Cys Gln Ser
    165                 170                 175

agc tgc tgc aag ccc tgc tgc tcc cag tcc aga tgc tgt gtc cct gtg      631
Ser Cys Cys Lys Pro Cys Cys Ser Gln Ser Arg Cys Cys Val Pro Val
180                 185                 190                 195

tgc tac cag tgc aag atc tga ggctctagtg ggaaacctca ggtagctcct         682
Cys Tyr Gln Cys Lys Ile
                200

gaagatctgt gctttccaac aagtgactac ccttgaagca catccccttc tg            734
```

<210> SEQ ID NO 41
<211> LENGTH: 201
<212> TYPE: PRT
<213> ORGANISM: Homo sapiens

<400> SEQUENCE: 41

```
Met Trp Asp Ile Lys Ser Arg Gly Ser Gly Gly Ser Thr Pro Ala Pro
1               5                   10                  15

Pro Ser His Leu Leu Leu Tyr Leu Leu His Pro Gln Ser Thr Arg Thr
            20                  25                  30

Met Gly Cys Cys Gly Cys Ser Gly Gly Cys Gly Ser Ser Cys Gly Gly
        35                  40                  45

Cys Asp Ser Ser Cys Gly Ser Cys Gly Ser Gly Cys Arg Gly Cys Gly
    50                  55                  60

Pro Ser Cys Cys Ala Pro Val Tyr Cys Cys Lys Pro Val Cys Cys Cys
65                  70                  75                  80

Val Pro Ala Cys Ser Cys Ser Ser Cys Gly Lys Arg Gly Cys Gly Ser
                85                  90                  95

Cys Gly Gly Ser Lys Gly Gly Cys Gly Ser Cys Gly Cys Ser Gln Cys
            100                 105                 110

Ser Cys Cys Lys Pro Cys Cys Cys Ser Ser Gly Cys Gly Ser Ser Cys
        115                 120                 125

Cys Gln Cys Ser Cys Cys Lys Pro Tyr Cys Ser Gln Cys Ser Cys Cys
    130                 135                 140

Lys Pro Cys Cys Ser Ser Ser Gly Arg Gly Ser Ser Cys Cys Gln Ser
145                 150                 155                 160

Ser Cys Cys Lys Pro Cys Cys Ser Ser Ser Gly Cys Gly Ser Ser Cys
                165                 170                 175

Cys Gln Ser Ser Cys Cys Lys Pro Cys Cys Ser Gln Ser Arg Cys Cys
            180                 185                 190

Val Pro Val Cys Tyr Gln Cys Lys Ile
        195                 200
```

<210> SEQ ID NO 42
<211> LENGTH: 5000
<212> TYPE: DNA
<213> ORGANISM: Homo sapiens

<400> SEQUENCE: 42

```
aaggagaagc ttaaatcagc cgtgggccgg gaagagtccc tgtctgagga gcagccgggc      60

tctttagctc accagggact catgatgtcc ccagctctgg acgagctgtg gggaagctac     120

ataccaccca gacaagttac cagggcccac ctgactgcca tatatccagt gatcttattt     180

cagcacattg acctctcgtg gctttggaca ctgctctctt ctctctcctt gaaaagtgga     240

ccatccccccg ctcctcagtc tcctgcagca ctcgattctc tattgtcagt gtctatttgc    300

tggtctgtcc agtgctgcct cccatcaccc tgtgtttggt gcttccccac tgccctggac     360

tctcctcctt actcttgtgc atggctgcgg ccactctgtg gtttgcttct gccttgtgtt     420

ctgtgattcc tgcatctaac agccgtggct gtggcttccc tcctctgtcc atgtctacac     480

tggcactttg tgtctgtatt aatcctgatc ttcatgatct tctctagtaa actaaatggt     540

gaggtttgtg ttttctagat gaggaaactt gcttggagag gtgttaagta acttgccacc     600

ggtctcacgg gaagggcaaa gccagttttg gagggctctt ggcttttgag cacacccttt     660

cccaccctca agcagcctct gcagaactca gatgtccagc gctggcctca ctgtctctcc     720
```

-continued

```
ccaaaccagc gcctctatcc ccatttttaa tatttttatt tattttaaga catggggtct    780
cactctgtca cccagactgc agtgcagtgg tgtgatcata gctcattgta acctcaacct    840
cctgggctta agggatcctc ctgcttcagt ctcctaagtc actgggacta tagacacaca    900
ccaccatgcc ccagctgcat ccccatcttt gtgacacaat ccttgtcagc ctgaccagaa    960
aactcttccc tcccccatcc agtcagtctc gagtcccctc tattctctcc ccatcatctt   1020
tctgaaatct gtcccctcat aataatagca gtgatgagga taatagcagc tcttgccaat   1080
taagcacttg ttatgagaca agcctgtgtt cattctcttc atgctcacaa tcagcccttc   1140
taggaggtac tgtttataga aatgaggaaa ctgaggctca gagtggtcag gtaacatacc   1200
tggggtcaca cagtaaatgg ctgagccagg ccttcagcag cagtggtctg actaaatcct   1260
gtgtgcttcc ctggctcagt gcacgttctc ttccctgagt tattccagcc attcccagtt   1320
ggtctctatc ttgctattct gatctgggct ctgcctcctg tcaggactag cataggtgtg   1380
atcctgttgc ttctggccta agaaacgccc actggctcct ggtctaagtc caagacttag   1440
ccatgctaag acagtctgtg ctctggcctc tccccaatcc cccctctttc ctcccctctt   1500
ccccctctcc cctcttgcct ttctcctccc cactccccca ttccccctcc ctgtcccccc   1560
tccctgttga gtgtctgcat cccagcaaca ttccatttcc tcccattccc cagacacacc   1620
atgcccctcc cgttcagtga cctggcacat gctggctccc cagctggcac ctctcctgca   1680
caaggccagt tcccacctgc aggcttaggt ccactgttgc tcccacctca agcagaggtg   1740
gtctgggggc tccccagccc ctgccttcta acctgttttg cccttgtgtg tggcctggtc   1800
tattcatcta ctgtcccgtg aatgtgttag ggcagggccc aagtatgatt tccccctttg   1860
tccccagcac ttagcacagg acccaacttg gaacatggca agaggtctaa gtttgagcca   1920
gtgtgatatg accaggcttc tggctcctaa ggagtataag tggccctagc ttgagcactt   1980
tcctgaaagt cctgtccttt gtgtgtgggg taggggcgca agtgctggga gagtctgaag   2040
ccaagtaatg aggctgttgg tgccaaaagt aggatgaatt ttaggctgtt cccaggattc   2100
ctgtctcccc acaggccagg gccacctctg agaggaccct cgaactcctg tgctccaagg   2160
cttcaaacct taaagggatt ttcaggccac ggtgggaact gtggctcttg cggacccgtt   2220
actctctgtt cctatctccc gtccgctctc tctttgcttc tcacatgtgg ttagggcctg   2280
caagtgtctc agggagagag acagctgcag ggagcagagc tggcaggccc aagttggggc   2340
agctgttgag gtgttggggc agctggcagg ctgctggggc tgttctgggt ctcggatgga   2400
agagggcagg gaggaaggtt cagcctggag cagagggctt cctctgcatc tctgcatcgc   2460
tgagcccagg acttaagggg cccggagctg tactgttccc ctcagagaag gtcttctcca   2520
ggcctggggt aggggtgaca gttgggagca aaataacttt ggcccctggc cccctttagg   2580
aatcctacgc caacgtgaag cagtggctgc aggagattga ccgctatgcc agcgagaacg   2640
tcaataagct cctggtgggc aacaagagcg acctcaccac caagaaggtg gtggacaaca   2700
ccacagccaa ggtagcagac gggccggtct gcccggggtc ggggcgctgg ggcctgctgc   2760
ccctcacctg ctctcccctc ctcttctctc ccctcctctt ctctcctctc ccttgtcagg   2820
agtttgcaga ctctctgggc atccccttct tggagacgag cgccaagaat gccaccaatg   2880
tcgagcaggc gttcatgacc atggctgctg aaatcaaaaa gcggatgggg cctggagcag   2940
cctctggggg cgagcggccc aatctcaaga tcgacagcac ccctgtaaag ccggctggcg   3000
gtggctgttg ctaggagggg cacatggagt gggacaggag ggggcacctt ctccagatga   3060
tgtccctgga gggggcagga ggtacctccc tctccctctc ctggggcatt tgagtctgtg   3120
```

gctttggggt gtcctgggct ccccatctcc ttctggccca tctgcctgct gccctgagcc 3180
ccggttctgt cagggtccct aagggaggac actcagggcc tgtggccagg cagggcggag 3240
gcctgctgtg ctgttgcctc taggtgactt tccaagatgc ccccctacac acctttcttt 3300
ggaacgaggg ctcttctgtc ggtgtccctc ccaccccccat gtatgctgca ctgggttctc 3360
tccttcttct tcctgctgtc ctgcccaaga actgagggtc tccccggcct ctactgccct 3420
ggctgcagtc agtgcccagg gcgaggaatg tggccagggg atccaggacc tgggatccag 3480
ggccctgggc tggacctcag gacaggcatg gaggccacag gggcccagca gcccaccctt 3540
tcctctcccc actgcctcct ctcccttcct acactcccag ctcgagccgt ccagctgcgg 3600
tgggatctga gtatatctag ggcgggtggg cgggtagcag tgctgggcct gtgtcttgag 3660
cctggaggga gtctgctcct gccgccctct gccctgccag agacagaccc atgcgctgcc 3720
tgcccaccgt gccccttgt ccccatgtca ggcggaggcg gaaggcccac cgtgccagag 3780
gctgggcacc agccttaacc ctcactctgc tagcacctcc tccctttccc caaggtagca 3840
catctggctc actccccact ccgtctctgg agcccaccag ggaaggccct catcccctgc 3900
cgctacttct ctggggaatg tgggttccat ccaggattgg gggcctctct gctcacccac 3960
tctgcaccca ggatcctagt cccctgccct ctggcacagc tgcttcctgc aagaaagcaa 4020
gtctttggtc tccctgagaa gccatgtccc tcgtgctgtc tcttgcctgt cccacctgtg 4080
ccctgccctc cagcttgtat ttaagtccct gggctgcccc cttggggtgc cccccgctcc 4140
caggttcccc tctggtgtca tgtcaggcat tttgcaagga aaagccactt ggggaaagat 4200
ggaaaaggac aaaaaaaatt aataaatttc cattggccct cgggtgagct gagggttttt 4260
gcaaggaagt tgtggtggcc aagtgtggtc tgtggtctaa gcccagcctt ggggtggggg 4320
gatggaactg gaaccctggg cttggtgggg tgcacggggg tcctggcttg gtttctgtgt 4380
cctaaggctg ctggcaaaag cccttgaccc cgtttcctga ggccaggaaa gctgcttgtg 4440
cttctgtggt ctgtccccaa gggcccagca ccgttctgtc agggaaagag gcaggcggcc 4500
atcagctcat acctggcgtg ccgccgccaa ctcccgcggg gcacacggca gaggtgtggg 4560
gtcgcgcagc cgctgagagg gcccccactg cacctggccc aacctccttc agcgcccccc 4620
aaaaccccac tgctcccatt cagcccctgt cctggcgtca ttgtgtgtcc cagccaggtg 4680
cttctgccgt ctccgacagt gacaagtgcc tcgcacttca gcctttgccc tgagcgcccg 4740
cccgaggggg ccgagtgcgg ctgtgccggt ggctggagtg ccgaggggtg cggggtgccg 4800
ggggcggccg cgtctacgct gtccggaggg tgaacggccg cgggcttgtc ggggctgggg 4860
gtggcgcccg agccgggcgg gcagacgagg ggcccgcgga gacccagccc cgcccgaggc 4920
cgctcgcgcg gcggccccgc ccccggctcc gccccgccgg cttcgcgggc tggagagcga 4980
gggagccgcg ggcgagggat 5000

<210> SEQ ID NO 43
<211> LENGTH: 5000
<212> TYPE: DNA
<213> ORGANISM: Homo sapiens

<400> SEQUENCE: 43
tcacagtggc gctgcatatt caaacccagg actcgctgcc ccaaacccat cctccactgt 60
gccgtgctag cactcggcaa accgcacaca ggagacagca ggcccacctc agccaggagg 120
gatggatcct tgcactggct attgtgggtt ctggtcctgg ctctgccctg atttgctgtg 180

-continued

```
tggacttggc tatatctctg ccctctctgg gccttgattc ttggtcctgt tggtttggga    240
agccagggtg gaaggggtct gaggtgtaaa cagcatgggc tttggagttc cactgcccag    300
gagccagtgc tggctccact acttactgta tgacttgggc aggtccctca tcctctctgg    360
acctcaattt cctcatctgt aaactggttc tattgtgagg attcaacaag atcatatgtg    420
tgaagaagtg agcacagggt ctggccatgg gaataaatat gatcaccatt accctgagac    480
tccctctggt cccttgttcc atagggactc agaagtctcg gcagaggctt ttgagttgat    540
gagaaagagg gagcctcaag aacgggggag gtgcgagtct tggggtgggg agcagatgga    600
gggccatcct ccactcccca tctgtgctga gcaagggggt gggacacagc tactgggcag    660
caggggccac tccctggctc agagggcttg ccacaccctc cctggcaggg ctgccagcct    720
agccacctca ccctcaggtg ccatggagag agaagcaggt agggataaag tggggcgagg    780
ggaagggtaa aaaggggagg aaaaaagtgg aaacaacaaa agggggggtta aggggccacc    840
tctcctaccc cagacctacc aggcctccag aggcccaaga ggagaggaac cacccccctag    900
cccagcccag atacagcctg tccccatcac ccagcatggg agcacagcgc cagctgacct    960
gcaaggcctg tcaggtgcac acacacttgt ccacgcccct ccaacacatg ctcatcacag   1020
acccacccac cgtggagggc cacactgcct gtcacccagg aaactccaga ccctcgcctg   1080
tccccagggc acagactccc agaaccgtag catggtacac acacatacac acacacacgc   1140
acacaccaca tacccatcca ccacaggaca cacacgtgca catacacgtt gcacgtgcag   1200
tgaagcccag agacatacca gaccttcacc tgaccacagt gcacatctcc ccaccccccca   1260
ctgcaaactg acccccaggc tcctcagact ccacagggag agacctgccc acaaagggac   1320
tcactcacat gcgcacacct agaccactgg gtgacaaccc gagccaggca cccactcgcc   1380
cctcacctga ctacagggcg cacacaccca attcacacac ccacacaaca cacacacaga   1440
agcaggctac attcacccaa atgcatgcac agccccactc accaccctat caccccacac   1500
atcactcggg gccccaggtc ctgcagacct tcctggctag ggctgaggag gggccgtcgg   1560
gggtcccagc cagcagaatg ggccctcaat cctcacctcg aggacaagga gaaggggtac   1620
ccaggcgcct cccttcctct tcccctcctc ccctctaggc tctgcgactg ctgctgcatt   1680
gcaggcgctg cccggacacc tcgtgagcgg ctgggccggg ctggggacct gaccccgcgg   1740
ccctgggggt gggggcagca tccccccgctg cgctgcggca ctgggacgcg tgggggccag   1800
gcactgacgt cacaggacgg gcgaggctgg atgaggggac gccgggggcg gaagtcgccc   1860
cgcatattgc tgtccagccg ccccacccct acccccaacg cgggcccctg gacccttggc   1920
agggcgcagg tgaccccaat gacgtcattg gccgtagggg ctctgggact tccctcctca   1980
gcccctctct tggggtcgcc ttttgcactg gtccctctca cgccgcccca ggcccggctc   2040
cggccccccc agcgccggta cctcttcccg cagcggctcg ccgtccggga tgagcgcggg   2100
cacctccccg ccgtcgccag cgccgtcctc gggcatggtg tcctggctgc ttgggcggcc   2160
ccagcctggg caccgggcat gatagggggg agcacggagg gctgcgacgc ggcccccggg   2220
ggcgtccgct cggctcagcg gccgcggagg gagtgcgcgg agctcgagcc cgagcgcggc   2280
ggcagcggcg gcggcggcgt tggcggcccg ggtgccaggc gccccgccct ccgctgaccc   2340
cgcccccgcg gcaccggcgg cgccgccggc agcgcctggc accgcgggcg ctccgcccgt   2400
ccccgagaag cccccgctgg gcggctggac ccctgggttc tcctccggcc gcgctcgcgc   2460
tcgcgacctt gagctggtct aaccctctgg cgcctgagct tcccgggctg taaaaccctc   2520
gaggaaggag aatctccaag gtgggtgggc gctcgcgggg tcccatctct aaggagtagg   2580
```

-continued

```
cccagagtta agcccaccca gatcccatcc ctgaagcctc acttggagaa gagggtagtt   2640
acagctgaga aaagcgtgac gagtctcact ggctgggcag gggtgctggg ctcagcttag   2700
gacaggcagg ctggggccag gacacaaggg accctaggct gcgtgacctt gggccagcat   2760
gctccactct caacctcagt tttcccatct gaaaaatggg gataaaagct ggactgagtg   2820
gctcatgcct gtaatcccag cactttggga gaccgaggtg ggaggatcac tggagtccag   2880
gaattccagc agccttggaa acatggcgaa accctgccta tacaaaaaat taaaaaatga   2940
gctgggcatg atggtgtggt gtgcacctgt attcccagct acttgggagg ctaagacagg   3000
aggatcaatt gagtctggga gtaagaggct gcagtgagct gtgtttgcac cactgttctc   3060
cagctgcgtg ataaagtgag accctgccta gaaggagaag aagaatgaga aggagaagga   3120
gaagaagaag aagacagaaa gaaagggaga aaaagaaata aagaaagaaa gaaggaaaag   3180
aaaagacata gaaaggtttt ggattcagtt tacaagtatc cattgtgccc tgcagtgaca   3240
tgggaactga cttgcattag atgacccct cccaggtaca cgtggcccca gtgctacctc    3300
ctagccctcc agggcctcag atcttcacat ctgtgtctgg gtctggcttt gctcccaaac   3360
tagacaatat gggcagaaaa tgagctgcaa tactggtggg ttaattcatt tttgtatgtg   3420
cgtgtgttca ggcaaagagc aactcaaaga ccattcaatt aaacatcctt acccacttaa   3480
agattaggta attgagatgt ggacacagga aaggactggt ccagggtttt atctatttat   3540
tatgaatttc ttggacacag atgtttattg ggtgtcttcc atatgcaagt attgtgcttg   3600
gcactgggaa gacaagggtg gaagtggaga atgacaacag ggcctgtcct catggaactt   3660
acatgcaggg caaattgggt gcacccagag ggggcctaga acccaaccta tgacctccac   3720
ccctgaccgg gtcaggtctc tgtccccttt gtccctctga gaggcacgag atgaactaac   3780
tcttaaagat aactaggctt atggacaagt ggatatgagg gggaagggca tcccaggtgg   3840
aggggacctc tgggcaatgg cactgcaatc agaccacgtg ggctgagttt ggggagcagg   3900
aaggtcatct ggtgtaactg gatacctggt agctaattag agaggtcgca gagaacctgc   3960
tcatgctctc tagaaagcgg tggctgaagg tctgtgagag ggaggcccct gaagactgtc   4020
tccgcggggt tgggagtgat cagaacctgg gtggagagaa aggaaccccc gggactacaa   4080
gtgaggctta ggggcctcac ttcaagaaga ccacaggccc ggcgatgact caggagttta   4140
ggctgcagct tcaggacgca aatcagcaca cctctgcccc caaatctgct ggactacggg   4200
agagtctatg ggacaggccc ggggcaggat cctgccccac ctataccacc caatctctca   4260
gacttcggat cctctgggcc ccagttttgc agtatgcgtg tatgtgtgcg tgcggccacg   4320
cgctcgctag gagcgtgtgg ttcgagaccc caaatcttcc catacgcagg cccccgggag   4380
tctacaggat ggcggctgag gcgggaggac attttcagca ccggacgacg gacagcaccc   4440
gcgcggagaa gaggagtggg aggcgggtgg agtcagcatc ctggggcttg cttggcagct   4500
ctgtcactga taggtccggc ctcccaccac cacctccggg tctgccgggg ctccgttcca   4560
agattgggtg aagtgtaggt gacgggggag gaaaacaagc ccagagaggg agaaacaggc   4620
gccccgaagg gcagggcttg gttggaactc gaccgccccg ttccctcctg gagtacgtcc   4680
caccaaggaa gctttgctcc tgactccggc tgcaggttac ctctcgactc cctggtgtag   4740
tcgtggcagg gtgcgtcaag tgcctcaccg cgcaggcgcg caaataattc tcgcccacct   4800
tctttcttaa ctcttctatt ggctgttccc accgtgaact ggcaagcccg tgatccaatc   4860
ccaggcaccg caagtcgctc cgcctgtccc tcacccggat gttgccttct gccgaatccg   4920
```

ctcaggccag agctcgtcag tggccaattg ggagagggga ggggcgagcc ggcgccgccg 4980
aagagccaat ggcaggcgcg 5000

<210> SEQ ID NO 44
<211> LENGTH: 5000
<212> TYPE: DNA
<213> ORGANISM: Homo sapiens

<400> SEQUENCE: 44
tatttatttt ttatttgaga cagagtttca ctcttgatgc ccaggctgga gtgcaatggc 60
acgattttgg ctcactacaa cctccacctc ccaggttcaa gcaattctcc tgcctcagcc 120
tcctaactag ctgggattac aggcatgagc caccatgccc agataatttt gtatttttag 180
tagagacagg gtttcaccat gttggccagg ttggttttga actcctgacc tcagatgatc 240
cacccacctc ggcctcctaa agtgctggga ttacaggcgt gagccaccac acccggccct 300
tctttgtctt taatgctaag acagtctggc ttcaaaataa atattttaag aacaaaccag 360
atgaacaaat tgatgattgg ggacagaaaa tctccccaaa gctttatttc agattaataa 420
tttgtatcaa tagtgttgat ttttgtagca catataattg ttcaaggctt tgcaaatatt 480
tttgaagtta gaaattaaaa cctacgctct tctgtataag cctccatgtc cacgggcttt 540
attctgtaag tggtcattta tttttctcac cgcgttatct attttcctat ccaaaagata 600
tatttatttt attttatttc agctaatgaa atttatgctc aaaaatgtgt tttaaatatg 660
tactgataag agaacagttc ccttatttgg gaggtgtttg taatctaatg ttaagtgggc 720
agggagaagg atattacatt gtttatatat taaattatgt ttatatgaaa attcaaggga 780
aaaataataa aattagcaaa aatcagttgg tggacagggt gaactgtttt ttttggcttg 840
ctgtctttcc ctttttccta tattccaagt gttgtgtgat ttcatttgct tatttaaaaa 900
acctaaaaat taaagacatc ttcagaacaa aataatacga agtctattta atttcatcca 960
ccaaaaacat ttttttatgc ttataacata acttatgttc attgtgcaaa caaacatgag 1020
atgttccaaa aaatataaat gaggacatta aaaaaatcac tgtcattcca aaatctagct 1080
atattctcta tgaacatttt gctgtacttg ctttcactct tttttctctt cctttttttct 1140 tttctggttt tttgtttgtt tgtttgtttg tttgttttgt ttgagatagg gtctcgttct 1200
gttgcccagg ctggagtgca gtggcacgat cacggtttac tgcagcctca atttcctgag 1260
aacaagcaat cctctcgcct tagcctccca agtagctggg actacaggag cacactaccg 1320
tgcctggcta atttttttcta ttttttttgta gagatgaagt ctcactatgt tacctagctt 1380
ggtcttgaac tctgggttca agcaatcttt ccaccttggc ctcccaaagt gttggattat 1440
acgtgtgagt cacctcacct ggctactctc attcttttga aatagtgttt agtgtgattg 1500
caattcgagt atatgtagag tgtttttttt tctttttctt tttctttctt tttatgtttt 1560
tgagatgaga tttcactctg ttgccctggc ctggctgcag tggagtggta tggtcatagc 1620
tcactgcagc ctcacataga ggattttttt ttctttttct tgaaatatca tgggcatttt 1680
ccatgatgtt acttttgttg aaatattatt tgtaatggtt gcttaggagt cttcaacatg 1740
aatagcctac aatacatgtc ataattccac cattttgtca atgtagctgc tttccttgcc 1800
ttgcctttta caaatcgtgt tgcactgaac aacactgtac ataatatttt gacttgtctt 1860
tgattatttc ctagagatga agtcttagaa gtgaaatgac taggtccagg ggcaaaaaaa 1920 aacttttttta ttctattttt gaggcagagt ctcattctgt cgcccagtct ggagtgcagt 1980
ggcacaatct cggctcactg caacctccac ctcccaggtt caagcaattc tcctgcctca 2040

-continued

```
gcctctagaa tagctgggac tacaggagcg tgccaccaca cccggctaat tttgttttt   2100
agtagagacg aagtttcact gtttggccag gctgatctgg aactggtgac ctcaggtgat   2160
ccacccacct tgacttccca aagtgctggg attacaggcg tgacccacca cgcctagcta   2220
gtaaaaacaa acaaacaaac aaacaaacaa acaaacaaaa tatatatata tataatgccc   2280
ttcctatgtt tttgaactgc ctgaccaaga ggtgtcttca atgtatgcac ttgtgctcat   2340
taagagtatc ttttaattct aaaaaaggag aaaaagaact taagctattt taaaagataa   2400
aaaatgcatc tcattattct ttctcagcat tgctttggtt actagtgagg ctgcgtctgc   2460
ttttcctgat tggccagctg ttgctctttc tgtgaataat gtttcaagtc cttttttttc   2520
cccgttagga tgtatttatt taaataaata catgtattta aataaactct ttaccagaat   2580
tattatttct ttagttacaa tatttatgac aaatatttcc ccatattgtt ctttaacttt   2640
aaattttgtt tcttatcact tttggtacac acaagtttgc atttttacat ggtaaaatgt   2700
tggttttgct tgctgagaat tccttcatgg cttttatgtg ttaaaagagc atcttcatac   2760
ttgtctgaat gttccaccta gatttttttaa tgtactttat tttatttatt tatttattta   2820
tttttatttt attttatttt ttttgagata gagtctcgct ctgtcaccca ggctggagta   2880
gagtagcgcg atctcggctc attgcaagct ccacttccca ggttcatgcc attctcctgc   2940
ctcagcctcc caagtagctg ggactacagg tacacgtcac catgccccac taattttttt   3000
tttttgtatt ttttggtaga gacggggttt caccatgtta gccaggatgg tctcgatctc   3060
ctgacctcat gatccgcccg cctcggcctc ccaaagtgct gggattacag gcaaaatgtg   3120
ctttattcat ttatttattt agagatggag ttttgctctt gttgcccagg ctggggtgca   3180
atggtgtgat ctcggctcac tgcaacctct gtctcctggg ttctcctgcc tcagcctccc   3240
gagtagctgg gcttacaggc atgcaccacc acgccaggct aattttgtag ttttagtaca   3300
gacggggttt ctccatgttg gtcaggctgg tctcgaactc cctaactctg gttatccacc   3360
tgcctgggcc tcccaaagtg ctgggattac aggcgtgagc caccgtgccc agccaatgtg   3420
cttaattttt ttaagttaac tctttaactc atctggaatt attttgatga atggtgtgag   3480
gcataaatgg aaccaagctt ttcccaaaca accaattttc cattatagtt attagttaat   3540
atttcctttc tccaattaat ttgtaattct tctttttacc acatgagaag gctttacatc   3600
tatgagagtc cattgtctgg gccatttact ttatttcact ggtctgccac ttcttgaacc   3660
aacataccac aatatttata ttgacacttt atcttttcat atctgatatg aaaatcattt   3720
ttttctaaaa catcttagtt atttttatta gtttattcat acggatgaaa aagtttagga   3780
ttttgacaca ttttaccaga tctcatggaa ttttctttgg tactgcactt gttcagttcc   3840
ccaatcctca atcatggtag agctgtagtt ttccttatat gggtcctgct caaattgtta   3900
gaaattctta tttctaagaa atgtattatg actatcataa ggcgattttc ccatcaccac   3960
ccctgctcag gttactacca attattgttg gaataacaga aagtgttttt ttccctattc   4020
atcatacaca tagctacttg ctgcgattat ggattctgag aacgtcttag gtgactattt   4080
gggttttcca cgtgggccat catatctgca aatagtagta tttctgcctt tttttttttt   4140
tttttttttt tttggtattt ccacttcttg cttcatgttt tactgcattg gccagggctg   4200
gtagaaagat gttcagtggt cacgtgaggt tttactactg actttattag gaatgcttct   4260
ggtgtttctc atctgagttc cgttgtcgct tagactttga aatccctttt taaaaatcgt   4320
gttcagaaag cacatctcat ggaaatgaca aatatgagaa ctaaaaccga caaatttctg   4380
```

```
cccaaaatcc cacatgcaga gcctcctggc ctggagcctc ctgaggcgtc ggttctttga   4440
tgacttccca tttcttttcc cttttttttt ttttttttga cggagtctgg ctctgtcgcc   4500
agtctggagt gcagtggtgc gatctcggct cactgcaacc tccgcctccc agcttccagt   4560
gattctcctg cctcagcctc ccgagtagct gggattacag gcgcctgcca ccatgcccgg   4620
ctaatttttg tattttcagt aaagacgagg tttcaccatg ttggccaggc tggtctcgaa   4680
ctcccgaact caggtgatcc gcgcgcctcg gcctcccaaa gtgctgggat gacaggcgtg   4740
agccaccgcg ccagctgatg acttcccatt tcttccttgg ttctttcgga gccactttgg   4800
gaaattcggt tctatctgca gtggtaaaat acaggtcggc tctccacgcg cgcggccaat   4860
ggacgctccc agcgcggaca gacaggccct ttgctggagc tgggcagggc gaaaggaccc   4920
cagggcgggg cttcagtcga ggccggcccc gcccaccgct gcagccgcgc atgcgccatg   4980
tacaggctgc tttgggccct                                               5000
```

<210> SEQ ID NO 45
<211> LENGTH: 5000
<212> TYPE: DNA
<213> ORGANISM: Homo sapiens

<400> SEQUENCE: 45

```
cagatcagtc tccctgagca tttggggagc agagttttta agggcaactt ggtgggtggg     60
gagaagccag tgatccagga gtgctgattg gtcagggatg aaatcacaag gagtcgaagc    120
catcttcttg cactgagtca gttcctgggt gggggccaca agatcagatg agccagttta    180
ttgatctggg tggtgctacc tgatccatca agtgcaggga gggtcagaat cttgtaaatg    240
acctctggct acatgactcc taaactgtaa tttctaatct tgtggctaat gttagtctag    300
tccccaggca agaaggtggt ctgctttggg aaagggttgt tactgtcttt gtttaaacta    360
taaactacca actaaatttc tcccaaagtt agttcagcca acacccagga atgaacaagg    420
acagcttgga gattagaagc aaggtggagt gggctaagtt agatctctca ctgtctcagt    480
cataactttg caaaggcggt ttcaagccca gctgccaacc agaggaactc actcaacacg    540
tgagcagcag gcagaagcaa gagccttccc ctgagaaata ggaaggaaat cctagcctcg    600
cccccgcaac cactgactga acgggacccc tcttggccaa gggggtgtcg acaaaaagtg    660
tcaaactctg taaaatattt taaaagattc tgagccgaac atgactgaca aatggcccgt    720
gacacagccc tcaggaggtc ctgagagcag gtgcccaaga ggtttggggt gcagcttggt    780
tttatatatt ttagggagac atgagacttt aatcaaatac atttaagaaa tactaaggcc    840
taaactctgt tgttgttttt tttaatcttg ctcaaattcc tatctaaggg gtctgcgcat    900
gccctacaaa tcataaactc tcaacagaca ggttttgttt agccctaaat attgtgactt    960
actttccaac ccgactctgg cataacatta tgagacaagg aagaaaatca aaatacttta   1020
ccccaaaaca tgtttctttg ctgtattttg aaatggccct gcagagcgtc ctttgtgggg   1080
gaaaatttgg atctgcaaag aatctctatt aacatagcta gatctttttc ttccagaccc   1140
tcccagtcct aaagagatta actaaggtct gaataggaaa catttgtcat ctattgtctc   1200
taagggcagc cactatcaga cttcaaaaga actttggtct ccacaatctt tatcttaact   1260
tgaactttcc cttcctatcc atcccaggtc tttagacaaa ctcaaccaac cgtgaaccag   1320
aaaatgttta aatttaccta tagcctggaa ccccctcacc ccccatcccc caccacccgc   1380
tttgagttgt cccgcctttc tggaccaaac caatgtaatt ttgaaatgta tttgattgat   1440
gtctcctgcc tccctaaaat gtgtaaaacc aagctgtacc atgaccacct tgggcccatg   1500
```

-continued

```
ttctcaggac ctcctgaggg ttgtgtctca ggccatggtc actcatattg ggcccagaat   1560
aaatctctct tcaaatattt tacagagttt gactcttttt gtcgacatta cattggtttg   1620
gtccagaaaa gtgggacaac ttgaagggtg gggagtgctt ccaggctata ggtagatgta   1680
aaaattttcc ggttgacagt tggttgagct tgtctaaaga cctgggatca acagaaagga   1740
atgtctgggt taggataaag gatcatggag acccaggttg ttatttgcag aggaagcctt   1800
taggtagcag gcttcagaga gaagaggttg tgagacgttt gttatcggac ttaaagtctg   1860
tgtggatgtt aatgccagag aggtagaatg aggcatgtct gacccccact gcccatcata   1920
gtgtctcagg ttaaatttta aaacagccct ggctgaggag gaagtccatt cagatggtcg   1980
gggaggaggt cttagaatgt tatgtttggt taaccgggaa accttggaag ctgagttcct   2040
ggctacgggg ggatgggaag ctggacttgc gcccttctcc tactccctgg ccagccatga   2100
cccagctccc tcccctcagg gaaaacagaa accaattctg tggagactgc actgaggaga   2160
tcagtgtacc cctgacattg ccccctcctt cttgatagga gatccaccac ggagaggccc   2220
tggccattct acggaagagg cgcaaggaag tcttctgagt ccgctgcttc accttttgac   2280
atcagagggc caaaagctcc accctcagat caggctaaca cctctggttt ttgcacatag   2340
agagggggtg aagctggatt gcgcatatgc ctggttttgg gtctgcagtt ggttcctgct   2400
ggtgggttcg tggtctcgct gacttcaaga atgcacccat ggactttcac ggaccttcgc   2460
agtgagtgtt acagctctta aagatggcac agacccaaag agtcagtggc agcaaggttt   2520
attgtttatt cgcgaaagga caaagcttcc acagcgtgga agtagacccg agtgggttgc   2580
cgctgctggc tgtgtggcca gcttttattc ccctattggc cccgcccatg ttccgtttct   2640
gtcctatcag agtgcctttt tttcaatcct ccctgcgatt ggctactttc agaatcctgt   2700
gcagattggt gtgttttaca atcctcttgc aagacaggaa agttcctgat tggtgcattt   2760
tacaatcctc ttgtaagaca gaaaagttcc ccaagtcccc acgggaccca agaagtccag   2820
ctggcctcat gtctcagttt ctcctcttat caatattcat gtccctccca cagcttattg   2880
aatatgcata ttcagccacc cccactcagt gtagatctct gctttattct tccctccctc   2940
caagtgtctg tttccagctt cctaccagag gctgcgcctc ccaaccagtc agaacagcca   3000
cactcagccc gcagcacttt atgagaagta aagcgctcct ttccaaattg acgacctcgt   3060
ccttcttcag ttaacacctc cctctctcaa tgacgatgat ggagcatgtc caggtgttgg   3120
tgacacagct acatggctgc gtgtgggata aagtcgctgc cccttcagaa ctcacacccc   3180
cctggagtgg gacacacacc tctaagaaca aacaaggatg agagcagagc cagcttggca   3240
tcgtgggaat caataaatga aacagaaagt gcaaggtggt gggggtagct atctcgggac   3300
ggggtgtcag aggtggatct gagttgggca gacaggaggg acgcagtcca gggcggtcct   3360
gggtgagtct gttccatgta aggaactgcc agcacacagg tcgtaaggag gagtgcggtg   3420
tggccccggc accaatccag ggctggatga agaatgattg aggcagtctg aagatgacac   3480
caagtcattc tcctcccacg gagaggtgga ctttctcttc tctctgcaat ctgggctggc   3540
ctcagtgact tgaggaggga gaaatactct aggattccta ggctgggtca taaggcacct   3600
tctagcctct gctcgagtga cctcctagga agtacagctg ccctgagccc accatgctgt   3660
gaggaagccc aagccagccg tgggaagagg ccgtgaggtg ggggagggga gggagatctg   3720
tccggcctca cctgttgtag ccatcccata ggtgtgtgaa cacagcatct tggacaagcc   3780
agccccagct gacataattt acagaaaaac caaggaaccc tgcagacagc cggaactgag   3840
```

-continued

```
gtcccaaaat acagcccagc caagccatgc tgccatcgtt agccattggt accttcccaa   3900
ttgagacccc acaaatcatg cggcctgtgc caccatccag tgccggatct gaactactga   3960
tccactgagc tttgggctga ttggttctgc aacgatgggt ggccaaggcc acggtcaaat   4020
ccagctggag aggtggatgg ggccagtgtc aggggtttgg atttcacccc aagtcagctg   4080
aggcacactg gaatgtcgta agcctgcaca tccactcatc acacatttta accgcatctg   4140
agtgtggacc gtaccgatgg gttcctgcac ctgcagcctc cacaccattg ctggtgccct   4200
gcctcctagc tggagtatcc ttcctgtctc ttggctgctc tttgtaccca tcatggtccc   4260
cctaccaccc tccaagttct gctccaagct ttgttttcct ccaagagaag aacctgtcca   4320
gacaatagtt tcaaagcagc gggaagctct gctcacgtgt ccccaaggac catgctgtgt   4380
gaaattccct tctgtaatca cagagcccat tgccctggcc tattcctggt ccaggaatag   4440
ggaggaggta gacagaggat gcctccttcc ccactgctga gaaccctgcc atcctcagcc   4500
acagttgcca cagagaagat accacatccc tgggggaatc agcaggaatc aggtagagag   4560
tggcactgct ctggggaggg agggcgtctc acagcatcaa acgtcaaaaa cccacaacat   4620
tgacccagtc ctgccaagac ggaaccctgc atgagcatgg gggatgggga gttggggtgt   4680
tgcaaaagac gcaatacatg aatgatctca ggtaattctc aggcaacccc cggaggctgg   4740
tgttgctagc acccctctgc aggagaagaa gctggggctc gggagctgac tggatctgct   4800
caaaggccca ggaagaataa gagttaggaa ctgggacaga ccttgaggaa gctgcacttc   4860
ctcctgaggt gagccagcgt tggagctgtt tttcctttca gtatgaattc cacaaggaaa   4920
tcatctcagg aggaagggct catacttgga tccagaaaat atcaacatag ccaaagaaaa   4980
acaatcaaga catacctcca                                               5000
```